US012692314B2

(12) United States Patent
Pihlgren Bosch et al.

(10) Patent No.: US 12,692,314 B2
(45) Date of Patent: Jul. 28, 2026

(54) CD3/BCMA/CD38 TRISPECIFIC ANTIBODIES

(71) Applicant: IGI THERAPEUTICS SA, Neuchâtel (CH)

(72) Inventors: Maria Pihlgren Bosch, La Chaux-de-Fonds (CH); Mario Perro, La Chaux-de-Fonds (CH); Olivia Hall, La Chaux-de-Fonds (CH); Laura Carretero Iglesia, La Chaux-de-Fonds (CH); Adam Drake, La Chaux-de-Fonds (CH); Daniela Pais, La Chaux-de-Fonds (CH); Rebecca Croasdale-Wood, La Chaux-de-Fonds (CH); Carole Estoppey, La Chaux-de-Fonds (CH); Michael Dyson, La Chaux-de-Fonds (CH); Thierry Monney, La Chaux-de-Fonds (CH)

(73) Assignee: IGI THERAPEUTICS SA, Neuchâtel (CH)

( * ) Notice: Subject to any disclaimer, the term of this patent is extended or adjusted under 35 U.S.C. 154(b) by 469 days.

(21) Appl. No.: 18/312,519

(22) Filed: May 4, 2023

(65) Prior Publication Data

US 2024/0132615 A1 Apr. 25, 2024
US 2024/0228650 A9 Jul. 11, 2024

(30) Foreign Application Priority Data

May 6, 2022 (EP) .................................... 22172090
Jul. 26, 2022 (EP) .................................... 22186879
Nov. 16, 2022 (EP) .................................... 22207756
Dec. 8, 2022 (EP) .................................... 22212233

(51) Int. Cl.
*C07K 16/28* (2006.01)
*A61P 35/00* (2006.01)

(52) U.S. Cl.
CPC .......... *C07K 16/2809* (2013.01); *A61P 35/00* (2018.01); *C07K 16/2878* (2013.01); *C07K 16/2896* (2013.01); *C07K 2317/31* (2013.01); *C07K 2317/515* (2013.01); *C07K 2317/55* (2013.01); *C07K 2317/565* (2013.01); *C07K 2317/622* (2013.01); *C07K 2317/70* (2013.01); *C07K 2317/71* (2013.01); *C07K 2317/72* (2013.01); *C07K 2317/76* (2013.01); *C07K 2317/94* (2013.01)

(58) Field of Classification Search
CPC ............ C07K 16/2809; C07K 16/2878; C07K 16/2896; C07K 2317/31; C07K 2317/515; C07K 2317/55; C07K 2317/565; C07K 2317/622; C07K 2317/70; C07K 2317/71; C07K 2317/72; C07K 2317/76; C07K 2317/94; A61P 35/00
See application file for complete search history.

(56) References Cited

U.S. PATENT DOCUMENTS 8,883,981 B2 * 11/2014 Shitara ............... C07K 16/2887 530/387.3
9,209,965 B2 12/2015 Rahbar et al.
10,882,922 B2 1/2021 Yang et al.
11,124,577 B2 9/2021 Vu et al.
2017/0027488 A1 2/2017 Enenkel et al.
2020/0048348 A1 * 2/2020 Trinklein ........... C07K 16/2809
2020/0399386 A1 * 12/2020 Abbasian ........... C07K 16/2878
2021/0163620 A1 6/2021 Granda et al.
2021/0284749 A1 * 9/2021 Park ....................... C07K 16/30
2022/0089767 A1 * 3/2022 Bouchez .............. C07K 16/468
2022/0348659 A1 * 11/2022 Sato ........................ A61P 31/12
2023/0242656 A1 * 8/2023 Li ...................... C07K 16/2878 424/144.1
2025/0206823 A1 * 6/2025 Qu ......................... A61K 47/68

FOREIGN PATENT DOCUMENTS

WO WO-1999051642 A1 10/1999
WO WO-2012131555 A2 10/2012
WO WO-2012135345 A1 10/2012
WO WO-2019195535 A1 * 10/2019 ......... C07K 16/2803
WO WO-2020204708 A1 10/2020

OTHER PUBLICATIONS

Blythe (Protein Science (2005) 14:246-248) (Year: 2005).*
Gershoni (Biodrugs (2007) 21(3): 145-156) (Year: 2007).*
Sela-Culang (Frontiers in Immunology (2013) 4: 302) (Year: 2013).*
Almagro (Frontiers in Immunology (2018) 8: 1751) (Year: 2018).*
Ni (The Protein Journal (2024) 43: 683-696) (Year: 2024).*
Anderson, K.C., et al., "Clinically relevant end points and new drug approvals for myeloma," Leukemia. 22(2):231-9, Nature Publishing Group, United Kingdom (Feb. 2008).
Arnett, K., et al., "Crystal structure of a human CD3-epsilon/delta dimer in complex with a UCHT1 single-chain antibody fragment," Proc. Natl. Acad. Sci. USA. 101(46):16268-73, PNAS, United States (Nov. 2004).
Bird, R.E., et al., "Single-chain antigen-binding proteins," Science 242:423-426, American Association for the Advancement of Science, United States (Oct. 1988).

(Continued)

*Primary Examiner* — Brad Duffy
*Assistant Examiner* — Elizabeth A Shupe
(74) *Attorney, Agent, or Firm* — MARSHALL, GERSTEIN & BORUN LLP

(57) ABSTRACT

The present invention relates to novel trispecific heterodimeric immunoglobulins. More specifically the present invention relates to trispecific heterodimeric immunoglobulins that target human CD3 antigen, human BCMA and human CD38 antigen. The present invention also relates to this novel class of trispecific heterodimeric immunoglobulins for use in the treatment of proliferative diseases and in particular cancers such as hematological cancer. The present invention relates to novel trispecific antibody for use in treating multiple myeloma.

10 Claims, 138 Drawing Sheets

Figure 1A:
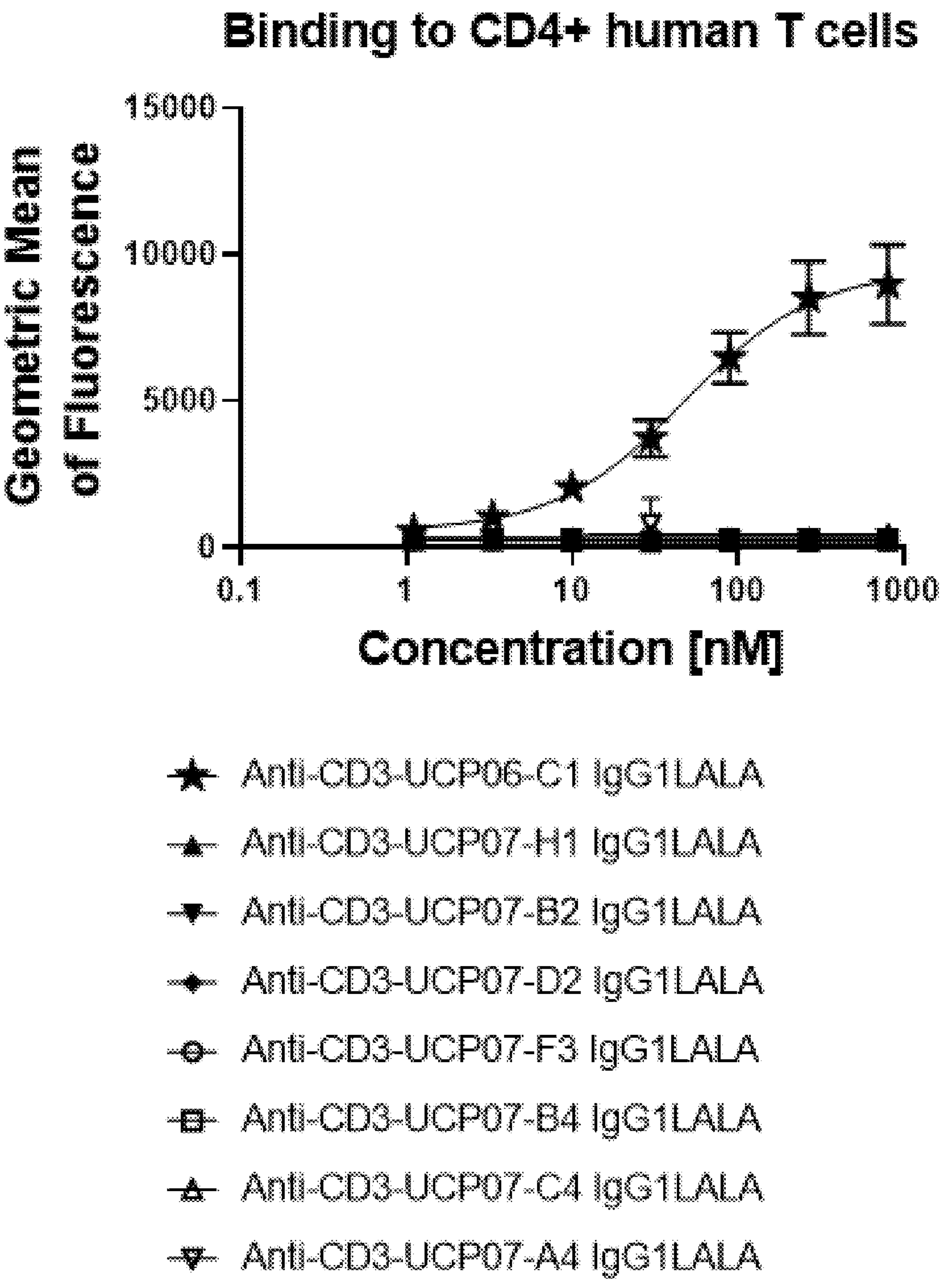

Specification includes a Sequence Listing.

(56) References Cited

OTHER PUBLICATIONS

Cohen, A.D., et al., "B cell maturation antigen—specific Car T cells are clinically active in multiple myeloma," The Journal of Clinical Investigation 129:2210-2221, The American Society for Clinical Investigation, United States (Jun. 2016).
Coloma, M.J., and Morrison, S.L., "Design and production of novel tetravalent bispecific antibodies," Nat. Biotechnol. 15(2):159-62, Nature Publishing Group, United States (Feb. 1997).
Frankel, SR., and Baeuerle, PA., "Targeting T cells to tumor cells using bispecific antibodies," Current Opinion in Chemical Biology 17(3):385-92, Elsevier, Netherlands (2013).
Frerichs. K.A., et al., "Preclinical Activity of JNJ-7957, a Novel BCMA×CD3 Bispecific Antibody for the Treatment of Multiple Myeloma, Is Potentiated by Daratumumab," Clin. Cancer Res. 26(9):2203-2215, American Association for Cancer Research, United States (May 2020).
Hezareh, M., et al., "Effector Function Activities of a Panel of Mutants of a Broadly Neutralizing Antibody against Human Immunodeficiency Virus Type 1," J. Virol. 75(24):12161-12168, American Society for Microbiology, United States (Dec. 2001).
Hinton, P.R., et al., "An engineered human IgG1 antibody with longer serum half-life," J. Immunol. 176(1):346-56, American Associated of Immunologists, United States (Jan. 2006).
Holliger. P., et al., "'Diabodies': small bivalent and bispecific antibody fragments," Proc. Natl. Acad. Sci. US. 90:6444-48, PNAS, United States (Jul. 1993).
Huston, J.S., et al., "Protein engineering of antibody binding sites: recovery of specific activity in an anti-digoxin single-chain Fv analogue produced in *Escherichia coli*," Proc. Natl. Acad. Sci. US. 85:5879-83, PNAS, United States (Aug. 1988).
Kalim, M., et al., "Intracellular trafficking of new anticancer therapeutics: antibody-drug conjugates," Drug Des. Devel. Ther. 11:2265-2276, Dove Medical Press, New Zealand (Aug. 2017).
Laabi, Y.,et al., "A new gene, BCM, on chromosome 16 is fused to the interleukin 2 gene by a t(4;16) (q26;p13) translocation in a malignant T cell lymphoma," The EMBO Journal 11(11):3897-3904, Oxford University Press, United Kingdom (1992).
Labrijn, A.F., et al., "Controlled Fab-arm exchange for the generation of stable bispecific IgG1," Nat. Protoc. 9(10):2450-63, Nature Publishing Group, United Kingdom (Oct. 2014).
Ferrero, E.,., et al., "A Natural History of the Human CD38 Gene," pp. 65-79 in *Cyclic ADP-Ribose and NAADP*, eds. Lee, H., et al., Springer Publishing, Boston, Massachusetts, United States (2002).
Liu, Y., et al., "High-throughput screening for developability during early-stage antibody discovery using self-interaction nanoparticle spectroscopy," mABs 6(2):483-92, Landes Bioscience, United States (Apr. 2014).
Madry, C., et al., "The characterization of murine BCMA gene defines it as a new member of the tumor necrosis factor receptor superfamily," International Immunology 10(11):1693-1702, Oxford University Press, United Kingdom (Jun. 1998).
May, C., et al., "Advances in bispecific biotherapeutics for the treatment of cancer," Biochemical Pharmacology. 84(9):1105-12, Elsevier, Netherlands (2012).
Moreau, P., et al., "Teclistamab in Relapsed or Refractory Multiple Myeloma," The New England Journal of Medicine, 6:495-505, Massachusetts Medical Society, United States (Jun. 2022).
Moreaux, J., et al., "BAFF and APRIL protect myeloma cell from apoptosis induced by interleukin 6 deprivation and dexamethasone," Blood. 103(8):3148-3157, Elsevier, Netherlands (Apr. 2004).
Munshi, N.C., et al., "Idecabtagene Vicleucel in Relapsed and Refractory Multiple Myeloma," The New England Journal of Medicine 384:705-716, Massachusetts Medical Society, United States (Mar. 2021).
Nie, S., et al., "Biology drives the discovery of bispecific antibodies as innovative therapeutics," Antibody Therapeutics 3(1):17-62, National Library of Medicine, United Kingdom (2020).
Nijhof, I.S., et al., "CD38 expression and complement inhibitors affect response and resistance to daratumumab therapy in myeloma," Blood 128:7, Elsevier, Netherlands (Aug. 2016).
Parslow, A.C., et al., "Antibody-Drug Conjugated for Cancer Therapy," Biomedicines 4(3):14, MDPI, Switzerland (Jul. 2016).
Pillarisetti, K., et al., "Teclistamab is an active T cell-redirecting bispecific antibody against B-cell maturation antigen for multiple myeloma," Blood Adv. 4(18):4538-4549, Elsevier, Netherlands (Sep. 2020).
Ran, F.A., et al., "Double nicking by RNA-guided CRISPR Cas9 for enhanced genome editing specificity," Cell. 154(6)1380-9, Elsevier, Netherlands (Sep. 2013).
Rodriguez-Lobato, L. G., et al., "Why Immunotherapy Fails in Multiple Myeloma," Hemato. 2(1):1-42, MDPI, Switzerland (Dec. 2020).
Schlothauer. T., et al., "Novel human IgG1 and IgG4 Fc-engineered antibodies with completely abolished immune effector functions," Protein Eng. Des. Sel. 29(10):457-466, Oxford University Press, United Kingdom (Jul. 2016).
Seckinger, A., et al., "Target Expression, Generation, Preclinical Activity, and Pharmacokinetics of the BCMA-T Cell Bispecific Antibody EM801 for Multiple Myeloma Treatment," Cancer Cell. 31(3):396-410, Cell Press, United States (Mar. 2017).
Shields, R.L., et al., "High resolution mapping of the binding site on human IgGI for Fc gamma RI, Fc gamma RII, Fc gamma RIII, and FcRn and design of IgGI variants with improved binding to the Fc gamma R," J. Biol. Chem. 276(9):6591-604, Elsevier, Netherlands (Mar. 2001).
Skegro, D., et al., "Immunoglobin domain interface exchange as a platform technology for the generation of Fc heterodimers and bispecific antibodies," J. Biol. Chem. 292(23):9745-9759, Elsevier, Netherlands (Jun. 2017).
Smith, E.J., et al., "A novel, native-format bispecific antibody triggering T-cell killing of B-cells is robustly active in mouse tumor models and cynomolgus monkeys," Sci. Rep. 5:17943, Nature Publishing Group, United Kingdom (Dec. 2015).
Sondergeld, P., et al., "Monoclonal antibodies in myeloma," Clin. Adv. Hermatol. Oncol. 13(9):599-609, Millennium Medical Publishing, United States (Sep. 2015).
Sonneveld, P., and Broji, A., "Treatment of relapsed and refractory multiple myeloma," Haematologica. 101(4):396-404, Ferrata Storti Foundation, Italy (Apr. 2016).
Stutz, C., et al., "A single mutation increases heavy-chain heterodimer assembly of bispecific antibodies by inducing structural disorder in one homodimer species," J. Biol. Chem. 295(28):9392-9408, Elsevier, Netherlands (May 2020).
Szlasa, W., et al., "Targeting CD38 in Neoplasms and Non-Cancer Diseases," Cancers 14(17):4169, MDPI, Switzerland (Aug. 2022).
Tai, Y.T., et al., "Anti-CS1 humanized monoclonal antibody HuLuc63 inhibits myeloma cell adhesion and induces antibody-dependent cellular cytotoxicity in the bone marrow milieu," Blood. 113(4):1329-37, The American Society of Hematology, United States (Aug. 2008).
Tandon, B., and Duncavage, E.J., "The utility of next-generation sequencing in diagnosis and monitoring of acute myeloid leukemia and myelodysplastic syndromes," Int. J. Lab. Hematol. 1:115-21, Wiley, United Kingdom (May 2015).
Tomlinson, I., and Holliger, P., "Methods for generating multivalent and bispecific antibody fragments," Methods Enzymol. 326:461-79, Elsevier, Netherlands (2000).
Uhlen, M., et al., "A pathology atlas of the human cancer transcriptome," Science. 357(6352):eaan2507, American Association for the Advancement of Science, United States (Aug. 2017).
UniProtKB, "A0A2K5UD97_MACFA," Accession No. A0A2K5UD97, accessed at https://www.uniprot.org/uniprotkb/A0A2K5UD97/, accessed on Jul. 6, 2023, 6 pages.
UniProtKB, "CD38_HUMAN," Accession No. P28907, accessed at https://www.uniprot.org/uniprotkb/P28907, accessed on Jul. 6, 2023, 9 pages.
UniProtKB, "CD38_MACFA," Accession No. Q5VANO, accessed at https://www.uniprot.org/uniprotkb/Q5VAN0/, accessed on Jul. 6, 2023, 6 pages.
UniProtKB, "CD3D_HUMAN," Accession No. P04234, accessed at https://www.uniprot.org/uniprotkb/P04234/, accessed on Jul. 6, 2023, 12 pages.

(56) References Cited

OTHER PUBLICATIONS

UniProtKB, "CD3D_MACDA," Accession No. Q95LI8, accessed at https://www.uniprot.org/uniprotkb/Q95LI8/, accessed on Jul. 6, 2023, 8 pages.
UniProtKB, "CD3E_HUMAN," Accession No. P07766, accessed at https://www.uniprot.org/uniprotkb/P07766/, accessed on Jul. 6, 2023, 12 pages.
UniProtKB, "CD3E_MACFA," Accession No. Q95LI5, accessed at https://www.uniprot.org/uniprotkb/Q95LI5/, accessed on Jul. 6, 2023, 8 pages.
UniProtKB, "CD3G_HUMAN," Accession No. P09693, accessed at https://www.uniprot.org/uniprotkb/P09693, accessed on Jul. 6, 2023, 12 pages.
UniProtKB, "CD80_MOUSE," Accession No. Q00609, accessed at https://www.uniprot.org/uniprotkb/Q00609/, accessed on Jul. 6, 2023, 10 pages.
UniProtKB, "TNR17_HUMAN," Accession No. Q02223, accessed at https://www.uniprot.org/uniprotkb/Q02223/, accessed on Jul. 6, 2023, 8 pages.
Ward, E.S., et al., "Binding activities of a repertoire of single immunoglobulin variable domains secreted from *Escherichia coli*," Nature 341:544-546, Nature Publishing Group, United Kingdom (Oct. 1989).
Wines, B.D., et al., "The interaction of Fc alpha RI with IgA and its implications for ligand binding by immunoreceptors of the leukocyte receptor cluster," J Immunol. 166(3):1781-9, The American Association of Immunologists, United States (Feb. 2001).
Zun De Zafra, C.L., et al., "Targeting Multiple Myeloma with AMG 424, a Novel Anti-CD38/CD3 Bispecific T-cell-recruiting Antibody Optimized for Cytotoxicity and Cytokine Release," Clin Cancer Res. 25(13):3921-3933, American Association for Cancer Research, United States (Jul. 2019).

* cited by examiner

Binding to CD4+ human T cells

★ Anti-CD3-UCP06-C1 IgG1LALA

▲ Anti-CD3-UCP07-H1 IgG1LALA

▼ Anti-CD3-UCP07-B2 IgG1LALA

◆ Anti-CD3-UCP07-D2 IgG1LALA

○ Anti-CD3-UCP07-F3 IgG1LALA

▣ Anti-CD3-UCP07-B4 IgG1LALA

△ Anti-CD3-UCP07-C4 IgG1LALA

▽ Anti-CD3-UCP07-A4 IgG1LALA

Human T cell activation

- ★ Anti-CD3-UCP06-C1 IgG1LALA
- ⬟ Anti-CD3-UCP07-H1 IgG1LALA
- ▼ Anti-CD3-UCP07-B2 IgG1LALA
- ◆ Anti-CD3-UCP07-D2 IgG1LALA
- ○ Anti-CD3-UCP07-F3 IgG1LALA
- ☐ Anti-CD3-UCP07-B4 IgG1LALA
- △ Anti-CD3-UCP07-C4 IgG1LALA
- ▽ Anti-CD3-UCP07-A4 IgG1LALA

NCI-H929 Killing

- ◆ Anti-CD3-C1-UCP01-D6 x BCMA
- ◇ Anti-CD3-C1-UCP01-E10 x BCMA
- ✴ Anti-CD3-C1-UCP01-H10 x BCMA
- ⊠ Anti-CD3-C1-UCP01-F10 x BCMA
- ✕ Anti-CD3-C1-UCP01-E12 x BCMA
- ◈ TNB-F2B BEAT Fc
- ⊙ 83A10-TCBcv_aCD3xTNB-BCMA BEAT Fc
- — Negative control
- �ꟷ No Antibody

T cell activation

- ◆ Anti-CD3-C1-UCP01-D6 x BCMA
- ◇ Anti-CD3-C1-UCP01-E10 x BCMA
- ✳ Anti-CD3-C1-UCP01-H10 x BCMA
- ⊠ Anti-CD3-C1-UCP01-F10 x BCMA
- ✕ Anti-CD3-C1-UCP01-E12 x BCMA
- ◆ TNB-F2B BEAT Fc
- ○ 83A10-TCBcv_aCD3xTNB-BCMA BEAT Fc
- — Negative control
- ╁ No Antibody Anti-CD3 «Fc distal»

Anti-CD38

Anti-BCMA « Fc proximal»

A   B

IgG3 BEAT (A) CH3 [A(-)]          Anti-BCMA VH

IgG1 BEAT (B) CH3 [A(+)]          Anti-CD38 VH

IgG1          Anti-CD3 VH cLc VL

Anti-BCMA «Fc distal»

Anti-CD3

Anti-CD38 « Fc proximal»

A   B

⬤ IgG3 BEAT (A) CH3 [A(-)]          ⬤ Anti-BCMA VH

⬤ IgG1 BEAT (B) CH3 [A(+)]          ⬤ Anti-CD38 VH

◯ IgG1                               ⬤ Anti-CD3 VH

⬤ cLc VL

- --★-- Daratumumab
- -⊗- Isatuximab
- -■- 83A10-TCBcv
- -△- CD3/BCMA/CD38_119
- -□- CD3/BCMA/CD38_118
- △ Isotype IgG1

- ✕ Isotype TREAT
- ⊛ No antibody

■ Vehicle

▨ 0.1 mg/kg CD3/BCMA/CD38-118

▨ 0.02 mg/kg CD3/BCMA/CD38-118

▨ 2.5 mg/kg BEAT CD3/CD38

▨ 0.1 mg/kg BEAT CD3/CD38

▨ 2.5 mg/kg Teclistamab

▨ 0.1 mg/kg Teclistamab

Figure 46A:
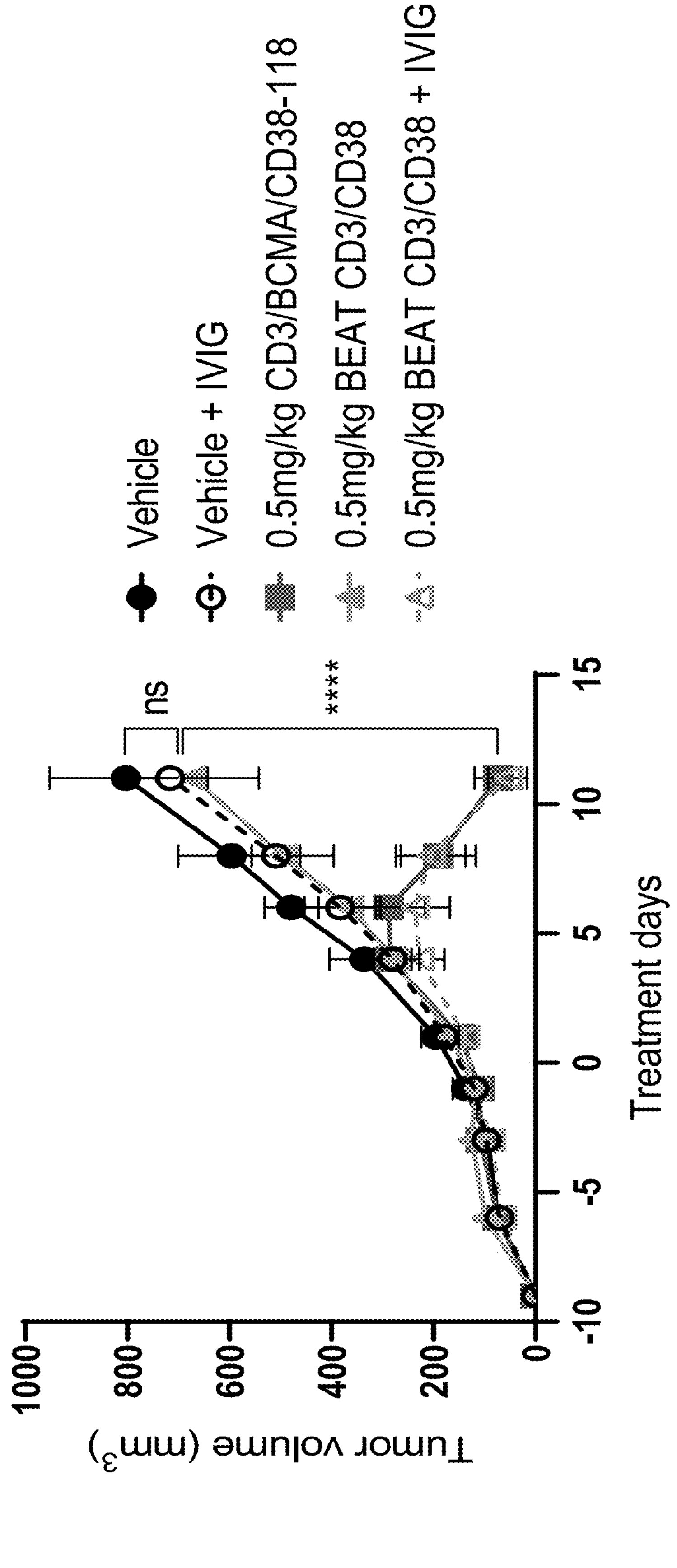
Figure 46B:
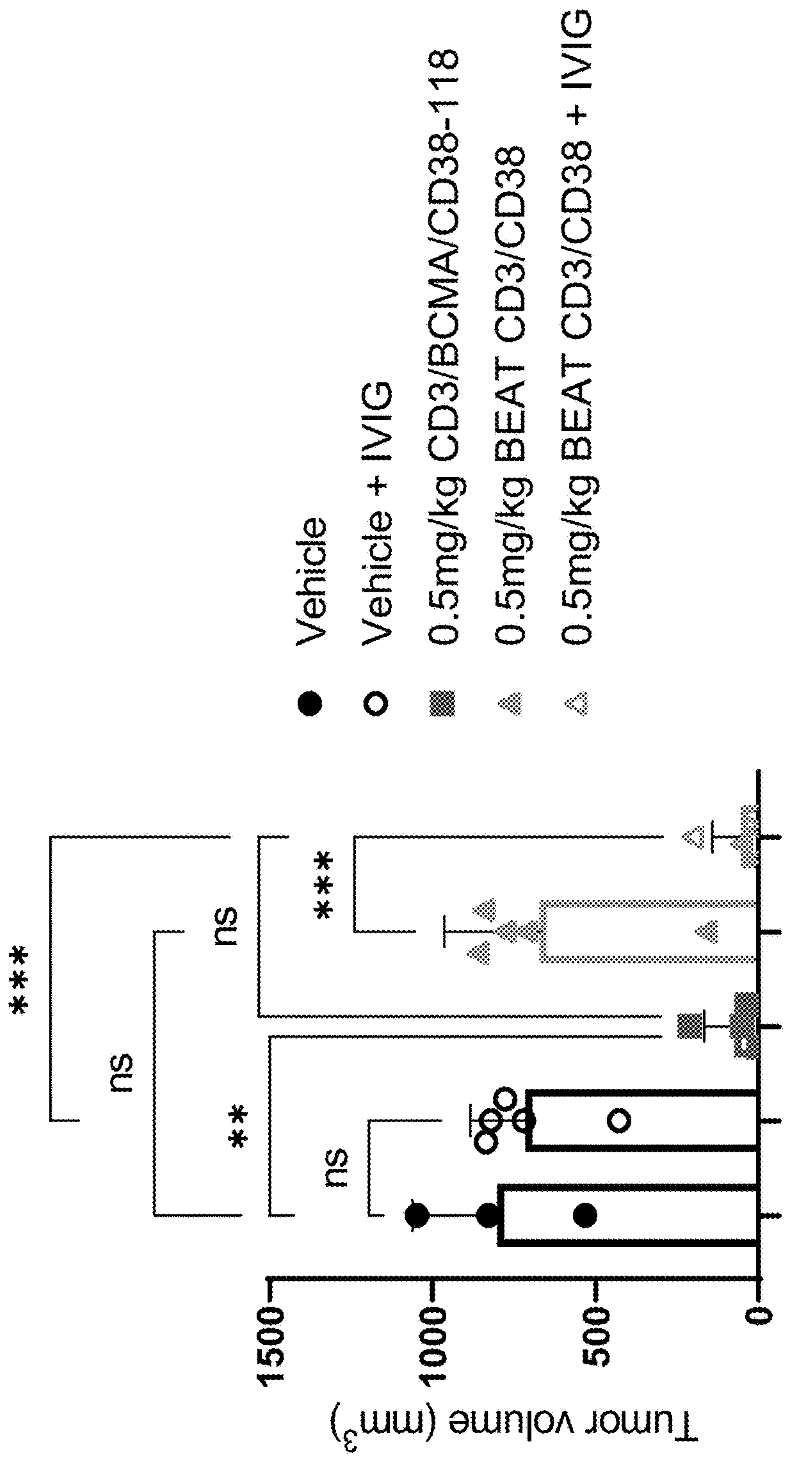
Figure 46C:
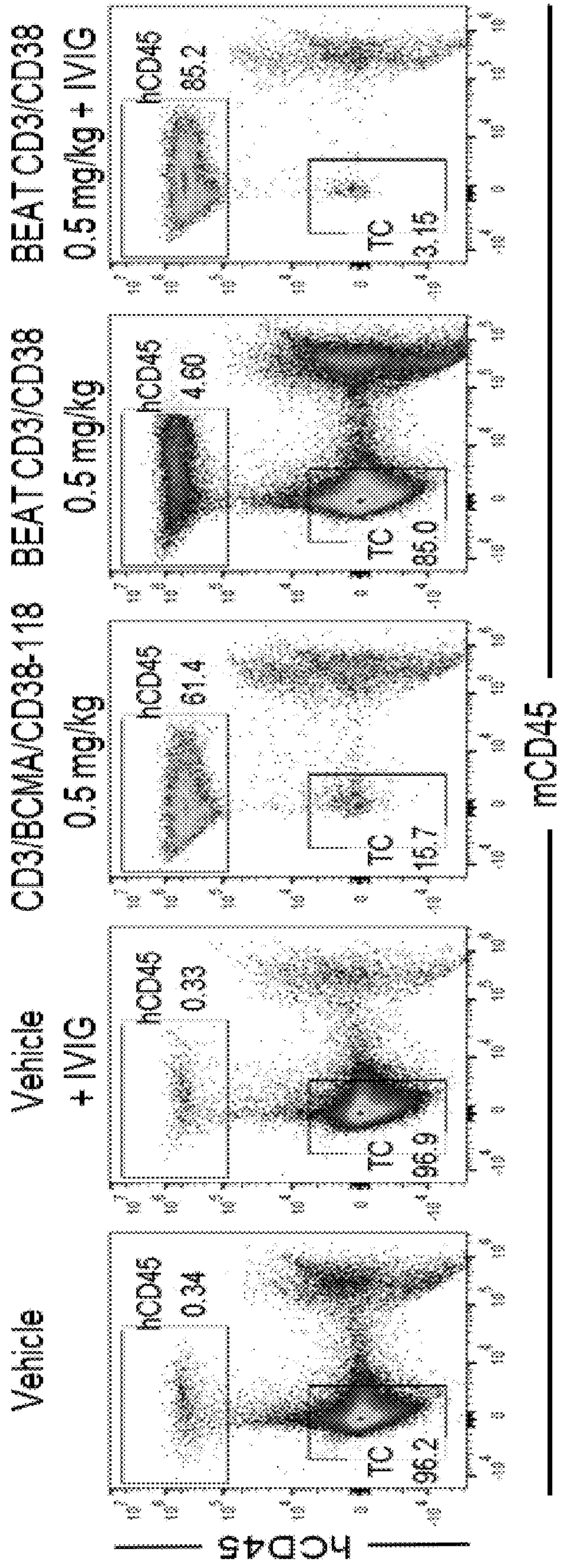
Figure 46D:
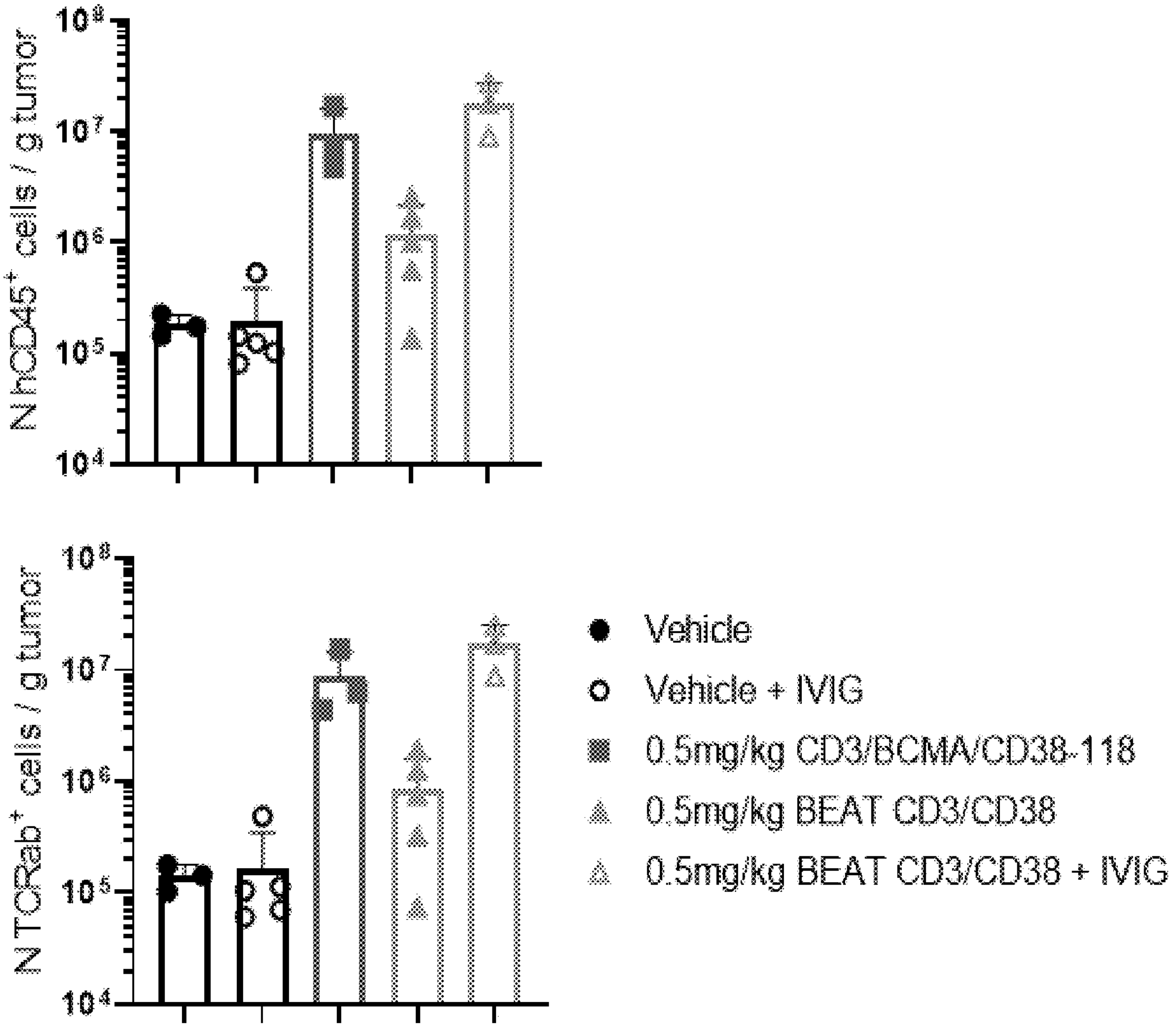

FIG. 46D (continuation)
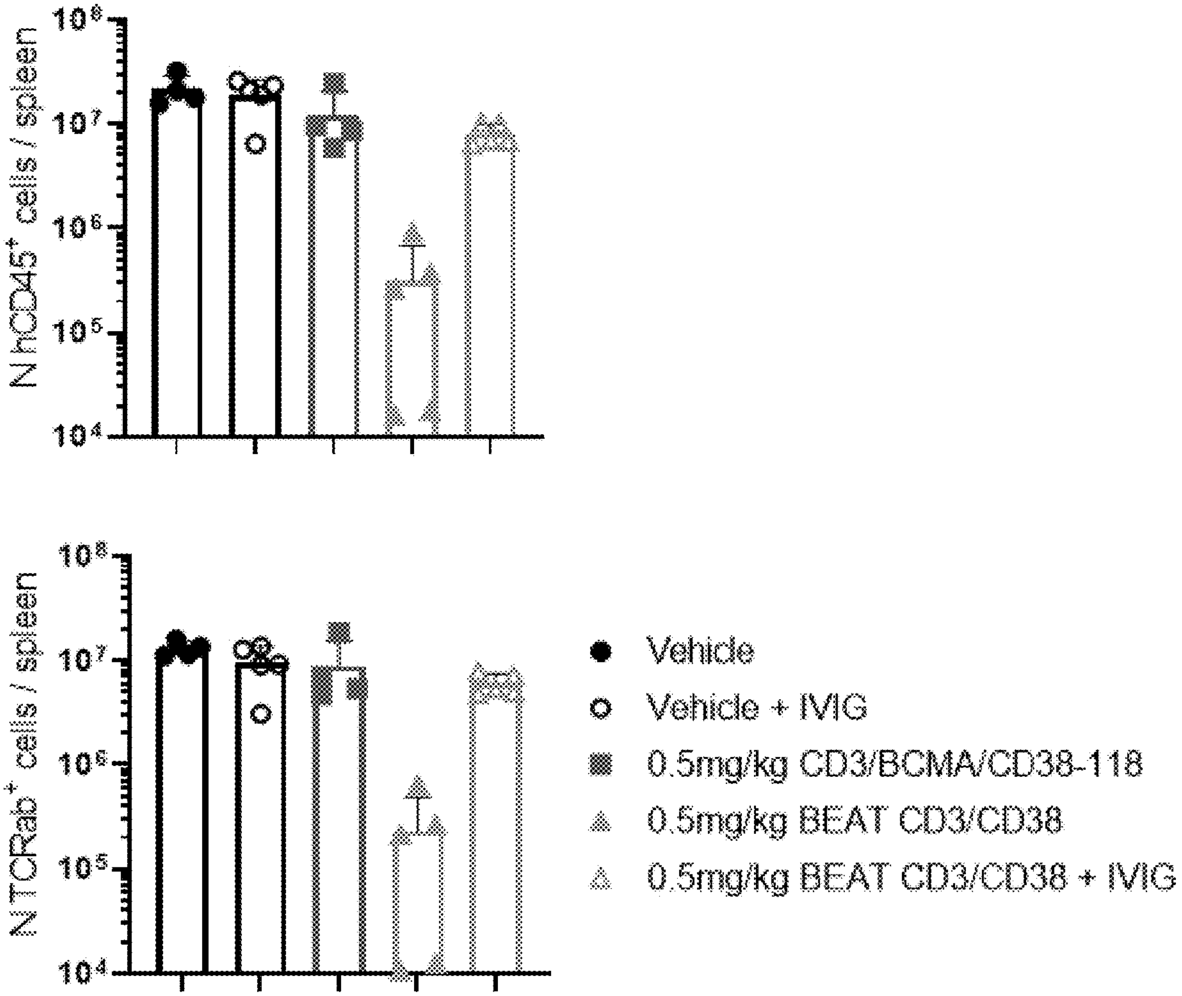

Tumor volume (mm³)

Treatment days

● Vehicle
0.1 mg/kg CD3/BCMA/CD38-118
0.1 mg/kg BEAT CD3/CD38
0.1 mg/kg Teclistamab Tumor volume (mm³)

Treatment days

● Vehicle
0.5 mg/kg CD3/BCMA/CD38-118
0.5 mg/kg BEAT CD3/CD38
0.5 mg/kg Teclistamab

SEQUENCE LISTING

```
Sequence total quantity: 729
SEQ ID NO: 1            moltype = AA  length = 214
FEATURE                 Location/Qualifiers
REGION                  1..214
                        note = SEQ ID NO: 1 - Vk35 /Jk1 Light Chain
source                  1..214
                        mol_type = protein
                        organism = synthetic construct
SEQUENCE: 1
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 2            moltype = AA  length = 451
FEATURE                 Location/Qualifiers
REGION                  1..451
                        note = SEQ ID NO: 2 - anti-CD3-UCP02-A3 IgG1 LALA Heavy
                         Chain
source                  1..451
                        mol_type = protein
                        organism = synthetic construct
SEQUENCE: 2
EVQLVESGGG LIQPGGSLRL SCAASGFTFR RYYMTWVRQA PGKGLEWVSV IFPQGGTSYA  60
DSVKGRFTIS RDNSKNTLYL QMNSLRAEDT AVYYCARVHD VLDDVEWFDH WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 3            moltype = AA  length = 448
FEATURE                 Location/Qualifiers
REGION                  1..448
                        note = SEQ ID NO: 3 - anti-CD3-UCP02-B2 IgG1 LALA Heavy
                         Chain
source                  1..448
                        mol_type = protein
                        organism = synthetic construct
SEQUENCE: 3
EVQLLESGGG LVQPGGSLRL SCAASGFTFS HYVLNWVRQA PGKGLEWVSG ISLTGIATIY  60
ADSVKGRFTI SRDNSKNTLY LQMNSLRAED TAVYYCARGD PTSAFDVWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 4            moltype = AA  length = 451
FEATURE                 Location/Qualifiers
REGION                  1..451
                        note = SEQ ID NO: 4 - anti-CD3-UCP02-D2 IgG1 LALA Heavy
                         Chain
source                  1..451
                        mol_type = protein
                        organism = synthetic construct
SEQUENCE: 4
EVQLVESGGG LVKPGGSLRL SCAASGFTFN KAWMGWVRQA PGKGLEWVGR IKSVTDGGIT  60
VYAAPVKGRF TISRDDSKNT LYLQMNSLKT EDTAVYYCAR VTARYYYFDN WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 5            moltype = AA  length = 448
FEATURE                 Location/Qualifiers
REGION                  1..448
                        note = SEQ ID NO: 5 - anti-CD3-UCP02-F2 IgG1 LALA Heavy
                         Chain
source                  1..448
                        mol_type = protein
                        organism = synthetic construct
SEQUENCE: 5
EVQLVESGGG LIQPGGSLRL SCAASGLKVS GNYMNWVRQA PGKGLEWVSV IYSDGQTYYA  60
```

```
DSVKGRFTIS RDNSKNTLYL QMNSLRAEDT AVYYCARDPY YLGPFDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 6            moltype = AA  length = 447
FEATURE                 Location/Qualifiers
REGION                  1..447
                        note = SEQ ID NO: 6 - anti-CD3-UCP02-H2 IgG1 LALA Heavy
                         Chain
source                  1..447
                        mol_type = protein
                        organism = synthetic construct
SEQUENCE: 6
EVQLVESGGG LIQPGGSLRL SCAASGFTVS GYYMHWVRQA PGKGLEWVSI IYVDGRTEYA  60
DSVKGRFTIS RDNSKNTLYL QMNSLRAEDT AVYYCARASY AGPFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 7            moltype = AA  length = 452
FEATURE                 Location/Qualifiers
REGION                  1..452
                        note = SEQ ID NO: 7 - anti-CD3-UCP03-A3 IgG1 LALA Heavy
                         Chain
source                  1..452
                        mol_type = protein
                        organism = synthetic construct
SEQUENCE: 7
EVQLLESGGG LVQPGGSLRL SCAASGFTFS SNAMSWVRQA PGKGLEWVSA VGKYGGATSY  60
ADSVKGRFTI SRDNSKNTLY LQMNSLRAED TAVYYCARGG PGYSTFYEFD NWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 8            moltype = AA  length = 448
FEATURE                 Location/Qualifiers
REGION                  1..448
                        note = SEQ ID NO: 8 - anti-CD3-UCP03-A4 IgG1 LALA Heavy
                         Chain
source                  1..448
                        mol_type = protein
                        organism = synthetic construct
SEQUENCE: 8
EVQLVESGGG LIQPGGSLRL SCAASGFTVS GNYMTWVRQA PGKGLEWVSL IYTDGRTLYA  60
DSVKGRFTIS RDNSKNTLYL QMNSLRAEDT AVYYCARVSW SYGPFDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 9            moltype = AA  length = 446
FEATURE                 Location/Qualifiers
REGION                  1..446
                        note = SEQ ID NO: 9 - anti-CD3-UCP03-B1 IgG1 LALA Heavy
                         Chain
source                  1..446
                        mol_type = protein
                        organism = synthetic construct
SEQUENCE: 9
EVQLLESGGG LVQPGGSLRL SCAASGFTFS RYAMTWVRQA PGKGLEWVSG ISKYGGATAY  60
ADSVKGRFTI SRDNSKNTLY LQMNSLRAED TAVYYCARGG TRFDIWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446
```

-continued

```
SEQ ID NO: 10          moltype = AA  length = 454
FEATURE                Location/Qualifiers
REGION                 1..454
                       note = SEQ ID NO: 10 - anti-CD3-UCP03-C1 IgG1 LALA Heavy
                        Chain
source                 1..454
                       mol_type = protein
                       organism = synthetic construct
SEQUENCE: 10
EVQLLESGGG LVQPGGSLRL SCAASGFTFS QYAMSWVRQA PGKGLEWVSV ISPSGATAVY  60
ADSVKGRFTI SRDNSKNTLY LQMNSLRAED TAVYYCARGQ YDDLDKSGYE FDHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 11          moltype = AA  length = 447
FEATURE                Location/Qualifiers
REGION                 1..447
                       note = SEQ ID NO: 11 - anti-CD3-UCP03-C3 IgG1 LALA Heavy
                        Chain
source                 1..447
                       mol_type = protein
                       organism = synthetic construct
SEQUENCE: 11
QVQLVQSGAE VKKPGSSVKV SCKASGGLFS SYTISWVRQA PGQGLEWMGG IIPNTGSSYY  60
AQKFQGRVTI TADESTSTAY MELSSLRSED TAVYYCARDR YSVLDIWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 12          moltype = AA  length = 450
FEATURE                Location/Qualifiers
REGION                 1..450
                       note = SEQ ID NO: 12 - anti-CD3-UCP03-C5 IgG1 LALA Heavy
                        Chain
source                 1..450
                       mol_type = protein
                       organism = synthetic construct
SEQUENCE: 12
EVQLVESGGG LIQPGGSLRL SCAASGFTVS DNDMSWVRQA PGKGLEWVSL IYSNGGTHYA  60
DSVKGRFTIS RDNSKNTLYL QMNSLRAEDT AVYYCARWGI SLGEPYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 13          moltype = AA  length = 452
FEATURE                Location/Qualifiers
REGION                 1..452
                       note = SEQ ID NO: 13 - anti-CD3-UCP03-E1 IgG1 LALA Heavy
                        Chain
source                 1..452
                       mol_type = protein
                       organism = synthetic construct
SEQUENCE: 13
EVQLLESGGG LVQPGGSLRL SCAASGFTFS QYAMNWVRQA PGKGLEWVSA ISRKGGSTIY  60
ADSVKGRFTI SRDNSKNTLY LQMNSLRAED TAVYYCARAG YISGDSAAFD VWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 14          moltype = AA  length = 450
FEATURE                Location/Qualifiers
REGION                 1..450
                       note = SEQ ID NO: 14 - anti-CD3-UCP03-E2 IgG1 LALA Heavy
                        Chain
source                 1..450
```

-continued

```
                      mol_type = protein
                      organism = synthetic construct
SEQUENCE: 14
EVQLVESGGG LIQPGGSLRL SCAASGISVG NNYMSWVRQA PGKGLEWVSV IYPNGRIKYA  60
DSVKGRFTIS RDNSKNTLYL QMNSLRAEDT AVYYCARGVI DGSYLDFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 15         moltype = AA  length = 448
FEATURE               Location/Qualifiers
REGION                1..448
                      note = SEQ ID NO: 15 - anti-CD3-UCP03-E4 IgG1 LALA Heavy
                       Chain
source                1..448
                      mol_type = protein
                      organism = synthetic construct
SEQUENCE: 15
EVQLVESGGG LIQPGGSLRL SCAASGFTVS GYYMSWVRQA PGKGLEWVSV IGGAGQTDYA  60
DSVKGRFTIS RDNSKNTLYL QMNSLRAEDT AVYYCAREPW HTGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 16         moltype = AA  length = 451
FEATURE               Location/Qualifiers
REGION                1..451
                      note = SEQ ID NO: 16 - anti-CD3-UCP03-F1 IgG1 LALA Heavy
                       Chain
source                1..451
                      mol_type = protein
                      organism = synthetic construct
SEQUENCE: 16
EVQLLESGGG LVQPGGSLRL SCAASGFPFS HHVMTWVRQA PGKGLEWVSA ITQRGEYTLY  60
ADSVKGRFTI SRDNSKNTLY LQMNSLRAED TAVYYCARGP VPGGDHAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 17         moltype = AA  length = 448
FEATURE               Location/Qualifiers
REGION                1..448
                      note = SEQ ID NO: 17 - anti-CD3-UCP03-F2 IgG1 LALA Heavy
                       Chain
source                1..448
                      mol_type = protein
                      organism = synthetic construct
SEQUENCE: 17
EVQLLESGGG LVQPGGSLRL SCAASGFAFS HYAMTWVRQA PGKGLELVSA ISQHGGYTAY  60
ADSVKGRFTI SRDNSKNTLY LQMNSLRAED TAVYYCARGH PVHAFDFWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 18         moltype = AA  length = 449
FEATURE               Location/Qualifiers
REGION                1..449
                      note = SEQ ID NO: 18 - anti-CD3-UCP03-F4 IgG1 LALA Heavy
                       Chain
source                1..449
                      mol_type = protein
                      organism = synthetic construct
SEQUENCE: 18
EVQLVESGGG LIQPGGSLRL SCAASGFTFS DNYMSWVRQA PGKGLEWVSV IYSQGRTFYA  60
DSVKGRFTIS RDNSKNTLYL QMNSLRAEDT AVYYCARIPY RPSVYKDVWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
```

-continued

```
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 19          moltype = AA  length = 451
FEATURE                Location/Qualifiers
REGION                 1..451
                       note = SEQ ID NO: 19 - anti-CD3-UCP03-G2 IgG1 LALA Heavy
                        Chain
source                 1..451
                       mol_type = protein
                       organism = synthetic construct
SEQUENCE: 19
QVQLVQSGAE VKKPGSSVKV SCKASGYGFN LYAINWVRQA PGQGLEWMGR IIPEYGHTRY  60
AQKFQGRVTI TADESTSTAY MELSSLRSED TAVYYCARDR YSTYSGGMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 20          moltype = AA  length = 447
FEATURE                Location/Qualifiers
REGION                 1..447
                       note = SEQ ID NO: 20 - anti-CD3-UCP03-G3 IgG1 LALA Heavy
                        Chain
source                 1..447
                       mol_type = protein
                       organism = synthetic construct
SEQUENCE: 20
QVLLVQSGAE VKKPGSSVKV SCKASGGFFR YYAISWVRQA PGQGLEWMGG IIPVTGSTHY  60
AQKFQGRVTI TADESTSTAY MELSSLRSED TAVYYCARDR FGAFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 21          moltype = AA  length = 448
FEATURE                Location/Qualifiers
REGION                 1..448
                       note = SEQ ID NO: 21 - anti-CD3-UCP03-G4 IgG1 LALA Heavy
                        Chain
source                 1..448
                       mol_type = protein
                       organism = synthetic construct
SEQUENCE: 21
EVQLLESGGG LVQPGGSLRL SCAASGFNFD DYAMSWVRQA PGKGLEWVSI ISHKGDFTSY  60
ADSVKGRFTI SRDNSKNTLY LQMNSLRAED TAVYYCARVL LGDFFDVWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 22          moltype = AA  length = 446
FEATURE                Location/Qualifiers
REGION                 1..446
                       note = SEQ ID NO: 22 - anti-CD3-UCP03-H2 IgG1 LALA Heavy
                        Chain
source                 1..446
                       mol_type = protein
                       organism = synthetic construct
SEQUENCE: 22
EVQLVESGGG LIQPGGSLRL SCAASGFTVR DSYMHWVRQA PGKGLEWVSI IYYTGKTHYA  60
DSVKGRFTIS RDNSKNTLYL QMNSLRAEDT AVYYCARSQY GYFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 23          moltype = AA  length = 445
FEATURE                Location/Qualifiers
```

```
REGION                  1..445
                        note = SEQ ID NO: 23 - anti-CD3-UCP03-H3 IgG1 LALA Heavy
                         Chain
source                  1..445
                        mol_type = protein
                        organism = synthetic construct
SEQUENCE: 23
EVQLVESGGG LIQPGGSLRL SCAASGFTVR DTYMSWVRQA PGKGLEWVSI IYGHGKTTYA  60
DSVKGRFTIS RDNSKNTLYL QMNSLRAEDT AVYYCARGYQ LFDIWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                       445

SEQ ID NO: 24           moltype = AA  length = 447
FEATURE                 Location/Qualifiers
REGION                  1..447
                        note = SEQ ID NO: 24 - anti-CD3-UCP05-A1 IgG1 LALA Heavy
                         Chain
source                  1..447
                        mol_type = protein
                        organism = synthetic construct
SEQUENCE: 24
EVQLLESGGG LVQPGGSLRL SCAASGFTFS TYAMSWVRQA PGKGLELVSA ISRHGGFSRY  60
ADSVKGRFTI SRDNSKNTLY LQMNSLRAED TAVYYCARAS SYGYDPWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 25           moltype = AA  length = 449
FEATURE                 Location/Qualifiers
REGION                  1..449
                        note = SEQ ID NO: 25 - anti-CD3-UCP05-A2 IgG1 LALA Heavy
                         Chain
source                  1..449
                        mol_type = protein
                        organism = synthetic construct
SEQUENCE: 25
EVQLLESGGG LVQPGGSLRL SCAASGFSFK IYAMGWVRQA PGKGLEWVSA ITQQGGATVY  60
ADSVKGRFTI SRDNSKNTLY LQMNSLRAED TAVYYCARPG DLGGGFDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 26           moltype = AA  length = 452
FEATURE                 Location/Qualifiers
REGION                  1..452
                        note = SEQ ID NO: 26 - anti-CD3-UCP05-C1 IgG1 LALA Heavy
                         Chain
source                  1..452
                        mol_type = protein
                        organism = synthetic construct
SEQUENCE: 26
QVQLVQSGAE VKKPGSSVKV SCKASGGRFS RQALTWVRQA PGQGLEWMGG IIPDHGRPIY  60
AQKFQGRVTI TADESTSTAY MELSSLRSED TAVYYCARGK GGSVAGWKFD VWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 27           moltype = AA  length = 452
FEATURE                 Location/Qualifiers
REGION                  1..452
                        note = SEQ ID NO: 27 - anti-CD3-UCP05-D1 IgG1 LALA Heavy
                         Chain
source                  1..452
                        mol_type = protein
                        organism = synthetic construct
SEQUENCE: 27
```

-continued

```
EVQLLESGGG LVQPGGSLRL SCAASGFTFN QYAMSWVRQA PGKGLEWVSA ISQFGGYTKY  60
ADSVKGRFTI SRDNSKNTLY LQMNSLRAED TAVYYCARHG RLSHDDYAFD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 28          moltype = AA  length = 448
FEATURE                Location/Qualifiers
REGION                 1..448
                       note = SEQ ID NO: 28 - anti-CD3-UCP05-D2 IgG1 LALA Heavy
                        Chain
source                 1..448
                       mol_type = protein
                       organism = synthetic construct
SEQUENCE: 28
EVQLLESGGG LVQPGGSLRL SCAASGFTFN IYALGWVRQA PGKGLEWVSA ISQNGGYTLY  60
ADSVKGRFTI SRDNSKNTLY LQMNSLRAED TAVYYCARLR GGSGMDVWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 29          moltype = AA  length = 449
FEATURE                Location/Qualifiers
REGION                 1..449
                       note = SEQ ID NO: 29 - anti-CD3-UCP05-F1 IgG1 LALA Heavy
                        Chain
source                 1..449
                       mol_type = protein
                       organism = synthetic construct
SEQUENCE: 29
EVQLLESGGG LVQPGGSLRL SCAASGFTFR HYAMTWVRQA PGKGLEWVSA ITQRGGYTYY  60
ADSVKGRFTI SRDNSKNTLY LQMNSLRAED TAVYYCARAG PSGGGFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 30          moltype = AA  length = 458
FEATURE                Location/Qualifiers
REGION                 1..458
                       note = SEQ ID NO: 30 - anti-CD3-UCP05-G2 IgG1 LALA Heavy
                        Chain
source                 1..458
                       mol_type = protein
                       organism = synthetic construct
SEQUENCE: 30
QVQLVQSGAE VKKPGSSVKV SCKASGGVFN FYAISWVRQA PGQGLEWMGG ITPDGGFVKY  60
AQKFQGRVTI TADESTSTAY MELSSLRSED TAVYYCARSP VSLYYGKYYV YYGAFDVWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKKVEPKS CDKTHTCPPC  240
PAPEAAGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSRDELT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 31          moltype = AA  length = 447
FEATURE                Location/Qualifiers
REGION                 1..447
                       note = SEQ ID NO: 31 - anti-CD3-UCP05-H1 IgG1 LALA Heavy
                        Chain
source                 1..447
                       mol_type = protein
                       organism = synthetic construct
SEQUENCE: 31
EVQLLESGGG LVQPGGSLRL SCAASGFAFS NSAMSWVRQA PGKGLELVSA ISTKGGKTLY  60
ADSVKGRFTI SRDNSKNTLY LQMNSLRAED TAVYYCARSS PYGFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
```

-continued

```
NVFSCSVMHE ALHNHYTQKS LSLSPGK                                    447

SEQ ID NO: 32          moltype = AA  length = 447
FEATURE                Location/Qualifiers
REGION                 1..447
                       note = SEQ ID NO: 32 - anti-CD3-UCP05-H2 IgG1 LALA Heavy
                        Chain
source                 1..447
                       mol_type = protein
                       organism = synthetic construct
SEQUENCE: 32
QVQLVQSGAE VKKPGSSVKV SCKASGGGFS HYALNWVRQA PGQGLEWMGG IIPLTGKTAY  60
AQKFQGRVTI TADESTSTAY MELSSLRSED TAVYYCARKI SSARDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                    447

SEQ ID NO: 33          moltype = AA  length = 455
FEATURE                Location/Qualifiers
REGION                 1..455
                       note = SEQ ID NO: 33 - anti-CD3-UCP06-A1 IgG1 LALA Heavy
                        Chain
source                 1..455
                       mol_type = protein
                       organism = synthetic construct
SEQUENCE: 33
QVQLVQSGAE VKKPGSSVKV SCKASGGHFR GYGISWVRQA PGQGLEWMGE IIPLRGFTIY  60
AQKFQGRVTI TADESTSTAY MELSSLRSED TAVYYCARGS YVDSSYYYYD GFDVWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                            455

SEQ ID NO: 34          moltype = AA  length = 448
FEATURE                Location/Qualifiers
REGION                 1..448
                       note = SEQ ID NO: 34 - anti-CD3-UCP06-C1 IgG1 LALA Heavy
                        Chain
source                 1..448
                       mol_type = protein
                       organism = synthetic construct
SEQUENCE: 34
QVQLVQSGAE VKKPGSSVKV SCKASGGKFS RYAISWVRQA PGQGLEWMGG IIPKGGYAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                   448

SEQ ID NO: 35          moltype = AA  length = 452
FEATURE                Location/Qualifiers
REGION                 1..452
                       note = SEQ ID NO: 35 - anti-CD3-UCP07-A1 IgG1 LALA Heavy
                        Chain
source                 1..452
                       mol_type = protein
                       organism = synthetic construct
SEQUENCE: 35
EVQLVESGGG LVKPGGSLRL SCAASGFTFS DYAVNWVRQA PGKGLEWVGR IKSKNEGGTG  60
YAAPVKGRFT ISRDDSKNTL YLQMNSLKTE DTAVYYCARE PSYYRDGAAD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 36          moltype = AA  length = 448
FEATURE                Location/Qualifiers
REGION                 1..448
                       note = SEQ ID NO: 36 - anti-CD3-UCP07-A3 IgG1 LALA Heavy
                        Chain
```

-continued

```
source                  1..448
                        mol_type = protein
                        organism = synthetic construct
SEQUENCE: 36
EVQLLESGGG LVQPGGSLRL SCAASGVSFR EYVMAWVRQA PGKGLEWVSV ISQYGGNTYY  60
ADSVKGRFTI SRDNSKNTLY LQMNSLRAED TAVYYCARSG GSVPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 37           moltype = AA  length = 447
FEATURE                 Location/Qualifiers
REGION                  1..447
                        note = SEQ ID NO: 37 - anti-CD3-UCP07-A4 IgG1 LALA Heavy
                         Chain
source                  1..447
                        mol_type = protein
                        organism = synthetic construct
SEQUENCE: 37
EVQLLESGGG LVQPGGSLRL SCAASGSTFR RYVMGWVRQA PGKGLEWVSA ISQQGGYTYY  60
ADSVKGRFTI SRDNSKNTLY LQMNSLRAED TAVYYCARSS SSAFDVWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 38           moltype = AA  length = 452
FEATURE                 Location/Qualifiers
REGION                  1..452
                        note = SEQ ID NO: 38 - anti-CD3-UCP07-B2 IgG1 LALA Heavy
                         Chain
source                  1..452
                        mol_type = protein
                        organism = synthetic construct
SEQUENCE: 38
EVQLVESGGG LVKPGGSLRL SCAASGFDFG KAWMAWVRQA PGKGLEWVGR IKSDFKGGDT  60
IYAAPVKGRF TISRDDSKNT LYLQMNSLKT EDTAVYYCAR GRSRGVSEFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 39           moltype = AA  length = 451
FEATURE                 Location/Qualifiers
REGION                  1..451
                        note = SEQ ID NO: 39 - anti-CD3-UCP07-B3 IgG1 LALA Heavy
                         Chain
source                  1..451
                        mol_type = protein
                        organism = synthetic construct
SEQUENCE: 39
EVQLVESGGG LVKPGGSLRL SCAASGFDFN AAWMTWVRQA PGKGLEWVGR IKSEKNGGKS  60
VYAAPVKGRF TISRDDSKNT LYLQMNSLKT EDTAVYYCAR GGRLSSYFDP WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 40           moltype = AA  length = 458
FEATURE                 Location/Qualifiers
REGION                  1..458
                        note = SEQ ID NO: 40 - anti-CD3-UCP07-B4 IgG1 LALA Heavy
                         Chain
source                  1..458
                        mol_type = protein
                        organism = synthetic construct
SEQUENCE: 40
QVQLVQSGAE VKKPGSSVKV SCKASGGRFS RYVINWVRQA PGQGLEWMGR IVPIFGTANY  60
AQKFQGRVTI TADESTSTAY MELSSLRSED TAVYYCARDT SYRVRGYGYS SWSYFDIWGQ  120
GTLVTVSSAS TKGPSVFPLA PSSKSTSGGT AALGCLVKDY FPEPVTVSWN SGALTSGVHT  180
```

-continued

```
FPAVLQSSGL YSLSSVVTVP SSSLGTQTYI CNVNHKPSNT KVDKKVEPKS CDKTHTCPPC  240
PAPEAAGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSRDELT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 41          moltype = AA  length = 449
FEATURE                Location/Qualifiers
REGION                 1..449
                       note = SEQ ID NO: 41 - anti-CD3-UCP07-C3 IgG1 LALA Heavy
                        Chain
source                 1..449
                       mol_type = protein
                       organism = synthetic construct
SEQUENCE: 41
QVQLVQSGAE VKKPGSSVKV SCKASGGSFS RYAIGWVRQA PGQGLEWMGG IIPDVGIAFY  60
AQKFQGRVTI TADESTSTAY MELSSLRSED TAVYYCAREY HYVGAFDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 42          moltype = AA  length = 449
FEATURE                Location/Qualifiers
REGION                 1..449
                       note = SEQ ID NO: 42 - anti-CD3-UCP07-D1 IgG1 LALA Heavy
                        Chain
source                 1..449
                       mol_type = protein
                       organism = synthetic construct
SEQUENCE: 42
EVQLLESGGG LVQPGGSLRL SCAASGFNFN INVMSWVRQA PGKGLEWVSA ISQSGGYTLY  60
ADSVKGRFTI SRDNSKNTLY LQMNSLRAED TAVYYCARAS PYGGGFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 43          moltype = AA  length = 451
FEATURE                Location/Qualifiers
REGION                 1..451
                       note = SEQ ID NO: 43 - anti-CD3-UCP07-D2 IgG1 LALA Heavy
                        Chain
source                 1..451
                       mol_type = protein
                       organism = synthetic construct
SEQUENCE: 43
EVQLLESGGG LVQPGGSLRL SCAASGFTFD RDVMGWVRQA PGKGLEWVSA ISIRGGKTLY  60
ADSVKGRFTI SRDNSKNTLY LQMNSLRAED TAVYYCARSS SARTDVPFDV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 44          moltype = AA  length = 449
FEATURE                Location/Qualifiers
REGION                 1..449
                       note = SEQ ID NO: 44 - anti-CD3-UCP07-E1 IgG1 LALA Heavy
                        Chain
source                 1..449
                       mol_type = protein
                       organism = synthetic construct
SEQUENCE: 44
EVQLLESGGG LVQPGGSLRL SCAASGFTFS RNAMNWVRQA PGKGLEWVSS ISRIGGFTIY  60
ADSVKGRFTI SRDNSKNTLY LQMNSLRAED TAVYYCARVG SGGKAFDVWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 45          moltype = AA  length = 448
```

-continued

```
FEATURE                Location/Qualifiers
REGION                 1..448
                       note = SEQ ID NO: 45 - anti-CD3-UCP07-E2 IgG1 LALA Heavy
                        Chain
source                 1..448
                       mol_type = protein
                       organism = synthetic construct
SEQUENCE: 45
EVQLLESGGG LVQPGGSLRL SCAASGFPFS NYAMSWVRQA PGKGLEWVSA ISRKGGFTEY  60
ADSVKGRFTI SRDNSKNTLY LQMNSLRAED TAVYYCARAS YLGGFAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 46          moltype = AA  length = 452
FEATURE                Location/Qualifiers
REGION                 1..452
                       note = SEQ ID NO: 46 - anti-CD3-UCP07-F2 IgG1 LALA Heavy
                        Chain
source                 1..452
                       mol_type = protein
                       organism = synthetic construct
SEQUENCE: 46
QVQLVQSGAE VKKPGSSVKV SCKASGGKFN KYVIGWVRQA PGQGLEWMGG VIPLKGQSKY  60
AQKFQGRVTI TADESTSTAY MELSSLRSED TAVYYCARGR YYGDYSWKFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 47          moltype = AA  length = 451
FEATURE                Location/Qualifiers
REGION                 1..451
                       note = SEQ ID NO: 47 - anti-CD3-UCP07-F3 IgG1 LALA Heavy
                        Chain
source                 1..451
                       mol_type = protein
                       organism = synthetic construct
SEQUENCE: 47
EVQLLESGGG LVQPGGSLRL SCAASGFNFS GHAVGWVRQA PGKGLEWVSA ISQNGGYTLY  60
ADSVKGRFTI SRDNSKNTLY LQMNSLRAED TAVYYCARAA SYGLDYALDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 48          moltype = AA  length = 448
FEATURE                Location/Qualifiers
REGION                 1..448
                       note = SEQ ID NO: 48 - anti-CD3-UCP07-H1 IgG1 LALA Heavy
                        Chain
source                 1..448
                       mol_type = protein
                       organism = synthetic construct
SEQUENCE: 48
EVQLLESGGG LVQPGGSLRL SCAASGFAFS KYAMHWVRQA PGKGLEWVSG ISQSGGYTLY  60
ADSVKGRFTI SRDNSKNTLY LQMNSLRAED TAVYYCARSH RYSAFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 49          moltype = AA  length = 451
FEATURE                Location/Qualifiers
REGION                 1..451
                       note = SEQ ID NO: 49 - anti-CD3-UCP08-B1 IgG1 LALA Heavy
                        Chain
source                 1..451
                       mol_type = protein
                       organism = synthetic construct
```

-continued

```
SEQUENCE: 49
QVQLVQSGAE VKKPGSSVKV SCKASGGPSS HAISWVRQAP GQGLEWMGGI IPRSGKTYYA  60
QKFQGRVTIT ADESTSTAYM ELSSLRSEDT AVYYCARGPY GRYPDYLFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 50          moltype = AA  length = 448
FEATURE                Location/Qualifiers
REGION                 1..448
                       note = SEQ ID NO: 50 - anti-CD3-C1-UCP01-B6 IgG1 LALA
                        Heavy Chain
source                 1..448
                       mol_type = protein
                       organism = synthetic construct
SEQUENCE: 50
QVQLVQSGAE VKKPGSSVKV SCKASGGKFS RYAISWVRQA PGQGLEWMGG ISPYQGYASY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 51          moltype = AA  length = 449
FEATURE                Location/Qualifiers
REGION                 1..449
                       note = SEQ ID NO: 51 - anti-CD3-C1-UCP01-B9 IgG1 LALA
                        Heavy Chain
source                 1..449
                       mol_type = protein
                       organism = synthetic construct
SEQUENCE: 51
QVQLVQSGAE VKKPGSSVKV SCKASGGKFS RYAISWVRQA PGQGLEWMGG INAPVVRSPE  60
YAQKFQGRVT ITADESTSTA YMELSSLRSE DTAVYYCARY GYSLYMDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 52          moltype = AA  length = 448
FEATURE                Location/Qualifiers
REGION                 1..448
                       note = SEQ ID NO: 52 - anti-CD3-C1-UCP01-C11 IgG1 LALA
                        Heavy Chain
source                 1..448
                       mol_type = protein
                       organism = synthetic construct
SEQUENCE: 52
QVQLVQSGAE VKKPGSSVKV SCKASGGKFS RYAISWVRQA PGQGLEWMGG INPHVGAPEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 53          moltype = AA  length = 448
FEATURE                Location/Qualifiers
REGION                 1..448
                       note = SEQ ID NO: 53 - anti-CD3-C1-UCP01-D1 IgG1 LALA Heavy
                        Chain
source                 1..448
                       mol_type = protein
                       organism = synthetic construct
SEQUENCE: 53
QVQLVQSGAE VKKPGSSVKV SCKASGGKFS RYAISWVRQA PGQGLEWMGG INPLSDEAQY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
```

-continued

```
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 54          moltype = AA  length = 448
FEATURE                Location/Qualifiers
REGION                 1..448
                       note = SEQ ID NO: 54 - anti-CD3-C1-UCP01-D4 IgG1 LALA
                        Heavy Chain
source                 1..448
                       mol_type = protein
                       organism = synthetic construct
SEQUENCE: 54
QVQLVQSGAE VKKPGSSVKV SCKASGGKFS RYAISWVRQA PGQGLEWMGG INPIRGRPSY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 55          moltype = AA  length = 448
FEATURE                Location/Qualifiers
REGION                 1..448
                       note = SEQ ID NO: 55 - anti-CD3-C1-UCP01-D6 IgG1 LALA
                        Heavy Chain
source                 1..448
                       mol_type = protein
                       organism = synthetic construct
SEQUENCE: 55
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 56          moltype = AA  length = 449
FEATURE                Location/Qualifiers
REGION                 1..449
                       note = SEQ ID NO: 56 - anti-CD3-C1-UCP01-E6 IgG1 LALA
                        Heavy Chain
source                 1..449
                       mol_type = protein
                       organism = synthetic construct
SEQUENCE: 56
QVQLVQSGAE VKKPGSSVKV SCKASGGKFS RYAISWVRQA PGQGLEWMGG ITPPHVGIAD  60
YAQKFQGRVT ITADESTSTA YMELSSLRSE DTAVYYCARY GYSLYMDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 57          moltype = AA  length = 448
FEATURE                Location/Qualifiers
REGION                 1..448
                       note = SEQ ID NO: 57 - anti-CD3-C1-UCP01-E7 IgG1 LALA
                        Heavy Chain
source                 1..448
                       mol_type = protein
                       organism = synthetic construct
SEQUENCE: 57
QVQLVQSGAE VKKPGSSVKV SCKASGGKFS RYAISWVRQA PGQGLEWMGG INPHLGEAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 58          moltype = AA  length = 448
FEATURE                Location/Qualifiers
REGION                 1..448
                       note = SEQ ID NO: 58 - anti-CD3-C1-UCP01-E10 IgG1 LALA
```

-continued

```
                      Heavy Chain
source                1..448
                      mol_type = protein
                      organism = synthetic construct
SEQUENCE: 58
QVQLVQSGAE VKKPGSSVKV SCKASGGKFS RYAISWVRQA PGQGLEWMGG ISPFEGTPAY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 59         moltype = AA  length = 448
FEATURE               Location/Qualifiers
REGION                1..448
                      note = SEQ ID NO: 59 - anti-CD3-C1-UCP01-E11 IgG1 LALA
                      Heavy Chain
source                1..448
                      mol_type = protein
                      organism = synthetic construct
SEQUENCE: 59
QVQLVQSGAE VKKPGSSVKV SCKASGGKFS RYAISWVRQA PGQGLEWMGG INPFKGDAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 60         moltype = AA  length = 448
FEATURE               Location/Qualifiers
REGION                1..448
                      note = SEQ ID NO: 60 - anti-CD3-C1-UCP01-E12 IgG1 LALA
                      Heavy Chain
source                1..448
                      mol_type = protein
                      organism = synthetic construct
SEQUENCE: 60
QVQLVQSGAE VKKPGSSVKV SCKASGGKFS RYAISWVRQA PGQGLEWMGG INPLVGHAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 61         moltype = AA  length = 448
FEATURE               Location/Qualifiers
REGION                1..448
                      note = SEQ ID NO: 61 - anti-CD3-C1-UCP01-F1 IgG1 LALA
                      Heavy Chain
source                1..448
                      mol_type = protein
                      organism = synthetic construct
SEQUENCE: 61
QVQLVQSGAE VKKPGSSVKV SCKASGGKFS RYAISWVRQA PGQGLEWMGG INPRLGQAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 62         moltype = AA  length = 448
FEATURE               Location/Qualifiers
REGION                1..448
                      note = SEQ ID NO: 62 - anti-CD3-C1-UCP01-F10 IgG1 LALA
                      Heavy Chain
source                1..448
                      mol_type = protein
                      organism = synthetic construct
SEQUENCE: 62
QVQLVQSGAE VKKPGSSVKV SCKASGGKFS RYAISWVRQA PGQGLEWMGG INPHIRFPEY  60
AQKFQGRVTI TADESTSTAY MELSSLRSED TAVYYCARYG YSLYMDIWGQ GTLVTVSSAS  120
```

```
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 63          moltype = AA  length = 448
FEATURE                Location/Qualifiers
REGION                 1..448
                       note = SEQ ID NO: 63 - anti-CD3-C1-UCP01-F12 IgG1 LALA
                        Heavy Chain
source                 1..448
                       mol_type = protein
                       organism = synthetic construct
SEQUENCE: 63
QVQLVQSGAE VKKPGSSVKV SCKASGGKFS RYAISWVRQA PGQGLEWMGG ISPFRGHAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 64          moltype = AA  length = 448
FEATURE                Location/Qualifiers
REGION                 1..448
                       note = SEQ ID NO: 64 - anti-CD3-C1-UCP01-G12 IgG1 LALA
                        Heavy Chain
source                 1..448
                       mol_type = protein
                       organism = synthetic construct
SEQUENCE: 64
QVQLVQSGAK VKKPGSSVKV SCKASGGKFS RYAISWVRQA PGQGLEWMGG ISPHIGHPEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 65          moltype = AA  length = 448
FEATURE                Location/Qualifiers
REGION                 1..448
                       note = SEQ ID NO: 65 - anti-CD3-C1-UCP01-H9 IgG1 LALA
                        Heavy Chain
source                 1..448
                       mol_type = protein
                       organism = synthetic construct
SEQUENCE: 65
QVQLVQSGAE VKKPGSSVKV SCKASGGKFS RYAISWVRQA PGQGLEWMGG ISPHVGYAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 66          moltype = AA  length = 448
FEATURE                Location/Qualifiers
REGION                 1..448
                       note = SEQ ID NO: 66 - anti-CD3-C1-UCP01-H10 IgG1 LALA
                        Heavy Chain
source                 1..448
                       mol_type = protein
                       organism = synthetic construct
SEQUENCE: 66
QVQLVQSGAE VKKPGSSVKV SCKASGGKFS RYAISWVRQA PGQGLEWMGG ISPLVGYPQY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448
```

-continued

```
SEQ ID NO: 67          moltype = AA  length = 448
FEATURE                Location/Qualifiers
REGION                 1..448
                       note = SEQ ID NO: 67 - anti-CD3-C1-UCP02-E1 IgG1 LALA
                        Heavy Chain
source                 1..448
                       mol_type = protein
                       organism = synthetic construct
SEQUENCE: 67
QVQLVQSGAE VKKPGSSVKV SCKASGGKFS RYAISWVRQA PGQGLEWMGG ISPFKGYAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 68          moltype = AA  length = 224
FEATURE                Location/Qualifiers
REGION                 1..224
                       note = SEQ ID NO: 68 - anti-BCMA-UCP01-A8 FAB Heavy Chain
source                 1..224
                       mol_type = protein
                       organism = synthetic construct
SEQUENCE: 68
QVQLVQSGAE VKKPGSSVKV SCKASGGLFN YYIINWVRQA PGQGLEWMGG IIPTYGGAGY  60
AQKFQGRVTI TADESTSTAY MELSSLRSED TAVYYCARSS PSISGYAFDV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 69          moltype = AA  length = 224
FEATURE                Location/Qualifiers
REGION                 1..224
                       note = SEQ ID NO: 69 - anti-BCMA-UCP01-A10 FAB Heavy Chain
source                 1..224
                       mol_type = protein
                       organism = synthetic construct
SEQUENCE: 69
QVQLVQSGAE VKKPGSSVKV SCKASGYVFS DHIISWVRQA PGQGLEWMGG IIPHGGAPTY  60
AQKFQGRVTI TADESTSTAY MELSSLRSED TAVYYCARDL FDYYPQGFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 70          moltype = AA  length = 227
FEATURE                Location/Qualifiers
REGION                 1..227
                       note = SEQ ID NO: 70 - anti-BCMA-UCP01-C2 FAB Heavy Chain
source                 1..227
                       mol_type = protein
                       organism = synthetic construct
SEQUENCE: 70
EVQLLESGGG LVQPGGSLRL SCAASGFIFS QYDMSWVRQA PGKGLEWVSA ISLLGDFTSY  60
ADSVKGRFTI SRDNSKNTLY LQMNSLRAED TAVYYCARRL TDYISGGGDG FDVWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSC               227

SEQ ID NO: 71          moltype = AA  length = 228
FEATURE                Location/Qualifiers
REGION                 1..228
                       note =  SEQ ID NO: 71 - anti-BCMA-UCP01-E8 FAB Heavy Chain
source                 1..228
                       mol_type = protein
                       organism = synthetic construct
SEQUENCE: 71
QVQLVQSGAE VKKPGSSVKV SCKASGGQFS VQFISWVRQA PGQGLEWMGG IIPTSGDTYY  60
AQKFQGRVTI TADESTSTAY MELSSLRSED TAVYYCARSV VDLSYVTGYY YMDIWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSC              228

SEQ ID NO: 72          moltype = AA  length = 229
FEATURE                Location/Qualifiers
REGION                 1..229
                       note = SEQ ID NO: 72 - anti-BCMA-UCP01-E9 FAB Heavy Chain
source                 1..229
                       mol_type = protein
                       organism = synthetic construct
SEQUENCE: 72
EVQLLESGGG LVQPGGSLRL SCAASGFTFS NYAMSWVRQA PGKGLEWVSV ISERGAVTVY  60
```

-continued

```
ADSVKGRFTI SRDNSKNTLY LQMNSLRAED TAVYYCARSP YGYSSGVEGY FGFDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSC             229

SEQ ID NO: 73          moltype = AA  length = 218
FEATURE                Location/Qualifiers
REGION                 1..218
                       note = SEQ ID NO: 73 - anti-BCMA-UCP01-F9 FAB Heavy Chain
source                 1..218
                       mol_type = protein
                       organism = synthetic construct
SEQUENCE: 73
QVQLVQSGAE VKKPGSSVKV SCKASGYKFR TYAINWVRQA PGQGLEWMGG IVPISGETFY  60
AQKFQGRVTI TADESTSTAY MELSSLRSED TAVYYCARED YSDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSC                          218

SEQ ID NO: 74          moltype = AA  length = 225
FEATURE                Location/Qualifiers
REGION                 1..225
                       note = SEQ ID NO: 74 - anti-BCMA-PP02-A3 FAB Heavy Chain
source                 1..225
                       mol_type = protein
                       organism = synthetic construct
SEQUENCE: 74
EVQLLESGGG LVQPGGSLRL SCAASGFTFS QYAMSWVRQA PGKGLEWVSI ISQDGGVTVY  60
ADSVKGRFTI SRDNSKNTLY LQMNSLRAED TAVYYCARSP YGGGSYIPHD SWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                  225

SEQ ID NO: 75          moltype = AA  length = 224
FEATURE                Location/Qualifiers
REGION                 1..224
                       note = SEQ ID NO: 75 - anti-BCMA-PP02-B4 FAB Heavy Chain
source                 1..224
                       mol_type = protein
                       organism = synthetic construct
SEQUENCE: 75
EVQLLESGGG LVQPGGSLRL SCAASGFTFS NYDMSWVRQA PGKGLEWVSA ISVSGDFTQY  60
ADSVKGRFTI SRDNSKNTLY LQMNSLRAED TAVYYCARVG YYLLDSAFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 76          moltype = AA  length = 226
FEATURE                Location/Qualifiers
REGION                 1..226
                       note = SEQ ID NO: 76 - anti-BCMA-PP02-C2 FAB Heavy Chain
source                 1..226
                       mol_type = protein
                       organism = synthetic construct
SEQUENCE: 76
QVQLVQSGAE VKKPGSSVKV SCKASGGHFS SYAISWVRQA PGQGLEWMGG IIPQHGVPSY  60
AQKFQGRVTI TADESTSTAY MELSSLRSED TAVYYCARVL ITVDGSYGGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                 226

SEQ ID NO: 77          moltype = AA  length = 224
FEATURE                Location/Qualifiers
REGION                 1..224
                       note = SEQ ID NO: 77 - anti-BCMA-PP02-C4 FAB Heavy Chain
source                 1..224
                       mol_type = protein
                       organism = synthetic construct
SEQUENCE: 77
EVQLLESGGG LVQPGGSLRL SCAASGFTFT AYDMSWVRQA PGKGLEWVSA ISGFGGDTLY  60
ADSVKGRFTI SRDNSKNTLY LQMNSLRAED TAVYYCARIG YYYLDSAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 78          moltype = AA  length = 224
FEATURE                Location/Qualifiers
REGION                 1..224
                       note = SEQ ID NO: 78 - anti-BCMA-PP02-D3 FAB Heavy Chain
source                 1..224
                       mol_type = protein
                       organism = synthetic construct
SEQUENCE: 78
EVQLVESGGG LIQPGGSLRL SCAASGFIFS HYEMNWVRQA PGKGLEWVSA IGQGGNTVYA  60
DSVKGRFTIS RDNSKNTLYL QMNSLRAEDT AVYYCARVPY SYSGYSGADI WGQGTLVTVS  120
```

```
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 79          moltype = AA  length = 226
FEATURE                Location/Qualifiers
REGION                 1..226
                       note = SEQ ID NO: 79 - anti-BCMA-PP02-E6 FAB Heavy Chain
source                 1..226
                       mol_type = protein
                       organism = synthetic construct
SEQUENCE: 79
EVQLLESGGG LVQPGGSLRL SCAASGFTFS YYAMTWVRQA PGKGLEWVST ISQNGGQTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 80          moltype = AA  length = 231
FEATURE                Location/Qualifiers
REGION                 1..231
                       note = SEQ ID NO: 80 - anti-BCMA-PP02-F1 FAB Heavy Chain
source                 1..231
                       mol_type = protein
                       organism = synthetic construct
SEQUENCE: 80
EVQLLESGGG LVQPGGSLRL SCAASGFSFS EYAMSWVRQA PGKGLEWVSA LSLSGDVTSY  60
ADSVKGRFTI SRDNSKNTLY LQMNSLRAED TAVYYCARSP YSRVGDSYYY DYIGFDIWGQ  120
GTLVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKKVEPKS C           231

SEQ ID NO: 81          moltype = AA  length = 224
FEATURE                Location/Qualifiers
REGION                 1..224
                       note = SEQ ID NO: 81 - anti-BCMA-PP03-C4 FAB Heavy Chain
source                 1..224
                       mol_type = protein
                       organism = synthetic construct
SEQUENCE: 81
EVQLLESGGG LVQPGGSLRL SCAASGFTFT AYDMSWVRQA PGKGLEWVSA ISGFGGDTLY  60
ADSVKGRFTI SRDNSKNTLY LQMNSLRAED TAVYYCARIG YYYLDSAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 82          moltype = AA  length = 228
FEATURE                Location/Qualifiers
REGION                 1..228
                       note = SEQ ID NO: 82 - anti-BCMA-PP03-E4 FAB Heavy Chain
source                 1..228
                       mol_type = protein
                       organism = synthetic construct
SEQUENCE: 82
EVQLLESGGG LVQPGGSLRL SCAASGFALS YYAMSWVRQA PGKGLEWVSA ISEDGGRTSY  60
ADSVKGRFTI SRDNSKNTLY LQMNSLRAED TAVYYCARAS AYIPYSEFYA GFDVWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSC              228

SEQ ID NO: 83          moltype = AA  length = 225
FEATURE                Location/Qualifiers
REGION                 1..225
                       note = SEQ ID NO: 83 - anti-BCMA-D3-MP03-G7 FAB Heavy Chain
source                 1..225
                       mol_type = protein
                       organism = synthetic construct
SEQUENCE: 83
EVQLVESGGG LIQPGGSLRL SCAASGFIFS HYEMNWVRQA PGKGLEWVSI IGQRGHTTEY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 84          moltype = AA  length = 225
FEATURE                Location/Qualifiers
REGION                 1..225
                       note = SEQ ID NO: 84 - anti-BCMA-D3-MP04-A2 FAB Heavy Chain
source                 1..225
                       mol_type = protein
                       organism = synthetic construct
SEQUENCE: 84
EVQLVESGGG LIQPGGSLRL SCAASGFIFS HYEMNWVRQA PGKGLEWVSA IGQQGGNTVY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
```

```
SSGLYSLSSV VTVPSSSLGT QTYICNVNHK PSNTKVDKKV EPKSC                  225

SEQ ID NO: 85           moltype = AA  length = 224
FEATURE                 Location/Qualifiers
REGION                  1..224
                        note = SEQ ID NO: 85 - anti-BCMA-D3-MP04-B11a FAB Heavy
                         Chain
source                  1..224
                        mol_type = protein
                        organism = synthetic construct
SEQUENCE: 85
EVQLVESGGG LIQPGGSLRL SCAASGFIFS HYEMNWVRQA PGKGLEWVSA IGQVDGEVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 86           moltype = AA  length = 224
FEATURE                 Location/Qualifiers
REGION                  1..224
                        note = SEQ ID NO: 86 - anti-BCMA-D3-MP04-B11b FAB Heavy
                         Chain
source                  1..224
                        mol_type = protein
                        organism = synthetic construct
SEQUENCE: 86
EVQLVESGGG LIQPGGSLRL SCAASGFIFS HYEMNWVRQA PGKGLEWVSA IGQVDAEVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 87           moltype = AA  length = 224
FEATURE                 Location/Qualifiers
REGION                  1..224
                        note = SEQ ID NO: 87 - anti-BCMA-D3-MP04-B11c FAB Heavy
                         Chain
source                  1..224
                        mol_type = protein
                        organism = synthetic construct
SEQUENCE: 87
EVQLVESGGG LIQPGGSLRL SCAASGFIFS HYEMNWVRQA PGKGLEWVSA IGQVEGEVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 88           moltype = AA  length = 224
FEATURE                 Location/Qualifiers
REGION                  1..224
                        note = SEQ ID NO: 88 - anti-BCMA-D3-MP04-B11d FAB Heavy
                         Chain
source                  1..224
                        mol_type = protein
                        organism = synthetic construct
SEQUENCE: 88
EVQLVESGGG LIQPGGSLRL SCAASGFIFS HYEMNWVRQA PGKGLEWVSA IGQVAAEVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 89           moltype = AA  length = 225
FEATURE                 Location/Qualifiers
REGION                  1..225
                        note = SEQ ID NO: 89 - anti-BCMA-D3-MP04-C2 FAB Heavy Chain
source                  1..225
                        mol_type = protein
                        organism = synthetic construct
SEQUENCE: 89
EVQLVESGGG LIQPGGSLRL SCAASGFIFS HYEMNWVRQA PGKGLEWVSA IGQFGGNTVY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                  225

SEQ ID NO: 90           moltype = AA  length = 225
FEATURE                 Location/Qualifiers
REGION                  1..225
                        note = SEQ ID NO: 90 - anti-BCMA-D3-MP04-C8a FAB Heavy
                         Chain
source                  1..225
                        mol_type = protein
                        organism = synthetic construct
```

-continued

```
SEQUENCE: 90
EVQLVESGGG LIQPGGSLRL SCAASGFIFS HYEMNWVRQA PGKGLEWVSA IGQMGFGTLY  60
ADNVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 91          moltype = AA  length = 225
FEATURE                Location/Qualifiers
REGION                 1..225
                       note = SEQ ID NO: 91 - anti-BCMA-D3-MP04-C8b FAB Heavy
                        Chain
source                 1..225
                       mol_type = protein
                       organism = synthetic construct
SEQUENCE: 91
EVQLVESGGG LIQPGGSLRL SCAASGFIFS HYEMNWVRQA PGKGLEWVSA IGQIGFGTLY  60
ADNVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 92          moltype = AA  length = 225
FEATURE                Location/Qualifiers
REGION                 1..225
                       note = SEQ ID NO: 92 - anti-BCMA-D3-MP04-D4 FAB Heavy Chain
source                 1..225
                       mol_type = protein
                       organism = synthetic construct
SEQUENCE: 92
EVQLVESGGG LIQPGGSLRL SCAASGFIFS HYEMNWVRQA PGKGLEWVSA IGQVGGNTVY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 93          moltype = AA  length = 225
FEATURE                Location/Qualifiers
REGION                 1..225
                       note = SEQ ID NO: 93 - anti-BCMA-D3-MP04-E11 FAB Heavy
                        Chain
source                 1..225
                       mol_type = protein
                       organism = synthetic construct
SEQUENCE: 93
EVQLVESGGG LIQPGGSLRL SCAASGFIFS HYEMNWVRQA PGKGLEWVSA IGQLGGNTVY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 94          moltype = AA  length = 224
FEATURE                Location/Qualifiers
REGION                 1..224
                       note = SEQ ID NO: 94 - anti-BCMA-D3-MP04-F3 FAB Heavy Chain
source                 1..224
                       mol_type = protein
                       organism = synthetic construct
SEQUENCE: 94
EVQLVESGGG LIQPGGSLRL SCAASGFIFS HYEMNWVRQA PGKGLEWVSA IGQVGNTVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 95          moltype = AA  length = 224
FEATURE                Location/Qualifiers
REGION                 1..224
                       note = SEQ ID NO: 95 - anti-BCMA-D3-MP04-G7 FAB Heavy Chain
source                 1..224
                       mol_type = protein
                       organism = synthetic construct
SEQUENCE: 95
EVQLVESGGG LIQPGGSLRL SCAASGFIFS HYEMNWVRQA PGKGLEWVSA IGQRDGTVYA  60
DSVKGRFTIS RDNSKNTLYL QMNSLRAEDT AVYYCARVPY SYSGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 96          moltype = AA  length = 224
FEATURE                Location/Qualifiers
REGION                 1..224
                       note = SEQ ID NO: 96 - anti-BCMA-D3-MP05-A9 FAB Heavy Chain
source                 1..224
                       mol_type = protein
```

```
                        organism = synthetic construct
SEQUENCE: 96
EVQLVESGGG LIQPGGSLRL SCAASGFIFS HYEMNWVRQA PGKGLEWVSA IGQGGNTVYA  60
DSVKGRFTIS RDNSKNTLYL QMNSLRAEDT AVYYCARVPY SYAGYSGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 97           moltype = AA  length = 224
FEATURE                 Location/Qualifiers
REGION                  1..224
                        note = SEQ ID NO: 97 - anti-BCMA-D3-MP05-C1a FAB Heavy
                         Chain
source                  1..224
                        mol_type = protein
                        organism = synthetic construct
SEQUENCE: 97
EVQLVESGGG LIQPGGSLRL SCAASGFIFS HYEMNWVRQA PGKGLEWVSA IGQGGNTVYA  60
DSVKGRFTIS RDNSKNTLYL QMNSLRAEDT AVYYCARVPY SYMGYAGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 98           moltype = AA  length = 224
FEATURE                 Location/Qualifiers
REGION                  1..224
                        note = SEQ ID NO: 98 - anti-BCMA-D3-MP05-C1b FAB Heavy
                         Chain
source                  1..224
                        mol_type = protein
                        organism = synthetic construct
SEQUENCE: 98
EVQLVESGGG LIQPGGSLRL SCAASGFIFS HYEMNWVRQA PGKGLEWVSA IGQGGNTVYA  60
DSVKGRFTIS RDNSKNTLYL QMNSLRAEDT AVYYCARVPY SYIGYAGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 99           moltype = AA  length = 224
FEATURE                 Location/Qualifiers
REGION                  1..224
                        note = SEQ ID NO: 99 - anti-BCMA-D3-MP05-F4 FAB Heavy Chain
source                  1..224
                        mol_type = protein
                        organism = synthetic construct
SEQUENCE: 99
EVQLVESGGG LIQPGGSLRL SCAASGFIFS HYEMNWVRQA PGKGLEWVSA IGQGGNTVYA  60
DSVKGRFTIS RDNSKNTLYL QMNSLRAEDT AVYYCARVPY SYLGYQGADI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 100          moltype = AA  length = 226
FEATURE                 Location/Qualifiers
REGION                  1..226
                        note =  SEQ ID NO: 100 - anti-BCMA-E6-PP02-A3 FAB Heavy
                         Chain
source                  1..226
                        mol_type = protein
                        organism = synthetic construct
SEQUENCE: 100
EVQLLESGGG LVQPGGSLRL SCAASGFTFS YYAMTWVRQA PGKGLEWVST ISSQNDITKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC               226

SEQ ID NO: 101          moltype = AA  length = 226
FEATURE                 Location/Qualifiers
REGION                  1..226
                        note = SEQ ID NO: 101 - anti-BCMA-E6-PP02-B1 FAB Heavy
                         Chain
source                  1..226
                        mol_type = protein
                        organism = synthetic construct
SEQUENCE: 101
EVQLLESGGG LVQPGGSLRL SCAASGFTFS YYAMTWVRQA PGKGLEWVST VSQAGYDTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC               226

SEQ ID NO: 102          moltype = AA  length = 226
FEATURE                 Location/Qualifiers
REGION                  1..226
```

```
                         note = SEQ ID NO: 102 - anti-BCMA-E6-PP02-B4 FAB Heavy
                          Chain
source                   1..226
                         mol_type = protein
                         organism = synthetic construct
SEQUENCE: 102
EVQLLESGGG LVQPGGSLRL SCAASGFTFS YYAMTWVRQA PGKGLEWVST ISQPGFDAKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 103           moltype = AA  length = 226
FEATURE                  Location/Qualifiers
REGION                   1..226
                         note = SEQ ID NO: 103 - anti-BCMA-E6-PP02-C7 FAB Heavy
                          Chain
source                   1..226
                         mol_type = protein
                         organism = synthetic construct
SEQUENCE: 103
EVQLLESGGG LVQPGGSLRL SCAASGFTFS YYAMTWVRQA PGKGLEWVST ISQSGLVPKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 104           moltype = AA  length = 226
FEATURE                  Location/Qualifiers
REGION                   1..226
                         note = SEQ ID NO: 104 - anti-BCMA-E6-PP02-D2 FAB Heavy
                          Chain
source                   1..226
                         mol_type = protein
                         organism = synthetic construct
SEQUENCE: 104
EVQLLESGGG LVQPGGSLRL SCAASGFTFS YYAMTWVRQA PGKGLEWVST ISQQNEQTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 105           moltype = AA  length = 226
FEATURE                  Location/Qualifiers
REGION                   1..226
                         note = SEQ ID NO: 105 - anti-BCMA-E6-PP02-E6 FAB Heavy
                          Chain
source                   1..226
                         mol_type = protein
                         organism = synthetic construct
SEQUENCE: 105
EVQLLESGGG LVQPGGSLRL SCAASGFTFS YYAMTWVRQA PGKGLEWVST ISQAGRDFKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 106           moltype = AA  length = 226
FEATURE                  Location/Qualifiers
REGION                   1..226
                         note = SEQ ID NO: 106 - anti-BCMA-E6-PP02-F7 FAB Heavy
                          Chain
source                   1..226
                         mol_type = protein
                         organism = synthetic construct
SEQUENCE: 106
EVQLLESGGG LVQPGGSLRL SCAASGFTFS YYAMTWVRQA PGKGLEWVST IGQRGFQTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 107           moltype = AA  length = 227
FEATURE                  Location/Qualifiers
REGION                   1..227
                         note = SEQ ID NO: 107 - anti-BCMA-E6-PP02-G2 FAB Heavy
                          Chain
source                   1..227
                         mol_type = protein
                         organism = synthetic construct
SEQUENCE: 107
EVQLLESGGG LVQPGGSLRL SCAASGFTFS YYAMTWVRQA PGKGLEWVGT ISQSVGQVVK  60
YADSVKGRFT ISRDNSKNTL YLQMNSLRAE DTAVYYCARS PYSYLHGYYG FDYWGQGTLV  120
TVSSASTKGP SVFPLAPSSK STSGGTAALG CLVKDYFPEP VTVSWNSGAL TSGVHTFPAV  180
```

```
LQSSGLYSLS SVVTVPSSSL GTQTYICNVN HKPSNTKVDK KVEPKSC              227

SEQ ID NO: 108          moltype = AA  length = 226
FEATURE                 Location/Qualifiers
REGION                  1..226
                        note = SEQ ID NO: 108 - anti-BCMA-E6-PP02-G6 FAB Heavy
                         Chain
source                  1..226
                        mol_type = protein
                        organism = synthetic construct
SEQUENCE: 108
EVQLLESGGG LVQPGGSLRL SCAASGFTFS YYAMTWVRQA PGKGLEWVST IAQRGGQTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 109          moltype = AA  length = 226
FEATURE                 Location/Qualifiers
REGION                  1..226
                        note = SEQ ID NO: 109 - anti-BCMA-E6-PP02-G7 FAB Heavy
                         Chain
source                  1..226
                        mol_type = protein
                        organism = synthetic construct
SEQUENCE: 109
EVQLLESGGG LVQPGGSLRL SCAASGFTFS YYAMTWVRQA PGKGLEWVST ISQQWDVTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 110          moltype = AA  length = 224
FEATURE                 Location/Qualifiers
REGION                  1..224
                        note = SEQ ID NO: 110 - anti-CD38-UCP03-B3 FAB Heavy Chain
source                  1..224
                        mol_type = protein
                        organism = synthetic construct
SEQUENCE: 110
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 111          moltype = AA  length = 226
FEATURE                 Location/Qualifiers
REGION                  1..226
                        note = SEQ ID NO: 111 - anti-CD38-UCP01-E2 FAB Heavy Chain
source                  1..226
                        mol_type = protein
                        organism = synthetic construct
SEQUENCE: 111
QVQLVQSGAE VKKPGSSVKV SCKASGGSFS NYAIGWVRQA PGQGLEWMGR IIPVFGSAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 112          moltype = AA  length = 224
FEATURE                 Location/Qualifiers
REGION                  1..224
                        note = SEQ ID NO: 112 - anti-CD38-B3-PP11-A2 FAB Heavy
                         Chain
source                  1..224
                        mol_type = protein
                        organism = synthetic construct
SEQUENCE: 112
QVQLVQSGAE VKKPGSSVKV SCKASGQTTP MYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 113          moltype = AA  length = 224
FEATURE                 Location/Qualifiers
REGION                  1..224
                        note = SEQ ID NO: 113 - anti-CD38-B3-PP11-C11 FAB Heavy
                         Chain
source                  1..224
                        mol_type = protein
                        organism = synthetic construct
SEQUENCE: 113
```

-continued

```
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARST PTYGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 114         moltype = AA  length = 224
FEATURE                Location/Qualifiers
REGION                 1..224
                       note = SEQ ID NO: 114 - anti-CD38-B3-PP11-D1a FAB Heavy
                        Chain
source                 1..224
                       mol_type = protein
                       organism = synthetic construct
SEQUENCE: 114
QVQLVQSGAE VKKPGSSVKV SCKASGMQTR WYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 115         moltype = AA  length = 224
FEATURE                Location/Qualifiers
REGION                 1..224
                       note = SEQ ID NO: 115 - anti-CD38-B3-PP11-D1b FAB Heavy
                        Chain
source                 1..224
                       mol_type = protein
                       organism = synthetic construct
SEQUENCE: 115
QVQLVQSGAE VKKPGSSVKV SCKASGIQTR WYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 116         moltype = AA  length = 224
FEATURE                Location/Qualifiers
REGION                 1..224
                       note = SEQ ID NO: 116 - anti-CD38-B3-PP11-D11a FAB Heavy
                        Chain
source                 1..224
                       mol_type = protein
                       organism = synthetic construct
SEQUENCE: 116
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PILGNGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 117         moltype = AA  length = 224
FEATURE                Location/Qualifiers
REGION                 1..224
                       note = SEQ ID NO: 117 - anti-CD38-B3-PP11-E1 FAB Heavy
                        Chain
source                 1..224
                       mol_type = protein
                       organism = synthetic construct
SEQUENCE: 117
QVQLVQSGAE VKKPGSSVKV SCKASGQHKR VYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 118         moltype = AA  length = 224
FEATURE                Location/Qualifiers
REGION                 1..224
                       note = SEQ ID NO: 118 - anti-CD38-B3-PP11-E11 FAB Heavy
                        Chain
source                 1..224
                       mol_type = protein
                       organism = synthetic construct
SEQUENCE: 118
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PSYGKGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 119         moltype = AA  length = 224
FEATURE                Location/Qualifiers
REGION                 1..224
                       note = SEQ ID NO: 119 - anti-CD38-B3-PP11-H1a FAB Heavy
```

```
                           Chain
source                    1..224
                          mol_type = protein
                          organism = synthetic construct
SEQUENCE: 119
QVQLVQSGAE VKKPGSSVKV SCKASGQNER MYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 120            moltype = AA  length = 224
FEATURE                   Location/Qualifiers
REGION                    1..224
                          note = SEQ ID NO: 120 - anti-CD38-B3-PP11-H10 FAB Heavy
                           Chain
source                    1..224
                          mol_type = protein
                          organism = synthetic construct
SEQUENCE: 120
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PHYGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 121            moltype = AA  length = 226
FEATURE                   Location/Qualifiers
REGION                    1..226
                          note = SEQ ID NO: 121 - anti-CD38-E2-UCP01-A10 FAB Heavy
                           Chain
source                    1..226
                          mol_type = protein
                          organism = synthetic construct
SEQUENCE: 121
QVQLVQSGAE VKKPGSSVKV SCKASGLPDA TYAIGWVRQA PGQGLEWMGR IIPVFGSAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 122            moltype = AA  length = 226
FEATURE                   Location/Qualifiers
REGION                    1..226
                          note = SEQ ID NO: 122 - anti-CD38-E2-UCP02-A5 FAB Heavy
                           Chain
source                    1..226
                          mol_type = protein
                          organism = synthetic construct
SEQUENCE: 122
QVQLVQSGAE VKKPGSSVKV SCKASGGSFS NYAIGWVRQA PGQGLEWMGR IIPDLGAAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 123            moltype = AA  length = 226
FEATURE                   Location/Qualifiers
REGION                    1..226
                          note = SEQ ID NO: 123 - anti-CD38-E2-UCP02-D6 FAB Heavy
                           Chain
source                    1..226
                          mol_type = protein
                          organism = synthetic construct
SEQUENCE: 123
QVQLVQSGAE VKKPGSSVKV SCKASGGSFS NYAIGWVRQA PGQGLEWMGR IIPRLDAEHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 124            moltype = AA  length = 226
FEATURE                   Location/Qualifiers
REGION                    1..226
                          note = SEQ ID NO: 124 - anti-CD38-E2-UCP02-E7 FAB Heavy
                           Chain
source                    1..226
                          mol_type = protein
                          organism = synthetic construct
SEQUENCE: 124
QVQLVQSGAE VKKPGSSVKV SCKASGGSFS NYAIGWVRQA PGQGLEWMGR IIPALAATHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226
```

```
SEQ ID NO: 125          moltype = AA  length = 226
FEATURE                 Location/Qualifiers
REGION                  1..226
                        note = SEQ ID NO: 125 - anti-CD38-E2-UCP02-F3 FAB Heavy
                         Chain
source                  1..226
                        mol_type = protein
                        organism = synthetic construct
SEQUENCE: 125
QVQLVQSGAE VKKPGSSVKV SCKASGGSFS NYAIGWVRQA PGQGLEWMGR IIPVLDAAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                 226

SEQ ID NO: 126          moltype = AA  length = 226
FEATURE                 Location/Qualifiers
REGION                  1..226
                        note = SEQ ID NO: 126 - anti-CD38-E2-UCP02-F8 FAB Heavy
                         Chain
source                  1..226
                        mol_type = protein
                        organism = synthetic construct
SEQUENCE: 126
QVQLVQSGAE VKKPGSSVKV SCKASGGSFS NYAIGWVRQA PGQGLEWMGR IIPSLDAGHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                 226

SEQ ID NO: 127          moltype = AA  length = 226
FEATURE                 Location/Qualifiers
REGION                  1..226
                        note = SEQ ID NO: 127 - anti-CD38-E2-UCP02-G8 FAB Heavy
                         Chain
source                  1..226
                        mol_type = protein
                        organism = synthetic construct
SEQUENCE: 127
QVQLVQSGAE VKKPGSSVKV SCKASGGSFS NYAIGWVRQA PGQGLEWMGR IIPALGGVHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                 226

SEQ ID NO: 128          moltype = AA  length = 10
FEATURE                 Location/Qualifiers
REGION                  1..10
                        note = SEQ ID NO: 128 - anti-CD3-UCP02-A3 CDRH1
source                  1..10
                        mol_type = protein
                        organism = synthetic construct
SEQUENCE: 128
GFTFRRYYMT                                                         10

SEQ ID NO: 129          moltype = AA  length = 10
FEATURE                 Location/Qualifiers
REGION                  1..10
                        note = SEQ ID NO: 129 - anti-CD3-UCP02-B2 CDRH1
source                  1..10
                        mol_type = protein
                        organism = synthetic construct
SEQUENCE: 129
GFTFSHYVLN                                                         10

SEQ ID NO: 130          moltype = AA  length = 10
FEATURE                 Location/Qualifiers
REGION                  1..10
                        note = SEQ ID NO: 130 - anti-CD3-UCP02-D2 CDRH1
source                  1..10
                        mol_type = protein
                        organism = synthetic construct
SEQUENCE: 130
GFTFNKAWMG                                                         10

SEQ ID NO: 131          moltype = AA  length = 10
FEATURE                 Location/Qualifiers
REGION                  1..10
                        note = SEQ ID NO: 131 - anti-CD3-UCP02-F2 CDRH1
source                  1..10
                        mol_type = protein
```

```
                          organism = synthetic construct
SEQUENCE: 131
GLKVSGNYMN                                                                10

SEQ ID NO: 132            moltype = AA  length = 10
FEATURE                   Location/Qualifiers
REGION                    1..10
                          note = SEQ ID NO: 132 - anti-CD3-UCP02-H2 CDRH1
source                    1..10
                          mol_type = protein
                          organism = synthetic construct
SEQUENCE: 132
GFTVSGYYMH                                                                10

SEQ ID NO: 133            moltype = AA  length = 10
FEATURE                   Location/Qualifiers
REGION                    1..10
                          note = SEQ ID NO: 133 - anti-CD3-UCP03-A3 CDRH1
source                    1..10
                          mol_type = protein
                          organism = synthetic construct
SEQUENCE: 133
GFTFSSNAMS                                                                10

SEQ ID NO: 134            moltype = AA  length = 10
FEATURE                   Location/Qualifiers
REGION                    1..10
                          note = SEQ ID NO: 134 - anti-CD3-UCP03-A4 CDRH1
source                    1..10
                          mol_type = protein
                          organism = synthetic construct
SEQUENCE: 134
GFTVSGNYMT                                                                10

SEQ ID NO: 135            moltype = AA  length = 10
FEATURE                   Location/Qualifiers
REGION                    1..10
                          note = SEQ ID NO: 135 - anti-CD3-UCP03-B1 CDRH1
source                    1..10
                          mol_type = protein
                          organism = synthetic construct
SEQUENCE: 135
GFTFSRYAMT                                                                10

SEQ ID NO: 136            moltype = AA  length = 10
FEATURE                   Location/Qualifiers
REGION                    1..10
                          note = SEQ ID NO: 136 - anti-CD3-UCP03-C1 CDRH1
source                    1..10
                          mol_type = protein
                          organism = synthetic construct
SEQUENCE: 136
GFTFSQYAMS                                                                10

SEQ ID NO: 137            moltype = AA  length = 10
FEATURE                   Location/Qualifiers
REGION                    1..10
                          note = SEQ ID NO: 137 - anti-CD3-UCP03-C3 CDRH1
source                    1..10
                          mol_type = protein
                          organism = synthetic construct
SEQUENCE: 137
GGLFSSYTIS                                                                10

SEQ ID NO: 138            moltype = AA  length = 10
FEATURE                   Location/Qualifiers
REGION                    1..10
                          note = SEQ ID NO: 138 - anti-CD3-UCP03-C5 CDRH1
source                    1..10
                          mol_type = protein
                          organism = synthetic construct
SEQUENCE: 138
GFTVSDNDMS                                                                10

SEQ ID NO: 139            moltype = AA  length = 10
FEATURE                   Location/Qualifiers
REGION                    1..10
                          note = SEQ ID NO: 139 - anti-CD3-UCP03-E1 CDRH1
source                    1..10
```

```
                        mol_type = protein
                        organism = synthetic construct
SEQUENCE: 139
GFTFSQYAMN                                                      10

SEQ ID NO: 140          moltype = AA  length = 10
FEATURE                 Location/Qualifiers
REGION                  1..10
                        note = SEQ ID NO: 140 - anti-CD3-UCP03-E2 CDRH1
source                  1..10
                        mol_type = protein
                        organism = synthetic construct
SEQUENCE: 140
GISVGNNYMS                                                      10

SEQ ID NO: 141          moltype = AA  length = 10
FEATURE                 Location/Qualifiers
REGION                  1..10
                        note = SEQ ID NO: 141 - anti-CD3-UCP03-E4 CDRH1
source                  1..10
                        mol_type = protein
                        organism = synthetic construct
SEQUENCE: 141
GFTVSGYYMS                                                      10

SEQ ID NO: 142          moltype = AA  length = 10
FEATURE                 Location/Qualifiers
REGION                  1..10
                        note = SEQ ID NO: 142 - anti-CD3-UCP03-F1 CDRH1
source                  1..10
                        mol_type = protein
                        organism = synthetic construct
SEQUENCE: 142
GFPFSHHVMT                                                      10

SEQ ID NO: 143          moltype = AA  length = 10
FEATURE                 Location/Qualifiers
REGION                  1..10
                        note = SEQ ID NO: 143 - anti-CD3-UCP03-F2 CDRH1
source                  1..10
                        mol_type = protein
                        organism = synthetic construct
SEQUENCE: 143
GFAFSHYAMT                                                      10

SEQ ID NO: 144          moltype = AA  length = 10
FEATURE                 Location/Qualifiers
REGION                  1..10
                        note = SEQ ID NO: 144 - anti-CD3-UCP03-F4 CDRH1
source                  1..10
                        mol_type = protein
                        organism = synthetic construct
SEQUENCE: 144
GFTFSDNYMS                                                      10

SEQ ID NO: 145          moltype = AA  length = 10
FEATURE                 Location/Qualifiers
REGION                  1..10
                        note = SEQ ID NO: 145 - anti-CD3-UCP03-G2 CDRH1
source                  1..10
                        mol_type = protein
                        organism = synthetic construct
SEQUENCE: 145
GYGFNLYAIN                                                      10

SEQ ID NO: 146          moltype = AA  length = 10
FEATURE                 Location/Qualifiers
REGION                  1..10
                        note = SEQ ID NO: 146 - anti-CD3-UCP03-G3 CDRH1
source                  1..10
                        mol_type = protein
                        organism = synthetic construct
SEQUENCE: 146
GGFFRYYAIS                                                      10

SEQ ID NO: 147          moltype = AA  length = 10
FEATURE                 Location/Qualifiers
REGION                  1..10
                        note = SEQ ID NO: 147 - anti-CD3-UCP03-G4 CDRH1
```

```
source                  1..10
                        mol_type = protein
                        organism = synthetic construct
SEQUENCE: 147
GFNFDDYAMS                                                                10

SEQ ID NO: 148          moltype = AA  length = 10
FEATURE                 Location/Qualifiers
REGION                  1..10
                        note = SEQ ID NO: 148 - anti-CD3-UCP03-H2 CDRH1
source                  1..10
                        mol_type = protein
                        organism = synthetic construct
SEQUENCE: 148
GFTVRDSYMH                                                                10

SEQ ID NO: 149          moltype = AA  length = 10
FEATURE                 Location/Qualifiers
REGION                  1..10
                        note = SEQ ID NO: 149 - anti-CD3-UCP03-H3 CDRH1
source                  1..10
                        mol_type = protein
                        organism = synthetic construct
SEQUENCE: 149
GFTVRDTYMS                                                                10

SEQ ID NO: 150          moltype = AA  length = 10
FEATURE                 Location/Qualifiers
REGION                  1..10
                        note = SEQ ID NO: 150 - anti-CD3-UCP05-A1 CDRH1
source                  1..10
                        mol_type = protein
                        organism = synthetic construct
SEQUENCE: 150
GFTFSTYAMS                                                                10

SEQ ID NO: 151          moltype = AA  length = 10
FEATURE                 Location/Qualifiers
REGION                  1..10
                        note = SEQ ID NO: 151 - anti-CD3-UCP05-A2 CDRH1
source                  1..10
                        mol_type = protein
                        organism = synthetic construct
SEQUENCE: 151
GFSFKIYAMG                                                                10

SEQ ID NO: 152          moltype = AA  length = 10
FEATURE                 Location/Qualifiers
REGION                  1..10
                        note = SEQ ID NO: 152 - anti-CD3-UCP05-C1 CDRH1
source                  1..10
                        mol_type = protein
                        organism = synthetic construct
SEQUENCE: 152
GGRFSRQALT                                                                10

SEQ ID NO: 153          moltype = AA  length = 10
FEATURE                 Location/Qualifiers
REGION                  1..10
                        note = SEQ ID NO: 153 - anti-CD3-UCP05-D1 CDRH1
source                  1..10
                        mol_type = protein
                        organism = synthetic construct
SEQUENCE: 153
GFTFNQYAMS                                                                10

SEQ ID NO: 154          moltype = AA  length = 10
FEATURE                 Location/Qualifiers
REGION                  1..10
                        note = SEQ ID NO: 154 - anti-CD3-UCP05-D2 CDRH1
source                  1..10
                        mol_type = protein
                        organism = synthetic construct
SEQUENCE: 154
GFTFNIYALG                                                                10

SEQ ID NO: 155          moltype = AA  length = 10
FEATURE                 Location/Qualifiers
REGION                  1..10
```

```
                        note = SEQ ID NO: 155 - anti-CD3-UCP05-F1 CDRH1
source                  1..10
                        mol_type = protein
                        organism = synthetic construct
SEQUENCE: 155
GFTFRHYAMT                                                                  10

SEQ ID NO: 156          moltype = AA  length = 10
FEATURE                 Location/Qualifiers
REGION                  1..10
                        note = SEQ ID NO: 156 - anti-CD3-UCP05-G2 CDRH1
source                  1..10
                        mol_type = protein
                        organism = synthetic construct
SEQUENCE: 156
GGVFNFYAIS                                                                  10

SEQ ID NO: 157          moltype = AA  length = 10
FEATURE                 Location/Qualifiers
REGION                  1..10
                        note = SEQ ID NO: 157 - anti-CD3-UCP05-H1 CDRH1
source                  1..10
                        mol_type = protein
                        organism = synthetic construct
SEQUENCE: 157
GFAFSNSAMS                                                                  10

SEQ ID NO: 158          moltype = AA  length = 10
FEATURE                 Location/Qualifiers
REGION                  1..10
                        note = SEQ ID NO: 158 - anti-CD3-UCP05-H2 CDRH1
source                  1..10
                        mol_type = protein
                        organism = synthetic construct
SEQUENCE: 158
GGGFSHYALN                                                                  10

SEQ ID NO: 159          moltype = AA  length = 10
FEATURE                 Location/Qualifiers
REGION                  1..10
                        note = SEQ ID NO: 159 - anti-CD3-UCP06-A1 CDRH1
source                  1..10
                        mol_type = protein
                        organism = synthetic construct
SEQUENCE: 159
GGHFRGYGIS                                                                  10

SEQ ID NO: 160          moltype = AA  length = 10
FEATURE                 Location/Qualifiers
REGION                  1..10
                        note = SEQ ID NO: 160 - anti-CD3-UCP06-C1 CDRH1
source                  1..10
                        mol_type = protein
                        organism = synthetic construct
SEQUENCE: 160
GGKFSRYAIS                                                                  10

SEQ ID NO: 161          moltype = AA  length = 10
FEATURE                 Location/Qualifiers
REGION                  1..10
                        note = SEQ ID NO: 161 - anti-CD3-UCP07-A1 CDRH1
source                  1..10
                        mol_type = protein
                        organism = synthetic construct
SEQUENCE: 161
GFTFSDYAVN                                                                  10

SEQ ID NO: 162          moltype = AA  length = 10
FEATURE                 Location/Qualifiers
REGION                  1..10
                        note = SEQ ID NO: 162 - anti-CD3-UCP07-A3 CDRH1
source                  1..10
                        mol_type = protein
                        organism = synthetic construct
SEQUENCE: 162
GVSFREYVMA                                                                  10

SEQ ID NO: 163          moltype = AA  length = 10
FEATURE                 Location/Qualifiers
```

```
REGION                  1..10
                        note = SEQ ID NO: 163 - anti-CD3-UCP07-A4 CDRH1
source                  1..10
                        mol_type = protein
                        organism = synthetic construct
SEQUENCE: 163
GSTFRRYVMG                                                            10

SEQ ID NO: 164          moltype = AA  length = 10
FEATURE                 Location/Qualifiers
REGION                  1..10
                        note = SEQ ID NO: 164 - anti-CD3-UCP07-B2 CDRH1
source                  1..10
                        mol_type = protein
                        organism = synthetic construct
SEQUENCE: 164
GFDFGKAWMA                                                            10

SEQ ID NO: 165          moltype = AA  length = 10
FEATURE                 Location/Qualifiers
REGION                  1..10
                        note = SEQ ID NO: 165 - anti-CD3-UCP07-B3 CDRH1
source                  1..10
                        mol_type = protein
                        organism = synthetic construct
SEQUENCE: 165
GFDFNAAWMT                                                            10

SEQ ID NO: 166          moltype = AA  length = 10
FEATURE                 Location/Qualifiers
REGION                  1..10
                        note = SEQ ID NO: 166 - anti-CD3-UCP07-B4 CDRH1
source                  1..10
                        mol_type = protein
                        organism = synthetic construct
SEQUENCE: 166
GGRFSRYVIN                                                            10

SEQ ID NO: 167          moltype = AA  length = 10
FEATURE                 Location/Qualifiers
REGION                  1..10
                        note = SEQ ID NO: 167 - anti-CD3-UCP07-C3 CDRH1
source                  1..10
                        mol_type = protein
                        organism = synthetic construct
SEQUENCE: 167
GGSFSRYAIG                                                            10

SEQ ID NO: 168          moltype = AA  length = 10
FEATURE                 Location/Qualifiers
REGION                  1..10
                        note = SEQ ID NO: 168 - anti-CD3-UCP07-D1 CDRH1
source                  1..10
                        mol_type = protein
                        organism = synthetic construct
SEQUENCE: 168
GFNFNINVMS                                                            10

SEQ ID NO: 169          moltype = AA  length = 10
FEATURE                 Location/Qualifiers
REGION                  1..10
                        note = SEQ ID NO: 169 - anti-CD3-UCP07-D2 CDRH1
source                  1..10
                        mol_type = protein
                        organism = synthetic construct
SEQUENCE: 169
GFTFDRDVMG                                                            10

SEQ ID NO: 170          moltype = AA  length = 10
FEATURE                 Location/Qualifiers
REGION                  1..10
                        note = SEQ ID NO: 170 - anti-CD3-UCP07-E1 CDRH1
source                  1..10
                        mol_type = protein
                        organism = synthetic construct
SEQUENCE: 170
GFTFSRNAMN                                                            10

SEQ ID NO: 171          moltype = AA  length = 10
```

```
FEATURE                 Location/Qualifiers
REGION                  1..10
                        note = SEQ ID NO: 171 - anti-CD3-UCP07-E2 CDRH1
source                  1..10
                        mol_type = protein
                        organism = synthetic construct
SEQUENCE: 171
GFPFSNYAMS                                                    10

SEQ ID NO: 172          moltype = AA  length = 10
FEATURE                 Location/Qualifiers
REGION                  1..10
                        note = SEQ ID NO: 172 - anti-CD3-UCP07-F2 CDRH1
source                  1..10
                        mol_type = protein
                        organism = synthetic construct
SEQUENCE: 172
GGKFNKYVIG                                                    10

SEQ ID NO: 173          moltype = AA  length = 10
FEATURE                 Location/Qualifiers
REGION                  1..10
                        note = SEQ ID NO: 173 - anti-CD3-UCP07-F3 CDRH1
source                  1..10
                        mol_type = protein
                        organism = synthetic construct
SEQUENCE: 173
GFNFSGHAVG                                                    10

SEQ ID NO: 174          moltype = AA  length = 10
FEATURE                 Location/Qualifiers
REGION                  1..10
                        note = SEQ ID NO: 174 - anti-CD3-UCP07-H1 CDRH1
source                  1..10
                        mol_type = protein
                        organism = synthetic construct
SEQUENCE: 174
GFAFSKYAMH                                                    10

SEQ ID NO: 175          moltype = AA  length = 9
FEATURE                 Location/Qualifiers
REGION                  1..9
                        note = SEQ ID NO: 175 - anti-CD3-UCP08-B1 CDRH1
source                  1..9
                        mol_type = protein
                        organism = synthetic construct
SEQUENCE: 175
GGPSSHAIS                                                     9

SEQ ID NO: 176          moltype = AA  length = 10
FEATURE                 Location/Qualifiers
REGION                  1..10
                        note = SEQ ID NO: 176 - anti-CD3-C1-UCP01-B6 CDRH1
source                  1..10
                        mol_type = protein
                        organism = synthetic construct
SEQUENCE: 176
GGKFSRYAIS                                                    10

SEQ ID NO: 177          moltype = AA  length = 10
FEATURE                 Location/Qualifiers
REGION                  1..10
                        note = SEQ ID NO: 177 - anti-CD3-C1-UCP01-B9 CDRH1
source                  1..10
                        mol_type = protein
                        organism = synthetic construct
SEQUENCE: 177
GGKFSRYAIS                                                    10

SEQ ID NO: 178          moltype = AA  length = 10
FEATURE                 Location/Qualifiers
REGION                  1..10
                        note = SEQ ID NO: 178 - anti-CD3-C1-UCP01-C11 CDRH1
source                  1..10
                        mol_type = protein
                        organism = synthetic construct
SEQUENCE: 178
GGKFSRYAIS                                                    10
```

```
SEQ ID NO: 179          moltype = AA  length = 10
FEATURE                 Location/Qualifiers
REGION                  1..10
                        note = SEQ ID NO: 179 - anti-CD3-C1-UCP01-D1 CDRH1
source                  1..10
                        mol_type = protein
                        organism = synthetic construct
SEQUENCE: 179
GGKFSRYAIS                                                    10

SEQ ID NO: 180          moltype = AA  length = 10
FEATURE                 Location/Qualifiers
REGION                  1..10
                        note = SEQ ID NO: 180 - anti-CD3-C1-UCP01-D4 CDRH1
source                  1..10
                        mol_type = protein
                        organism = synthetic construct
SEQUENCE: 180
GGKFSRYAIS                                                    10

SEQ ID NO: 181          moltype = AA  length = 10
FEATURE                 Location/Qualifiers
REGION                  1..10
                        note = SEQ ID NO: 181 - anti-CD3-C1-UCP01-D6 CDRH1
source                  1..10
                        mol_type = protein
                        organism = synthetic construct
SEQUENCE: 181
GGKFSRYAIS                                                    10

SEQ ID NO: 182          moltype = AA  length = 10
FEATURE                 Location/Qualifiers
REGION                  1..10
                        note = SEQ ID NO: 182 - anti-CD3-C1-UCP01-E6 CDRH1
source                  1..10
                        mol_type = protein
                        organism = synthetic construct
SEQUENCE: 182
GGKFSRYAIS                                                    10

SEQ ID NO: 183          moltype = AA  length = 10
FEATURE                 Location/Qualifiers
REGION                  1..10
                        note = SEQ ID NO: 183 - anti-CD3-C1-UCP01-E7 CDRH1
source                  1..10
                        mol_type = protein
                        organism = synthetic construct
SEQUENCE: 183
GGKFSRYAIS                                                    10

SEQ ID NO: 184          moltype = AA  length = 10
FEATURE                 Location/Qualifiers
REGION                  1..10
                        note = SEQ ID NO: 184 - anti-CD3-C1-UCP01-E10 CDRH1
source                  1..10
                        mol_type = protein
                        organism = synthetic construct
SEQUENCE: 184
GGKFSRYAIS                                                    10

SEQ ID NO: 185          moltype = AA  length = 10
FEATURE                 Location/Qualifiers
REGION                  1..10
                        note = SEQ ID NO: 185 - anti-CD3-C1-UCP01-E11 CDRH1
source                  1..10
                        mol_type = protein
                        organism = synthetic construct
SEQUENCE: 185
GGKFSRYAIS                                                    10

SEQ ID NO: 186          moltype = AA  length = 10
FEATURE                 Location/Qualifiers
REGION                  1..10
                        note = SEQ ID NO: 186 - anti-CD3-C1-UCP01-E12 CDRH1
source                  1..10
                        mol_type = protein
                        organism = synthetic construct
SEQUENCE: 186
GGKFSRYAIS                                                    10
```

```
SEQ ID NO: 187          moltype = AA  length = 10
FEATURE                 Location/Qualifiers
REGION                  1..10
                        note = SEQ ID NO: 187 - anti-CD3-C1-UCP01-F1 CDRH1
source                  1..10
                        mol_type = protein
                        organism = synthetic construct
SEQUENCE: 187
GGKFSRYAIS                                                    10

SEQ ID NO: 188          moltype = AA  length = 10
FEATURE                 Location/Qualifiers
REGION                  1..10
                        note = SEQ ID NO: 188 - anti-CD3-C1-UCP01-F10 CDRH1
source                  1..10
                        mol_type = protein
                        organism = synthetic construct
SEQUENCE: 188
GGKFSRYAIS                                                    10

SEQ ID NO: 189          moltype = AA  length = 10
FEATURE                 Location/Qualifiers
REGION                  1..10
                        note = SEQ ID NO: 189 - anti-CD3-C1-UCP01-F12 CDRH1
source                  1..10
                        mol_type = protein
                        organism = synthetic construct
SEQUENCE: 189
GGKFSRYAIS                                                    10

SEQ ID NO: 190          moltype = AA  length = 10
FEATURE                 Location/Qualifiers
REGION                  1..10
                        note = SEQ ID NO: 190 - anti-CD3-C1-UCP01-G12 CDRH1
source                  1..10
                        mol_type = protein
                        organism = synthetic construct
SEQUENCE: 190
GGKFSRYAIS                                                    10

SEQ ID NO: 191          moltype = AA  length = 10
FEATURE                 Location/Qualifiers
REGION                  1..10
                        note = SEQ ID NO: 191 - anti-CD3-C1-UCP01-H9 CDRH1
source                  1..10
                        mol_type = protein
                        organism = synthetic construct
SEQUENCE: 191
GGKFSRYAIS                                                    10

SEQ ID NO: 192          moltype = AA  length = 10
FEATURE                 Location/Qualifiers
REGION                  1..10
                        note = SEQ ID NO: 192 - anti-CD3-C1-UCP01-H10 CDRH1
source                  1..10
                        mol_type = protein
                        organism = synthetic construct
SEQUENCE: 192
GGKFSRYAIS                                                    10

SEQ ID NO: 193          moltype = AA  length = 10
FEATURE                 Location/Qualifiers
REGION                  1..10
                        note = SEQ ID NO: 193 - anti-CD3-C1-UCP02-E1 CDRH1
source                  1..10
                        mol_type = protein
                        organism = synthetic construct
SEQUENCE: 193
GGKFSRYAIS                                                    10

SEQ ID NO: 194          moltype = AA  length = 10
FEATURE                 Location/Qualifiers
REGION                  1..10
                        note = SEQ ID NO: 194 - anti-BCMA-UCP01-A8 CDRH1
source                  1..10
                        mol_type = protein
                        organism = synthetic construct
SEQUENCE: 194
```

```
GGLFNYYIIN                                                  10

SEQ ID NO: 195          moltype = AA  length = 10
FEATURE                 Location/Qualifiers
REGION                  1..10
                        note = SEQ ID NO: 195 - anti-BCMA-UCP01-A10 CDRH1
source                  1..10
                        mol_type = protein
                        organism = synthetic construct
SEQUENCE: 195
GYVFSDHIIS                                                  10

SEQ ID NO: 196          moltype = AA  length = 10
FEATURE                 Location/Qualifiers
REGION                  1..10
                        note = SEQ ID NO: 196 - anti-BCMA-UCP01-C2 CDRH1
source                  1..10
                        mol_type = protein
                        organism = synthetic construct
SEQUENCE: 196
GFIFSQYDMS                                                  10

SEQ ID NO: 197          moltype = AA  length = 10
FEATURE                 Location/Qualifiers
REGION                  1..10
                        note = SEQ ID NO: 197 - anti-BCMA-UCP01-E8 CDRH1
source                  1..10
                        mol_type = protein
                        organism = synthetic construct
SEQUENCE: 197
GGQFSVQFIS                                                  10

SEQ ID NO: 198          moltype = AA  length = 10
FEATURE                 Location/Qualifiers
REGION                  1..10
                        note = SEQ ID NO: 198 - anti-BCMA-UCP01-E9 CDRH1
source                  1..10
                        mol_type = protein
                        organism = synthetic construct
SEQUENCE: 198
GFTFSNYAMS                                                  10

SEQ ID NO: 199          moltype = AA  length = 10
FEATURE                 Location/Qualifiers
REGION                  1..10
                        note = SEQ ID NO: 199 - anti-BCMA-UCP01-F9 CDRH1
source                  1..10
                        mol_type = protein
                        organism = synthetic construct
SEQUENCE: 199
GYKFRTYAIN                                                  10

SEQ ID NO: 200          moltype = AA  length = 10
FEATURE                 Location/Qualifiers
REGION                  1..10
                        note = SEQ ID NO: 200 - anti-BCMA-PP02-A3 CDRH1
source                  1..10
                        mol_type = protein
                        organism = synthetic construct
SEQUENCE: 200
GFTFSQYAMS                                                  10

SEQ ID NO: 201          moltype = AA  length = 10
FEATURE                 Location/Qualifiers
REGION                  1..10
                        note = SEQ ID NO: 201 - anti-BCMA-PP02-B4 CDRH1
source                  1..10
                        mol_type = protein
                        organism = synthetic construct
SEQUENCE: 201
GFTFSNYDMS                                                  10

SEQ ID NO: 202          moltype = AA  length = 10
FEATURE                 Location/Qualifiers
REGION                  1..10
                        note = SEQ ID NO: 202 - anti-BCMA-PP02-C2 CDRH1
source                  1..10
                        mol_type = protein
                        organism = synthetic construct
```

```
SEQUENCE: 202
GGHFSSYAIS                                                             10

SEQ ID NO: 203          moltype = AA  length = 10
FEATURE                 Location/Qualifiers
REGION                  1..10
                        note = SEQ ID NO: 203 - anti-BCMA-PP02-C4 CDRH1
source                  1..10
                        mol_type = protein
                        organism = synthetic construct
SEQUENCE: 203
GFTFTAYDMS                                                             10

SEQ ID NO: 204          moltype = AA  length = 10
FEATURE                 Location/Qualifiers
REGION                  1..10
                        note = SEQ ID NO: 204 - anti-BCMA-PP02-D3 CDRH1
source                  1..10
                        mol_type = protein
                        organism = synthetic construct
SEQUENCE: 204
GFIFSHYEMN                                                             10

SEQ ID NO: 205          moltype = AA  length = 10
FEATURE                 Location/Qualifiers
REGION                  1..10
                        note = SEQ ID NO: 205 - anti-BCMA-PP02-E6 CDRH1
source                  1..10
                        mol_type = protein
                        organism = synthetic construct
SEQUENCE: 205
GFTFSYYAMT                                                             10

SEQ ID NO: 206          moltype = AA  length = 10
FEATURE                 Location/Qualifiers
REGION                  1..10
                        note = SEQ ID NO: 206 - anti-BCMA-PP02-F1 CDRH1
source                  1..10
                        mol_type = protein
                        organism = synthetic construct
SEQUENCE: 206
GFSFSEYAMS                                                             10

SEQ ID NO: 207          moltype = AA  length = 10
FEATURE                 Location/Qualifiers
REGION                  1..10
                        note = SEQ ID NO: 207 - anti-BCMA-PP03-C4 CDRH1
source                  1..10
                        mol_type = protein
                        organism = synthetic construct
SEQUENCE: 207
GFTFTAYDMS                                                             10

SEQ ID NO: 208          moltype = AA  length = 10
FEATURE                 Location/Qualifiers
REGION                  1..10
                        note = SEQ ID NO: 208 - anti-BCMA-PP03-E4 CDRH1
source                  1..10
                        mol_type = protein
                        organism = synthetic construct
SEQUENCE: 208
GFALSYYAMS                                                             10

SEQ ID NO: 209          moltype = AA  length = 10
FEATURE                 Location/Qualifiers
REGION                  1..10
                        note = SEQ ID NO: 209 - anti-BCMA-D3-MP03-G7 CDRH1
source                  1..10
                        mol_type = protein
                        organism = synthetic construct
SEQUENCE: 209
GFIFSHYEMN                                                             10

SEQ ID NO: 210          moltype = AA  length = 10
FEATURE                 Location/Qualifiers
REGION                  1..10
                        note = SEQ ID NO: 210 - anti-BCMA-D3-MP04-A2 CDRH1
source                  1..10
                        mol_type = protein
```

-continued

```
                        organism = synthetic construct
SEQUENCE: 210
GFIFSHYEMN                                                                10

SEQ ID NO: 211          moltype = AA  length = 10
FEATURE                 Location/Qualifiers
REGION                  1..10
                        note = SEQ ID NO: 211 - anti-BCMA-D3-MP04-B11a CDRH1
source                  1..10
                        mol_type = protein
                        organism = synthetic construct
SEQUENCE: 211
GFIFSHYEMN                                                                10

SEQ ID NO: 212          moltype = AA  length = 10
FEATURE                 Location/Qualifiers
REGION                  1..10
                        note = SEQ ID NO: 212 - anti-BCMA-D3-MP04-B11b CDRH1
source                  1..10
                        mol_type = protein
                        organism = synthetic construct
SEQUENCE: 212
GFIFSHYEMN                                                                10

SEQ ID NO: 213          moltype = AA  length = 10
FEATURE                 Location/Qualifiers
REGION                  1..10
                        note = SEQ ID NO: 213 - anti-BCMA-D3-MP04-B11c CDRH1
source                  1..10
                        mol_type = protein
                        organism = synthetic construct
SEQUENCE: 213
GFIFSHYEMN                                                                10

SEQ ID NO: 214          moltype = AA  length = 10
FEATURE                 Location/Qualifiers
REGION                  1..10
                        note = SEQ ID NO: 214 - anti-BCMA-D3-MP04-B11d CDRH1
source                  1..10
                        mol_type = protein
                        organism = synthetic construct
SEQUENCE: 214
GFIFSHYEMN                                                                10

SEQ ID NO: 215          moltype = AA  length = 10
FEATURE                 Location/Qualifiers
REGION                  1..10
                        note = SEQ ID NO: 215 - anti-BCMA-D3-MP04-C2 CDRH1
source                  1..10
                        mol_type = protein
                        organism = synthetic construct
SEQUENCE: 215
GFIFSHYEMN                                                                10

SEQ ID NO: 216          moltype = AA  length = 10
FEATURE                 Location/Qualifiers
REGION                  1..10
                        note = SEQ ID NO: 216 - antii-BCMA-D3-MP04-C8a CDRH1
source                  1..10
                        mol_type = protein
                        organism = synthetic construct
SEQUENCE: 216
GFIFSHYEMN                                                                10

SEQ ID NO: 217          moltype = AA  length = 10
FEATURE                 Location/Qualifiers
REGION                  1..10
                        note = SEQ ID NO: 217 - anti-BCMA-D3-MP04-C8b CDRH1
source                  1..10
                        mol_type = protein
                        organism = synthetic construct
SEQUENCE: 217
GFIFSHYEMN                                                                10

SEQ ID NO: 218          moltype = AA  length = 10
FEATURE                 Location/Qualifiers
REGION                  1..10
                        note = SEQ ID NO: 218 - anti-BCMA-D3-MP04-D4 CDRH1
source                  1..10
```

```
                          mol_type = protein
                          organism = synthetic construct
SEQUENCE: 218
GFIFSHYEMN                                                         10

SEQ ID NO: 219            moltype = AA  length = 10
FEATURE                   Location/Qualifiers
REGION                    1..10
                          note = SEQ ID NO: 219 - anti-BCMA-D3-MP04-E11 CDRH1
source                    1..10
                          mol_type = protein
                          organism = synthetic construct
SEQUENCE: 219
GFIFSHYEMN                                                         10

SEQ ID NO: 220            moltype = AA  length = 10
FEATURE                   Location/Qualifiers
REGION                    1..10
                          note = SEQ ID NO: 220 - anti-BCMA-D3-MP04-F3 CDRH1
source                    1..10
                          mol_type = protein
                          organism = synthetic construct
SEQUENCE: 220
GFIFSHYEMN                                                         10

SEQ ID NO: 221            moltype = AA  length = 10
FEATURE                   Location/Qualifiers
REGION                    1..10
                          note = SEQ ID NO: 221 - anti-BCMA-D3-MP04-G7 CDRH1
source                    1..10
                          mol_type = protein
                          organism = synthetic construct
SEQUENCE: 221
GFIFSHYEMN                                                         10

SEQ ID NO: 222            moltype = AA  length = 10
FEATURE                   Location/Qualifiers
REGION                    1..10
                          note = SEQ ID NO: 222 - anti-BCMA-D3-MP05-A9 CDRH1
source                    1..10
                          mol_type = protein
                          organism = synthetic construct
SEQUENCE: 222
GFIFSHYEMN                                                         10

SEQ ID NO: 223            moltype = AA  length = 10
FEATURE                   Location/Qualifiers
REGION                    1..10
                          note = SEQ ID NO: 223 - anti-BCMA-D3-MP05-C1a CDRH1
source                    1..10
                          mol_type = protein
                          organism = synthetic construct
SEQUENCE: 223
GFIFSHYEMN                                                         10

SEQ ID NO: 224            moltype = AA  length = 10
FEATURE                   Location/Qualifiers
REGION                    1..10
                          note = SEQ ID NO: 224 - antii-BCMA-D3-MP05-C1b CDRH1
source                    1..10
                          mol_type = protein
                          organism = synthetic construct
SEQUENCE: 224
GFIFSHYEMN                                                         10

SEQ ID NO: 225            moltype = AA  length = 10
FEATURE                   Location/Qualifiers
REGION                    1..10
                          note = SEQ ID NO: 225 - anti-BCMA-D3-MP05-F4 CDRH1
source                    1..10
                          mol_type = protein
                          organism = synthetic construct
SEQUENCE: 225
GFIFSHYEMN                                                         10

SEQ ID NO: 226            moltype = AA  length = 10
FEATURE                   Location/Qualifiers
REGION                    1..10
                          note = SEQ ID NO: 226 - anti-BCMA-E6-PP02-A3 CDRH1
```

```
source                  1..10
                        mol_type = protein
                        organism = synthetic construct
SEQUENCE: 226
GFTFSYYAMT                                                                    10

SEQ ID NO: 227          moltype = AA  length = 10
FEATURE                 Location/Qualifiers
REGION                  1..10
                        note = SEQ ID NO: 227 - anti-BCMA-E6-PP02-B1 CDRH1
source                  1..10
                        mol_type = protein
                        organism = synthetic construct
SEQUENCE: 227
GFTFSYYAMT                                                                    10

SEQ ID NO: 228          moltype = AA  length = 10
FEATURE                 Location/Qualifiers
REGION                  1..10
                        note = SEQ ID NO: 228 - anti-BCMA-E6-PP02-B4 CDRH1
source                  1..10
                        mol_type = protein
                        organism = synthetic construct
SEQUENCE: 228
GFTFSYYAMT                                                                    10

SEQ ID NO: 229          moltype = AA  length = 10
FEATURE                 Location/Qualifiers
REGION                  1..10
                        note = SEQ ID NO: 229 - anti-BCMA-E6-PP02-C7 CDRH1
source                  1..10
                        mol_type = protein
                        organism = synthetic construct
SEQUENCE: 229
GFTFSYYAMT                                                                    10

SEQ ID NO: 230          moltype = AA  length = 10
FEATURE                 Location/Qualifiers
REGION                  1..10
                        note = SEQ ID NO: 230 - anti-BCMA-E6-PP02-D2 CDRH1
source                  1..10
                        mol_type = protein
                        organism = synthetic construct
SEQUENCE: 230
GFTFSYYAMT                                                                    10

SEQ ID NO: 231          moltype = AA  length = 10
FEATURE                 Location/Qualifiers
REGION                  1..10
                        note = SEQ ID NO: 231 - anti-BCMA-E6-PP02-E6 CDRH1
source                  1..10
                        mol_type = protein
                        organism = synthetic construct
SEQUENCE: 231
GFTFSYYAMT                                                                    10

SEQ ID NO: 232          moltype = AA  length = 10
FEATURE                 Location/Qualifiers
REGION                  1..10
                        note = SEQ ID NO: 232 - anti-BCMA-E6-PP02-F7 CDRH1
source                  1..10
                        mol_type = protein
                        organism = synthetic construct
SEQUENCE: 232
GFTFSYYAMT                                                                    10

SEQ ID NO: 233          moltype = AA  length = 10
FEATURE                 Location/Qualifiers
REGION                  1..10
                        note = SEQ ID NO: 233 - anti-BCMA-E6-PP02-G2 CDRH1
source                  1..10
                        mol_type = protein
                        organism = synthetic construct
SEQUENCE: 233
GFTFSYYAMT                                                                    10

SEQ ID NO: 234          moltype = AA  length = 10
FEATURE                 Location/Qualifiers
REGION                  1..10
```

-continued

```
                        note = SEQ ID NO: 234 - anti-BCMA-E6-PP02-G6 CDRH1
source                  1..10
                        mol_type = protein
                        organism = synthetic construct
SEQUENCE: 234
GFTFSYYAMT                                                                10

SEQ ID NO: 235          moltype = AA  length = 10
FEATURE                 Location/Qualifiers
REGION                  1..10
                        note = SEQ ID NO: 235 - anti-BCMA-E6-PP02-G7 CDRH1
source                  1..10
                        mol_type = protein
                        organism = synthetic construct
SEQUENCE: 235
GFTFSYYAMT                                                                10

SEQ ID NO: 236          moltype = AA  length = 10
FEATURE                 Location/Qualifiers
REGION                  1..10
                        note = SEQ ID NO: 236 - anti-CD38-UCP03-B3 CDRH1
source                  1..10
                        mol_type = protein
                        organism = synthetic construct
SEQUENCE: 236
GGDFTLYSIS                                                                10

SEQ ID NO: 237          moltype = AA  length = 10
FEATURE                 Location/Qualifiers
REGION                  1..10
                        note = SEQ ID NO: 237 - anti-CD38-UCP01-E2 CDRH1
source                  1..10
                        mol_type = protein
                        organism = synthetic construct
SEQUENCE: 237
GGSFSNYAIG                                                                10

SEQ ID NO: 238          moltype = AA  length = 10
FEATURE                 Location/Qualifiers
REGION                  1..10
                        note = SEQ ID NO: 238 - anti-CD38-B3-PP11-A2 CDRH1
source                  1..10
                        mol_type = protein
                        organism = synthetic construct
SEQUENCE: 238
GQTTPMYSIS                                                                10

SEQ ID NO: 239          moltype = AA  length = 10
FEATURE                 Location/Qualifiers
REGION                  1..10
                        note = SEQ ID NO: 239 - anti-CD38-B3-PP11-C11 CDRH1
source                  1..10
                        mol_type = protein
                        organism = synthetic construct
SEQUENCE: 239
GGDFTLYSIS                                                                10

SEQ ID NO: 240          moltype = AA  length = 10
FEATURE                 Location/Qualifiers
REGION                  1..10
                        note = SEQ ID NO: 240 - anti-CD38-B3-PP11-D1a CDRH1
source                  1..10
                        mol_type = protein
                        organism = synthetic construct
SEQUENCE: 240
GMQTRWYSIS                                                                10

SEQ ID NO: 241          moltype = AA  length = 10
FEATURE                 Location/Qualifiers
REGION                  1..10
                        note = SEQ ID NO: 241 - anti-CD38-B3-PP11-D1b CDRH1
source                  1..10
                        mol_type = protein
                        organism = synthetic construct
SEQUENCE: 241
GIQTRWYSIS                                                                10

SEQ ID NO: 242          moltype = AA  length = 10
FEATURE                 Location/Qualifiers
```

```
REGION                 1..10
                       note = SEQ ID NO: 242 - anti-CD38-B3-PP11-D11a CDRH1
source                 1..10
                       mol_type = protein
                       organism = synthetic construct
SEQUENCE: 242
GGDFTLYSIS                                                            10

SEQ ID NO: 243         moltype = AA  length = 10
FEATURE                Location/Qualifiers
REGION                 1..10
                       note = SEQ ID NO: 243 - anti-CD38-B3-PP11-E1 CDRH1
source                 1..10
                       mol_type = protein
                       organism = synthetic construct
SEQUENCE: 243
GQHKRVYSIS                                                            10

SEQ ID NO: 244         moltype = AA  length = 10
FEATURE                Location/Qualifiers
REGION                 1..10
                       note = SEQ ID NO: 244 - anti-CD38-B3-PP11-E11 CDRH1
source                 1..10
                       mol_type = protein
                       organism = synthetic construct
SEQUENCE: 244
GGDFTLYSIS                                                            10

SEQ ID NO: 245         moltype = AA  length = 10
FEATURE                Location/Qualifiers
REGION                 1..10
                       note = SEQ ID NO: 245 - anti-CD38-B3-PP11-H1a CDRH1
source                 1..10
                       mol_type = protein
                       organism = synthetic construct
SEQUENCE: 245
GQNERMYSIS                                                            10

SEQ ID NO: 246         moltype = AA  length = 10
FEATURE                Location/Qualifiers
REGION                 1..10
                       note = SEQ ID NO: 246 - anti-CD38-B3-PP11-H10 CDRH1
source                 1..10
                       mol_type = protein
                       organism = synthetic construct
SEQUENCE: 246
GGDFTLYSIS                                                            10

SEQ ID NO: 247         moltype = AA  length = 10
FEATURE                Location/Qualifiers
REGION                 1..10
                       note = SEQ ID NO: 247 - anti-CD38-E2-UCP01-A10 CDRH1
source                 1..10
                       mol_type = protein
                       organism = synthetic construct
SEQUENCE: 247
GLPDATYAIG                                                            10

SEQ ID NO: 248         moltype = AA  length = 10
FEATURE                Location/Qualifiers
REGION                 1..10
                       note = SEQ ID NO: 248 - anti-CD38-E2-UCP02-A5 CDRH1
source                 1..10
                       mol_type = protein
                       organism = synthetic construct
SEQUENCE: 248
GGSFSNYAIG                                                            10

SEQ ID NO: 249         moltype = AA  length = 10
FEATURE                Location/Qualifiers
REGION                 1..10
                       note = SEQ ID NO: 249 - anti-CD38-E2-UCP02-D6 CDRH1
source                 1..10
                       mol_type = protein
                       organism = synthetic construct
SEQUENCE: 249
GGSFSNYAIG                                                            10

SEQ ID NO: 250         moltype = AA  length = 10
```

```
FEATURE                Location/Qualifiers
REGION                 1..10
                       note = SEQ ID NO: 250 - anti-CD38-E2-UCP02-E7 CDRH1
source                 1..10
                       mol_type = protein
                       organism = synthetic construct
SEQUENCE: 250
GGSFSNYAIG                                                             10

SEQ ID NO: 251         moltype = AA  length = 10
FEATURE                Location/Qualifiers
REGION                 1..10
                       note = SEQ ID NO: 251 - anti-CD38-E2-UCP02-F3 CDRH1
source                 1..10
                       mol_type = protein
                       organism = synthetic construct
SEQUENCE: 251
GGSFSNYAIG                                                             10

SEQ ID NO: 252         moltype = AA  length = 10
FEATURE                Location/Qualifiers
REGION                 1..10
                       note = SEQ ID NO: 252 - anti-CD38-E2-UCP02-F8 CDRH1
source                 1..10
                       mol_type = protein
                       organism = synthetic construct
SEQUENCE: 252
GGSFSNYAIG                                                             10

SEQ ID NO: 253         moltype = AA  length = 10
FEATURE                Location/Qualifiers
REGION                 1..10
                       note = SEQ ID NO: 253 - anti-CD38-E2-UCP02-G8 CDRH1
source                 1..10
                       mol_type = protein
                       organism = synthetic construct
SEQUENCE: 253
GGSFSNYAIG                                                             10

SEQ ID NO: 254         moltype = AA  length = 9
FEATURE                Location/Qualifiers
REGION                 1..9
                       note = SEQ ID NO: 254 - anti-CD3-UCP02-A3 CDRH2
source                 1..9
                       mol_type = protein
                       organism = synthetic construct
SEQUENCE: 254
VIFPQGGTS                                                              9

SEQ ID NO: 255         moltype = AA  length = 10
FEATURE                Location/Qualifiers
REGION                 1..10
                       note = SEQ ID NO: 255 - anti-CD3-UCP02-B2 CDRH2
source                 1..10
                       mol_type = protein
                       organism = synthetic construct
SEQUENCE: 255
GISLTGIATI                                                             10

SEQ ID NO: 256         moltype = AA  length = 12
FEATURE                Location/Qualifiers
REGION                 1..12
                       note = SEQ ID NO: 256 - anti-CD3-UCP02-D2 CDRH2
source                 1..12
                       mol_type = protein
                       organism = synthetic construct
SEQUENCE: 256
RIKSVTDGGI TV                                                          12

SEQ ID NO: 257         moltype = AA  length = 9
FEATURE                Location/Qualifiers
REGION                 1..9
                       note = SEQ ID NO: 257 - anti-CD3-UCP02-F2 CDRH2
source                 1..9
                       mol_type = protein
                       organism = synthetic construct
SEQUENCE: 257
VIYSDGQTY                                                              9
```

```
SEQ ID NO: 258          moltype = AA  length = 9
FEATURE                 Location/Qualifiers
REGION                  1..9
                        note = SEQ ID NO: 258 - anti-CD3-UCP02-H2 CDRH2
source                  1..9
                        mol_type = protein
                        organism = synthetic construct
SEQUENCE: 258
IIYVDGRTE                                                                  9

SEQ ID NO: 259          moltype = AA  length = 10
FEATURE                 Location/Qualifiers
REGION                  1..10
                        note = SEQ ID NO: 259 - anti-CD3-UCP03-A3 CDRH2
source                  1..10
                        mol_type = protein
                        organism = synthetic construct
SEQUENCE: 259
AVGKYGGATS                                                                 10

SEQ ID NO: 260          moltype = AA  length = 9
FEATURE                 Location/Qualifiers
REGION                  1..9
                        note = SEQ ID NO: 260 - anti-CD3-UCP03-A4 CDRH2
source                  1..9
                        mol_type = protein
                        organism = synthetic construct
SEQUENCE: 260
LIYTDGRTL                                                                  9

SEQ ID NO: 261          moltype = AA  length = 10
FEATURE                 Location/Qualifiers
REGION                  1..10
                        note = SEQ ID NO: 261 - anti-CD3-UCP03-B1 CDRH2
source                  1..10
                        mol_type = protein
                        organism = synthetic construct
SEQUENCE: 261
GISKYGGATA                                                                 10

SEQ ID NO: 262          moltype = AA  length = 10
FEATURE                 Location/Qualifiers
REGION                  1..10
                        note = SEQ ID NO: 262 - anti-CD3-UCP03-C1 CDRH2
source                  1..10
                        mol_type = protein
                        organism = synthetic construct
SEQUENCE: 262
VISPSGATAV                                                                 10

SEQ ID NO: 263          moltype = AA  length = 10
FEATURE                 Location/Qualifiers
REGION                  1..10
                        note = SEQ ID NO: 263 - anti-CD3-UCP03-C3 CDRH2
source                  1..10
                        mol_type = protein
                        organism = synthetic construct
SEQUENCE: 263
GIIPNTGSSY                                                                 10

SEQ ID NO: 264          moltype = AA  length = 9
FEATURE                 Location/Qualifiers
REGION                  1..9
                        note = SEQ ID NO: 264 - anti-CD3-UCP03-C5 CDRH2
source                  1..9
                        mol_type = protein
                        organism = synthetic construct
SEQUENCE: 264
LIYSNGGTH                                                                  9

SEQ ID NO: 265          moltype = AA  length = 10
FEATURE                 Location/Qualifiers
REGION                  1..10
                        note = SEQ ID NO: 265 - anti-CD3-UCP03-E1 CDRH2
source                  1..10
                        mol_type = protein
                        organism = synthetic construct
SEQUENCE: 265
AISRKGGSTI                                                                 10
```

```
SEQ ID NO: 266          moltype = AA  length = 9
FEATURE                 Location/Qualifiers
REGION                  1..9
                        note = SEQ ID NO: 266 - anti-CD3-UCP03-E2 CDRH2
source                  1..9
                        mol_type = protein
                        organism = synthetic construct
SEQUENCE: 266
VIYPNGRIK                                                                9

SEQ ID NO: 267          moltype = AA  length = 9
FEATURE                 Location/Qualifiers
REGION                  1..9
                        note = SEQ ID NO: 267 - anti-CD3-UCP03-E4 CDRH2
source                  1..9
                        mol_type = protein
                        organism = synthetic construct
SEQUENCE: 267
VIGGAGQTD                                                                9

SEQ ID NO: 268          moltype = AA  length = 10
FEATURE                 Location/Qualifiers
REGION                  1..10
                        note = SEQ ID NO: 268 - anti-CD3-UCP03-F1 CDRH2
source                  1..10
                        mol_type = protein
                        organism = synthetic construct
SEQUENCE: 268
AITQRGEYTL                                                               10

SEQ ID NO: 269          moltype = AA  length = 10
FEATURE                 Location/Qualifiers
REGION                  1..10
                        note = SEQ ID NO: 269 - anti-CD3-UCP03-F2 CDRH2
source                  1..10
                        mol_type = protein
                        organism = synthetic construct
SEQUENCE: 269
AISQHGGYTA                                                               10

SEQ ID NO: 270          moltype = AA  length = 9
FEATURE                 Location/Qualifiers
REGION                  1..9
                        note = SEQ ID NO: 270 - anti-CD3-UCP03-F4 CDRH2
source                  1..9
                        mol_type = protein
                        organism = synthetic construct
SEQUENCE: 270
VIYSQGRTF                                                                9

SEQ ID NO: 271          moltype = AA  length = 10
FEATURE                 Location/Qualifiers
REGION                  1..10
                        note = SEQ ID NO: 271 - anti-CD3-UCP03-G2 CDRH2
source                  1..10
                        mol_type = protein
                        organism = synthetic construct
SEQUENCE: 271
RIIPEYGHTR                                                               10

SEQ ID NO: 272          moltype = AA  length = 10
FEATURE                 Location/Qualifiers
REGION                  1..10
                        note = SEQ ID NO: 272 - anti-CD3-UCP03-G3 CDRH2
source                  1..10
                        mol_type = protein
                        organism = synthetic construct
SEQUENCE: 272
GIIPVTGSTH                                                               10

SEQ ID NO: 273          moltype = AA  length = 10
FEATURE                 Location/Qualifiers
REGION                  1..10
                        note =  SEQ ID NO: 273 - anti-CD3-UCP03-G4 CDRH2
source                  1..10
                        mol_type = protein
                        organism = synthetic construct
SEQUENCE: 273
```

-continued

```
IISHKGDFTS                                                      10

SEQ ID NO: 274         moltype = AA  length = 9
FEATURE                Location/Qualifiers
REGION                 1..9
                       note = SEQ ID NO: 274 - anti-CD3-UCP03-H2 CDRH2
source                 1..9
                       mol_type = protein
                       organism = synthetic construct
SEQUENCE: 274
IIYYTGKTH                                                       9

SEQ ID NO: 275         moltype = AA  length = 9
FEATURE                Location/Qualifiers
REGION                 1..9
                       note = SEQ ID NO: 275 - anti-CD3-UCP03-H3 CDRH2
source                 1..9
                       mol_type = protein
                       organism = synthetic construct

SEQUENCE: 275
IIYGHGKTT                                                       9

SEQ ID NO: 276         moltype = AA  length = 10
FEATURE                Location/Qualifiers
REGION                 1..10
                       note = SEQ ID NO: 276 - anti-CD3-UCP05-A1 CDRH2
source                 1..10
                       mol_type = protein
                       organism = synthetic construct
SEQUENCE: 276
AISRHGGFSR                                                      10

SEQ ID NO: 277         moltype = AA  length = 10
FEATURE                Location/Qualifiers
REGION                 1..10
                       note = SEQ ID NO: 277 - anti-CD3-UCP05-A2 CDRH2
source                 1..10
                       mol_type = protein
                       organism = synthetic construct
SEQUENCE: 277
AITQQGGATV                                                      10

SEQ ID NO: 278         moltype = AA  length = 10
FEATURE                Location/Qualifiers
REGION                 1..10
                       note = SEQ ID NO: 278 - anti-CD3-UCP05-C1 CDRH2
source                 1..10
                       mol_type = protein
                       organism = synthetic construct
SEQUENCE: 278
GIIPDHGRPI                                                      10

SEQ ID NO: 279         moltype = AA  length = 10
FEATURE                Location/Qualifiers
REGION                 1..10
                       note = SEQ ID NO: 279 - anti-CD3-UCP05-D1 CDRH2
source                 1..10
                       mol_type = protein
                       organism = synthetic construct
SEQUENCE: 279
AISQFGGYTK                                                      10

SEQ ID NO: 280         moltype = AA  length = 10
FEATURE                Location/Qualifiers
REGION                 1..10
                       note = SEQ ID NO: 280 - anti-CD3-UCP05-D2 CDRH2
source                 1..10
                       mol_type = protein
                       organism = synthetic construct
SEQUENCE: 280
AISQNGGYTL                                                      10

SEQ ID NO: 281         moltype = AA  length = 10
FEATURE                Location/Qualifiers
REGION                 1..10
                       note = SEQ ID NO: 281 - anti-CD3-UCP05-F1 CDRH2
source                 1..10
                       mol_type = protein
                       organism = synthetic construct
```

```
SEQUENCE: 281
AITQRGGYTY                                                      10

SEQ ID NO: 282          moltype = AA  length = 10
FEATURE                 Location/Qualifiers
REGION                  1..10
                        note = SEQ ID NO: 282 - anti-CD3-UCP05-G2 CDRH2
source                  1..10
                        mol_type = protein
                        organism = synthetic construct
SEQUENCE: 282
GITPDGGFVK                                                      10

SEQ ID NO: 283          moltype = AA  length = 10
FEATURE                 Location/Qualifiers
REGION                  1..10
                        note = SEQ ID NO: 283 - anti-CD3-UCP05-H1 CDRH2
source                  1..10
                        mol_type = protein
                        organism = synthetic construct
SEQUENCE: 283
AISTKGGKTL                                                      10

SEQ ID NO: 284          moltype = AA  length = 10
FEATURE                 Location/Qualifiers
REGION                  1..10
                        note = SEQ ID NO: 284 - anti-CD3-UCP05-H2 CDRH2
source                  1..10
                        mol_type = protein
                        organism = synthetic construct
SEQUENCE: 284
GIIPLTGKTA                                                      10

SEQ ID NO: 285          moltype = AA  length = 10
FEATURE                 Location/Qualifiers
REGION                  1..10
                        note = SEQ ID NO: 285 - anti-CD3-UCP06-A1 CDRH2
source                  1..10
                        mol_type = protein
                        organism = synthetic construct
SEQUENCE: 285
EIIPLRGFTI                                                      10

SEQ ID NO: 286          moltype = AA  length = 10
FEATURE                 Location/Qualifiers
REGION                  1..10
                        note = SEQ ID NO: 286 - anti-CD3-UCP06-C1 CDRH2
source                  1..10
                        mol_type = protein
                        organism = synthetic construct
SEQUENCE: 286
GIIPKGGYAE                                                      10

SEQ ID NO: 287          moltype = AA  length = 11
FEATURE                 Location/Qualifiers
REGION                  1..11
                        note = SEQ ID NO: 287 - anti-CD3-UCP07-A1 CDRH2
source                  1..11
                        mol_type = protein
                        organism = synthetic construct
SEQUENCE: 287
RIKSKNEGGT G                                                    11

SEQ ID NO: 288          moltype = AA  length = 10
FEATURE                 Location/Qualifiers
REGION                  1..10
                        note = SEQ ID NO: 288 - anti-CD3-UCP07-A3 CDRH2
source                  1..10
                        mol_type = protein
                        organism = synthetic construct
SEQUENCE: 288
VISQYGGNTY                                                      10

SEQ ID NO: 289          moltype = AA  length = 10
FEATURE                 Location/Qualifiers
REGION                  1..10
                        note = SEQ ID NO: 289 - anti-CD3-UCP07-A4 CDRH2
source                  1..10
                        mol_type = protein
```

```
                          organism = synthetic construct
SEQUENCE: 289
AISQQGGYTY                                                         10

SEQ ID NO: 290            moltype = AA  length = 12
FEATURE                   Location/Qualifiers
REGION                    1..12
                          note = SEQ ID NO: 290 - anti-CD3-UCP07-B2 CDRH2
source                    1..12
                          mol_type = protein
                          organism = synthetic construct
SEQUENCE: 290
RIKSDFKGGD TI                                                      12

SEQ ID NO: 291            moltype = AA  length = 12
FEATURE                   Location/Qualifiers
REGION                    1..12
                          note = SEQ ID NO: 291 - anti-CD3-UCP07-B3 CDRH2
source                    1..12
                          mol_type = protein
                          organism = synthetic construct
SEQUENCE: 291
RIKSEKNGGK SV                                                      12

SEQ ID NO: 292            moltype = AA  length = 10
FEATURE                   Location/Qualifiers
REGION                    1..10
                          note = SEQ ID NO: 292 - anti-CD3-UCP07-B4 CDRH2
source                    1..10
                          mol_type = protein
                          organism = synthetic construct
SEQUENCE: 292
RIVPIFGTAN                                                         10

SEQ ID NO: 293            moltype = AA  length = 10
FEATURE                   Location/Qualifiers
REGION                    1..10
                          note = SEQ ID NO: 293 - anti-CD3-UCP07-C3 CDRH2
source                    1..10
                          mol_type = protein
                          organism = synthetic construct
SEQUENCE: 293
GIIPDVGIAF                                                         10

SEQ ID NO: 294            moltype = AA  length = 10
FEATURE                   Location/Qualifiers
REGION                    1..10
                          note = SEQ ID NO: 294 - anti-CD3-UCP07-D1 CDRH2
source                    1..10
                          mol_type = protein
                          organism = synthetic construct
SEQUENCE: 294
AISQSGGYTL                                                         10

SEQ ID NO: 295            moltype = AA  length = 10
FEATURE                   Location/Qualifiers
REGION                    1..10
                          note = SEQ ID NO: 295 - anti-CD3-UCP07-D2 CDRH2
source                    1..10
                          mol_type = protein
                          organism = synthetic construct
SEQUENCE: 295
AISIRGGKTL                                                         10

SEQ ID NO: 296            moltype = AA  length = 10
FEATURE                   Location/Qualifiers
REGION                    1..10
                          note = SEQ ID NO: 296 - anti-CD3-UCP07-E1 CDRH2
source                    1..10
                          mol_type = protein
                          organism = synthetic construct
SEQUENCE: 296
SISRIGGFTI                                                         10

SEQ ID NO: 297            moltype = AA  length = 10
FEATURE                   Location/Qualifiers
REGION                    1..10
                          note = SEQ ID NO: 297 - anti-CD3-UCP07-E2 CDRH2
source                    1..10
```

```
                        mol_type = protein
                        organism = synthetic construct
SEQUENCE: 297
AISRKGGFTE                                                      10

SEQ ID NO: 298          moltype = AA  length = 10
FEATURE                 Location/Qualifiers
REGION                  1..10
                        note = SEQ ID NO: 298 - anti-CD3-UCP07-F2 CDRH2
source                  1..10
                        mol_type = protein
                        organism = synthetic construct
SEQUENCE: 298
GVIPLKGQSK                                                      10

SEQ ID NO: 299          moltype = AA  length = 10
FEATURE                 Location/Qualifiers
REGION                  1..10
                        note = SEQ ID NO: 299 - anti-CD3-UCP07-F3 CDRH2
source                  1..10
                        mol_type = protein
                        organism = synthetic construct
SEQUENCE: 299
AISQNGGYTL                                                      10

SEQ ID NO: 300          moltype = AA  length = 10
FEATURE                 Location/Qualifiers
REGION                  1..10
                        note = SEQ ID NO: 300 - anti-CD3-UCP07-H1 CDRH2
source                  1..10
                        mol_type = protein
                        organism = synthetic construct
SEQUENCE: 300
GISQSGGYTL                                                      10

SEQ ID NO: 301          moltype = AA  length = 10
FEATURE                 Location/Qualifiers
REGION                  1..10
                        note = SEQ ID NO: 301 - anti-CD3-UCP08-B1 CDRH2
source                  1..10
                        mol_type = protein
                        organism = synthetic construct
SEQUENCE: 301
GIIPRSGKTY                                                      10

SEQ ID NO: 302          moltype = AA  length = 10
FEATURE                 Location/Qualifiers
REGION                  1..10
                        note = SEQ ID NO: 302 - anti-CD3-C1-UCP01-B6 CDRH2
source                  1..10
                        mol_type = protein
                        organism = synthetic construct
SEQUENCE: 302
GISPYQGYAS                                                      10

SEQ ID NO: 303          moltype = AA  length = 11
FEATURE                 Location/Qualifiers
REGION                  1..11
                        note = SEQ ID NO: 303 - anti-CD3-C1-UCP01-B9 CDRH2
source                  1..11
                        mol_type = protein
                        organism = synthetic construct
SEQUENCE: 303
GINAPVVRSP E                                                    11

SEQ ID NO: 304          moltype = AA  length = 10
FEATURE                 Location/Qualifiers
REGION                  1..10
                        note = SEQ ID NO: 304 - anti-CD3-C1-UCP01-C11 CDRH2
source                  1..10
                        mol_type = protein
                        organism = synthetic construct
SEQUENCE: 304
GINPHVGAPE                                                      10

SEQ ID NO: 305          moltype = AA  length = 10
FEATURE                 Location/Qualifiers
REGION                  1..10
                        note = SEQ ID NO: 305 - anti-CD3-C1-UCP01-D1 CDRH2
```

```
source                  1..10
                        mol_type = protein
                        organism = synthetic construct
SEQUENCE: 305
GINPLSDEAQ                                                                  10

SEQ ID NO: 306          moltype = AA  length = 10
FEATURE                 Location/Qualifiers
REGION                  1..10
                        note = SEQ ID NO: 306 - anti-CD3-C1-UCP01-D4 CDRH2
source                  1..10
                        mol_type = protein
                        organism = synthetic construct
SEQUENCE: 306
GINPIRGRPS                                                                  10

SEQ ID NO: 307          moltype = AA  length = 10
FEATURE                 Location/Qualifiers
REGION                  1..10
                        note = SEQ ID NO: 307 - anti-CD3-C1-UCP01-D6 CDRH2
source                  1..10
                        mol_type = protein
                        organism = synthetic construct
SEQUENCE: 307
GITALGGYPN                                                                  10

SEQ ID NO: 308          moltype = AA  length = 11
FEATURE                 Location/Qualifiers
REGION                  1..11
                        note = SEQ ID NO: 308 - anti-CD3-C1-UCP01-E6 CDRH2
source                  1..11
                        mol_type = protein
                        organism = synthetic construct
SEQUENCE: 308
GITPPHVGIA D                                                                11

SEQ ID NO: 309          moltype = AA  length = 10
FEATURE                 Location/Qualifiers
REGION                  1..10
                        note = SEQ ID NO: 309 - anti-CD3-C1-UCP01-E7 CDRH2
source                  1..10
                        mol_type = protein
                        organism = synthetic construct
SEQUENCE: 309
GINPHLGEAE                                                                  10

SEQ ID NO: 310          moltype = AA  length = 10
FEATURE                 Location/Qualifiers
REGION                  1..10
                        note = SEQ ID NO: 310 - anti-CD3-C1-UCP01-E10 CDRH2
source                  1..10
                        mol_type = protein
                        organism = synthetic construct
SEQUENCE: 310
GISPFEGTPA                                                                  10

SEQ ID NO: 311          moltype = AA  length = 10
FEATURE                 Location/Qualifiers
REGION                  1..10
                        note = SEQ ID NO: 311 - anti-CD3-C1-UCP01-E11 CDRH2
source                  1..10
                        mol_type = protein
                        organism = synthetic construct
SEQUENCE: 311
GINPFKGDAE                                                                  10

SEQ ID NO: 312          moltype = AA  length = 10
FEATURE                 Location/Qualifiers
REGION                  1..10
                        note = SEQ ID NO: 312 - anti-CD3-C1-UCP01-E12 CDRH2
source                  1..10
                        mol_type = protein
                        organism = synthetic construct
SEQUENCE: 312
GINPLVGHAE                                                                  10

SEQ ID NO: 313          moltype = AA  length = 10
FEATURE                 Location/Qualifiers
REGION                  1..10
```

```
                        note = SEQ ID NO: 313 - anti-CD3-C1-UCP01-F1 CDRH2
source                  1..10
                        mol_type = protein
                        organism = synthetic construct
SEQUENCE: 313
GINPRLGQAE                                                        10

SEQ ID NO: 314          moltype = AA  length = 10
FEATURE                 Location/Qualifiers
REGION                  1..10
                        note = SEQ ID NO: 314 - anti-CD3-C1-UCP01-F10 CDRH2
source                  1..10
                        mol_type = protein
                        organism = synthetic construct
SEQUENCE: 314
GINPHIRFPE                                                        10

SEQ ID NO: 315          moltype = AA  length = 10
FEATURE                 Location/Qualifiers
REGION                  1..10
                        note = SEQ ID NO: 315 - anti-CD3-C1-UCP01-F12 CDRH2
source                  1..10
                        mol_type = protein
                        organism = synthetic construct
SEQUENCE: 315
GISPFRGHAE                                                        10

SEQ ID NO: 316          moltype = AA  length = 10
FEATURE                 Location/Qualifiers
REGION                  1..10
                        note = SEQ ID NO: 316 - anti-CD3-C1-UCP01-G12 CDRH2
source                  1..10
                        mol_type = protein
                        organism = synthetic construct
SEQUENCE: 316
GISPHIGHPE                                                        10

SEQ ID NO: 317          moltype = AA  length = 10
FEATURE                 Location/Qualifiers
REGION                  1..10
                        note = SEQ ID NO: 317 - anti-CD3-C1-UCP01-H9 CDRH2
source                  1..10
                        mol_type = protein
                        organism = synthetic construct
SEQUENCE: 317
GISPHVGYAE                                                        10

SEQ ID NO: 318          moltype = AA  length = 10
FEATURE                 Location/Qualifiers
REGION                  1..10
                        note = SEQ ID NO: 318 - anti-CD3-C1-UCP01-H10 CDRH2
source                  1..10
                        mol_type = protein
                        organism = synthetic construct
SEQUENCE: 318
GISPLVGYPQ                                                        10

SEQ ID NO: 319          moltype = AA  length = 10
FEATURE                 Location/Qualifiers
REGION                  1..10
                        note = SEQ ID NO: 319 - anti-CD3-C1-UCP02-E1 CDRH2
source                  1..10
                        mol_type = protein
                        organism = synthetic construct
SEQUENCE: 319
GISPFKGYAE                                                        10

SEQ ID NO: 320          moltype = AA  length = 10
FEATURE                 Location/Qualifiers
REGION                  1..10
                        note = SEQ ID NO: 320 - anti-BCMA-UCP01-A8 CDRH2
source                  1..10
                        mol_type = protein
                        organism = synthetic construct
SEQUENCE: 320
GIIPTYGGAG                                                        10

SEQ ID NO: 321          moltype = AA  length = 10
FEATURE                 Location/Qualifiers
```

```
REGION                1..10
                      note = SEQ ID NO: 321 - anti-BCMA-UCP01-A10 CDRH2
source                1..10
                      mol_type = protein
                      organism = synthetic construct
SEQUENCE: 321
GIIPHGGAPT                                                           10

SEQ ID NO: 322        moltype = AA  length = 10
FEATURE               Location/Qualifiers
REGION                1..10
                      note = SEQ ID NO: 322 - anti-BCMA-UCP01-C2 CDRH2
source                1..10
                      mol_type = protein
                      organism = synthetic construct
SEQUENCE: 322
AISLLGDFTS                                                           10

SEQ ID NO: 323        moltype = AA  length = 10
FEATURE               Location/Qualifiers
REGION                1..10
                      note = SEQ ID NO: 323 - anti-BCMA-UCP01-E8 CDRH2
source                1..10
                      mol_type = protein
                      organism = synthetic construct
SEQUENCE: 323
GIIPTSGDTY                                                           10

SEQ ID NO: 324        moltype = AA  length = 10
FEATURE               Location/Qualifiers
REGION                1..10
                      note = SEQ ID NO: 324 - anti-BCMA-UCP01-E9 CDRH2
source                1..10
                      mol_type = protein
                      organism = synthetic construct
SEQUENCE: 324
VISERGAVTV                                                           10

SEQ ID NO: 325        moltype = AA  length = 10
FEATURE               Location/Qualifiers
REGION                1..10
                      note = SEQ ID NO: 325 - anti-BCMA-UCP01-F9 CDRH2
source                1..10
                      mol_type = protein
                      organism = synthetic construct
SEQUENCE: 325
GIVPISGETF                                                           10

SEQ ID NO: 326        moltype = AA  length = 10
FEATURE               Location/Qualifiers
REGION                1..10
                      note = SEQ ID NO: 326 - anti-BCMA-PP02-A3 CDRH2
source                1..10
                      mol_type = protein
                      organism = synthetic construct
SEQUENCE: 326
IISQDGGVTV                                                           10

SEQ ID NO: 327        moltype = AA  length = 10
FEATURE               Location/Qualifiers
REGION                1..10
                      note = SEQ ID NO: 327 - anti-BCMA-PP02-B4 CDRH2
source                1..10
                      mol_type = protein
                      organism = synthetic construct
SEQUENCE: 327
AISVSGDFTQ                                                           10

SEQ ID NO: 328        moltype = AA  length = 10
FEATURE               Location/Qualifiers
REGION                1..10
                      note = SEQ ID NO: 328 - anti-BCMA-PP02-C2 CDRH2
source                1..10
                      mol_type = protein
                      organism = synthetic construct
SEQUENCE: 328
GIIPQHGVPS                                                           10

SEQ ID NO: 329        moltype = AA  length = 10
```

-continued

```
FEATURE                Location/Qualifiers
REGION                 1..10
                       note = SEQ ID NO: 329 - anti-BCMA-PP02-C4 CDRH2
source                 1..10
                       mol_type = protein
                       organism = synthetic construct
SEQUENCE: 329
AISGFGGDTL                                                            10

SEQ ID NO: 330         moltype = AA  length = 9
FEATURE                Location/Qualifiers
REGION                 1..9
                       note = SEQ ID NO: 330 - anti-BCMA-PP02-D3 CDRH2
source                 1..9
                       mol_type = protein
                       organism = synthetic construct
SEQUENCE: 330
AIGQGGNTV                                                             9

SEQ ID NO: 331         moltype = AA  length = 10
FEATURE                Location/Qualifiers
REGION                 1..10
                       note = SEQ ID NO: 331 - anti-BCMA-PP02-E6 CDRH2
source                 1..10
                       mol_type = protein
                       organism = synthetic construct
SEQUENCE: 331
TISQNGGQTK                                                            10

SEQ ID NO: 332         moltype = AA  length = 10
FEATURE                Location/Qualifiers
REGION                 1..10
                       note = SEQ ID NO: 332 - anti-BCMA-PP02-F1 CDRH2
source                 1..10
                       mol_type = protein
                       organism = synthetic construct
SEQUENCE: 332
ALSLSGDVTS                                                            10

SEQ ID NO: 333         moltype = AA  length = 10
FEATURE                Location/Qualifiers
REGION                 1..10
                       note = SEQ ID NO: 333 - anti-BCMA-PP03-C4 CDRH2
source                 1..10
                       mol_type = protein
                       organism = synthetic construct
SEQUENCE: 333
AISGFGGDTL                                                            10

SEQ ID NO: 334         moltype = AA  length = 10
FEATURE                Location/Qualifiers
REGION                 1..10
                       note = SEQ ID NO: 334 - anti-BCMA-PP03-E4 CDRH2
source                 1..10
                       mol_type = protein
                       organism = synthetic construct
SEQUENCE: 334
AISEDGGRTS                                                            10

SEQ ID NO: 335         moltype = AA  length = 10
FEATURE                Location/Qualifiers
REGION                 1..10
                       note = SEQ ID NO: 335 - anti-BCMA-D3-MP03-G7 CDRH2
source                 1..10
                       mol_type = protein
                       organism = synthetic construct
SEQUENCE: 335
IIGQRGHTTE                                                            10

SEQ ID NO: 336         moltype = AA  length = 10
FEATURE                Location/Qualifiers
REGION                 1..10
                       note = SEQ ID NO: 336 - anti-BCMA-D3-MP04-A2 CDRH2
source                 1..10
                       mol_type = protein
                       organism = synthetic construct
SEQUENCE: 336
AIGQQGGNTV                                                            10
```

```
SEQ ID NO: 337          moltype = AA  length = 9
FEATURE                 Location/Qualifiers
REGION                  1..9
                        note = SEQ ID NO: 337 - anti-BCMA-D3-MP04-B11a CDRH2
source                  1..9
                        mol_type = protein
                        organism = synthetic construct
SEQUENCE: 337
AIGQVDGEV                                                                   9

SEQ ID NO: 338          moltype = AA  length = 9
FEATURE                 Location/Qualifiers
REGION                  1..9
                        note = SEQ ID NO: 338 - anti-BCMA-D3-MP04-B11b CDRH2
source                  1..9
                        mol_type = protein
                        organism = synthetic construct
SEQUENCE: 338
AIGQVDAEV                                                                   9

SEQ ID NO: 339          moltype = AA  length = 9
FEATURE                 Location/Qualifiers
REGION                  1..9
                        note = SEQ ID NO: 339 - anti-BCMA-D3-MP04-B11c CDRH2
source                  1..9
                        mol_type = protein
                        organism = synthetic construct
SEQUENCE: 339
AIGQVEGEV                                                                   9

SEQ ID NO: 340          moltype = AA  length = 9
FEATURE                 Location/Qualifiers
REGION                  1..9
                        note = SEQ ID NO: 340 - anti-BCMA-D3-MP04-B11d CDRH2
source                  1..9
                        mol_type = protein
                        organism = synthetic construct
SEQUENCE: 340
AIGQVAAEV                                                                   9

SEQ ID NO: 341          moltype = AA  length = 10
FEATURE                 Location/Qualifiers
REGION                  1..10
                        note = SEQ ID NO: 341 - anti-BCMA-D3-MP04-C2 CDRH2
source                  1..10
                        mol_type = protein
                        organism = synthetic construct
SEQUENCE: 341
AIGQFGGNTV                                                                  10

SEQ ID NO: 342          moltype = AA  length = 10
FEATURE                 Location/Qualifiers
REGION                  1..10
                        note = SEQ ID NO: 342 - antii-BCMA-D3-MP04-C8a CDRH2
source                  1..10
                        mol_type = protein
                        organism = synthetic construct
SEQUENCE: 342
AIGQMGFGTL                                                                  10

SEQ ID NO: 343          moltype = AA  length = 10
FEATURE                 Location/Qualifiers
REGION                  1..10
                        note = SEQ ID NO: 343 - anti-BCMA-D3-MP04-C8b CDRH2
source                  1..10
                        mol_type = protein
                        organism = synthetic construct
SEQUENCE: 343
AIGQIGFGTL                                                                  10

SEQ ID NO: 344          moltype = AA  length = 10
FEATURE                 Location/Qualifiers
REGION                  1..10
                        note = SEQ ID NO: 344 - anti-BCMA-D3-MP04-D4 CDRH2
source                  1..10
                        mol_type = protein
                        organism = synthetic construct
SEQUENCE: 344
AIGQVGGNTV                                                                  10
```

```
SEQ ID NO: 345          moltype = AA  length = 10
FEATURE                 Location/Qualifiers
REGION                  1..10
                        note = SEQ ID NO: 345 - anti-BCMA-D3-MP04-E11 CDRH2
source                  1..10
                        mol_type = protein
                        organism = synthetic construct
SEQUENCE: 345
AIGQLGGNTV                                                          10

SEQ ID NO: 346          moltype = AA  length = 9
FEATURE                 Location/Qualifiers
REGION                  1..9
                        note = SEQ ID NO: 346 - anti-BCMA-D3-MP04-F3 CDRH2
source                  1..9
                        mol_type = protein
                        organism = synthetic construct
SEQUENCE: 346
AIGQVGNTV                                                           9

SEQ ID NO: 347          moltype = AA  length = 9
FEATURE                 Location/Qualifiers
REGION                  1..9
                        note = SEQ ID NO: 347 - anti-BCMA-D3-MP04-G7 CDRH2
source                  1..9
                        mol_type = protein
                        organism = synthetic construct
SEQUENCE: 347
AIGQRDGTV                                                           9

SEQ ID NO: 348          moltype = AA  length = 9
FEATURE                 Location/Qualifiers
REGION                  1..9
                        note = SEQ ID NO: 348 - anti-BCMA-D3-MP05-A9 CDRH2
source                  1..9
                        mol_type = protein
                        organism = synthetic construct
SEQUENCE: 348
AIGQGGNTV                                                           9

SEQ ID NO: 349          moltype = AA  length = 9
FEATURE                 Location/Qualifiers
REGION                  1..9
                        note = SEQ ID NO: 349 - anti-BCMA-D3-MP05-C1a CDRH2
source                  1..9
                        mol_type = protein
                        organism = synthetic construct
SEQUENCE: 349
AIGQGGNTV                                                           9

SEQ ID NO: 350          moltype = AA  length = 9
FEATURE                 Location/Qualifiers
REGION                  1..9
                        note = SEQ ID NO: 350 - antii-BCMA-D3-MP05-C1b CDRH2
source                  1..9
                        mol_type = protein
                        organism = synthetic construct
SEQUENCE: 350
AIGQGGNTV                                                           9

SEQ ID NO: 351          moltype = AA  length = 9
FEATURE                 Location/Qualifiers
REGION                  1..9
                        note = SEQ ID NO: 351 - anti-BCMA-D3-MP05-F4 CDRH2
source                  1..9
                        mol_type = protein
                        organism = synthetic construct
SEQUENCE: 351
AIGQGGNTV                                                           9

SEQ ID NO: 352          moltype = AA  length = 10
FEATURE                 Location/Qualifiers
REGION                  1..10
                        note = SEQ ID NO: 352 - anti-BCMA-E6-PP02-A3 CDRH2
source                  1..10
                        mol_type = protein
                        organism = synthetic construct
SEQUENCE: 352
```

```
TISSQNDITK                                                    10

SEQ ID NO: 353          moltype = AA  length = 10
FEATURE                 Location/Qualifiers
REGION                  1..10
                        note = SEQ ID NO: 353 - anti-BCMA-E6-PP02-B1 CDRH2
source                  1..10
                        mol_type = protein
                        organism = synthetic construct
SEQUENCE: 353
TVSQAGYDTK                                                    10

SEQ ID NO: 354          moltype = AA  length = 10
FEATURE                 Location/Qualifiers
REGION                  1..10
                        note = SEQ ID NO: 354 - anti-BCMA-E6-PP02-B4 CDRH2
source                  1..10
                        mol_type = protein
                        organism = synthetic construct
SEQUENCE: 354
TISQPGFDAK                                                    10

SEQ ID NO: 355          moltype = AA  length = 10
FEATURE                 Location/Qualifiers
REGION                  1..10
                        note = SEQ ID NO: 355 - anti-BCMA-E6-PP02-C7 CDRH2
source                  1..10
                        mol_type = protein
                        organism = synthetic construct
SEQUENCE: 355
TISQSGLVPK                                                    10

SEQ ID NO: 356          moltype = AA  length = 10
FEATURE                 Location/Qualifiers
REGION                  1..10
                        note = SEQ ID NO: 356 - anti-BCMA-E6-PP02-D2 CDRH2
source                  1..10
                        mol_type = protein
                        organism = synthetic construct
SEQUENCE: 356
TISQQNEQTK                                                    10

SEQ ID NO: 357          moltype = AA  length = 10
FEATURE                 Location/Qualifiers
REGION                  1..10
                        note = SEQ ID NO: 357 - anti-BCMA-E6-PP02-E6 CDRH2
source                  1..10
                        mol_type = protein
                        organism = synthetic construct
SEQUENCE: 357
TISQAGRDFK                                                    10

SEQ ID NO: 358          moltype = AA  length = 10
FEATURE                 Location/Qualifiers
REGION                  1..10
                        note = SEQ ID NO: 358 - anti-BCMA-E6-PP02-F7 CDRH2
source                  1..10
                        mol_type = protein
                        organism = synthetic construct
SEQUENCE: 358
TIGQRGFQTK                                                    10

SEQ ID NO: 359          moltype = AA  length = 11
FEATURE                 Location/Qualifiers
REGION                  1..11
                        note = SEQ ID NO: 359 - anti-BCMA-E6-PP02-G2 CDRH2
source                  1..11
                        mol_type = protein
                        organism = synthetic construct
SEQUENCE: 359
TISQSVGQVV K                                                  11

SEQ ID NO: 360          moltype = AA  length = 10
FEATURE                 Location/Qualifiers
REGION                  1..10
                        note = SEQ ID NO: 360 - anti-BCMA-E6-PP02-G6 CDRH2
source                  1..10
                        mol_type = protein
                        organism = synthetic construct
```

```
SEQUENCE: 360
TIAQRGGQTK                                                         10

SEQ ID NO: 361         moltype = AA  length = 10
FEATURE                Location/Qualifiers
REGION                 1..10
                       note = SEQ ID NO: 361 - anti-BCMA-E6-PP02-G7 CDRH2
source                 1..10
                       mol_type = protein
                       organism = synthetic construct
SEQUENCE: 361
TISQQWDVTK                                                         10

SEQ ID NO: 362         moltype = AA  length = 10
FEATURE                Location/Qualifiers
REGION                 1..10
                       note = SEQ ID NO: 362 - anti-CD38-UCP03-B3 CDRH2
source                 1..10
                       mol_type = protein
                       organism = synthetic construct
SEQUENCE: 362
RIIPTGANAN                                                         10

SEQ ID NO: 363         moltype = AA  length = 10
FEATURE                Location/Qualifiers
REGION                 1..10
                       note = SEQ ID NO: 363 - anti-CD38-UCP01-E2 CDRH2
source                 1..10
                       mol_type = protein
                       organism = synthetic construct
SEQUENCE: 363
RIIPVFGSAH                                                         10

SEQ ID NO: 364         moltype = AA  length = 10
FEATURE                Location/Qualifiers
REGION                 1..10
                       note = SEQ ID NO: 364 - anti-CD38-B3-PP11-A2 CDRH2
source                 1..10
                       mol_type = protein
                       organism = synthetic construct
SEQUENCE: 364
RIIPTGANAN                                                         10

SEQ ID NO: 365         moltype = AA  length = 10
FEATURE                Location/Qualifiers
REGION                 1..10
                       note = SEQ ID NO: 365 - anti-CD38-B3-PP11-C11 CDRH2
source                 1..10
                       mol_type = protein
                       organism = synthetic construct
SEQUENCE: 365
RIIPTGANAN                                                         10

SEQ ID NO: 366         moltype = AA  length = 10
FEATURE                Location/Qualifiers
REGION                 1..10
                       note = SEQ ID NO: 366 - anti-CD38-B3-PP11-D1a CDRH2
source                 1..10
                       mol_type = protein
                       organism = synthetic construct
SEQUENCE: 366
RIIPTGANAN                                                         10

SEQ ID NO: 367         moltype = AA  length = 10
FEATURE                Location/Qualifiers
REGION                 1..10
                       note = SEQ ID NO: 367 - anti-CD38-B3-PP11-D1b CDRH2
source                 1..10
                       mol_type = protein
                       organism = synthetic construct
SEQUENCE: 367
RIIPTGANAN                                                         10

SEQ ID NO: 368         moltype = AA  length = 10
FEATURE                Location/Qualifiers
REGION                 1..10
                       note = SEQ ID NO: 368 - anti-CD38-B3-PP11-D11a CDRH2
source                 1..10
                       mol_type = protein
```

```
                         organism = synthetic construct
SEQUENCE: 368
RIIPTGANAN                                                                    10

SEQ ID NO: 369           moltype = AA  length = 10
FEATURE                  Location/Qualifiers
REGION                   1..10
                         note = SEQ ID NO: 369 - anti-CD38-B3-PP11-E1 CDRH2
source                   1..10
                         mol_type = protein
                         organism = synthetic construct
SEQUENCE: 369
RIIPTGANAN                                                                    10

SEQ ID NO: 370           moltype = AA  length = 10
FEATURE                  Location/Qualifiers
REGION                   1..10
                         note = SEQ ID NO: 370 - anti-CD38-B3-PP11-E11 CDRH2
source                   1..10
                         mol_type = protein
                         organism = synthetic construct
SEQUENCE: 370
RIIPTGANAN                                                                    10

SEQ ID NO: 371           moltype = AA  length = 10
FEATURE                  Location/Qualifiers
REGION                   1..10
                         note = SEQ ID NO: 371 - anti-CD38-B3-PP11-H1a CDRH2
source                   1..10
                         mol_type = protein
                         organism = synthetic construct
SEQUENCE: 371
RIIPTGANAN                                                                    10

SEQ ID NO: 372           moltype = AA  length = 10
FEATURE                  Location/Qualifiers
REGION                   1..10
                         note = SEQ ID NO: 372 - anti-CD38-B3-PP11-H10 CDRH2
source                   1..10
                         mol_type = protein
                         organism = synthetic construct
SEQUENCE: 372
RIIPTGANAN                                                                    10

SEQ ID NO: 373           moltype = AA  length = 10
FEATURE                  Location/Qualifiers
REGION                   1..10
                         note = SEQ ID NO: 373 - anti-CD38-E2-UCP01-A10 CDRH2
source                   1..10
                         mol_type = protein
                         organism = synthetic construct
SEQUENCE: 373
RIIPVFGSAH                                                                    10

SEQ ID NO: 374           moltype = AA  length = 10
FEATURE                  Location/Qualifiers
REGION                   1..10
                         note = SEQ ID NO: 374 - anti-CD38-E2-UCP02-A5 CDRH2
source                   1..10
                         mol_type = protein
                         organism = synthetic construct
SEQUENCE: 374
RIIPDLGAAH                                                                    10

SEQ ID NO: 375           moltype = AA  length = 10
FEATURE                  Location/Qualifiers
REGION                   1..10
                         note = SEQ ID NO: 375 - anti-CD38-E2-UCP02-D6 CDRH2
source                   1..10
                         mol_type = protein
                         organism = synthetic construct
SEQUENCE: 375
RIIPRLDAEH                                                                    10

SEQ ID NO: 376           moltype = AA  length = 10
FEATURE                  Location/Qualifiers
REGION                   1..10
                         note = SEQ ID NO: 376 - anti-CD38-E2-UCP02-E7 CDRH2
source                   1..10
```

```
                        mol_type = protein
                        organism = synthetic construct
SEQUENCE: 376
RIIPALAATH                                                      10

SEQ ID NO: 377          moltype = AA  length = 10
FEATURE                 Location/Qualifiers
REGION                  1..10
                        note = SEQ ID NO: 377 - anti-CD38-E2-UCP02-F3 CDRH2
source                  1..10
                        mol_type = protein
                        organism = synthetic construct
SEQUENCE: 377
RIIPVLDAAH                                                      10

SEQ ID NO: 378          moltype = AA  length = 10
FEATURE                 Location/Qualifiers
REGION                  1..10
                        note = SEQ ID NO: 378 - anti-CD38-E2-UCP02-F8 CDRH2
source                  1..10
                        mol_type = protein
                        organism = synthetic construct
SEQUENCE: 378
RIIPSLDAGH                                                      10

SEQ ID NO: 379          moltype = AA  length = 10
FEATURE                 Location/Qualifiers
REGION                  1..10
                        note = SEQ ID NO: 379 - anti-CD38-E2-UCP02-G8 CDRH2
source                  1..10
                        mol_type = protein
                        organism = synthetic construct
SEQUENCE: 379
RIIPALGGVH                                                      10

SEQ ID NO: 380          moltype = AA  length = 11
FEATURE                 Location/Qualifiers
REGION                  1..11
                        note = SEQ ID NO: 380 - anti-CD3-UCP02-A3 CDRH3
source                  1..11
                        mol_type = protein
                        organism = synthetic construct
SEQUENCE: 380
ARVHDVLDDV E                                                    11

SEQ ID NO: 381          moltype = AA  length = 11
FEATURE                 Location/Qualifiers
REGION                  1..11
                        note = SEQ ID NO: 381 - anti-CD3-UCP02-B2 CDRH3
source                  1..11
                        mol_type = protein
                        organism = synthetic construct
SEQUENCE: 381
ARGDPTSAFD V                                                    11

SEQ ID NO: 382          moltype = AA  length = 12
FEATURE                 Location/Qualifiers
REGION                  1..12
                        note = SEQ ID NO: 382 - anti-CD3-UCP02-D2 CDRH3
source                  1..12
                        mol_type = protein
                        organism = synthetic construct
SEQUENCE: 382
ARVTARYYYF DN                                                   12

SEQ ID NO: 383          moltype = AA  length = 12
FEATURE                 Location/Qualifiers
REGION                  1..12
                        note = SEQ ID NO: 383 - anti-CD3-UCP02-F2 CDRH3
source                  1..12
                        mol_type = protein
                        organism = synthetic construct
SEQUENCE: 383
ARDPYYLGPF DI                                                   12

SEQ ID NO: 384          moltype = AA  length = 11
FEATURE                 Location/Qualifiers
REGION                  1..11
                        note = SEQ ID NO: 384 - anti-CD3-UCP02-H2 CDRH3
```

```
source                  1..11
                        mol_type = protein
                        organism = synthetic construct
SEQUENCE: 384
ARASYAGPFD Y                                                    11

SEQ ID NO: 385          moltype = AA  length = 15
FEATURE                 Location/Qualifiers
REGION                  1..15
                        note = SEQ ID NO: 385 - anti-CD3-UCP03-A3 CDRH3
source                  1..15
                        mol_type = protein
                        organism = synthetic construct
SEQUENCE: 385
ARGGPGYSTF YEFDN                                                15

SEQ ID NO: 386          moltype = AA  length = 12
FEATURE                 Location/Qualifiers
REGION                  1..12
                        note = SEQ ID NO: 386 - anti-CD3-UCP03-A4 CDRH3
source                  1..12
                        mol_type = protein
                        organism = synthetic construct
SEQUENCE: 386
ARVSWSYGPF DI                                                   12

SEQ ID NO: 387          moltype = AA  length = 9
FEATURE                 Location/Qualifiers
REGION                  1..9
                        note = SEQ ID NO: 387 - anti-CD3-UCP03-B1 CDRH3
source                  1..9
                        mol_type = protein
                        organism = synthetic construct
SEQUENCE: 387
ARGGTRFDI                                                       9

SEQ ID NO: 388          moltype = AA  length = 17
FEATURE                 Location/Qualifiers
REGION                  1..17
                        note = SEQ ID NO: 388 - anti-CD3-UCP03-C1 CDRH3
source                  1..17
                        mol_type = protein
                        organism = synthetic construct
SEQUENCE: 388
ARGQYDDLDK SGYEFDH                                              17

SEQ ID NO: 389          moltype = AA  length = 10
FEATURE                 Location/Qualifiers
REGION                  1..10
                        note = SEQ ID NO: 389 - anti-CD3-UCP03-C3 CDRH3
source                  1..10
                        mol_type = protein
                        organism = synthetic construct
SEQUENCE: 389
ARDRYSVLDI                                                      10

SEQ ID NO: 390          moltype = AA  length = 14
FEATURE                 Location/Qualifiers
REGION                  1..14
                        note = SEQ ID NO: 390 - anti-CD3-UCP03-C5 CDRH3
source                  1..14
                        mol_type = protein
                        organism = synthetic construct
SEQUENCE: 390
ARWGISLGEP YFDY                                                 14

SEQ ID NO: 391          moltype = AA  length = 15
FEATURE                 Location/Qualifiers
REGION                  1..15
                        note = SEQ ID NO: 391 - anti-CD3-UCP03-E1 CDRH3
source                  1..15
                        mol_type = protein
                        organism = synthetic construct
SEQUENCE: 391
ARAGYISGDS AAFDV                                                15

SEQ ID NO: 392          moltype = AA  length = 14
FEATURE                 Location/Qualifiers
REGION                  1..14
```

```
                        note = SEQ ID NO: 392 - anti-CD3-UCP03-E2 CDRH3
source                  1..14
                        mol_type = protein
                        organism = synthetic construct
SEQUENCE: 392
ARGVIDGSYL DFAY                                                           14

SEQ ID NO: 393          moltype = AA  length = 12
FEATURE                 Location/Qualifiers
REGION                  1..12
                        note = SEQ ID NO: 393 - anti-CD3-UCP03-E4 CDRH3
source                  1..12
                        mol_type = protein
                        organism = synthetic construct
SEQUENCE: 393
AREPWHTGPF DY                                                             12

SEQ ID NO: 394          moltype = AA  length = 14
FEATURE                 Location/Qualifiers
REGION                  1..14
                        note = SEQ ID NO: 394 - anti-CD3-UCP03-F1 CDRH3
source                  1..14
                        mol_type = protein
                        organism = synthetic construct
SEQUENCE: 394
ARGPVPGGDH AFDY                                                           14

SEQ ID NO: 395          moltype = AA  length = 11
FEATURE                 Location/Qualifiers
REGION                  1..11
                        note = SEQ ID NO: 395 - anti-CD3-UCP03-F2 CDRH3
source                  1..11
                        mol_type = protein
                        organism = synthetic construct
SEQUENCE: 395
ARGHPVHAFD F                                                              11

SEQ ID NO: 396          moltype = AA  length = 13
FEATURE                 Location/Qualifiers
REGION                  1..13
                        note = SEQ ID NO: 396 - anti-CD3-UCP03-F4 CDRH3
source                  1..13
                        mol_type = protein
                        organism = synthetic construct
SEQUENCE: 396
ARIPYRPSVY KDV                                                            13

SEQ ID NO: 397          moltype = AA  length = 14
FEATURE                 Location/Qualifiers
REGION                  1..14
                        note = SEQ ID NO: 397 - anti-CD3-UCP03-G2 CDRH3
source                  1..14
                        mol_type = protein
                        organism = synthetic construct
SEQUENCE: 397
ARDRYSTYSG GMDY                                                           14

SEQ ID NO: 398          moltype = AA  length = 10
FEATURE                 Location/Qualifiers
REGION                  1..10
                        note = SEQ ID NO: 398 - anti-CD3-UCP03-G3 CDRH3
source                  1..10
                        mol_type = protein
                        organism = synthetic construct
SEQUENCE: 398
ARDRFGAFDY                                                                10

SEQ ID NO: 399          moltype = AA  length = 9
FEATURE                 Location/Qualifiers
REGION                  1..9
                        note = SEQ ID NO: 399 - anti-CD3-UCP03-G4 CDRH3
source                  1..9
                        mol_type = protein
                        organism = synthetic construct
SEQUENCE: 399
VLLGDFFDV                                                                 9

SEQ ID NO: 400          moltype = AA  length = 10
FEATURE                 Location/Qualifiers
```

```
REGION                  1..10
                        note = SEQ ID NO: 400 - anti-CD3-UCP03-H2 CDRH3
source                  1..10
                        mol_type = protein
                        organism = synthetic construct
SEQUENCE: 400
ARSQYGYFDY                                                          10

SEQ ID NO: 401          moltype = AA  length = 9
FEATURE                 Location/Qualifiers
REGION                  1..9
                        note = SEQ ID NO: 401 - anti-CD3-UCP03-H3 CDRH3
source                  1..9
                        mol_type = protein
                        organism = synthetic construct
SEQUENCE: 401
ARGYQLFDI                                                           9

SEQ ID NO: 402          moltype = AA  length = 10
FEATURE                 Location/Qualifiers
REGION                  1..10
                        note = SEQ ID NO: 402 - anti-CD3-UCP05-A1 CDRH3
source                  1..10
                        mol_type = protein
                        organism = synthetic construct
SEQUENCE: 402
ARASSYGYDP                                                          10

SEQ ID NO: 403          moltype = AA  length = 12
FEATURE                 Location/Qualifiers
REGION                  1..12
                        note = SEQ ID NO: 403 - anti-CD3-UCP05-A2 CDRH3
source                  1..12
                        mol_type = protein
                        organism = synthetic construct
SEQUENCE: 403
ARPGDLGGGF DI                                                       12

SEQ ID NO: 404          moltype = AA  length = 15
FEATURE                 Location/Qualifiers
REGION                  1..15
                        note = SEQ ID NO: 404 - anti-CD3-UCP05-C1 CDRH3
source                  1..15
                        mol_type = protein
                        organism = synthetic construct
SEQUENCE: 404
ARGKGGSVAG WKFDV                                                    15

SEQ ID NO: 405          moltype = AA  length = 15
FEATURE                 Location/Qualifiers
REGION                  1..15
                        note = SEQ ID NO: 405 - anti-CD3-UCP05-D1 CDRH3
source                  1..15
                        mol_type = protein
                        organism = synthetic construct
SEQUENCE: 405
ARHGRLSHDD YAFDI                                                    15

SEQ ID NO: 406          moltype = AA  length = 11
FEATURE                 Location/Qualifiers
REGION                  1..11
                        note = SEQ ID NO: 406 - anti-CD3-UCP05-D2 CDRH3
source                  1..11
                        mol_type = protein
                        organism = synthetic construct
SEQUENCE: 406
ARLRGGSGMD V                                                        11

SEQ ID NO: 407          moltype = AA  length = 12
FEATURE                 Location/Qualifiers
REGION                  1..12
                        note = SEQ ID NO: 407 - anti-CD3-UCP05-F1 CDRH3
source                  1..12
                        mol_type = protein
                        organism = synthetic construct
SEQUENCE: 407
ARAGPSGGGF DY                                                       12

SEQ ID NO: 408          moltype = AA  length = 21
```

-continued

```
FEATURE                Location/Qualifiers
REGION                 1..21
                       note = SEQ ID NO: 408 - anti-CD3-UCP05-G2 CDRH3
source                 1..21
                       mol_type = protein
                       organism = synthetic construct
SEQUENCE: 408
ARSPVSLYYG KYYVYYGAFD V                                              21

SEQ ID NO: 409         moltype = AA  length = 10
FEATURE                Location/Qualifiers
REGION                 1..10
                       note = SEQ ID NO: 409 - anti-CD3-UCP05-H1 CDRH3
source                 1..10
                       mol_type = protein
                       organism = synthetic construct
SEQUENCE: 409
ARSSPYGFDY                                                           10

SEQ ID NO: 410         moltype = AA  length = 10
FEATURE                Location/Qualifiers
REGION                 1..10
                       note = SEQ ID NO: 410 - anti-CD3-UCP05-H2 CDRH3
source                 1..10
                       mol_type = protein
                       organism = synthetic construct
SEQUENCE: 410
ARKISSARDY                                                           10

SEQ ID NO: 411         moltype = AA  length = 18
FEATURE                Location/Qualifiers
REGION                 1..18
                       note = SEQ ID NO: 411 - anti-CD3-UCP06-A1 CDRH3
source                 1..18
                       mol_type = protein
                       organism = synthetic construct
SEQUENCE: 411
ARGSYVDSSY YYYDGFDV                                                  18

SEQ ID NO: 412         moltype = AA  length = 11
FEATURE                Location/Qualifiers
REGION                 1..11
                       note = SEQ ID NO: 412 - anti-CD3-UCP06-C1 CDRH3
source                 1..11
                       mol_type = protein
                       organism = synthetic construct
SEQUENCE: 412
ARYGYSLYMD I                                                         11

SEQ ID NO: 413         moltype = AA  length = 14
FEATURE                Location/Qualifiers
REGION                 1..14
                       note = SEQ ID NO: 413 - anti-CD3-UCP07-A1 CDRH3
source                 1..14
                       mol_type = protein
                       organism = synthetic construct
SEQUENCE: 413
AREPSYYRDG AADY                                                      14

SEQ ID NO: 414         moltype = AA  length = 11
FEATURE                Location/Qualifiers
REGION                 1..11
                       note = SEQ ID NO: 414 - anti-CD3-UCP07-A3 CDRH3
source                 1..11
                       mol_type = protein
                       organism = synthetic construct
SEQUENCE: 414
ARSGGSVPFD Y                                                         11

SEQ ID NO: 415         moltype = AA  length = 10
FEATURE                Location/Qualifiers
REGION                 1..10
                       note = SEQ ID NO: 415 - anti-CD3-UCP07-A4 CDRH3
source                 1..10
                       mol_type = protein
                       organism = synthetic construct
SEQUENCE: 415
ARSSSSAFDV                                                           10
```

```
SEQ ID NO: 416          moltype = AA  length = 13
FEATURE                 Location/Qualifiers
REGION                  1..13
                        note = SEQ ID NO: 416 - anti-CD3-UCP07-B2 CDRH3
source                  1..13
                        mol_type = protein
                        organism = synthetic construct
SEQUENCE: 416
ARGRSRGVSE FDY                                                      13

SEQ ID NO: 417          moltype = AA  length = 12
FEATURE                 Location/Qualifiers
REGION                  1..12
                        note = SEQ ID NO: 417 - anti-CD3-UCP07-B3 CDRH3
source                  1..12
                        mol_type = protein
                        organism = synthetic construct
SEQUENCE: 417
ARGGRLSSYF DP                                                       12

SEQ ID NO: 418          moltype = AA  length = 21
FEATURE                 Location/Qualifiers
REGION                  1..21
                        note = SEQ ID NO: 418 - anti-CD3-UCP07-B4 CDRH3
source                  1..21
                        mol_type = protein
                        organism = synthetic construct
SEQUENCE: 418
ARDTSYRVRG YGYSSWSYFD I                                             21

SEQ ID NO: 419          moltype = AA  length = 12
FEATURE                 Location/Qualifiers
REGION                  1..12
                        note = SEQ ID NO: 419 - anti-CD3-UCP07-C3 CDRH3
source                  1..12
                        mol_type = protein
                        organism = synthetic construct
SEQUENCE: 419
AREYHYVGAF DI                                                       12

SEQ ID NO: 420          moltype = AA  length = 12
FEATURE                 Location/Qualifiers
REGION                  1..12
                        note = SEQ ID NO: 420 - anti-CD3-UCP07-D1 CDRH3
source                  1..12
                        mol_type = protein
                        organism = synthetic construct
SEQUENCE: 420
ARASPYGGGF DY                                                       12

SEQ ID NO: 421          moltype = AA  length = 14
FEATURE                 Location/Qualifiers
REGION                  1..14
                        note = SEQ ID NO: 421 - anti-CD3-UCP07-D2 CDRH3
source                  1..14
                        mol_type = protein
                        organism = synthetic construct
SEQUENCE: 421
ARSSSARTDV PFDV                                                     14

SEQ ID NO: 422          moltype = AA  length = 12
FEATURE                 Location/Qualifiers
REGION                  1..12
                        note = SEQ ID NO: 422 - anti-CD3-UCP07-E1 CDRH3
source                  1..12
                        mol_type = protein
                        organism = synthetic construct
SEQUENCE: 422
ARVGSGGKAF DV                                                       12

SEQ ID NO: 423          moltype = AA  length = 11
FEATURE                 Location/Qualifiers
REGION                  1..11
                        note = SEQ ID NO: 423 - anti-CD3-UCP07-E2 CDRH3
source                  1..11
                        mol_type = protein
                        organism = synthetic construct
SEQUENCE: 423
ARASYLGGFA Y                                                        11
```

```
SEQ ID NO: 424          moltype = AA  length = 15
FEATURE                 Location/Qualifiers
REGION                  1..15
                        note = SEQ ID NO: 424 - anti-CD3-UCP07-F2 CDRH3
source                  1..15
                        mol_type = protein
                        organism = synthetic construct
SEQUENCE: 424
ARGRYYGDYS WKFDY                                                   15

SEQ ID NO: 425          moltype = AA  length = 14
FEATURE                 Location/Qualifiers
REGION                  1..14
                        note = SEQ ID NO: 425 - anti-CD3-UCP07-F3 CDRH3
source                  1..14
                        mol_type = protein
                        organism = synthetic construct
SEQUENCE: 425
ARAASYGLDY ALDI                                                    14

SEQ ID NO: 426          moltype = AA  length = 11
FEATURE                 Location/Qualifiers
REGION                  1..11
                        note = SEQ ID NO: 426 - anti-CD3-UCP07-H1 CDRH3
source                  1..11
                        mol_type = protein
                        organism = synthetic construct
SEQUENCE: 426
ARSHRYSAFD Y                                                       11

SEQ ID NO: 427          moltype = AA  length = 15
FEATURE                 Location/Qualifiers
REGION                  1..15
                        note = SEQ ID NO: 427 - anti-CD3-UCP08-B1 CDRH3
source                  1..15
                        mol_type = protein
                        organism = synthetic construct
SEQUENCE: 427
ARGPYGRYPD YLFDY                                                   15

SEQ ID NO: 428          moltype = AA  length = 11
FEATURE                 Location/Qualifiers
REGION                  1..11
                        note = SEQ ID NO: 428 - anti-CD3-C1-UCP01-B6 CDRH3
source                  1..11
                        mol_type = protein
                        organism = synthetic construct
SEQUENCE: 428
ARYGYSLYMD I                                                       11

SEQ ID NO: 429          moltype = AA  length = 11
FEATURE                 Location/Qualifiers
REGION                  1..11
                        note = SEQ ID NO: 429 - anti-CD3-C1-UCP01-B9 CDRH3
source                  1..11
                        mol_type = protein
                        organism = synthetic construct
SEQUENCE: 429
ARYGYSLYMD I                                                       11

SEQ ID NO: 430          moltype = AA  length = 11
FEATURE                 Location/Qualifiers
REGION                  1..11
                        note = SEQ ID NO: 430 - anti-CD3-C1-UCP01-C11 CDRH3
source                  1..11
                        mol_type = protein
                        organism = synthetic construct
SEQUENCE: 430
ARYGYSLYMD I                                                       11

SEQ ID NO: 431          moltype = AA  length = 11
FEATURE                 Location/Qualifiers
REGION                  1..11
                        note = SEQ ID NO: 431 - anti-CD3-C1-UCP01-D1 CDRH3
source                  1..11
                        mol_type = protein
                        organism = synthetic construct
SEQUENCE: 431
```

```
ARYGYSLYMD I                                                    11

SEQ ID NO: 432          moltype = AA  length = 11
FEATURE                 Location/Qualifiers
REGION                  1..11
                        note = SEQ ID NO: 432 - anti-CD3-C1-UCP01-D4 CDRH3
source                  1..11
                        mol_type = protein
                        organism = synthetic construct
SEQUENCE: 432
ARYGYSLYMD I                                                    11

SEQ ID NO: 433          moltype = AA  length = 11
FEATURE                 Location/Qualifiers
REGION                  1..11
                        note = SEQ ID NO: 433 - anti-CD3-C1-UCP01-D6 CDRH3
source                  1..11
                        mol_type = protein
                        organism = synthetic construct
SEQUENCE: 433
ARYGYSLYMD I                                                    11

SEQ ID NO: 434          moltype = AA  length = 11
FEATURE                 Location/Qualifiers
REGION                  1..11
                        note = SEQ ID NO: 434 - anti-CD3-C1-UCP01-E6 CDRH3
source                  1..11
                        mol_type = protein
                        organism = synthetic construct
SEQUENCE: 434
ARYGYSLYMD I                                                    11

SEQ ID NO: 435          moltype = AA  length = 11
FEATURE                 Location/Qualifiers
REGION                  1..11
                        note = SEQ ID NO: 435 - anti-CD3-C1-UCP01-E7 CDRH3
source                  1..11
                        mol_type = protein
                        organism = synthetic construct
SEQUENCE: 435
ARYGYSLYMD I                                                    11

SEQ ID NO: 436          moltype = AA  length = 11
FEATURE                 Location/Qualifiers
REGION                  1..11
                        note = SEQ ID NO: 436 - anti-CD3-C1-UCP01-E10 CDRH3
source                  1..11
                        mol_type = protein
                        organism = synthetic construct
SEQUENCE: 436
ARYGYSLYMD I                                                    11

SEQ ID NO: 437          moltype = AA  length = 11
FEATURE                 Location/Qualifiers
REGION                  1..11
                        note = SEQ ID NO: 437 - anti-CD3-C1-UCP01-E11 CDRH3
source                  1..11
                        mol_type = protein
                        organism = synthetic construct
SEQUENCE: 437
ARYGYSLYMD I                                                    11

SEQ ID NO: 438          moltype = AA  length = 11
FEATURE                 Location/Qualifiers
REGION                  1..11
                        note = SEQ ID NO: 438 - anti-CD3-C1-UCP01-E12 CDRH3
source                  1..11
                        mol_type = protein
                        organism = synthetic construct
SEQUENCE: 438
ARYGYSLYMD I                                                    11

SEQ ID NO: 439          moltype = AA  length = 11
FEATURE                 Location/Qualifiers
REGION                  1..11
                        note = SEQ ID NO: 439 - anti-CD3-C1-UCP01-F1 CDRH3
source                  1..11
                        mol_type = protein
                        organism = synthetic construct
```

```
SEQUENCE: 439
ARYGYSLYMD I                                                      11

SEQ ID NO: 440          moltype = AA  length = 11
FEATURE                 Location/Qualifiers
REGION                  1..11
                        note = SEQ ID NO: 440 - anti-CD3-C1-UCP01-F10 CDRH3
source                  1..11
                        mol_type = protein
                        organism = synthetic construct
SEQUENCE: 440
ARYGYSLYMD I                                                      11

SEQ ID NO: 441          moltype = AA  length = 11
FEATURE                 Location/Qualifiers
REGION                  1..11
                        note = SEQ ID NO: 441 - anti-CD3-C1-UCP01-F12 CDRH3
source                  1..11
                        mol_type = protein
                        organism = synthetic construct
SEQUENCE: 441
ARYGYSLYMD I                                                      11

SEQ ID NO: 442          moltype = AA  length = 11
FEATURE                 Location/Qualifiers
REGION                  1..11
                        note = SEQ ID NO: 442 - anti-CD3-C1-UCP01-G12 CDRH3
source                  1..11
                        mol_type = protein
                        organism = synthetic construct
SEQUENCE: 442
ARYGYSLYMD I                                                      11

SEQ ID NO: 443          moltype = AA  length = 11
FEATURE                 Location/Qualifiers
REGION                  1..11
                        note = SEQ ID NO: 443 - anti-CD3-C1-UCP01-H9 CDRH3
source                  1..11
                        mol_type = protein
                        organism = synthetic construct
SEQUENCE: 443
ARYGYSLYMD I                                                      11

SEQ ID NO: 444          moltype = AA  length = 11
FEATURE                 Location/Qualifiers
REGION                  1..11
                        note = SEQ ID NO: 444 - anti-CD3-C1-UCP01-H10 CDRH3
source                  1..11
                        mol_type = protein
                        organism = synthetic construct
SEQUENCE: 444
ARYGYSLYMD I                                                      11

SEQ ID NO: 445          moltype = AA  length = 11
FEATURE                 Location/Qualifiers
REGION                  1..11
                        note = SEQ ID NO: 445 - anti-CD3-C1-UCP02-E1 CDRH3
source                  1..11
                        mol_type = protein
                        organism = synthetic construct
SEQUENCE: 445
ARYGYSLYMD I                                                      11

SEQ ID NO: 446          moltype = AA  length = 14
FEATURE                 Location/Qualifiers
REGION                  1..14
                        note = SEQ ID NO: 446 - anti-BCMA-UCP01-A8 CDRH3
source                  1..14
                        mol_type = protein
                        organism = synthetic construct
SEQUENCE: 446
ARSSPSISGY AFDV                                                   14

SEQ ID NO: 447          moltype = AA  length = 14
FEATURE                 Location/Qualifiers
REGION                  1..14
                        note = SEQ ID NO: 447 - anti-BCMA-UCP01-A10 CDRH3
source                  1..14
                        mol_type = protein
```

```
                         organism = synthetic construct
SEQUENCE: 447
ARDLFDYYPQ GFDY                                                  14

SEQ ID NO: 448           moltype = AA  length = 17
FEATURE                  Location/Qualifiers
REGION                   1..17
                         note = SEQ ID NO: 448 - anti-BCMA-UCP01-C2 CDRH3
source                   1..17
                         mol_type = protein
                         organism = synthetic construct
SEQUENCE: 448
ARRLTDYISG GGDGFDV                                               17

SEQ ID NO: 449           moltype = AA  length = 18
FEATURE                  Location/Qualifiers
REGION                   1..18
                         note = SEQ ID NO: 449 - anti-BCMA-UCP01-E8 CDRH3
source                   1..18
                         mol_type = protein
                         organism = synthetic construct
SEQUENCE: 449
ARSVVDLSYV TGYYYMDI                                              18

SEQ ID NO: 450           moltype = AA  length = 19
FEATURE                  Location/Qualifiers
REGION                   1..19
                         note = SEQ ID NO: 450 - anti-BCMA-UCP01-E9 CDRH3
source                   1..19
                         mol_type = protein
                         organism = synthetic construct
SEQUENCE: 450
ARSPYGYSSG VEGYFGFDV                                             19

SEQ ID NO: 451           moltype = AA  length = 8
FEATURE                  Location/Qualifiers
REGION                   1..8
                         note = SEQ ID NO: 451 - anti-BCMA-UCP01-F9 CDRH3
source                   1..8
                         mol_type = protein
                         organism = synthetic construct
SEQUENCE: 451
AREDYSDY                                                         8

SEQ ID NO: 452           moltype = AA  length = 15
FEATURE                  Location/Qualifiers
REGION                   1..15
                         note = SEQ ID NO: 452 - anti-BCMA-PP02-A3 CDRH3
source                   1..15
                         mol_type = protein
                         organism = synthetic construct
SEQUENCE: 452
ARSPYGGGSY IPHDS                                                 15

SEQ ID NO: 453           moltype = AA  length = 14
FEATURE                  Location/Qualifiers
REGION                   1..14
                         note = SEQ ID NO: 453 - anti-BCMA-PP02-B4 CDRH3
source                   1..14
                         mol_type = protein
                         organism = synthetic construct
SEQUENCE: 453
ARVGYYLLDS AFDI                                                  14

SEQ ID NO: 454           moltype = AA  length = 16
FEATURE                  Location/Qualifiers
REGION                   1..16
                         note = SEQ ID NO: 454 - anti-BCMA-PP02-C2 CDRH3
source                   1..16
                         mol_type = protein
                         organism = synthetic construct
SEQUENCE: 454
ARVLITVDGS YGGFDY                                                16

SEQ ID NO: 455           moltype = AA  length = 14
FEATURE                  Location/Qualifiers
REGION                   1..14
                         note = SEQ ID NO: 455 - anti-BCMA-PP02-C4 CDRH3
source                   1..14
```

```
                        mol_type = protein
                        organism = synthetic construct
SEQUENCE: 455
ARIGYYYLDS AFDY                                                              14

SEQ ID NO: 456          moltype = AA  length = 15
FEATURE                 Location/Qualifiers
REGION                  1..15
                        note = SEQ ID NO: 456 - anti-BCMA-PP02-D3 CDRH3
source                  1..15
                        mol_type = protein
                        organism = synthetic construct
SEQUENCE: 456
ARVPYSYSGY SGADI                                                             15

SEQ ID NO: 457          moltype = AA  length = 16
FEATURE                 Location/Qualifiers
REGION                  1..16
                        note = SEQ ID NO: 457 - anti-BCMA-PP02-E6 CDRH3
source                  1..16
                        mol_type = protein
                        organism = synthetic construct
SEQUENCE: 457
ARSPYSYLHG YYGFDY                                                            16

SEQ ID NO: 458          moltype = AA  length = 21
FEATURE                 Location/Qualifiers
REGION                  1..21
                        note = SEQ ID NO: 458 - anti-BCMA-PP02-F1 CDRH3
source                  1..21
                        mol_type = protein
                        organism = synthetic construct
SEQUENCE: 458
ARSPYSRVGD SYYYDYIGFD I                                                      21

SEQ ID NO: 459          moltype = AA  length = 14
FEATURE                 Location/Qualifiers
REGION                  1..14
                        note = SEQ ID NO: 459 - anti-BCMA-PP03-C4 CDRH3
source                  1..14
                        mol_type = protein
                        organism = synthetic construct
SEQUENCE: 459
ARIGYYYLDS AFDY                                                              14

SEQ ID NO: 460          moltype = AA  length = 18
FEATURE                 Location/Qualifiers
REGION                  1..18
                        note = SEQ ID NO: 460 - anti-BCMA-PP03-E4 CDRH3
source                  1..18
                        mol_type = protein
                        organism = synthetic construct
SEQUENCE: 460
ARASAYIPYS EFYAGFDV                                                          18

SEQ ID NO: 461          moltype = AA  length = 15
FEATURE                 Location/Qualifiers
REGION                  1..15
                        note = SEQ ID NO: 461 - anti-BCMA-D3-MP03-G7 CDRH3
source                  1..15
                        mol_type = protein
                        organism = synthetic construct
SEQUENCE: 461
ARVPYSYSGY SGADI                                                             15

SEQ ID NO: 462          moltype = AA  length = 15
FEATURE                 Location/Qualifiers
REGION                  1..15
                        note = SEQ ID NO: 462 - anti-BCMA-D3-MP04-A2 CDRH3
source                  1..15
                        mol_type = protein
                        organism = synthetic construct
SEQUENCE: 462
ARVPYSYSGY SGADI                                                             15

SEQ ID NO: 463          moltype = AA  length = 15
FEATURE                 Location/Qualifiers
REGION                  1..15
                        note = SEQ ID NO: 463 - anti-BCMA-D3-MP04-B11a CDRH3
```

```
source                 1..15
                       mol_type = protein
                       organism = synthetic construct
SEQUENCE: 463
ARVPYSYSGY SGADI                                                15

SEQ ID NO: 464         moltype = AA  length = 15
FEATURE                Location/Qualifiers
REGION                 1..15
                       note = SEQ ID NO: 464 - anti-BCMA-D3-MP04-B11b CDRH3
source                 1..15
                       mol_type = protein
                       organism = synthetic construct
SEQUENCE: 464
ARVPYSYSGY SGADI                                                15

SEQ ID NO: 465         moltype = AA  length = 15
FEATURE                Location/Qualifiers
REGION                 1..15
                       note = SEQ ID NO: 465 - anti-BCMA-D3-MP04-B11c CDRH3
source                 1..15
                       mol_type = protein
                       organism = synthetic construct
SEQUENCE: 465
ARVPYSYSGY SGADI                                                15

SEQ ID NO: 466         moltype = AA  length = 15
FEATURE                Location/Qualifiers
REGION                 1..15
                       note = SEQ ID NO: 466 - anti-BCMA-D3-MP04-B11d CDRH3
source                 1..15
                       mol_type = protein
                       organism = synthetic construct
SEQUENCE: 466
ARVPYSYSGY SGADI                                                15

SEQ ID NO: 467         moltype = AA  length = 15
FEATURE                Location/Qualifiers
REGION                 1..15
                       note = SEQ ID NO: 467 - anti-BCMA-D3-MP04-C2 CDRH3
source                 1..15
                       mol_type = protein
                       organism = synthetic construct
SEQUENCE: 467
ARVPYSYSGY SGADI                                                15

SEQ ID NO: 468         moltype = AA  length = 15
FEATURE                Location/Qualifiers
REGION                 1..15
                       note = SEQ ID NO: 468 - antii-BCMA-D3-MP04-C8a CDRH3
source                 1..15
                       mol_type = protein
                       organism = synthetic construct
SEQUENCE: 468
ARVPYSYSGY SGADI                                                15

SEQ ID NO: 469         moltype = AA  length = 15
FEATURE                Location/Qualifiers
REGION                 1..15
                       note = SEQ ID NO: 469 - anti-BCMA-D3-MP04-C8b CDRH3
source                 1..15
                       mol_type = protein
                       organism = synthetic construct
SEQUENCE: 469
ARVPYSYSGY SGADI                                                15

SEQ ID NO: 470         moltype = AA  length = 15
FEATURE                Location/Qualifiers
REGION                 1..15
                       note = SEQ ID NO: 470 - anti-BCMA-D3-MP04-D4 CDRH3
source                 1..15
                       mol_type = protein
                       organism = synthetic construct
SEQUENCE: 470
ARVPYSYSGY SGADI                                                15

SEQ ID NO: 471         moltype = AA  length = 15
FEATURE                Location/Qualifiers
REGION                 1..15
```

```
                        note = SEQ ID NO: 471 - anti-BCMA-D3-MP04-E11 CDRH3
source                  1..15
                        mol_type = protein
                        organism = synthetic construct
SEQUENCE: 471
ARVPYSYSGY SGADI                                                    15

SEQ ID NO: 472          moltype = AA  length = 15
FEATURE                 Location/Qualifiers
REGION                  1..15
                        note = SEQ ID NO: 472 - anti-BCMA-D3-MP04-F3 CDRH3
source                  1..15
                        mol_type = protein
                        organism = synthetic construct
SEQUENCE: 472
ARVPYSYSGY SGADI                                                    15

SEQ ID NO: 473          moltype = AA  length = 15
FEATURE                 Location/Qualifiers
REGION                  1..15
                        note = SEQ ID NO: 473 - anti-BCMA-D3-MP04-G7 CDRH3
source                  1..15
                        mol_type = protein
                        organism = synthetic construct
SEQUENCE: 473
ARVPYSYSGY SGADI                                                    15

SEQ ID NO: 474          moltype = AA  length = 15
FEATURE                 Location/Qualifiers
REGION                  1..15
                        note = SEQ ID NO: 474 - anti-BCMA-D3-MP05-A9 CDRH3
source                  1..15
                        mol_type = protein
                        organism = synthetic construct
SEQUENCE: 474
ARVPYSYAGY SGADI                                                    15

SEQ ID NO: 475          moltype = AA  length = 15
FEATURE                 Location/Qualifiers
REGION                  1..15
                        note = SEQ ID NO: 475 - anti-BCMA-D3-MP05-C1a CDRH3
source                  1..15
                        mol_type = protein
                        organism = synthetic construct
SEQUENCE: 475
ARVPYSYMGY AGADI                                                    15

SEQ ID NO: 476          moltype = AA  length = 15
FEATURE                 Location/Qualifiers
REGION                  1..15
                        note = SEQ ID NO: 476 - antii-BCMA-D3-MP05-C1b CDRH3
source                  1..15
                        mol_type = protein
                        organism = synthetic construct
SEQUENCE: 476
ARVPYSYIGY AGADI                                                    15

SEQ ID NO: 477          moltype = AA  length = 15
FEATURE                 Location/Qualifiers
REGION                  1..15
                        note = SEQ ID NO: 477 - anti-BCMA-D3-MP05-F4 CDRH3
source                  1..15
                        mol_type = protein
                        organism = synthetic construct
SEQUENCE: 477
ARVPYSYLGY QGADI                                                    15

SEQ ID NO: 478          moltype = AA  length = 16
FEATURE                 Location/Qualifiers
REGION                  1..16
                        note = SEQ ID NO: 478 - anti-BCMA-E6-PP02-A3 CDRH3
source                  1..16
                        mol_type = protein
                        organism = synthetic construct
SEQUENCE: 478
ARSPYSYLHG YYGFDY                                                   16

SEQ ID NO: 479          moltype = AA  length = 16
FEATURE                 Location/Qualifiers
```

```
REGION                  1..16
                        note = SEQ ID NO: 479 - anti-BCMA-E6-PP02-B1 CDRH3
source                  1..16
                        mol_type = protein
                        organism = synthetic construct
SEQUENCE: 479
ARSPYSYLHG YYGFDY                                                           16

SEQ ID NO: 480          moltype = AA  length = 16
FEATURE                 Location/Qualifiers
REGION                  1..16
                        note = SEQ ID NO: 480 - anti-BCMA-E6-PP02-B4 CDRH3
source                  1..16
                        mol_type = protein
                        organism = synthetic construct
SEQUENCE: 480
ARSPYSYLHG YYGFDY                                                           16

SEQ ID NO: 481          moltype = AA  length = 16
FEATURE                 Location/Qualifiers
REGION                  1..16
                        note = SEQ ID NO: 481 - anti-BCMA-E6-PP02-C7 CDRH3
source                  1..16
                        mol_type = protein
                        organism = synthetic construct
SEQUENCE: 481
ARSPYSYLHG YYGFDY                                                           16

SEQ ID NO: 482          moltype = AA  length = 16
FEATURE                 Location/Qualifiers
REGION                  1..16
                        note = SEQ ID NO: 482 - anti-BCMA-E6-PP02-D2 CDRH3
source                  1..16
                        mol_type = protein
                        organism = synthetic construct
SEQUENCE: 482
ARSPYSYLHG YYGFDY                                                           16

SEQ ID NO: 483          moltype = AA  length = 16
FEATURE                 Location/Qualifiers
REGION                  1..16
                        note = SEQ ID NO: 483 - anti-BCMA-E6-PP02-E6 CDRH3
source                  1..16
                        mol_type = protein
                        organism = synthetic construct
SEQUENCE: 483
ARSPYSYLHG YYGFDY                                                           16

SEQ ID NO: 484          moltype = AA  length = 16
FEATURE                 Location/Qualifiers
REGION                  1..16
                        note = SEQ ID NO: 484 - anti-BCMA-E6-PP02-F7 CDRH3
source                  1..16
                        mol_type = protein
                        organism = synthetic construct
SEQUENCE: 484
ARSPYSYLHG YYGFDY                                                           16

SEQ ID NO: 485          moltype = AA  length = 16
FEATURE                 Location/Qualifiers
REGION                  1..16
                        note = SEQ ID NO: 485 - anti-BCMA-E6-PP02-G2 CDRH3
source                  1..16
                        mol_type = protein
                        organism = synthetic construct
SEQUENCE: 485
ARSPYSYLHG YYGFDY                                                           16

SEQ ID NO: 486          moltype = AA  length = 16
FEATURE                 Location/Qualifiers
REGION                  1..16
                        note = SEQ ID NO: 486 - anti-BCMA-E6-PP02-G6 CDRH3
source                  1..16
                        mol_type = protein
                        organism = synthetic construct
SEQUENCE: 486
ARSPYSYLHG YYGFDY                                                           16

SEQ ID NO: 487          moltype = AA  length = 16
```

```
FEATURE              Location/Qualifiers
REGION               1..16
                     note = SEQ ID NO: 487 - anti-BCMA-E6-PP02-G7 CDRH3
source               1..16
                     mol_type = protein
                     organism = synthetic construct
SEQUENCE: 487
ARSPYSYLHG YYGFDY                                                    16

SEQ ID NO: 488       moltype = AA  length = 14
FEATURE              Location/Qualifiers
REGION               1..14
                     note = SEQ ID NO: 488 - anti-CD38-UCP03-B3 CDRH3
source               1..14
                     mol_type = protein
                     organism = synthetic construct
SEQUENCE: 488
ARSWPSLGSG WFDI                                                      14

SEQ ID NO: 489       moltype = AA  length = 16
FEATURE              Location/Qualifiers
REGION               1..16
                     note = SEQ ID NO: 489 - anti-CD38-UCP01-E2 CDRH3
source               1..16
                     mol_type = protein
                     organism = synthetic construct
SEQUENCE: 489
ARGLGYYLYS SYYFDI                                                    16

SEQ ID NO: 490       moltype = AA  length = 14
FEATURE              Location/Qualifiers
REGION               1..14
                     note = SEQ ID NO: 490 - anti-CD38-B3-PP11-A2 CDRH3
source               1..14
                     mol_type = protein
                     organism = synthetic construct
SEQUENCE: 490
ARSWPSLGSG WFDI                                                      14

SEQ ID NO: 491       moltype = AA  length = 14
FEATURE              Location/Qualifiers
REGION               1..14
                     note = SEQ ID NO: 491 - anti-CD38-B3-PP11-C11 CDRH3
source               1..14
                     mol_type = protein
                     organism = synthetic construct
SEQUENCE: 491
ARSTPTYGSG WFDI                                                      14

SEQ ID NO: 492       moltype = AA  length = 14
FEATURE              Location/Qualifiers
REGION               1..14
                     note = SEQ ID NO: 492 - anti-CD38-B3-PP11-D1a CDRH3
source               1..14
                     mol_type = protein
                     organism = synthetic construct
SEQUENCE: 492
ARSWPSLGSG WFDI                                                      14

SEQ ID NO: 493       moltype = AA  length = 14
FEATURE              Location/Qualifiers
REGION               1..14
                     note = SEQ ID NO: 493 - anti-CD38-B3-PP11-D1b CDRH3
source               1..14
                     mol_type = protein
                     organism = synthetic construct
SEQUENCE: 493
ARSWPSLGSG WFDI                                                      14

SEQ ID NO: 494       moltype = AA  length = 14
FEATURE              Location/Qualifiers
REGION               1..14
                     note = SEQ ID NO: 494 - anti-CD38-B3-PP11-D11a CDRH3
source               1..14
                     mol_type = protein
                     organism = synthetic construct
SEQUENCE: 494
ARSWPILGNG WFDI                                                      14
```

```
SEQ ID NO: 495          moltype = AA  length = 14
FEATURE                 Location/Qualifiers
REGION                  1..14
                        note = SEQ ID NO: 495 - anti-CD38-B3-PP11-E1 CDRH3
source                  1..14
                        mol_type = protein
                        organism = synthetic construct
SEQUENCE: 495
ARSWPSLGSG WFDI                                                     14

SEQ ID NO: 496          moltype = AA  length = 14
FEATURE                 Location/Qualifiers
REGION                  1..14
                        note = SEQ ID NO: 496 - anti-CD38-B3-PP11-E11 CDRH3
source                  1..14
                        mol_type = protein
                        organism = synthetic construct
SEQUENCE: 496
ARSWPSYGKG WFDI                                                     14

SEQ ID NO: 497          moltype = AA  length = 14
FEATURE                 Location/Qualifiers
REGION                  1..14
                        note = SEQ ID NO: 497 - anti-CD38-B3-PP11-H1a CDRH3
source                  1..14
                        mol_type = protein
                        organism = synthetic construct
SEQUENCE: 497
ARSWPSLGSG WFDI                                                     14

SEQ ID NO: 498          moltype = AA  length = 14
FEATURE                 Location/Qualifiers
REGION                  1..14
                        note = SEQ ID NO: 498 - anti-CD38-B3-PP11-H10 CDRH3
source                  1..14
                        mol_type = protein
                        organism = synthetic construct
SEQUENCE: 498
ARSWPHYGSG WFDI                                                     14

SEQ ID NO: 499          moltype = AA  length = 16
FEATURE                 Location/Qualifiers
REGION                  1..16
                        note = SEQ ID NO: 499 - anti-CD38-E2-UCP01-A10 CDRH3
source                  1..16
                        mol_type = protein
                        organism = synthetic construct
SEQUENCE: 499
ARGLGYYLYS SYYFDI                                                   16

SEQ ID NO: 500          moltype = AA  length = 16
FEATURE                 Location/Qualifiers
REGION                  1..16
                        note = SEQ ID NO: 500 - anti-CD38-E2-UCP02-A5 CDRH3
source                  1..16
                        mol_type = protein
                        organism = synthetic construct
SEQUENCE: 500
ARGLGYYLYS SYYFDI                                                   16

SEQ ID NO: 501          moltype = AA  length = 16
FEATURE                 Location/Qualifiers
REGION                  1..16
                        note = SEQ ID NO: 501 - anti-CD38-E2-UCP02-D6 CDRH3
source                  1..16
                        mol_type = protein
                        organism = synthetic construct
SEQUENCE: 501
ARGLGYYLYS SYYFDI                                                   16

SEQ ID NO: 502          moltype = AA  length = 16
FEATURE                 Location/Qualifiers
REGION                  1..16
                        note = SEQ ID NO: 502 - anti-CD38-E2-UCP02-E7 CDRH3
source                  1..16
                        mol_type = protein
                        organism = synthetic construct
SEQUENCE: 502
ARGLGYYLYS SYYFDI                                                   16
```

```
SEQ ID NO: 503          moltype = AA  length = 16
FEATURE                 Location/Qualifiers
REGION                  1..16
                        note = SEQ ID NO: 503 - anti-CD38-E2-UCP02-F3 CDRH3
source                  1..16
                        mol_type = protein
                        organism = synthetic construct
SEQUENCE: 503
ARGLGYYLYS SYYFDI                                                  16

SEQ ID NO: 504          moltype = AA  length = 16
FEATURE                 Location/Qualifiers
REGION                  1..16
                        note = SEQ ID NO: 504 - anti-CD38-E2-UCP02-F8 CDRH3
source                  1..16
                        mol_type = protein
                        organism = synthetic construct
SEQUENCE: 504
ARGLGYYLYS SYYFDI                                                  16

SEQ ID NO: 505          moltype = AA  length = 16
FEATURE                 Location/Qualifiers
REGION                  1..16
                        note = SEQ ID NO: 505 - anti-CD38-E2-UCP02-G8 CDRH3
source                  1..16
                        mol_type = protein
                        organism = synthetic construct
SEQUENCE: 505
ARGLGYYLYS SYYFDI                                                  16

SEQ ID NO: 506          moltype = AA  length = 454
FEATURE                 Location/Qualifiers
REGION                  1..454
                        note = SEQ ID NO: 506 -
                         83A10-TCBcv_aCD3-G65S-VH-BTA1113_LALA
source                  1..454
                        mol_type = protein
                        organism = synthetic construct
SEQUENCE: 506
EVQLLESGGG LVQPGGSLRL SCAASGFTFS TYAMNWVRQA PGKGLEWVSR IRSKYNNYAT  60
YYADSVKSRF TISRDDSKNT LYLQMNSLRA EDTAVYYCVR HGNFGNSYVS WFAYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPAVYTLP  360
PSREEMTKNQ VKLVCLVTGF YPSDIAVEWE SSGQPENNYY TTPPMLDSDG SFSLVSWLNV  420
DKSRWQQGNI FSCSVMHEAL HNRFTQKSLS LSPG                              454

SEQ ID NO: 507          moltype = AA  length = 474
FEATURE                 Location/Qualifiers
REGION                  1..474
                        note = SEQ ID NO: 507 - BCMA_dAbx2_G65S_BTB_D401Q_LALA
source                  1..474
                        mol_type = protein
                        organism = synthetic construct
SEQUENCE: 507
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 508          moltype = AA  length = 216
FEATURE                 Location/Qualifiers
REGION                  1..216
                        note = SEQ ID NO: 508 - 83A10-TCBcv_aCD3-LC
source                  1..216
                        mol_type = protein
                        organism = synthetic construct
SEQUENCE: 508
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216
```

```
SEQ ID NO: 509          moltype = AA  length = 447
FEATURE                 Location/Qualifiers
REGION                  1..447
                        note = SEQ ID NO: 509 - 180-C1-UCP01-E10-BTA1113-LALA
source                  1..447
                        mol_type = protein
                        organism = synthetic construct
SEQUENCE: 509
QVQLVQSGAE VKKPGSSVKV SCKASGGKFS RYAISWVRQA PGQGLEWMGG ISPFEGTPAY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 510          moltype = AA  length = 474
FEATURE                 Location/Qualifiers
REGION                  1..474
                        note = SEQ ID NO: 510 - BCMA_dAbx2_G65S_BTB_D401Q_LALA
source                  1..474
                        mol_type = protein
                        organism = synthetic construct
SEQUENCE: 510
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 511          moltype = AA  length = 447
FEATURE                 Location/Qualifiers
REGION                  1..447
                        note = SEQ ID NO: 511 - 180-C1-UCP01-F10-BTA1113-LALA
source                  1..447
                        mol_type = protein
                        organism = synthetic construct
SEQUENCE: 511
QVQLVQSGAE VKKPGSSVKV SCKASGGKFS RYAISWVRQA PGQGLEWMGG INPHIRFPEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 512          moltype = AA  length = 474
FEATURE                 Location/Qualifiers
REGION                  1..474
                        note = SEQ ID NO: 512 - BCMA_dAbx2_G65S_BTB_D401Q_LALA
source                  1..474
                        mol_type = protein
                        organism = synthetic construct
SEQUENCE: 512
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 513          moltype = AA  length = 447
FEATURE                 Location/Qualifiers
REGION                  1..447
                        note = SEQ ID NO: 513 - 180-C1-UCP01-H10-BTA1113-LALA
source                  1..447
                        mol_type = protein
                        organism = synthetic construct
SEQUENCE: 513
QVQLVQSGAE VKKPGSSVKV SCKASGGKFS RYAISWVRQA PGQGLEWMGG ISPLVGYPQY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
```

```
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                    447

SEQ ID NO: 514          moltype = AA  length = 474
FEATURE                 Location/Qualifiers
REGION                  1..474
                        note = SEQ ID NO: 514 - BCMA_dAbx2_G65S_BTB_D401Q_LALA
source                  1..474
                        mol_type = protein
                        organism = synthetic construct
SEQUENCE: 514
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 515          moltype = AA  length = 447
FEATURE                 Location/Qualifiers
REGION                  1..447
                        note = SEQ ID NO: 515 - 180-C1-UCP01-D6-BTA1113-LALA
source                  1..447
                        mol_type = protein
                        organism = synthetic construct
SEQUENCE: 515
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                    447

SEQ ID NO: 516          moltype = AA  length = 474
FEATURE                 Location/Qualifiers
REGION                  1..474
                        note = SEQ ID NO: 516 - BCMA_dAbx2_G65S_BTB_D401Q_LALA
source                  1..474
                        mol_type = protein
                        organism = synthetic construct
SEQUENCE: 516
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 517          moltype = AA  length = 447
FEATURE                 Location/Qualifiers
REGION                  1..447
                        note = SEQ ID NO: 517 - 180-C1-UCP01-E12-BTA1113-LALA
source                  1..447
                        mol_type = protein
                        organism = synthetic construct
SEQUENCE: 517
QVQLVQSGAE VKKPGSSVKV SCKASGGKFS RYAISWVRQA PGQGLEWMGG INPLVGHAEY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                    447

SEQ ID NO: 518          moltype = AA  length = 474
FEATURE                 Location/Qualifiers
REGION                  1..474
                        note = SEQ ID NO: 518 - BCMA_dAbx2_G65S_BTB_D401Q_LALA
source                  1..474
```

```
                        mol_type = protein
                        organism = synthetic construct
SEQUENCE: 518
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 519          moltype = AA  length = 445
FEATURE                 Location/Qualifiers
REGION                  1..445
                        note = SEQ ID NO: 519 - ABC_VH_BTA113LALA
source                  1..445
                        mol_type = protein
                        organism = synthetic construct
SEQUENCE: 519
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKSY GAFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPAVYTL PPSREEMTKN  360
QVKLVCLVTG FYPSDIAVEW ESSGQPENNY YTTPPMLDSD GSFSLVSWLN VDKSRWQQGN  420
IFSCSVMHEA LHNRFTQKSL SLSPG                                        445

SEQ ID NO: 520          moltype = AA  length = 474
FEATURE                 Location/Qualifiers
REGION                  1..474
                        note = SEQ ID NO: 520 -
                         TNB383b_BCMA_dAbx2_G65S_BTB_D401Q_LALA
source                  1..474
                        mol_type = protein
                        organism = synthetic construct
SEQUENCE: 520
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 521          moltype = AA  length = 214
FEATURE                 Location/Qualifiers
REGION                  1..214
                        note = SEQ ID NO: 521 - ABCLC
source                  1..214
                        mol_type = protein
                        organism = synthetic construct
SEQUENCE: 521
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPNTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 522          moltype = AA  length = 452
FEATURE                 Location/Qualifiers
REGION                  1..452
                        note = SEQ ID NO: 522 - E2-BTA
source                  1..452
                        mol_type = protein
                        organism = synthetic construct
SEQUENCE: 522
QVQLVQSGAE VKKPGSSVKV SCKASGGSFS NYAIGWVRQA PGQGLEWMGR IIPVFGSAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALAAPIEK TISKAKGQPR EPAVYTLPPS  360
REEMTKNQVK LVCLVTGFYP SDIAVEWESS GQPENNYYTT PPMLDSDGSF SLVSWLNVDK  420
SRWQQGNIFS CSVMHEALHN RFTQKSLSLS PG                                452

SEQ ID NO: 523          moltype = AA  length = 687
FEATURE                 Location/Qualifiers
```

-continued

```
REGION                  1..687
                        note = SEQ ID NO: 523 - C1-D6-3x-D3-E11-BTB
source                  1..687
                        mol_type = protein
                        organism = synthetic construct
SEQUENCE: 523
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SGGGGSEVQL  240
VESGGGLIQP GGSLRLSCAA SGFIFSHYEM NWVRQAPGKG LEWVSAIGQL GGNTVYADSV  300
KGRFTISRDN SKNTLYLQMN SLRAEDTAVY YCARVPYSYS GYSGADIWGQ GTLVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALA APIEKTISKA KGQPREPEVA TFPPSRDELT  600
KNQVTLVCLV TGFYPSDIAV EWESNGQPEN NYKTDPPLLE SQGSFALSSR LRVDKSRWQQ  660
GNVFSCSVMH EALHNHYTQK SLSLSPG                                    687

SEQ ID NO: 524          moltype = AA  length = 451
FEATURE                 Location/Qualifiers
REGION                  1..451
                        note = SEQ ID NO: 524 - D3-E11-BTA
source                  1..451
                        mol_type = protein
                        organism = synthetic construct
SEQUENCE: 524
EVQLVESGGG LIQPGGSLRL SCAASGFIFS HYEMNWVRQA PGKGLEWVSA IGQLGGNTVY  60
ADSVKSRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALAAPIEKT ISKAKGQPRE PAVYTLPPSR  360
EEMTKNQVKL VCLVTGFYPS DIAVEWESSG QPENNYYTTP PMLDSDGSFS LVSWLNVDKS  420
RWQQGNIFSC SVMHEALHNR FTQKSLSLSP G                               451

SEQ ID NO: 525          moltype = AA  length = 447
FEATURE                 Location/Qualifiers
REGION                  1..447
                        note = SEQ ID NO: 525 - C1-D6-BTB
source                  1..447
                        mol_type = protein
                        organism = synthetic construct
SEQUENCE: 525
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPEVA TFPPSRDELT  360
KNQVTLVCLV TGFYPSDIAV EWESNGQPEN NYKTDPPLLE SQGSFALSSR LRVDKSRWQQ  420
GNVFSCSVMH EALHNHYTQK SLSLSPG                                    447

SEQ ID NO: 526          moltype = AA  length = 447
FEATURE                 Location/Qualifiers
REGION                  1..447
                        note = SEQ ID NO: 526 - C1-D6-BTA
source                  1..447
                        mol_type = protein
                        organism = synthetic construct
SEQUENCE: 526
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                    447

SEQ ID NO: 527          moltype = AA  length = 694
FEATURE                 Location/Qualifiers
REGION                  1..694
                        note = SEQ ID NO: 527 - G6DU-2x-G6DU-BTB
source                  1..694
                        mol_type = protein
                        organism = synthetic construct
SEQUENCE: 527
QVQLVQSGAE VKKPGSSVKV SCKASGVDFT KYAIHWVRQA PGQGLEWMGG IVPAEGDANY  60
```

-continued

```
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCG GGGSGGGGSQ  240
VQLVQSGAEV KKPGSSVKVS CKASGVDFTK YAIHWVRQAP GQGLEWMGGI VPAEGDANYA  300
QKFQGRVTIT ADESTSTAYM ELSSLRSEDT AVYYCARDVL SAGDGYYLYD LMDVWGQGTL  360
VTVSSASTKG PSVFPLAPSS KSTSGGTAAL GCLVKDYFPE PVTVSWNSGA LTSGVHTFPA  420
VLQSSGLYSL SSVVTVPSSS LGTQTYICNV NHKPSNTKVD KKVEPKSCDK THTCPPCPAP  480
EAAGGPSVFL FPPKPKDTLM ISRTPEVTCV VVDVSHEDPE VKFNWYVDGV EVHNAKTKPR  540
EEQYNSTYRV VSVLTVLHQD WLNGKEYKCK VSNKALAAPI EKTISKAKGQ PREPEVATFP  600
PSRDELTKNQ VTLVCLVTGF YPSDIAVEWE SNGQPENNYK TDPPLLESQG SFALSSRLRV  660
DKSRWQQGNV FSCSVMHEAL HNHYTQKSLS LSPG                             694

SEQ ID NO: 528         moltype = AA  length = 455
FEATURE                Location/Qualifiers
REGION                 1..455
                       note = SEQ ID NO: 528 - G6DU-BTA
source                 1..455
                       mol_type = protein
                       organism = synthetic construct
SEQUENCE: 528
QVQLVQSGAE VKKPGSSVKV SCKASGVDFT KYAIHWVRQA PGQGLEWMGG IVPAEGDANY  60
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALAAP IEKTISKAKG QPREPAVYTL  360
PPSREEMTKN QVKLVCLVTG FYPSDIAVEW ESSGQPENNY YTTPPMLDSD GSFSLVSWLN  420
VDKSRWQQGN IFSCSVMHEA LHNRFTQKSL SLSPG                            455

SEQ ID NO: 529         moltype = AA  length = 694
FEATURE                Location/Qualifiers
REGION                 1..694
                       note = SEQ ID NO: 529 - G6DU-2x-G6DU-BTB
source                 1..694
                       mol_type = protein
                       organism = synthetic construct
SEQUENCE: 529
QVQLVQSGAE VKKPGSSVKV SCKASGVDFT KYAIHWVRQA PGQGLEWMGG IVPAEGDANY  60
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCG GGGSGGGGSQ  240
VQLVQSGAEV KKPGSSVKVS CKASGVDFTK YAIHWVRQAP GQGLEWMGGI VPAEGDANYA  300
QKFQGRVTIT ADESTSTAYM ELSSLRSEDT AVYYCARDVL SAGDGYYLYD LMDVWGQGTL  360
VTVSSASTKG PSVFPLAPSS KSTSGGTAAL GCLVKDYFPE PVTVSWNSGA LTSGVHTFPA  420
VLQSSGLYSL SSVVTVPSSS LGTQTYICNV NHKPSNTKVD KKVEPKSCDK THTCPPCPAP  480
EAAGGPSVFL FPPKPKDTLM ISRTPEVTCV VVDVSHEDPE VKFNWYVDGV EVHNAKTKPR  540
EEQYNSTYRV VSVLTVLHQD WLNGKEYKCK VSNKALAAPI EKTISKAKGQ PREPEVATFP  600
PSRDELTKNQ VTLVCLVTGF YPSDIAVEWE SNGQPENNYK TDPPLLESQG SFALSSRLRV  660
DKSRWQQGNV FSCSVMHEAL HNHYTQKSLS LSPG                             694

SEQ ID NO: 530         moltype = AA  length = 447
FEATURE                Location/Qualifiers
REGION                 1..447
                       note = SEQ ID NO: 530 - C1-D6-BTA
source                 1..447
                       mol_type = protein
                       organism = synthetic construct
SEQUENCE: 530
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 531         moltype = AA  length = 685
FEATURE                Location/Qualifiers
REGION                 1..685
                       note = SEQ ID NO: 531 - D3-E11-2x-B3-C11-BTB
source                 1..685
                       mol_type = protein
                       organism = synthetic construct
SEQUENCE: 531
EVQLVESGGG LIQPGGSLRL SCAASGFIFS HYEMNWVRQA PGKGLEWVSA IGQLGGNTVY  60
ADSVKGRFTI SRDNSKNTLY LQMNSLRAED TAVYYCARVP YSYSGYSGAD IWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCGGGGS GGGGSQVQLV  240
```

-continued

```
QSGAEVKKPG SSVKVSCKAS GGDFTLYSIS WVRQAPGQGL EWMGRIIPTG ANANYAQKFQ  300
GRVTITADES TSTAYMELSS LRSEDTAVYY CARSTPTYGS GWFDIWGQGT LVTVSSASTK  360
GPSVFPLAPS SKSTSGGTAA LGCLVKDYFP EPVTVSWNSG ALTSGVHTFP AVLQSSGLYS  420
LSSVVTVPSS SLGTQTYICN VNHKPSNTKV DKKVEPKSCD KTHTCPPCPA PEAAGGPSVF  480
LFPPKPKDTL MISRTPEVTC VVVDVSHEDP EVKFNWYVDG VEVHNAKTKP REEQYNSTYR  540
VVSVLTVLHQ DWLNGKEYKC KVSNKALAAP IEKTISKAKG QPREPEVATF PPSRDELTKN  600
QVTLVCLVTG FYPSDIAVEW ESNGQPENNY KTDPPLLESQ GSFALSSRLR VDKSRWQQGN  660
VFSCSVMHEA LHNHYTQKSL SLSPG                                       685

SEQ ID NO: 532          moltype = AA  length = 447
FEATURE                 Location/Qualifiers
REGION                  1..447
                        note = SEQ ID NO: 532 - C1-D6-BTA
source                  1..447
                        mol_type = protein
                        organism = synthetic construct
SEQUENCE: 532
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 533          moltype = AA  length = 686
FEATURE                 Location/Qualifiers
REGION                  1..686
                        note = SEQ ID NO: 533 - E6-E6-2x-B3-C11-BTB
source                  1..686
                        mol_type = protein
                        organism = synthetic construct
SEQUENCE: 533
EVQLLESGGG LVQPGGSLRL SCAASGFTFS YYAMTWVRQA PGKGLEWVST ISQAGRDFKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSTPTYG SGWFDIWGQG TLVTVSSAST  360
KGPSVFPLAP SSKSTSGGTA ALGCLVKDYF PEPVTVSWNS GALTSGVHTF PAVLQSSGLY  420
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                      686

SEQ ID NO: 534          moltype = AA  length = 447
FEATURE                 Location/Qualifiers
REGION                  1..447
                        note = SEQ ID NO: 534 - C1-D6-BTA
source                  1..447
                        mol_type = protein
                        organism = synthetic construct
SEQUENCE: 534
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 535          moltype = AA  length = 686
FEATURE                 Location/Qualifiers
REGION                  1..686
                        note = SEQ ID NO: 535 - E6-G6-2x-B3-C11-BTB
source                  1..686
                        mol_type = protein
                        organism = synthetic construct
SEQUENCE: 535
EVQLLESGGG LVQPGGSLRL SCAASGFTFS YYAMTWVRQA PGKGLEWVST IAQRGGQTKY  60
ADSVKGRFTI SRDNSKNTLY LQMNSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSTPTYG SGWFDIWGQG TLVTVSSAST  360
KGPSVFPLAP SSKSTSGGTA ALGCLVKDYF PEPVTVSWNS GALTSGVHTF PAVLQSSGLY  420
```

```
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                      686

SEQ ID NO: 536          moltype = AA  length = 447
FEATURE                 Location/Qualifiers
REGION                  1..447
                        note = SEQ ID NO: 536 - C1-D6-BTA
source                  1..447
                        mol_type = protein
                        organism = synthetic construct
SEQUENCE: 536
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 537          moltype = AA  length = 686
FEATURE                 Location/Qualifiers
REGION                  1..686
                        note = SEQ ID NO: 537 - E6-B1-N82aS-2x-B3-C11-BTB
source                  1..686
                        mol_type = protein
                        organism = synthetic construct
SEQUENCE: 537
EVQLLESGGG LVQPGGSLRL SCAASGFTFS YYAMTWVRQA PGKGLEWVST VSQAGYDTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSTPTYG SGWFDIWGQG TLVTVSSAST  360
KGPSVFPLAP SSKSTSGGTA ALGCLVKDYF PEPVTVSWNS GALTSGVHTF PAVLQSSGLY  420
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                      686

SEQ ID NO: 538          moltype = AA  length = 447
FEATURE                 Location/Qualifiers
REGION                  1..447
                        note = SEQ ID NO: 538 - C1-D6-BTA
source                  1..447
                        mol_type = protein
                        organism = synthetic construct
SEQUENCE: 538
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                     447

SEQ ID NO: 539          moltype = AA  length = 688
FEATURE                 Location/Qualifiers
REGION                  1..688
                        note = SEQ ID NO: 539 - E6-G6-N82aS-2x-E2-A5-BTB
source                  1..688
                        mol_type = protein
                        organism = synthetic construct
SEQUENCE: 539
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGSFSNYAI GWVRQAPGQG LEWMGRIIPD LGAAHYAQKF  300
QGRVTITADE STSTAYMELS SLRSEDTAVY YCARGLGYYL YSSYYFDIWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL AAPIEKTISK AKGQPREPEV ATFPPSRDEL  600
```

```
TKNQVTLVCL VTGFYPSDIA VEWESNGQPE NNYKTDPPLL ESQGSFALSS RLRVDKSRWQ  660
QGNVFSCSVM HEALHNHYTQ KSLSLSPG                                     688

SEQ ID NO: 540          moltype = AA  length = 447
FEATURE                 Location/Qualifiers
REGION                  1..447
                        note = SEQ ID NO: 540 - C1-D6-BTA
source                  1..447
                        mol_type = protein
                        organism = synthetic construct
SEQUENCE: 540
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                      447

SEQ ID NO: 541          moltype = AA  length = 686
FEATURE                 Location/Qualifiers
REGION                  1..686
                        note = SEQ ID NO: 541 - E6-G6-N82aS-2x-B3-C11-BTB
source                  1..686
                        mol_type = protein
                        organism = synthetic construct
SEQUENCE: 541
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSTPTYG SGWFDIWGQG TLVTVSSAST  360
KGPSVFPLAP SSKSTSGGTA ALGCLVKDYF PEPVTVSWNS GALTSGVHTF PAVLQSSGLY  420
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                       686

SEQ ID NO: 542          moltype = AA  length = 447
FEATURE                 Location/Qualifiers
REGION                  1..447
                        note = SEQ ID NO: 542 - C1-D6-BTA
source                  1..447
                        mol_type = protein
                        organism = synthetic construct
SEQUENCE: 542
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                      447

SEQ ID NO: 543          moltype = AA  length = 686
FEATURE                 Location/Qualifiers
REGION                  1..686
                        note = SEQ ID NO: 543 - E6-G6-N82aS-2x-B3-BTB
source                  1..686
                        mol_type = protein
                        organism = synthetic construct
SEQUENCE: 543
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSWPSLG SGWFDIWGQG TLVTVSSAST  360
KGPSVFPLAP SSKSTSGGTA ALGCLVKDYF PEPVTVSWNS GALTSGVHTF PAVLQSSGLY  420
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                       686
```

```
SEQ ID NO: 544         moltype = AA  length = 452
FEATURE                Location/Qualifiers
REGION                 1..452
                       note = SEQ ID NO: 544 - E2-A5-BTA
source                 1..452
                       mol_type = protein
                       organism = synthetic construct
SEQUENCE: 544
QVQLVQSGAE VKKPGSSVKV SCKASGGSFS NYAIGWVRQA PGQGLEWMGR IIPDLGAAHY  60
AQKFQGRVTI TADESTSTAY MELSSLRSED TAVYYCARGL GYYLYSSYYF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALAAPIEK TISKAKGQPR EPAVYTLPPS  360
REEMTKNQVK LVCLVTGFYP SDIAVEWESS GQPENNYYTT PPMLDSDGSF SLVSWLNVDK  420
SRWQQGNIFS CSVMHEALHN RFTQKSLSLS PG                               452

SEQ ID NO: 545         moltype = AA  length = 688
FEATURE                Location/Qualifiers
REGION                 1..688
                       note = SEQ ID NO: 545 - C1-D6-3x-E6-G6-N82aS-BTB
source                 1..688
                       mol_type = protein
                       organism = synthetic construct
SEQUENCE: 545
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SGGGGSEVQL  240
LESGGGLVQP GGSLRLSCAA SGFTFSYYAM TWVRQAPGKG LEWVSTIAQR GGQTKYADSV  300
KGRFTISRDN SKNTLYLQMS SLRAEDTAVY YCARSPYSYL HGYYGFDYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL AAPIEKTISK AKGQPREPEV ATFPPSRDEL  600
TKNQVTLVCL VTGFYPSDIA VEWESNGQPE NNYKTDPPLL ESQGSFALSS RLRVDKSRWQ  660
QGNVFSCSVM HEALHNHYTQ KSLSLSPG                                    688

SEQ ID NO: 546         moltype = AA  length = 450
FEATURE                Location/Qualifiers
REGION                 1..450
                       note = SEQ ID NO: 546 - B3-C11-BTA
source                 1..450
                       mol_type = protein
                       organism = synthetic construct
SEQUENCE: 546
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARST PTYGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALAAPIEKTI SKAKGQPREP AVYTLPPSRE  360
EMTKNQVKLV CLVTGFYPSD IAVEWESSGQ PENNYYTTPP MLDSDGSFSL VSWLNVDKSR  420
WQQGNIFSCS VMHEALHNRF TQKSLSLSPG                                  450

SEQ ID NO: 547         moltype = AA  length = 688
FEATURE                Location/Qualifiers
REGION                 1..688
                       note = SEQ ID NO: 547 - C1-D6-3x-E6-G6-N82aS-BTB
source                 1..688
                       mol_type = protein
                       organism = synthetic construct
SEQUENCE: 547
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SGGGGSEVQL  240
LESGGGLVQP GGSLRLSCAA SGFTFSYYAM TWVRQAPGKG LEWVSTIAQR GGQTKYADSV  300
KGRFTISRDN SKNTLYLQMS SLRAEDTAVY YCARSPYSYL HGYYGFDYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL AAPIEKTISK AKGQPREPEV ATFPPSRDEL  600
TKNQVTLVCL VTGFYPSDIA VEWESNGQPE NNYKTDPPLL ESQGSFALSS RLRVDKSRWQ  660
QGNVFSCSVM HEALHNHYTQ KSLSLSPG                                    688

SEQ ID NO: 548         moltype = AA  length = 450
FEATURE                Location/Qualifiers
REGION                 1..450
```

```
                        note = SEQ ID NO: 548 - B3-BTA
source                  1..450
                        mol_type = protein
                        organism = synthetic construct
SEQUENCE: 548
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PSLGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALAAPIEKTI SKAKGQPREP AVYTLPPSRE  360
EMTKNQVKLV CLVTGFYPSD IAVEWESSGQ PENNYYTTPP MLDSDGSFSL VSWLNVDKSR  420
WQQGNIFSCS VMHEALHNRF TQKSLSLSPG                                  450

SEQ ID NO: 549          moltype = AA  length = 688
FEATURE                 Location/Qualifiers
REGION                  1..688
                        note = SEQ ID NO: 549 - C1-D6-3x-E6-G6-N82aS-BTB
source                  1..688
                        mol_type = protein
                        organism = synthetic construct
SEQUENCE: 549
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SGGGGSEVQL  240
LESGGGLVQP GGSLRLSCAA SGFTFSYYAM TWVRQAPGKG LEWVSTIAQR GGQTKYADSV  300
KGRFTISRDN SKNTLYLQMS SLRAEDTAVY YCARSPYSYL HGYYGFDYWG QGTLVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPEAAGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL AAPIEKTISK AKGQPREPEV ATFPPSRDEL  600
TKNQVTLVCL VTGFYPSDIA VEWESNGQPE NNYKTDPPLL ESQGSFALSS RLRVDKSRWQ  660
QGNVFSCSVM HEALHNHYTQ KSLSLSPG                                    688

SEQ ID NO: 550          moltype = AA  length = 455
FEATURE                 Location/Qualifiers
REGION                  1..455
                        note = SEQ ID NO: 550 - G6DU-BTA
source                  1..455
                        mol_type = protein
                        organism = synthetic construct
SEQUENCE: 550
QVQLVQSGAE VKKPGSSVKV SCKASGVDFT KYAIHWVRQA PGQGLEWMGG IVPAEGDANY  60
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALAAP IEKTISKAKG QPREPAVYTL  360
PPSREEMTKN QVKLVCLVTG FYPSDIAVEW ESSGQPENNY YTTPPMLDSD GSFSLVSWLN  420
VDKSRWQQGN IFSCSVMHEA LHNRFTQKSL SLSPG                            455

SEQ ID NO: 551          moltype = AA  length = 686
FEATURE                 Location/Qualifiers
REGION                  1..686
                        note = SEQ ID NO: 551 - E6-G6-N82aS-2x-B3-C11
source                  1..686
                        mol_type = protein
                        organism = synthetic construct
SEQUENCE: 551
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQVQL  240
VQSGAEVKKP GSSVKVSCKA SGGDFTLYSI SWVRQAPGQG LEWMGRIIPT GANANYAQKF  300
QGRVTITADE STSTAYMELS SLRSEDTAVY YCARSTPTYG SGWFDIWGQG TLVTVSSAST  360
KGPSVFPLAP SSKSTSGGTA ALGCLVKDYF PEPVTVSWNS GALTSGVHTF PAVLQSSGLY  420
SLSSVVTVPS SSLGTQTYIC NVNHKPSNTK VDKKVEPKSC DKTHTCPPCP APEAAGGPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALAA PIEKTISKAK GQPREPEVAT FPPSRDELTK  600
NQVTLVCLVT GFYPSDIAVE WESNGQPENN YKTDPPLLES QGSFALSSRL RVDKSRWQQG  660
NVFSCSVMHE ALHNHYTQKS LSLSPG                                      686

SEQ ID NO: 552          moltype = AA  length = 450
FEATURE                 Location/Qualifiers
REGION                  1..450
                        note = SEQ ID NO: 552 - B3-C11-BTA
source                  1..450
                        mol_type = protein
```

```
                         organism = synthetic construct
SEQUENCE: 552
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARST PTYGSGWFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALAAPIEKTI SKAKGQPREP EVATFPPSRD  360
ELTKNQVTLV CLVTGFYPSD IAVEWESNGQ PENNYKTDPP LLESQGSFAL SSRLRVDKSR  420
WQQGNVFSCS VMHEALHNHY TQKSLSLSPG                                  450

SEQ ID NO: 553           moltype = AA  length = 696
FEATURE                  Location/Qualifiers
REGION                   1..696
                         note = SEQ ID NO: 553 - G6DU-E6-G6-N82aS-BTB
source                   1..696
                         mol_type = protein
                         organism = synthetic construct
SEQUENCE: 553
QVQLVQSGAE VKKPGSSVKV SCKASGVDFT KYAIHWVRQA PGQGLEWMGG IVPAEGDANY  60
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCG GGGSGGGGSG  240
GGGSEVQLLE SGGGLVQPGG SLRLSCAASG FTFSYYAMTW VRQAPGKGLE WVSTIAQRGG  300
QTKYADSVKG RFTISRDNSK NTLYLQMSSL RAEDTAVYYC ARSPYSYLHG YYGFDYWGQG  360
TLVTVSSAST KGPSVFPLAP SSKSTSGGTA ALGCLVKDYF PEPVTVSWNS GALTSGVHTF  420
PAVLQSSGLY SLSSVVTVPS SSLGTQTYIC NVNHKPSNTK VDKKVEPKSC DKTHTCPPCP  480
APEAAGGPSV FLFPPKPKDT LMISRTPEVT CVVVDVSHED PEVKFNWYVD GVEVHNAKTK  540
PREEQYNSTY RVVSVLTVLH QDWLNGKEYK CKVSNKALAA PIEKTISKAK GQPREPEVAT  600
FPPSRDELTK NQVTLVCLVT GFYPSDIAVE WESNGQPENN YKTDPPLLES QGSFALSSRL  660
RVDKSRWQQG NVFSCSVMHE ALHNHYTQKS LSLSPG                            696

SEQ ID NO: 554           moltype = AA  length = 455
FEATURE                  Location/Qualifiers
REGION                   1..455
                         note = SEQ ID NO: 554 - G6DU-BTA
source                   1..455
                         mol_type = protein
                         organism = synthetic construct
SEQUENCE: 554
QVQLVQSGAE VKKPGSSVKV SCKASGVDFT KYAIHWVRQA PGQGLEWMGG IVPAEGDANY  60
AQKFQGRVTI TADESTSTAY MELSSLRSED TAVYYCARDV LSAGDGYYLY DLMDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALAAP IEKTISKAKG QPREPAVYTL  360
PPSREEMTKN QVKLVCLVTG FYPSDIAVEW ESSGQPENNY YTTPPMLDSD GSFSLVSWLN  420
VDKSRWQQGN IFSCSVMHEA LHNRFTQKSL SLSPG                             455

SEQ ID NO: 555           moltype = AA  length = 691
FEATURE                  Location/Qualifiers
REGION                   1..691
                         note = SEQ ID NO: 555 - C1-D6-2x-G6DU-BTB
source                   1..691
                         mol_type = protein
                         organism = synthetic construct
SEQUENCE: 555
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SGGGGSQVQL  240
VQSGAEVKKP GSSVKVSCKA SGVDFTKYAI HWVRQAPGQG LEWMGGIVPA EGDANYAQKF  300
QGRVTITADE STSTAYMELS SLRSEDTAVY YCARDVLSAG DGYYLYDLMD VWGQGTLVTV  360
SSASTKGPSV FPLAPSSKST SGGTAALGCL VKDYFPEPVT VSWNSGALTS GVHTFPAVLQ  420
SSGLYSLSSV VTVPSSSLGT QTYICNVNHK PSNTKVDKKV EPKSCDKTHT CPPCPAPEAA  480
GGPSVFLFPP KPKDTLMISR TPEVTCVVVD VSHEDPEVKF NWYVDGVEVH NAKTKPREEQ  540
YNSTYRVVSV LTVLHQDWLN GKEYKCKVSN KALAAPIEKT ISKAKGQPRE PEVATFPPSR  600
DELTKNQVTL VCLVTGFYPS DIAVEWESNG QPENNYKTDP PLLESQGSFA LSSRLRVDKS  660
RWQQGNVFSC SVMHEALHNH YTQKSLSLSP G                                 691

SEQ ID NO: 556           moltype = AA  length = 447
FEATURE                  Location/Qualifiers
REGION                   1..447
                         note = SEQ ID NO: 556 - C1-D6-BTA
source                   1..447
                         mol_type = protein
                         organism = synthetic construct
SEQUENCE: 556
QVQLVQSGAE VKKPGSSVKV SCKASGGKFS RYAISWVRQA PGQGLEWMGG ITALGGYPNY  60
```

```
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALA APIEKTISKA KGQPREPAVY TLPPSREEMT  360
KNQVKLVCLV TGFYPSDIAV EWESSGQPEN NYYTTPPMLD SDGSFSLVSW LNVDKSRWQQ  420
GNIFSCSVMH EALHNRFTQK SLSLSPG                                       447

SEQ ID NO: 557         moltype = AA  length = 452
FEATURE                Location/Qualifiers
REGION                 1..452
                       note = SEQ ID NO: 557 - E6-G6-N82aS-BTB
source                 1..452
                       mol_type = protein
                       organism = synthetic construct
SEQUENCE: 557
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALAAPIEK TISKAKGQPR EPEVATFPPS  360
RDELTKNQVT LVCLVTGFYP SDIAVEWESN GQPENNYKTD PPLLESQGSF ALSSRLRVDK  420
SRWQQGNVFS CSVMHEALHN HYTQKSLSLS PG                                 452

SEQ ID NO: 558         moltype = AA  length = 669
FEATURE                Location/Qualifiers
REGION                 1..669
                       note = SEQ ID NO: 558 - 83A10TCBcv-HC1
source                 1..669
                       mol_type = protein
                       organism = synthetic construct
SEQUENCE: 558
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKVL GWFDYWGQGT LVTVSSASTK  120
GPSVFPLAPS SKSTSGGTAA LGCLVEDYFP EPVTVSWNSG ALTSGVHTFP AVLQSSGLYS  180
LSSVVTVPSS SLGTQTYICN VNHKPSNTKV DEKVEPKSCD GGGGSGGGGS QAVVTQEPSL  240
TVSPGGTVTL TCGSSTGAVT TSNYANWVQE KPGQAFRGLI GGTNKRAPGT PARFSGSLLG  300
GKAALTLSGA QPEDEAEYYC ALWYSNLWVF GGGTKLTVLS SASTKGPSVF PLAPSSKSTS  360
GGTAALGCLV KDYFPEPVTV SWNSGALTSG VHTFPAVLQS SGLYSLSSVV TVPSSSLGTQ  420
TYICNVNHKP SNTKVDKKVE PKSCDKTHTC PPCPAPEAAG GPSVFLFPPK PKDTLMISRT  480
PEVTCVVVDV SHEDPEVKFN WYVDGVEVHN AKTKPREEQY NSTYRVVSVL TVLHQDWLNG  540
KEYKCKVSNK ALGAPIEKTI SKAKGQPREP QVYTLPPCRD ELTKNQVSLW CLVKGFYPSD  600
IAVEWESNGQ PENNYKTTPP VLDSDGSFFL YSKLTVDKSR WQQGNVFSCS VMHEALHNHY  660
TQKSLSLSP                                                           669

SEQ ID NO: 559         moltype = AA  length = 444
FEATURE                Location/Qualifiers
REGION                 1..444
                       note = SEQ ID NO: 559 - 83A10TCBcv-HC2
source                 1..444
                       mol_type = protein
                       organism = synthetic construct
SEQUENCE: 559
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKVL GWFDYWGQGT LVTVSSASTK  120
GPSVFPLAPS SKSTSGGTAA LGCLVEDYFP EPVTVSWNSG ALTSGVHTFP AVLQSSGLYS  180
LSSVVTVPSS SLGTQTYICN VNHKPSNTKV DEKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVCTL PPSRDELTKN  360
QVSLSCAVKG FYPSDIAVEW ESNGQPENNY KTTPPVLDSD GSFFLVSKLT VDKSRWQQGN  420
VFSCSVMHEA LHNHYTQKSL SLSP                                          444

SEQ ID NO: 560         moltype = AA  length = 216
FEATURE                Location/Qualifiers
REGION                 1..216
                       note = SEQ ID NO: 560 - 83A10TCBcv-LC1
source                 1..216
                       mol_type = protein
                       organism = synthetic construct
SEQUENCE: 560
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGYPPDFTF GQGTKVEIKR TVAAPSVFIF  120
PPSDRKLKSG TASVVCLLNN FYPREAKVQW KVDNALQSGN SQESVTEQDS KDSTYSLSST  180
LTLSKADYEK HKVYACEVTH QGLSSPVTKS FNRGEC                             216

SEQ ID NO: 561         moltype = AA  length = 232
FEATURE                Location/Qualifiers
REGION                 1..232
```

```
                        note = SEQ ID NO: 561 - 83A10TCBcv-LC2
source                  1..232
                        mol_type = protein
                        organism = synthetic construct
SEQUENCE: 561
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSSASVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 562          moltype = AA  length = 451
FEATURE                 Location/Qualifiers
REGION                  1..451
                        note = SEQ ID NO: 562 - 9G7-BTA
source                  1..451
                        mol_type = protein
                        organism = synthetic construct
SEQUENCE: 562
QVTLKESGPT LVKPTQTLTL TCTFSGLSLS TSGKGVGWIR QPPGKALEWL AHIWWDDDKR  60
YNPALKSRLT ITKDTSKNQV VLTMTNMDPV DTATYYCARI ELGRSYVMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVQFK WYVDGVEVHN AKTKPREEQY  300
NSTFRVVSVL TVLHQDWLNG KEYKCKVSNK ALPAPIEKTI SKTKGQPREP AVYTLPPSRE  360
EMTKNQVKLV CLVTGFYPSD IAVEWESSGQ PENNYYTTPP MLDSDGSFSL VSWLNVDKSR  420
WQQGNIFSCS VMHEALHNRF TQKSLSLSPG K                                 451

SEQ ID NO: 563          moltype = AA  length = 214
FEATURE                 Location/Qualifiers
REGION                  1..214
                        note = SEQ ID NO: 563 - 9G7-LC
source                  1..214
                        mol_type = protein
                        organism = synthetic construct
SEQUENCE: 563
DIQMTQSPSS LSASVGDRVT ITCQASQDVI TSVAWYQQKP GKAPKLLIYS ASYRYTGVPS  60
RFSGSGSGTD FTFTISSLQP EDIATYYCQQ HYTIPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 564          moltype = AA  length = 482
FEATURE                 Location/Qualifiers
REGION                  1..482
                        note = SEQ ID NO: 564 - SP34v3-BTB
source                  1..482
                        mol_type = protein
                        organism = synthetic construct
SEQUENCE: 564
EVQLVESGGG LVQPGGSLRL SCAASGFTFN TYAMNWVRQA PGKGLEWVAR IRSKYNNYAT  60
YYADSVKGRF TISRDDSKNT LYLQMNSLRA EDTAVYYCVR HGNFGNSYVS YFAYWGQGTT  120
VTVSSGGGGS GGGGSGGGGS EIVVTQSPAT LSVSPGERAT LSCRSSTGAV TESNYANWVQ  180
EKPGQAFRGL IGGANKRAPG VPARFSGSLS GDEATLTISS LQSEDFAVYY CALFYSNTWV  240
FGQGTKLEIK GGGGTDKTHT CPPCPAPEAA GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
KALPAPIEKT ISKAKGQPRE PEVATFPPSR DELTKNQVTL VCLVTGFYPS DIAVEWESNG  420
QPENNYKTDP PLLESQGSFA LSSRLRVDKS RWQQGNVFSC SVMHEALHNH YTQKSLSLSP  480
GK                                                                482

SEQ ID NO: 565          moltype = AA  length = 452
FEATURE                 Location/Qualifiers
REGION                  1..452
                        note = SEQ ID NO: 565 - daratumumabHC
source                  1..452
                        mol_type = protein
                        organism = synthetic construct
SEQUENCE: 565
EVQLLESGGG LVQPGGSLRL SCAVSGFTFN SFAMSWVRQA PGKGLEWVSA ISGSGGGTYY  60
ADSVKGRFTI SRDNSKNTLY LQMNSLRAED TAVYFCAKDK ILWFGEPVFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 566          moltype = AA  length = 214
FEATURE                 Location/Qualifiers
REGION                  1..214
                        note = SEQ ID NO: 566 - daratumumabLC
```

```
source                  1..214
                        mol_type = protein
                        organism = synthetic construct
SEQUENCE: 566
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 567          moltype = AA  length = 444
FEATURE                 Location/Qualifiers
REGION                  1..444
                        note = SEQ ID NO: 567 - h5F9 IgG4HS heavy chain
source                  1..444
                        mol_type = protein
                        organism = synthetic construct
SEQUENCE: 567
QVQLVQSGAE VKKPGASVKV SCKASGYTFT NYNMHWVRQA PGQRLEWMGT IYPGNDDTSY  60
NQKFKDRVTI TADTSASTAY MELSSLRSED TAVYYCARGG YRAMDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 568          moltype = AA  length = 219
FEATURE                 Location/Qualifiers
REGION                  1..219
                        note = SEQ ID NO: 568 - h5F9 IgG4 HS lightchain
source                  1..219
                        mol_type = protein
                        organism = synthetic construct
SEQUENCE: 568
DIVMTQSPLS LPVTPGEPAS ISCRSSQSIV YSNGNTYLGW YLQKPGQSPQ LLIYKVSNRF  60
SGVPDRFSGS GSGTDFTLKI SRVEAEDVGV YYCFQGSHVP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 569          moltype = AA  length = 450
FEATURE                 Location/Qualifiers
REGION                  1..450
                        note = SEQ ID NO: 569 - isatuximabHC
source                  1..450
                        mol_type = protein
                        organism = synthetic construct
SEQUENCE: 569
QVQLVQSGAE VAKPGTSVKL SCKASGYTFT DYWMQWVKQR PGQGLEWIGT IYPGDGDTGY  60
AQKFQGKATL TADKSSKTVY MHLSSLASED SAVYYCARGD YYGSNSLDYW GQGTSVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 570          moltype = AA  length = 214
FEATURE                 Location/Qualifiers
REGION                  1..214
                        note = SEQ ID NO: 570 - isatuximabLC
source                  1..214
                        mol_type = protein
                        organism = synthetic construct
SEQUENCE: 570
DIVMTQSHLS MSTSLGDPVS ITCKASQDVS TVVAWYQQKP GQSPRRLIYS ASYRYIGVPD  60
RFTGSGAGTD FTFTISSVQA EDLAVYYCQQ HYSPPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 571          moltype = AA  length = 452
FEATURE                 Location/Qualifiers
REGION                  1..452
                        note = SEQ ID NO: 571 - TNB-F2B BEAT Fc HC1
source                  1..452
                        mol_type = protein
                        organism = synthetic construct
SEQUENCE: 571
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDS RGYGDYRLGG AYWGQGTLVT  120
```

```
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPAVYTLPPS  360
REEMTKNQVK LVCLVTGFYP SDIAVEWESS GQPENNYYTT PPMLDSDGSF SLVSWLNVDK  420
SRWQQGNIFS CSVMHEALHN RFTQKSLSLS PG                               452

SEQ ID NO: 572         moltype = AA  length = 474
FEATURE                Location/Qualifiers
REGION                 1..474
                       note = SEQ ID NO: 572 - TNB-F2B BEAT Fc HC2
source                 1..474
                       mol_type = protein
                       organism = synthetic construct
SEQUENCE: 572
EVQLLESGGG LVQPGGSLRL SCAASGFTVS SYGMSWVRQA PGKGPEWVSG IRGSDGSTYY  60
ADSVKSRFTI SRDNSKNTLY LQMNSLRAED TAVYYCAKQG ENDGPFDHRG QGTLVTVSSG  120
GGGSEVQLLE SGGGLVQPGG SLRLSCAASG FTVSSYGMSW VRQAPGKGPE WVSGIRGSDG  180
STYYADSVKS RFTISRDNSK NTLYLQMNSL RAEDTAVYYC AKQGENDGPF DHRGQGTLVT  240
VSSGGGGTDK THTCPPCPAP EAAGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPEVATFP PSRDELTKNQ VTLVCLVTGF YPSDIAVEWE SNGQPENNYK  420
TDPPLLESQG SFALSSRLRV DKSRWQQGNV FSCSVMHEAL HNHYTQKSLS LSPG        474

SEQ ID NO: 573         moltype = AA  length = 10
FEATURE                Location/Qualifiers
REGION                 1..10
                       note = SEQ ID NO: 573 - D3-E11CDR-H1
source                 1..10
                       mol_type = protein
                       organism = synthetic construct
SEQUENCE: 573
GFIFSHYEMN                                                        10

SEQ ID NO: 574         moltype = AA  length = 10
FEATURE                Location/Qualifiers
REGION                 1..10
                       note = SEQ ID NO: 574 - D3-E11CDR-H2
source                 1..10
                       mol_type = protein
                       organism = synthetic construct
SEQUENCE: 574
AIGQLGGNTV                                                        10

SEQ ID NO: 575         moltype = AA  length = 17
FEATURE                Location/Qualifiers
REGION                 1..17
                       note = SEQ ID NO: 575 - D3-E11CDR-H3
source                 1..17
                       mol_type = protein
                       organism = synthetic construct
SEQUENCE: 575
YCARVPYSYS GYSGADI                                                17

SEQ ID NO: 576         moltype = AA  length = 10
FEATURE                Location/Qualifiers
REGION                 1..10
                       note = SEQ ID NO: 576 - E6-G6CDR-H1
source                 1..10
                       mol_type = protein
                       organism = synthetic construct
SEQUENCE: 576
GFTFSYYAMT                                                        10

SEQ ID NO: 577         moltype = AA  length = 10
FEATURE                Location/Qualifiers
REGION                 1..10
                       note = SEQ ID NO: 577 - E6-G6CDR-H2
source                 1..10
                       mol_type = protein
                       organism = synthetic construct
SEQUENCE: 577
TIAQRGGQTK                                                        10

SEQ ID NO: 578         moltype = AA  length = 16
FEATURE                Location/Qualifiers
REGION                 1..16
                       note = SEQ ID NO: 578 - E6-G6CDR-H3
source                 1..16
```

```
                        mol_type = protein
                        organism = synthetic construct
SEQUENCE: 578
ARSPYSYLHG YYGFDY                                                16

SEQ ID NO: 579          moltype = AA  length = 10
FEATURE                 Location/Qualifiers
REGION                  1..10
                        note = SEQ ID NO: 579 - C1-D6CDR-H1
source                  1..10
                        mol_type = protein
                        organism = synthetic construct
SEQUENCE: 579
GGKFSRYAIS                                                       10

SEQ ID NO: 580          moltype = AA  length = 10
FEATURE                 Location/Qualifiers
REGION                  1..10
                        note = SEQ ID NO: 580 - C1-D6CDR-H2
source                  1..10
                        mol_type = protein
                        organism = synthetic construct
SEQUENCE: 580
GITALGGYPN                                                       10

SEQ ID NO: 581          moltype = AA  length = 11
FEATURE                 Location/Qualifiers
REGION                  1..11
                        note = SEQ ID NO: 581 - C1-D6CDR-H3
source                  1..11
                        mol_type = protein
                        organism = synthetic construct
SEQUENCE: 581
ARYGYSLYMD I                                                     11

SEQ ID NO: 582          moltype = AA  length = 10
FEATURE                 Location/Qualifiers
REGION                  1..10
                        note = SEQ ID NO: 582 - B3CDR-H1
source                  1..10
                        mol_type = protein
                        organism = synthetic construct
SEQUENCE: 582
GGDFTLYSIS                                                       10

SEQ ID NO: 583          moltype = AA  length = 10
FEATURE                 Location/Qualifiers
REGION                  1..10
                        note = SEQ ID NO: 583 - B3CDR-H2
source                  1..10
                        mol_type = protein
                        organism = synthetic construct
SEQUENCE: 583
RIIPTGANAN                                                       10

SEQ ID NO: 584          moltype = AA  length = 14
FEATURE                 Location/Qualifiers
REGION                  1..14
                        note = SEQ ID NO: 584 - B3CDR-H3
source                  1..14
                        mol_type = protein
                        organism = synthetic construct
SEQUENCE: 584
ARSWPSLGSG WFDI                                                  14

SEQ ID NO: 585          moltype = AA  length = 10
FEATURE                 Location/Qualifiers
REGION                  1..10
                        note = SEQ ID NO: 585 - B3-C11CDR-H1
source                  1..10
                        mol_type = protein
                        organism = synthetic construct
SEQUENCE: 585
GGDFTLYSIS                                                       10

SEQ ID NO: 586          moltype = AA  length = 10
FEATURE                 Location/Qualifiers
REGION                  1..10
                        note = SEQ ID NO: 586 - B3-C11CDR-H2
```

```
source                  1..10
                        mol_type = protein
                        organism = synthetic construct
SEQUENCE: 586
RIIPTGANAN                                                       10

SEQ ID NO: 587          moltype = AA  length = 14
FEATURE                 Location/Qualifiers
REGION                  1..14
                        note = SEQ ID NO: 587 - B3-C11CDR-H3
source                  1..14
                        mol_type = protein
                        organism = synthetic construct
SEQUENCE: 587
ARSTPTYGSG WFDI                                                  14

SEQ ID NO: 588          moltype = AA  length = 10
FEATURE                 Location/Qualifiers
REGION                  1..10
                        note = SEQ ID NO: 588 - E2-A5CDR-H1
source                  1..10
                        mol_type = protein
                        organism = synthetic construct
SEQUENCE: 588
GGSFSNYAIG                                                       10

SEQ ID NO: 589          moltype = AA  length = 10
FEATURE                 Location/Qualifiers
REGION                  1..10
                        note = SEQ ID NO: 589 - E2-A5CDR-H2
source                  1..10
                        mol_type = protein
                        organism = synthetic construct
SEQUENCE: 589
RIIPDLGAAH                                                       10

SEQ ID NO: 590          moltype = AA  length = 16
FEATURE                 Location/Qualifiers
REGION                  1..16
                        note = SEQ ID NO: 590 - E2-A5CDR-H3
source                  1..16
                        mol_type = protein
                        organism = synthetic construct
SEQUENCE: 590
ARGLGYYLYS SYYFDI                                                16

SEQ ID NO: 591          moltype = AA  length = 123
FEATURE                 Location/Qualifiers
REGION                  1..123
                        note = SEQ ID NO: 591 - E6-G6VH(N82aS)
source                  1..123
                        mol_type = protein
                        organism = synthetic construct
SEQUENCE: 591
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSS                                                              123

SEQ ID NO: 592          moltype = AA  length = 118
FEATURE                 Location/Qualifiers
REGION                  1..118
                        note = SEQ ID NO: 592 - C1-D6VH
source                  1..118
                        mol_type = protein
                        organism = synthetic construct
SEQUENCE: 592
QVQLVQSGAE VKKPGSSVKV SCKASGGKFS RYAISWVRQA PGQGLEWMGG ITALGGYPNY  60
AQKFQGRVTI TADESTSTAY MELSSLRSED TAVYYCARYG YSLYMDIWGQ GTLVTVSS    118

SEQ ID NO: 593          moltype = AA  length = 121
FEATURE                 Location/Qualifiers
REGION                  1..121
                        note = SEQ ID NO: 593 - B3VH
source                  1..121
                        mol_type = protein
                        organism = synthetic construct
SEQUENCE: 593
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARSW PSLGSGWFDI WGQGTLVTVS  120
```

```
S                                                                 121

SEQ ID NO: 594         moltype = AA  length = 121
FEATURE                Location/Qualifiers
REGION                 1..121
                       note = SEQ ID NO: 594 - B3-C11VH
source                 1..121
                       mol_type = protein
                       organism = synthetic construct
SEQUENCE: 594
QVQLVQSGAE VKKPGSSVKV SCKASGGDFT LYSISWVRQA PGQGLEWMGR IIPTGANANY  60
AQKFQGRVTI TADESTSTAY MELSSLRSED TAVYYCARST PTYGSGWFDI WGQGTLVTVS  120
S                                                                 121

SEQ ID NO: 595         moltype = AA  length = 123
FEATURE                Location/Qualifiers
REGION                 1..123
                       note = SEQ ID NO: 595 - E2-A5VH
source                 1..123
                       mol_type = protein
                       organism = synthetic construct
SEQUENCE: 595
QVQLVQSGAE VKKPGSSVKV SCKASGGSFS NYAIGWVRQA PGQGLEWMGR IIPDLGAAHY  60
AQKFQGRVTI TADESTSTAY MELSSLRSED TAVYYCARGL GYYLYSSYYF DIWGQGTLVT  120
VSS                                                               123

SEQ ID NO: 596         moltype = AA  length = 122
FEATURE                Location/Qualifiers
REGION                 1..122
                       note = SEQ ID NO: 596 - D3-E11VH
source                 1..122
                       mol_type = protein
                       organism = synthetic construct
SEQUENCE: 596
EVQLVESGGG LIQPGGSLRL SCAASGFIFS HYEMNWVRQA PGKGLEWVSA IGQLGGNTVY  60
ADSVKGRFTI SRDNSKNTLY LQMNSLRAED TAVYYCARVP YSYSGYSGAD IWGQGTLVTV  120
SS                                                                122

SEQ ID NO: 597         moltype = AA  length = 329
FEATURE                Location/Qualifiers
REGION                 1..329
                       note = SEQ ID NO: 597 - BTBFcLALAP329AD401Q
source                 1..329
                       mol_type = protein
                       organism = synthetic construct
SEQUENCE: 597
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LAAPIEKTIS KAKGQPREPE VATFPPSRDE  240
LTKNQVTLVC LVTGFYPSDI AVEWESNGQP ENNYKTDPPL LESQGSFALS SRLRVDKSRW  300
QQGNVFSCSV MHEALHNHYT QKSLSLSPG                                   329

SEQ ID NO: 598         moltype = AA  length = 329
FEATURE                Location/Qualifiers
REGION                 1..329
                       note = SEQ ID NO: 598 - BTAFcLALAP329A
source                 1..329
                       mol_type = protein
                       organism = synthetic construct
SEQUENCE: 598
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LAAPIEKTIS KAKGQPREPA VYTLPPSREE  240
MTKNQVKLVC LVTGFYPSDI AVEWESSGQP ENNYYTTPPM LDSDGSFSLV SWLNVDKSRW  300
QQGNIFSCSV MHEALHNRFT QKSLSLSPG                                   329

SEQ ID NO: 599         moltype = AA  length = 185
FEATURE                Location/Qualifiers
REGION                 1..185
                       note = SEQ ID NO: 599 - human FcgR3a-C-His
source                 1..185
                       mol_type = protein
                       organism = synthetic construct
SEQUENCE: 599
GMRTEDLPKA VVFLEPQWYR VLEKDSVTLK CQGAYSPEDN STQWFHNESL ISSQASSYFI  60
DAATVDDSGE YRCQTNLSTL SDPVQLEVHI GWLLLQAPRW VFKEEDPIHL RCHSWKNTAL  120
HKVTYLQNGK GRKYFHHNSD FYIPKATLKD SGSYFCRGLV GSKNVSSETV NITNTQGSAH  180
```

```
HHHHH                                                                   185

SEQ ID NO: 600          moltype = AA  length = 179
FEATURE                 Location/Qualifiers
REGION                  1..179
                        note = SEQ ID NO: 600 - human FcgR2b-C-His
source                  1..179
                        mol_type = protein
                        organism = synthetic construct
SEQUENCE: 600
AAPPKAVLKL EPQWINVLQE DSVTLTCRGT HSPESDSIQW FHNGNLIPTH TQPSYRFKAN  60
NNDSGEYTCQ TGQTSLSDPV HLTVLSEWLV LQTPHLEFQE GETIVLRCHS WKDKPLVKVT  120
FFQNGKSKKF SRSDPNFSIP QANHSHSGDY HCTGNIGYTL YSSKPVTITV QAPHHHHHH   179

SEQ ID NO: 601          moltype = AA  length = 185
FEATURE                 Location/Qualifiers
REGION                  1..185
                        note = SEQ ID NO: 601 - Human FcgR2a-C-10His
source                  1..185
                        mol_type = protein
                        organism = synthetic construct
SEQUENCE: 601
QAAAPPKAVL KLEPPWINVL QEDSVTLTCQ GARSPESDSI QWFHNGNLIP THTQPSYRFK  60
ANNNDSGEYT CQTGQTSLSD PVHLTVLSEW LVLQTPHLEF QEGETIMLRC HSWKDKPLVK  120
VTFFQNGKSQ KFSRLDPTFS IPQANHSHSG DYHCTGNIGY TLFSSKPVTI TVQVPHHHHH  180
HHHHH                                                                   185

SEQ ID NO: 602          moltype = AA  length = 308
FEATURE                 Location/Qualifiers
REGION                  1..308
                        note = SEQ ID NO: 602 - human FcRn-Avi-His
source                  1..308
                        mol_type = protein
                        organism = synthetic construct
SEQUENCE: 602
AESHLSLLYH LTAVSSPAPG TPAFWVSGWL GPQQYLSYNS LRGEAEPCGA WVWENQVSWY  60
WEKETTDLRI KEKLFLEAFK ALGGKGPYTL QGLLGCELGP DNTSVPTAKF ALNGEEFMNF  120
DLKQGTWGGD WPEALAISQR WQQQDKAANK ELTFLLFSCP HRLREHLERG RGNLEWKEPP  180
SMRLKARPSS PGFSVLTCSA FSFYPPELQL RFLRNGLAAG TGQGDFGPNS DGSFHASSSL  240
TVKSGDEHHY CCIVQHAGLA QPLRVELESP AKSSGGGGTG GLNDIFEAQK IEWHEGGGHH  300
HHHHHHHH                                                                308

SEQ ID NO: 603          moltype = AA  length = 99
FEATURE                 Location/Qualifiers
REGION                  1..99
                        note = SEQ ID NO: 603 - human beta 2-microglobulin
source                  1..99
                        mol_type = protein
                        organism = synthetic construct
SEQUENCE: 603
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDM                          99

SEQ ID NO: 604          moltype = AA  length = 10
FEATURE                 Location/Qualifiers
REGION                  1..10
                        note = SEQ ID NO: 604 - G4Sx2 linker
source                  1..10
                        mol_type = protein
                        organism = synthetic construct
SEQUENCE: 604
GGGGSGGGGS                                                              10

SEQ ID NO: 605          moltype = AA  length = 15
FEATURE                 Location/Qualifiers
REGION                  1..15
                        note = SEQ ID NO: 605 - G4Sx3 linker
source                  1..15
                        mol_type = protein
                        organism = synthetic construct
SEQUENCE: 605
GGGGSGGGGS GGGGS                                                        15

SEQ ID NO: 606          moltype = AA  length = 204
FEATURE                 Location/Qualifiers
REGION                  1..204
                        note = SEQ ID NO: 606 - recombinant human CD3
                         proteinCD3(Q23-103)-linker-CD3(D23-V118)
source                  1..204
```

```
                         mol_type = protein
                         organism = synthetic construct
SEQUENCE: 606
MQSIKGNHLV KVYDYQEDGS VLLTCDAEAK NITWFKDGKM IGFLTEDKKK WNLGSNAKDP  60
RGMYQCKGSQ NKSKPLQVYY RMGSADDAKK DAAKKDDAKK DDAKKDGSDG NEEMGGITQT  120
PYKVSISGTT VILTCPQYPG SEILWQHNDK NIGGDEDDKN IGSDEDHLSL KEFSELEQSG  180
YYVCYPRGSK PEDANFYLYL RARV                                         204

SEQ ID NO: 607           moltype = AA  length = 264
FEATURE                  Location/Qualifiers
REGION                   1..264
                         note = SEQ ID NO: 607 - human CD38-ECD-C-His
source                   1..264
                         mol_type = protein
                         organism = synthetic construct
SEQUENCE: 607
VPRWRQQWSG PGTTKRFPET VLARCVKYTE IHPEMRHVDC QSVWDAFKGA FISKHPCNIT  60
EEDYQPLMKL GTQTVPCNKI LLWSRIKDLA HQFTQVQRDM FTLEDTLLGY LADDLTWCGE  120
FNTSKINYQS CPDWRKDCSN NPVSVFWKTV SRRFAEAACD VVHVMLNGSR SKIFDKNSTF  180
GSVEVHNLQP EKVQTLEAWV IHGGREDSRD LCQDPTIKEL ESIISKRNIQ FSCKNIYRPD  240
KFLQCVKNPE DSSCTSEIHH HHHH                                         264

SEQ ID NO: 608           moltype = AA  length = 264
FEATURE                  Location/Qualifiers
REGION                   1..264
                         note = SEQ ID NO: 608 - cynomolgus monkey CD38-ECD-C-His
source                   1..264
                         mol_type = protein
                         organism = synthetic construct
SEQUENCE: 608
VPRWRQQWSG SGTTSRFPET VLARCVKYTE VHPEMRHVDC QSVWDAFKGA FISKYPCNIT  60
EEDYQPLVKL GTQTVPCNKT LLWSRIKDLA HQFTQVQRDM FTLEDMLLGY LADDLTWCGE  120
FNTFEINYQS CPDWRKDCSN NPVSVFWKTV SRRFAETACG VVHVMLNGSR SKIFDKNSTF  180
GSVEVHNLQP EKVQALEAWV IHGGREDSRD LCQDPTIKEL ESIISKRNIR FFCKNIYRPD  240
KFLQCVKNPE DSSCLSGIHH HHHH                                         264

SEQ ID NO: 609           moltype = AA  length = 225
FEATURE                  Location/Qualifiers
REGION                   1..225
                         note = SEQ ID NO: 609 - daratumumab Fab VH-CH1
source                   1..225
                         mol_type = protein
                         organism = synthetic construct
SEQUENCE: 609
EVQLLESGGG LVQPGGSLRL SCAVSGFTFN SFAMSWVRQA PGKGLEWVSA ISGSGGGTYY  60
ADSVKGRFTI SRDNSKNTLY LQMNSLRAED TAVYFCAKDK ILWFGEPVFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                  225

SEQ ID NO: 610           moltype = AA  length = 201
FEATURE                  Location/Qualifiers
REGION                   1..201
                         note = SEQ ID NO: 610 - human CD3e(M1-D126)-B7.1
source                   1..201
                         mol_type = protein
                         organism = synthetic construct
SEQUENCE: 610
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDGGGG SPPEDPPDSK NTLVLFGAGF GAVITVVVIV VIIKCFCKHR SCFRRNEASR  180
ETNNSLTFGP EEALAEQTVF L                                            201

SEQ ID NO: 611           moltype = AA  length = 180
FEATURE                  Location/Qualifiers
REGION                   1..180
                         note = SEQ ID NO: 611 - human CD3d(M1-A105)-B7.1
source                   1..180
                         mol_type = protein
                         organism = synthetic construct
SEQUENCE: 611
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGGGGS PPEDPPDSKN  120
TLVLFGAGFG AVITVVVIVV IIKCFCKHRS CFRRNEASRE TNNSLTFGPE EALAEQTVFL  180

SEQ ID NO: 612           moltype = AA  length = 191
FEATURE                  Location/Qualifiers
REGION                   1..191
                         note = SEQ ID NO: 612 - human CD3g(M1-S116)-B7.1
source                   1..191
```

```
                        mol_type = protein
                        organism = synthetic construct
SEQUENCE: 612
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGGGG  120
SPPEDPPDSK NTLVLFGAGF GAVITVVVIV VIIKCFCKHR SCFRRNEASR ETNNSLTFGP  180
EEALAEQTVF L                                                       191

SEQ ID NO: 613          moltype = AA  length = 192
FEATURE                 Location/Qualifiers
REGION                  1..192
                        note = SEQ ID NO: 613 - cynoCD3d(M1-A105)-B7.1
source                  1..192
                        mol_type = protein
                        organism = synthetic construct
SEQUENCE: 613
MQSGTRWRVL GLCLLSIGVW GQDGNEEMGS ITQTPYQVSI SGTTVILTCS QHLGSEAQWQ  60
HNGKNKEDSG DRLFLPEFSE MEQSGYYVCY PRGSNPEDAS HHLYLKARVC ENCMEMDGGG  120
GSPPEDPPDS KNTLVLFGAG FGAVITVVVI VVIIKCFCKH RSCFRRNEAS RETNNSLTFG  180
PEEALAEQTV FL                                                      192

SEQ ID NO: 614          moltype = AA  length = 180
FEATURE                 Location/Qualifiers
REGION                  1..180
                        note = SEQ ID NO: 614 - cynoCD3e(M1-D117)-B7.1
source                  1..180
                        mol_type = protein
                        organism = synthetic construct
SEQUENCE: 614
MEHSTFLSGL VLATLLSQVS PFKIPVEELE DRVFVKCNTS VTWVEGTVGT LLTNNTRLDL  60
GKRILDPRGI YRCNGTDIYK DKESAVQVHY RMCQNCVELD PATLAGGGGS PPEDPPDSKN  120
TLVLFGAGFG AVITVVVIVV IIKCFCKHRS CFRRNEASRE TNNSLTFGPE EALAEQTVFL  180

SEQ ID NO: 615          moltype = AA  length = 184
FEATURE                 Location/Qualifiers
REGION                  1..184
                        note = SEQ ID NO: 615 - human BCMA
source                  1..184
                        mol_type = protein
                        organism = synthetic construct
SEQUENCE: 615
MLQMAGQCSQ NEYFDSLLHA CIPCQLRCSS NTPPLTCQRY CNASVTNSVK GTNAILWTCL  60
GLSLIISLAV FVLMFLLRKI NSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                               184

SEQ ID NO: 616          moltype = AA  length = 183
FEATURE                 Location/Qualifiers
REGION                  1..183
                        note = SEQ ID NO: 616 - cyno BCMA
source                  1..183
                        mol_type = protein
                        organism = synthetic construct
SEQUENCE: 616
MLQMARQCSQ NEYFDSLLHD CKPCQLRCSS TPPLTCQRYC NASMTNSVKG MNAILWTCLG  60
LSLIISLAVF VLTFLLRKMS SEPLKDEFKN TGSGLLGMAN IDLEKGRTGD EIVLPRGLEY  120
TVEECTCEDC IKNKPKVDSD HCFPLPAMEE GATILVTTKT NDYCNSLSAA LSVTEIEKSI  180
SAR                                                                183

SEQ ID NO: 617          moltype = AA  length = 299
FEATURE                 Location/Qualifiers
REGION                  1..299
                        note = SEQ ID NO: 617 - Full-length human CD38
source                  1..299
                        mol_type = protein
                        organism = synthetic construct
SEQUENCE: 617
ANCEFSPVSG DKPCCRLSRR AQLCLGVSIL VLILVVVLAV VVPRWRQQWS GPGTTKRFPE  60
TVLARCVKYT EIHPEMRHVD CQSVWDAFKG AFISKHPCNI TEEDYQPLMK LGTQTVPCNK  120
ILLWSRIKDL AHQFTQVQRD MFTLEDTLLG YLADDLTWCG EFNTSKINYQ SCPDWRKDCS  180
NNPVSVFWKT VSRRFAEAAC DVVHVMLNGS RSKIFDKNST FGSVEVHNLQ PEKVQTLEAW  240
VIHGGREDSR DLCQDPTIKE LESIISKRNI QFSCKNIYRP DKFLQCVKNP EDSSCTSEI   299

SEQ ID NO: 618          moltype = AA  length = 300
FEATURE                 Location/Qualifiers
REGION                  1..300
                        note = SEQ ID NO: 618 - Full-length cynomolgus monkey CD38
source                  1..300
                        mol_type = protein
```

```
                         organism = synthetic construct
SEQUENCE: 618
ANCEFSPVSG DKPCCRLSRR AQVCLGVCLL VLLILVVVVA VVLPRWRQQW SGSGTTSRFP  60
ETVLARCVKY TEVHPEMRHV DCQSVWDAFK GAFISKYPCN ITEEDYQPLV KLGTQTVPCN  120
KTLLWSRIKD LAHQFTQVQR DMFTLEDMLL GYLADDLTWC GEFNTFEINY QSCPDWRKDC  180
SNNPVSVFWK TVSRRFAETA CGVVHVMLNG SRSKIFDKNS TFGSVEVHNL QPEKVQALEA  240
WVIHGGREDS RDLCQDPTIK ELESIISKRN IRFFCKNIYR PDKFLQCVKN PEDSSCLSGI  300

SEQ ID NO: 619           moltype = AA  length = 227
FEATURE                  Location/Qualifiers
REGION                   1..227
                         note = SEQ ID NO: 619 - anti-CD38-UCP01-B1 FAB heavy chain
source                   1..227
                         mol_type = protein
                         organism = synthetic construct
SEQUENCE: 619
QVQLVQSGAE VKKPGSSVKV SCKASGGDFD QYYISWVRQA PGQGLEWMGR IIPTLGDSQY  60
AQKFQGRVTI TADESTSTAY MELSSLRSED TAVYYCARAV IVSPYYYIYV FDVWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSC                227

SEQ ID NO: 620           moltype = AA  length = 223
FEATURE                  Location/Qualifiers
REGION                   1..223
                         note = SEQ ID NO: 620 - anti-CD38-UCP01-D1 FAB heavy chain
source                   1..223
                         mol_type = protein
                         organism = synthetic construct
SEQUENCE: 620
QVQLVQSGAE VKKPGSSVKV SCKASGGIFN GYLISWVRQA PGQGLEWMGG IIPVNGLADY  60
AQKFQGRVTI TADESTSTAY MELSSLRSED TAVYYCARTI GRYIIAFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSC                    223

SEQ ID NO: 621           moltype = AA  length = 224
FEATURE                  Location/Qualifiers
REGION                   1..224
                         note = SEQ ID NO: 621 - anti-CD38-UCP01-F1 FAB heavy chain
source                   1..224
                         mol_type = protein
                         organism = synthetic construct
SEQUENCE: 621
QVQLVQSGAE VKKPGSSVKV SCKASGGVFS LYTITWVRQA PGQGLEWMGS IIPLLGDPEY  60
AQKFQGRVTI TADESTSTAY MELSSLRSED TAVYYCARYP YPYGSKYFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                   224

SEQ ID NO: 622           moltype = AA  length = 225
FEATURE                  Location/Qualifiers
REGION                   1..225
                         note = SEQ ID NO: 622 - anti-CD38-UCP01-G1 FAB heavy chain
source                   1..225
                         mol_type = protein
                         organism = synthetic construct
SEQUENCE: 622
QVQLVQSGAE VKKPGSSVKV SCKASGGGFS KYFITWVRQA PGQGLEWMGG VIPKIGYTSY  60
AQKFQGRVTI TADESTSTAY MELSSLRSED TAVYYCARGS DDYASYSPLD SWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                  225

SEQ ID NO: 623           moltype = AA  length = 220
FEATURE                  Location/Qualifiers
REGION                   1..220
                         note = SEQ ID NO: 623 - anti-CD38-UCP01-H1 FAB heavy chain
source                   1..220
                         mol_type = protein
                         organism = synthetic construct
SEQUENCE: 623
QVQLVQSGAE VKKPGSSVKV SCKASGDFFS GYAINWVRQA PGQGLEWMGR IIPLLGDTYY  60
AQKFQGRVTI TADESTSTAY MELSSLRSED TAVYYCARSA AGWFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC                        220

SEQ ID NO: 624           moltype = AA  length = 219
FEATURE                  Location/Qualifiers
REGION                   1..219
                         note = SEQ ID NO: 624 - anti-CD38-UCP01-C2 FAB heavy chain
source                   1..219
                         mol_type = protein
```

```
                         organism = synthetic construct
SEQUENCE: 624
QVQLVQSGAE VKKPGSSVKV SCKASGGYLG IYAISWVRQA PGQGLEWMGR IIPILGEADY  60
AQKFQGRVTI TADESTSTAY MELSSLRSED TAVYYCARGG VWWDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSC                       219

SEQ ID NO: 625           moltype = AA  length = 226
FEATURE                  Location/Qualifiers
REGION                   1..226
                         note = SEQ ID NO: 625 - anti-CD38-UCP02-A7 FAB heavy chain
source                   1..226
                         mol_type = protein
                         organism = synthetic construct
SEQUENCE: 625
EVQLLESGGG LVQPGGSLRL SCAASGFTFS FYDMSWVRQA PGKGLEWVST ITLHGGDTYY  60
ADSVKGRFTI SRDNSKNTLY LQMNSLRAED TAVYYCARDP SYIYSTSGYF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 626           moltype = AA  length = 228
FEATURE                  Location/Qualifiers
REGION                   1..228
                         note = SEQ ID NO: 626 - anti-CD38-UCP02-B1 FAB heavy chain
source                   1..228
                         mol_type = protein
                         organism = synthetic construct
SEQUENCE: 626
QVQLVQSGAE VKKPGSSVKV SCKASGGQFS FYAINWVRQA PGQGLEWMGE IIPDYGVTHY  60
AQKFQGRVTI TADESTSTAY MELSSLRSED TAVYYCARWS YTYGIRYYYK LFDPWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSC              228

SEQ ID NO: 627           moltype = AA  length = 225
FEATURE                  Location/Qualifiers
REGION                   1..225
                         note = SEQ ID NO: 627 - anti-CD38-UCP02-B7 FAB heavy chain
source                   1..225
                         mol_type = protein
                         organism = synthetic construct
SEQUENCE: 627
EVQLVESGGG LVKPGGSLRL SCAASGFSFN EAWMTWVRQA PGKGLEWVGR IKSYSDGGYT  60
GYAAPVKGRF TISRDDSKNT LYLQMNSLKT EDTAVYYCAR SPGIPYHYFD VWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                 225

SEQ ID NO: 628           moltype = AA  length = 224
FEATURE                  Location/Qualifiers
REGION                   1..224
                         note = SEQ ID NO: 628 - anti-CD38-UCP02-C3 FAB heavy chain
source                   1..224
                         mol_type = protein
                         organism = synthetic construct
SEQUENCE: 628
QVQLVQSGAE VKKPGSSVKV SCKASGDYFN NYAINWVRQA PGQGLEWMGR IIPFLDDANY  60
AQKFQGRVTI TADESTSTAY MELSSLRSED TAVYYCARAT SPLYSYYFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                  224

SEQ ID NO: 629           moltype = AA  length = 227
FEATURE                  Location/Qualifiers
REGION                   1..227
                         note = SEQ ID NO: 629 - anti-CD38-UCP02-D1 FAB heavy chain
source                   1..227
                         mol_type = protein
                         organism = synthetic construct
SEQUENCE: 629
QVQLVQSGAE VKKPGSSVKV SCKASGGDFD QYYISWVRQA PGQGLEWMGR IIPTLGDSQY  60
AQKFQGRVTI TADESTSTAY MELSSLRSED TAVYYCARAV IVSPYYYIYV FDVWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSC               227

SEQ ID NO: 630           moltype = AA  length = 225
FEATURE                  Location/Qualifiers
REGION                   1..225
                         note = SEQ ID NO: 630 - anti-CD38-UCP02-D5 FAB heavy chain
source                   1..225
                         mol_type = protein
                         organism = synthetic construct
```

```
SEQUENCE: 630
QVQLVQSGAE VKKPGSSVKV SCKASGGIFS VHAIHWVRQA PGQGLEWMGE IIPVIGEADY  60
AQKFQGRVTI TADESTSTAY MELSSLRSED TAVYYCAREQ YYYALGGGFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC                225

SEQ ID NO: 631          moltype = AA  length = 220
FEATURE                 Location/Qualifiers
REGION                  1..220
                        note = SEQ ID NO: 631 - anti-CD38-UCP02-E5 FAB heavy chain
source                  1..220
                        mol_type = protein
                        organism = synthetic construct
SEQUENCE: 631
QVQLVQSGAE VKKPGSSVKV SCKASGGGFR HYFISWVRQA PGQGLEWMGG IIPAAATPYY  60
AQKFQGRVTI TADESTSTAY MELSSLRSED TAVYYCARGY WHWFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC                      220

SEQ ID NO: 632          moltype = AA  length = 224
FEATURE                 Location/Qualifiers
REGION                  1..224
                        note = SEQ ID NO: 632 - anti-CD38-UCP02-F2 FAB heavy chain
source                  1..224
                        mol_type = protein
                        organism = synthetic construct
SEQUENCE: 632
QVQLVQSGAE VKKPGSSVKV SCKASGDVFS LLAIGWVRQA PGQGLEWMGR IIPSLDATHY  60
AQKFQGRVTI TADESTSTAY MELSSLRSED TAVYYCARGR DVLRSYYFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 633          moltype = AA  length = 224
FEATURE                 Location/Qualifiers
REGION                  1..224
                        note = SEQ ID NO: 633 - anti-CD38-UCP02-F5 FAB heavy chain
source                  1..224
                        mol_type = protein
                        organism = synthetic construct
SEQUENCE: 633
QVQLVQSGAE VKKPGSSVKV SCKASGGVFS YYTISWVRQA PGQGLEWMGR IIPSLGATHY  60
AQKFQGRVTI TADESTSTAY MELSSLRSED TAVYYCARSD SFYYAYYMDL WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                 224

SEQ ID NO: 634          moltype = AA  length = 226
FEATURE                 Location/Qualifiers
REGION                  1..226
                        note = SEQ ID NO: 634 - anti-CD38-UCP02-F6 FAB heavy chain
source                  1..226
                        mol_type = protein
                        organism = synthetic construct
SEQUENCE: 634
EVQLLESGGG LVQPGGSLRL SCAASGFTFS FYDMSWVRQA PGKGLEWVSA VSLYGDETYY  60
ADSVKGRFTI SRDNSKNTLY LQMNSLRAED TAVYYCAREP VSYDYYGSYF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC               226

SEQ ID NO: 635          moltype = AA  length = 223
FEATURE                 Location/Qualifiers
REGION                  1..223
                        note = SEQ ID NO: 635 - anti-CD38-UCP02-H1 FAB heavy chain
source                  1..223
                        mol_type = protein
                        organism = synthetic construct
SEQUENCE: 635
QVQLVQSGAE VKKPGSSVKV SCKASGDKFN TYAISWVRQA PGQGLEWMGG ITPRYDYAHY  60
AQKFQGRVTI TADESTSTAY MELSSLRSED TAVYYCARSW GFRAGYLDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSC                  223

SEQ ID NO: 636          moltype = AA  length = 224
FEATURE                 Location/Qualifiers
REGION                  1..224
                        note = SEQ ID NO: 636 - anti-CD38-UCP03-C3 FAB heavy chain
source                  1..224
                        mol_type = protein
                        organism = synthetic construct
SEQUENCE: 636
```

```
QVQLVQSGAE VKKPGSSVKV SCKASGGKFS NYAISWVRQA PGQGLEWMGR IIPQIGDAAY  60
AQKFQGRVTI TADESTSTAY MELSSLRSED TAVYYCARAS FLYYSYYFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 637          moltype = AA  length = 218
FEATURE                 Location/Qualifiers
REGION                  1..218
                        note = SEQ ID NO: 637 - anti-CD38-UCP03-H5 FAB heavy chain
source                  1..218
                        mol_type = protein
                        organism = synthetic construct
SEQUENCE: 637
QVQLVQSGAE VKKPGSSVKV SCKASGGLFS FYAISWVRQA PGQGLEWMGG IIPFFGEPQY  60
AQKFQGRVTI TADESTSTAY MELSSLRSED TAVYYCARGS YRFDVWGQGT LVTVSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSC                       218

SEQ ID NO: 638          moltype = AA  length = 224
FEATURE                 Location/Qualifiers
REGION                  1..224
                        note = SEQ ID NO: 638 - anti-CD38-UCP03-B6 FAB heavy chain
source                  1..224
                        mol_type = protein
                        organism = synthetic construct
SEQUENCE: 638
QVQLVQSGAE VKKPGSSVKV SCKASGGHIS NSAINWVRQA PGQGLEWMGR VIPVIDDAYY  60
AQKFQGRVTI TADESTSTAY MELSSLRSED TAVYYCARSR GYYGSFYFDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 639          moltype = AA  length = 225
FEATURE                 Location/Qualifiers
REGION                  1..225
                        note = SEQ ID NO: 639 - anti-CD38-UCP03-E3 FAB heavy chain
source                  1..225
                        mol_type = protein
                        organism = synthetic construct
SEQUENCE: 639
QVQLVQSGAE VKKPGSSVKV SCKASGGSFS IYAISWVRQA PGQGLEWMGG IIPNSGDTDY  60
AQKFQGRVTI TADESTSTAY MELSSLRSED TAVYYCARGP YDSYGESYFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSC               225

SEQ ID NO: 640          moltype = AA  length = 224
FEATURE                 Location/Qualifiers
REGION                  1..224
                        note = SEQ ID NO: 640 - anti-CD38-UCP03-A6 FAB heavy chain
source                  1..224
                        mol_type = protein
                        organism = synthetic construct
SEQUENCE: 640
QVQLVQSGAE VKKPGSSVKV SCKASGGDFS LYAISWVRQA PGQGLEWMGG IIPLLGEPVY  60
AQKFQGRVTI TADESTSTAY MELSSLRSED TAVYYCARGH RVYSSSPFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 641          moltype = AA  length = 224
FEATURE                 Location/Qualifiers
REGION                  1..224
                        note = SEQ ID NO: 641 - anti-CD38-UCP03-C2 FAB heavy chain
source                  1..224
                        mol_type = protein
                        organism = synthetic construct
SEQUENCE: 641
QVQLVQSGAE VKKPGSSVKV SCKASGGTFS NYAISWVRQA PGQGLEWMGG IIPAFGDAGY  60
AQKFQGRVTI TADESTSTAY MELSSLRSED TAVYYCARGR VLYYSYYFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSC                224

SEQ ID NO: 642          moltype = AA  length = 223
FEATURE                 Location/Qualifiers
REGION                  1..223
                        note = SEQ ID NO: 642 - anti-CD38-UCP03-H2 FAB heavy chain
source                  1..223
                        mol_type = protein
                        organism = synthetic construct
SEQUENCE: 642
QVQLVQSGAE VKKPGSSVKV SCKASGGEFS IYVISWVRQA PGQGLEWMGR VIPSTGDTNY  60
```

```
AQKFQGRVTI TADESTSTAY MELSSLRSED TAVYYCARGK AYYSGWLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSC                   223

SEQ ID NO: 643         moltype = AA  length = 218
FEATURE                Location/Qualifiers
REGION                 1..218
                       note = SEQ ID NO: 643 - anti-CD38-UCP03-H3 FAB heavy chain
source                 1..218
                       mol_type = protein
                       organism = synthetic construct
SEQUENCE: 643
QVQLVQSGAE VKKPGSSVKV SCKASGGVFS QFPISWVRQA PGQGLEWMGG IIAGYGATEY  60
AQKFQGRVTI TADESTSTAY MELSSLRSED TAVYYCARVY GGIDWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSC                         218

SEQ ID NO: 644         moltype = AA  length = 10
FEATURE                Location/Qualifiers
REGION                 1..10
                       note = SEQ ID NO: 644 - anti-CD38-UCP01-B1 CDRH1
source                 1..10
                       mol_type = protein
                       organism = synthetic construct
SEQUENCE: 644
GGDFDQYYIS                                                        10

SEQ ID NO: 645         moltype = AA  length = 10
FEATURE                Location/Qualifiers
REGION                 1..10
                       note = SEQ ID NO: 645 - anti-CD38-UCP01-D1 CDRH1
source                 1..10
                       mol_type = protein
                       organism = synthetic construct
SEQUENCE: 645
GGIFNGYLIS                                                        10

SEQ ID NO: 646         moltype = AA  length = 10
FEATURE                Location/Qualifiers
REGION                 1..10
                       note = SEQ ID NO: 646 - anti-CD38-UCP01-F1 CDRH1
source                 1..10
                       mol_type = protein
                       organism = synthetic construct
SEQUENCE: 646
GGVFSLYTIT                                                        10

SEQ ID NO: 647         moltype = AA  length = 10
FEATURE                Location/Qualifiers
REGION                 1..10
                       note = SEQ ID NO: 647 - anti-CD38-UCP01-G1 CDRH1
source                 1..10
                       mol_type = protein
                       organism = synthetic construct
SEQUENCE: 647
GGGFSKYFIT                                                        10

SEQ ID NO: 648         moltype = AA  length = 10
FEATURE                Location/Qualifiers
REGION                 1..10
                       note = SEQ ID NO: 648 - anti-CD38-UCP01-H1 CDRH1
source                 1..10
                       mol_type = protein
                       organism = synthetic construct
SEQUENCE: 648
GDFFSGYAIN                                                        10

SEQ ID NO: 649         moltype = AA  length = 10
FEATURE                Location/Qualifiers
REGION                 1..10
                       note = SEQ ID NO: 649 - anti-CD38-UCP01-C2 CDRH1
source                 1..10
                       mol_type = protein
                       organism = synthetic construct
SEQUENCE: 649
GGYLGIYAIS                                                        10

SEQ ID NO: 650         moltype = AA  length = 10
FEATURE                Location/Qualifiers
```

```
REGION                  1..10
                        note = SEQ ID NO: 650 - anti-CD38-UCP02-A7 CDRH1
source                  1..10
                        mol_type = protein
                        organism = synthetic construct
SEQUENCE: 650
GFTFSFYDMS                                                            10

SEQ ID NO: 651          moltype = AA  length = 10
FEATURE                 Location/Qualifiers
REGION                  1..10
                        note = SEQ ID NO: 651 - anti-CD38-UCP02-B1 CDRH1
source                  1..10
                        mol_type = protein
                        organism = synthetic construct
SEQUENCE: 651
GGQFSFYAIN                                                            10

SEQ ID NO: 652          moltype = AA  length = 10
FEATURE                 Location/Qualifiers
REGION                  1..10
                        note = SEQ ID NO: 652 - anti-CD38-UCP02-B7 CDRH1
source                  1..10
                        mol_type = protein
                        organism = synthetic construct
SEQUENCE: 652
GFSFNEAWMT                                                            10

SEQ ID NO: 653          moltype = AA  length = 10
FEATURE                 Location/Qualifiers
REGION                  1..10
                        note = SEQ ID NO: 653 - anti-CD38-UCP02-C3 CDRH1
source                  1..10
                        mol_type = protein
                        organism = synthetic construct
SEQUENCE: 653
GDYFNNYAIN                                                            10

SEQ ID NO: 654          moltype = AA  length = 10
FEATURE                 Location/Qualifiers
REGION                  1..10
                        note = SEQ ID NO: 654 - anti-CD38-UCP02-D1 CDRH1
source                  1..10
                        mol_type = protein
                        organism = synthetic construct
SEQUENCE: 654
GGDFDQYYIS                                                            10

SEQ ID NO: 655          moltype = AA  length = 10
FEATURE                 Location/Qualifiers
REGION                  1..10
                        note = SEQ ID NO: 655 - anti-CD38-UCP02-D5 CDRH1
source                  1..10
                        mol_type = protein
                        organism = synthetic construct
SEQUENCE: 655
GGIFSVHAIH                                                            10

SEQ ID NO: 656          moltype = AA  length = 10
FEATURE                 Location/Qualifiers
REGION                  1..10
                        note = SEQ ID NO: 656 - anti-CD38-UCP02-E5 CDRH1
source                  1..10
                        mol_type = protein
                        organism = synthetic construct
SEQUENCE: 656
GGGFRHYFIS                                                            10

SEQ ID NO: 657          moltype = AA  length = 10
FEATURE                 Location/Qualifiers
REGION                  1..10
                        note = SEQ ID NO: 657 - anti-CD38-UCP02-F2 CDRH1
source                  1..10
                        mol_type = protein
                        organism = synthetic construct
SEQUENCE: 657
GDVFSLLAIG                                                            10

SEQ ID NO: 658          moltype = AA  length = 10
```

```
FEATURE                 Location/Qualifiers
REGION                  1..10
                        note = SEQ ID NO: 658 - anti-CD38-UCP02-F5 CDRH1
source                  1..10
                        mol_type = protein
                        organism = synthetic construct
SEQUENCE: 658
GGVFSYYTIS                                                      10

SEQ ID NO: 659          moltype = AA  length = 10
FEATURE                 Location/Qualifiers
REGION                  1..10
                        note = SEQ ID NO: 659 - anti-CD38-UCP02-F6 CDRH1
source                  1..10
                        mol_type = protein
                        organism = synthetic construct
SEQUENCE: 659
GFTFSFYDMS                                                      10

SEQ ID NO: 660          moltype = AA  length = 10
FEATURE                 Location/Qualifiers
REGION                  1..10
                        note = SEQ ID NO: 660 - anti-CD38-UCP02-H1 CDRH1
source                  1..10
                        mol_type = protein
                        organism = synthetic construct
SEQUENCE: 660
GDKFNTYAIS                                                      10

SEQ ID NO: 661          moltype = AA  length = 10
FEATURE                 Location/Qualifiers
REGION                  1..10
                        note = SEQ ID NO: 661 - anti-CD38-UCP03-C3 CDRH1
source                  1..10
                        mol_type = protein
                        organism = synthetic construct
SEQUENCE: 661
GGKFSNYAIS                                                      10

SEQ ID NO: 662          moltype = AA  length = 10
FEATURE                 Location/Qualifiers
REGION                  1..10
                        note = SEQ ID NO: 662 - anti-CD38-UCP03-H5 CDRH1
source                  1..10
                        mol_type = protein
                        organism = synthetic construct
SEQUENCE: 662
GGLFSFYAIS                                                      10

SEQ ID NO: 663          moltype = AA  length = 10
FEATURE                 Location/Qualifiers
REGION                  1..10
                        note = SEQ ID NO: 663 - anti-CD38-UCP03-B6 CDRH1
source                  1..10
                        mol_type = protein
                        organism = synthetic construct
SEQUENCE: 663
GGHISNSAIN                                                      10

SEQ ID NO: 664          moltype = AA  length = 10
FEATURE                 Location/Qualifiers
REGION                  1..10
                        note = SEQ ID NO: 664 - anti-CD38-UCP03-E3 CDRH1
source                  1..10
                        mol_type = protein
                        organism = synthetic construct
SEQUENCE: 664
GGSFSIYAIS                                                      10

SEQ ID NO: 665          moltype = AA  length = 10
FEATURE                 Location/Qualifiers
REGION                  1..10
                        note = SEQ ID NO: 665 - anti-CD38-UCP03-A6 CDRH1
source                  1..10
                        mol_type = protein
                        organism = synthetic construct
SEQUENCE: 665
GGDFSLYAIS                                                      10
```

```
SEQ ID NO: 666          moltype = AA  length = 10
FEATURE                 Location/Qualifiers
REGION                  1..10
                        note = SEQ ID NO: 666 - anti-CD38-UCP03-C2 CDRH1
source                  1..10
                        mol_type = protein
                        organism = synthetic construct
SEQUENCE: 666
GGTFSNYAIS                                                        10

SEQ ID NO: 667          moltype = AA  length = 10
FEATURE                 Location/Qualifiers
REGION                  1..10
                        note = SEQ ID NO: 667 - anti-CD38-UCP03-H2 CDRH1
source                  1..10
                        mol_type = protein
                        organism = synthetic construct
SEQUENCE: 667
GGEFSIYVIS                                                        10

SEQ ID NO: 668          moltype = AA  length = 10
FEATURE                 Location/Qualifiers
REGION                  1..10
                        note = SEQ ID NO: 668 - anti-CD38-UCP03-H3 CDRH1
source                  1..10
                        mol_type = protein
                        organism = synthetic construct
SEQUENCE: 668
GGVFSQFPIS                                                        10

SEQ ID NO: 669          moltype = AA  length = 10
FEATURE                 Location/Qualifiers
REGION                  1..10
                        note = SEQ ID NO: 669 - anti-CD38-UCP01-B1 CDRH2
source                  1..10
                        mol_type = protein
                        organism = synthetic construct
SEQUENCE: 669
RIIPTLGDSQ                                                        10

SEQ ID NO: 670          moltype = AA  length = 10
FEATURE                 Location/Qualifiers
REGION                  1..10
                        note = SEQ ID NO: 670 - anti-CD38-UCP01-D1 CDRH2
source                  1..10
                        mol_type = protein
                        organism = synthetic construct
SEQUENCE: 670
GIIPVNGLAD                                                        10

SEQ ID NO: 671          moltype = AA  length = 10
FEATURE                 Location/Qualifiers
REGION                  1..10
                        note = SEQ ID NO: 671 - anti-CD38-UCP01-F1 CDRH2
source                  1..10
                        mol_type = protein
                        organism = synthetic construct
SEQUENCE: 671
SIIPLLGDPE                                                        10

SEQ ID NO: 672          moltype = AA  length = 10
FEATURE                 Location/Qualifiers
REGION                  1..10
                        note = SEQ ID NO: 672 - anti-CD38-UCP01-G1 CDRH2
source                  1..10
                        mol_type = protein
                        organism = synthetic construct
SEQUENCE: 672
GVIPKIGYTS                                                        10

SEQ ID NO: 673          moltype = AA  length = 10
FEATURE                 Location/Qualifiers
REGION                  1..10
                        note = SEQ ID NO: 673 - anti-CD38-UCP01-H1 CDRH2
source                  1..10
                        mol_type = protein
                        organism = synthetic construct
SEQUENCE: 673
RIIPLLGDTY                                                        10
```

```
SEQ ID NO: 674          moltype = AA  length = 10
FEATURE                 Location/Qualifiers
REGION                  1..10
                        note = SEQ ID NO: 674 - anti-CD38-UCP01-C2 CDRH2
source                  1..10
                        mol_type = protein
                        organism = synthetic construct
SEQUENCE: 674
RIIPILGEAD                                                    10

SEQ ID NO: 675          moltype = AA  length = 10
FEATURE                 Location/Qualifiers
REGION                  1..10
                        note = SEQ ID NO: 675 - anti-CD38-UCP02-A7 CDRH2
source                  1..10
                        mol_type = protein
                        organism = synthetic construct
SEQUENCE: 675
TITLHGGDTY                                                    10

SEQ ID NO: 676          moltype = AA  length = 10
FEATURE                 Location/Qualifiers
REGION                  1..10
                        note = SEQ ID NO: 676 - anti-CD38-UCP02-B1 CDRH2
source                  1..10
                        mol_type = protein
                        organism = synthetic construct
SEQUENCE: 676
EIIPDYGVTH                                                    10

SEQ ID NO: 677          moltype = AA  length = 12
FEATURE                 Location/Qualifiers
REGION                  1..12
                        note = SEQ ID NO: 677 - anti-CD38-UCP02-B7 CDRH2
source                  1..12
                        mol_type = protein
                        organism = synthetic construct
SEQUENCE: 677
RIKSYSDGGY TG                                                 12

SEQ ID NO: 678          moltype = AA  length = 10
FEATURE                 Location/Qualifiers
REGION                  1..10
                        note = SEQ ID NO: 678 - anti-CD38-UCP02-C3 CDRH2
source                  1..10
                        mol_type = protein
                        organism = synthetic construct
SEQUENCE: 678
RIIPFLDDAN                                                    10

SEQ ID NO: 679          moltype = AA  length = 10
FEATURE                 Location/Qualifiers
REGION                  1..10
                        note = SEQ ID NO: 679 - anti-CD38-UCP02-D1 CDRH2
source                  1..10
                        mol_type = protein
                        organism = synthetic construct
SEQUENCE: 679
RIIPTLGDSQ                                                    10

SEQ ID NO: 680          moltype = AA  length = 10
FEATURE                 Location/Qualifiers
REGION                  1..10
                        note = SEQ ID NO: 680 - anti-CD38-UCP02-D5 CDRH2
source                  1..10
                        mol_type = protein
                        organism = synthetic construct
SEQUENCE: 680
EIIPVIGEAD                                                    10

SEQ ID NO: 681          moltype = AA  length = 10
FEATURE                 Location/Qualifiers
REGION                  1..10
                        note = SEQ ID NO: 681 - anti-CD38-UCP02-E5 CDRH2
source                  1..10
                        mol_type = protein
                        organism = synthetic construct
SEQUENCE: 681
```

```
GIIPAAATPY                                                        10

SEQ ID NO: 682          moltype = AA  length = 10
FEATURE                 Location/Qualifiers
REGION                  1..10
                        note = SEQ ID NO: 682 - anti-CD38-UCP02-F2 CDRH2
source                  1..10
                        mol_type = protein
                        organism = synthetic construct
SEQUENCE: 682
RIIPSLDATH                                                        10

SEQ ID NO: 683          moltype = AA  length = 10
FEATURE                 Location/Qualifiers
REGION                  1..10
                        note = SEQ ID NO: 683 - anti-CD38-UCP02-F5 CDRH2
source                  1..10
                        mol_type = protein
                        organism = synthetic construct
SEQUENCE: 683
RIIPSLGATH                                                        10

SEQ ID NO: 684          moltype = AA  length = 10
FEATURE                 Location/Qualifiers
REGION                  1..10
                        note = SEQ ID NO: 684 - anti-CD38-UCP02-F6 CDRH2
source                  1..10
                        mol_type = protein
                        organism = synthetic construct
SEQUENCE: 684
AVSLYGDETY                                                        10

SEQ ID NO: 685          moltype = AA  length = 10
FEATURE                 Location/Qualifiers
REGION                  1..10
                        note = SEQ ID NO: 685 - anti-CD38-UCP02-H1 CDRH2
source                  1..10
                        mol_type = protein
                        organism = synthetic construct
SEQUENCE: 685
GITPRYDYAH                                                        10

SEQ ID NO: 686          moltype = AA  length = 10
FEATURE                 Location/Qualifiers
REGION                  1..10
                        note = SEQ ID NO: 686 - anti-CD38-UCP03-C3 CDRH2
source                  1..10
                        mol_type = protein
                        organism = synthetic construct
SEQUENCE: 686
RIIPQIGDAA                                                        10

SEQ ID NO: 687          moltype = AA  length = 10
FEATURE                 Location/Qualifiers
REGION                  1..10
                        note = SEQ ID NO: 687 - anti-CD38-UCP03-H5 CDRH2
source                  1..10
                        mol_type = protein
                        organism = synthetic construct
SEQUENCE: 687
GIIPFFGEPQ                                                        10

SEQ ID NO: 688          moltype = AA  length = 10
FEATURE                 Location/Qualifiers
REGION                  1..10
                        note = SEQ ID NO: 688 - anti-CD38-UCP03-B6 CDRH2
source                  1..10
                        mol_type = protein
                        organism = synthetic construct
SEQUENCE: 688
RVIPVIDDAY                                                        10

SEQ ID NO: 689          moltype = AA  length = 10
FEATURE                 Location/Qualifiers
REGION                  1..10
                        note = SEQ ID NO: 689 - anti-CD38-UCP03-E3 CDRH2
source                  1..10
                        mol_type = protein
                        organism = synthetic construct
```

```
SEQUENCE: 689
GIIPNSGDTD                                                          10

SEQ ID NO: 690         moltype = AA  length = 10
FEATURE                Location/Qualifiers
REGION                 1..10
                       note = SEQ ID NO: 690 - anti-CD38-UCP03-A6 CDRH2
source                 1..10
                       mol_type = protein
                       organism = synthetic construct
SEQUENCE: 690
GIIPLLGEPV                                                          10

SEQ ID NO: 691         moltype = AA  length = 10
FEATURE                Location/Qualifiers
REGION                 1..10
                       note = SEQ ID NO: 691 - anti-CD38-UCP03-C2 CDRH2
source                 1..10
                       mol_type = protein
                       organism = synthetic construct
SEQUENCE: 691
GIIPAFGDAG                                                          10

SEQ ID NO: 692         moltype = AA  length = 10
FEATURE                Location/Qualifiers
REGION                 1..10
                       note = SEQ ID NO: 692 - anti-CD38-UCP03-H2 CDRH2
source                 1..10
                       mol_type = protein
                       organism = synthetic construct
SEQUENCE: 692
RVIPSTGDTN                                                          10

SEQ ID NO: 693         moltype = AA  length = 10
FEATURE                Location/Qualifiers
REGION                 1..10
                       note = SEQ ID NO: 693 - anti-CD38-UCP03-H3 CDRH2
source                 1..10
                       mol_type = protein
                       organism = synthetic construct
SEQUENCE: 693
GIIAGYGATE                                                          10

SEQ ID NO: 694         moltype = AA  length = 17
FEATURE                Location/Qualifiers
REGION                 1..17
                       note = SEQ ID NO: 694 - anti-CD38-UCP01-B1 CDRH3
source                 1..17
                       mol_type = protein
                       organism = synthetic construct
SEQUENCE: 694
ARAVIVSPYY YIYVFDV                                                  17

SEQ ID NO: 695         moltype = AA  length = 13
FEATURE                Location/Qualifiers
REGION                 1..13
                       note = SEQ ID NO: 695 - anti-CD38-UCP01-D1 CDRH3
source                 1..13
                       mol_type = protein
                       organism = synthetic construct
SEQUENCE: 695
ARTIGRYIIA FDY                                                      13

SEQ ID NO: 696         moltype = AA  length = 14
FEATURE                Location/Qualifiers
REGION                 1..14
                       note = SEQ ID NO: 696 - anti-CD38-UCP01-F1 CDRH3
source                 1..14
                       mol_type = protein
                       organism = synthetic construct
SEQUENCE: 696
ARYPYPYGSK YFDI                                                     14

SEQ ID NO: 697         moltype = AA  length = 15
FEATURE                Location/Qualifiers
REGION                 1..15
                       note = SEQ ID NO: 697 - anti-CD38-UCP01-G1 CDRH3
source                 1..15
                       mol_type = protein
```

```
                        organism = synthetic construct
SEQUENCE: 697
ARGSDDYASY SPLDS                                                    15

SEQ ID NO: 698          moltype = AA  length = 10
FEATURE                 Location/Qualifiers
REGION                  1..10
                        note = SEQ ID NO: 698 - anti-CD38-UCP01-H1 CDRH3
source                  1..10
                        mol_type = protein
                        organism = synthetic construct
SEQUENCE: 698
ARSAAGWFAY                                                          10

SEQ ID NO: 699          moltype = AA  length = 9
FEATURE                 Location/Qualifiers
REGION                  1..9
                        note = SEQ ID NO: 699 - anti-CD38-UCP01-C2 CDRH3
source                  1..9
                        mol_type = protein
                        organism = synthetic construct
SEQUENCE: 699
ARGGVWWDY                                                           9

SEQ ID NO: 700          moltype = AA  length = 16
FEATURE                 Location/Qualifiers
REGION                  1..16
                        note = SEQ ID NO: 700 - anti-CD38-UCP01-E2 CDRH3
source                  1..16
                        mol_type = protein
                        organism = synthetic construct
SEQUENCE: 700
ARGLGYYLYS SYYFDI                                                   16

SEQ ID NO: 701          moltype = AA  length = 16
FEATURE                 Location/Qualifiers
REGION                  1..16
                        note = SEQ ID NO: 701 - anti-CD38-UCP02-A7 CDRH3
source                  1..16
                        mol_type = protein
                        organism = synthetic construct
SEQUENCE: 701
ARDPSYIYST SGYFDY                                                   16

SEQ ID NO: 702          moltype = AA  length = 18
FEATURE                 Location/Qualifiers
REGION                  1..18
                        note = SEQ ID NO: 702 - anti-CD38-UCP02-B1 CDRH3
source                  1..18
                        mol_type = protein
                        organism = synthetic construct
SEQUENCE: 702
ARWSYTYGIR YYYKLFDP                                                 18

SEQ ID NO: 703          moltype = AA  length = 13
FEATURE                 Location/Qualifiers
REGION                  1..13
                        note = SEQ ID NO: 703 - anti-CD38-UCP02-B7 CDRH3
source                  1..13
                        mol_type = protein
                        organism = synthetic construct
SEQUENCE: 703
ARSPGIPYHY FDV                                                      13

SEQ ID NO: 704          moltype = AA  length = 14
FEATURE                 Location/Qualifiers
REGION                  1..14
                        note = SEQ ID NO: 704 - anti-CD38-UCP02-C3 CDRH3
source                  1..14
                        mol_type = protein
                        organism = synthetic construct
SEQUENCE: 704
ARATSPLYSY YFDY                                                     14

SEQ ID NO: 705          moltype = AA  length = 17
FEATURE                 Location/Qualifiers
REGION                  1..17
                        note = SEQ ID NO: 705 - anti-CD38-UCP02-D1 CDRH3
source                  1..17
```

```
                        mol_type = protein
                        organism = synthetic construct
SEQUENCE: 705
ARAVIVSPYY YIYVFDV                                              17

SEQ ID NO: 706          moltype = AA  length = 15
FEATURE                 Location/Qualifiers
REGION                  1..15
                        note = SEQ ID NO: 706 - anti-CD38-UCP02-D5 CDRH3
source                  1..15
                        mol_type = protein
                        organism = synthetic construct
SEQUENCE: 706
AREQYYYALG GGFDY                                                15

SEQ ID NO: 707          moltype = AA  length = 10
FEATURE                 Location/Qualifiers
REGION                  1..10
                        note = SEQ ID NO: 707 - anti-CD38-UCP02-E5 CDRH3
source                  1..10
                        mol_type = protein
                        organism = synthetic construct
SEQUENCE: 707
ARGYWHWFDY                                                      10

SEQ ID NO: 708          moltype = AA  length = 14
FEATURE                 Location/Qualifiers
REGION                  1..14
                        note = SEQ ID NO: 708 - anti-CD38-UCP02-F2 CDRH3
source                  1..14
                        mol_type = protein
                        organism = synthetic construct
SEQUENCE: 708
ARGRDVLRSY YFDI                                                 14

SEQ ID NO: 709          moltype = AA  length = 14
FEATURE                 Location/Qualifiers
REGION                  1..14
                        note = SEQ ID NO: 709 - anti-CD38-UCP02-F5 CDRH3
source                  1..14
                        mol_type = protein
                        organism = synthetic construct
SEQUENCE: 709
ARSDSFYYAY YMDL                                                 14

SEQ ID NO: 710          moltype = AA  length = 16
FEATURE                 Location/Qualifiers
REGION                  1..16
                        note = SEQ ID NO: 710 - anti-CD38-UCP02-F6 CDRH3
source                  1..16
                        mol_type = protein
                        organism = synthetic construct
SEQUENCE: 710
AREPVSYDYY GSYFDY                                               16

SEQ ID NO: 711          moltype = AA  length = 13
FEATURE                 Location/Qualifiers
REGION                  1..13
                        note = SEQ ID NO: 711 - anti-CD38-UCP02-H1 CDRH3
source                  1..13
                        mol_type = protein
                        organism = synthetic construct
SEQUENCE: 711
ARSWGFRAGY LDY                                                  13

SEQ ID NO: 712          moltype = AA  length = 14
FEATURE                 Location/Qualifiers
REGION                  1..14
                        note = SEQ ID NO: 712 - anti-CD38-UCP03-B3 CDRH3
source                  1..14
                        mol_type = protein
                        organism = synthetic construct
SEQUENCE: 712
ARSWPSLGSG WFDI                                                 14

SEQ ID NO: 713          moltype = AA  length = 14
FEATURE                 Location/Qualifiers
REGION                  1..14
                        note = SEQ ID NO: 713 - anti-CD38-UCP03-C3 CDRH3
```

```
source                  1..14
                        mol_type = protein
                        organism = synthetic construct
SEQUENCE: 713
ARASFLYYSY YFDY                                                             14

SEQ ID NO: 714          moltype = AA  length = 9
FEATURE                 Location/Qualifiers
REGION                  1..9
                        note = SEQ ID NO: 714 - anti-CD38-UCP03-H5 CDRH3
source                  1..9
                        mol_type = protein
                        organism = synthetic construct
SEQUENCE: 714
ARGSYRFDV                                                                   9

SEQ ID NO: 715          moltype = AA  length = 14
FEATURE                 Location/Qualifiers
REGION                  1..14
                        note = SEQ ID NO: 715 - anti-CD38-UCP03-B6 CDRH3
source                  1..14
                        mol_type = protein
                        organism = synthetic construct
SEQUENCE: 715
ARSRGYYGSF YFDI                                                             14

SEQ ID NO: 716          moltype = AA  length = 15
FEATURE                 Location/Qualifiers
REGION                  1..15
                        note = SEQ ID NO: 716 - anti-CD38-UCP03-E3 CDRH3
source                  1..15
                        mol_type = protein
                        organism = synthetic construct
SEQUENCE: 716
ARGPYDSYGE SYFDY                                                            15

SEQ ID NO: 717          moltype = AA  length = 14
FEATURE                 Location/Qualifiers
REGION                  1..14
                        note = SEQ ID NO: 717 - anti-CD38-UCP03-A6 CDRH3
source                  1..14
                        mol_type = protein
                        organism = synthetic construct
SEQUENCE: 717
ARGHRVYSSS PFDY                                                             14

SEQ ID NO: 718          moltype = AA  length = 14
FEATURE                 Location/Qualifiers
REGION                  1..14
                        note = SEQ ID NO: 718 - anti-CD38-UCP03-C2 CDRH3
source                  1..14
                        mol_type = protein
                        organism = synthetic construct
SEQUENCE: 718
ARGRVLYYSY YFDY                                                             14

SEQ ID NO: 719          moltype = AA  length = 13
FEATURE                 Location/Qualifiers
REGION                  1..13
                        note = SEQ ID NO: 719 - anti-CD38-UCP03-H2 CDRH3
source                  1..13
                        mol_type = protein
                        organism = synthetic construct
SEQUENCE: 719
ARGKAYYSGW LAI                                                              13

SEQ ID NO: 720          moltype = AA  length = 8
FEATURE                 Location/Qualifiers
REGION                  1..8
                        note = SEQ ID NO: 720 - anti-CD38-UCP03-H3 CDRH3
source                  1..8
                        mol_type = protein
                        organism = synthetic construct
SEQUENCE: 720
ARVYGGID                                                                    8

SEQ ID NO: 721          moltype = AA  length = 11
FEATURE                 Location/Qualifiers
REGION                  1..11
```

```
                         note = CDR-L1
source                   1..11
                         mol_type = protein
                         organism = synthetic construct
SEQUENCE: 721
RASQSVSSNL A                                                 11

SEQ ID NO: 722           moltype = AA  length = 7
FEATURE                  Location/Qualifiers
REGION                   1..7
                         note = CDR-L2
source                   1..7
                         mol_type = protein
                         organism = synthetic construct
SEQUENCE: 722
GASTRAT                                                      7

SEQ ID NO: 723           moltype = AA  length = 9
FEATURE                  Location/Qualifiers
REGION                   1..9
                         note = CDR-L3
source                   1..9
                         mol_type = protein
                         organism = synthetic construct
SEQUENCE: 723
QQYNNWPWT                                                    9

SEQ ID NO: 724           moltype = AA  length = 4
FEATURE                  Location/Qualifiers
REGION                   1..4
                         note = Linker 1
source                   1..4
                         mol_type = protein
                         organism = synthetic construct
SEQUENCE: 724
GGGT                                                         4

SEQ ID NO: 725           moltype = AA  length = 5
FEATURE                  Location/Qualifiers
REGION                   1..5
                         note = Linker 2
source                   1..5
                         mol_type = protein
                         organism = synthetic construct
SEQUENCE: 725
GGGGS                                                        5

SEQ ID NO: 726           moltype = AA  length = 16
FEATURE                  Location/Qualifiers
REGION                   1..16
                         note = Epitope
source                   1..16
                         mol_type = protein
                         organism = synthetic construct
SEQUENCE: 726
YVCYPRGSKP EDANFY                                            16

SEQ ID NO: 727           moltype = AA  length = 452
FEATURE                  Location/Qualifiers
source                   1..452
                         mol_type = protein
                         organism = synthetic construct
SEQUENCE: 727
EVQLLESGGG LVQPGGSLRL SCAASGFTFS YYAMTWVRQA PGKGLEWVST IAQRGGQTKY  60
ADSVKGRFTI SRDNSKNTLY LQMSSLRAED TAVYYCARSP YSYLHGYYGF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALAAPIEK TISKAKGQPR EPAVYTLPPS  360
REEMTKNQVK LVCLVTGFYP SDIAVEWESS GQPENNYYTT PPMLDSDGSF SLVSWLNVDK  420
SRWQQGNIFS CSVMHEALHN RFTQKSLSLS PG                          452

SEQ ID NO: 728           moltype = AA  length = 681
FEATURE                  Location/Qualifiers
source                   1..681
                         mol_type = protein
                         organism = synthetic construct
SEQUENCE: 728
QVQLVQSGAE VKKPGSSVKV SCKASGGKFS RYAISWVRQA PGQGLEWMGG ITALGGYPNY  60
```

-continued

```
AQKFQGRVTI TADESTSTAY MELSSLRSED TAVYYCARYG YSLYMDIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SQVQLVQSGA  240
EVKKPGSSVK VSCKASGGDF TLYSISWVRQ APGQGLEWMG RIIPTGANAN YAQKFQGRVT  300
ITADESTSTA YMELSSLRSE DTAVYYCARS TPTYGSGWFD IWGQGTLVTV SSASTKGPSV  360
FPLAPSSKST SGGTAALGCL VKDYFPEPVT VSWNSGALTS GVHTFPAVLQ SSGLYSLSSV  420
VTVPSSSLGT QTYICNVNHK PSNTKVDKKV EPKSCDKTHT CPPCPAPEAA GGPSVFLFPP  480
KPKDTLMISR TPEVTCVVVD VSHEDPEVKF NWYVDGVEVH NAKTKPREEQ YNSTYRVVSV  540
LTVLHQDWLN GKEYKCKVSN KALAAPIEKT ISKAKGQPRE PEVATFPPSR DELTKNQVTL  600
VCLVTGFYPS DIAVEWESNG QPENNYKTDP PLLESQGSFA LSSRLRVDKS RWQQGNVFSC  660
SVMHEALHNH YTQKSLSLSP G                                           681

SEQ ID NO: 729          moltype = AA  length = 264
FEATURE                 Location/Qualifiers
source                  1..264
                        mol_type = protein
                        organism = synthetic construct
SEQUENCE: 729
RWRQQWSGPG TTKRFPETVL ARCVKYTEIH PEMRHVDCQS VWDAFKGAFI SKHPCDITEE  60
DYQPLMKLGT QTVPCNKILL WSRIKDLAHQ FTQVQRDMFT LEDTLLGYLA DDLTWCGEFA  120
TSKINYQSCP DWRKDCSNNP VSVFWKTVSR RFAEAACDVV HVMLDGSRSK IFDKDSTFGS  180
VEVHNLQPEK VQTLEAWVIH GGREDSRDLC QDPTIKELES IISKRNIQFS CKNIYRPDKF  240
LQCVKNPEDS SCTSEIHHHH HHHH                                        264
```

CD3/BCMA/CD38 TRISPECIFIC ANTIBODIES

CROSS REFERENCE TO RELATED APPLICATIONS

This application claims priority to EP Application No. 22172090.7, filed May 6, 2022; EP Application No. 22186879.7, filed Jul. 26, 2022; EP Application No. 22207756.2, filed Nov. 16, 2022; and EP Application No. 22212233.5, filed Dec. 8, 2022, the contents of each of which are incorporated herein by reference in their entirety.

REFERENCE TO A SEQUENCE LISTING SUBMITTED ELECTRONICALLY VIA EFS-WEB

The content of the electronically submitted sequence listing (Name 3305_0400004_Seqlisting_ST26.xml; Size: 1,016,135 bytes; and Date of Creation: Sep. 12, 2023) is incorporated herein by reference in its entirety.

FIELD OF THE INVENTION

The present invention relates to novel trispecific heterodimeric immunoglobulins. More specifically the present invention relates to trispecific heterodimeric immunoglobulins that target an epitope of the human CD3 antigen, an epitope of the human BCMA and an epitope of the human CD38 antigen. The present invention also relates to this novel class of trispecific heterodimeric immunoglobulins for use in the treatment of proliferative diseases and in particular cancers such as hematological cancer.

BACKGROUND OF THE INVENTION

Multispecific antibodies that target one or more immune-related molecules and one or more tumor antigens to recruit immune cells, such as T cells, to tumor cells, have been developed in the past decades for cancer immunotherapy. For instance, antibodies bispecific for CD3 on T cells and for a surface target antigen on cancer cells are capable of connecting a T cell to a cancer cell, independently of T-cell receptor specificity, costimulation, or peptide antigen presentation (WO2020204708A1). Trispecific T-cell engaging antibodies have also showed promising results for the treatment of various cancers including breast cancer, lymphoma and multiple myeloma when two proteins are targeted on T cells and one on a tumor cell (U.S. Ser. No. 10/882,922B2). Additionally, tumor cell lysis has been proposed using trispecific binding molecules that engage two tumor-associated antigens expressed on cancer cells in addition to CD3 or other component of a TCR complex on T-cells (US20210163620A1).

Multispecific, immune cell redirecting antibodies have been shown to mediate T cell redirection both in pre-clinical and clinical investigations (May C et al., (2012) Biochem Pharmacol, 84(9): 1105-12; Frankel S R & Baeuerle P A, (2013) Curr Opin Chem Biol, 17(3): 385-92; Nie et al., (2020) Antibody Therapeutics, 3(1), 17-62), thus demonstrating their importance for new drug development and for the treatment of complex diseases such as inflammatory diseases, autoimmune disorders and cancer, such as hematological cancers, including Multiple Myeloma (MM) for which a curing treatment remains a need. Multiple myeloma is a neoplastic plasma-cell disorder characterized by clonal proliferation of malignant plasma cells in the bone marrow (BM) microenvironment, monoclonal protein in the blood or urine and associated organ dysfunction. Multiple myeloma accounts for 1-2% of all new cancer diagnoses and approximately 20% of all deaths from blood malignancies. The disease is slightly more common in males and African Americans than the general population. Multiple myeloma remains an incurable cancer, although recent improved understanding of the pathogenesis of myeloma has led to the development of new treatments and improved survival.

The diagnosis of multiple myeloma requires the presence of one or more myeloma defining events (MDE) in addition to evidence of either 10% or more clonal plasma cells on BM examination or a biopsy-proven plasmacytoma. MDE include so-called CRAB (hypercalcemia, renal failure, anemia, or lytic bone lesions) features as well as three specific biomarkers: clonal BM plasma cells >60%, serum free light chain (sFLC) ratio >100 (provided involved sFLC level is >100 mg/L), and more than 1 focal lesion on magnetic resonance imaging. Several genetic abnormalities that occur in tumor plasma cells play major roles in the pathogenesis of myeloma and determine disease prognosis.

The uncontrolled growth of myeloma cells has many consequences, including skeletal destruction, BM failure, increased plasma volume and viscosity, suppression of normal immunoglobulin production, and renal impairment.

Symptomatic (active) disease should be treated immediately, whereas asymptomatic (smoldering) myeloma requires only clinical observation, since early treatment with conventional chemotherapy has shown no clear benefit yet. Investigational trials are currently evaluating the ability of immunomodulatory drugs to delay the progression from asymptomatic to symptomatic myeloma. For active myeloma, current data support the initiation of induction therapy regimens including thalidomide, lenalidomide, and/or bortezomib followed by autologous hematopoietic stem-cell transplantation (HSCT) after major disease response for patients who can tolerate auto-HSCT conditioning regimens. Considerations of physiologic age, which may differ from chronologic age, and the presence of coexisting conditions drive decisions of treatment choice and drug dose. For example, less intensive approaches are desirable for patients with significant comorbidities, including cardiopulmonary or hepatic impairment, limiting treatment-related mortality, and mitigating risk of treatment interruption.

Treatment of relapsed/refractory multiple myeloma (RRMM) presents a special therapeutic challenge, due to the heterogeneity of disease at relapse and the absence of clear biological based recommendations regarding the choice of salvage therapies at various time points of disease progression. With increasing recognition of the inherent clonal heterogeneity and genomic instability of the plasma cells influencing both inherent and acquired therapeutic resistance, the identification of the optimal choice and sequence of therapies has become critical. New agents have gained approval by United States (US) Food and Drug Administration (FDA) for relapsed/refractory myeloma in recent years, including proteasome inhibitors (carfilzomib and ixazomib), immunomodulatory drugs such as the thalidomide derivatives pomalidomide and lenalidomide, and the histone deacetylase inhibitor panobinostat. Other molecularly targeted therapies directed at specific cell signaling pathways, as well as survival and proliferation controls (including P13K/AKT/mTOR inhibitors, Hsp90 inhibitors, cyclin-dependent kinase inhibitors, kinesin spindle protein inhibitors) are currently in development. Despite advances in the management of multiple myeloma, relapse is inevitable in almost all patients. Recurrence of myeloma is typically more aggressive with each relapse, which is associated with a shorter survival. Thus, additional treatment options are needed.

In recent years, multiple myeloma patients have benefited from new treatments targeting MM associated antigens such as CD38 and BCMA.

CD38 (UniProt P28907) was first identified in 1980 as a surface marker (cluster of differentiation) of thymus cell lymphocytes [Lee, H. C., ed. (2002). A Natural History of the Human CD38 Gene. Cyclic ADP-Ribose and NAADP. Springer Publishing]. In 1992, it was additionally described as a surface marker on B cells, monocytes, and natural killer cells (NK cells). About the same time, CD38 was discovered to be a marker of activated of B cells and T cells. Daratumumab (Darzalex), as well as isatuximab (SARCLISA) which target CD38 have been approved for the treatment of multiple myeloma.

B-cell maturation antigen, also known as BCMA, CD269, TNFRSF17 (UniProt Q02223), is a member of the tumor necrosis receptor superfamily that is preferentially expressed in differentiated plasma cells [Laabi et al. (1992) EMBO J 11(11):3897-3904; Madry et al. (1998) Int Immunol 10(11):1693-1702]. BCMA is a non-glycosylated type I transmembrane protein, which is involved in B cell maturation, growth, and survival. BCMA is a receptor for two ligands of the TNF superfamily: APRIL (a proliferation-inducing ligand, CD256, TNFSFi3), the high-affinity ligand to BCMA and the B cell activation factor BAFF (THANK, BlyS, B lymphocyte stimulator, TALL-1 and zTNF4), the low-affinity ligand to BCMA. APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g., Bcl-2, Bcl-xL, Bcl-w, Mcl-1, A1) and down regulates expression of pro-apoptotic factors (e.g., Bid, Bad, Bik, Bim, etc.), thus inhibiting apoptosis and promoting survival. This combined action promotes B cell differentiation, proliferation, survival, and antibody production (as reviewed in Rickert R C et al., Immunol Rev (2011) 244 (1): 115-133). In line with this finding, BCMA also supports growth and survival of malignant human B cells, including multiple myeloma cells.

Bispecific antibodies binding CD3 and BCMA for the treatment of MM, such as teclistamab, have been developed to induce T-cell mediated cytotoxicity against BCMA expressing MM cells and/or RRMM cells, alone or in combination with an immunotherapeutic drug such as thalidomide or an immunotherapeutic derivative such as an anti-PD-1 antibody and an anti-PD-L1 antibody (U.S. Ser. No. 11/124,577B2).

Exceptional overall response rate has been observed using bispecific antibodies or chimeric antigen receptor (CAR) T cells immunotherapy, in which T lymphocytes are engineered with synthetic chimeric antigen receptors. Nevertheless, durable responses beyond 2 years are still limited (Progression-free survival is below 40% for treatment with idecabtagene vicleucel (Munshi, N. C. et al. Idecabtagene Vicleucel in Relapsed and Refractory Multiple Myeloma. N. Engl. J. Med. 384, 705-716 (2021)) or teclistamab (Moreau, P. et al. Teclistamab in Relapsed or Refractory Multiple Myeloma. N. Engl. J. Med. NEJMoa2203478 (2022) doi: 10.1056/NEJMoa2203478). It has been proposed that one of the potential reasons for patient relapse may be downregulation of the target or expansion of clones lacking sufficient expression of targets (Rodriguez-Lobato, L. G., Oliver-Caldés, A., Moreno, D. F., Fernandez de Larrea, C. & Blade, J. Why Immunotherapy Fails in Multiple Myeloma. Hemato 2, 1-42 (2020)). This low expression of targets in the MM population has been observed after treatment with CD38-targeted daratumumab (Nijhof, I. S. et al. CD38 expression and complement inhibitors affect response and resistance to daratumumab therapy in myeloma. 128, 12 (2016)), and BCMA specific CAR T cells (Cohen, A. D. et al. B cell maturation antigen-specific CAR T cells are clinically active in multiple myeloma. J. Clin. Invest. 129, 2210-2221 (2019)). Consequently, the development of approaches that prevent tumor escape, often associated with lower surface expression of targeted tumor associated antigens remain a challenge.

Although promising treatments of hematological cancers, such as multiple myeloma, are nowadays available, the improvement of therapies, for instance effector cell redirecting antibody-based therapies, still remains a need. In fact, despite the increasing number of available treatments, the prognosis for multiple myeloma and relapsed/refractory multiple myeloma patients is still poor given the increasing evidence of resistance to the currently available treatments, and the necessity to maximise the therapeutic window.

DETAILED DESCRIPTION

The present invention relates to a trispecific antibody or antibody fragment thereof comprising at least three binding portions, at least one of which binds to human CD3, at least one which binds to human BCMA and at least one of which binds to human CD38.

The present invention also relates to a trispecific antibody or antibody fragment thereof comprising a common light chain.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain CDR set comprising an amino acid sequence selected from the group comprising: SEQ ID NO: 181, SEQ ID NO: 307, and SEQ ID NO: 433; SEQ ID NO: 184, SEQ ID NO: 310, and SEQ ID NO: 436; SEQ ID NO: 186, SEQ ID NO: 312, and SEQ ID NO: 438; SEQ ID NO: 188, SEQ ID NO: 314, and SEQ ID NO: 440; SEQ ID NO: 192, SEQ ID NO: 318, and SEQ ID NO: 444.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human BCMA comprises a heavy chain CDR set comprising an amino acid sequence selected from the group comprising: SEQ ID NO: 234, SEQ ID NO: 360, and SEQ ID NO: 486; SEQ ID NO: 219, SEQ ID NO: 345, and SEQ ID NO: 471; SEQ ID NO: 227, SEQ ID NO: 353, and SEQ ID NO: 479; SEQ ID NO: 231, SEQ ID NO: 357, and SEQ ID NO: 483.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD38 comprises a heavy chain CDR set comprising an amino acid sequence comprising: SEQ ID NO: 236, SEQ ID NO: 362, and SEQ ID NO: 712; SEQ ID NO: 239, SEQ ID NO: 365, and SEQ ID NO: 491; SEQ ID NO: 237, SEQ ID NO: 363, and SEQ ID NO: 700; SEQ ID NO: 248, SEQ ID NO: 374, and SEQ ID NO: 500.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain variable region of a heavy chain comprising an amino acid sequence that is at least about 85%, 86%, 87%, 88%, 89%, 90%, 91%, 92%, 93%, 94%, 95%, 96%, 97%, 98%, 99% or 100% identical to the amino acid sequence selected from the group comprising SEQ ID NOs: 55; 58; 60; 62 and 66.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 592.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human BCMA comprises a heavy chain variable region of a heavy chain comprising an amino acid sequence that is at least about 85%, 86%, 87%, 89%, 90%, 91%, 92%, 93%, 94%, 95%, 96%, 97%, 98%, 99% or 100% identical to the amino acid sequence selected from the group comprising SEQ ID NOs: 93, 101, 105 and 108.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human BCMA comprises a heavy chain variable region of a heavy chain comprising an amino acid sequence that is at least about 85%, 86%, 87%, 89%, 90%, 91%, 92%, 93%, 94%, 95%, 96%, 97%, 98%, 99% or 100% identical to the amino acid sequence selected from the group comprising SEQ ID NOs: 93, 101, 105 and 108, wherein said amino acid sequences of SEQ ID NOs: 93, 101, 105 and 108 further comprise the substitution N82aS.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human BCMA comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 591.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD38 comprises a heavy chain variable region of a heavy chain comprising an amino acid sequence that is at least about 85%, 86%, 87%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD38 comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 593 or 594.

The present invention also relates to a trispecific antibody or antibody fragment thereof further comprising a light chain variable region of a light chain comprising an amino acid sequence that is at least about 85%, 86%, 87%, 89%, 90%, 91%, 92%, 93%, 94%, 95%, 96%, 97%, 98%, 99% or 100% identical to an amino acid sequence of SEQ ID NO: 1.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain comprising an amino acid sequence that is at least about 85%, 86%, 87%, 88%, 89%, 90%, 91%, 92%, 93%, 94%, 95%, 96%, 97%, 98%, 99% or 100% identical to the amino acid sequence selected from the group comprising SEQ ID NOs: 55; 58; 60; 62 and 66.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human BCMA comprises a heavy chain comprising an amino acid sequence that is at least about 85%, 86%, 87%, 89%, 90%, 91%, 92%, 93%, 94%, 95%, 96%, 97%, 98%, 99% or 100% identical to the amino acid sequence selected from the group comprising SEQ ID NOs: 93, 101, 105 and 108; or to an amino acid sequence selected from the group comprising SEQ ID NOs: 93, 101, 105 and 108, wherein said amino acid sequences of SEQ ID NOs: 93, 101, 105 and 108 further comprise the substitution N82aS.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD38 comprises a heavy chain comprising an amino acid sequence that is at least about 85%, 86%, 87%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111.

The present invention also relates to a trispecific antibody or antibody fragment thereof further comprising a light chain comprising an amino acid sequence that is at least about 85%, 86%, 87%, 89%, 90%, 91%, 92%, 93%, 94%, 95%, 96%, 97%, 98%, 99% or 100% identical to an amino acid sequence of SEQ ID NO: 1.

The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain CDR set comprising an amino acid sequence of SEQ ID NO: 181, SEQ ID NO: 307, and SEQ ID NO: 433, and a light chain CDR set comprising amino acid sequence of SEQ ID NO: 721, SEQ ID NO: 722 and SEQ ID NO: 723; said at least one binding portion which binds to BCMA comprises a heavy chain CDR set comprising amino acid sequence of SEQ ID NO: 234, SEQ ID NO: 360, and SEQ ID NO: 486, and a light chain CDR set comprising amino acid sequence of SEQ ID NO: 721, SEQ ID NO: 722 and SEQ ID NO: 723; and said at least one binding portion which binds to human CD38 comprises a heavy chain CDR set comprising amino acid sequence of SEQ ID NO: 239, SEQ ID NO: 365, and SEQ ID NO: 491, and a light chain CDR set comprising amino acid sequence of SEQ ID NO: 721, SEQ ID NO: 722 and SEQ ID NO: 723.

The present invention also relates to a trispecific antibody or antibody fragment thereof, wherein said at least one binding portion which binds to human CD3 comprises a heavy chain CDR set comprising amino acid sequence of SEQ ID NO: 181, SEQ ID NO: 307, and SEQ ID NO: 433, and a light chain CDR set comprising amino acid sequence of SEQ ID NO: 721, SEQ ID NO: 722 and SEQ ID NO: 723; said at least one binding portion which binds to BCMA comprises a heavy chain CDR set comprising amino acid sequence of SEQ ID NO: 234, SEQ ID NO: 360, and SEQ ID NO: 486, and a light chain CDR set comprising amino acid sequence of SEQ ID NO: 721, SEQ ID NO: 722 and SEQ ID NO: 723; and said at least one binding portion which binds to human CD38 comprises a heavy chain CDR set comprising amino acid sequence of SEQ ID NO: 236, SEQ ID NO: 362, and SEQ ID NO: 712, and a light chain CDR set comprising amino acid sequence of SEQ ID NO: 721, SEQ ID NO: 722 and SEQ ID NO: 723.

The present invention also relates to a trispecific antibody or antibody fragment thereof, wherein said at least one binding portion which binds to human CD3 and/or said at least one binding portion which binds to human BCMA and/or said at least one binding portion which binds to human CD38 is a Fab fragment.

The present invention also relates to a trispecific antibody or antibody fragment thereof, wherein said at least one binding portion which binds to human CD3 and said at least one binding portion which binds to human BCMA, or said at least one binding portion which binds to human CD3 and said at least one binding portion which binds to human CD38, or said at least one binding portion which binds to human BCMA and said at least one binding portion which binds to human CD38, are fused to each other.

The present invention also relates to a trispecific antibody or antibody fragment thereof, wherein said at least one binding portion which binds to human BCMA is fused at the N-terminus to the C-terminus of said at least one binding portion which binds to human CD3, or wherein said at least one binding portion which binds to human BCMA is fused at the N-terminus to the C-terminus said at least one binding portion which binds to human CD38.

The present invention also relates to a trispecific antibody or antibody fragment thereof, wherein said at least one binding portion which binds to human BCMA is fused at the C-terminus to the N-terminus of said at least one binding portion which binds to human CD3, or wherein said at least one binding portion which binds to human BCMA is fused at the C-terminus to the N-terminus said at least one binding portion which binds to human CD38.

The present invention also relates to a trispecific antibody or antibody fragment thereof, wherein said at least one binding portion which binds to human CD3 and said at least one binding portion which binds to human BCMA, or said at least one binding portion which binds to human CD3 and said at least one binding portion which binds to human CD38, or said at least one binding portion which binds to human BCMA and said at least one binding portion which binds to human CD38, are fused to each other via a peptide linker.

The present invention also relates to a trispecific antibody or antibody fragment thereof, wherein said trispecific antibody or antibody fragment thereof comprises a non-naturally occurring Fc domain.

The present invention also relates to a trispecific antibody or antibody fragment thereof comprising a set of three amino acid chains comprising an amino acid sequence selected from the group comprising: SEQ ID NO: 522, SEQ ID NO: 523 and SEQ ID NO: 1; SEQ ID NO: 530, SEQ ID NO: 531 and SEQ ID NO: 1; SEQ ID NO: 532, SEQ ID NO: 533 and SEQ ID NO: 1; SEQ ID NO: 534, SEQ ID NO: 535 and SEQ ID NO: 1; SEQ ID NO: 536, SEQ ID NO: 537 and SEQ ID NO: 1; SEQ ID NO: 538, SEQ ID NO: 539 and SEQ ID NO: 1; SEQ ID NO: 540, SEQ ID NO: 541 and SEQ ID NO: 1; SEQ ID NO: 542, SEQ ID NO: 543 and SEQ ID NO: 1; SEQ ID NO: 544, SEQ ID NO: 545 and SEQ ID NO: 1; SEQ ID NO: 546, SEQ ID NO: 547 and SEQ ID NO: 1; and SEQ ID NO: 548, SEQ ID NO:549 and SEQ ID NO:1.

Preferably the present invention relates to a trispecific antibody or antibody fragment thereof comprising three amino acid chains having an amino acid sequence selected from the group comprising: SEQ ID NO: 546, SEQ ID NO: 547 and SEQ ID NO: 1; and SEQ ID NO: 548, SEQ ID NO:549 and SEQ ID NO:1.

More preferably, the trispecific antibody or antibody fragment thereof disclosed herein, comprises three amino acid chains having amino acid sequences of SEQ ID NO: 546, SEQ ID NO: 547 and SEQ ID NO: 1.

The present invention also relates to a trispecific antibody or antibody fragment thereof, wherein said trispecific antibody or antibody fragment thereof is a hetero-dimeric immunoglobulin comprising a first engineered immunoglobulin chain comprising a first engineered domain and a second engineered immunoglobulin chain comprising a second engineered domain wherein said hetero-dimeric immunoglobulin heterodimerize through said first and second engineered domains.

In particular, wherein said non-naturally occurring Fc domain comprises a first engineered CH3 domain and a second engineered CH3 domain.

More in particular, wherein said first engineered CH3 domain comprises the substitutions of the group comprising: Q347A, S364K, T366V, K370T, K392Y, F405S, Y407V, K409W, T411N (EU numbering), and said second engineered CH3 domain comprises the substitutions of the group comprising: Q347E, Y349A, L351F, S364T, T366V, K370T, T394D, V397L, D399E, F405A, Y407S, K409R, T411R (EU numbering).

The present invention further relates to a trispecific antibody or antibody fragment thereof for use as a medicament.

In particular, for use in treating multiple myeloma, relapsed multiple myeloma, refractory multiple myeloma, relapsed/refractory multiple myeloma, smoldering multiple myeloma, active multiple myeloma, acute lymphoblastic leukemia, chronic lymphocytic leukemia, acute myeloid leukemia, lymphoma, breast cancer such as Her2+ breast cancer, prostate cancer, cervical cancer, germinal center B-cell lymphoma or B-cell acute lymphoblastic leukemia, Chronic lymphocytic leukemia (CLL), Myelodisplastic syndrome (MDS), Non-Hodgkin lymphoma, diffuse large B-cell lymphoma, non-small cell lung cancer (NSCLC), Hepatocellular carcinoma (HCC), High-grade serous ovarian carcinoma, peritoneal cancer.

The present invention also relates to an epitope on the human CD38 extracellular domain which is bound by the trispecific antibody or antibody fragment thereof disclosed herein.

More particularly, the present invention also relates to an epitope on the human CD38 extracellular domain comprising the residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270, as detected by X-ray crystallography. In particular, as detected by X-ray crystallography, having resolution of at least 5 Å, preferably of at least A, even more preferably of at least 3.5 Å. In a most preferred example, the resolution is about 3.4 Å.

More particularly, the present invention also relates to an epitope on the human CD38 extracellular domain which is bound by the antibody of any one of the preceding claims and comprising the residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270, as detected by X-ray crystallography. In particular, as detected by X-ray crystallography, having resolution of at least 5 Å, preferably of at least Å, even more preferably of at least 3.5 Å. In a most preferred example, the resolution is about 3.4 Å.

The present invention also relates to an epitope on the human BCMA extracellular domain which is bound by the trispecific antibody or antibody fragment thereof disclosed herein.

The present invention also relates to an epitope on the human CD3 extracellular domain which is bound by the trispecific antibody or antibody fragment thereof disclosed herein.

The present invention also relates to an antibody or antibody fragment thereof or antigen-binding fragment which binds to the same epitope on CD3, and/or BCMA, and/or CD38 as a reference antibody or antibody fragment thereof wherein the reference antibody or antibody fragment thereof is a trispecific antibody or antibody fragment thereof, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 239, SEQ ID NO: 365, and SEQ ID NO: 491, and a light chain CDR set comprising SEQ ID NO: 721, SEQ ID NO: 722 and SEQ ID NO: 723.

The present invention also relates to an antibody or antigen-binding fragment which binds to the same epitope on CD3 as a reference antibody wherein the reference antibody is a trispecific antibody, wherein said at least one binding portion which binds to human CD3, and/or BCMA, and/or CD38 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 236, SEQ ID NO: 362, and SEQ ID NO: 712, and a light chain CDR set comprising SEQ ID NO: 721, SEQ ID NO: 722 and SEQ ID NO: 723.

The present invention also relates to an antibody or antigen-binding fragment which binds an epitope on the human CD3, wherein said epitope on CD3 comprises the amino acid sequence of SEQ ID NO: 726.

The present invention also relates to an antibody or antigen-binding fragment which binds an epitope on the human CD38, wherein said epitope on CD3 comprises the residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270, as detected by X-ray crystallography. In particular, as detected by X-ray crystallography, having resolution of at least 5 Å, preferably of at least A, even more preferably of at least 3.5 Å. In a most preferred example, the resolution is about 3.4 Å.

The present invention also relates to an isolated nucleic acid encoding the trispecific antibody disclosed herein.

The present invention also relates to a host cell comprising the isolated nucleic acid.

The present invention further relates to an antibody or antibody fragment thereof that binds to human CD3, comprising a heavy chain CDR set comprising an amino acid sequence selected from the group comprising: SEQ ID NO: 181, SEQ ID NO: 307, and SEQ ID NO: 433; SEQ ID NO: 184, SEQ ID NO: 310, and SEQ ID NO: 436; SEQ ID NO: 186, SEQ ID NO: 312, and SEQ ID NO: 438; SEQ ID NO: 188, SEQ ID NO: 314, and SEQ ID NO: 440; SEQ ID NO: 192, SEQ ID NO: 318, and SEQ ID NO: 444, and a light chain CDR set comprising the amino acid sequences of SEQ ID NO: 721, SEQ ID NO: 722 and SEQ ID NO: 723.

The present invention further relates to an antibody or antibody fragment thereof that binds to human BCMA, comprising a heavy chain CDR set comprising an amino acid sequence selected from the group comprising: SEQ ID NO: 234, SEQ ID NO: 360, and SEQ ID NO: 486; SEQ ID NO: 219, SEQ ID NO: 345, and SEQ ID NO: 471; SEQ ID NO: 227, SEQ ID NO: 353, and SEQ ID NO: 479; SEQ ID NO: 231, SEQ ID NO: 357, and SEQ ID NO: 483, and a light chain CDR set comprising the amino acid sequences of SEQ ID NO: 721, SEQ ID NO: 722 and SEQ ID NO: 723.

The present invention further relates to a trispecific hetero-dimeric antibody comprising a first and a second engineered CH3 domain, wherein said first engineered CH3 domain comprises one or more substitutions selected from the group comprising: Q347A, S364K, T366V, K370T, K392Y, F405S, Y407V, K409W, T411N (EU numbering) and said second engineered CH3 domain comprises one or more substitutions selected from the group comprising: Q347E, Y349A, L351F, S364T, T366V, K370T, T394D, V397L, D399E, F405A, Y407S, K409R, T411R (EU numbering), and wherein said trispecific hetero-dimeric immunoglobulin or hetero-dimeric fragment heterodimerize through said first and second engineered CH3 domains, characterized in that said trispecific hetero-dimeric antibody comprises at least three binding portions each binding portion which binds to a different antigen.

Particularly, the present invention relates to a trispecific hetero-dimeric antibody comprising a first and a second engineered CH3 domain, wherein said first engineered CH3 domain comprises the substitutions of the group comprising: Q347A, S364K, T366V, K370T, K392Y, F405S, Y407V, K409W, T411N (EU numbering), and said second engineered CH3 domain comprises the substitutions of the group comprising: Q347E, Y349A, L351F, S364T, T366V, K370T, T394D, V397L, D399E, F405A, Y407S, K409R, T411R (EU numbering), and wherein said trispecific hetero-dimeric immunoglobulin or hetero-dimeric fragment heterodimerize through said first and second engineered CH3 domains, characterized in that said trispecific hetero-dimeric antibody or antibody fragment thereof comprises at least three binding portions each binding portion which binds to a different antigen.

Provided herein are antibodies that immunospecifically bind to human BCMA, CD38 and CD3 and antigen-binding fragments thereof. Also described are related polynucleotides capable of encoding the provided BCMA-specific, CD38-specific, and CD3-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the BCMA-specific antibodies and/or CD38-specific antibodies and antigen-binding fragments may be used to diagnose or monitor BCMA-expressing cancer and/or CD38-expressing cancer progression, regression, or stability; to determine whether or not a patient should be treated for cancer; or to determine whether or not a subject is afflicted with BCMA-expressing cancer and/or CD38-expressing cancer and thus may be amenable to treatment with a BCMA-specific anti-cancer therapeutic and/or CD38-expressing cancer, such as the multispecific antibodies against BCMA, CD38 and CD3 described herein.

Further provided herein are multispecific antibodies that immunospecifically bind to BCMA, CD38 and CD3 and multispecific antigen-binding fragments thereof. Also described are related polynucleotides capable of encoding the provided BCMA×CD38×CD3-multispecific antibodies, cells expressing the provided antibodies, as well as associated vectors and detectably labeled multispecific antibodies. In addition, methods of using the provided multispecific antibodies are described. For example, the BCMA×CD38×CD3-multispecific antibodies may be used to diagnose or monitor BCMA-expressing cancer and/or CD38-expressing cancer progression, regression, or stability, to determine whether or not a patient should be treated for cancer; or to determine whether or not a subject is afflicted with BCMA-expressing cancer and/or CD38-expressing cancer and thus may be amenable to treatment with a BCMA-specific anti-cancer therapeutic and/or CD38-specific anti-cancer therapeutic, such as the BCMA×CD38×CD3-multispecific antibodies described herein.

As utilized in accordance with the present disclosure, the following terms, unless otherwise indicated, shall be understood to have the following meanings. Unless otherwise required by context, singular terms shall include pluralities and plural terms shall include the singular. As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that aspects and embodiments of the present disclosure described herein include "comprising", "consisting" and "consisting essentially" of aspects and embodiments.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature.

Such an isolated polypeptide can be encoded by genomic DNA, cDNA, mRNA, or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

The present invention relates to a multispecific binding molecule, for instance a multispecific binding protein, such as an antibody or antibody fragment thereof, comprising at least three binding portions, at least one of which binds to human CD3, at least one which binds to human BCMA and at least one of which binds to human CD38.

The term "binding protein" or "binding molecule" as used herein refers to a non-naturally occurring or recombinant or engineered molecule, e.g., a protein, such as a non-naturally occurring or recombinant or engineered antibody, that specifically binds to at least one target antigen, e.g., a CD38 polypeptide, a BCMA polypeptide, or a CD3 polypeptide of the present disclosure.

A "recombinant" molecule is one that has been prepared, expressed, created, or isolated by recombinant means.

The terms "antibody" and "immunoglobulin" as referred to herein are used interchangeably and include whole antibodies and any antigen binding fragments or single chains thereof. Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain (VH) and three constant domains (CH1, CH2, and CH3), wherein the VH domain is at the amino-terminus of the polypeptide and the CH3 domain is at the carboxyl-terminus, and a full-length light chain immunoglobulin polypeptide includes a variable domain (VL) and a constant domain (CL), wherein the VL domain is at the amino-terminus of the polypeptide and the CL domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al, SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, J. Mol Biol. 196: 901-17; Chothia et al, 1989, Nature 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, FASEB J. 9: 133-39; MacCallum, 1996, J. Mol. Biol. 262(5): 732-45; and Lefranc, 2003, Dev. Comp. Immunol. 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," In Antibody Engineering, Vol. 2. Kontermann R., Dubel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, Nucleic Acids Res. 22: 4673-80. Molecular models are conventionally used to correctly delineate framework and CDR regions and thus correct the sequence-based assignments. All such alternative definitions are encompassed by the current invention and the sequences provided in this specification are not intended to exclude alternatively defined CDR sequences which may only comprise a portion of the CDR sequences provided in the sequence listing. In a preferred embodiment of the present invention, CDRH1, corresponds to Kabat positions 26-35, CDRH2 corresponds to Kabat positions 50-58 and CDRH3, corresponding to Kabat positions 93-102. In another preferred embodiment, CDRL1, corresponds to Kabat positions 24-34, CDRL2 corresponds to Kabat positions 50-56 and CDRL3, corresponding to Kabat positions 89-97.

The term "antibody fragment" as used herein, includes a portion of a full-length antibody. Non limiting examples of antibody fragments include: (i) the fragment crystallizable (Fc) composed by two constant heavy chain fragments which consist of CH2 and CH3 domains, in IgA, IgD and IgG, and of CH2, CH3 and CH4 domains, in IgE and IgM, and which are paired by disulfide bonds and non-covalent interactions; (ii) the fragment antigen binding (Fab), consisting of VL, CL and VH, CH1 connected by disulfide bonds; (iii) Fab', consisting of VL, CL and VH, CH1 connected by disulfide bonds, and of one or more cysteine residues from the hinge region; (iv) Fab'-SH, which is a Fab' fragment in which the cysteine residues contain a free sulfhydryl group; (v) F(ab')2 consisting of two Fab fragments connected at the hinge region by a disulfides bond; (vi) the variable fragments (Fv), consisting of VL and VH chains, paired together by non-covalent interactions; (vii) the single chain variable fragments (scFv), consisting of VL and VH chains paired together by a linker; (ix) the bispecific single chain Fv dimers, (x) the scFv-Fc fragment; (xi) a Fd fragment consisting of the VH and CH1 domains; (xii) the single domain antibody, dAb, consisting of a VH domain or a VL domain; (xiii) diabodies, consisting of two scFv fragments in which VH and VL domains are connected by a short peptide that prevent their pairing in the same chain and allows the non-covalent dimerization of the two scFvs; (xiv) the trivalent triabodies, where three scFv, with VH and VL domains connected by a short peptide, form a trimer; and the like thereof.

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins. Fc molecules are made up of monomeric polypeptides that can be linked into dimeric or multimeric forms by covalent {i.e., disulfide bonds) and non-covalent association. The number of intermolecular disulfide bonds between monomeric subunits of native Fc molecules ranges from 1 to 4 depending on class {e.g., IgG, IgA, and IgE) or subclass {e.g., IgG1, IgG2, IgG3, IgA1, IgGA2, and IgG4). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the VH and CH1 domains of one heavy chain, wherein the VH-CH1 heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a CH1 domain.

A F(ab') fragment typically includes one light chain and a portion of one heavy chain that contains more of the constant region (between the CH1 and CH2 domains), such that an interchain disulfide bond can be formed between two heavy chains to form a F(ab')2 molecule.

One embodiment of the disclosure provides binding proteins having biological and immunological specificity to between one and three target antigens.

The term "antigen" or "target antigen" or "antigen target" as used herein refers to a molecule or a portion of a molecule that is capable of being bound by a binding protein, and/or additionally is capable of being used in an animal to produce antibodies capable of binding to an epitope of that antigen. A target antigen may have one or more epitopes. With respect to each target antigen recognized by a binding protein, the binding protein is capable of competing with an intact antibody and/or an antibody fragment thereof that recognizes the target antigen. The antigen is bound by a binding protein, such as an antibody, via an antigen binding site, also referred herein as "binding portion" or "binding domain".

In certain embodiments of the present invention, one or more binding portion of the antibody disclosed herein are an antibody fragment selected from the non-limiting example of antibody fragments listed above. In particular embodiments, one or more binding portions of the antibody disclosed herein are Fab fragments. In a more particular embodiment, all the binding portions of the antibody of the present invention are Fab fragments.

Based on the number of antigen binding sites, a binding protein, such as an antibody or an antibody fragment can be classified as monovalent or multivalent. The term "valence" is used herein to indicate the number of binding sites. The term "monovalent binding protein" refers to a binding protein that has one antigen binding site. For instance, a monovalent antibody is one that has one antigen binding site.

The term "multivalent binding protein" refers to a binding protein that has more than one antigen binding site. For instance, a multivalent antibody is one that has more than one antigen binding site. Non limiting examples of multivalent binding proteins are bivalent and trivalent. The term "bivalent binding protein" refers to a binding protein that has two antigen binding sites. For instance, a bivalent antibody is one that has two antigen binding sites. The term "trispecific binding protein" refers to a binding protein that specifically binds to three different antigen targets. For instance, a trivalent antibody is one that three antigen binding sites.

The term "monospecific binding protein" refers to a binding protein that specifically binds to one antigen target.

The term "multispecific binding protein" as used herein, refers to any binding protein, including an antibody or antibody fragment thereof, having more than one binding site and that binds different epitopes of the same antigen, or different antigen targets.

The term "bispecific binding protein" refers to a binding protein, including an antibody or antibody fragment thereof, that specifically binds to two different antigen targets. In some embodiments, a bispecific binding protein, such as an antibody or antibody fragment thereof, binds to two different antigens. In some embodiments, a bispecific binding protein binds to two different epitopes on the same antigen.

In some embodiments, a trispecific binding protein, such as an antibody or antibody fragment thereof, binds to three different antigens. In some embodiments, a trispecific binding protein binds to one, two, or three different epitopes on the same antigen.

A trivalent binding protein can bind to one antigen target (i.e., monospecific trivalent binding protein). In other embodiments, the trivalent binding protein can bind to two antigen targets (i.e., bispecific trivalent binding protein). In other embodiments, the trivalent binding protein can bind to three antigen targets (i.e., trispecific trivalent binding protein).

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant ($K_D$) is for instance $<10^{-8}$M, more preferably when the equilibrium dissociation constant is $<10^{-9}$M, and most preferably when the dissociation constant is $<10^{-10}$M.

In a preferred embodiment of the present invention, the antibody disclosed herein is trivalent, preferably is trispecific, more preferably is a trispecific antibody comprising at least three binding portions; in a particular embodiment, the antibody of the present invention is a trispecific antibody or antibody fragment thereof, comprising at least three binding portions, at least one of which binds to human CD3, at least one which binds to human BCMA and at least one of which binds to human CD38.

"CD3" is cluster of differentiation 3, a multimeric protein complex composed of four polypeptide chains: epsilon (ε), gamma (γ), delta (δ) and zeta (ζ), that assemble and function as three pairs of dimers (εγ, εδ, ζζ. In some embodiments, a binding protein of the present disclosure binds the extracellular domain of one or more CD3 polypeptide chain i.e., CD3ε, CD3γ, CD3δ and CD3ζ. Exemplary CD3 extracellular domain polypeptide sequences include, but are not limited to, the extracellular domain of human CD3ε (e.g., as represented by SEQ ID NO: 610) and the extracellular domain of cynomolgus monkey CD3ε (e.g., as represented by SEQ ID NO: 614); the extracellular domain of human CD3δ (e.g., as represented by SEQ ID NO: 611) and the extracellular domain of cynomolgus monkey CD3δ (e.g., as represented by SEQ ID NO: 613); the extracellular domain of human CD3γ (e.g., as represented by SEQ ID NO: 612) and the extracellular domain of cynomolgus monkey CD3γ; the extracellular domain of human CD3 (and the extracellular domain of cynomolgus monkey CD3ζ.

"BCMA" is the B-cell maturation antigen, also known as tumor necrosis factor receptor superfamily member 17; BCMA is expressed by mature B lymphocytes and overexpressed in malignant plasma cells. In some embodiments, a binding protein of the present disclosure binds the extracellular domain of one or more BCMA polypeptide. Exemplary BCMA extracellular domain polypeptide sequences include, but are not limited to, the extracellular domain of human BCMA (e.g., as represented by SEQ ID NO: 615) and the extracellular domain of cynomolgus monkey BCMA (e.g., as represented by SEQ ID NO: 616).

"CD38" is cluster of differentiation 38 polypeptide, a glycoprotein found on the surface of many immune cells. In some embodiments, a binding protein of the present disclosure binds the extracellular domain of one or more CD38 polypeptide. Exemplary CD38 extracellular domain polypeptide sequences include, but are not limited to, the extracellular domain of human CD38 (e.g., as represented by SEQ ID NO: 617) and the extracellular domain of cynomolgus monkey CD38 (e.g., as represented by SEQ ID NO: 618).

The term "T-cell engager" refers to binding proteins directed to a host's immune system, more specifically the T cells' cytotoxic activity as well as directed to a tumor target protein.

In preferred embodiments, the present invention provides a trispecific antibody or antibody fragment thereof that binds to a human CD3 and to a human BCMA, and to human CD38. In preferred embodiment of the present invention the antibody is monoclonal.

In a particular embodiment, the trispecific antibody of the present disclosure comprises a common light chain.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present {i.e., on a molar basis it is more abundant than any other individual species in the composition). In some embodiments, a substantially purified fraction is a composition wherein the species comprises at least about 50%) (on a molar basis) of all macromolecular species present. In other embodiments, a substantially pure composition will comprise more than about 80%>, 85%>, 90%, 95%, or 99% of all macromolecular species present in the composition. In still other embodiments, the species is purified to essential homogeneity (contaminant species cannot be detected in the composition by conventional detection methods) wherein the composition consists essentially of a single macromolecular species.

A nucleic acid is "isolate" or "substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g., F. Ausubel, et al., ed. (1987) Current Protocols in Molecular Biology, Greene Publishing and Wiley Interscience, New York. A nucleic acid of the invention can be, for example, DNA or RNA and may or may not contain intron sequences.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (GE). Surface plasmon analysis can also be performed by immobilizing the analyte (binding protein on a biosensor matrix) and presenting the ligand (target antigen). The term "Ko" as used herein refers to the dissociation constant of the interaction between a particular binding protein or a binding portion of a binding protein or an antibody or antibody fragment thereof and a target antigen and/or antigen epitope.

The term "binds to" as used herein in reference to a binding protein refers to the ability of a binding protein or an antigen-binding fragment thereof to bind to an antigen containing an epitope with an $K_D$ of at least about $1\times10^{-6}$M, $1\times10^{-7}$M, $1\times10^{-8}$M, $1\times10^{-9}$M, $1\times10^{-10}$M, $1\times10^{-11}$M, $1\times10^{-2}$M, or less and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. A linker might be inserted at the transition between variable domains or between variable and constant domains, respectively, at the sequence level.

The transition between domains can be identified because the approximate size of the immunoglobulin domains is well understood. The precise location of a domain transition can be determined by locating peptide stretches that do not form secondary structural elements such as beta-sheets or alpha-helices as demonstrated by experimental data or as can be assumed by techniques of modeling or secondary structure prediction.

Certain embodiments, the disclosure provides nucleic acid molecules comprising nucleotide sequences encoding polypeptide chains that form the binding proteins of the present invention. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "vector" as used herein refers to any molecule (e.g., nucleic acid, plasmid) or other means (e.g., a virus) that is used to transfer and or provide coding information to a host cell. The term "vector" includes a nucleic acid molecule that is capable of transporting another nucleic acid to which it has been linked. One type of vector is a "plasmid" which refers to a circular double-stranded DNA molecule into which additional DNA segments may be inserted. Another type of vector is a viral vector, wherein additional DNA segments may be inserted into the viral genome, in particular wherein nucleic acids facilitating viral assembly are combined with coding information to facilitate transfer to the host cell by virus like particles. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-, α-di substituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetyl serine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction, and the right-hand direction is the carboxyl-terminal direction, in accordance with standard usage and convention.

Naturally occurring residues may be divided into classes based on common side chain properties:

(1) hydrophobic: Met, Ala, Val, Leu, lie, Phe, Trp, Tyr, Pro;
(2) polar hydrophilic: Arg, Asn, Asp, Gln, Glu, His, Lys, Ser, Thr;
(3) aliphatic: Ala, Gly, lie, Leu, Val, Pro;
(4) aliphatic hydrophobic: Ala, lie, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term percent "identity," in the context of two or more nucleic acids or polypeptide sequences, refers to two or more sequences that are the same. Two sequences are "substantially identical" if two sequences have a specified percentage of amino acid residues or nucleotides that are the same (e.g., at least 60% identity, for instance 60%, 61%, 62%, 63%, 64%, 65%, 66%, 67% 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity), when compared and aligned for maximum correspondence over over a specified region, or, when not specified, over the entire sequence. For sequence comparison, typically one sequence acts as a reference sequence, to which test sequences are compared. Methods of alignment of sequences for comparison are well known by a person skilled in the art. Non-limiting examples of algorithms that are suitable for determining percent sequence identity and sequence similarity are the BLAST and BLAST 2.0 algorithms, which are described in Altschul et al., 1977, Nuc. Acids Res. 25:3389-3402; and Altschul et al., 1990, J. Mol. Biol. 215:403-410, respectively. Software for performing BLAST analyses is publicly available through the National Center for Biotechnology Information; Clustal Omega algorithm (Sievers F, Higgins D G. Clustal Omega for making accurate alignments of many protein sequences. Protein Sci. 2018 Jan. 27(1):135-145.); MUSCULE algorithm (Edgar, R. C. MUSCLE: a multiple sequence alignment method with reduced time and space complexity. BMC Bioinformatics 5, 113 (2004). doi.org/10.1186/1471-2105-5-113).

The terms "patient" or "subject" are used herein interchangeably. The term "patient" as used herein includes human and animal subjects. Animals subjects include all vertebrates, e.g., mammals and non-mammals, such as non-human primates, sheep, dog, cow, chickens.

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments of the present invention, the disorder is characterized by expression, e.g., overexpression of BCMA, and/or expression, e.g., overexpression of CD38, including in cancer and in non-cancer diseases such as gastrointestinal, neurological and pulmonary system disorders (Szlasa W at al., Targeting CD38 in Neoplasms and Non-Cancer Diseases. Cancers. 2022 Aug. 28; 14(17):4169); for instance the antibody or antibody fragment thereof according to the present invention can be used for treating B cell malignancies and autoimmune disorders. In other particular embodiments, the antibody or antibody fragment thereof of the present invention can be used to treat humans with cancer, or humans susceptible to cancer, or ameliorate cancer in a human subject. The antibody can also be used to prevent cancer in a human patient. In more particular embodiments, the antibody or antibody fragment thereof of the present invention is used to treat the cancer, such as hematological malignancies. In preferred embodiments the cancer is a BCMA-expressing cancer and/or CD38 expressing cancer. Non limiting examples of cancers treated by the antibody or antibody fragment thereof of the present invention comprise leukemia, such as acute lymphoblastic leukemia, chronic lymphocytic leukemia, acute myeloid leukemia, acute promyelocytic leukemia, acute myeloblastic leukemia, acute monocytic leukemia and acute megakaryoblastic leukemia, chronic myelogenous leukemia, chronic lymphocytic leukemia, multiple myeloma, relapsed multiple myeloma, refractory multiple myeloma, relapsed/refractory multiple myeloma, smoldering multiple myeloma, active multiple myeloma, plasma cell leukemia, lymphoma, germinal center B-cell lymphoma or B-cell acute lymphoblastic leukemia, Hodgkin lymphoma, Non-Hodgkin lymphoma, diffuse large B-cell lymphoma, Myelodisplastic syndrome (MDS), breast cancer such as Her2+ breast cancer, prostate cancer, cervical cancer, non-small cell lung cancer (NSCLC), Hepatocellular carcinoma (HCC), High-grade serous ovarian carcinoma, peritoneal cancer, smoldering myeloma, glioma.

The present invention also relates to a trispecific antibody or antibody fragment thereof for use as a medicament. In particular, for use in the treatment of the above-mentioned disorders; particularly for use in the treatment of cancer and autoimmune disorders, more particularly for use in the treatment of hematological cancers, including but not limited to the ones mentioned above. In a preferred embodiment, the trispecific antibody of the present invention is for use in the treatment of Multiple Myeloma, including relapsed multiple myeloma, refractory multiple myeloma, relapsed/refractory multiple myeloma, smoldering multiple myeloma, active multiple myeloma.

The present invention also relates to the use of the trispecific antibody or antibody fragment thereof of the present invention for the treatment of the above-mentioned disorders; particularly for the treatment of cancer and autoimmune disorders, more particularly for the treatment of hematological cancers, including but not limited to the ones mentioned above. In a preferred embodiment, the present invention relates to a use of the trispecific antibody disclosed herein for the treatment of Multiple Myeloma, including relapsed multiple myeloma, refractory multiple myeloma, relapsed/refractory multiple myeloma, smoldering multiple myeloma, active multiple myeloma.

The present invention also relates to methods of treating a cancer and autoimmune disorders comprising the step of administering to a patient in need thereof a therapeutically effective amount of the trispecific antibody of the present invention. In particular, the present invention also relates to methods of treating a hematological cancer comprising the step of administering to a patient in need thereof a therapeutically effective amount of the trispecific antibody or antibody fragment thereof of the present invention. More in particular, the hematological cancer is selected from the list comprising but not limited to the ones mentioned above. In a preferred embodiment, the present invention relates to methods of treating Multiple Myeloma, including relapsed multiple myeloma, refractory multiple myeloma, relapsed/refractory multiple myeloma, smoldering multiple myeloma, active multiple myeloma, comprising the step of administering to a patient in need thereof a therapeutically effective amount of the trispecific antibody or antibody fragment thereof disclosed herein.

The present invention also relates to pharmaceutical compositions comprising the trispecific antibody, and for example containing one or more pharmaceutically acceptable excipients or carriers. To prepare pharmaceutical or sterile compositions comprising the trispecific antibody or antibody fragment thereof of the present disclosure a MBM preparation can be combined with one or more pharmaceutically acceptable excipient or pharmaceutically acceptable carrier.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

Anti-CD3 Binding Proteins

Certain aspects of the present disclosure relate to binding proteins that comprise an antigen binding site that binds a CD3 polypeptide (e.g., human and cynomolgus monkey CD3 polypeptides). In some embodiments, an antigen binding domain and/or binding protein of the present disclosure "cross reacts" with human and cynomolgus monkey CD3 polypeptides.

In some embodiments, the binding proteins disclosed herein are monospecific, or bispecific, or trispecific, or multispecific and/or monovalent, bivalent, trivalent, or multivalent and comprise a binding portion which binds to CD3, e.g., to human CD3.

In certain embodiments, the antibody or antibody fragment of the present invention comprises a binding portion which binds to human CD3 that comprises a heavy chain CDR set comprising an amino acid sequence selected from the group comprising: SEQ ID NO: 160, SEQ ID NO: 286 and SEQ ID NO: 412; SEQ ID NO: 176, SEQ ID NO: 302 and SEQ ID NO: 428; SEQ ID NO: 177, SEQ ID NO: 303 and SEQ ID NO: 429; SEQ ID NO: 178, SEQ ID NO: 304 and SEQ ID NO: 430; SEQ ID NO: 179, SEQ ID NO: 305 and SEQ ID NO: 431; SEQ ID NO: 180, SEQ ID NO: 306 and SEQ ID NO: 432; SEQ ID NO: 181, SEQ ID NO: 307 and SEQ ID NO: 433; SEQ ID NO: 182, SEQ ID NO: 308 and SEQ ID NO: 434; SEQ ID NO: 183, SEQ ID NO: 309 and SEQ ID NO: 435; SEQ ID NO: 184, SEQ ID NO: 310 and SEQ ID NO: 436; SEQ ID NO: 185, SEQ ID NO: 311 and SEQ ID NO: 437; SEQ ID NO: 186, SEQ ID NO: 312 and SEQ ID NO: 438; SEQ ID NO: 187, SEQ ID NO: 313 and SEQ ID NO: 439; SEQ ID NO: 188, SEQ ID NO: 314 and SEQ ID NO: 440; SEQ ID NO: 189, SEQ ID NO: 315 and SEQ ID NO: 441; SEQ ID NO: 190, SEQ ID NO: 316 and SEQ ID NO: 442; SEQ ID NO: 191, SEQ ID NO: 317 and SEQ ID NO: 443; SEQ ID NO: 192, SEQ ID NO: 318 and SEQ ID NO: 444; and SEQ ID NO: 193, SEQ ID NO: 319 and SEQ ID NO: 445. In more particular embodiments, the binding portion which binds to human CD3 also comprises a CDR set of the common light chain comprising the amino acid sequence of SEQ ID NO: 1. More particularly, the light chain CDR set comprising the amino acid sequences of SEQ ID NO: 721, SEQ ID NO:722 and SEQ ID NO:723.

Preferably, the binding portion which binds to human CD3 comprises a heavy chain CDR set comprising an amino acid sequence selected from the group comprising SEQ ID NO: 181, SEQ ID NO: 307, and SEQ ID NO: 433; SEQ ID NO: 184, SEQ ID NO: 310, and SEQ ID NO: 436; SEQ ID NO: 186, SEQ ID NO: 312, and SEQ ID NO: 438; SEQ ID NO: 188, SEQ ID NO: 314, and SEQ ID NO: 440; SEQ ID NO: 192, SEQ ID NO: 318, and SEQ ID NO: 444. More preferably, the binding portion which binds to human CD3 comprises the CDR set comprising SEQ ID NO: 181, SEQ ID NO: 307, and SEQ ID NO: 433. In more particular embodiments, the binding portion which binds to human CD3 also comprises a CDR set of the common light chain comprising the amino acid sequence of SEQ ID NO: 1. More particularly, the light chain CDR set comprising the amino acid sequences of SEQ ID NO: 721, SEQ ID NO:722 and SEQ ID NO:723. More preferably, the binding portion which binds to human CD3 comprises a heavy chain CDR set comprising an amino acid sequence of SEQ ID NO: 181, SEQ ID NO: 307, and SEQ ID NO: 433; and the light chain CDR set comprising the amino acid sequences of SEQ ID NO: 721, SEQ ID NO:722 and SEQ ID NO:723 In other embodiments, the binding portion which binds to human CD3 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 34, and 50 to 67. In more particular embodiments, the binding portion which binds to human CD3 also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human CD3 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 55, 58, 60, 62, and 66. In more particular embodiments, the binding portion which binds to human CD3 also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

In certain embodiments, the binding portion which binds to human CD3 comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 592.

In other embodiments, the binding portion which binds to human CD3 comprises an heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 34, and 50 to 67. In more particular embodiments, the binding portion which binds to human CD3 also comprises a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human CD3 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 55, 58, 60, 62, and 66; and a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

The present invention relates to a multispecific, e.g., bispecific or trispecific and multivalent, e.g., bivalent, or trivalent antibody or antibody fragment thereof comprising any of the binding portions that binds to human CD3 described above. In any of the bispecific or trispecific binding proteins described supra, the target antigen other than CD3 can be any of the following exemplary antigen targets: A2AR, APRIL, ATPDase, BAFF, BAFFR, BCMA, BIYS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CCR7, CD19, CD20, CD23 (also known as FCER2, a receptor for IgE), CD24, CD27, CD28, CD38, CD39, CD40, CD47, CD48, CD70, CD80 (also known as B7-1), CD86 (also known as B7-2), CD122, CD123, CD137 (also known as 41BB), CD137L, CD152 (also known as CTLA4), CD154 (also known as CD40L), CD160, CD272, CD273 (also known as PD-L2), CD274 (also known as PD-L1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, GPRC5D, Her2, HHLA2, HMGB1, HVEM, ICOSLG, IDO, IFNa, IgE, IGF1R, IL2Rbeta, IL1, IL1RAP, ILILIA, IL1B, IL1F10, IL2, IL4, IL4Ra, IL5, IL5R, IL6, IL7, IL7Ra, IL8, IL9, RAP, IL9R, IL10, rILI0, IL12, IL13, IL13RaI, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, KG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1), XCL1 and XCL2. In some embodiments, one or more of the above antigen targets are human antigen targets. In a preferred embodiment, the antibody or antibody fragment thereof of the present invention is a trivalent bispecific antibody comprising at least two binding portions, at least one of which binds to human CD3 and at least one of which binds to BCMA, preferably at least two which bind to BCMA. In a more preferred embodiment, the antibody of the present invention is a trivalent trispecific antibody comprising at least three binding portions, at least one of which binds to human CD3, at least one of which binds to BCMA and at least one that binds to CD38.

The present invention also relates to monospecific antibody or antibody fragment thereof comprising any of the binding portion that binds to CD3, e.g., to human CD3, described above.

In a particular aspect, the present invention relates to an antibody or antibody fragment thereof that binds to human CD3, comprising a heavy chain CDR set comprising an amino acid sequence selected from the group comprising SEQ ID NO: 160, SEQ ID NO: 286 and SEQ ID NO: 412; SEQ ID NO: 176, SEQ ID NO: 302 and SEQ ID NO: 428; SEQ ID NO: 177, SEQ ID NO: 303 and SEQ ID NO: 429; SEQ ID NO: 178, SEQ ID NO: 304 and SEQ ID NO: 430; SEQ ID NO: 179, SEQ ID NO: 305 and SEQ ID NO: 431; SEQ ID NO: 180, SEQ ID NO: 306 and SEQ ID NO: 432; SEQ ID NO: 181, SEQ ID NO: 307 and SEQ ID NO: 433; SEQ ID NO: 182, SEQ ID NO: 308 and SEQ ID NO: 434; SEQ ID NO: 183, SEQ ID NO: 309 and SEQ ID NO: 435; SEQ ID NO: 184, SEQ ID NO: 310 and SEQ ID NO: 436; SEQ ID NO: 185, SEQ ID NO: 311 and SEQ ID NO: 437; SEQ ID NO: 186, SEQ ID NO: 312 and SEQ ID NO: 438; SEQ ID NO: 187, SEQ ID NO: 313 and SEQ ID NO: 439; SEQ ID NO: 188, SEQ ID NO: 314 and SEQ ID NO: 440; SEQ ID NO: 189, SEQ ID NO: 315 and SEQ ID NO: 441; SEQ ID NO: 190, SEQ ID NO: 316 and SEQ ID NO: 442; SEQ ID NO: 191, SEQ ID NO: 317 and SEQ ID NO: 443; SEQ ID NO: 192, SEQ ID NO: 318 and SEQ ID NO: 444; and SEQ ID NO: 193, SEQ ID NO: 319 and SEQ ID NO: 445; and a light chain CDR set of the common light chain comprising the amino acid sequence of SEQ ID NO: 1; in particular, the light chain CDR set comprising the amino acid sequences of SEQ ID NO: 721, SEQ ID NO:722 and SEQ ID NO:723.

In a preferred aspect, the antibody or antibody fragment that binds to human CD3, comprises a heavy chain CDR set comprising an amino acid sequence selected from the group comprising SEQ ID NO: 181, SEQ ID NO: 307, and SEQ ID NO: 433; SEQ ID NO: 184, SEQ ID NO: 310, and SEQ ID NO: 436; SEQ ID NO: 186, SEQ ID NO: 312, and SEQ ID NO: 438; SEQ ID NO: 188, SEQ ID NO: 314, and SEQ ID NO: 440; SEQ ID NO: 192, SEQ ID NO: 318, and SEQ ID NO: 444, and a light chain CDR set comprising the amino acid sequences of SEQ ID NO: 721, SEQ ID NO: 722 and SEQ ID NO: 723.

In preferred embodiments, the antibody disclosed herein, comprising a binding portion that binds human CD3, as described above is monoclonal.

Anti-BCMA Binding Proteins

Certain aspects of the present disclosure relate to binding proteins that comprise an antigen binding site that binds a BCMA polypeptide (e.g., human and cynomolgus monkey BCMA polypeptides). In some embodiments, an antigen binding domain and/or binding protein of the present disclosure "cross reacts" with human and cynomolgus monkey BCMA polypeptides.

In some embodiments, the binding proteins disclosed herein are monospecific, or bispecific, or trispecific, or multispecific and/or monovalent, bivalent, trivalent, or multivalent and comprise a binding portion which binds to BCMA, e.g., to human BCMA.

In certain embodiments, the antibody or antibody fragment of the present invention comprises a binding portion which binds to human BCMA that comprises a heavy chain CDR set comprising an amino acid sequence selected from the group comprising: SEQ ID NO:209, SEQ ID NO: 335, and SEQ ID NO: 461; SEQ ID NO:210, SEQ ID NO: 336, and SEQ ID NO: 462; SEQ ID NO:211, SEQ ID NO: 337, and SEQ ID NO: 463; SEQ ID NO:212, SEQ ID NO: 338, and SEQ ID NO: 464; SEQ ID NO:213, SEQ ID NO: 339, and SEQ ID NO: 465; SEQ ID NO:214, SEQ ID NO: 340, and SEQ ID NO: 466; SEQ ID NO:215, SEQ ID NO: 341, and SEQ ID NO: 467; SEQ ID NO:216, SEQ ID NO: 342, and SEQ ID NO: 468; SEQ ID NO:217, SEQ ID NO: 343, and SEQ ID NO: 469; SEQ ID NO:218, SEQ ID NO: 344, and SEQ ID NO: 470; SEQ ID NO:219, SEQ ID NO: 345, and SEQ ID NO: 471; SEQ ID NO:220, SEQ ID NO: 346, and SEQ ID NO: 472; SEQ ID NO:221, SEQ ID NO: 347, and SEQ ID NO: 473; SEQ ID NO:222, SEQ ID NO: 348, and SEQ ID NO: 474; SEQ ID NO:223, SEQ ID NO: 349, and SEQ ID NO: 475; SEQ ID NO:224, SEQ ID NO: 350, and SEQ ID NO: 476; SEQ ID NO:225, SEQ ID NO: 351, and SEQ ID NO: 477; SEQ ID NO:226, SEQ ID NO: 352, and SEQ ID NO: 478; SEQ ID NO:227, SEQ ID NO: 353, and SEQ ID NO: 479; SEQ ID NO:228, SEQ ID NO: 354, and SEQ ID NO: 480; SEQ ID NO:229, SEQ ID NO: 355, and SEQ ID NO: 481; SEQ ID NO:230, SEQ ID NO: 356, and SEQ ID NO: 482; SEQ ID NO:231, SEQ ID NO: 357, and SEQ ID NO: 483; SEQ ID NO:232, SEQ ID NO: 358, and SEQ ID NO: 484; SEQ ID NO:233, SEQ ID NO: 359, and SEQ ID NO: 485; SEQ ID NO:234, SEQ ID NO: 360, and SEQ ID NO: 486; and SEQ ID NO:235, SEQ ID NO: 361, and SEQ ID NO: 487. In more particular embodiments, the binding portion which binds to human BCMA also comprises a CDR set of the common light chain comprising the amino acid sequence of SEQ ID NO: 1. More particularly, the light chain CDR set comprising the amino acid sequences of SEQ ID NO: 721, SEQ ID NO:722 and SEQ ID NO:723.

In more particular embodiments, the binding portion which binds to human BCMA comprises a heavy chain CDR set comprising an amino acid sequence selected from the group comprising: SEQ ID NO: 234, SEQ ID NO: 360, and SEQ ID NO: 486; SEQ ID NO: 219, SEQ ID NO: 345, and SEQ ID NO: 471; SEQ ID NO: 227, SEQ ID NO: 353, and SEQ ID NO: 479; SEQ ID NO: 231, SEQ ID NO: 357, and SEQ ID NO: 483. Preferably, the binding portion which binds to human BCMA comprising the CDR set comprising SEQ ID NO: 234, SEQ ID NO: 360, and SEQ ID NO: 486. In more particular embodiments, the binding portion which binds to human CD3 also comprises a CDR set of the common light chain comprising the amino acid sequence of SEQ ID NO: 1. More particularly, the light chain CDR set comprising the amino acid sequences of SEQ ID NO: 721, SEQ ID NO:722 and SEQ ID NO:723. Preferably, the binding portion which binds to human BCMA comprises a heavy chain CDR set comprising an amino acid sequence of SEQ ID NO: 234, SEQ ID NO: 360, and SEQ ID NO: 486; and the light chain CDR set comprising the amino acid sequences of SEQ ID NO: 721, SEQ ID NO:722 and SEQ ID NO:723.

In other embodiments, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 83 to 109. In more particular embodiments, the binding portion which binds to human BCMA also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

In other embodiments, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 83 to 109, wherein the amino acid sequences of SEQ ID NOs: 83 to 109 further comprise the mutation N82aS. In more particular embodiments, the binding portion which binds to human BCMA also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 93, 101, 105, and 108. In more particular embodiments, the binding portion which binds to human BCMA also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 93, 101, 105, and 108, wherein an amino acid sequences of SEQ ID NOs: 93, 101, 105, and 108 further comprise the substitution N82aS. In more particular embodiments, the binding portion which binds to human BCMA also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

In a more particular embodiment, the binding portion which binds to human BCMA comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 591.

In other embodiments, the binding portion which binds to human BCMA comprises an heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 83 to 109. In more particular embodiments, the binding portion which binds to human BCMA also comprises a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

In other embodiments, the binding portion which binds to human BCMA comprises an heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 83 to 109, wherein the amino acid sequences of SEQ ID NOs: 83 to 109 further comprise the mutation N82aS. In more particular embodiments, the binding portion which binds to human BCMA also comprises a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 93, 101, 105, and 108; and a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human BCMA comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 93, 101, 105, 108, wherein the amino acid sequences of SEQ ID NOs: 93, 101, 105, and 108 further comprise the amino acid substitution N82aS; and a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

The present invention relates to a multispecific, e.g., bispecific or trispecific and multivalent, e.g., bivalent, or trivalent antibody or antibody fragment thereof comprising any of the binding portions that binds to human BCMA described above. In any of the bispecific or trispecific binding proteins described supra, the target antigen other than BCMA can be any of the following exemplary antigen targets: A2AR, APRIL, ATPDase, BAFF, BAFFR, BCMA, BIYS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CCR7, CD19, CD20, CD23 (also known as FCER2, a receptor for IgE), CD24, CD27, CD28, CD38, CD39, CD40, CD47, CD48, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PD-L2), CD274 (also known as PD-L1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, GPRC5D, Her2, HHLA2, HMGB1, HVEM, ICOSLG, IDO, IFNa, IgE, IGF1R, IL2Rbeta, IL1, IL1RAP, ILILIA, IL1B, IL1F10, IL2, IL4, IL4Ra, IL5, IL5R, IL6, IL7, IL7Ra, IL8, IL9, RAP, IL9R, IL10, rILI0, IL12, IL13, IL13RaI, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, KG2D, NTPDase-1, OX40, OX40L, PD-1H, platelet receptor, PROM1, 5152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1), XCL1 and XCL2. In some embodiments, one or more of the above antigen targets are human antigen targets. In a preferred embodiment, the antibody or antibody fragment thereof of the present invention is a trivalent bispecific antibody comprising at least two binding portions, at least one of which binds to human CD3 and at least one of which binds to BCMA, preferably at least two which bind to BCMA. In a more preferred embodiment, the antibody of the present invention is a trivalent trispecific antibody comprising at least three binding portions, at least one of which binds to human CD3, at least one of which binds to BCMA and at least one that binds to CD38.

The present invention also relates to monospecific antibody or antibody fragment thereof comprising any of the binding portion that binds to BCMA, e.g., to human BCMA, described above.

In a particular aspect, the present invention relates to an antibody or antibody fragment thereof that binds to human BCMA, comprising a heavy chain CDR set comprising an amino acid sequence selected from the group comprising:
SEQ ID NO:209, SEQ ID NO: 335, and SEQ ID NO: 461;
SEQ ID NO:210, SEQ ID NO: 336, and SEQ ID NO: 462;
SEQ ID NO:211, SEQ ID NO: 337, and SEQ ID NO: 463;
SEQ ID NO:212, SEQ ID NO: 338, and SEQ ID NO: 464;
SEQ ID NO:213, SEQ ID NO: 339, and SEQ ID NO: 465;
SEQ ID NO:214, SEQ ID NO: 340, and SEQ ID NO: 466;
SEQ ID NO:215, SEQ ID NO: 341, and SEQ ID NO: 467;
SEQ ID NO:216, SEQ ID NO: 342, and SEQ ID NO: 468;
SEQ ID NO:217, SEQ ID NO: 343, and SEQ ID NO: 469;
SEQ ID NO:218, SEQ ID NO: 344, and SEQ ID NO: 470;
SEQ ID NO:219, SEQ ID NO: 345, and SEQ ID NO: 471;
SEQ ID NO:220, SEQ ID NO: 346, and SEQ ID NO: 472;
SEQ ID NO:221, SEQ ID NO: 347, and SEQ ID NO: 473;
SEQ ID NO:222, SEQ ID NO: 348, and SEQ ID NO: 474;
SEQ ID NO:223, SEQ ID NO: 349, and SEQ ID NO: 475;
SEQ ID NO:224, SEQ ID NO: 350, and SEQ ID NO: 476;
SEQ ID NO:225, SEQ ID NO: 351, and SEQ ID NO: 477;
SEQ ID NO:226, SEQ ID NO: 352, and SEQ ID NO: 478;
SEQ ID NO:227, SEQ ID NO: 353, and SEQ ID NO: 479;
SEQ ID NO:228, SEQ ID NO: 354, and SEQ ID NO: 480;
SEQ ID NO:229, SEQ ID NO: 355, and SEQ ID NO: 481;
SEQ ID NO:230, SEQ ID NO: 356, and SEQ ID NO: 482;
SEQ ID NO:231, SEQ ID NO: 357, and SEQ ID NO: 483;

SEQ ID NO:232, SEQ ID NO: 358, and SEQ ID NO: 484; SEQ ID NO:233, SEQ ID NO: 359, and SEQ ID NO: 485; SEQ ID NO:234, SEQ ID NO: 360, and SEQ ID NO: 486; and SEQ ID NO:235, SEQ ID NO: 361, and SEQ ID NO: 487; and a light chain CDR set comprising the amino acid sequences of SEQ ID NO: 721, SEQ ID NO: 722 and SEQ ID NO: 723.

In a more particular aspect, the present invention relates to an antibody or antibody fragment thereof that binds to human BCMA, comprising a heavy chain CDR set comprising an amino acid sequence selected from the group comprising: SEQ ID NO: 234, SEQ ID NO: 360, and SEQ ID NO: 486; SEQ ID NO: 219, SEQ ID NO: 345, and SEQ ID NO: 471; SEQ ID NO: 227, SEQ ID NO: 353, and SEQ ID NO: 479; SEQ ID NO: 231, SEQ ID NO: 357, and SEQ ID NO: 483, and a light chain CDR set comprising the amino acid sequences of SEQ ID NO: 721, SEQ ID NO: 722 and SEQ ID NO: 723.

In preferred embodiments, the antibody disclosed herein, comprising a binding portion that binds human BCMA, as described above is monoclonal.

Anti-CD38 Binding Proteins

Certain aspects of the present disclosure relate to binding proteins that comprise an antigen binding site that binds a CD38 polypeptide (e.g., human and cynomolgus monkey CD38 polypeptides). In some embodiments, an antigen binding domain and/or binding protein of the present disclosure "cross reacts" with human and cynomolgus monkey CD38 polypeptides.

In some embodiments, the binding proteins disclosed herein are monospecific, or bispecific, or trispecific, or multispecific and/or monovalent, bivalent, trivalent, or multivalent and comprise a binding portion which binds to CD38, e.g., to human CD38.

In certain embodiments, the antibody or antibody fragment of the present invention comprises a binding portion which binds to human CD38 that comprises a heavy chain CDR set comprising an amino acid sequence selected from the group comprising: SEQ ID NO: 238, SEQ ID NO: 364, and SEQ ID NO: 490; SEQ ID NO: 239, SEQ ID NO: 365, and SEQ ID NO: 491; SEQ ID NO: 240, SEQ ID NO: 366, and SEQ ID NO: 492; SEQ ID NO: 241, SEQ ID NO: 367, and SEQ ID NO: 493; SEQ ID NO: 242, SEQ ID NO: 368, and SEQ ID NO: 494; SEQ ID NO: 243, SEQ ID NO: 369, and SEQ ID NO: 495; SEQ ID NO: 244, SEQ ID NO: 370, and SEQ ID NO: 496; SEQ ID NO: 245, SEQ ID NO: 371, and SEQ ID NO: 497; SEQ ID NO: 246, SEQ ID NO: 372, and SEQ ID NO: 498; SEQ ID NO: 247, SEQ ID NO: 373, and SEQ ID NO: 499; SEQ ID NO: 248, SEQ ID NO: 374, and SEQ ID NO: 500; SEQ ID NO: 249, SEQ ID NO: 375, and SEQ ID NO: 501; SEQ ID NO: 250, SEQ ID NO: 376, and SEQ ID NO: 502; SEQ ID NO: 251, SEQ ID NO: 377, and SEQ ID NO: 503; SEQ ID NO: 252, SEQ ID NO: 378, and SEQ ID NO: 504; SEQ ID NO: 253, SEQ ID NO: 379, and SEQ ID NO: 505; SEQ ID NO: 236, SEQ ID NO: 362, and SEQ ID NO: 712; and SEQ ID NO: 237, SEQ ID NO: 363, and SEQ ID NO: 700. In more particular embodiments, the binding portion which binds to human CD38 also comprises a CDR set of the common light chain comprising the amino acid sequence of SEQ ID NO: 1. More particularly, the CDR set comprising the amino acid sequences of SEQ ID NO: 721, SEQ ID NO:722 and SEQ ID NO:723.

In more particular embodiments, the binding portion which binds to human CD38 comprises a heavy chain CDR set comprising an amino acid sequence selected from the group comprising: SEQ ID NO: 236, SEQ ID NO: 362, and SEQ ID NO: 712; SEQ ID NO: 239, SEQ ID NO: 365, and SEQ ID NO: 491; SEQ ID NO: 237, SEQ ID NO: 363, and SEQ ID NO: 700; SEQ ID NO: 248, SEQ ID NO: 374, and SEQ ID NO: 500. Preferably, the binding portion which binds to human CD38 comprising a CDR set comprising SEQ ID NO: 236, SEQ ID NO: 362, and SEQ ID NO: 712 or SEQ ID NO: 239, SEQ ID NO: 365, and SEQ ID NO: 491. In more particular embodiments, the binding portion which binds to human CD3 also comprises a CDR set of the common light chain comprising the amino acid sequence of SEQ ID NO: 1. More particularly, the light chain CDR set comprising the amino acid sequences of SEQ ID NO: 721, SEQ ID NO:722 and SEQ ID NO:723.

In other embodiments, the binding portion which binds to human CD38 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 110 to 127. In more particular embodiments, the binding portion which binds to human CD38 also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human CD38 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 110, 111, 113, and 122. In more particular embodiments, the binding portion which binds to human CD38 also comprises a light chain variable region of a light chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1. The present invention also relates to a trispecific antibody or antibody fragment thereof comprising at least three binding portions, at least one of which binds to human CD3, at least one which binds to human BCMA and at least one of which binds to human CD38, wherein said at least one binding portion which binds to human CD38 comprises a heavy chain variable region comprising an amino acid sequence that is at least about 85%, 86%, 87%, 89%, 90%, 91%, 92%, 93%, 94%, 95%, 96%, 97%, 98%, 99% or 100% identical to the amino acid sequence of SEQ ID NO: 593 or 594.

In other embodiments, the binding portion which binds to human CD38 comprises an heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 110 to 127. In more particular embodiments, the binding portion which binds to human BCMA also comprises a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

Preferably, the binding portion which binds to human CD38 comprises an heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence selected from the group comprising SEQ ID NOs: 110, 111, 113, and 122; and a light chain that is at least about 80%, 81%, 82%, 83, 84%, 85%, 86%, 87%, 88%, 89%, 90%, 91%, 92%, 93%, 94%, 95%, 96%, 99%, or 100% identical to the amino acid sequence of SEQ ID NO: 1.

The present invention relates to a multispecific, e.g., bispecific or trispecific and multivalent, e.g., bivalent, or trivalent antibody or antibody fragment thereof comprising any of the binding portions that binds to human CD38 described above.

In any of the trispecific binding proteins described supra, the target antigen other than CD38 can be any of the following exemplary antigen targets: A2AR, APRIL, ATPDase, BAFF, BAFFR, BCMA, BIYS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known asTECK), CCL26 (also known as eotaxin-3), CCR3, CCR4, CD3, CCR7, CD19, CD20, CD23 (also known as FCER2, a receptor for IgE), CD24, CD27, CD28, CD38, CD39, CD40, CD47, CD48, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PD-L2), CD274 (also known as PD-L1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, GPRC5D, Her2, HHLA2, HMGB1, HVEM, ICOSLG, IDO, IFNa, IgE, IGF1R, IL2Rbeta, IL1, IL1RAP, ILILIA, IL1B, IL1F10, IL2, IL4, IL4Ra, IL5, IL5R, IL6, IL7, IL7Ra, IL8, IL9, RAP, IL9R, IL10, rILI0, IL12, IL13, IL13RaI, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, KG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1), XCL1 and XCL2. In some embodiments, one or more of the above antigen targets are human antigen targets. In a preferred embodiment, the antibody of the present invention is a trivalent trispecific antibody comprising at least three binding portions, at least one of which binds to human CD3, at least one of which binds to BCMA and at least one that binds to CD38.

The present invention also relates to monospecific antibody or antibody fragment thereof comprising any of the binding portion that binds to CD38, e.g., to human CD38, described above.

In a particular aspect, the present invention relates to an antibody or antibody fragment thereof that binds to human BCMA, comprising a heavy chain CDR set comprising an amino acid sequence selected from the group comprising: SEQ ID NO: 238, SEQ ID NO: 364, and SEQ ID NO: 490; SEQ ID NO: 239, SEQ ID NO: 365, and SEQ ID NO: 491; SEQ ID NO: 240, SEQ ID NO: 366, and SEQ ID NO: 492; SEQ ID NO: 241, SEQ ID NO: 367, and SEQ ID NO: 493; SEQ ID NO: 242, SEQ ID NO: 368, and SEQ ID NO: 494; SEQ ID NO: 243, SEQ ID NO: 369, and SEQ ID NO: 495; SEQ ID NO: 244, SEQ ID NO: 370, and SEQ ID NO: 496; SEQ ID NO: 245, SEQ ID NO: 371, and SEQ ID NO: 497; SEQ ID NO: 246, SEQ ID NO: 372, and SEQ ID NO: 498; SEQ ID NO: 247, SEQ ID NO: 373, and SEQ ID NO: 499; SEQ ID NO: 248, SEQ ID NO: 374, and SEQ ID NO: 500; SEQ ID NO: 249, SEQ ID NO: 375, and SEQ ID NO: 501; SEQ ID NO: 250, SEQ ID NO: 376, and SEQ ID NO: 502; SEQ ID NO: 251, SEQ ID NO: 377, and SEQ ID NO: 503; SEQ ID NO: 252, SEQ ID NO: 378, and SEQ ID NO: 504; SEQ ID NO: 253, SEQ ID NO: 379, and SEQ ID NO: 505; SEQ ID NO: 236, SEQ ID NO: 362, and SEQ ID NO: 712; and SEQ ID NO: 237, SEQ ID NO: 363, and SEQ ID NO: 700; and a light chain CDR set comprising the amino acid sequences of SEQ ID NO: 721, SEQ ID NO: 722 and SEQ ID NO: 723.

In a more particular aspect, the present invention relates to an antibody or antibody fragment thereof that binds to human CD38, comprising a heavy chain CDR set comprising an amino acid sequence selected from the group comprising: SEQ ID NO: 236, SEQ ID NO: 362, and SEQ ID NO: 712; SEQ ID NO: 239, SEQ ID NO: 365, and SEQ ID NO: 491; SEQ ID NO: 237, SEQ ID NO: 363, and SEQ ID NO: 700; SEQ ID NO: 248, SEQ ID NO: 374, and SEQ ID NO: 500.

In preferred embodiments, the antibody disclosed herein, comprising a binding portion that binds human CD38, as described above is monoclonal.

Trivalent Bispecific Anti-CD3 and Anti-BCMA Antibodies

In certain aspects, the present invention relates to a trivalent bispecific antibody or antibody fragment thereof comprising at least two binding portions, at least one of which binds to human CD3 and at least one of which binds to BCMA, preferably at least two which bind to BCMA.

In particular embodiments of the present invention, the trivalent bispecific anti-CD3 and anti-BCMA antibody is an heterodimeric immunoglobulin, in particular it is constructed using the BEAT® heavy chain (Hc) heterodimerization technology previously described (Skegro et al., (2017) J Biol Chem 292(23): 9745-9759 and Stutz et al., (2020) J Biol Chem 295(28): 9392-9408, WO2012131555), comprises a BEAT(A) chain, also referred herein to as BTA, and a BEAT (B) chain, also referred herein to as BTB. More specifically, the trivalent bispecific anti-CD3 and anti-BCMA antibody is designed by the combination of the CD3 binders as Fab and BCMA double dAb from the art on a silenced BEAT Fc backbone (LALA mutations, Hezareh et al., 2001, J Virol, 75(24): 12161-12168).

In certain embodiments of the present invention, the trivalent bispecific anti-CD3 and anti-BCMA comprises a BTA chain comprising the amino acid sequence of SEQ ID NO: 515, a BTB chain comprising the amino acid sequence of SEQ ID NO: 516, and a common Light chain comprising the amino acid sequence of SEQ ID NO: 1; or a BTA chain comprising the amino acid sequence of SEQ ID NO: 509, a BTB chain comprising the amino acid sequence of SEQ ID NO: 510, and a common Light chain comprising the amino acid sequence of SEQ ID NO: 1; or a BTA chain comprising the amino acid sequence of SEQ ID NO: 513, a BTB chain comprising the amino acid sequence of SEQ ID NO: 514, and a common Light chain comprising the amino acid sequence of SEQ ID NO: 1; or a BTA chain comprising the amino acid sequence of SEQ ID NO: 511, a BTB chain comprising the amino acid sequence of SEQ ID NO: 512, and a common Light chain comprising the amino acid sequence of SEQ ID NO: 1; or a BTA chain comprising the amino acid sequence of SEQ ID NO: 517, a BTB chain comprising the amino acid sequence of SEQ ID NO: 518, and a common Light chain comprising the amino acid sequence of SEQ ID NO: 1. The present invention also discloses a trivalent bispecific anti-CD3 and anti-BCMA comprising a BTA chain and/or a BTB chain and/or a common light chain at least about 80%, 81%, 82%, 83, 84%, 85%, 86%, 87%, 88%, 89%, 90%, 91%, 92%, 93%, 94%, 95%, 96%, 99%, or 100% identical to the above mentioned amino acid sequences.

Trispecific Anti-CD3, Anti-BCMA and Anti-CD38 Proteins

The present invention relates to a trispecific antibody or antibody fragment thereof comprising at least three binding portions, at least one of which binds to human CD3, at least one which binds to human BCMA and at least one of which binds to human CD38, also called herein CD3/BCMA/CD38 antibodies. In preferred embodiments, the present invention provides a trispecific antibody or antibody fragment thereof that binds to a human CD3 and to a human BCMA, and to human CD38. In preferred embodiment of the present invention the antibody is monoclonal. Binding portions that bind CD3, BCMA or CD38, according to the present invention are described supra.

Trispecific antibodies are a group of engineered antibody derivatives which recognize three different target antigens. In particular embodiments of the present invention, the trispecific anti-CD3, anti-BCMA anti-CD38 antibody is a heterodimeric immunoglobulin, in particular it is constructed using the TREAT® trispecific antibody technology which is based on BEAT® platform. The BEAT® platform is based on the replacement of the protein-protein interface of the CH3 domain pair of the antibody Fc region with the protein-protein interface of the T cell receptor (TCR) α-β constant region. The resulting BEAT® interface drives preferential formation of heterodimeric bispecific or trispecific antibodies (bsAbs or TriAbs) over the homodimeric contaminants. In addition, CD3/BCMA/CD38 antibodies make use of a Fab CD38 binding arm as Fab unit, of a Fab BCMA binding arm and of a Fab CD3 binding arm that all utilize a common light chain to prevent light chain mispairing, a common challenge associated with bsAb and even more so TriAbs platforms. Additional engineering has also been performed to allow an easier and faster purification process, natural conformation in antibody structure, stability, and binding to neonatal Fc receptor (FcRn) was retained maximizing the serum half-life of CD3/BCMA/CD38 antibodies (Skegro et al., J Biol Chem, 2017, 292(23):9745-9759; Stutz et al., J Biol Chem, 2020, 295(28):9392-9408).

Binding portions that bind CD3, BCMA or CD38, according to the present invention can be any of the binding portions that bind CD3, BCMA or CD38 described above.

In certain particular embodiments, the at least one binding portion which binds to human CD3 comprises a heavy chain CDR set selected from the group comprising: SEQ ID NO: 181, SEQ ID NO: 307, and SEQ ID NO: 433; SEQ ID NO: 184, SEQ ID NO: 310, and SEQ ID NO: 436; SEQ ID NO: 186, SEQ ID NO: 312, and SEQ ID NO: 438; SEQ ID NO: 188, SEQ ID NO: 314, and SEQ ID NO: 440; SEQ ID NO: 192, SEQ ID NO: 318, and SEQ ID NO: 444.; the at least one which binds to BCMA comprises a heavy chain CDR set selected from the group comprising SEQ ID NO: 234, SEQ ID NO: 360, and SEQ ID NO: 486; SEQ ID NO: 219, SEQ ID NO: 345, and SEQ ID NO: 471; SEQ ID NO: 227, SEQ ID NO: 353, and SEQ ID NO: 479; SEQ ID NO: 231, SEQ ID NO: 357, and SEQ ID NO: 483; and the at least one binding portion which binds to human CD38 comprises a heavy chain CDR set comprising SEQ ID NO: 236, SEQ ID NO: 362, and SEQ ID NO: 712; SEQ ID NO: 239, SEQ ID NO: 365, and SEQ ID NO: 491; SEQ ID NO: 237, SEQ ID NO: 363, and SEQ ID NO: 700; SEQ ID NO: 248, SEQ ID NO: 374, and SEQ ID NO: 500.

More specifically, the trispecific antibody of the present invention comprises at least one binding portion which binds to human CD3 comprising a heavy chain CDR set comprising SEQ ID NO: 181, SEQ ID NO: 307, and SEQ ID NO: 433; at least one binding portion which binds to BCMA comprising a heavy chain CDR set comprising SEQ ID NO: 234, SEQ ID NO: 360, and SEQ ID NO: 486; and at least one binding portion which binds to human CD38 comprising a heavy chain CDR set comprising SEQ ID NO: 236, SEQ ID NO: 362, and SEQ ID NO: 712 or SEQ ID NO: 239, SEQ ID NO: 365, and SEQ ID NO: 491. In a particularly preferred embodiment, the at least one binding portion which binds to human CD38 comprises a heavy chain CDR set comprising the amino acid sequence of SEQ ID NO: 239, SEQ ID NO: 365, and SEQ ID NO: 491.

In certain embodiment, the trispecific antibody or antibody fragment thereof disclosed herein further comprises a light chain variable region comprising an amino acid sequence of SEQ ID NO: 1.

Even more specifically, the present invention relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 239, SEQ ID NO: 365, and SEQ ID NO: 491, and a light chain CDR set comprising SEQ ID NO: 721, SEQ ID NO: 722 and SEQ ID NO: 723.

Even more specifically, the present invention relates to a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 236, SEQ ID NO: 362, and SEQ ID NO: 712, and a light chain CDR set comprising SEQ ID NO: 721, SEQ ID NO: 722 and SEQ ID NO: 723.

The present invention also relates to an antibody or antibody fragment thereof or antigen-binding fragment which binds to the same epitope on CD3, and/or BCMA, and/or CD38 as a reference antibody wherein the reference antibody is a trispecific antibody comprising at least three binding portions, at least one of which binds to human CD3, at least one which binds to human BCMA and at least one of which binds to human CD38, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 239, SEQ ID NO: 365, and SEQ ID NO: 491, and a light chain CDR set comprising SEQ ID NO: 721, SEQ ID NO: 722 and SEQ ID NO: 723.

The present invention also relates to an antibody or antibody fragment thereof or antigen-binding fragment which binds to the same epitope on CD3, and/or BCMA, and/or CD38 as a reference antibody wherein the reference antibody is a trispecific antibody comprising at least three binding portions, at least one of which binds to human CD3, at least one which binds to human BCMA and at least one of which binds to human CD38, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 236, SEQ ID NO: 362, and SEQ ID NO: 712, and a light chain CDR set comprising SEQ ID NO: 721, SEQ ID NO: 722 and SEQ ID NO: 723.

In a particular aspect of the present invention, the trispecific antibody comprises at least one binding portion which binds to human CD3 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 55; 58; 60; 62 and 66; at least one binding portion which binds to human BCMA comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 93, 101, 105 and 108; and at least one binding portion which binds to human CD38 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111. In a more particular aspect, the trispecific antibody or antibody fragment thereof further comprises a light chain variable region of a light chain comprising an amino acid sequence of SEQ ID NO: 1.

In a particular aspect of the present invention, the trispecific antibody comprises at least one binding portion which binds to human CD3 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 55; 58; 60; 62 and 66; at least one binding portion which binds to human BCMA comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 93, 101, 105, and 108, wherein an amino acid sequence of SEQ ID NOs: 93, 101, 105, and 108 further comprises the substitution N82aS; and at least one binding portion which binds to human CD38 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111. In a more particular aspect, the trispecific antibody or antibody fragment thereof further comprises a light chain variable region of a light chain comprising an amino acid sequence of SEQ ID NO: 1.

In a particular aspect of the present invention, the trispecific antibody comprises at least one binding portion which binds to human CD3 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 55; 58; 60; 62 and 66; at least one binding portion which binds to human BCMA comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 93, 101, 105 and 108; and at least one binding portion which binds to human CD38 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111. In a more particular aspect, the trispecific antibody or antibody fragment thereof further comprises a light chain comprising an amino acid sequence of SEQ ID NOs: 1.

In a particular aspect of the present invention, the trispecific antibody comprises at least one binding portion which binds to human CD3 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 55; 58; 60; 62 and 66; at least one binding portion which binds to human BCMA comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 93, 101, 105 and 108, wherein an amino acid sequence of SEQ ID NOs: 93, 101, 105, and 108 further comprises the substitution N82aS; and at least one binding portion which binds to human CD38 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110; 113, 122 and 111. In a more particular aspect, the trispecific antibody or antibody fragment thereof further comprises a light chain comprising an amino acid sequence of SEQ ID NOs: 1.

More specifically, the trispecific antibody or antibody fragment thereof of the present invention comprises at least one binding portion which binds to human CD3 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 55; at least one binding portion which binds to human BCMA comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 108; and at least one binding portion which binds to human CD38 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110 and 113. In a more particular aspect, the trispecific antibody or antibody fragment thereof further comprises a light chain variable region of a light chain comprising an amino acid sequence of SEQ ID NO: 1.

More specifically, the trispecific antibody or antibody fragment thereof of the present invention comprises at least one binding portion which binds to human CD3 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 55; at least one binding portion which binds to human BCMA comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 108, wherein the amino acid sequence of SEQ ID NO: 108 further comprising the mutation N82aS; and at least one binding portion which binds to human CD38 comprising a heavy chain variable region of a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110 and 113. In a more particular aspect, the trispecific antibody or antibody fragment thereof further comprises a light chain variable region of a light chain comprising an amino acid sequence of SEQ ID NO: 1.

Even more specifically, the trispecific antibody or antibody fragment thereof of the present invention comprises at least one binding portion which binds to human CD3 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 55; at least one binding portion which binds to human BCMA comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NOs: 108; and at least one binding portion which binds to human CD38 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110 and 113, preferably of SEQ ID NO: 113. In a more particular aspect, the trispecific antibody or antibody fragment thereof further comprises a light chain comprising an amino acid sequence of SEQ ID NO: 1.

Even more specifically, the trispecific antibody or antibody fragment thereof of the present invention comprises at least one binding portion which binds to human CD3 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 55; at least one binding portion which binds to human BCMA comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 108, wherein the amino acid sequence of SEQ ID NO: 108 further comprising the mutation N82aS; and at least one binding portion which binds to human CD38 comprising a heavy chain comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 110 and 113, preferably of SEQ ID NO: 113. In a more particular aspect, the trispecific antibody or antibody fragment thereof further comprises a light chain comprising an amino acid sequence of SEQ ID NO: 1.

In a preferred embodiment, the trispecific antibody or antibody fragment thereof of the present invention comprises at least one binding portion which binds to human CD3 comprising a heavy chain comprising an amino acid sequence of SEQ ID NO: 55; at least one binding portion which binds to human BCMA comprising a heavy chain comprising an amino acid sequence of SEQ ID NO: 108; and at least one binding portion which binds to human CD38 comprising a heavy chain comprising an amino acid sequence of SEQ ID NO: 113; and a light chain comprising an amino acid sequence of SEQ ID NO: 1.

In a preferred embodiment, the trispecific antibody or antibody fragment thereof of the present invention comprises at least one binding portion which binds to human CD3 comprising a heavy chain comprising an amino acid sequence of SEQ ID NO: 55; at least one binding portion which binds to human BCMA comprising a heavy chain comprising an amino acid sequence of SEQ ID NO: 108, wherein the amino acid sequence of SEQ ID NO: 108 further comprising the mutation N82aS; and at least one binding portion which binds to human CD38 comprising a heavy chain comprising an amino acid sequence of SEQ ID NO: 113; and a light chain comprising an amino acid sequence of SEQ ID NO: 1.

In a preferred embodiment, the trispecific antibody or antibody fragment thereof of the present invention comprises at least one binding portion which binds to human CD3 comprising a heavy chain comprising an amino acid sequence of SEQ ID NO: 55; at least one binding portion which binds to human BCMA comprising a heavy chain comprising an amino acid sequence of SEQ ID NO: 108; and at least one binding portion which binds to human CD38 comprising a heavy chain comprising an amino acid sequence of SEQ ID NO: 110; and a light chain comprising an amino acid sequence of SEQ ID NO: 1.

In a preferred embodiment, the trispecific antibody or antibody fragment thereof of the present invention comprises at least one binding portion which binds to human CD3 comprising a heavy chain comprising an amino acid sequence of SEQ ID NOs: 55; at least one binding portion which binds to human BCMA comprising a heavy chain comprising an amino acid sequence of SEQ ID NO: 108, wherein the amino acid sequence of SEQ ID NO: 108 further comprising the mutation N82aS; and at least one binding portion which binds to human CD38 comprising a heavy chain comprising an amino acid sequence of SEQ ID NO: 110; and a light chain comprising an amino acid sequence of SEQ ID NO: 1.

In a more particular aspect of the present invention, the trispecific antibody comprises at least one binding portion which binds to human CD3 comprising a heavy chain variable region comprising an amino acid sequence that is at least about 80%, 81%, 82%, 83, 84%, 85%, 86%, 87%, 88%, 89%, 90%, 91%, 92%, 93%. 94%, 95%, 96%, 97%, 98%, 99% or 100% identical to the amino acid sequence of SEQ ID NO: 592; at least one binding portion which binds to human BCMA comprising a heavy chain variable region comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to the amino acid sequence of SEQ ID NO: 591; and at least one binding portion which binds to human CD38 comprising a heavy chain variable region comprising an amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to an amino acid sequence selected from the group comprising SEQ ID NOs: 593 and 594, preferably, of SEQ ID NO: 594. In a more particular aspect, the trispecific antibody or antibody fragment thereof further comprises a light chain variable region of a light chain comprising an amino acid sequence of SEQ ID NO: 1.

The present invention also relates to an antibody or antigen-binding fragment which binds an epitope on the human CD3, wherein said epitope on CD3 comprises the amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to SEQ ID NO: 726.

In particular, the present invention also relates to an antibody or antibody fragment thereof or antigen-binding fragment which binds to the same epitope on human CD3 as a reference antibody or antibody fragment thereof comprising the at least one binding portion which binds to human CD3, one binding portion which binds to human BCMA, and one binding portion which binds to CD38, whilst said antibody is bound to human CD3, to human BCMA, and to human CD38, wherein the reference antibody is a trispecific antibody or antibody fragment thereof comprising at least three binding portions, at least one of which binds to human CD3, at least one which binds to human BCMA and at least one of which binds to human CD38, wherein said at least one binding portion which binds to human CD3 comprises a heavy chain CDR set comprising SEQ ID NO: 181, SEQ ID NO: 307, and SEQ ID NO: 433, and a light chain CDR set comprising SEQ ID NO: 721, SEQ ID NO: 722 and SEQ ID NO: 723; said at least one binding portion which binds to BCMA comprises a heavy chain CDR set comprising SEQ ID NO: 234, SEQ ID NO: 360, and SEQ ID NO: 486, and a light chain CDR set comprising SEQ ID NO: 721, SEQ ID NO: 722 and SEQ ID NO: 723; and said at least one binding portion which binds to human CD38 comprises a heavy chain CDR set comprising SEQ ID NO: 239, SEQ ID NO: 365, and SEQ ID NO: 491, and a light chain CDR set comprising SEQ ID NO: 721, SEQ ID NO: 722 and SEQ ID NO: 723.

The present invention also relates to an epitope on the human CD3 comprising the amino acid sequence that is at least about 80%, 81%, 82%, 83, 84%, 85%, 86%, 87%, 88%, 89%, 90%, 91%, 92%, 93%, 94%, 95%, 96%, 97%, 98%, 99% or 100% identical to SEQ ID NO: 726.

The present invention also relates to an antibody or antigen-binding fragment which binds an epitope on the human CD38, wherein said epitope on CD38 comprises the residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270, as detected by X-ray crystallography. In particular, as detected by X-ray crystallography, having resolution of at least 5 Å, preferably of at least A, even more preferably of at least 3.5 Å. In a most preferred example, the resolution is about 3.4 Å.

The present invention also relates to an epitope on the human CD38 comprising the residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270, as detected by X-ray crystallography. In particular, as detected by X-ray crystallography, having resolution of at least 5 Å, preferably of at least A, even more preferably of at least 3.5 Å. In a most preferred example, the resolution is about 3.4 Å.

The present invention also provides full length antibodies as well as antibody fragments and/or binding portions that binds to a human CD3 and/or to a human BCMA, and/or to human CD38. Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward E S et al., (1989) Nature, 341: 544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird R E et al., (1988) Science 242: 423-426; Huston J S et al., (1988) Proc. Natl. Acad. Sci. USA, 85: 5879-83), (vii) bispecific single chain Fv dimers (PCT/US92/09965), (viii) "diabodies" or "triabodies", multivalent or multispecific fragments constructed by gene fusion (Tomlinson I & Hollinger P (2000) Methods Enzymol. 326: 461-79; WO94/13804; Holliger P et al., (1993) Proc. Natl. Acad. Sci. USA, 90: 6444-48) and (ix) scFv genetically fused to the same or a different antibody (Coloma M J & Morrison S L (1997) Nature Biotechnology, 15(2): 159-163).

In certain embodiments of the present invention, the trispecific antibody is a full-length antibody or an antibody fragment thereof, wherein the at least one binding portion which binds to human CD3, and/or the at least one binding portion which binds to human BCMA and/or the at least one binding portion which binds to human CD38 is an antibody fragment, such as a Fab region. The term “Fab” or “Fab region” or “Fab domain” as used herein includes the polypeptides that comprise the VH, CH1, VL, and CL immunoglobulin domains. Fab may refer to this region in isolation, or this region in the context of a full-length antibody or antibody fragment.

In certain embodiment of the present invention, the trispecific antibody comprises at least one binding portion which binds to human CD3 and at least one binding portion which binds to human BCMA fused to each other, or at least one binding portion which binds to human CD3 and at least one binding portion which binds to human CD38 fused to each other, or at least one binding portion which binds to human BCMA and at least one binding portion which binds to human CD38 fused to each other.

In a particular embodiment, the trispecific antibody has the at least one binding portion which binds to human BCMA fused at the N-terminus to the C-terminus of the at least one binding portion which binds to human CD3. In another embodiment, the trispecific antibody has the at least one binding portion which binds to human BCMA fused at the N-terminus to the C-terminus said at least one binding portion which binds to human CD38.

In another embodiment, the trispecific antibody has at least one binding portion which binds to human BCMA fused at the C-terminus to the N-terminus of the at least one binding portion which binds to human CD3. In a further embodiment, the trispecific antibody of the present invention has the at least one binding portion which binds to human BCMA fused at the C-terminus to the N-terminus said at least one binding portion which binds to human CD38.

In another embodiment, the trispecific antibody has at least one binding portion which binds to human CD3 fused at the C-terminus to the N-terminus of the at least one binding portion which binds to human CD38. In a further embodiment, the trispecific antibody of the present invention has the at least one binding portion which binds to human CD3 fused at the N-terminus to the C-terminus said at least one binding portion which binds to human CD38.

In a particular aspect, the binding portions above are fused to each other via a linker, e.g., a peptide linker.

In a specific aspect, the binding portions of the trispecific antibody of the present invention are Fab fragments.

In an even more specific embodiment, the antibody of the present invention has three binding portions which are Fab fragments, wherein the binding portion which binds to human BCMA is fused at the C-terminus to the N-terminus of the Fab heavy or light chain of the binding portion which binds to human CD3, or wherein the binding portion which binds to human BCMA is fused at the C-terminus to the N-terminus of the Fab heavy or light chain of said binding portion which binds to human CD38.

In an even more specific embodiment, the antibody of the present invention has three binding portions which are Fab fragments, wherein the binding portion which binds to human BCMA is fused at the N-terminus to the C-terminus of the Fab heavy or light chain of the binding portion which binds to human CD3, or wherein the binding portion which binds to human BCMA is fused at the N-terminus to the C-terminus of the Fab heavy or light chain of said binding portion which binds to human CD38.

In a particular aspect of the present invention the binding portions of the antibody fused as described above are fused via a peptide linker. Preferably the linker has a sequence selected from SEQ ID NOs: 604 and 605. Other preferred peptide linkers are listed below in paragraph “Linkers”.

Preferably the trispecific antibody according to the present invention comprises the a set of three amino acid chains of sequences that are at least about 80%, 81%, 82%, 83%, 84%, 85%, 86%, 87%, 89%, 90%, 91%, 92%, 93%, 94%, 95%, 96%, 97%, 98%, 99% or 100% identical to the amino acid sequence selected from the group comprising: SEQ ID NO: 522, SEQ ID NO: 523 and SEQ ID NO: 1; SEQ ID NO: 530, SEQ ID NO: 531 and SEQ ID NO: 1; SEQ ID NO: 532, SEQ ID NO: 533 and SEQ ID NO: 1; SEQ ID NO: 534, SEQ ID NO: 535 and SEQ ID NO: 1; SEQ ID NO: 536, SEQ ID NO: 537 and SEQ ID NO: 1; SEQ ID NO: 538, SEQ ID NO: 539 and SEQ ID NO: 1; SEQ ID NO: 540, SEQ ID NO: 541 and SEQ ID NO: 1; SEQ ID NO: 542, SEQ ID NO: 543 and SEQ ID NO: 1; SEQ ID NO: 544, SEQ ID NO: 545 and SEQ ID NO: 1; SEQ ID NO: 546, SEQ ID NO: 547 and SEQ ID NO: 1; and SEQ ID NO: 548, SEQ ID NO:549 and SEQ ID NO:1.

Preferably the present invention relates to a trispecific antibody comprising a set of three amino acid chains that are at least about 80%, 81%, 82%, 83%, 84%, 85%, 86%, 87%, 89%, 90%, 91%, 92%, 93%, 94%, 95%, 96%, 97%, 98%, 99% or 100% identical to the amino acid sequence of selected from the group comprising: SEQ ID NO: 546, SEQ ID NO: 547 and SEQ ID NO: 1; and SEQ ID NO: 548, SEQ ID NO:549 and SEQ ID NO:1.

In a more preferred embodiment, the trispecific antibody or antibody fragment thereof according to the present invention, comprises a set of three amino acid chains of amino acid sequences SEQ ID NO: 546, SEQ ID NO: 547 and SEQ ID NO: 1.

Nucleic acids Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.).

Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid molecules comprise a sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical.

Certain aspects of the present disclosure relate to kits of polynucleotides. In some embodiments, one or more of the polynucleotides is a vector {e.g., an expression vector). The kits may find use, inter alia, in producing one or more of the binding proteins described herein, e.g., a bi-, or trispecific binding protein of the present disclosure. In some embodiments, the kit comprises one, two, three, or four polynucleotides.

In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, polyomaviruses, such as Simian Virus 40 (SV40), and the like), from heterologous eukaryotic promoters (such as the actin promoter, an immunoglobulin promoter, from heat-shock promoters, and the like), the cytomegalovirus immediate-early enhancer/chicken β-actin CAG-promoter (Niwa et al., Gene 108(2): 193-9, 1991), the phosphoglycerate kinase (PGK)-promoter, a tetracycline-inducible promoter (Masui et al., Nucleic Acids Res. 33:e43, 2005), the lac system, the tip system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers, and other expression control elements (e.g., polyadenylation signals). Examples of suitable enhancers may include, but are not limited to, enhancer sequences from mammalian genes (such as globin, elastase, albumin, a-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth polypeptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, polynucleotide kits, vectors, and/or vector systems described herein. In some embodiments, the host cell is a bacterial cell (e.g., a *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture, and their variants 293T), Expi293™ cells, CHO cells, baby hamster kidney cells (e.g., BHK, ATCC CCL 10), mouse Sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3 Å, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell.

Methods of culturing host cells under conditions to express a protein are well known to one of ordinary skill in the art. Cell culture is a process cells are grown under controlled conditions in an artificial environment. The terms "cell culture" or "culture" or "host cell culture" refer to the growth and/or propagation and/or maintenance of cells in controlled artificial conditions. Optimal culturing conditions are obtained by the control and adjustment of several parameters including: the formulation of the cell culture medium, the bioreactor operating parameters, the nutrient supply modality and the culturing time period. The formulation of the culturing medium is optimized to favorite cell vitality and reproduction; examples of constituents of the cell culture medium include but are not limited to essential amino acids, salts, glucose, growth factors and antibiotics. Important bioreactor operating parameters are: temperature, pH, agitation speed, oxygenation and carbon dioxide levels. Nutrients can be supplied in different ways: in the batch mode culture all the necessary nutrients are present in the initial base medium and are used till exhausted while wastes accumulate; in the fed-batch culture additional feed medium is supplied to prevent nutrient depletion and prolong the culture; differently, in the perfusion modality, cells in culture are continuously supplemented with fresh medium containing nutrients that flows in the bioreactor removing cell wastes. A skilled person appreciate that the culturing period is important as it needs to be long enough to let the cells produce a consistent amount of product, but it cannot be too long to impair cell viability.

Methods of isolating proteins from cultured host cells are well known to one of ordinary skill in the art, including, for example, chromatography techniques. The term "chromatography" refers to the operation of separating compounds of a mixture based on their capability to interact with a stationary phase of a chromatography resin, from which they can be retained or eluted. Chromatography techniques are known in the art, for instance ion exchange chromatography separates ions and polar molecules based on their difference of charges, example of ion exchange chromatography techniques are cation exchange chromatography and anion exchange chromatography. Affinity chromatography relies on the specific interaction of the protein with an immobilized ligand. Non limiting examples of ligands which are useful for purification of an antibody by affinity chromatography are Protein A and Protein G. Protein A is a cell wall protein isolated from *Staphylococcus aureus*, which has the property of binding to the immunoglobulin Fc (and not binding to the antigen binding site). Herein, the term "Protein A chromatography" refers to an affinity chromatography wherein ligand binding the antibody is Protein A, wherein the term "Protein A" includes native Protein A, recombinant Protein A, and analogs or derivatives thereof. Both protein analogs and derivatives retain their binding activity to antibodies (e.g., IgG Fc). Protein G is a cell wall protein isolated from type G *Streptococcus*, and its N-terminal part is albumin binding domain, and its C-terminal part is IgG binding domain and cell wall binding domain. Herein, the term "Protein G chromatography" refers to an affinity chromatography wherein ligand binding the antibody is Protein G, wherein the term "protein G" includes native protein G, recombinant protein G, and analogs or derivatives thereof. Methods of isolating proteins from cultured host cells may include an affinity chromatography step (such as protein A affinity chromatography) followed by one or more step of ion exchange chromatography and/or size exclusion chromatography.

Antibody Architecture

In certain embodiments of the present invention, the binding portions of the trispecific antibody or antibody fragment thereof are fused (i.e., connected together) to each other. In particular embodiments, the at least one binding portion which binds to human CD3 and the at least one binding portion which binds to human BCMA, or the at least one binding portion which binds to human CD3 and the at least one binding portion which binds to human CD38, or the at least one binding portion which binds to human BCMA and the at least one binding portion which binds to human CD38, are fused to each other. In more particular embodiments, the at least one binding portion which binds to human CD3 and the at least one binding portion which binds to human BCMA, or the at least one binding portion which binds to human CD3 and the at least one binding portion which binds to human CD38, or the at least one binding portion which binds to human BCMA and the at least one binding portion which binds to human CD38, are fused to each other via a linker, e.g. a peptide linker.

In certain embodiments, the binding portion which binds to human BCMA is fused at the N-terminus to the C-terminus of the binding portion which binds to human CD3. In other embodiments, the binding portion which binds to human BCMA is fused at the N-terminus to the C-terminus of the binding portion which binds to human CD38. In other embodiments, the binding portion which binds to human BCMA is fused at the C-terminus to the N-terminus of the binding portion which binds to human CD3. In other embodiments, the binding portion which binds to human BCMA is fused at the C-terminus to the N-terminus of the binding portion which binds to human CD38.

In certain embodiments, the binding portion which binds to human CD3 is fused at the N-terminus to the C-terminus of the binding portion which binds to human BCMA. In other embodiments, the binding portion which binds to human CD3 is fused at the N-terminus to the C-terminus of the binding portion which binds to human CD38. In other embodiments, the binding portion which binds to human CD3 is fused at the C-terminus to the N-terminus of the binding portion which binds to human BCMA. In other embodiments, the binding portion which binds to human CD3 is fused at the C-terminus to the N-terminus of the binding portion which binds to human CD38.

In certain embodiments, the binding portion which binds to human CD38 is fused at the N-terminus to the C-terminus of the binding portion which binds to human BCMA. In other embodiments, the binding portion which binds to human CD38 is fused at the N-terminus to the C-terminus of the binding portion which binds to human CD3. In other embodiments, the binding portion which binds to human CD38 is fused at the C-terminus to the N-terminus of the binding portion which binds to human BCMA. In other embodiments, the binding portion which binds to human CD38 is fused at the C-terminus to the N-terminus of the binding portion which binds to human CD3.

In preferred embodiments, the binding portion which binds to human BCMA is fused at the N-terminus to the C-terminus of the binding portion which binds to human CD3, or the binding portion which binds to human BCMA is fused at the C-terminus to the N-terminus of the binding portion which binds to human CD38.

In preferred embodiments, the binding portions connected as described above are fused to each other via a linker, e.g. a peptide linker.

In preferred embodiments, the binding portion which binds to human BCMA is fused at the N-terminus to the C-terminus of the binding portion which binds to human CD3 via a peptide linker, or the binding portion which binds to human BCMA is fused at the C-terminus to the N-terminus of the binding portion which binds to human CD38 via a peptide linker.

In even more preferred embodiments, the binding portion which binds to human BCMA is fused at the N-terminus to the C-terminus of the binding portion which binds to human CD3 via a peptide linker of SEQ ID NO: 605, or the binding portion which binds to human BCMA is fused at the C-terminus to the N-terminus of the binding portion which binds to human CD38 via a peptide linker of SEQ ID NO: 604.

In particular embodiments of the present invention, the binding portions of the antibody disclosed herein are an antibody fragment selected from the previously mentioned non limiting list of "antibody fragments". In more particular embodiment, the binding portion which binds to human CD3 and/or the binding portion which binds to human BCMA and/or the binding portion which binds to human CD38 is a Fab domain.

In certain embodiment the antibody of the present invention comprises an Fc domain and at least three binding portions. In more particular embodiments, at least a first binding portion is fused at the N-terminus to the C-terminus of a second binding portion. In certain aspects, the first binding portion, e.g., a Fab domain, that is located between the antibody Fc domain and the second binding portion, e.g., a second Fab domain, is termed "Fc proximal", while the second binding portion is termed "Fc distal".

In particular embodiment the second binding portion, e.g., an Fc distal binding portion, is fused to the N-terminus of the VH (variable heavy) domain of the first binding portion, e.g., an Fc proximal binding portion.

In preferred embodiments, the binding portion that binds to CD38 is Fc proximal and the binding portion that binds CD3 or to the binding portion that binds BCMA is Fc distal; preferably the binding portion that binds to CD38 is proximal and the binding portion that binds to BCMA is Fc distal. In a preferred embodiment the binding portion that binds BCMA is Fc proximal and the binding portion that binds CD3 or the binding portion that binds CD38 is Fc distal; more preferably the binding portion that binds BCMA is Fc proximal to the binding portion that binds CD3 is Fc distal.

In particular embodiments of the present invention, the trispecific antibody or antibody fragment thereof of the present invention comprises a three binding portions, one that binds to human CD3, one that binds to human BCMA and one that binds to human CD38, said three binding portions are Fab fragments, and the antibody is constructed using the TREAT® trispecific antibody technology which is based on BEAT® platform as described above. In a particular embodiment, the binding portion that binds to human BCMA and the binding portion that binds to human CD38 are located on the same arm of the BEAT antibody, more in particular, the binding portion that binds to human BCMA binding arm is in the Fc distal position, and the binding portion that binds to human CD38 is in the Fc proximal position. In a more particular embodiment, the binding portion that binds to human BCMA and the binding portion that binds to human CD38 are fused via a flexible linker; preferably comprising an amino acid sequence of SEQ ID NO: 604. In a preferred particular embodiment, the binding portion that binds to human CD3 and the binding portion that binds to human BCMA are located on the same arm of the BEAT antibody, more in particular, the binding portion that binds to human CD3 binding arm is in the Fc distal position, and the binding portion that binds to human BCMA is in the Fc proximal position. In a more particular embodiment, the binding portion that binds to human CD3 and the binding portion that binds to human BCMA are fused via a flexible linker; preferably comprising an amino acid sequence of SEQ ID NO: 605.

Linkers

In some embodiments, the linkers of the present invention, e.g., L1, L2, L3 and L4, range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acid long. L1, L2, L3 and L4 in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues; a peptide with five glycine residues; a peptide with six glycine residues; a peptide with seven glycine residues; and a peptide with eight glycine residues. Other combinations of amino acid residues may be used such as the peptide GGGT, or the GGGGS, or repetitions of said peptides, such as the peptide GGGGS GGGGS GGGGS. In a preferred embodiment, the linker of the present invention linking different binding portions has an amino acid sequence of SEQ ID NO: 604 or 605 or an amino acid sequence of SEQ ID NO: 604 or 605 comprising one or more conservative substitutions thereof.

The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345 and International Application No. PCT/US2017/027488.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

Fc Regions and Constant Domains

The present invention also relates to a trispecific antibody comprising an Fc region. In some embodiments, a binding protein of the present disclosure comprises an antibody fragment, including but not limited to antibody Fab, (Fab')2, Fab'-SH, Fv, or scFv fragments. In some embodiments, a binding protein of the present disclosure comprises an antibody fragment, including but not limited to antibody Fab, (Fab')2, Fab'-SH, Fv, or scFv fragments, comprising an Fc region.

In some embodiments, a binding protein of the present disclosure comprises a full-length antibody heavy chain or a polypeptide chain comprising an Fc region. In some embodiments, the Fc region is a human Fc region, e.g., a human IgG1, IgG2, IgG3, or IgG4 Fc region. In some embodiments, the Fc region includes an antibody hinge, CH1, CH2, CH3, and optionally CH4 domains. In some embodiments, the Fc region is a human IgG1 Fc region. In some embodiments, the Fc region is a human IgG2 Fc region. In some embodiments, the Fc region is a human IgG3 Fc region in some embodiments, the Fc region is a human IgG4 Fc region. In some embodiments, the Fc region includes one or more of the mutations described herein.

In certain embodiment, the trispecific antibody or antibody fragment thereof of the present invention comprises a non-naturally occurring Fc domain.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "parent antibody" or "parent immunoglobulin" as used herein includes an unmodified antibody that is subsequently modified to generate a variant. Said parent antibody may be a naturally occurring antibody, a non-naturally occurring antibody, or a variant or engineered version of a naturally occurring antibody. Parent antibody may refer to the antibody itself, compositions that comprise the parent antibody, or the amino acid sequence that encodes it. In preferred embodiments of the present invention, the parent antibody comprises an Fc region. More specifically, the Fc region of the parent antibody according to the present invention is a human IgG1, IgG2, IgG3, or IgG4 Fc region; in some embodiments the Fc region of the parent antibody according to the present invention is a modified or not modified IgG1 Fc region.

In particular embodiments, the antibody of the present invention is a hetero-dimeric antibody or antibody fragment thereof with an engineered Fc comprising a first and a second engineered CH3 domain, wherein said first engineered CH3 domain comprises the substitutions that favor heterodimerization. In particular embodiments of the present invention, the antibody is constructed using the BEAT® heavy chain (Hc) heterodimerization technology previously described (Skegro et al., (2017) J Biol Chem 292(23): 9745-9759 and Stutz et al., (2020) J Biol Chem 295(28): 9392-9408, WO2012131555), wherein the BEAT(A) chain is also referred herein to as BEAT(A) and comprises a first engineered CH3 domain, and the BEAT (B) chain is also referred herein to as BEAT(B) and comprises a second engineered CH3 domain.

In a more particular embodiment the first engineered CH3 domain comprises one or more substitutions selected from the group comprising of the group comprising: Q347A, S364K, T366V, K370T, K392Y, F405S, Y407V, K409W, T411N (EU numbering); and said second engineered CH3 domain comprises the substitutions of the group comprising: Q347E, Y349A, L351F, S364T, T366V, K370T, T394D, V397L, D399E, F405A, Y407S, K409R, T411R (EU numbering); in specific aspects, the hetero-dimeric immunoglobulin or hetero-dimeric fragment heterodimerize through said first and second engineered CH3 domains.

In more particular embodiment, the present invention discloses a trispecific antibody or antibody fragment thereof constructed based on the BEAT® platform, wherein BEAT (A) CH3 domain comprises one or more substitutions selected from the group comprising: Q347A, S364K, T366V, K370T, K392Y, F405S, Y407V, K409W, T411N (EU numbering) and optionally BEAT(A) further comprises substitutions selected from the group comprising D356E, L358M, N384S, V397M, V4221, H435R, and Y436F (EU numbering); and BEAT(B) CH3 domain comprises one or more substitutions selected from the group comprising: Q347E, Y349A, L351F, S364T, T366V, K370T, T394D, V397L, D399E, F405A, Y407S, K409R, T411R (EU numbering), and optionally BEAT(b) further comprises the substitution D401Q (EU numbering).

In certain aspects, the present invention also relates to a trispecific hetero-dimeric antibody or antibody fragment thereof comprising a first and a second engineered CH3 domain, wherein said first engineered CH3 domain comprises the substitutions of the group comprising: Q347A, S364K, T366V, K370T, K392Y, F405S, Y407V, K409W, T411N (EU numbering), and said second engineered CH3 domain comprises the substitutions of the group comprising: Q347E, Y349A, L351F, S364T, T366V, K370T, T394D, V397L, D399E, F405A, Y407S, K409R, T411R (EU numbering), and wherein said trispecific hetero-dimeric immunoglobulin or hetero-dimeric fragment heterodimerize through said first and second engineered CH3 domains, characterized in that said trispecific hetero-dimeric antibody or antibody fragment thereof comprises at least three binding portions each binding portion which binds to a different antigen.

In certain aspects, the bispecific antibody of the present invention comprises a variant Fc region which comprises at least one amino acid modification relative to the Fc region of the parent antibody, whereas the antibody comprising the variant Fc region exhibits altered effector function compared to the parent antibody. More specifically the CH2 domain of the Fc region comprises at least one amino acid modification.

In particular embodiments of the present invention, BEAT (A) and BEAT(B) have been engineered to increase the Fc effector function. More specifically the CH2 domain of the Fc region has been engineered so as to comprise at least one amino acid modification. More specifically BEAT(A) comprises one or more substitutions at a position selected from the group comprising: 324, 334, 269, 298, 239, 332 and 333; and BEAT(B) comprises one or more substitutions at a position selected from the group comprising: 324, 334, 269, 298, 239, 332 and 333; preferably comprising 324, 334, 269, 289, 298, 333. Even more specifically BEAT(A) comprises one or more substitutions selected from the group comprising: S324N, K334E, K334A, E269D, S298A, S239D, 1332E and E333 Å; and BEAT(B) comprises one or more substitutions at a position selected from the group comprising: S324N, K334E, K334A, E269D, S289 Å, K334A, E333 Å. In certain particular embodiments, BEAT(A) comprises a set of mutations selected from the group comprising: S324N; or S324N and K334E; or E269D, S298A, S324N and K334A; or S239D, 1332E and S324N; or E269D, S298A, S324N and E334A; or S298A, S324N and E333A; or S298A, S324N and K334A; or S324N, S298A, E269D and E333A; or S324N, S298A, E269D and K334A. In other particular embodiments, BEAT(B) comprises a set of mutations selected from the group comprising: S324N; or S324N and K334E; or E269D, S298A, S324N and K334A; or S239D, 1332E and S324N; or E269D; or E269D, S298A, S324N and E334A; or S298A, S324N and E333A; or S298A, S324N and K334A; or S324N, S298A, E269D and E333A; or S324N, S298A, E269D and K334 Å. In certain preferred embodiments, BEAT(A) and BEAT(B) comprises the mutation S324N; or the mutations S324N and K334E; or the mutations E269D, S298A, S324N and K334 Å; or the mutations E269D, S298A, S324N and E334A; or the mutations S298A, S324N and E333A; or the mutations S298A, S324N and K334A; or the mutations S324N and K334E. In particularly preferred embodiments, BEAT(A) comprises the mutations S239D, 1332E and S324N, and BEAT(B) comprises the mutation S324N.

In some embodiments, the Fc region comprises one or more mutations that reduce or eliminate Fc receptor binding and/or effector function of the Fc region (e.g., Fc receptor-mediated antibody-dependent cellular phagocytosis (ADCP), complement-dependent cytotoxicity (CDC), and/or antibody-dependent cellular cytotoxicity (ADCC)).

In some embodiments, the Fc region is a human IgG1 Fc region comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298, 299, and/or 300 of human IgG1 according to EU Index. In some embodiments, the amino acid substitutions are S298N, T299A, and/or Y300S.

In some embodiments, the Fc region is a human IgG4 Fc region comprising one or more mutations that reduce or eliminate FcγI and/or FcγII binding. In some embodiments, the Fc region is a human IgG4 Fc region comprising one or more mutations that reduce or eliminate FcγI and/or FcγII binding but do not affect FcRn binding. In some embodiments, the Fc region is a human IgG4 Fc region comprising amino acid substitutions at positions corresponding to positions 228 and/or 409 of human IgG4 according to EU Index.

In some embodiments, the amino acid substitutions are S228P and/or R409K. In some embodiments, the Fc region is a human IgG4 Fc region comprising amino acid substitutions at positions corresponding to positions 234 and/or 235 of human IgG4 according to EU Index. In some embodiments, the amino acid substitutions are F234A and/or L235A. In some embodiments, the Fc region is a human IgG4 Fc region comprising amino acid substitutions at positions corresponding to positions 228, 234, 235, and/or 409 of human IgG4 according to EU Index. In some embodiments, the amino acid substitutions are S228P, F234A, L235A, and/or R409K. In some embodiments, the Fc region is a human IgG4 Fc region comprising amino acid substitutions at positions corresponding to positions 233-236 of human IgG4 according to EU Index.

In some embodiments, the amino acid substitutions are E233P, F234V, L235A, and a deletion at 236. In some embodiments, the Fc region is a human IgG4 Fc region comprising amino acid mutations at substitutions corresponding to positions 228, 233-236, and/or 409 of human IgG4 according to EU Index.

In some embodiments, the amino acid mutations are S228P; E233P, F234V, L235A, and a deletion at 236; and/or R409K.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) Sci. Rep. 5: 17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region CH2 and CH3 immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F.

To improve the yields of some binding proteins (e.g., bispecific or trispecific binding proteins), the CH domains can be altered by the BEAT technology which is described in detail with several examples in and in International Publication No. WO2012131555.

In some embodiments, a binding protein of the present disclosure comprises one or more mutations to improve serum half-life (See e.g., Hinton, P R. et al. (2006) J. Immunol. 176(1):346-56). In some embodiments, the mutation comprises substitutions at positions corresponding to positions 428 and 434 of human IgG1 or IgG4 according to EU Index, wherein the amino acid substitutions are M428L and N434S.

In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to CH1, the first Fc region comprising an immunoglobulin hinge region and CH2 and CH3 immunoglobulin heavy chain constant domains; wherein the third polypeptide chain further comprises a second Fc region linked to CH1, the second Fc region comprising an immunoglobulin hinge region and CH2 and CH3 immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235 Å. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235 Å. In some embodiments, the second polypeptide chain further comprises a first Fc region linked to CH1, the first Fc region comprising an immunoglobulin hinge region and CH2 and CH3 immunoglobulin heavy chain constant domains; wherein the third polypeptide chain further comprises a second Fc region linked to CH1, the second Fc region comprising an immunoglobulin hinge region and CH2 and CH3 immunoglobulin heavy chain constant domains; wherein the first and second Fc regions are human IgG1 Fc regions; and wherein the first and the second Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG4 Fc regions, and the Fc regions each comprise amino acid substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A.

In some embodiments, a binding protein of the present disclosure comprises knob and hole mutations and one or more mutations to reduce effector function. In some embodiments, the first and/or second Fc regions are human IgG1 Fc regions. In some embodiments, the first and/or second Fc regions are human IgG4 Fc regions. For further description of Fc mutations at position 329, see, e.g., Shields, R. L. et al. (2001) J. Biol. Chem. 276:6591-6604 and WO 1999051642.

In a specific embodiment, the trispecific antibody or antibody fragment thereof according to the present invention comprises a non-naturally occurring Fc domain comprising L234A/L235A(LALA)/P329A substitutions into the CH2 domain. More in particular, the trispecific antibody or antibody fragment thereof disclosed herein may comprise a Fc, wherein the Fc may comprise a first and a second BEAT CH3 domains as described above, or naturally occurring CHE domains, or as described above, or any other non-naturally occurring CH3 and CH2 domain that comprises L234A/L235A(LALA)/P329A substitutions.

Application of the Binding Protein

The antibody or antibody fragment thereof of the present invention can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in certain embodiments, binding proteins can be labeled with a detectable moiety. The detectable moiety can be anyone that is capable of producing, either directly or indirectly, a detectable signal. For example, the detectable moiety can be a radioisotope, such as 3H, 14C, 32P, 35S, 1251, 99Tc, U1In, or 67Ga; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

For clinical or research applications, in certain embodiments, binding proteins can be conjugated to a cytotoxic agent. A variety of antibodies coupled to cytotoxic agents {i.e., antibody-drug conjugates) have been used to target cytotoxic payloads to specific tumor cells. Cytotoxic agents and linkers that conjugate the agents to an antibody are known in the art; see, e.g., Parslow, A. C. et al. (2016) Biomedicines 4: 14 and Kalim, M. et al. (2017) Drug Des. Devel. Ther. 11:2265-2276.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically acceptable buffer, such as bacteriostatic water for injection (BWFI), phosphate-buffered saline, Ringer's solution, and dextrose solution. It may further include other materials desirable from a commercial and user standpoint, including other buffers, diluents, filters, needles, and syringes.

In some embodiments, a binding protein of the present disclosure is administered to a patient in need thereof for the treatment or prevention of cancer. In some embodiments, the present disclosure relates to a method of preventing and/or treating a proliferative disease or disorder (e.g., cancer). In some embodiments, the method comprises administering to a patient a therapeutically effective amount of the heterodimeric antibody, or pharmaceutical compositions related thereto, described herein. In some embodiments, the present disclosure relates to uses of the heterodimeric antibody, or pharmaceutical compositions related thereto, described herein for preventing and/or treating a proliferative disease or disorder (e.g., cancer) in a patient in need thereof. In some embodiments, the present disclosure relates to the heterodimeric antibody, or pharmaceutical compositions related thereto, described herein for use in the manufacture of a medicament for preventing and/or treating a proliferative disease or disorder (e.g., cancer) in a patient in need thereof. In some embodiments, the patient is a human. In some embodiments, the binding protein comprises one antigen binding site that binds a T-cell surface protein and another antigen binding site that binds the extracellular domain of a human CD38 polypeptide. In some embodiments, the binding protein comprises an antigen binding site that binds the extracellular domain of a human CD38 polypeptide, an antigen binding site that binds a human CD3 polypeptide and an antigen binding site that binds a human BCMA polypeptide.

In certain embodiments, the cancer is a BCMA-expressing cancer and/or CD38 expressing cancer. Examples of cancer comprises but are not limited to multiple myeloma, leukemia, such as acute lymphoblastic leukemia, chronic lymphocytic leukemia (CLL), acute myeloid leukemia, acute promyelocytic leukemia, acute myeloblastic leukemia, and acute megakaryoblastic leukemia, chronic myelogenous leukemia, multiple myeloma, plasma cell leukemia, lymphoma, breast cancer such as Her2+ breast cancer, prostate cancer, cervical cancer, germinal center B-cell lymphoma or B-cell acute lymphoblastic leukemia, Chronic lymphocytic leukemia (CLL), Hodgkin lymphoma, Non-Hodgkin lymphoma, diffuse large B-cell lymphoma, Myelodisplastic syndrome (MDS), breast cancer such as Her2+ breast cancer, prostate cancer, cervical cancer, non-small cell lung cancer (NSCLC), Hepatocellular carcinoma (HCC), High-grade serous ovarian carcinoma, peritoneal cancer, smoldering myeloma, glioma.

Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapol), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Further, the binding protein can be formulated as liquid formulation or as lyophilizate using appropriate excipients.

The pharmaceutical compositions of the disclosure can be selected for intravenous or subcutaneous. Alternatively, the compositions can be selected for inhalation or for delivery through the digestive tract, such as orally. The preparation of such pharmaceutically acceptable compositions is within the skill of the art.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized, and pre-systemic degradation is minimized.

Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations.

Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g., films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D (−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency depends upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; subcutaneous; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Therapeutic Regimen

The disclosure also provides a method of treating multiple myeloma in a subject in need thereof. The method employs a heterodimeric antibody that engages CD3, BCMA and CD38 in such a manner so as to transiently connect malignant cells with T cells which are engaged, thereby inducing T cell mediated killing of the bound malignant cell. The method described herein utilizes a heterodimeric antibody that binds CD3, BCMA and CD38 in such a manner so as to maximize destruction of target cells while reducing unwanted side effects (e.g., uncontrolled cytokine release).

The terms "treatment" or "treat" as used herein refer to both therapeutic treatment and prophylactic or preventative measures. The antibody of the present invention is administered to a subject in need; those in need of treatment include those having a disorder as well as those prone to have the disorder or those in which the disorder is to be prevented. The antibody of the present invention can be used to treat humans with cancer, or humans susceptible to cancer, or ameliorate cancer in a human subject, as well as to prevent cancer in a human patient. The antibody or antibody fragment thereof of the present invention is administered to a subject in need thereof, e.g., a human subject suffering from a BCMA-expressing cancer and/or CD38 expressing cancer, such as multiple myeloma, such as relapsed/refractory multiple myeloma. Relapsed myeloma is characterized as a recurrence of disease after prior response. Examples of laboratory and radiological criteria signaling the disease include, but are not limited to, >25% increase of the serum or urine monoclonal protein (M-protein) or >25% difference between involved and uninvolved serum free light chains from nadir, respectively, or the development of new plasmacytomas or hypercalcemia. Sonneveld et al., Haematologica. 2016 April; 101(4): 396-406.

In non-secretory disease patients, relapse is characterized by an increase of the bone marrow plasma cells. A signal for relapsed disease also is characterized by the appearance or reappearance of one or more CRAB criteria or a rapid and consistent biochemical relapse. Refractory myeloma is myeloma that is not responsive to treatment. Relapsed/refractory multiple myeloma refers to the disease which becomes non-responsive or progressive on therapy or within 60 days of the last treatment in patients who previously achieved at least a minimal response on previous therapy. Sonneveld, supra; Anderson et al., Leukemia. 2008; 22(2): 231-239.

The method of the disclosure comprises administering to the subject a dose between about 0.0001 mg/kg to about 200 mg/kg, for instance between about 0.0005 mg/kg to about 200 mg/kg, or between about 0.001 mg/kg to about 200 mg/kg, or between about 0.0015 mg/kg to about 200 mg/kg, or between about 0.005 mg/kg to about 200 mg/kg, or between about 0.01 mg/kg to about 200 mg/kg, or between about 0.015 mg/kg to about 200 mg/kg, or between about 0.03 mg/kg to about 200 mg/kg, or between about 0.05 mg/kg to about 200 mg/kg, or between about 0.06 mg/kg to about 200 mg/kg, or between about 0.09 mg/kg to about 200 mg/kg, or between about 0.1 mg/kg to about 200 mg/kg, or between about 0.12 mg/kg to about 200 mg/kg, or between about 0.15 mg/kg to about 200 mg/kg, or between about 0.18 mg/kg to about 200 mg/kg, or between about 0.2 mg/kg to about 200 mg/kg, or between about 0.3 mg/kg to about 200 mg/kg, or between about 0.36 mg/kg to about 200 mg/kg, or between about 0.5 mg/kg to about 200 mg/kg, or between about 0.6 mg/kg to about 200 mg/kg, or between about 0.7 mg/kg to about 200 mg/kg, or between about 1 mg/kg to about 200 mg/kg, or between about 1.2 mg/kg to about 200 mg/kg, or between about 1.5 mg/kg to about 200 mg/kg. For instance, between about 0.0001 mg/kg to about 20 mg/kg, or between about 0.0005 mg/kg to about 10 mg/kg, or between about 0.0005 mg/kg to about 5 mg/kg, or between about 0.0005 mg/kg to about 1.5 mg/kg, or between about 0.0005 mg/kg to about 1.2 mg/kg. The present disclosure also includes dosing ranges of any value included between the above disclosed intervals. For instance, the trispecific antibody of the present invention is administered to a patient in a single or multiple doses, selected from the group comprising at least about 0.0001 mg/kg, at least about 0.0005 mg/kg, at least about 0.001 mg/kg, at least about 0.0015 mg/kg, at least about 0.005 mg/kg, at least about 0.01 mg/kg, at least about 0.015 mg/kg, at least about 0.03 mg/kg, at least about 0.05 mg/kg, at least about 0.06 mg/kg, at least about 0.09 mg/kg, at least about 0.1 mg/kg, at least about 0.12 mg/kg, at least about 0.15 mg/kg, at least about 0.18 mg/kg, at least about 0.2 mg/kg, at least about 0.3 mg/kg, at least about 0.36 mg/kg, at least about 0.5 mg/kg, at least about 0.6 mg/kg, at least about 0.7 mg/kg, at least about 1 mg/kg, at least about 1.2 mg/kg, at least about 1.5 mg/kg, at least about 2 mg/kg, at least about 3 mg/kg, at least about 4 mg/kg, at least about 5 mg/kg, at least about 7 mg/kg, at least about 10 mg/kg, at least about 12 mg/kg, at least about 16 mg/kg, at least about 50 mg/kg, at least about 100 mg/kg, at least about 150 mg/kg, at least about 200 mg/kg.

In various aspects of the method, the dose is adjusted over the course of treatment. For example, the subject is administered an initial dose at one or more administrations, and a higher dose is used in one or more subsequent administrations. Put another way, the disclosure contemplates increasing the dose of trispecific antibody at least once over the course of treatment. Alternatively, the dose may be decreased over the course of treatment, such that amount of heterodimeric antibody is reduced as treatment progresses.

The disclosure contemplates a method wherein multiple (i.e., two or more) doses of the trispecific antibody are administered over the course of a treatment period. The individual doses may be administered at any interval, such as once a week, twice a week, three times a week, four times a week, or five times a week. Individual doses may be administered every two weeks, every three weeks, or every four weeks. In other words, in some aspects, a waiting period of at two weeks passes between heterodimeric antibody administrations to the subject. The waiting period between administrations of the doses need not be consistent over the course of the treatment period. In other words, the interval between doses can be adjusted over the course of treatment. In some aspects, the method comprises administering two doses of heterodimeric antibody per week to the subject in the first and second weeks of treatment (i.e., twice a week for weeks 1 and 2), administering one dose of heterodimeric antibody per week to the subject in the third and fourth weeks of treatment (i.e., once a week for weeks 3 and 4), and administering one dose of heterodimeric antibody every two weeks starting in week 5 through the end of treatment (i.e., there is a waiting period of two weeks between doses starting in week 5 through the end of treatment).

Alternatively, in various aspects, the method comprises administering one dose of the trispecific antibody per week for weeks 1-4 of treatment, and optionally administering one dose of the antibody every two weeks starting in week 5 through the end of treatment.

The multiple doses of heterodimeric antibody are administered over treatment period of, e.g., three months to about 18 months, or about three months to about 12 months, or about three months to about nine months, or about three months to about six months, or about three months to about eight months, or about six months to about 18 months, or about six months to about 12 months, or about eight months to about 12 months, or about six months to about eight months, or about eight months to about 12 months (e.g., about eight months). Optionally, the multiple (i.e., two or more) doses of the heterodimeric antibody are administered over a treatment period of about 12 weeks to about 52 weeks, or about 12 weeks to about 36 weeks, or about 24 weeks to about 32 weeks, with doses administered twice a week, once a week, once every two weeks, or once every four weeks.

By "treating" multiple myeloma is meant achievement of any positive therapeutic response with respect to the disease. For example, a positive therapeutic response includes one or more of the following improvements in the disease: (1) a reduction in the number of neoplastic cells; (2) an increase in neoplastic cell death; (3) inhibition of neoplastic cell survival; (4) reduction in paraprotein production by tumor cells; (5) inhibition (i.e., slowing to some extent, preferably halting) of tumor growth; (6) an increased patient survival rate; and (7) some relief from one or more symptoms associated with the disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. A complete therapeutic response (i.e., absence of clinically detectable disease with normalization of any previously abnormal radiographic studies, bone marrow, and cerebrospinal fluid (CSF) or abnormal monoclonal protein) is not required; any degree of improvement is contemplated.

The antibody or antibody fragment thereof may be administered via any suitable means to the subject, e.g., via intravenous, subcutaneous, intraarterial, intralymphatic, intrathecal, intracerebral, intraperitoneal, intracerobrospinal, intradermal, intraarticular, intrasynovial, oral, topical, or inhalation routes, osmotic pump, drug encapsulation, such as nanoparticle encapsulation, surface coating-mediated drug delivery. For example, the antibody may be administered via intravenous administration as a bolus or by continuous infusion over a period of time. In particular embodiments, antibody is administered via intravenous infusion, e.g., over a period of about 30 minutes to about four hours. Optionally, the time for infusion is decreased in subsequent administrations. For example, in one embodiment, the first dose of antibody is administered over a period of about four hours, and subsequent doses are administered over a period of two hours or less. In this regard, the first dose of the antibody is optionally administered over a period of about four hours, the second dose of the antibody is optionally administered over a period of about two hours, and subsequent doses are optionally administered over a period of about 30 minutes. In another particular embodiment, the trispecific antibody of the present invention is administered subcutaneously.

In some instances, the subject has previously been treated for a cancer, such as multiple myeloma. For example, the subject may have previously been administered an immunomodulatory drug (thalidomide, lenalidomide, pomalidomide), a proteasome inhibitor (such as pomalidomide, bortezomib, or carfilzomib), dexamethasone, doxorubicin, or combinations thereof.

Optionally, the subject was previously treated with an anti-CD38 monospecific antibody, such as daratumumab (DARZALEX®). In various embodiments, the subject is relapsed or refractory with prior anti-CD38 monospecific antibody treatment. The method may comprise a waiting period between the previous administration of anti-CD38 monospecific antibody and administration of the heterodimeric antibody.

Co-Therapy

Optionally, the antibody or antibody fragment thereof of the present invention is part of a therapeutic regimen that comprises administration of one or more other therapeutic agents, radiation therapy, stem cell transplantation, and the like.

The method of the disclosure optionally further comprises administering dexamethasone to the subject. The dexamethasone may be administered by any route, such as the routes described here. Preferably, the dexamethasone is administered intravenously or orally. When the dexamethasone is administered intravenously, it is optionally administered to the subject within one hour prior to administration of the antibody. The dexamethasone is optionally administered in an amount of about 8 mg or about 4 mg.

In various embodiments, the method of the disclosure further comprises administering a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase 11 inhibitors (e.g., etoposide, teniposide, and daunorubicin); alkylating agents (e.g., melphalan, chlorambucil, busulfan, thiotepa, ifosfamide, carmustine, lomustine, semustine, streptozocin, dacarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitabine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastine, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib, CEP-18770, MG132, peptide vinyl sulfones, peptide epoxyketones (such as epoxomicin and carfilzomib), beta-lactone inhibitors (such as lactacystin, MLN 519, NPI-0052, Salinosporamide A), compounds that create dithiocarbamate complexes with metals (such as Disulfiram), and certain antioxidants (such as Epigallocatechin-3-gallate, catechin-3-gallate, and Salinosporamide A); NF-κB inhibitors, including inhibitors of IKB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The therapeutic regimen may comprise administration of other antibody therapeutics, such as elotuzumab (a humanized monoclonal against SLAMF7; Tai et al., Blood, 2008; 112:1329-37); daratumumab, MOR202, and isatuximab that target CD38; nBT062-SMCC-DMI, nBT062-SPDB-DM4, and nBT062-SPP-DMI that target CD138; lucatumumab (also known as HCD122) and dacetuzumab (also known as SGN-40) that target CD40; lorvotuzumab which targets CD56. For a review of antibody therapeutics for the treatment of multiple myeloma, see, e.g., Tandon et al., Oncology & Hematology Review, 2015; 11(2):115-21, and Sondergeld et al., Clinical Advances in Hematology & Oncology, 2015; 13(9), 599, both incorporated by reference.

In some embodiments, the heterodimeric antibody is administered prior to, concurrent with, or after treatment with proteasome inhibitors (bortezomib, carfilzomib and ixazomib), immunomodulatory drugs (IMiDs) such as the thalidomide derivatives pomalidomide and lenalidomide, the histone deacetylase inhibitor Panobinostat, antibodies such as Daratumumab, Teclistamab, Isatuximab, Elotuzumab Talquetamab, Alnuctamab, Belantamab, Elranatamab or any other above cited compound and/or drug and/or biotherapeutics, also including venetoclax, mafodotin seliniexor, dexamethasone, doxorubicin, melflufen, CAR-T cell therapy and their combinations.

All cited references are herein expressly incorporated by reference in their entirety. Whereas particular embodiments of the invention have been described above for purposes of illustration, it will be appreciated by those skilled in the art that numerous variations of the details may be made without departing from the invention as described in the appended claims.

FIGURES

Figure 1B:
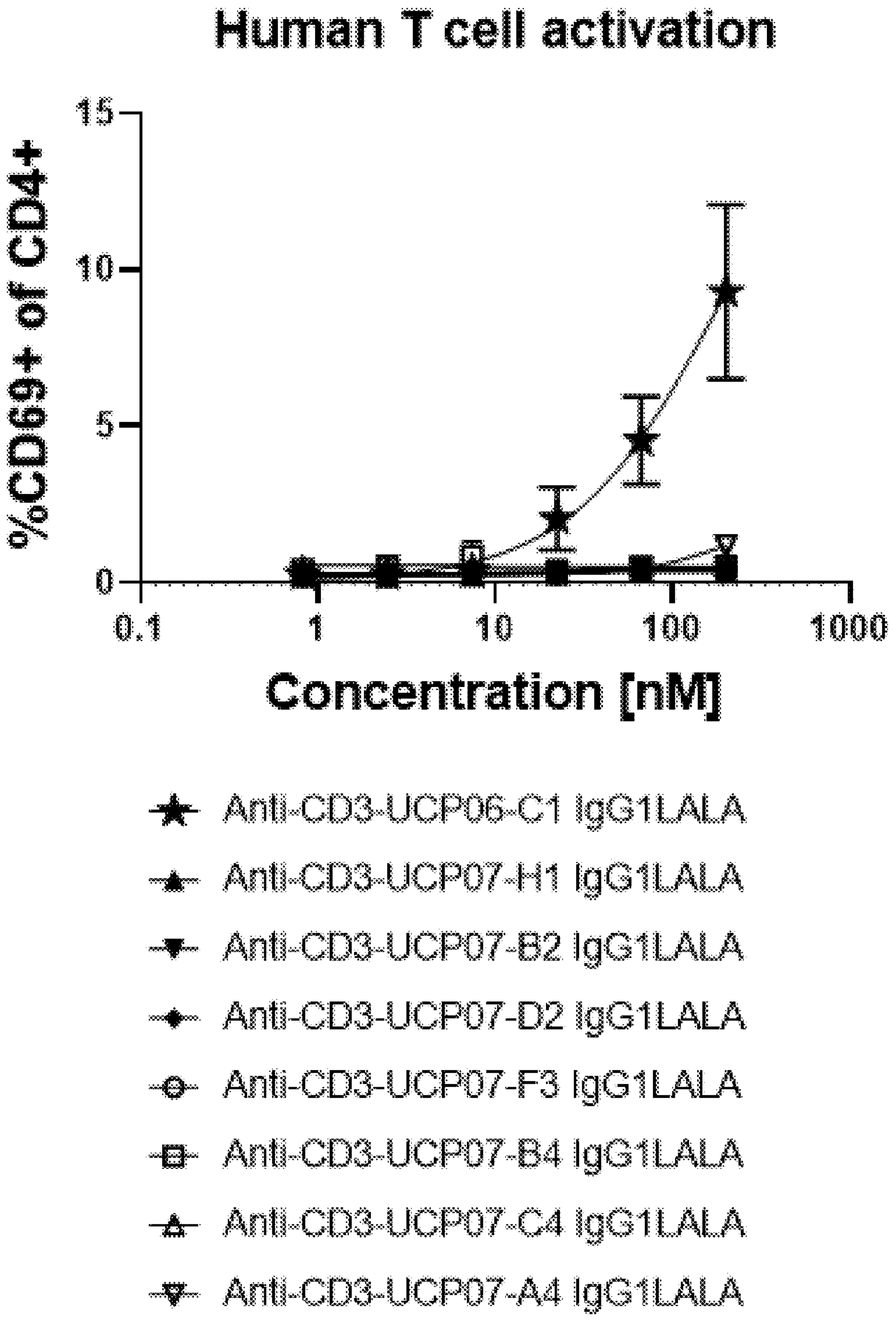

FIGS. 1A-1B. Anti-human CD3 C1 candidate binds to human CD3 and induces T cell activation. The binding of anti-CD3 candidates to human PBMCs was evaluated by flow cytometry (FIG. 1A). Concomitantly, the ability of anti-CD3 candidates to induce the activation of human purified T cells for 48h, via the upregulation of CD69 on $CD4^+$ T cells, was assessed by flow cytometry (FIG. 1B). Each point is the Mean+/−Standard Deviation of three independent measurements from one representative experiment. Experimental setup and analysis are described in Example 1.

Figure 2:
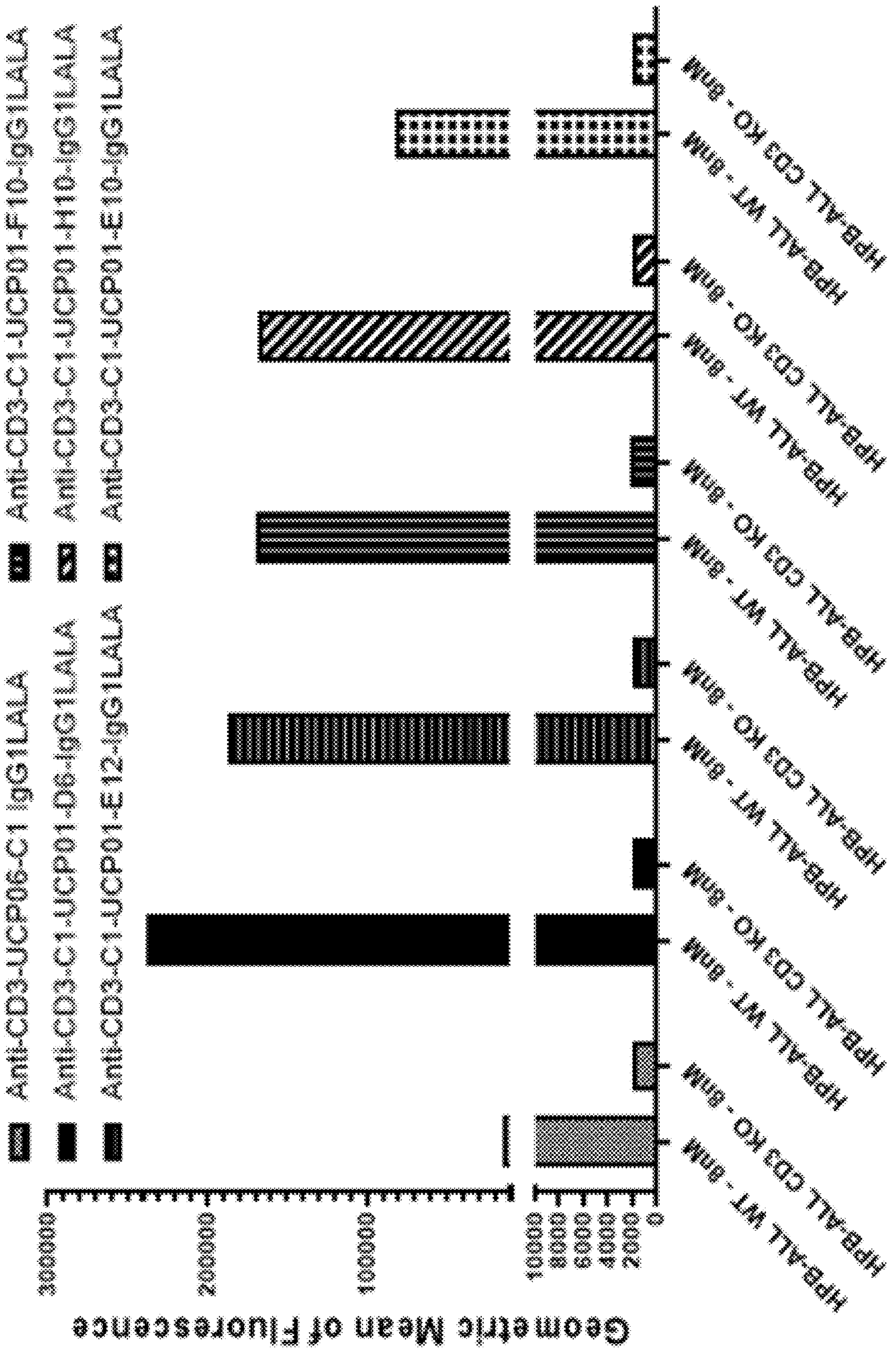

FIG. 2. Anti-CD3-C1 candidate and anti-CD3-C1-optimized candidates bind specifically to human CD3. The binding of anti-CD3 candidates to HPB-ALL wild-type and knocked-out for CD3 cell lines was evaluated by flow cytometry. Each bars represent the Geometric Mean of Fluorescence of one replicate tested at 8 nM from one representative experiment. Experimental setup and analysis are described in Example 2.

Figure 3:
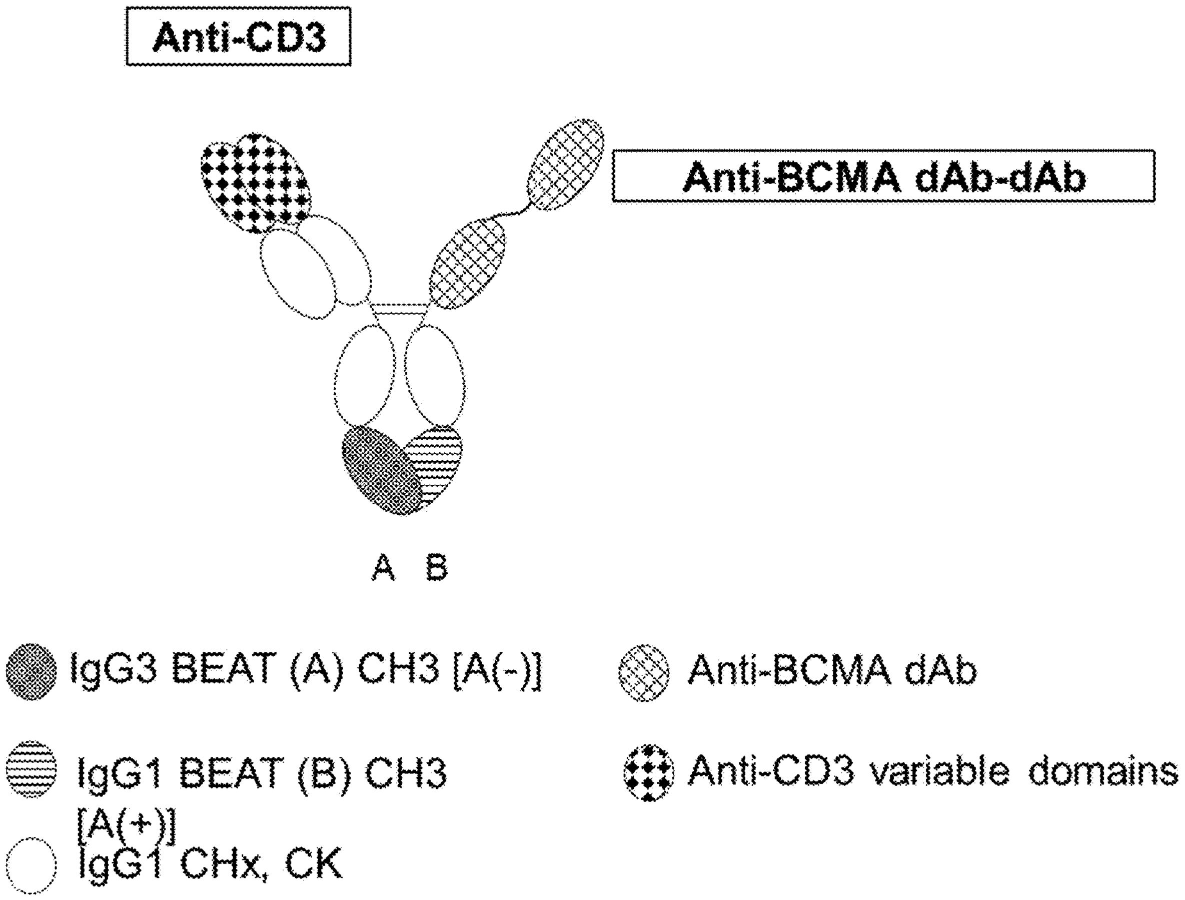

FIG. 3. Format of tool molecules used for assessment of T cell activation propensity of CD3 binders.

Figure 4A:
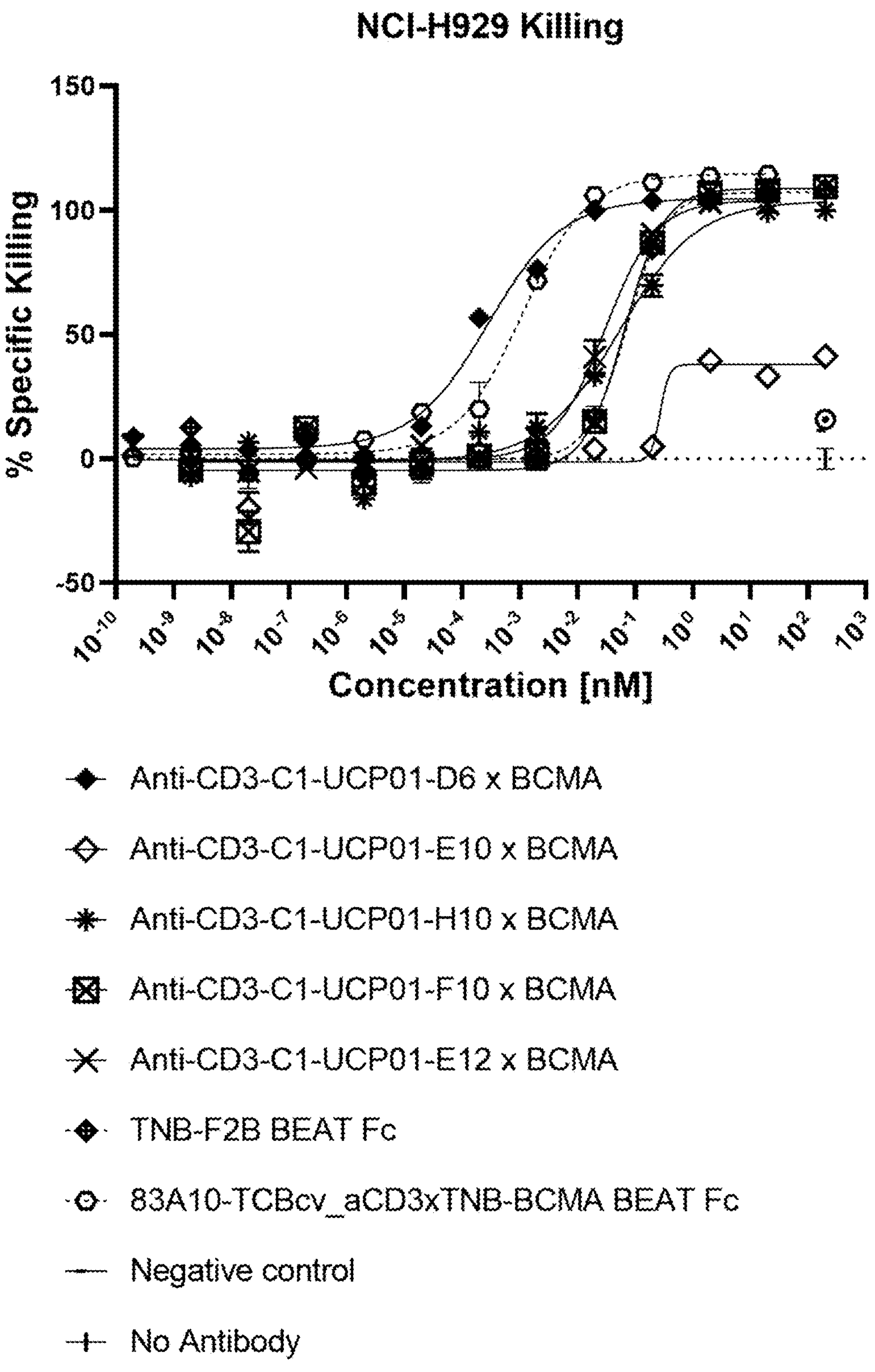
Figure 4B:
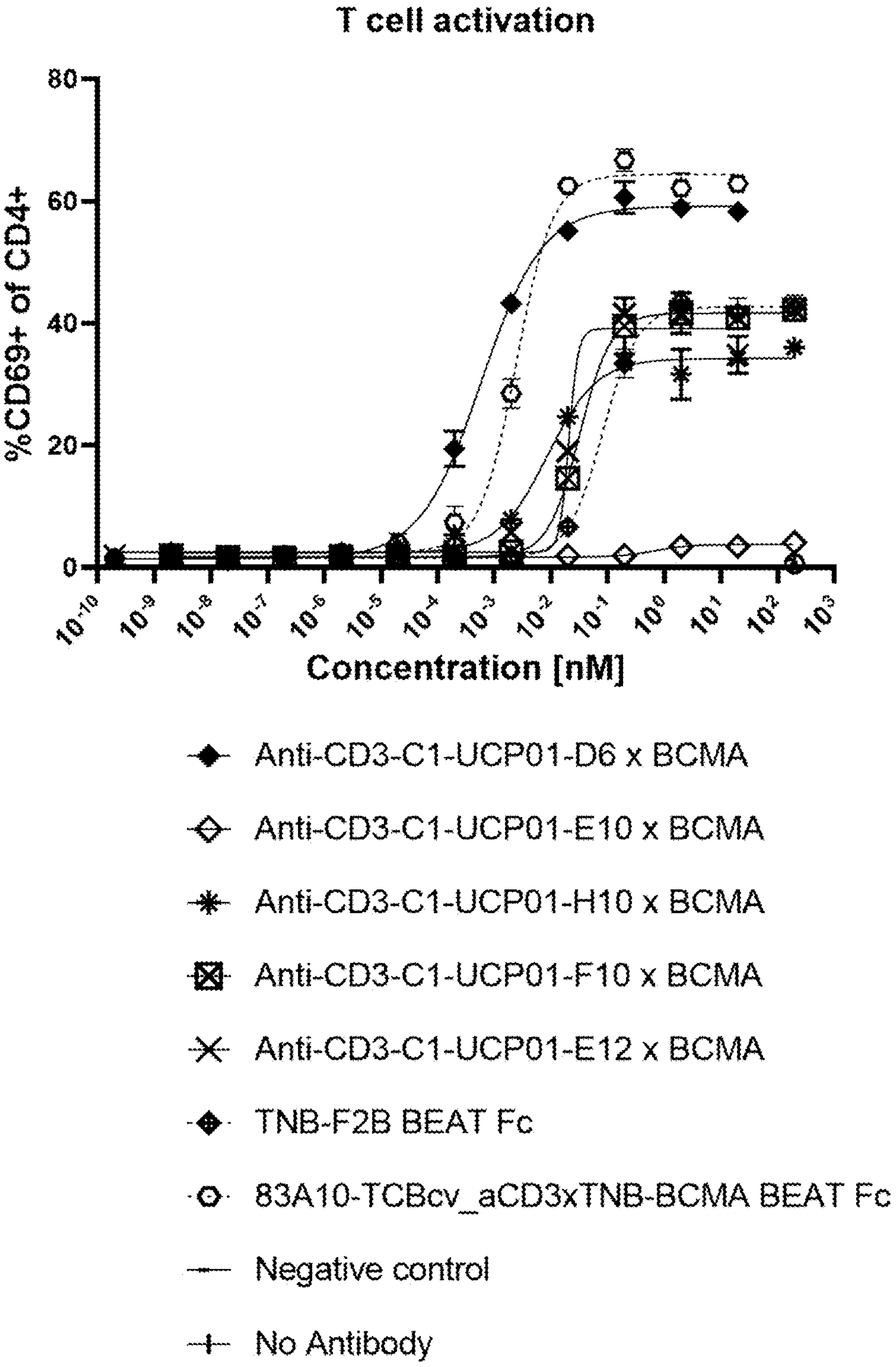

FIGS. 4A-4B. The 2+1 C1-D6/BCMA candidate triggers the most potent killing of tumor cells and activation of T cells in a Redirected Lysis assay. The ability of 2+1 CD3×BCMA-dAbx2 candidates to trigger T cell mediated killing of NCI-H929 tumor cells (FIG. 4A) was assessed in a Redirected Lysis assay with a 5:1 Effector-to-target ratio and measured by Flow Cytometry after 48 hours of incubation. In the same assay, the activation of human T cells was assessed by flow cytometry, measured by the percentage of CD69 upregulation on CD4 T cells (FIG. 4B). Each point is the Mean+/−Standard Deviation of two technical replicates from one representative donor. Experimental setup and analysis are described in Example 3.

Figure 5:
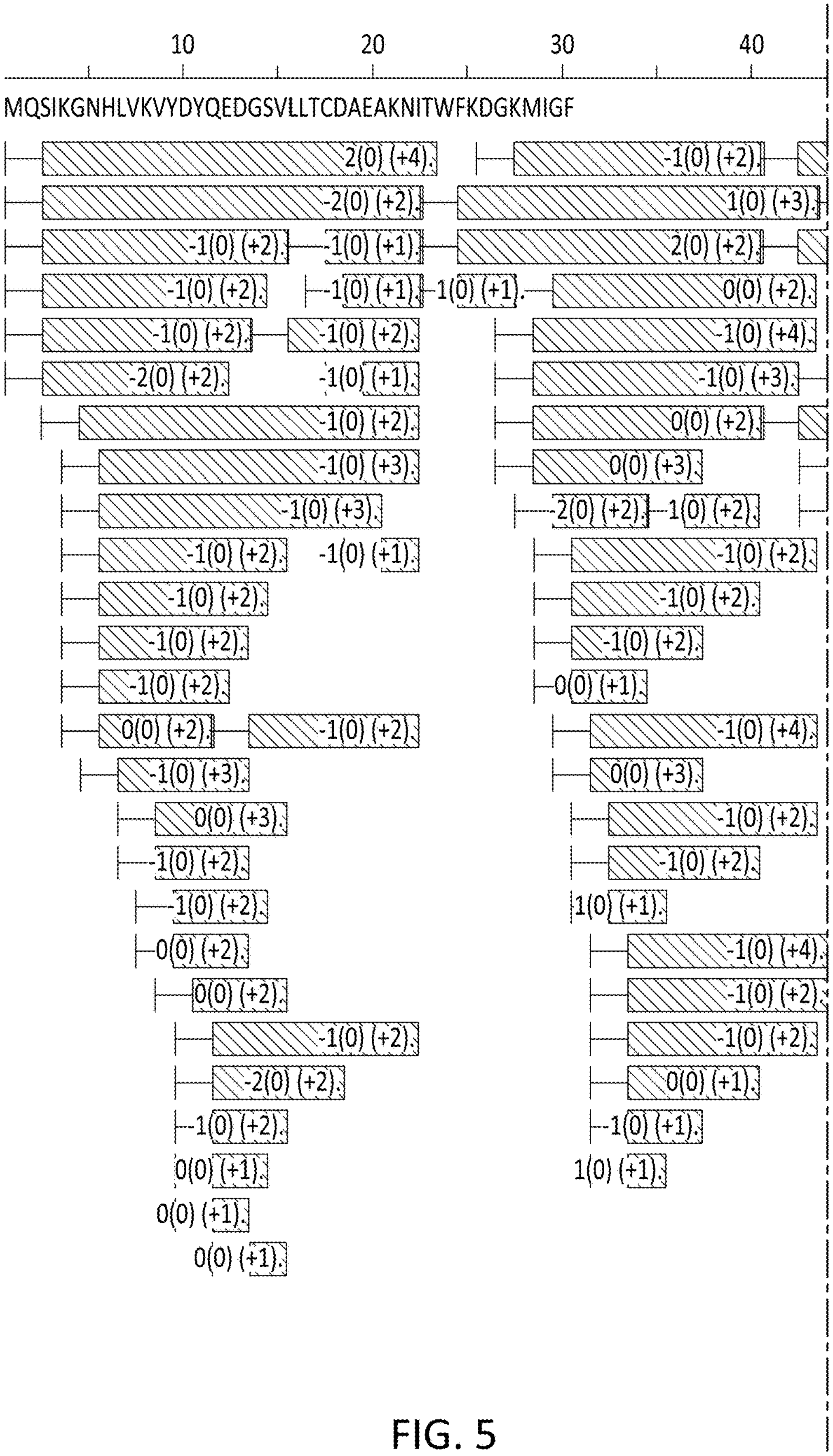
Figure 5:
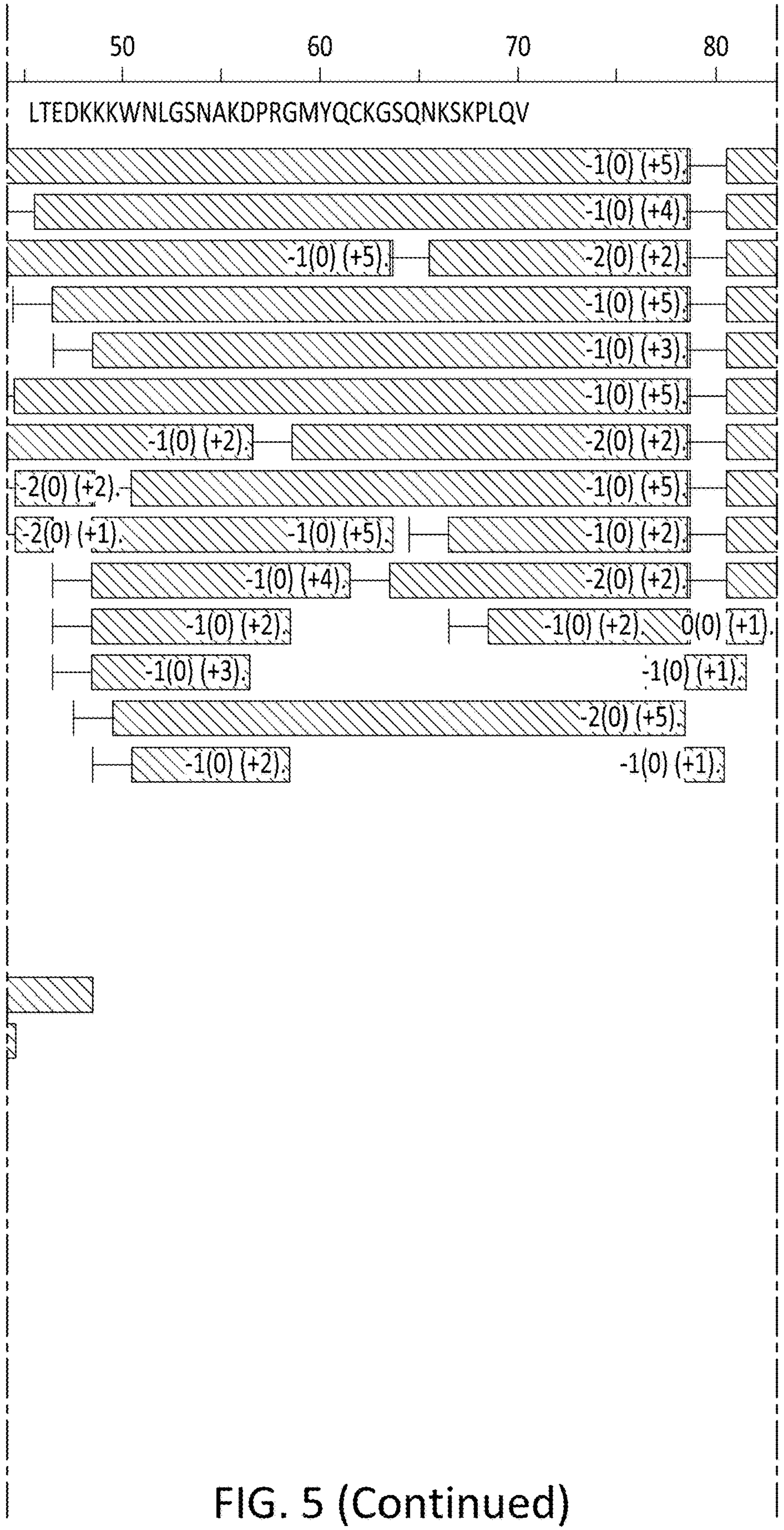
Figure 5:
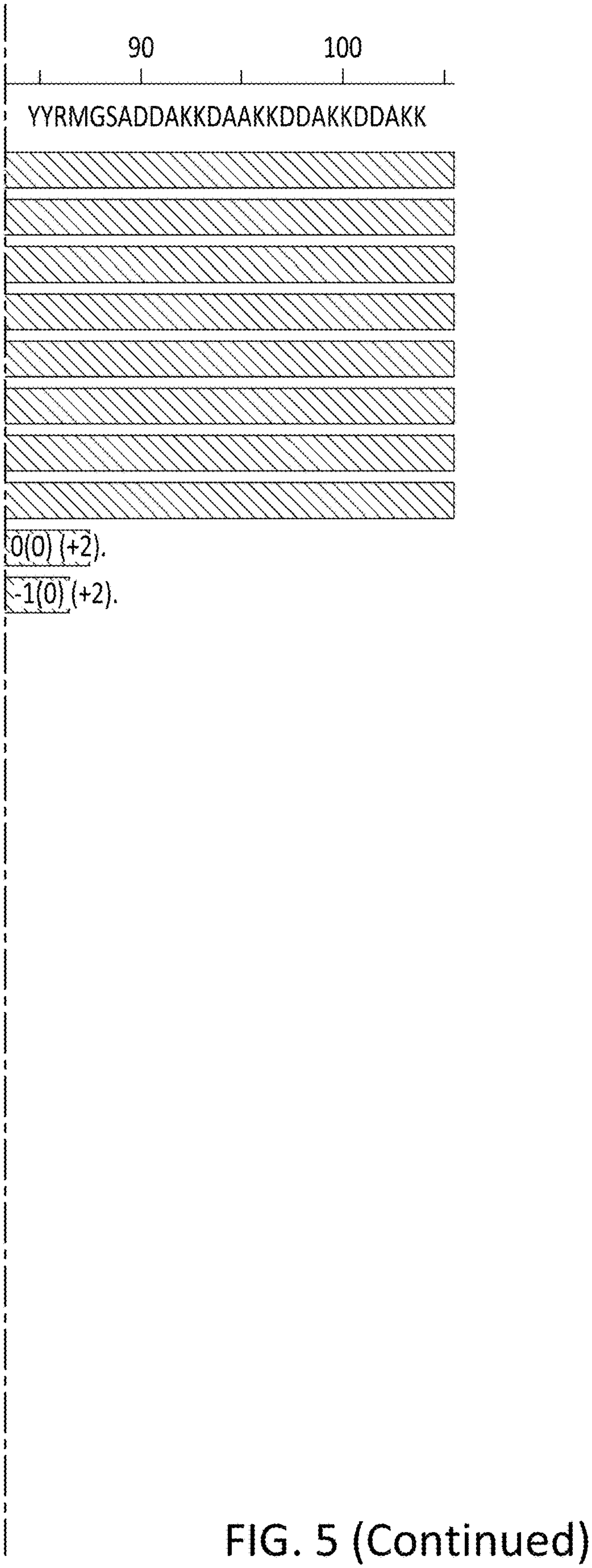
Figure 5:
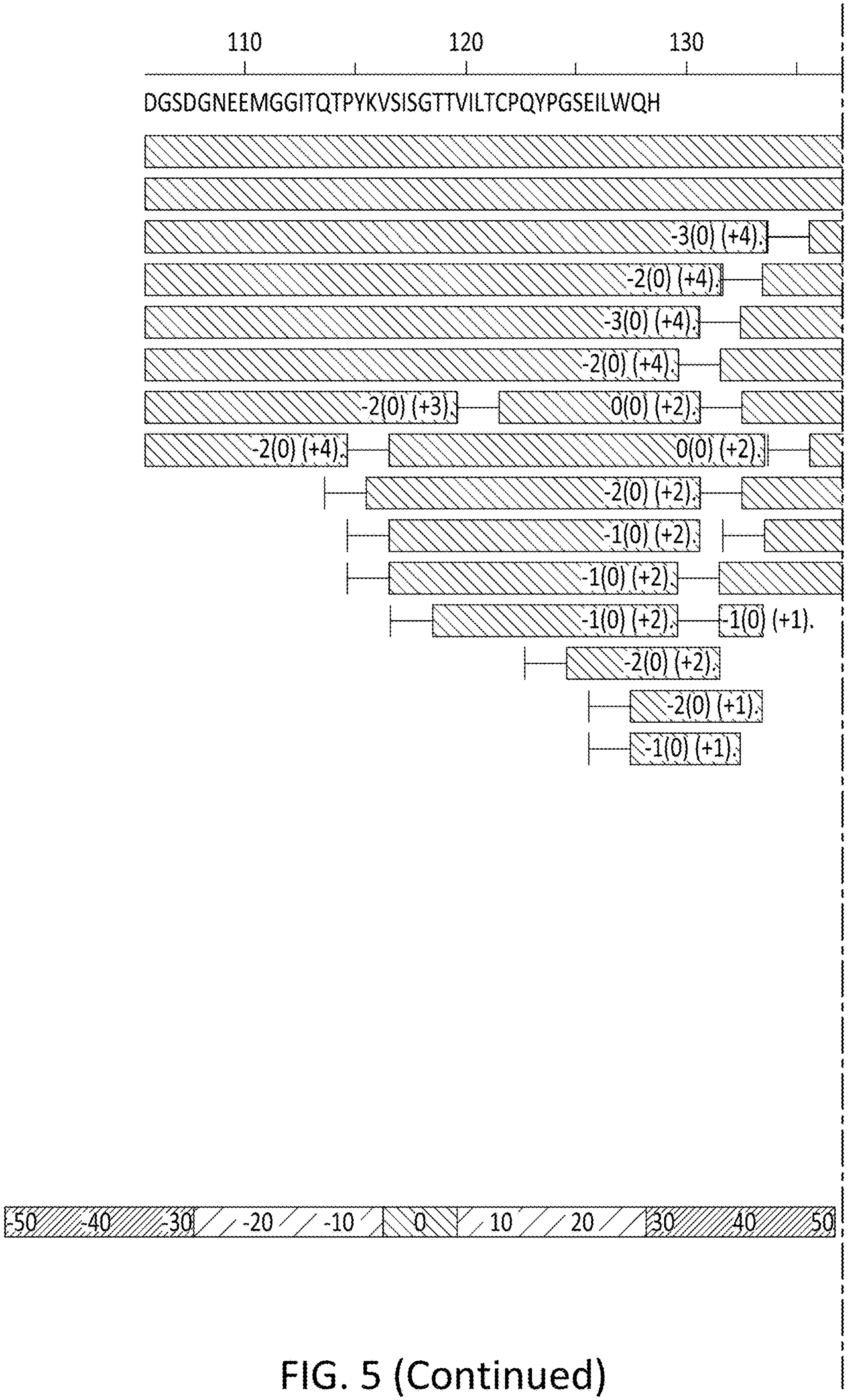
Figure 5:
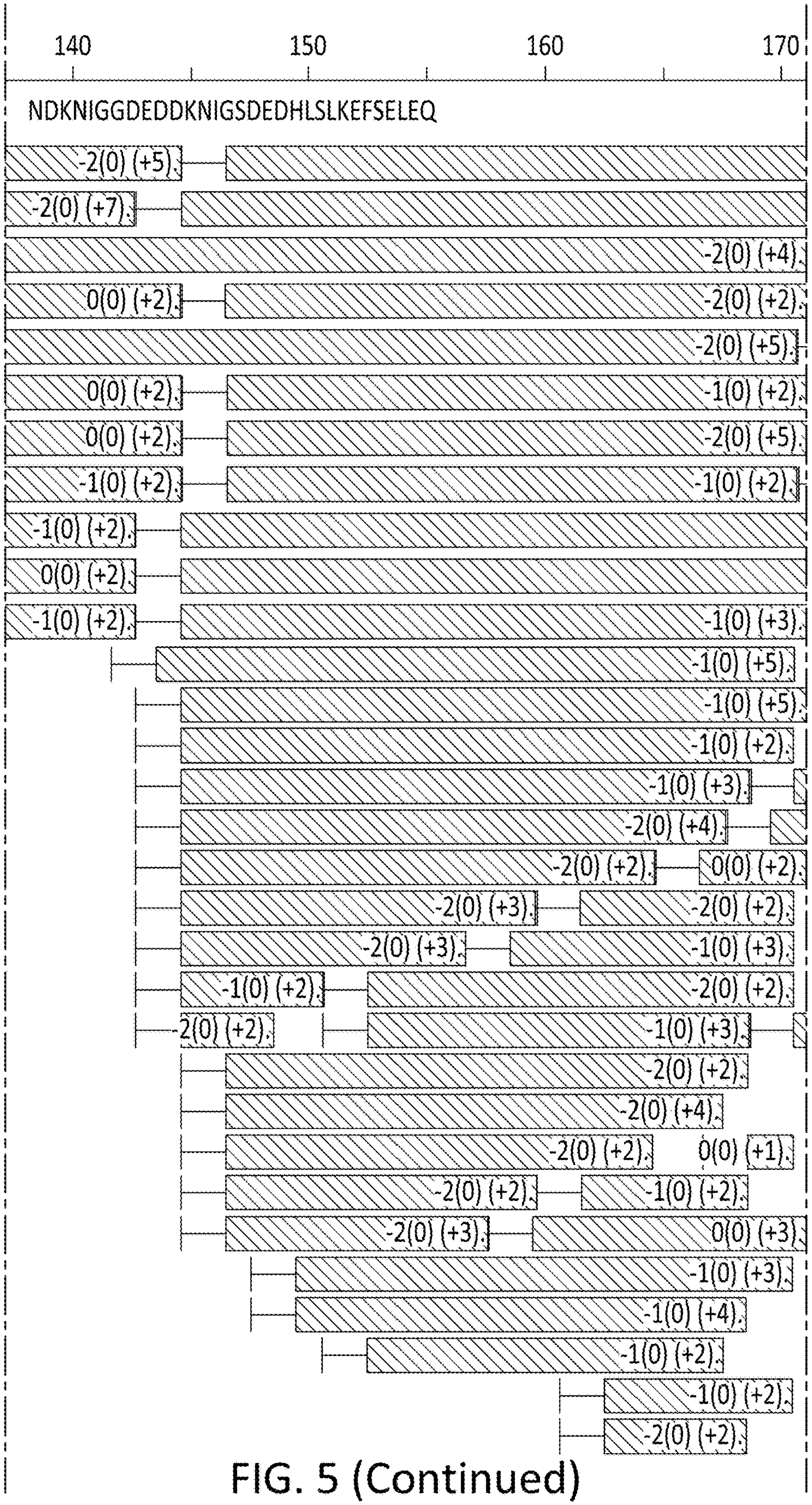
Figure 5:
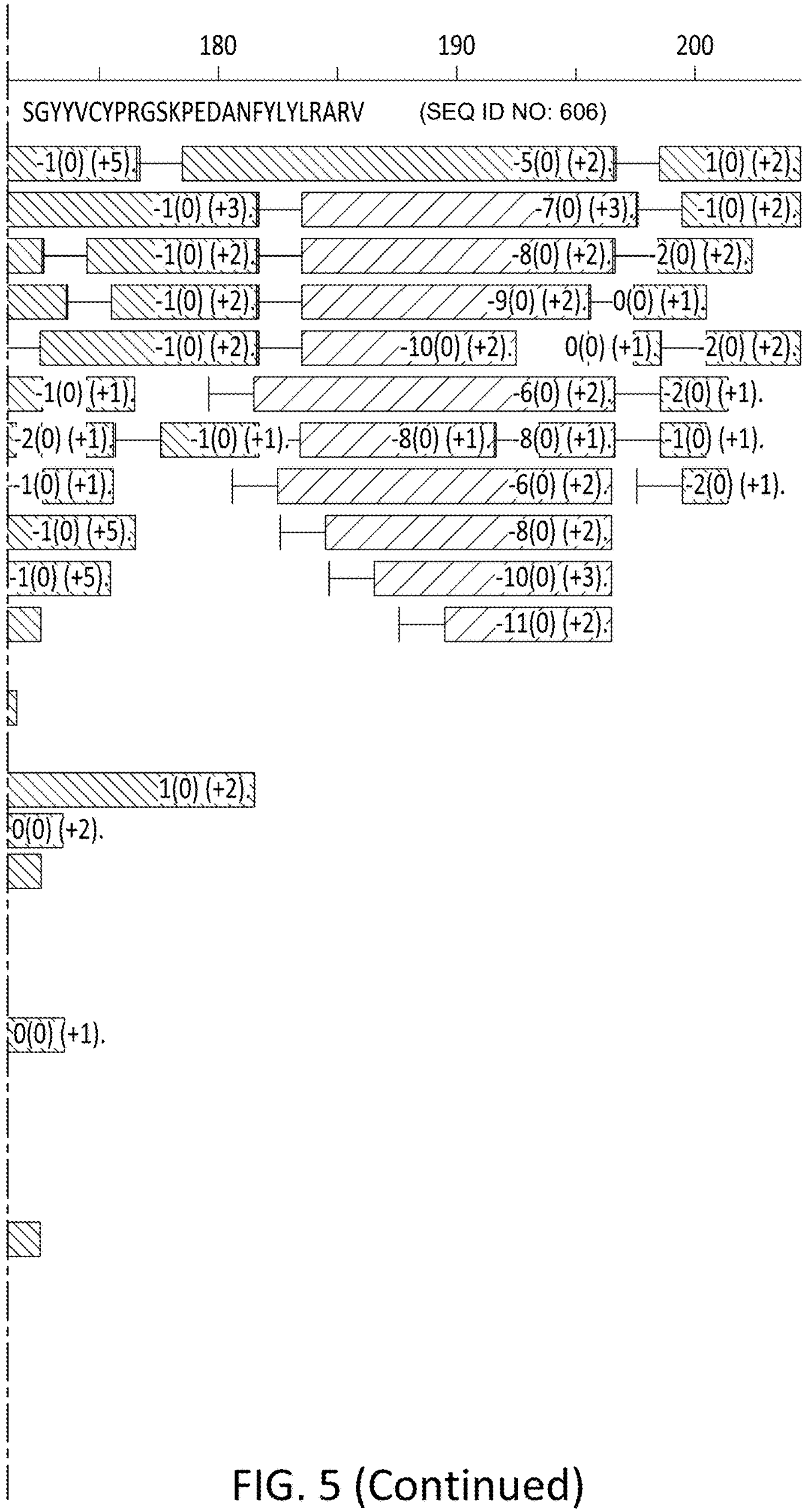

FIG. 5. HDX epitope mapping of C1-D6 binder onto hCD3γε (SEQ ID NO: 606). hCD3γε showed significant reduction in deuterium uptake (−10) upon binding to the IgG at AA182-197, YVCYPRGSKPEDANFY (SEQ ID NO: 726), indicating this was the main epitope. FIG. 5 shows the differential heat map comparing hydrogen/deuterium exchange of hsCD3 γ (23-103)-hsCD3 ε (23-118) alone to that of hsCD3 γ (23-103)-hsCD3 ε (23-118) & anti-CD3-C1-D6 IgG1 LALA.

Figure 6A:
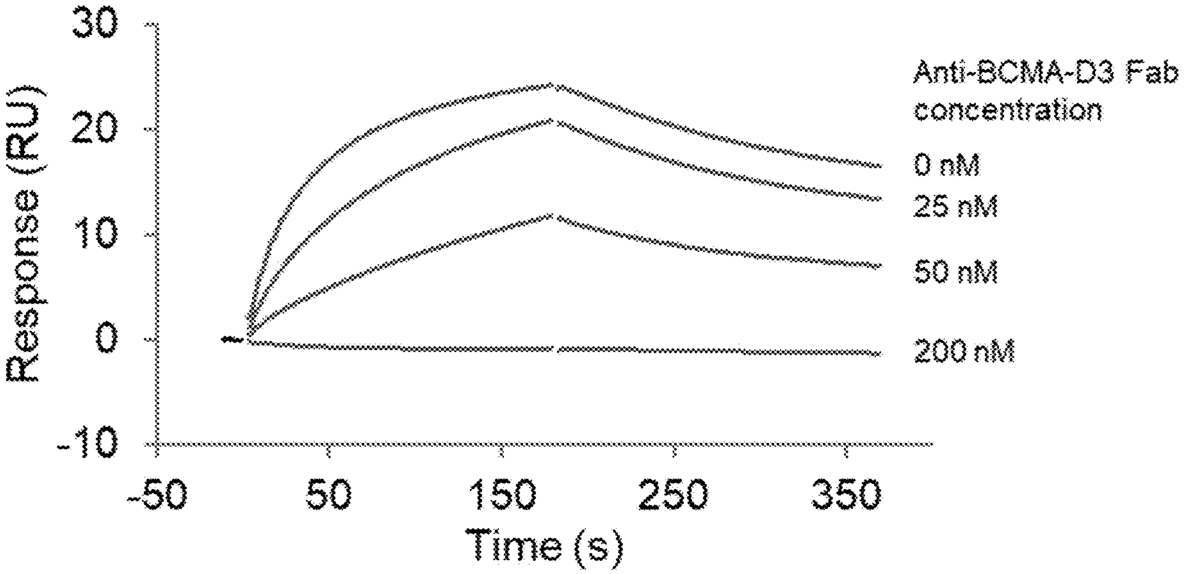
Figure 6B:
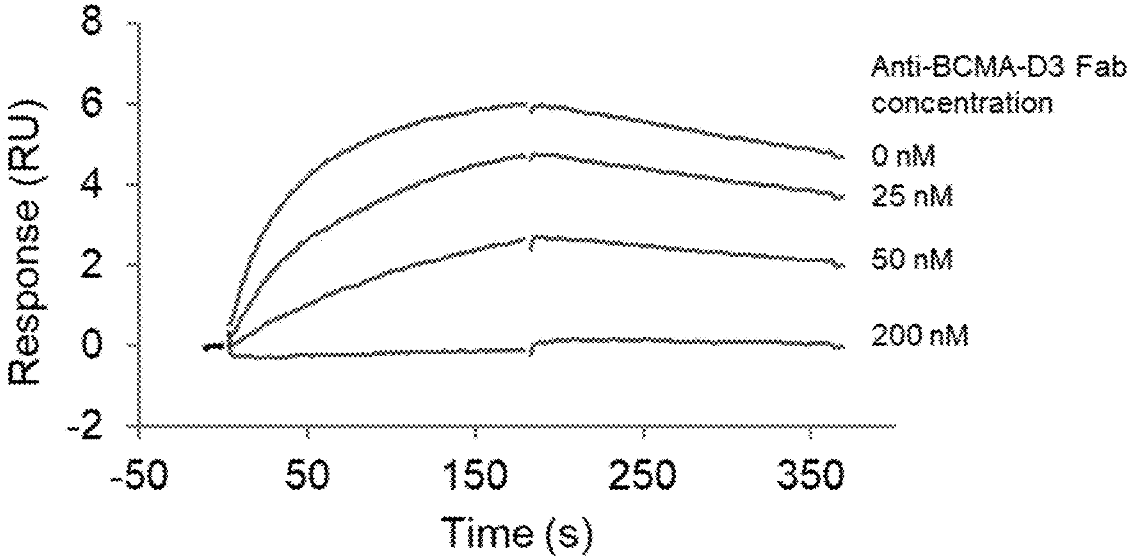
Figure 6C:
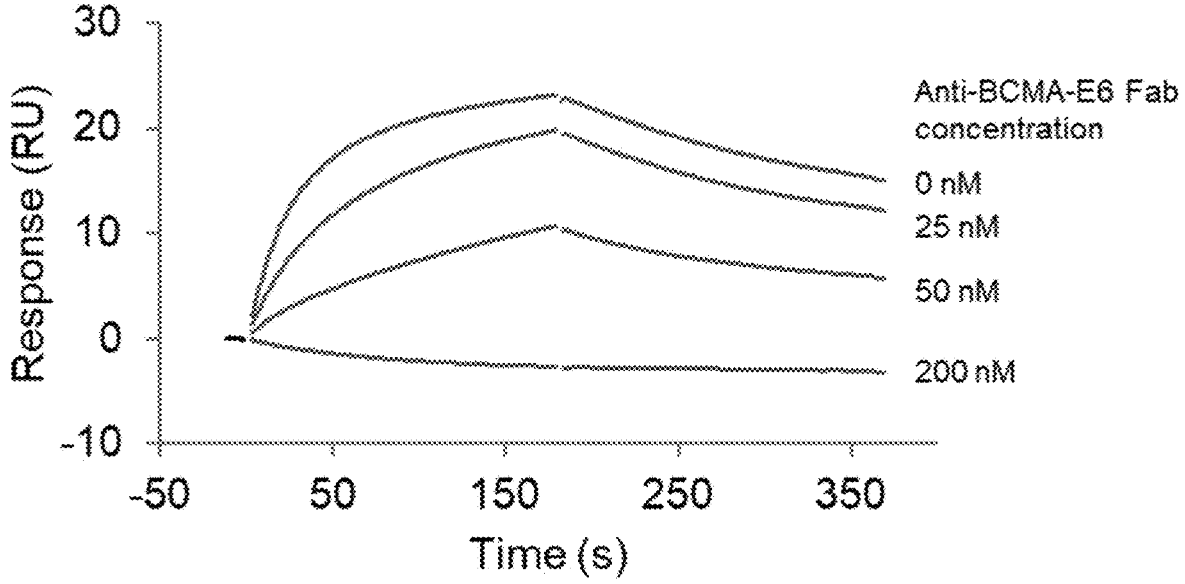
Figure 6D:
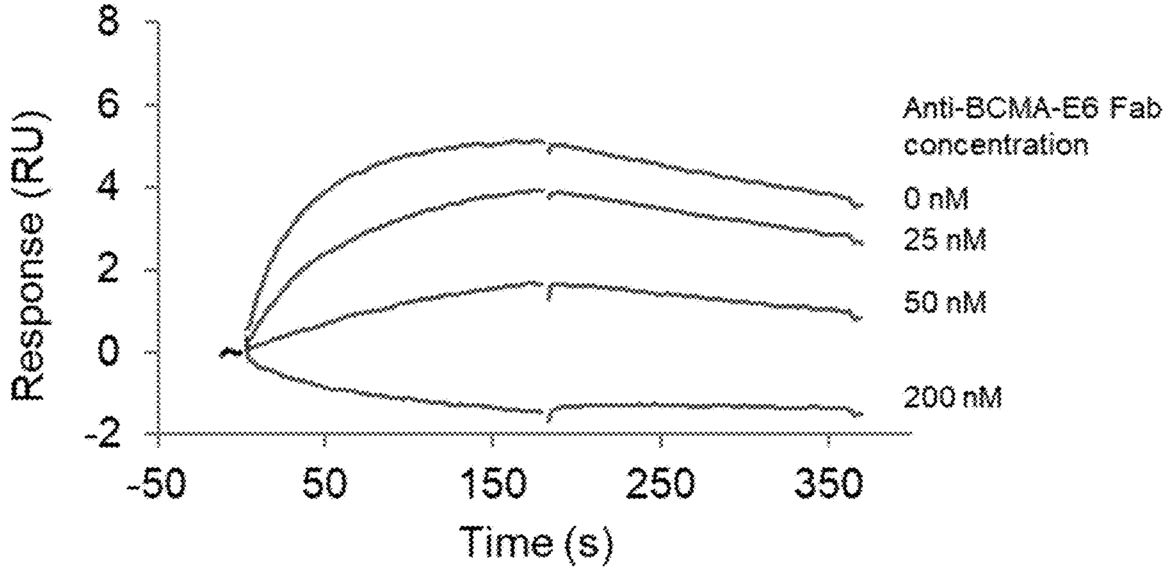

FIGS. 6A-6D. Blocking of the human BCMA/human APRIL interaction and blocking of the human BCMA/human BAFF interaction upon binding of anti-BCMA-D3 Fab and anti-BCMA-E6 Fab to human BCMA assessed by Surface Plasmon Resonance. Recombinant human APRIL-his protein or recombinant human BAFF-his protein was loaded on a CM5 sensor CHIP previously coated with anti-histidine antibody. A solution of 50 nM recombinant BCMA-Fc protein pre-mixed with varying concentrations (0 nM, 25 nM, 50 nM, or 200 nM) of anti-BCMA-D3 Fab in running buffer was injected over A) immobilized human APRIL (FIG. 6A) or B) immobilized human BAFF (FIG. 6B). Similarly, a solution of 50 nM recombinant BCMA-Fc protein pre-mixed with varying concentrations (0 nM, 25 nM, 50 nM, or 200 nM) of anti-BCMA-E6 Fab in running buffer was injected over C) immobilized human APRIL (FIG. 6C) or D) immobilized human BAFF (FIG. 6D). Plot shows data expressed as number of resonance units (abbreviated RU; Y axis) vs. time (X axis).

Figure 7:
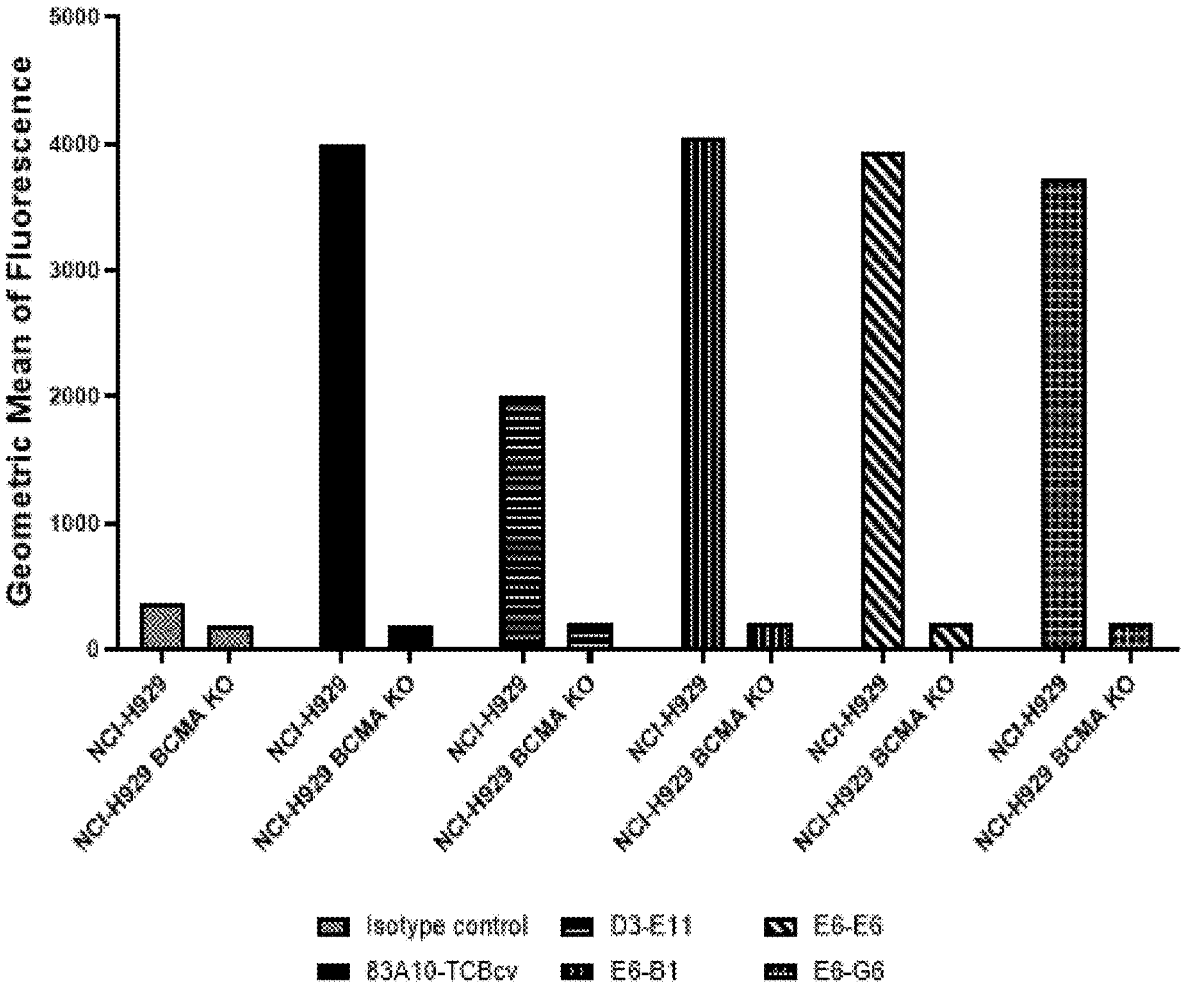

FIG. 7. Anti-BCMA-D3- and anti-BCMA-E6-affinity matured candidates bind specifically to BCMA. The binding of anti-BCMA candidates to NCI-H929 wild-type and knocked-out for BCMA cell lines was evaluated by flow cytometry. Each bar represents the Geometric Mean of Fluorescence of one replicate tested at 10 nM from one representative experiment. Experimental setup and analysis are described in Example 6.

Figure 8A:
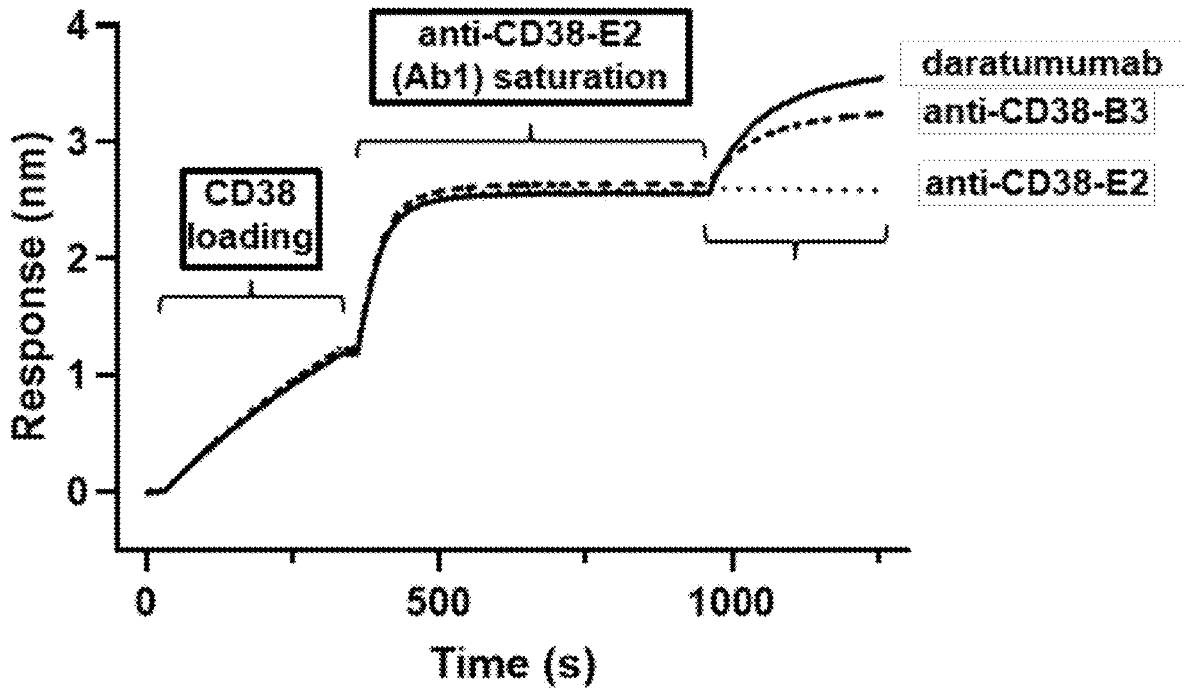
Figure 8B:
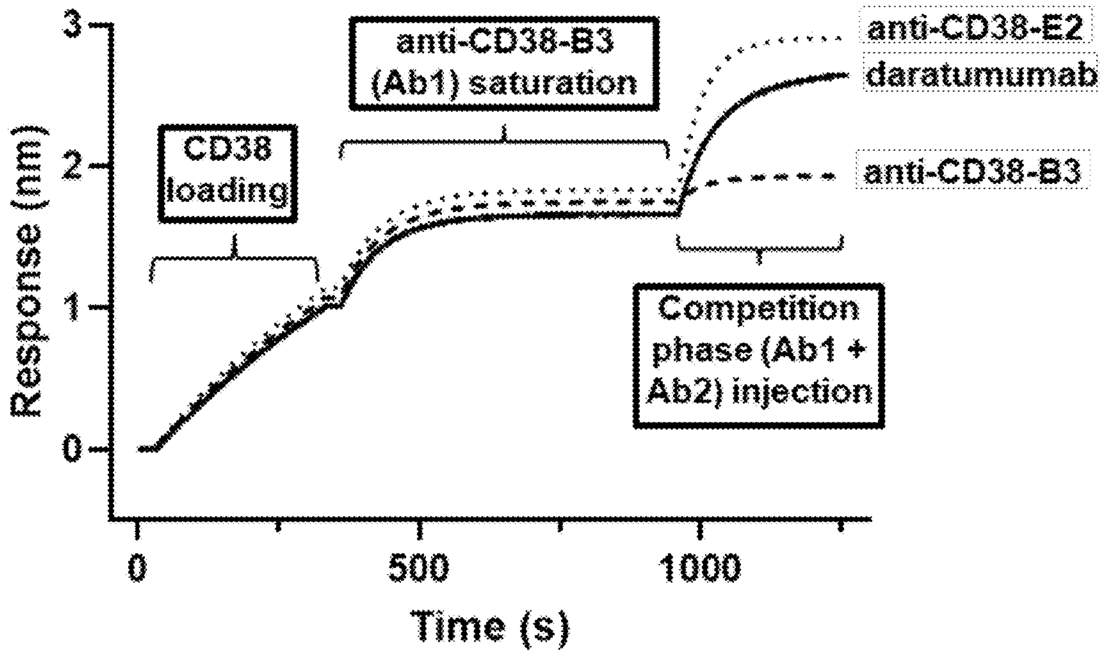
Figure 8C:
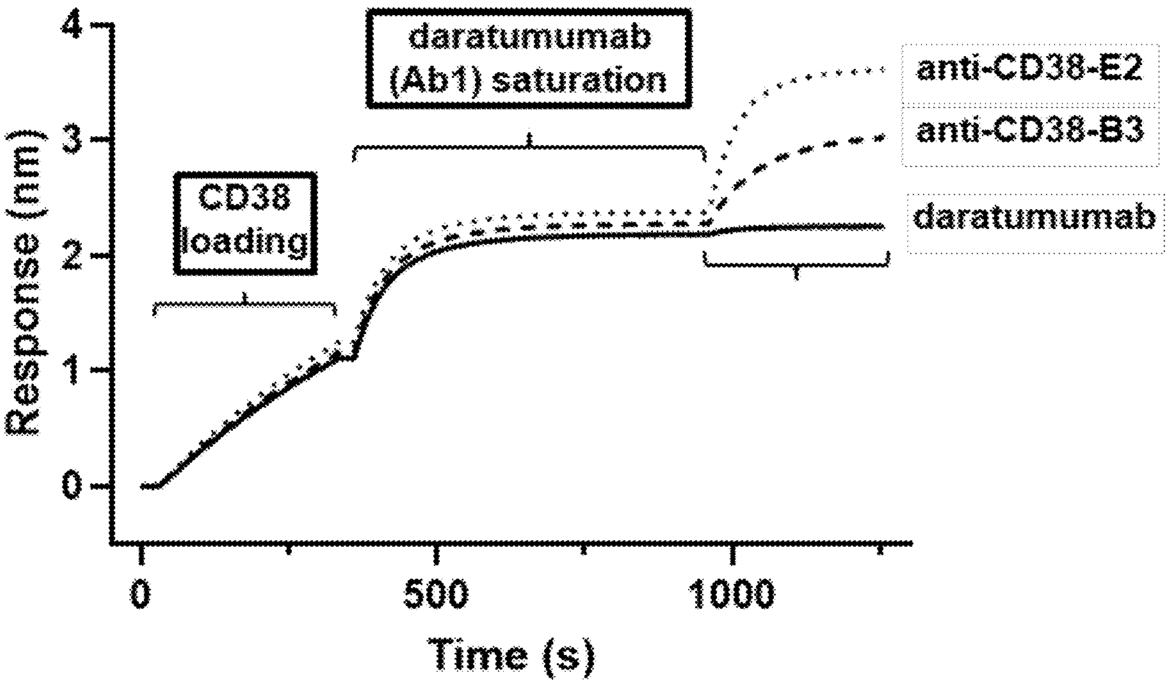

FIGS. 8A-8C. Epitope binning of anti-CD38-E2 Fab, anti-CD38-B3 Fab and daratumumab Fab to human CD38 using Octet Bio-Layer Interferometry. Biotinylated human CD38-avi-his protein was loaded on a streptavidin SA Biosensor. Fab antibody 1 (Ab1) was injected over immobilized human CD38 at 200 nM in kinetic buffer to reach saturation of the surface. Then, a pre-mixed solution of Ab1 and Fab antibody 2 (Ab2) at 200 nM final concentration each was injected over saturated surface (competition phase). Same experimental procedure was performed using Ab1 at 400 nM alone in the competition phase as control for surface saturation. Plot shows binding to the sensor tip as a wavelength shift (Response, in nm; Y axis) vs. time (X axis) for A) anti-CD38-E2 Fab as Ab1 (FIG. 8A), B) anti-CD38-B3 Fab as Ab1 (FIG. 8B), and C) daratumumab Fab as Ab1 (FIG. 8C). Curves are labelled by Ab2 clone name.

Figure 9A:
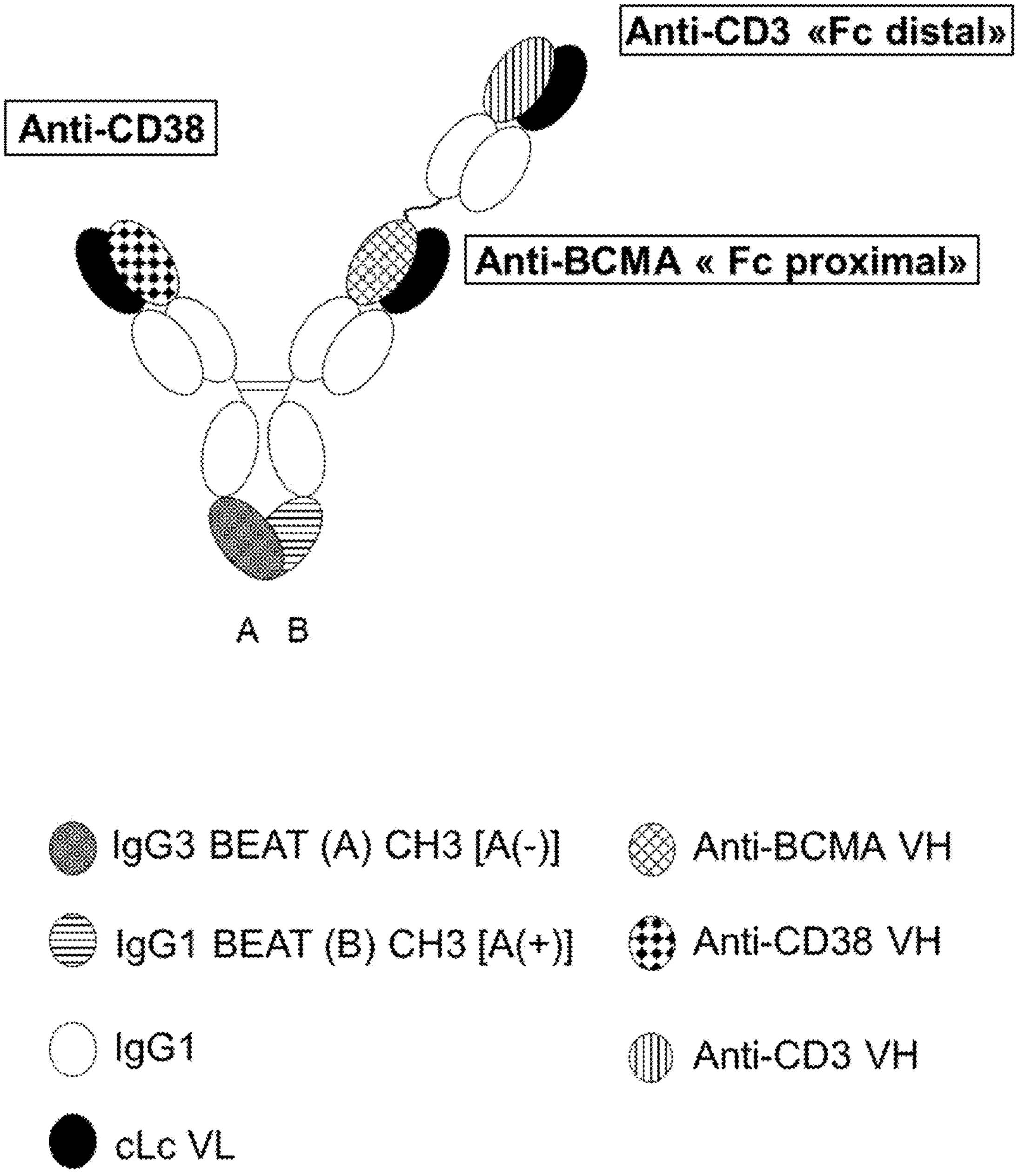
Figure 9B:
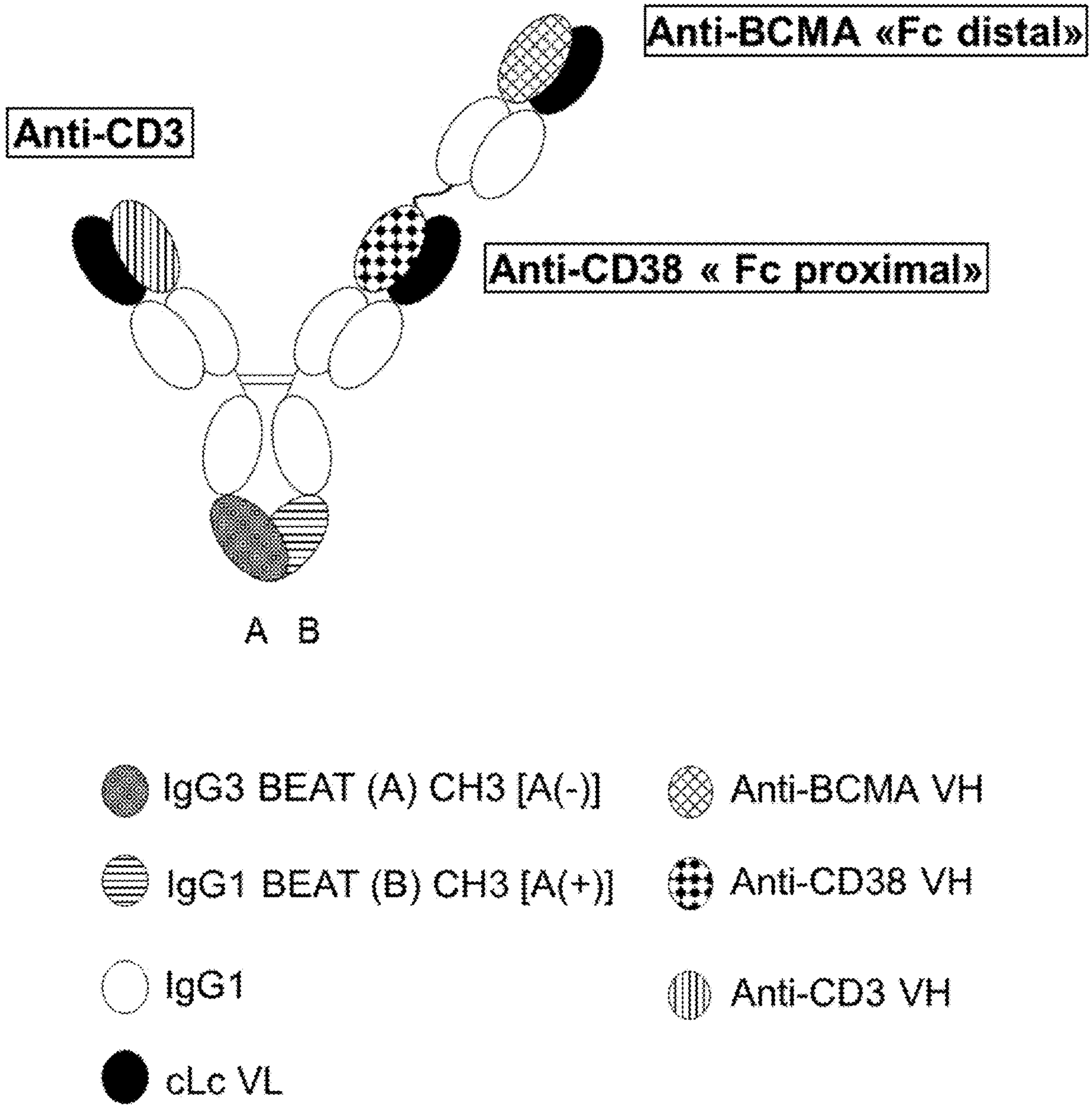

FIGS. 9A-9B. Schematic drawing of CD3/BCMA/CD38 trispecific antibodies. CD3/BCMA/CD38 antibodies were constructed with three Fabs targeting three separate antigens, whereby the "Fc distal" Fab domain was fused to the N-terminus of the VH domain of the "Fc proximal" Fab. A). Configuration BO (BTB Outer) CD3/BCMA/CD38 had the CD38 binder on arm A, the CD3 binding arm in the outer, Fc distal position of the B arm and the BCMA in the "Fc proximal" position of the B arm (FIG. 9A) while for B) Configuration C the CD3/BCMA/CD38 had the CD3 binding arm on arm A, the BCMA binder in the Fc distal position of arm B and the CD38 binder in the Fc proximal position of the B arm (FIG. 9B).

Figure 10A:
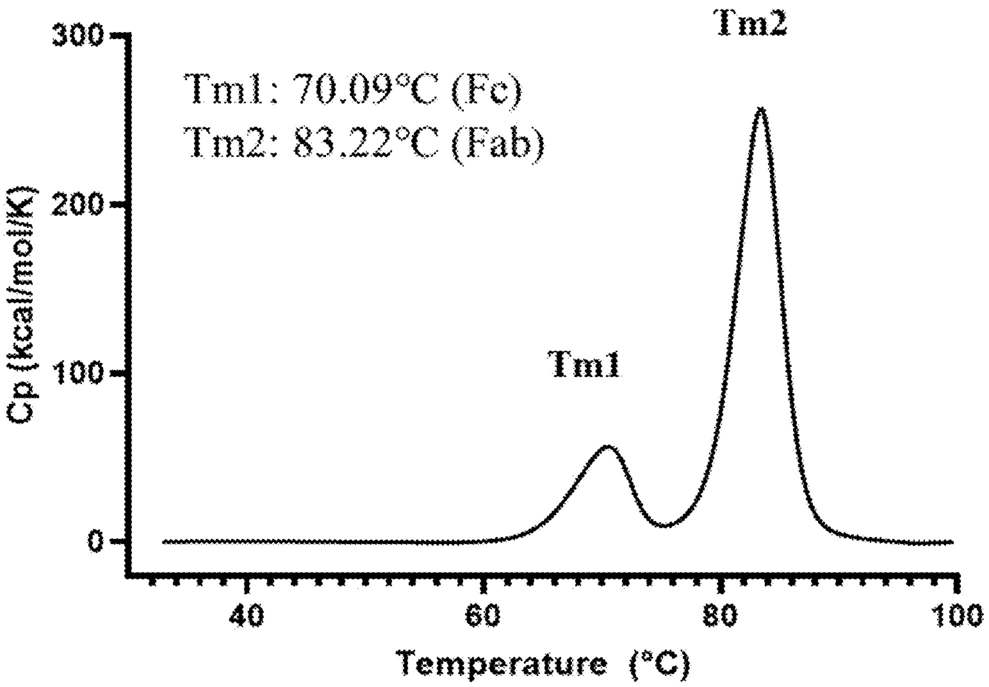
Figure 10B:
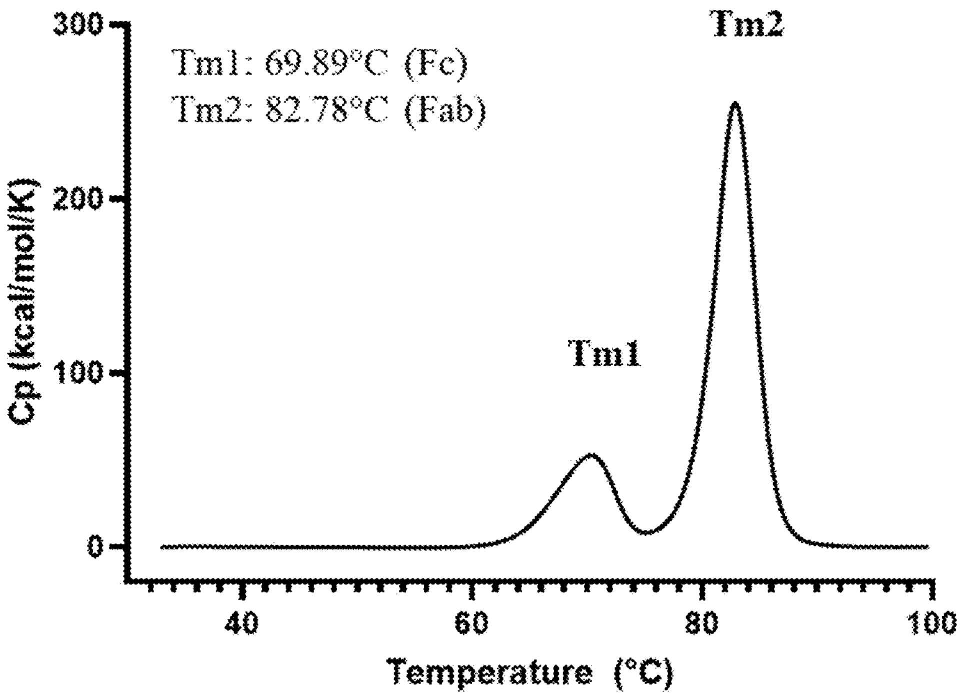
Figure 10C:
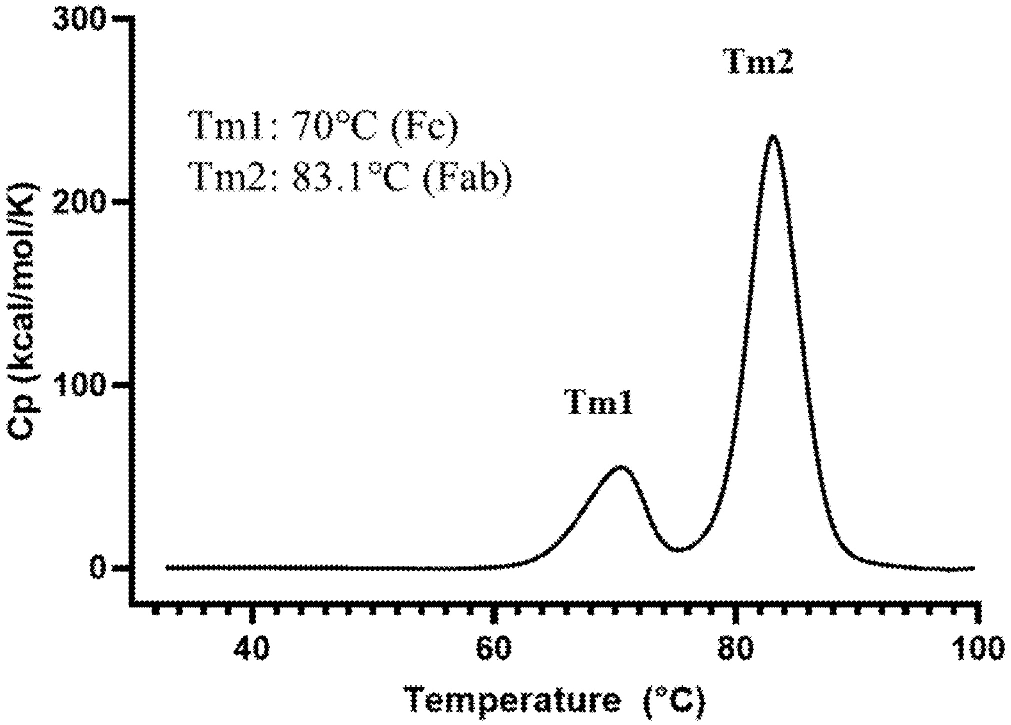
Figure 10D:
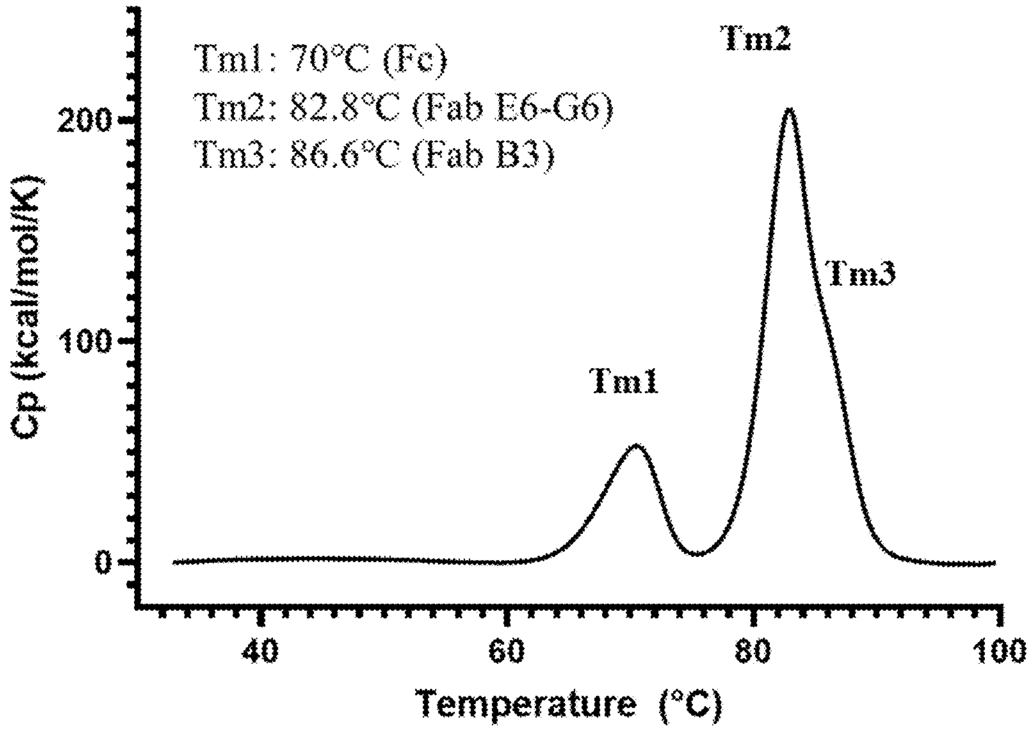

FIGS. 10A-10D. Thermograms obtained by differential scanning calorimetry (DSC) for CD3/BCMA/CD38 antibodies including thermal transition € analysis. Thermogram and thermal transition analysis of A. TREAT CD3/BCMA/CD38-115 (FIG. 10A); B. TREAT CD3/BCMA/CD38-117 (FIG. 10B); C. TREAT CD3/BCMA/CD38-118 (FIG. 10C) and D. TREAT CD3/BCMA/CD38-119 (FIG. 10D). The domains' unfolding corresponding to the different transitions were assigned in brackets after the corresponding temperatures.

Figure 11A:
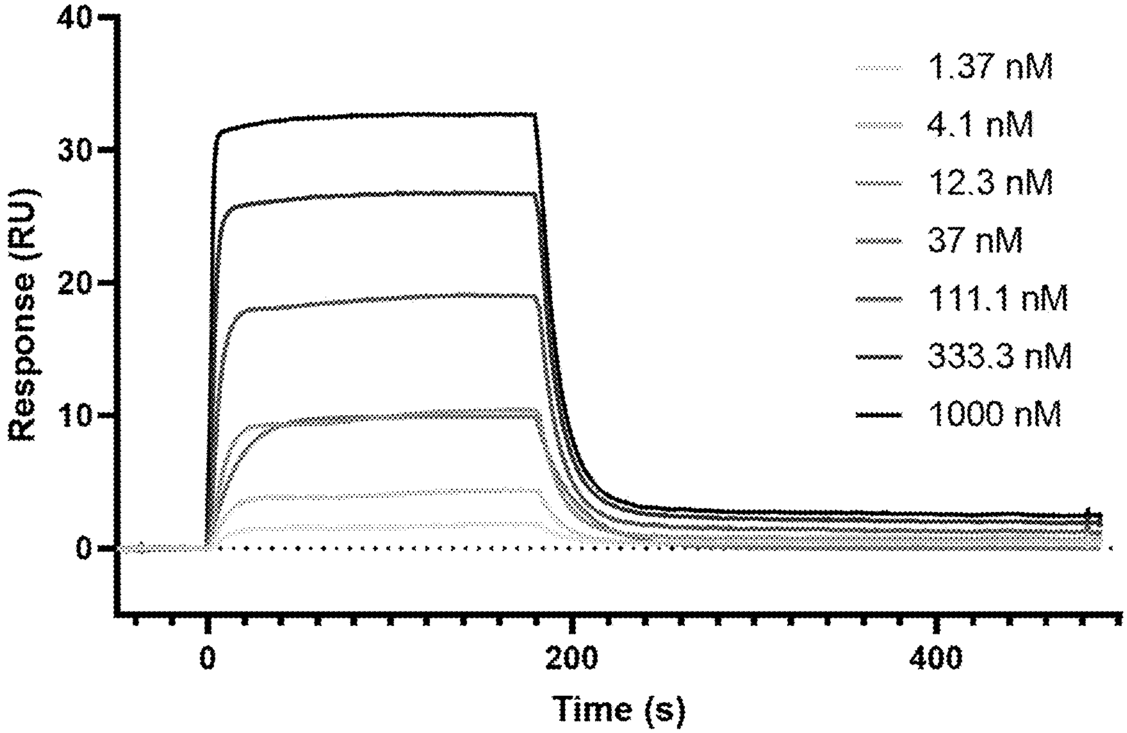
Figure 11B:
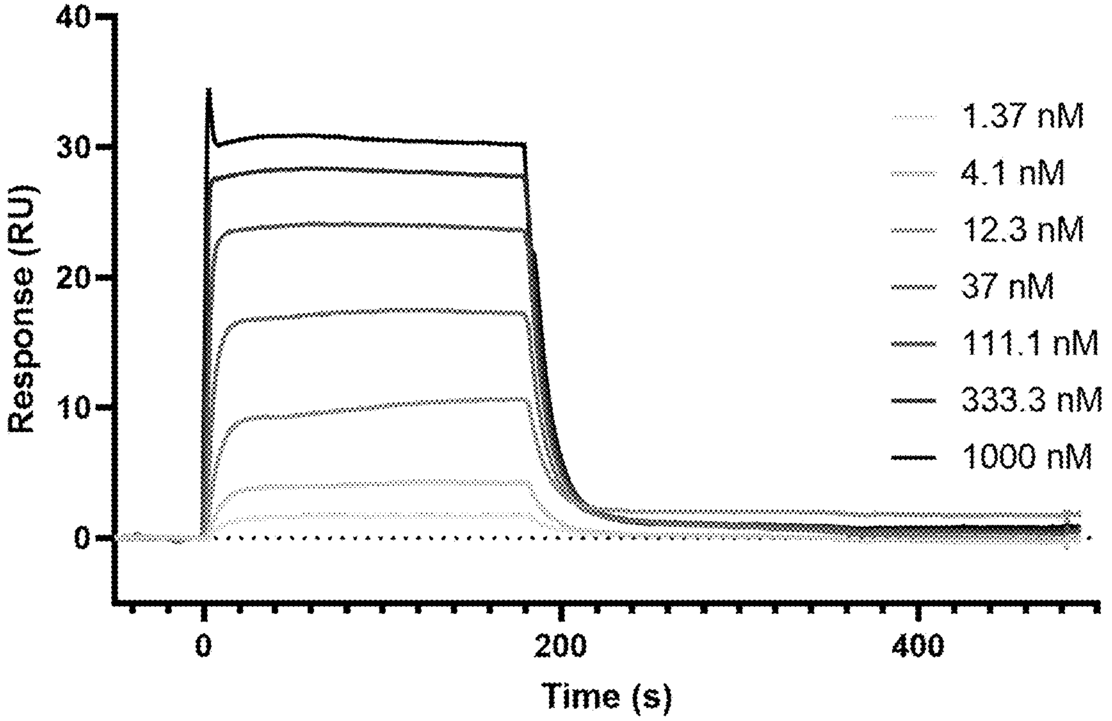
Figure 11C:
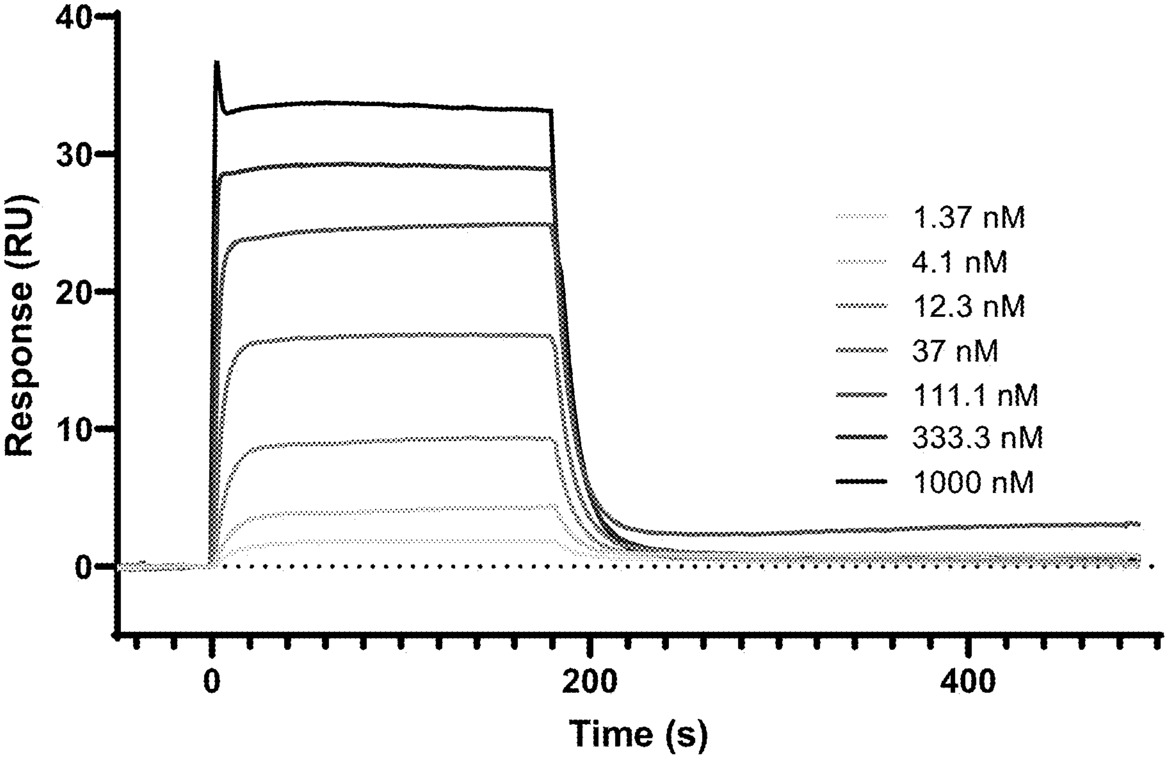
Figure 11D:
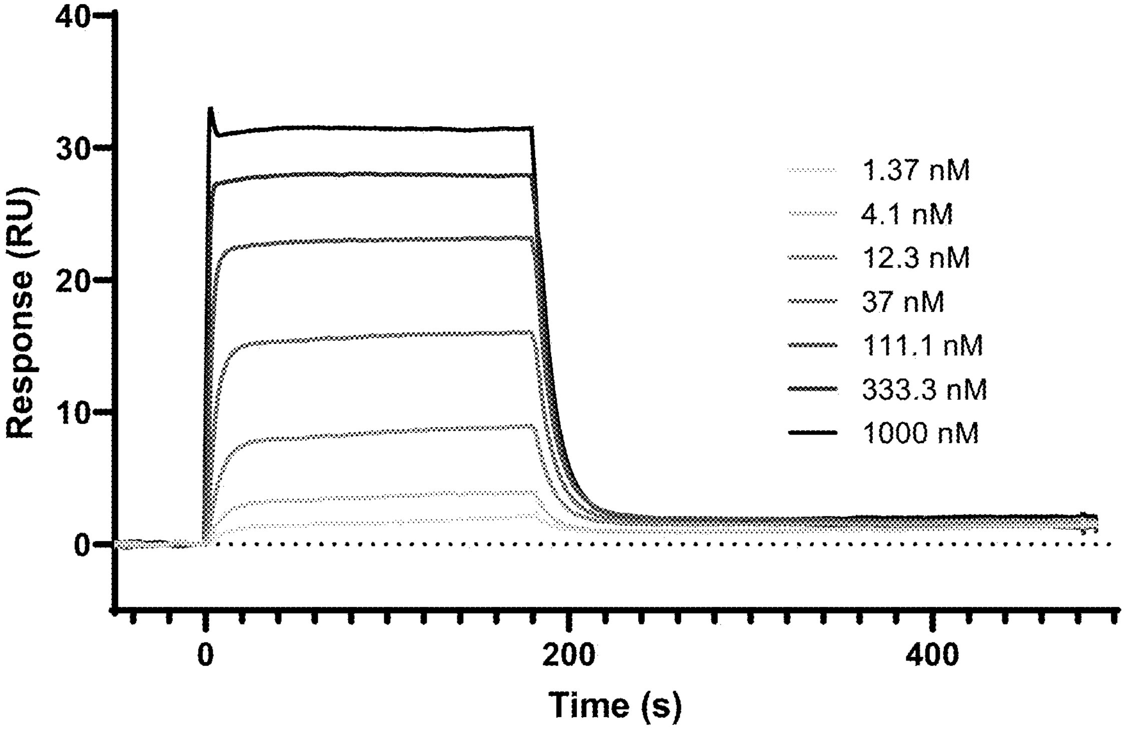

FIGS. 11A-11D. Surface Plasmon Resonance measurements of CD3/BCMA/CD38 antibodies to hCD3εδ. Biotinylated hCD3ε5 (CD3E & CD3D-377H, Creative Biomart, USA) was immobilized on the sensor surface via the Biotin CAPture Reagent, a modified streptavidin that can be reversibly attached to the CAP chip surface. CD3/BCMA/CD38 antibodies were injected in concentration series (as described in the figure) in HBS-EP+ buffer over immobilized hCD3εδ. Plots are showing data expressed as number of resonance units (abbreviated RU; Y axis) vs. time (s, X axis) for A. TREAT CD3/BCMA/CD38-115 (FIG. 11A); B. TREAT CD3/BCMA/CD38-117 (FIG. 11B); C. TREAT CD3/BCMA/CD38-118 (FIG. 11C) and D. TREAT CD3/BCMA/CD38-119 (FIG. 11D). Binding affinity to human CD3ε5 were measured using a steady state affinity model. This model uses the plot of the equilibrium response (Req; Y axis) vs. analyte concentration (M; X axis) for affinity calculation according to the following equation: $Req=K_A \times C \times Rmax/(K_A \times C \times n+1)$, concentration at 50% saturation is the equilibrium dissociation constant ($K_D$).

Figure 12A:
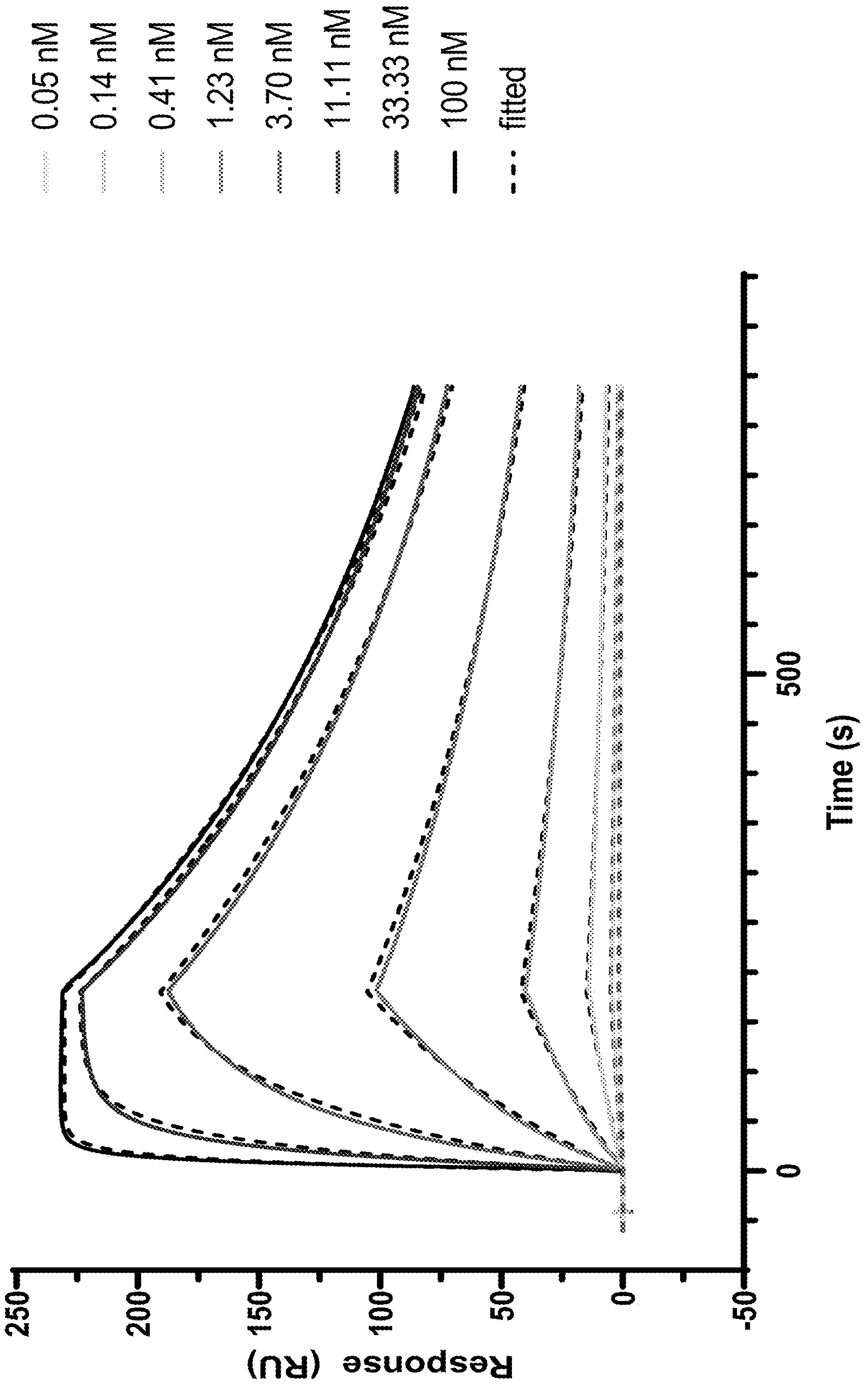
Figure 12B:
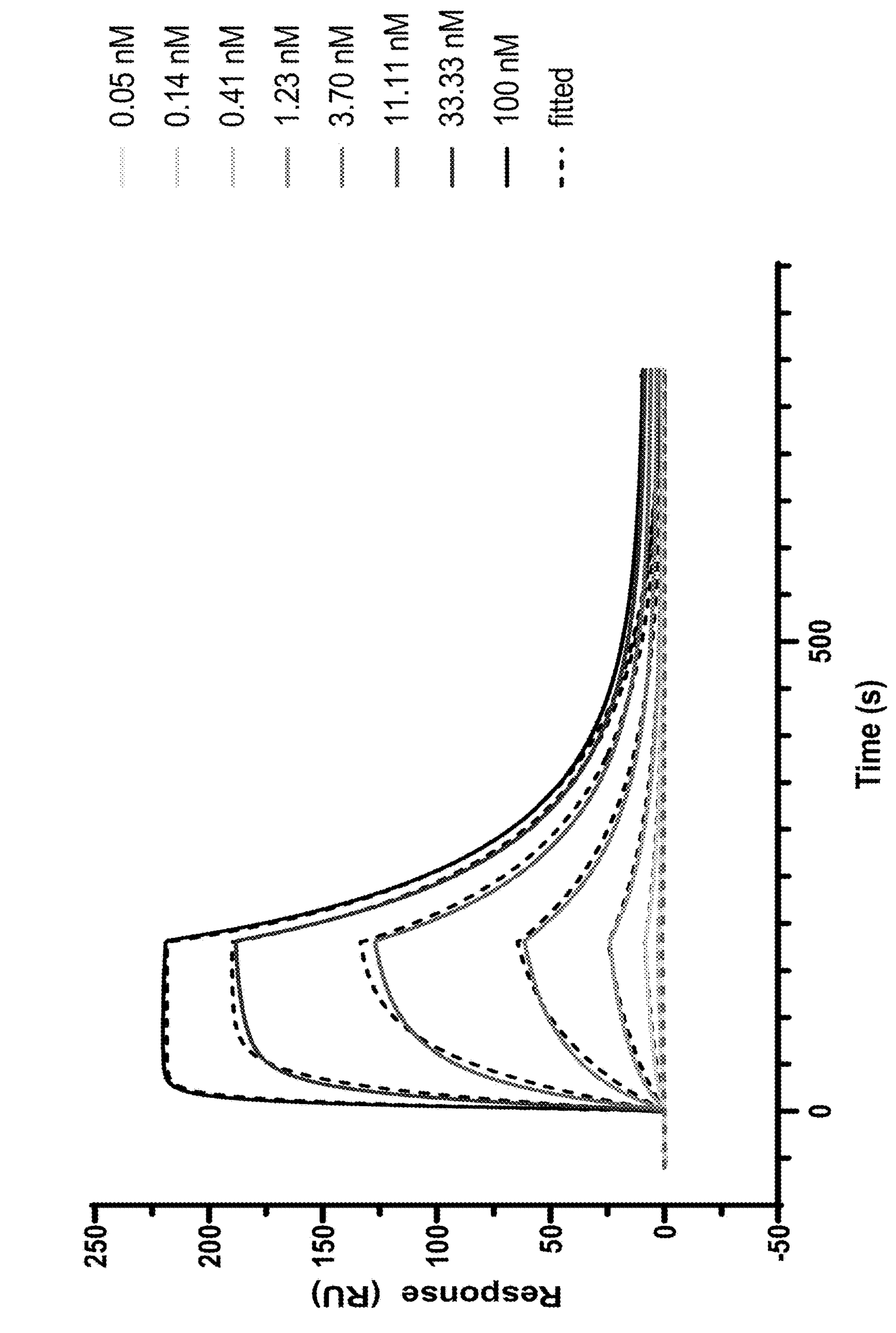
Figure 12C:
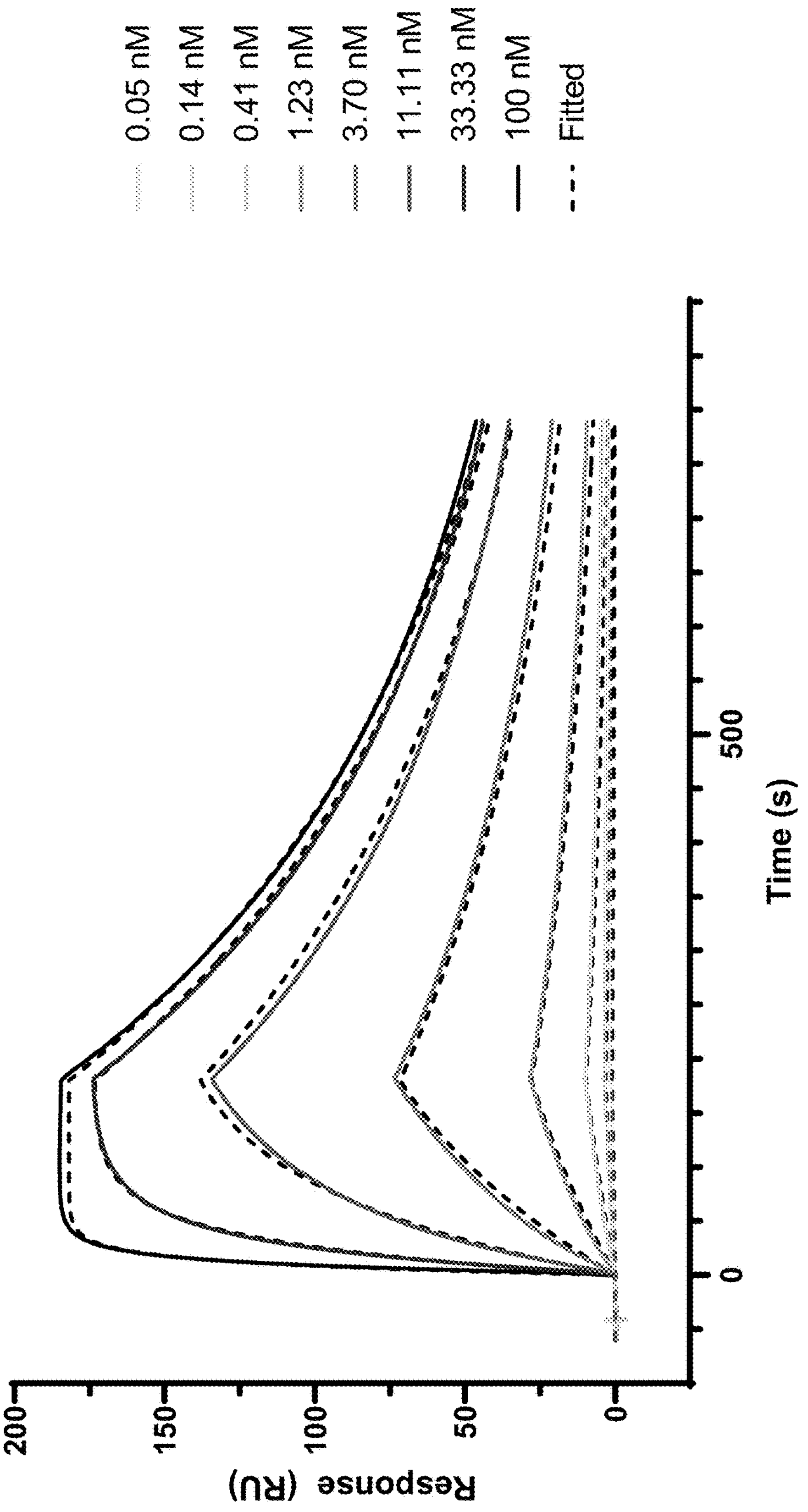
Figure 12D:
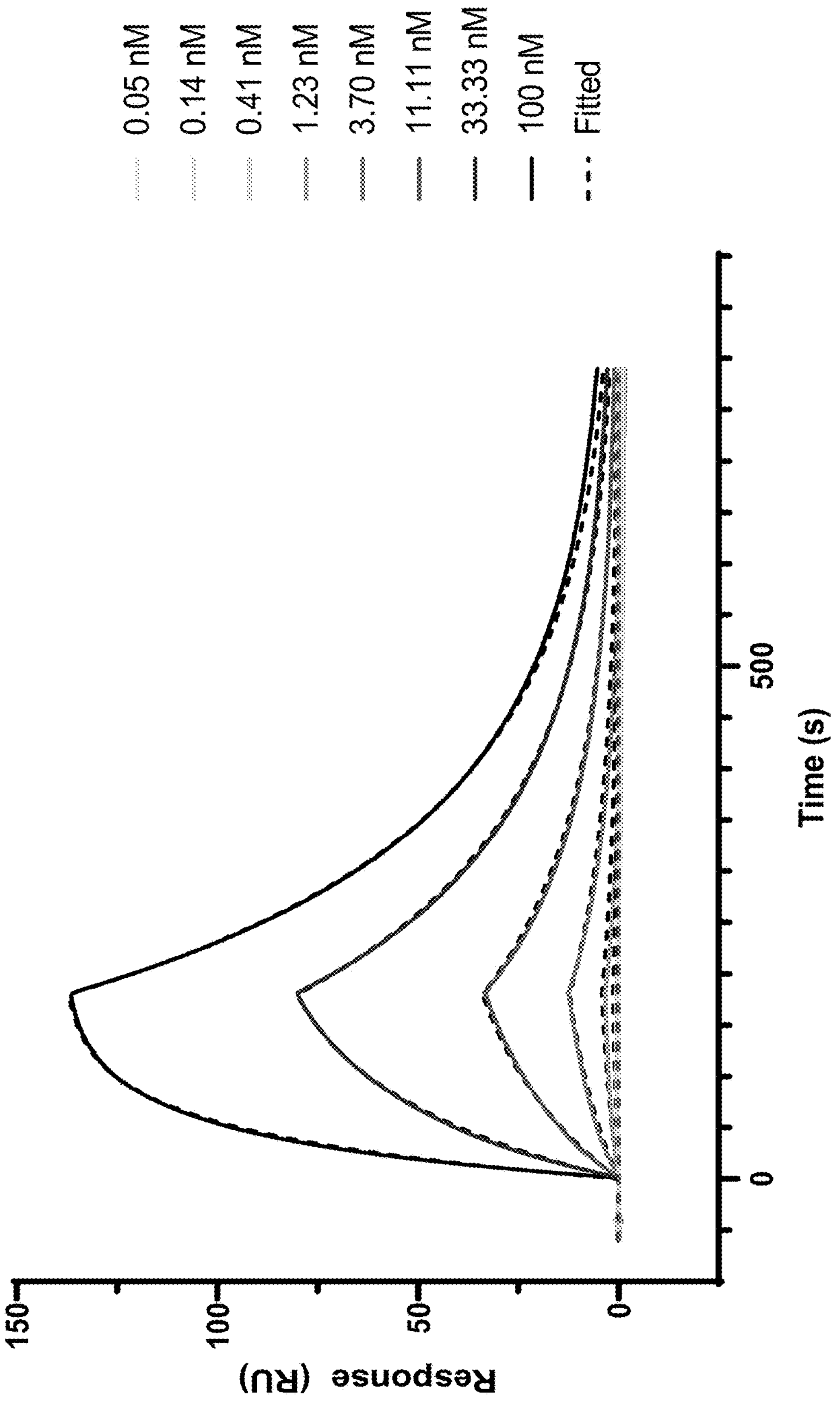

FIGS. 12A-12D. Surface Plasmon Resonance measurements of CD3/BCMA/CD38 antibodies to human CD38. Biotinylated hCD38 (Biotinylated Human CD38 Protein, Avitag™, His Tag, CD8-H82E7, Acrobiosystems, USA) was immobilized on the sensor surface via the Biotin CAPture Reagent, a modified streptavidin that can be reversibly attached to the CAP chip surface. CD3/BCMA/CD38 antibodies were injected in concentration series (as described in the figure) in HBS-EP+ buffer over immobilized hCD38. Plots are showing data expressed as number of resonance units (abbreviated RU; Y axis) vs. time (s, X axis) for A. TREAT CD3/BCMA/CD38-115 (FIG. 12A); B. TREAT CD3/BCMA/CD38-117 (FIG. 12B); C. TREAT CD3/BCMA/CD38-118 (FIG. 12C) and D. TREAT CD3/BCMA/CD38-119 (FIG. 12D). Binding affinities to human CD38 were measured using a 1:1 Langmuir binding model. This model assumes a 1:1 interaction between the ligand and analyte and determines the association rate constant ($k_a$), dissociation rate constant ($k_d$), and affinity ($K_D$) for each sample. Using this model, the $K_D$ is defined as the ratio between the included dissociation rate constant and the association rate constant, i.e., $K_D=k_d/k_a$. Measurements zero concentration samples for referencing. $Chi^2$ and residual values were used to evaluate the quality of fit between the experimental data (sensorgram fc2-fc1) and individual binding models. Solid lines represent the measured data while dotted lines represent simulated fits. Ko: equilibrium dissociation constant; $k_a$: association rate constant. $K_d$: dissociation rate constant.

Figure 13A:
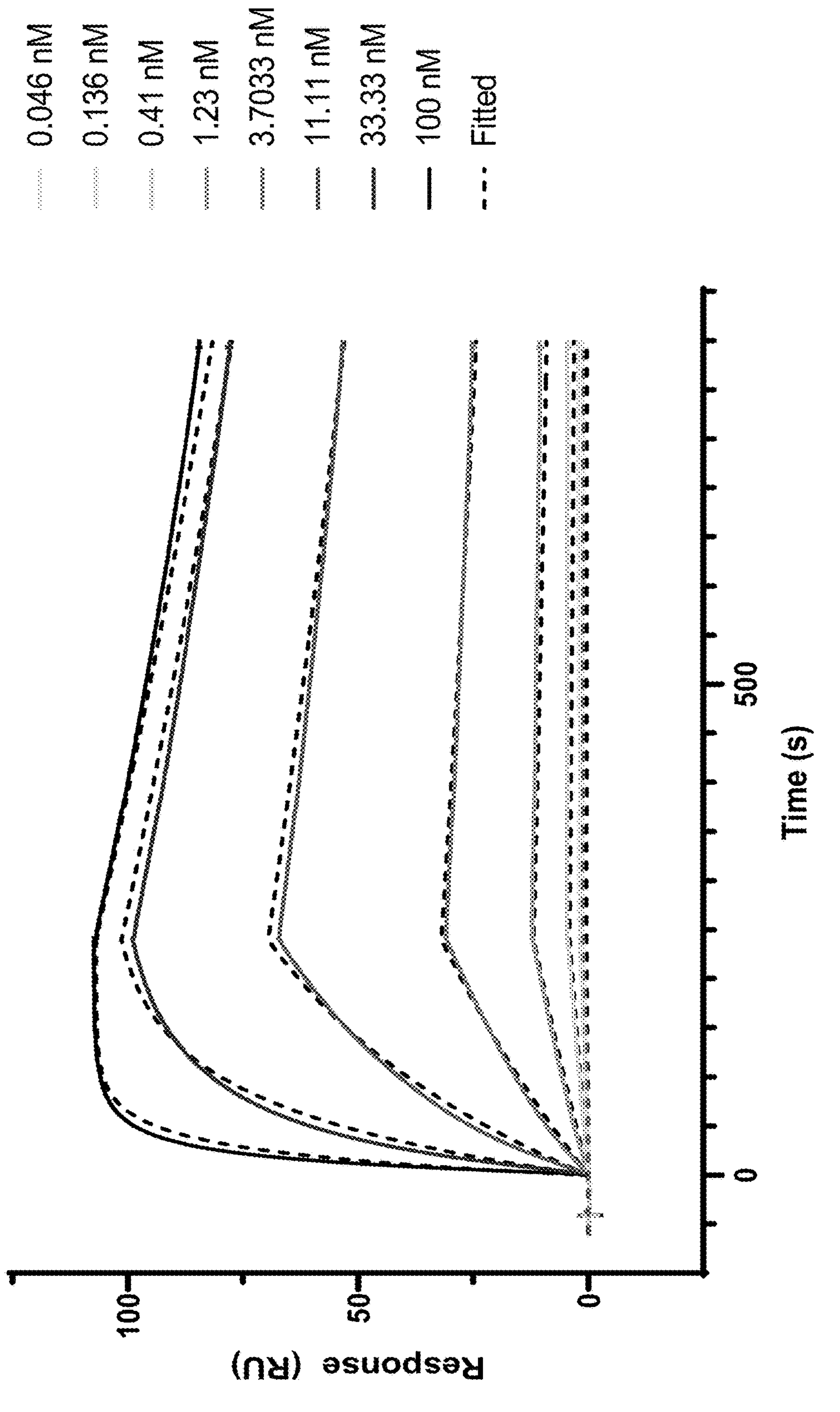
Figure 13B:
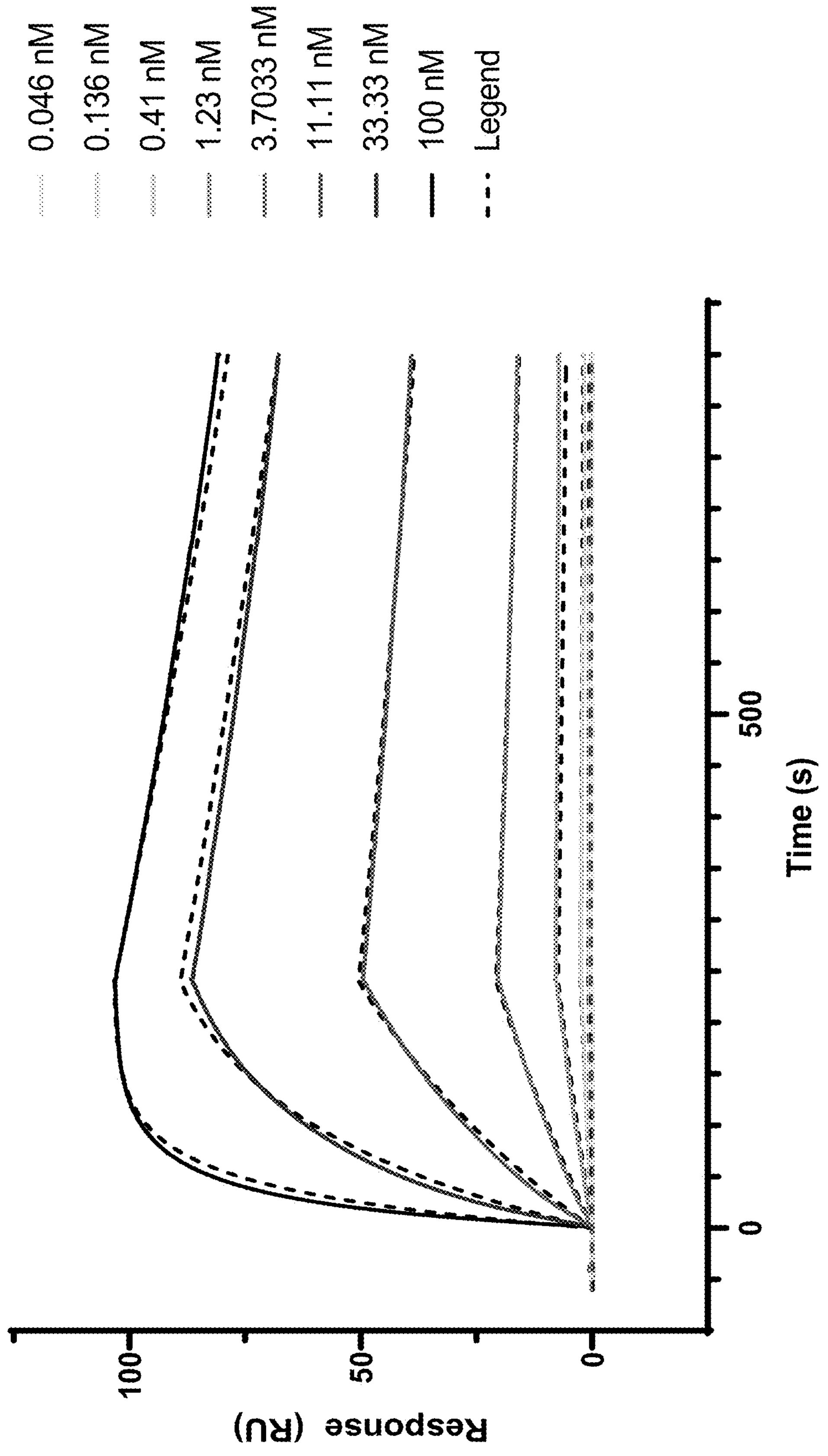
Figure 13C:
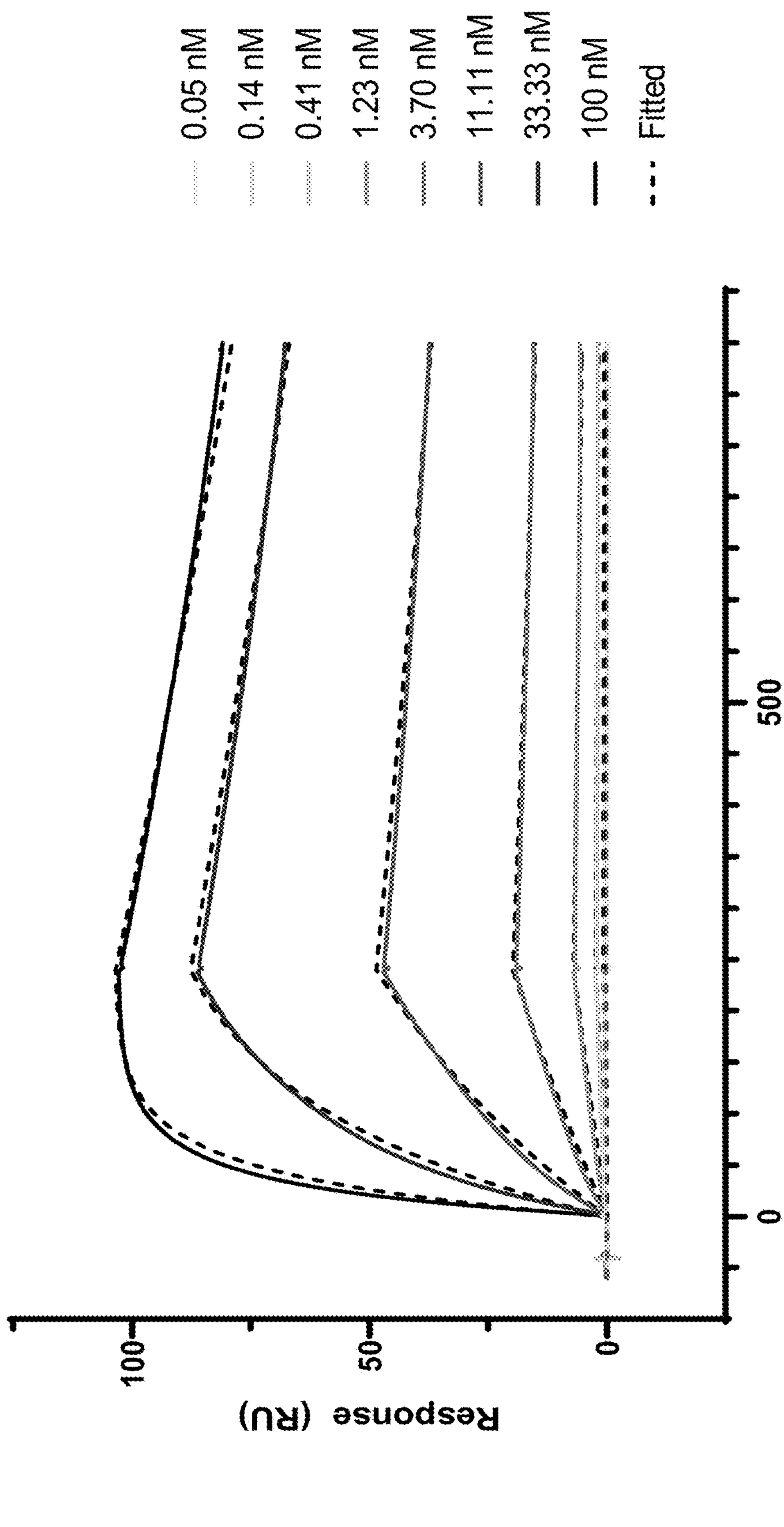
Figure 13D:
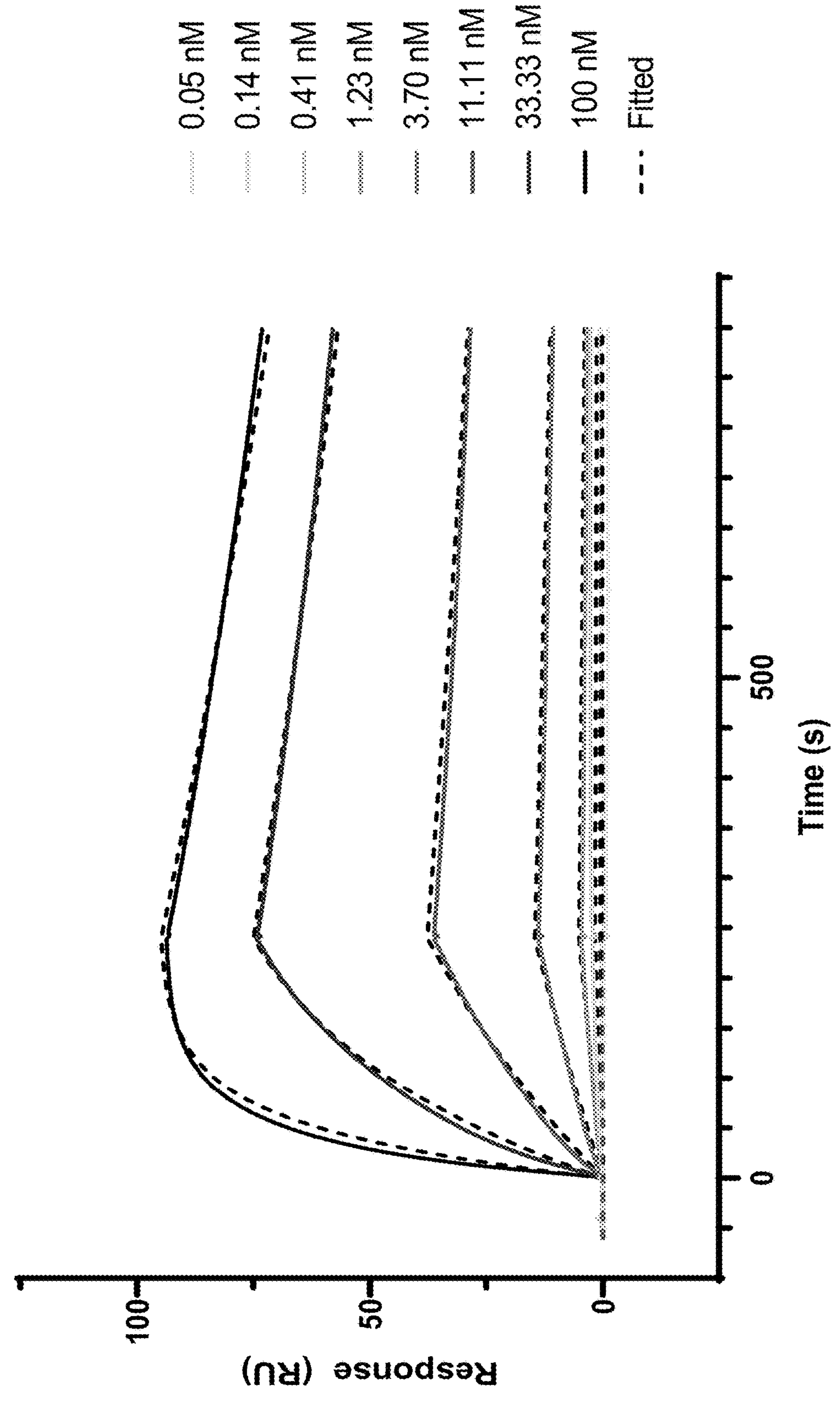

FIGS. 13A-13D. Surface Plasmon Resonance measurements of CD3/BCMA/CD38 antibodies to human BCMA. Biotinylated hBCMA (Biotinylated Human BCMA/TNFRSF17 Protein, His, Avitag™ DMF Filed, BCA-H82E4, Acrobiosystems, USA) was immobilized on the sensor surface via the Biotin CAPture Reagent, a modified streptavidin that can be reversibly attached to the CAP chip surface. CD3/BCMA/CD38 antibodies were injected in concentration series (as described in the figure) in HBS-EP+ buffer over immobilized hBCMA. Plots are showing data expressed as number of resonance units (abbreviated RU; Y axis) vs. time (s, X axis) for A. TREAT CD3/BCMA/CD38-115 (FIG. 13A); B. TREAT CD3/BCMA/CD38-117 (FIG. 13B); C. TREAT CD3/BCMA/CD38-118 (FIG. 13C) and D. TREAT CD3/BCMA/CD38-119 (FIG. 13D). Binding affinities to human CD38 were measured using a 1:1 Langmuir binding model. This model assumes a 1:1 interaction between the ligand and analyte and determines the association rate constant ($k_a$), dissociation rate constant ($k_d$), and affinity ($K_D$) for each sample. Using this model, the $K_D$ is defined as the ratio between the dissociation rate and the association rate, i.e., $K_D=k_d/k_a$. Measurements included zero concentration samples for referencing. $Chi^2$ and residual values were used to evaluate the quality of fit between the experimental data (sensorgram fc2-fc1) and individual binding models. Solid lines represent the measured data while dotted lines represent simulated fits. Ko: equilibrium dissociation constant; $k_a$ association rate constant; $k_d$: dissociation rate constant.

Figure 14A:
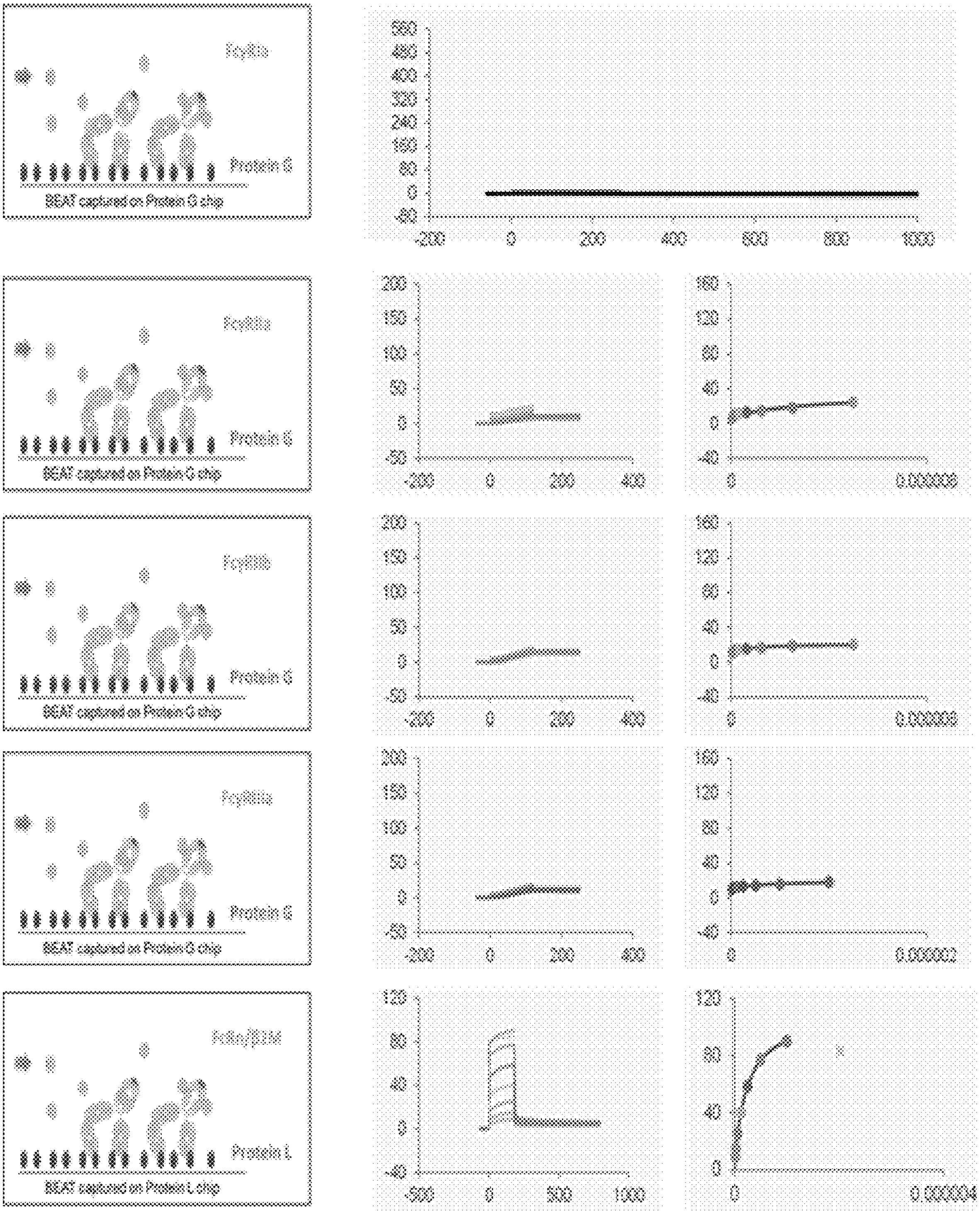
Figure 14B:
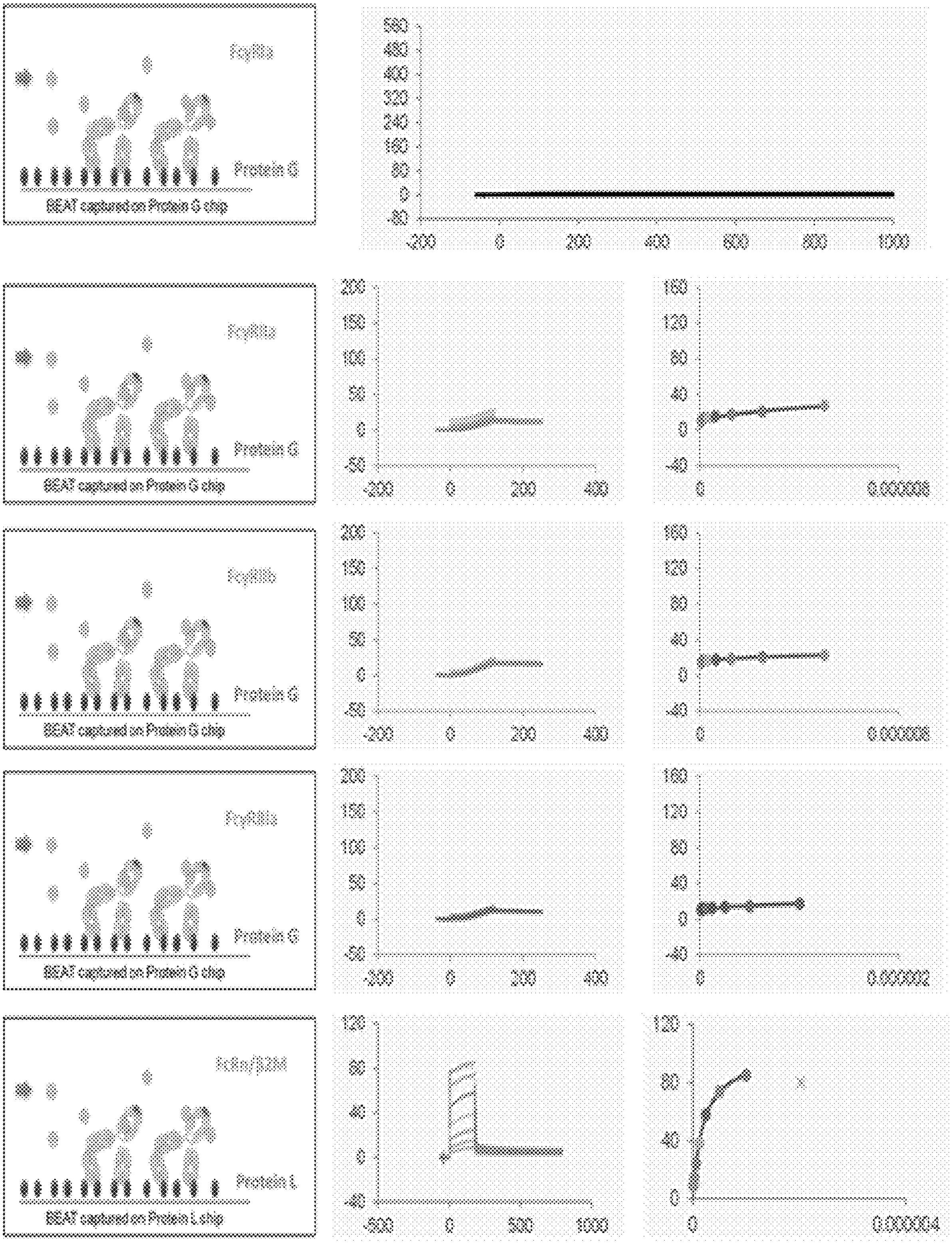
Figure 14C:
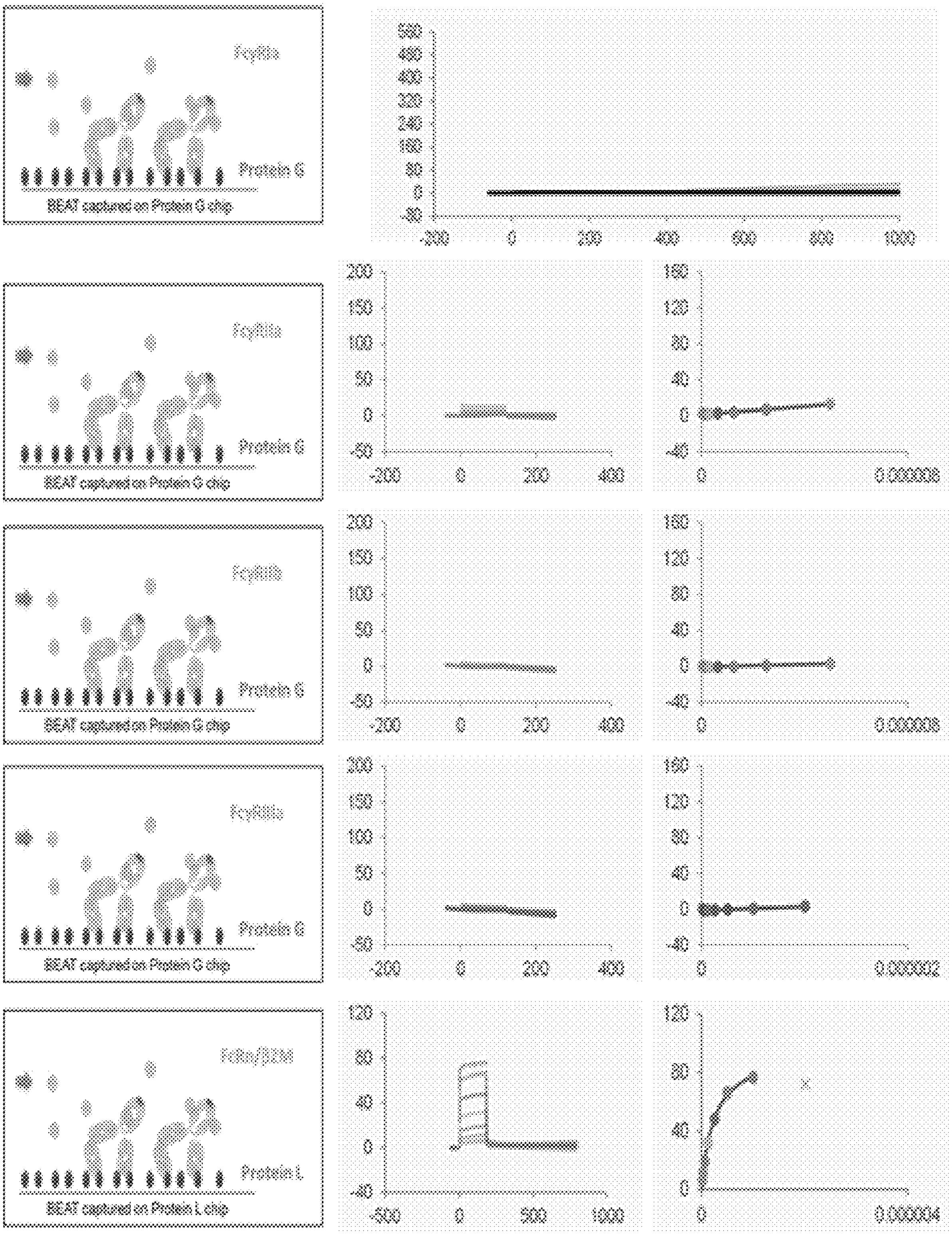
Figure 14D:
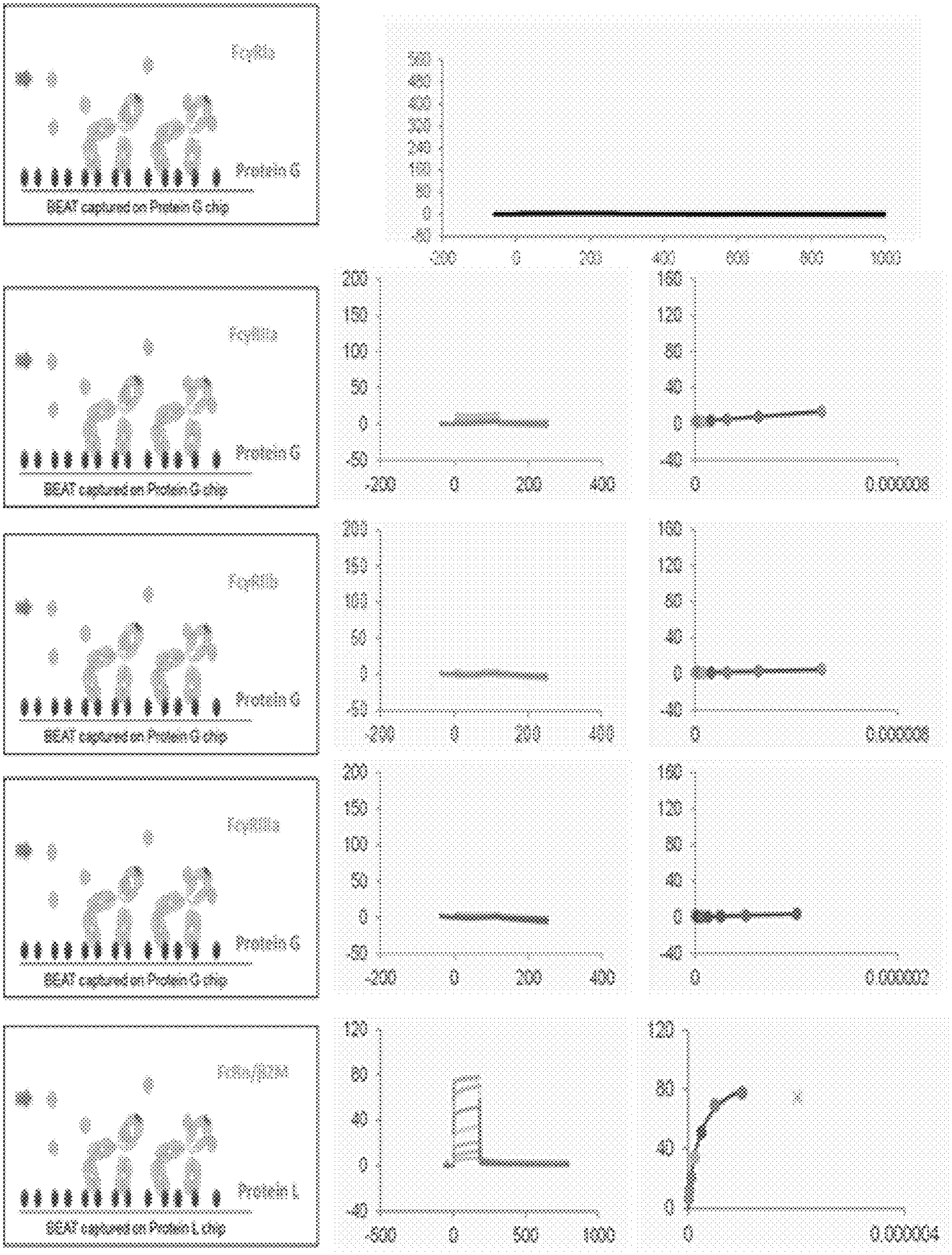
Figure 14E:
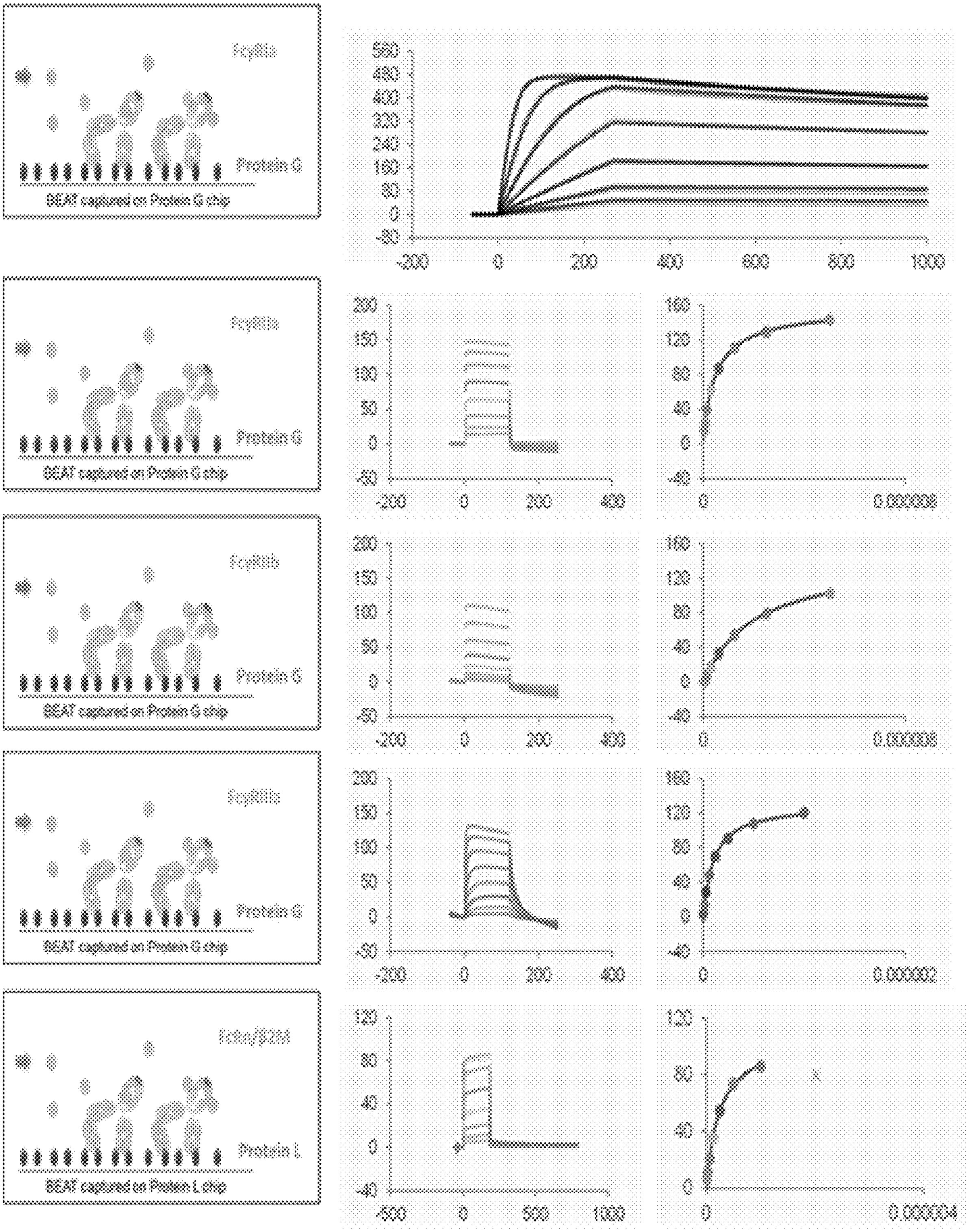

FIGS. 14A-14E. Surface Plasmon Resonance binding of selected TREAT CD3/BCMA/CD38 to Fc receptors compared to trastuzumab IgG1. (A) CD3/BCMA/CD38-115 (FIG. 14A), (B) CD3/BCMA/CD38-117 (FIG. 14B), (C) CD3/BCMA/CD38-118 (FIG. 14C), (D) CD3/BCMA/CD38-119 (FIG. 14D) and (E) trastuzumab IgG1 (FIG. 14E).

Figure 15:
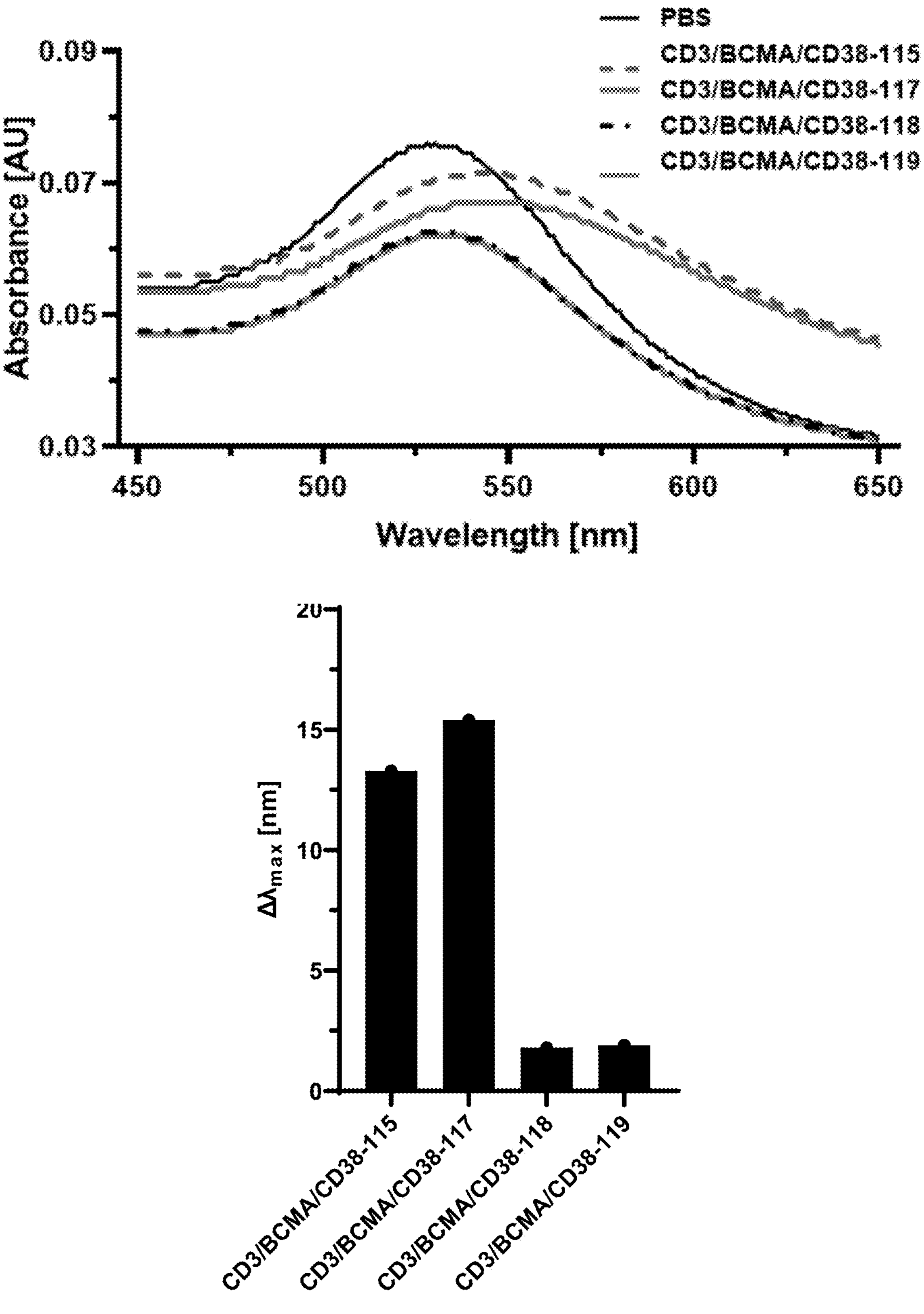

FIG. 15. AC-SINS profile of selected TREATs CD3/BCMA/CD38.

Figure 16A:
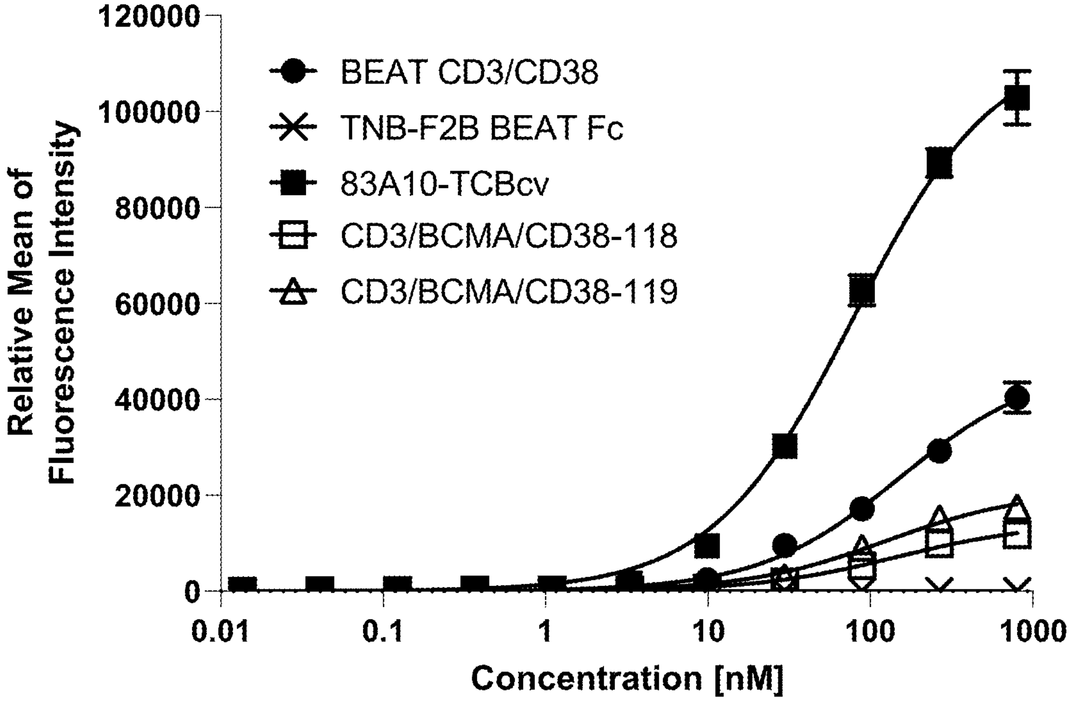
Figure 16B:
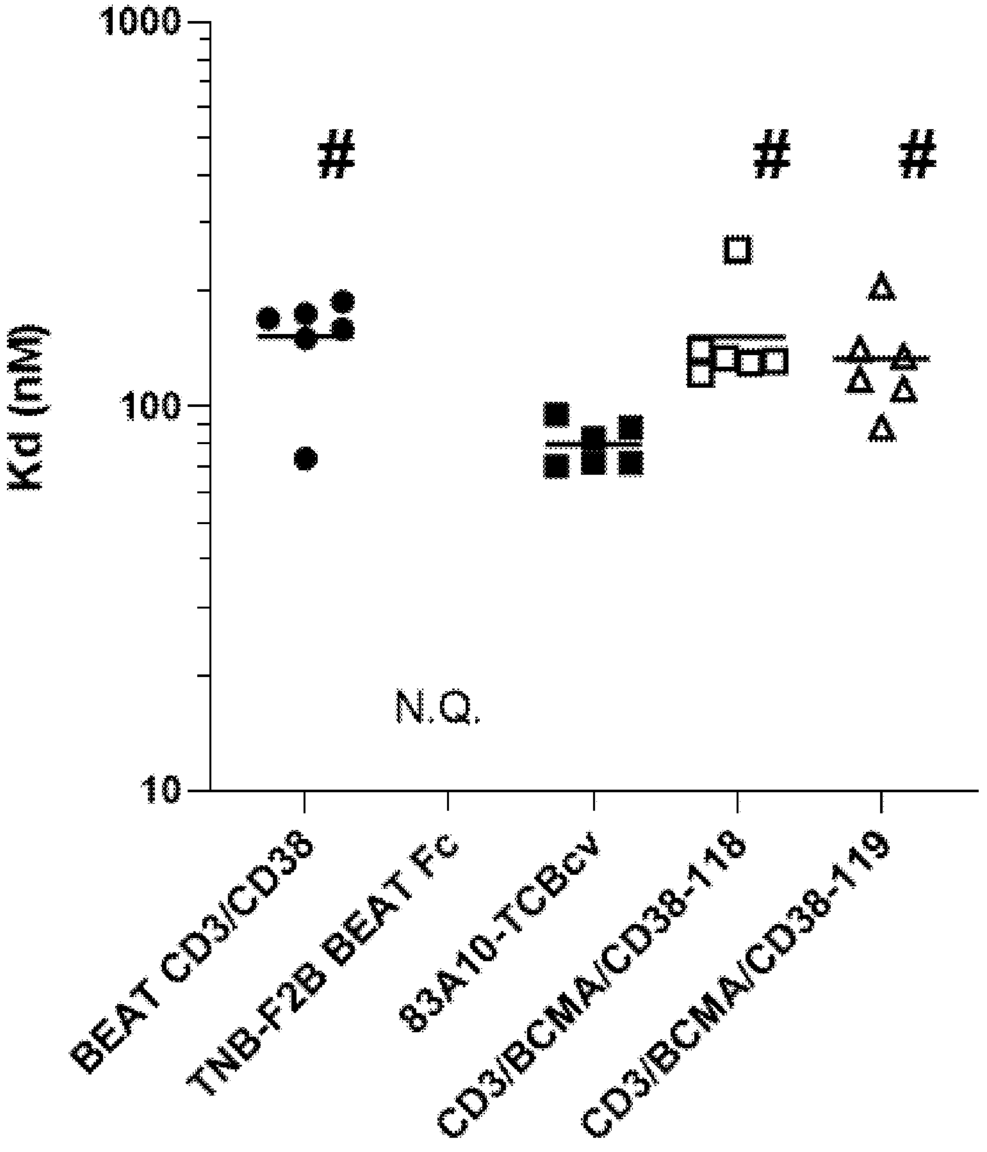

FIGS. 16A-16B. CD3/BCMA/CD38 candidates bind to human primary CD38-negative T cells. The binding of anti-CD3 candidates to CD38 negative human T cells was evaluated by flow cytometry, and binding curves are depicted in FIG. 16A. Each point represents the Mean+/−Standard Deviation of six measurements of independent T cell donors from two individual experiments. $K_D$ values determined from binding curves were plotted and compared to benchmarks in FIG. 16B using a paired One-way ANOVA followed by Tukey HSD post-hoc comparison. # stands for significantly different to 83A10-TCBcv. Experimental setup and analysis are described in Example 18.

Figure 17A:
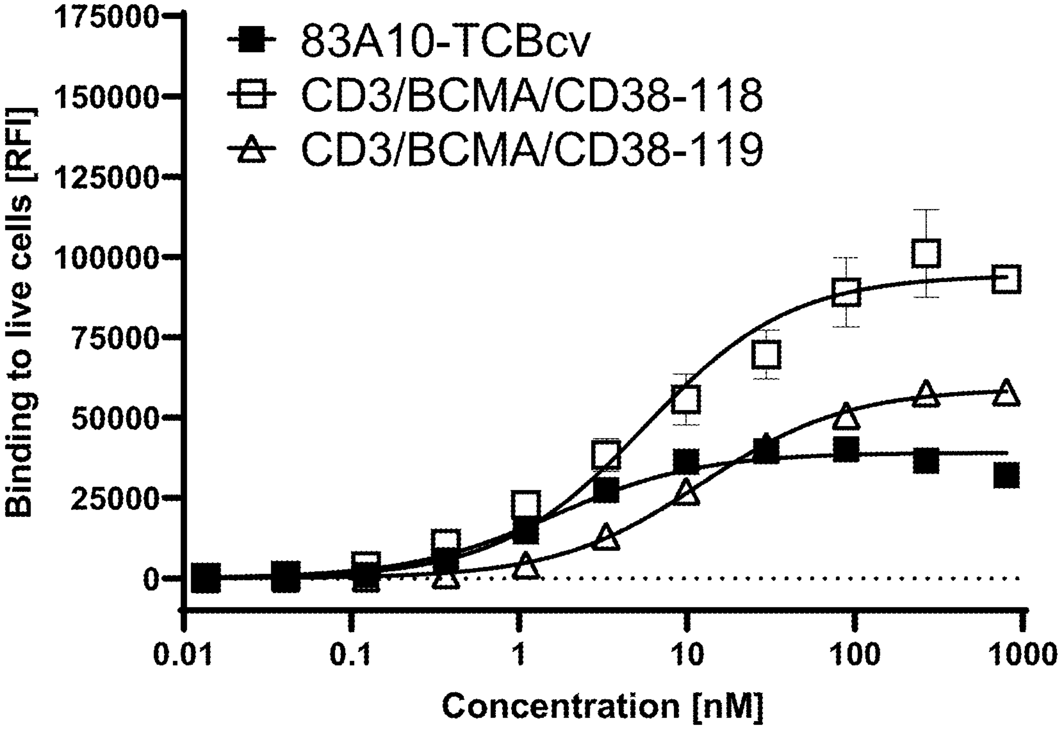
Figure 17B:
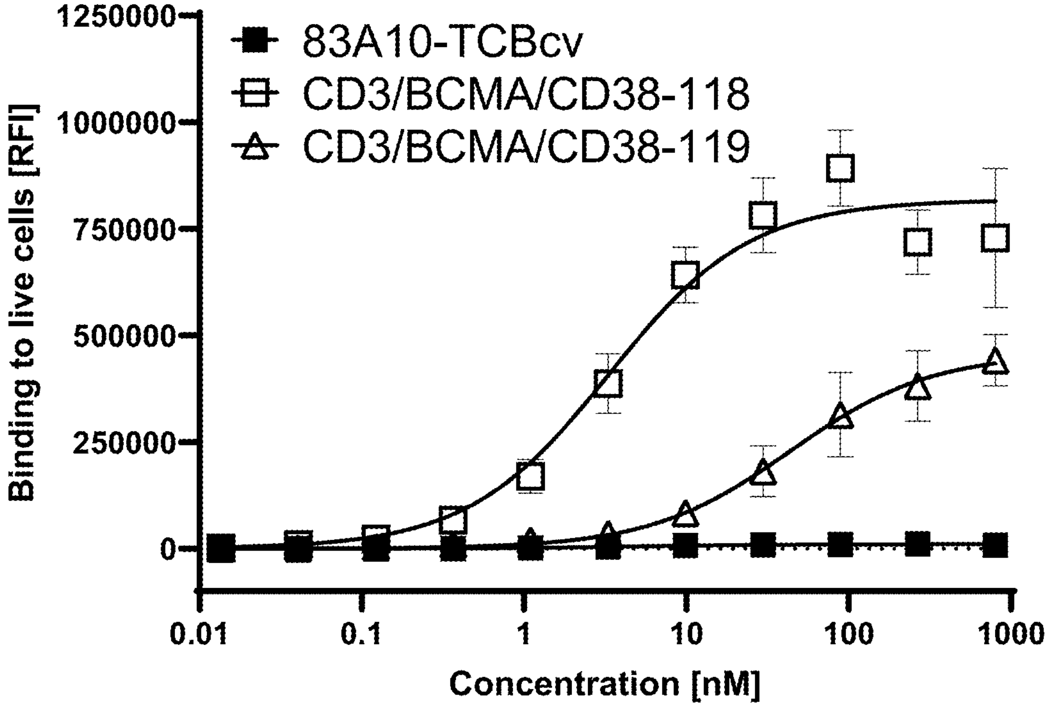
Figure 17C:
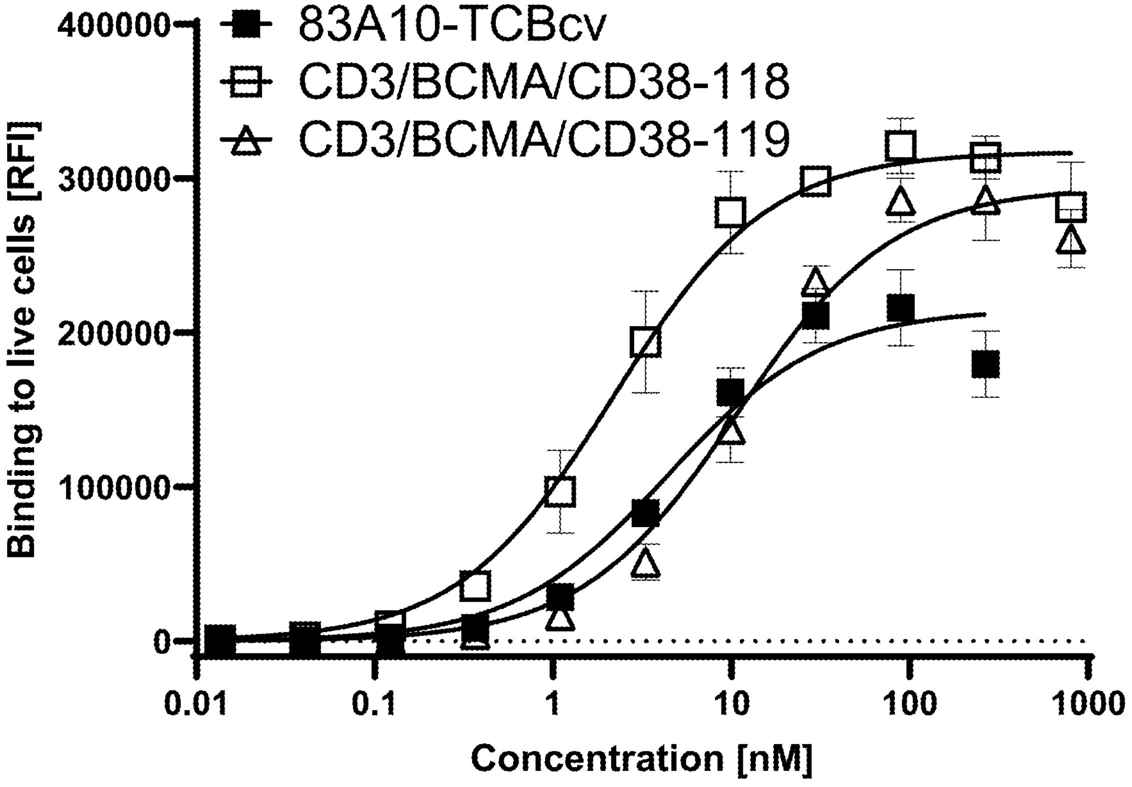

FIGS. 17A-17C. CD3/BCMA/CD38 candidates bind to cell lines displaying variable expression of CD38 and BCMA. The binding of candidates CD3/BCMA/CD38 candidates, −118, −119 and 83A10-TCBcv benchmark to CD38 and BCMA was evaluated by flow cytometry on different cell lines displaying variable expression of CD38 and BCMA, KMS-12-BM (FIG. 17A), MOLP-8 (FIG. 17B) and NCI-H929 (FIG. 17C). Each point is the Mean+/−Standard Deviation of three measurements from three individual experiments. Experimental setup and analysis are described in Example 18.

Figure 18C:
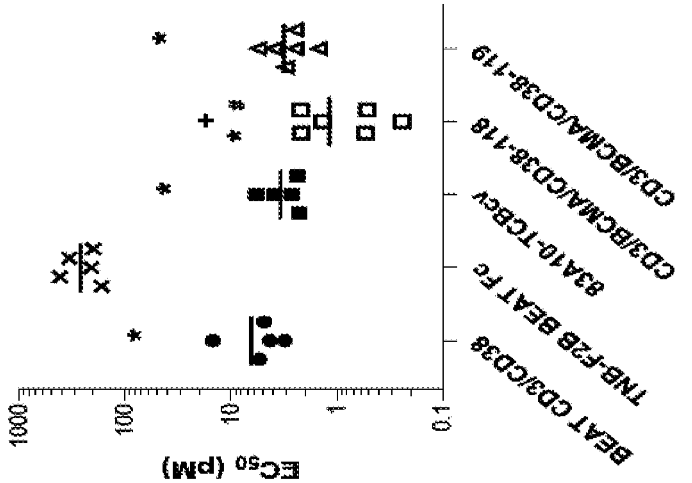
Figure 18B:
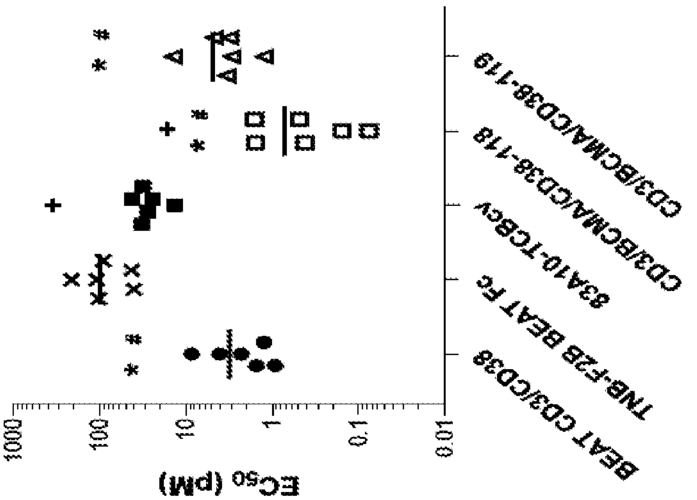
Figure 18A:
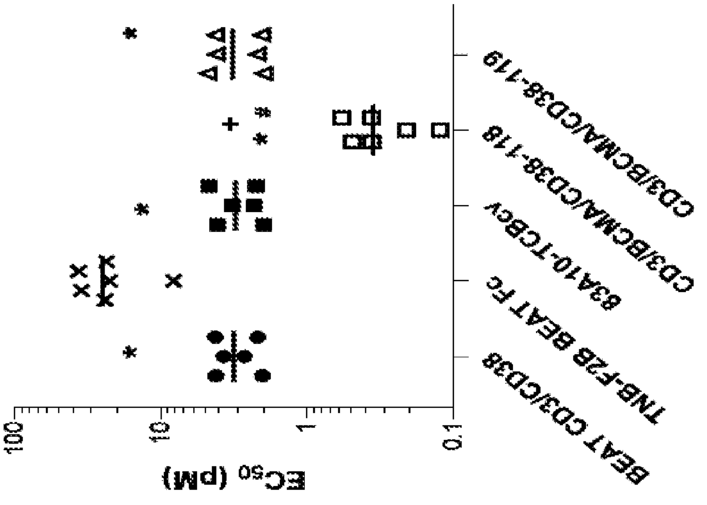

FIGS. 18A-18C. CD3/BCMA/CD38-118 candidate induces the most potent in vitro killing of Multiple Myeloma cell lines displaying variable expression of CD38 and BCMA. The ability of CD3/BCMA/CD38 candidates and benchmarks to trigger T cell mediated killing of KMS-12-BM (FIG. 18A), MOLP-8 (FIG. 18B) and NCI-H929 (FIG. 18C) tumor cells was assessed in a Redirected Lysis assay with a 5:1 Effector-to-target ratio and measured by Flow Cytometry after 72 hours of incubation. The half maximum effective killing concentration ($EC_{50}$) values were determined from Redirected Lysis assay. Each dot represents the $EC_{50}$ value for one individual donor. Means were compared using a paired One-way ANOVA followed by Tukey HSD post-hoc comparison. * stands for statistically significant compared to TNB-F2B BEAT Fc. # stands for statistically significant compared to 83A10-TCBcv. + stands for statistically significant compared to BEAT CD3/CD38. Three independent experiments were performed for each candidate with a total of 6 donors. Experimental setup and analysis are described in Example 18.

Figure 19:
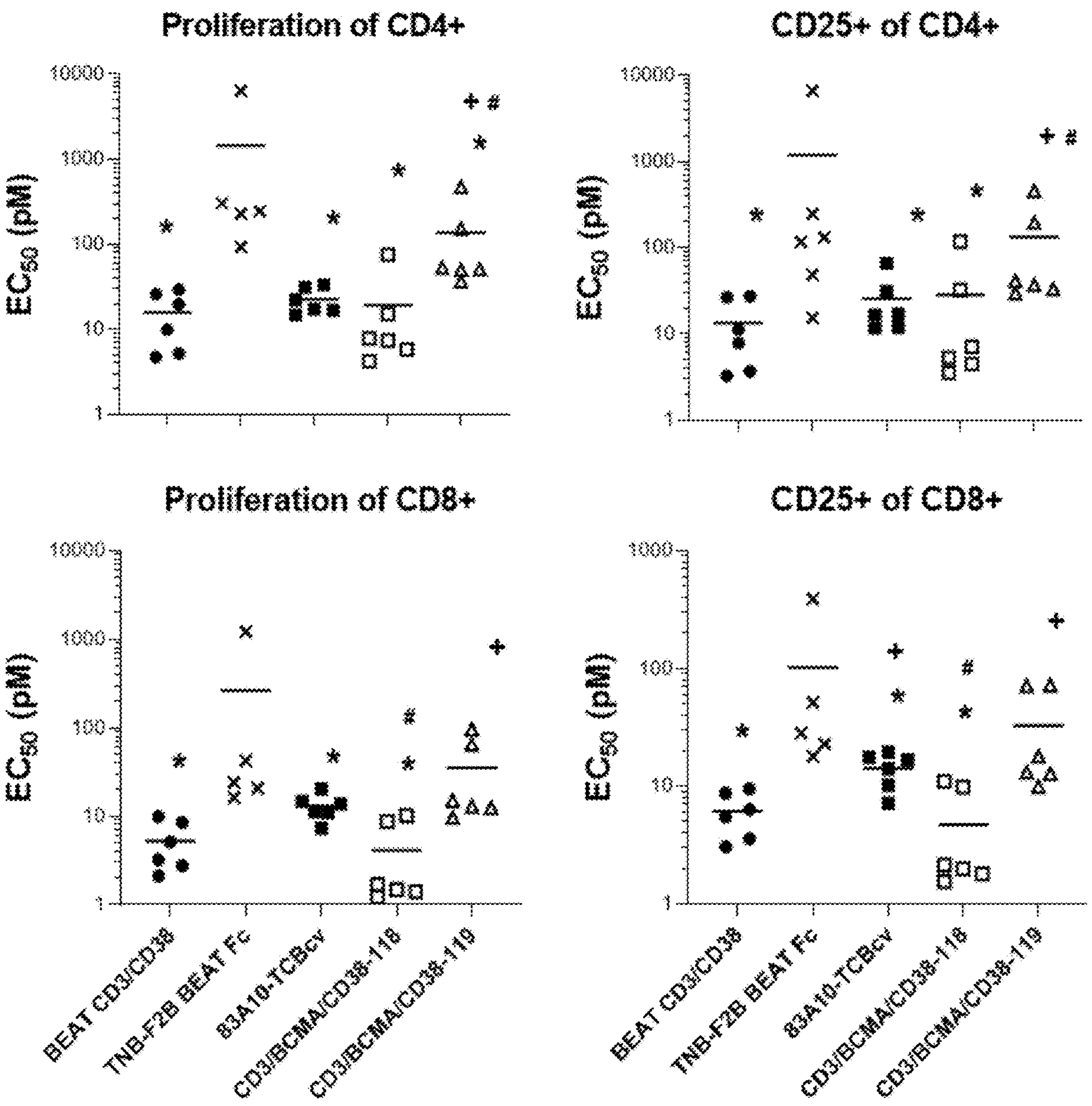
Figure 20A:
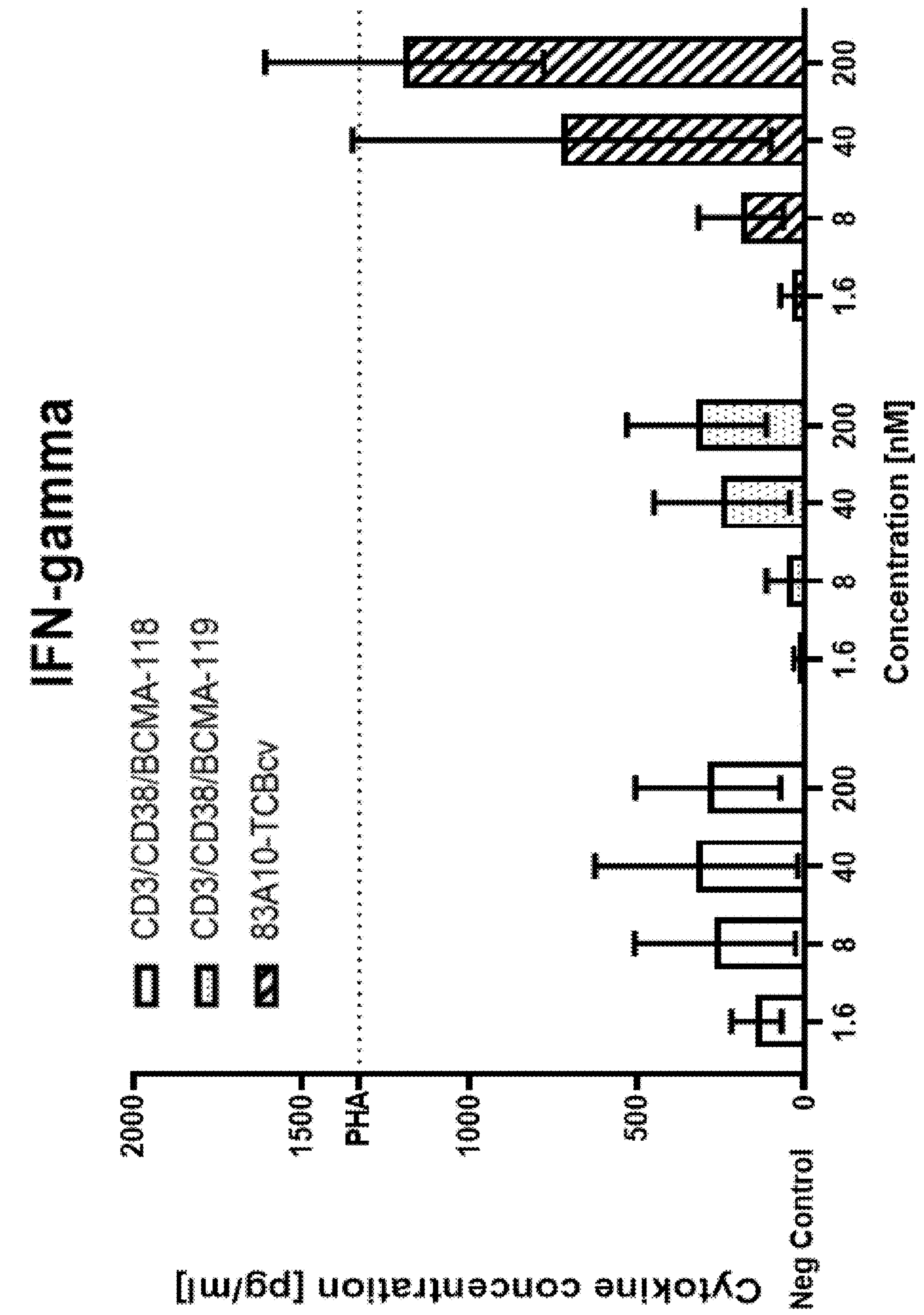
Figure 20B:
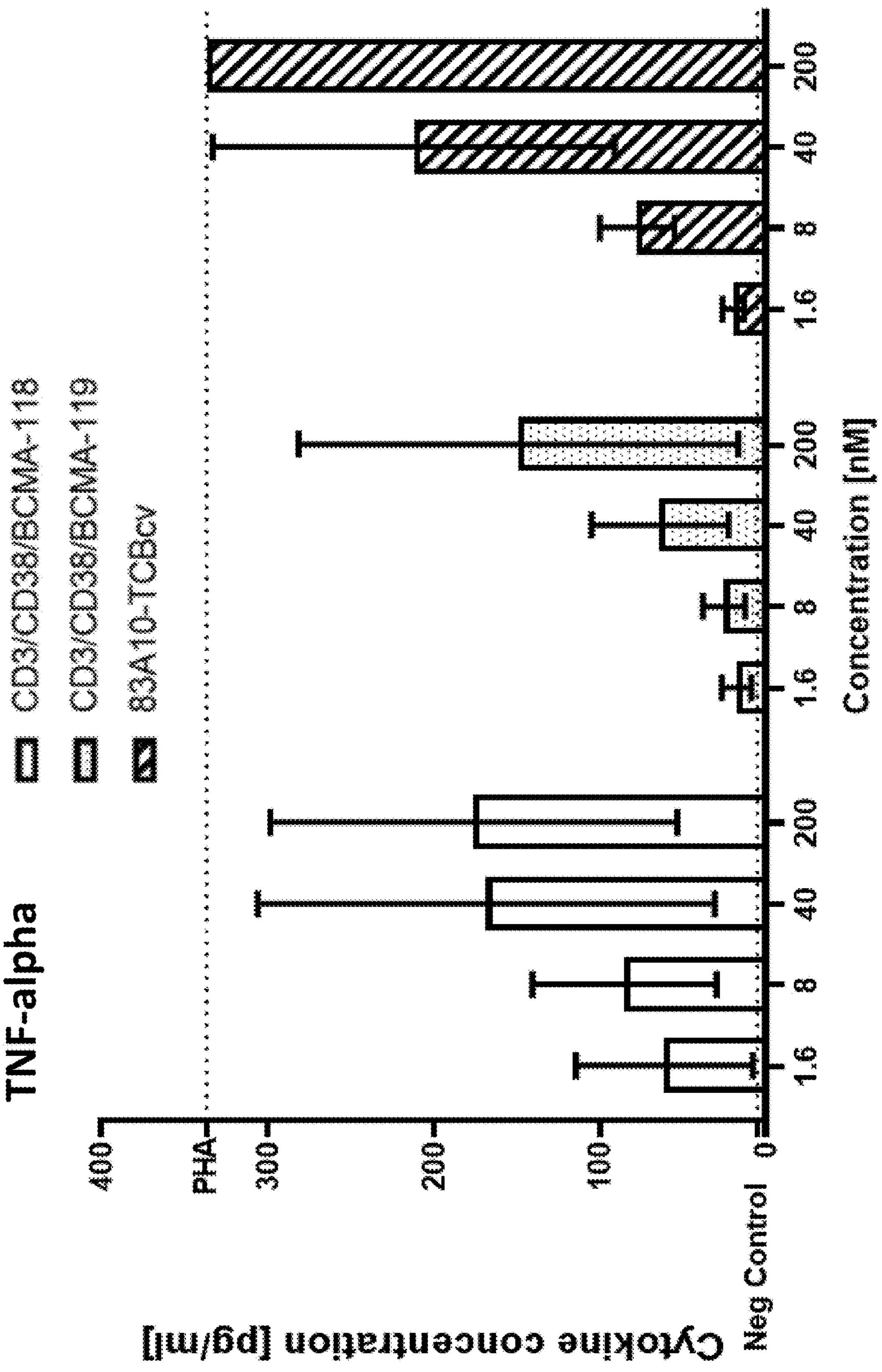
Figure 20C:
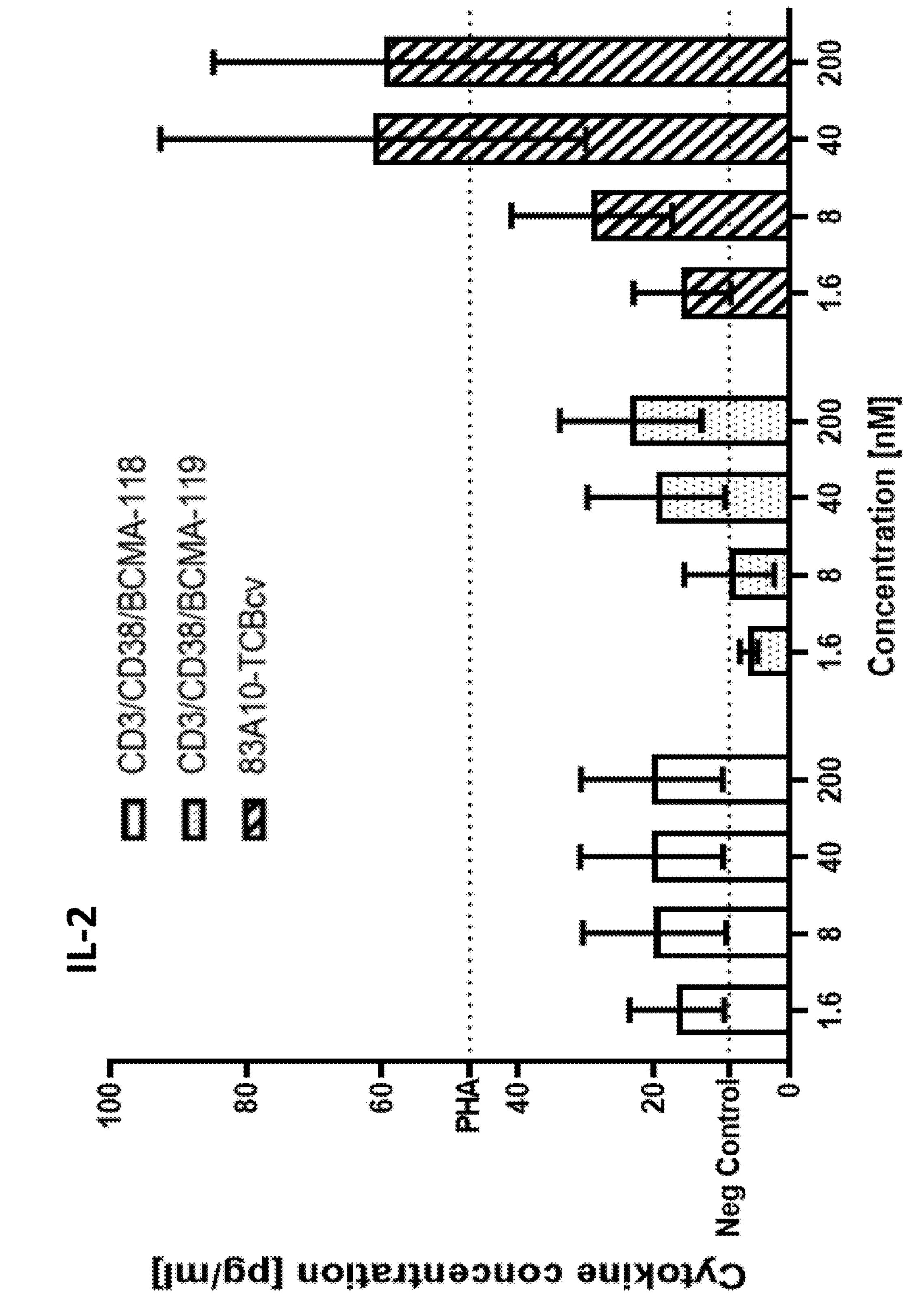
Figure 20D:
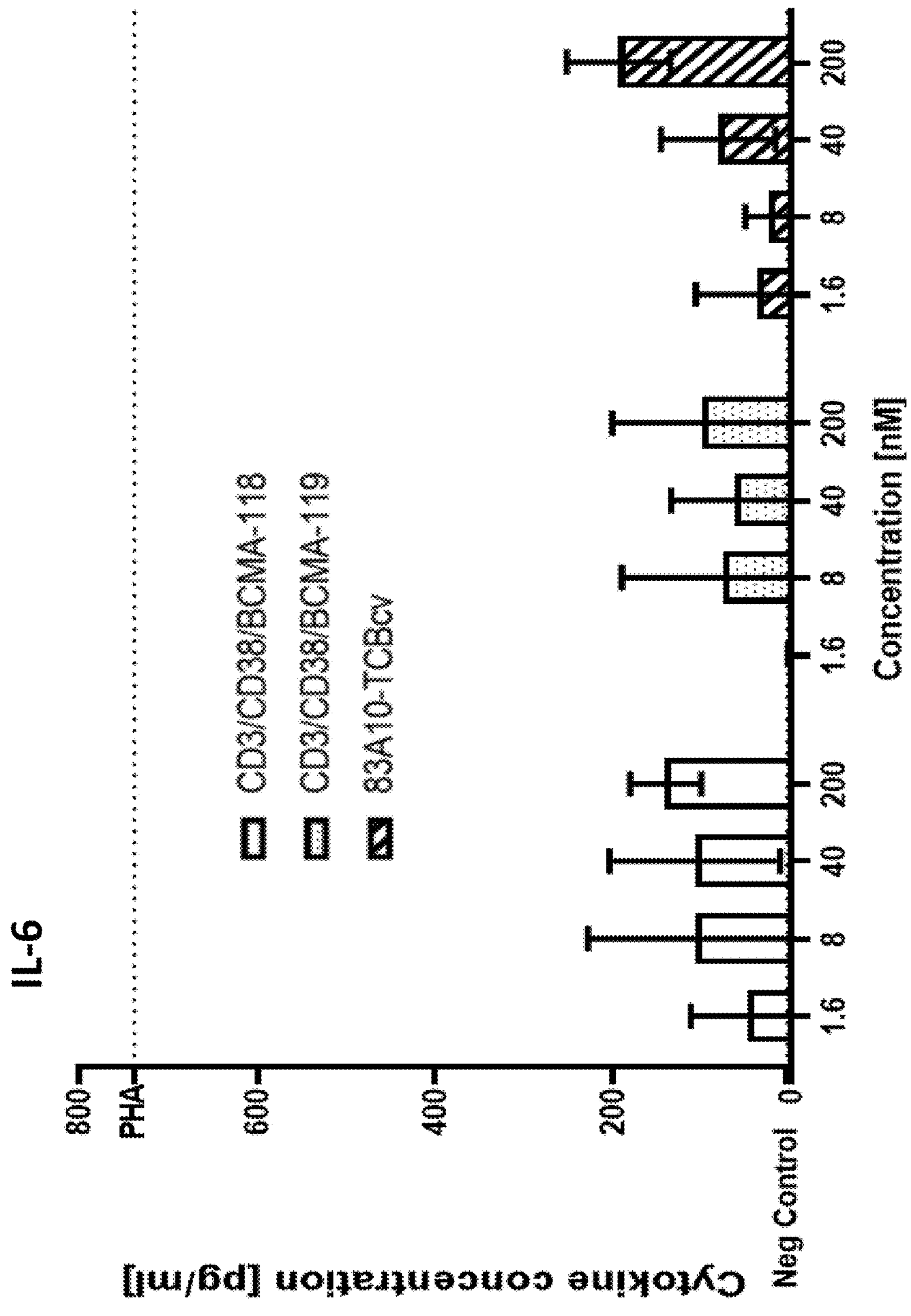
Figure 20E:
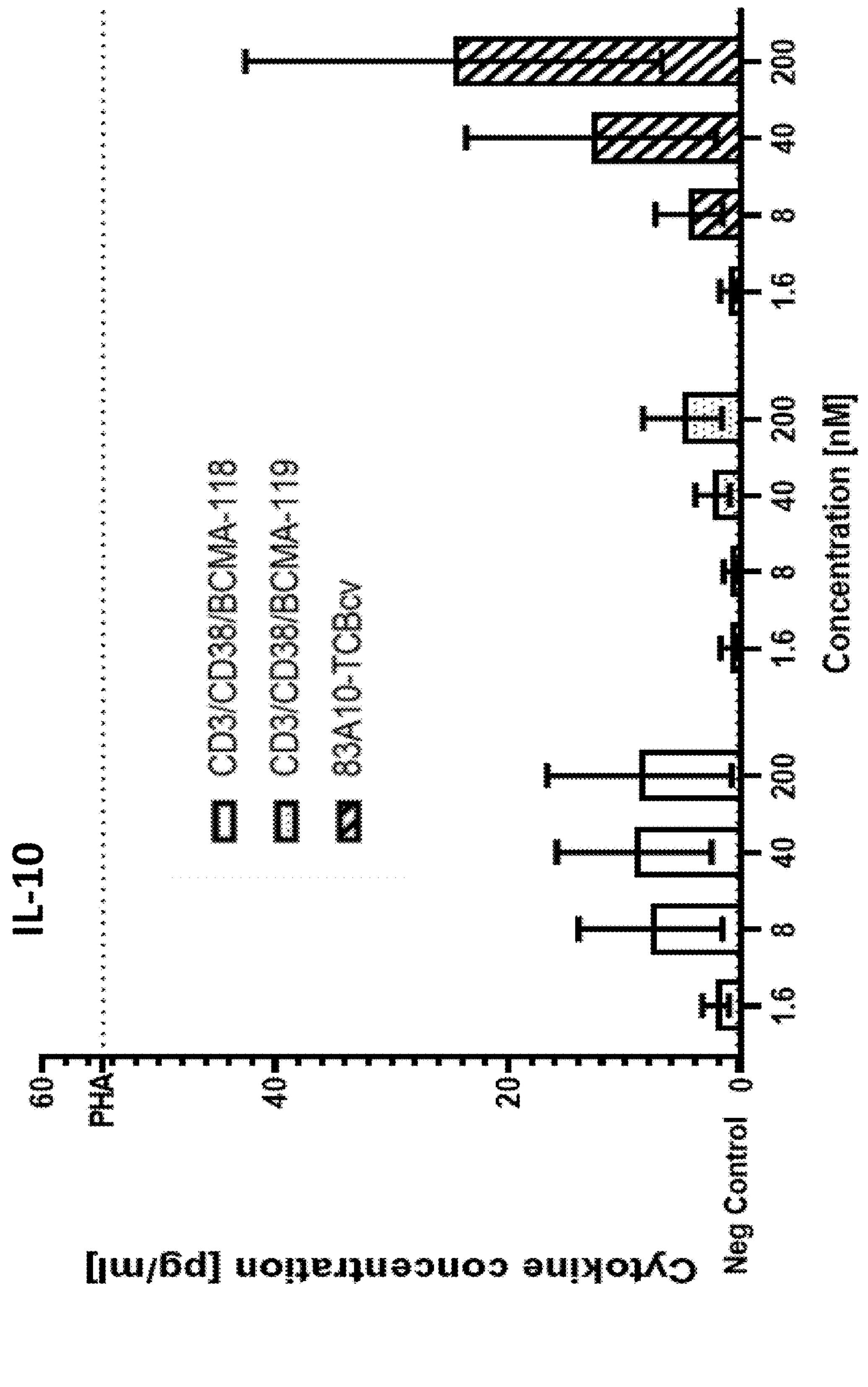

FIG. 19. CD3/BCMA/CD38 candidates induce strong T cell activation and proliferation associated with KMS-12-BM killing. The ability of CD3/BCMA/CD38 candidates and benchmarks to trigger T cell mediated killing of KMS-12-BM cells, and consequently T cell activation and proliferation, were assessed in a Redirected Lysis assay with a 5:1 Effector-to-target ratio. At endpoint, Proliferation and CD25 expression were assessed of $CD4^+$ and $CD8^+$ T cells. The figure shows $EC_{50}$ values for activation or proliferation. Each dot represents the EC50 value for one individual donor. Three independent experiments were performed for each candidate with a total of 6 donors. Means were compared using a paired One-way ANOVA followed by Tukey HSD post-hoc comparison. * stands for statistically significant compared to TNB-F2B BEAT Fc. # stands for statistically significant compared to 83A10-TCBcv+stands for statistically significant compared to BEAT CD3/CD38. Experimental setup and analysis are described in Example 18.

FIGS. 20A-20E. CD3/BCMA/CD38 candidates induce minimal cytokine release associated with on-target off-tumor activity compared to positive controls and benchmark 83A10-TCBcv. Cytokine release was evaluated in a High-Density assay. At endpoint, supernatants were stored at −80 and cytokine release was evaluated for IFN-gamma (FIG. 20A), TNF-alpha (FIG. 20B), IL-2 (FIG. 20C), IL-6 (FIG. 20D) and IL-10 (FIG. 20E) cytokines using Meso Scale Discovery (MSD) assay. Each bar is the Mean+/−Standard Deviation. A total of 4 PBMC donors were tested in two independent experiments. Dotted lines show a positive (PHA) and a negative control. Experimental setup and analysis are described in Example 18.

Figure 21A:
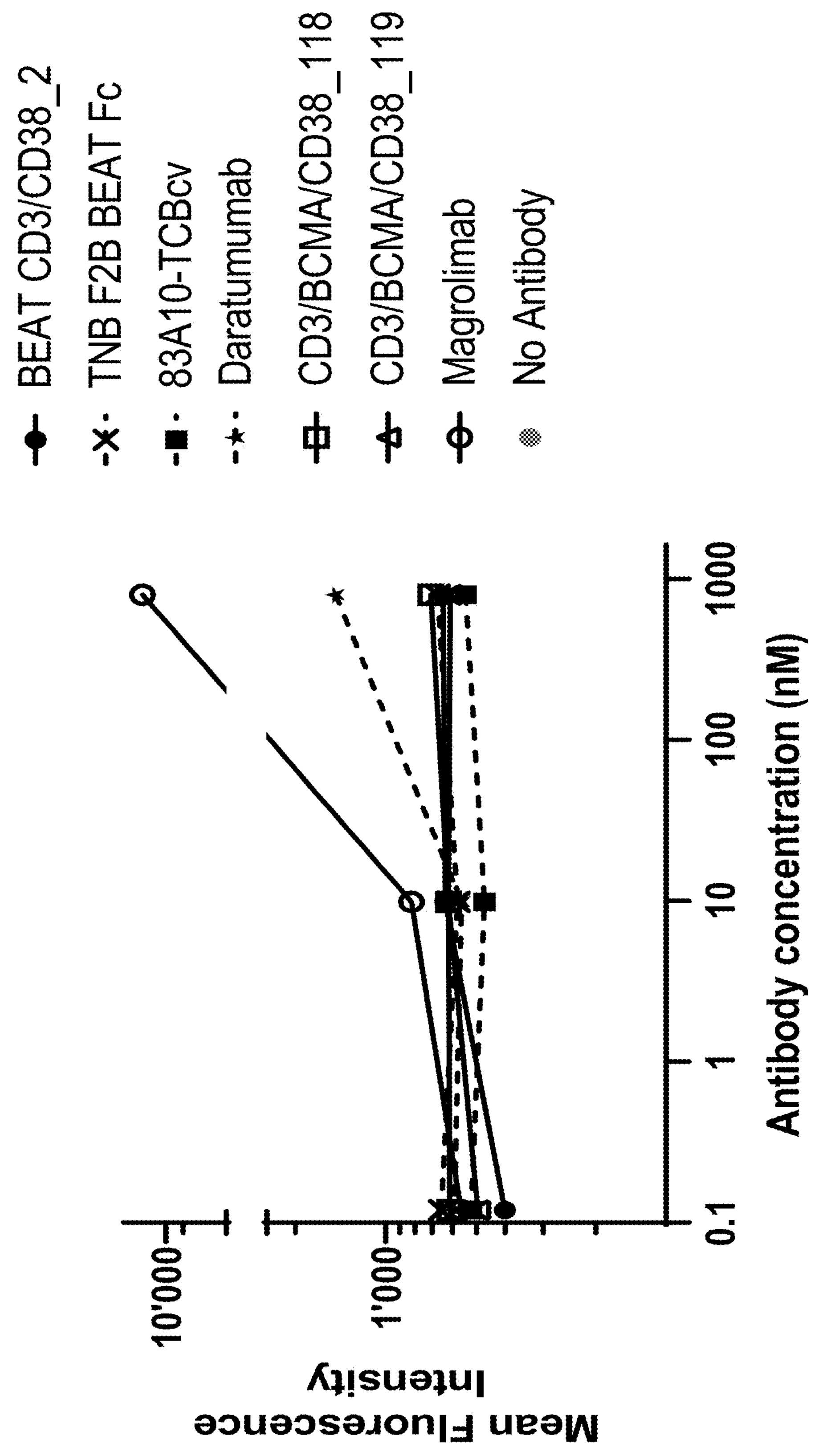
Figure 21B:
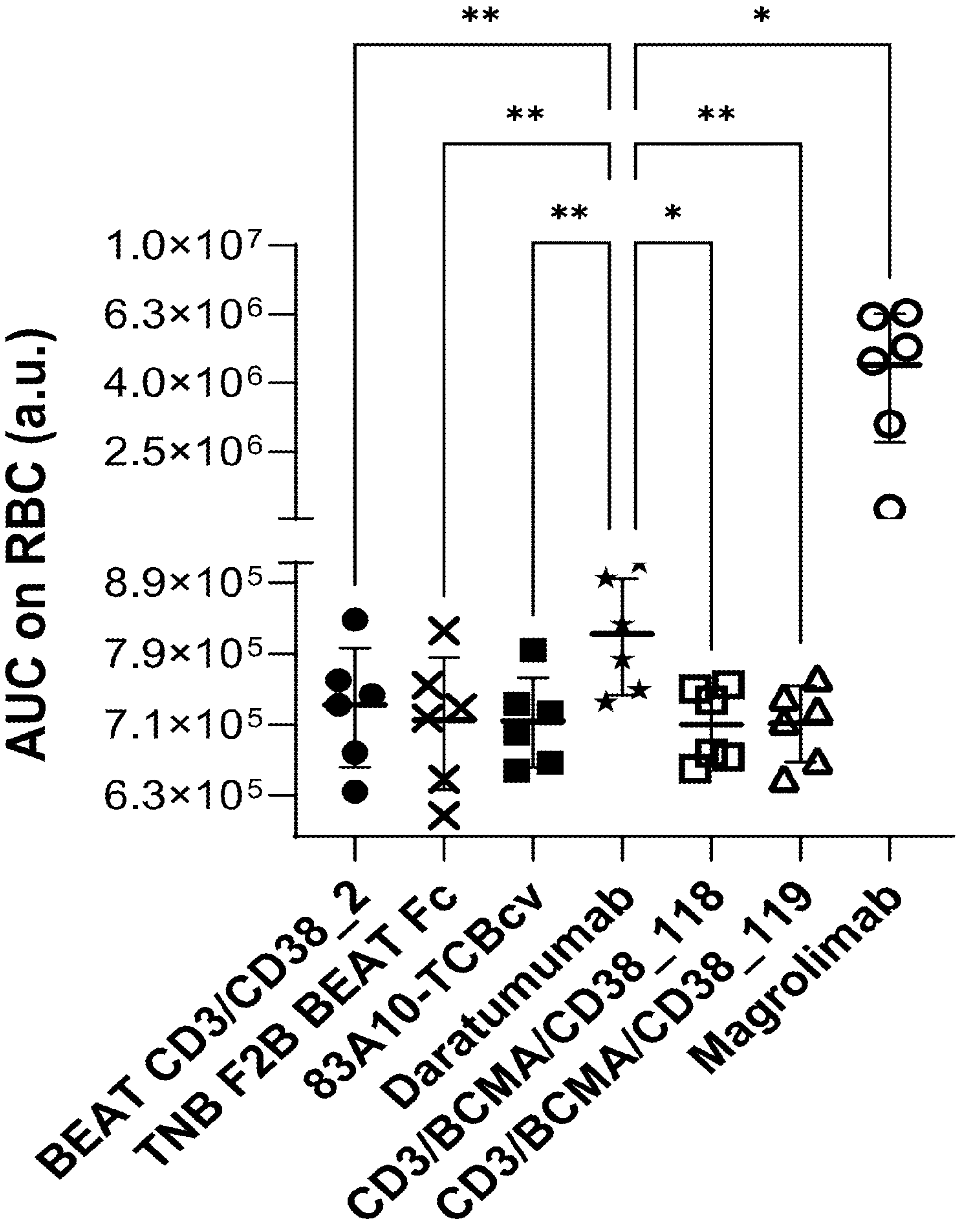

FIGS. 21A-21B. CD3/BCMA/CD38 candidates do not bind to Red Blood Cells compared to daratumumab and magrolimab. The binding of candidates CD3/BCMA/CD38 candidates and benchmarks to Red Blood Cells was evaluated by flow cytometry (FIG. 21A). Each dot represents the Area Under the Curve (AUC) of a dose response curve for each donor. Means were compared using a paired One-way ANOVA followed by Dunnett post-hoc comparison to daratumumab(*P<0.05) (FIG. 21B). Experimental setup and analysis are described in Example 18.

Figure 22:
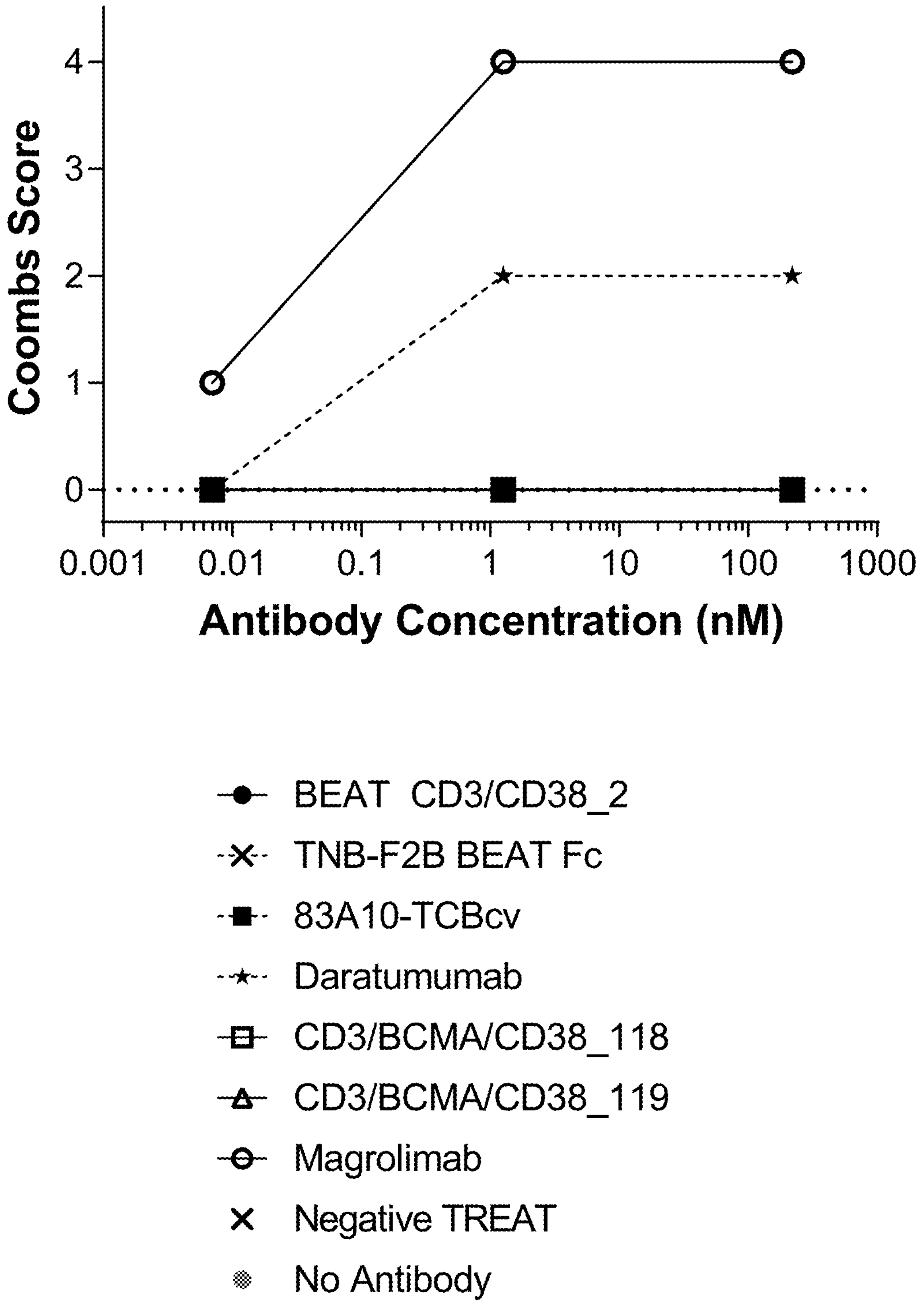

FIG. 22. CD3/BCMA/CD38 candidates do not induce hemagglutination. The propensity of candidates CD3/BCMA/CD38 candidates and benchmarks to induce hemagglutination was assessed in a Coombs assay. Each dot represents the Mean+/−Standard Deviation of Coombs for six donor. Experimental setup and analysis are described in Example 18.

Figure 23A:
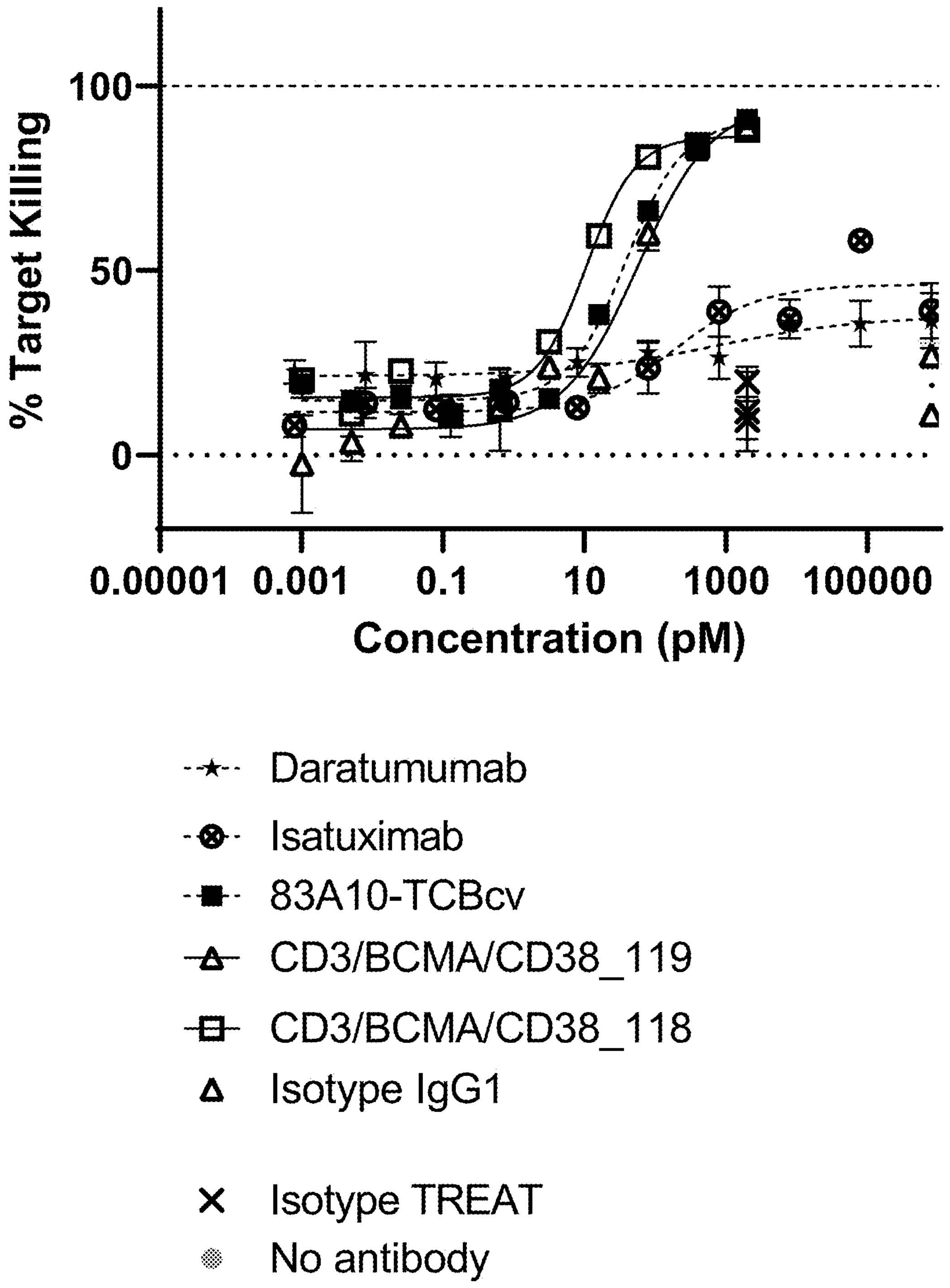
Figure 23B:
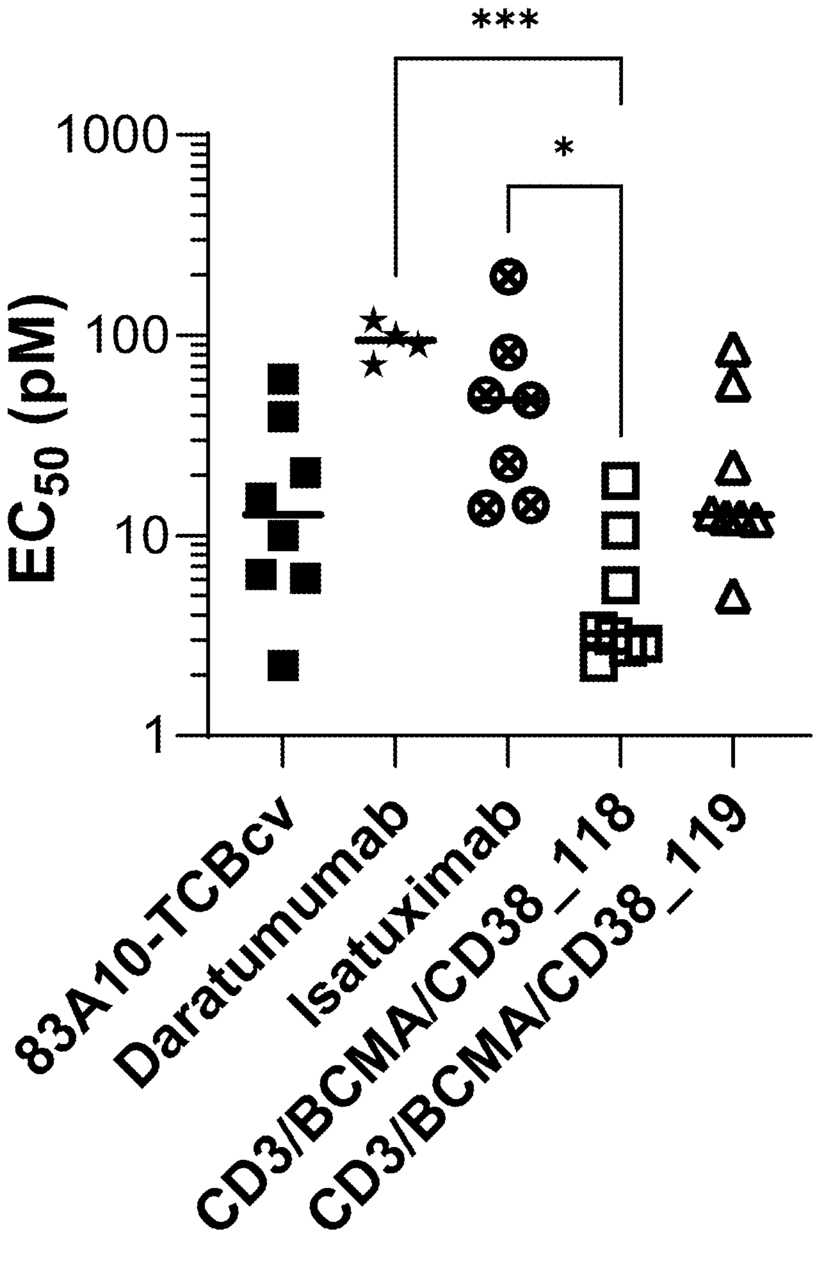
Figure 23C:
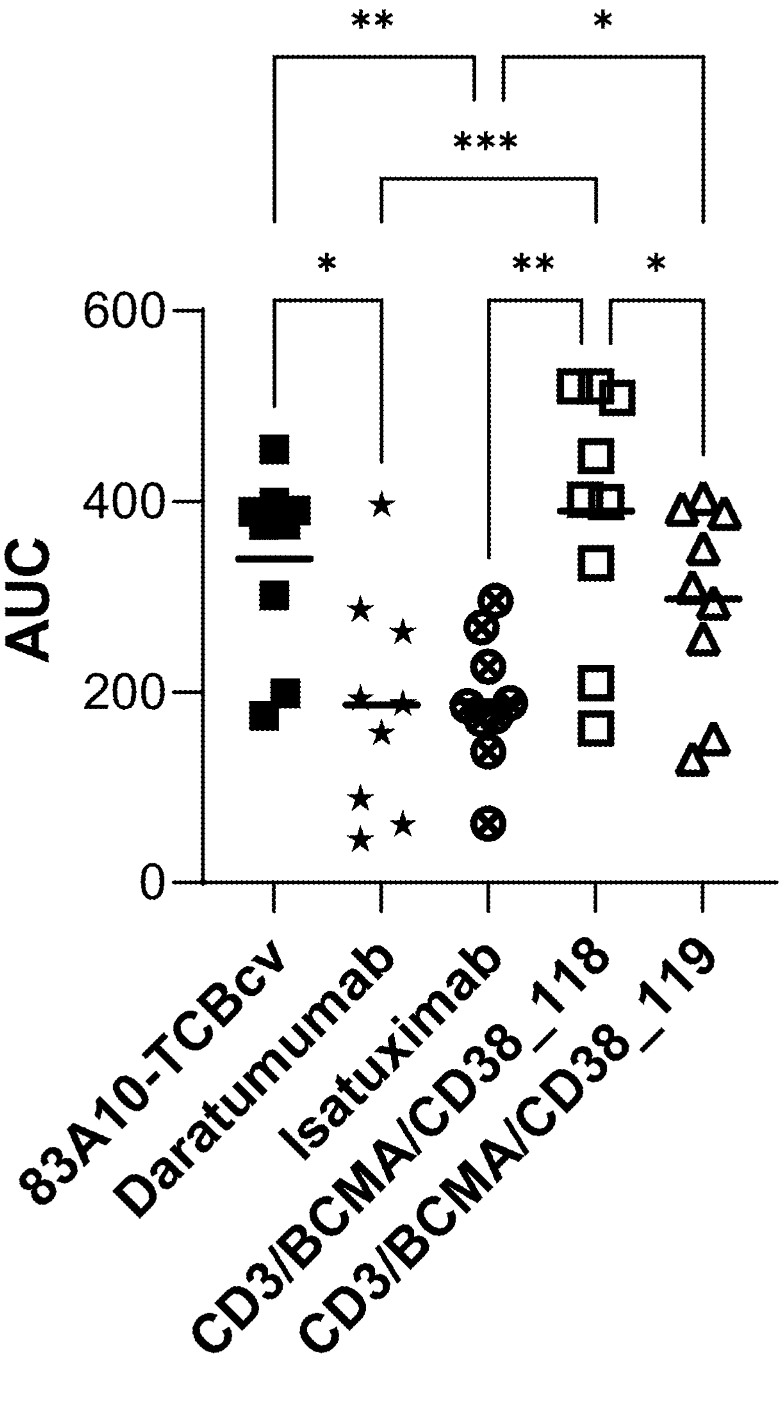

FIGS. 23A-23C. CD3/BCMA/CD38_118 shows superior killing of NCI-H929 in Multiple Modes of Action Killing compared to anti-CD38 benchmarks. The ability of CD3/BCMA/CD38 candidates and benchmarks to trigger NCI-H929 cells lysis was assessed in a Multiple Modes of Action Killing (MmoAK) assay in presence of human serum and IL-2. Each dot represents the Mean+/−Standard Error Mean of percentage of Target Killing (FIG. 23A), EC50 of killing (FIG. 23B) and the Area Under the Curve (AUC) of a dose response curve for each donor (FIG. 23C). Means (5-8 donors) were compared using Kruskal-Wallis followed by Dunn's post-hoc comparison or a paired One-way ANOVA test followed by Tukey's post-hoc comparison (*P<0.05, 0.01<P<0.05, *P<0.01). Experimental setup and analysis are described in Example 18.

Figure 24A:
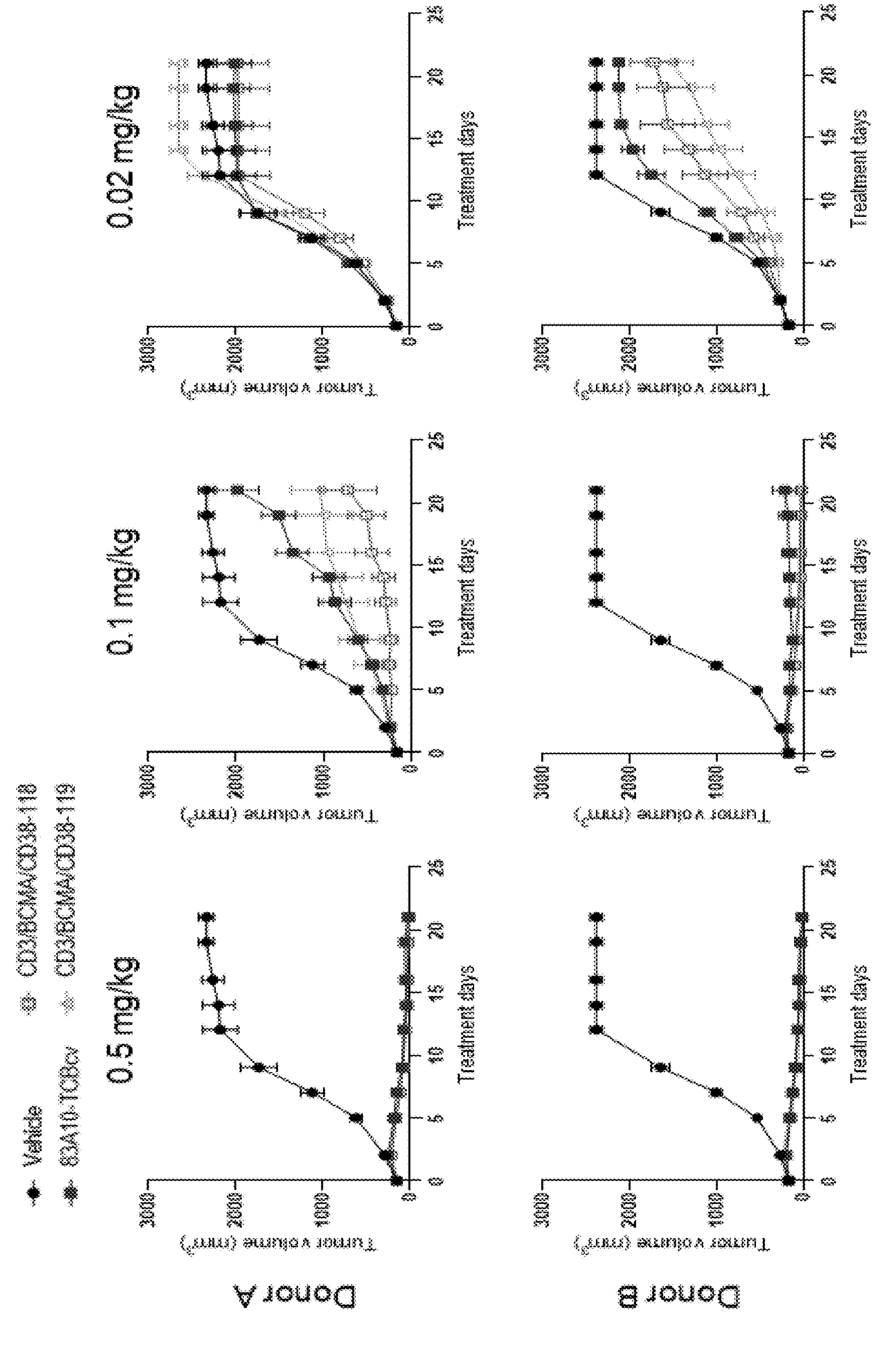
Figure 24B:
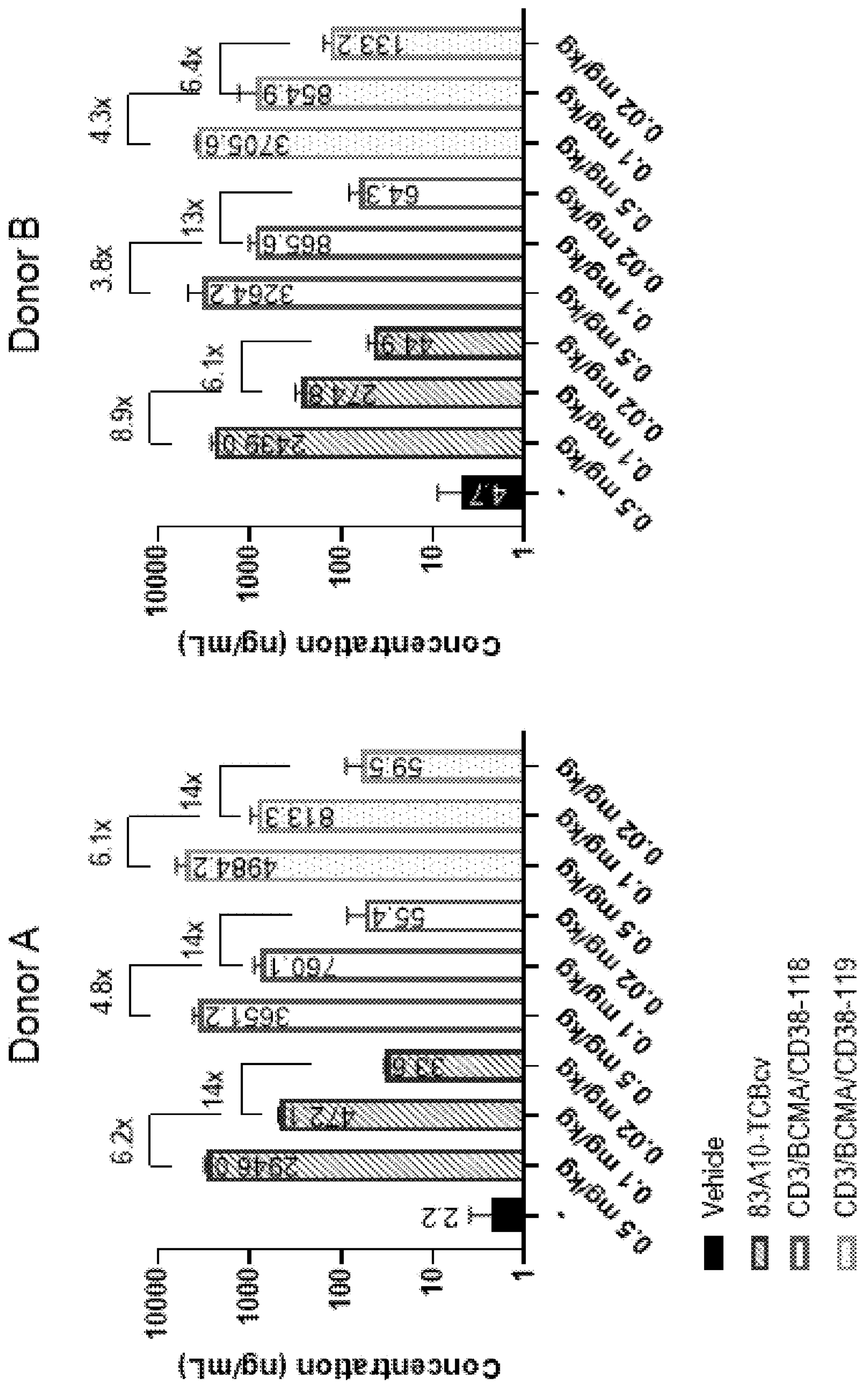

FIGS. 24A-24B. CD3/BCMA/CD38 candidates control NCI-H929 tumors in a dose dependent manner, with higher potency than benchmark 83A10-TCBcv at lower doses. NCG female mice were engrafted on day −10 s.c. with $1\times10^7$ NCI-H929 MM tumor cells (CD38++ and BCMA++) and inoculated i.p. with $1\times10^7$ PBMCs from 2 healthy human donors (Donor A: n=9 mice/group and Donor B: n=9 mice/group). Mice were randomized at day 0 when the average tumor volume reached around 150 $mm^3$ and treatments injected i.v. once per week for 3 weeks on days 0, 7 and 14. A. NCI-H929 tumor growth following treatment at 0.5 mg/kg dose (left); 0.1 mg/kg dose (middle) or 0.02 mg/kg dose (right) in NCG mice inoculated with Donor A (top) or Donor B (bottom) PBMCs (n=9 mice/group) (FIG. 24A). Mean±SEM are shown with Last Observation Carried Forward (LOCF). B. Plasma concentrations (ng/mL) of the indicated molecules at the indicated doses on day 13 or 14 post treatment (after two intravenous injections) in NCG mice inoculated with Donor A (left) or Donor B (right) PBMCs (n=3 mice/group) (FIG. 24B). Concentration of molecules was determined using a human BCMA-specific antigen capture ELISA (a method to quantify anti-BCMA human IgG). Mean±SD are shown, with values within bar representing mean concentrations and values above representing fold differences.

Figure 25A:
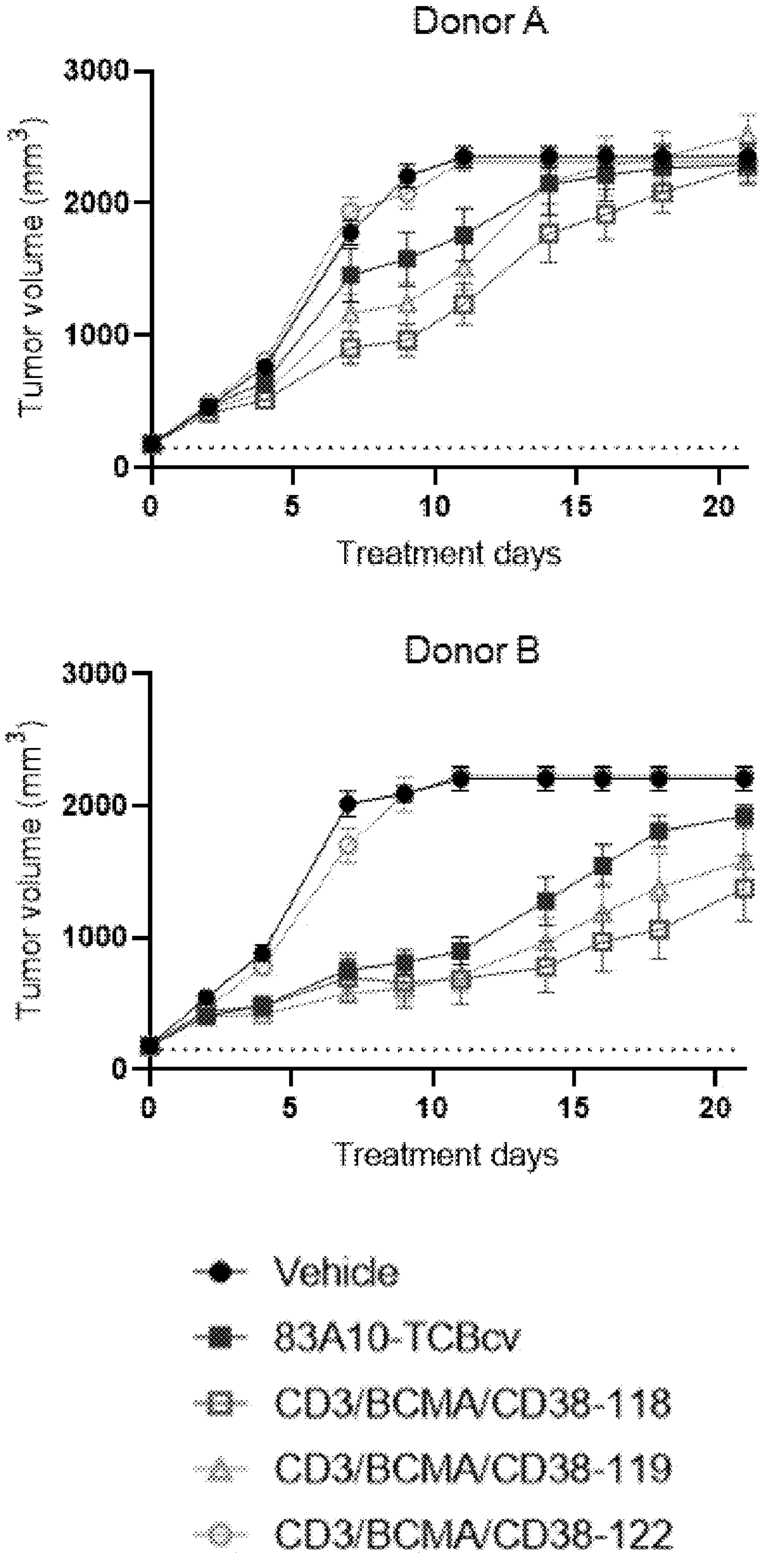
Figure 25B:
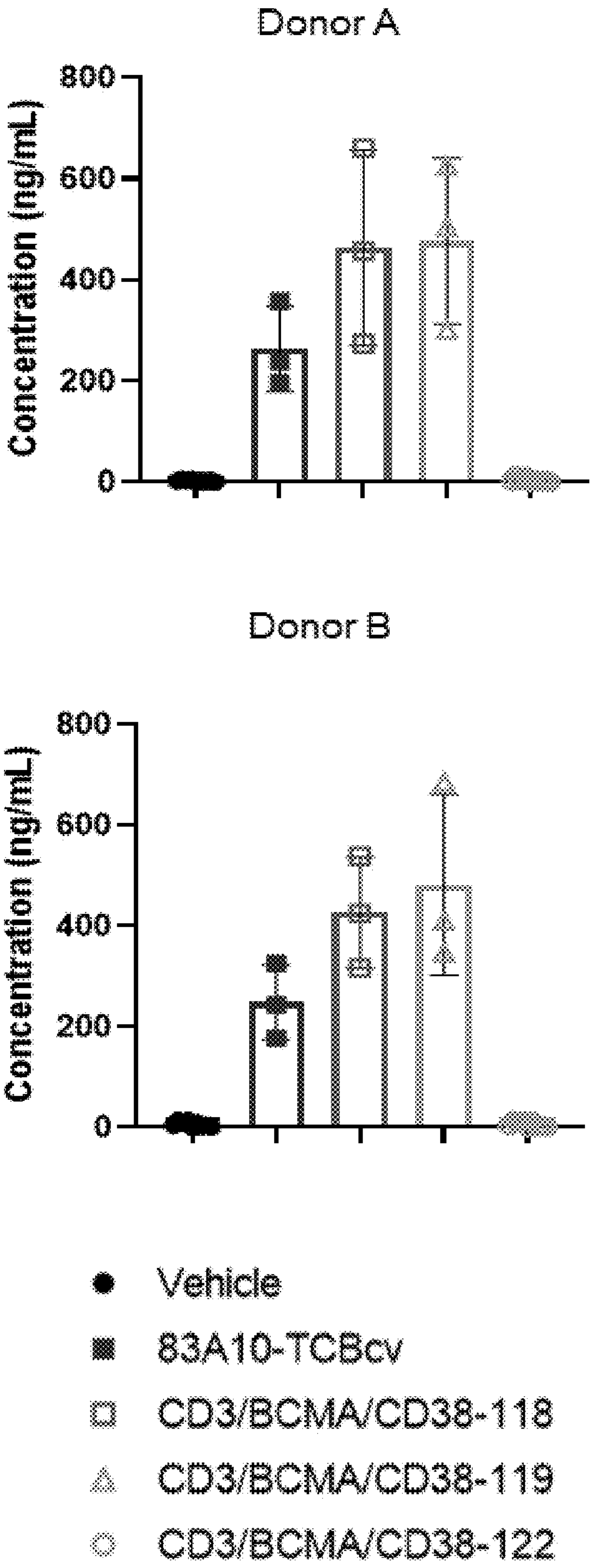

FIGS. 25A-25B. CD3/BCMA/CD38 candidates substantially delay the growth of NCI-H929 tumors at 0.1 mg/kg dosing, compared to vehicle or CD3 dummy control. NCG female mice were engrafted on day −11 s.c. with $1\times10^7$ NCI-H929 MM tumor cells (CD38++ and BCMA++) and inoculated i.p. with $1\times10^7$ PBMCs from 2 healthy human donors (Donor A: n=9 mice/group and Donor B: n=9 mice/group). Mice were randomized at day 0 when the average tumor volume reached around 180 $mm^3$ and treatments injected i.v. once per week for 3 weeks on days 0, 7 and 14. A. NCI-H929 tumor growth following treatment at 0.1 mg/kg dose in NCG mice inoculated with Donor A (top) or Donor B (bottom) PBMCs (n=9 mice/group) (FIG. 25A). Mean±SEM are shown with Last Observation Carried Forward (LOCF). B. Plasma concentrations (ng/mL) of the indicated molecules on day 10 (for vehicle and CD3/BCMA/CD38-122) or day 14 (for remaining groups) post treatment (after two intravenous injections) in NCG mice inoculated with Donor A (top) or Donor B (bottom) PBMCs (n=3 mice/group) (FIG. 25B). Concentration of molecules was determined using a human BCMA-specific antigen capture ELISA (a method to quantify anti-BCMA human IgG). Mean±SD are shown.

Figure 26A:
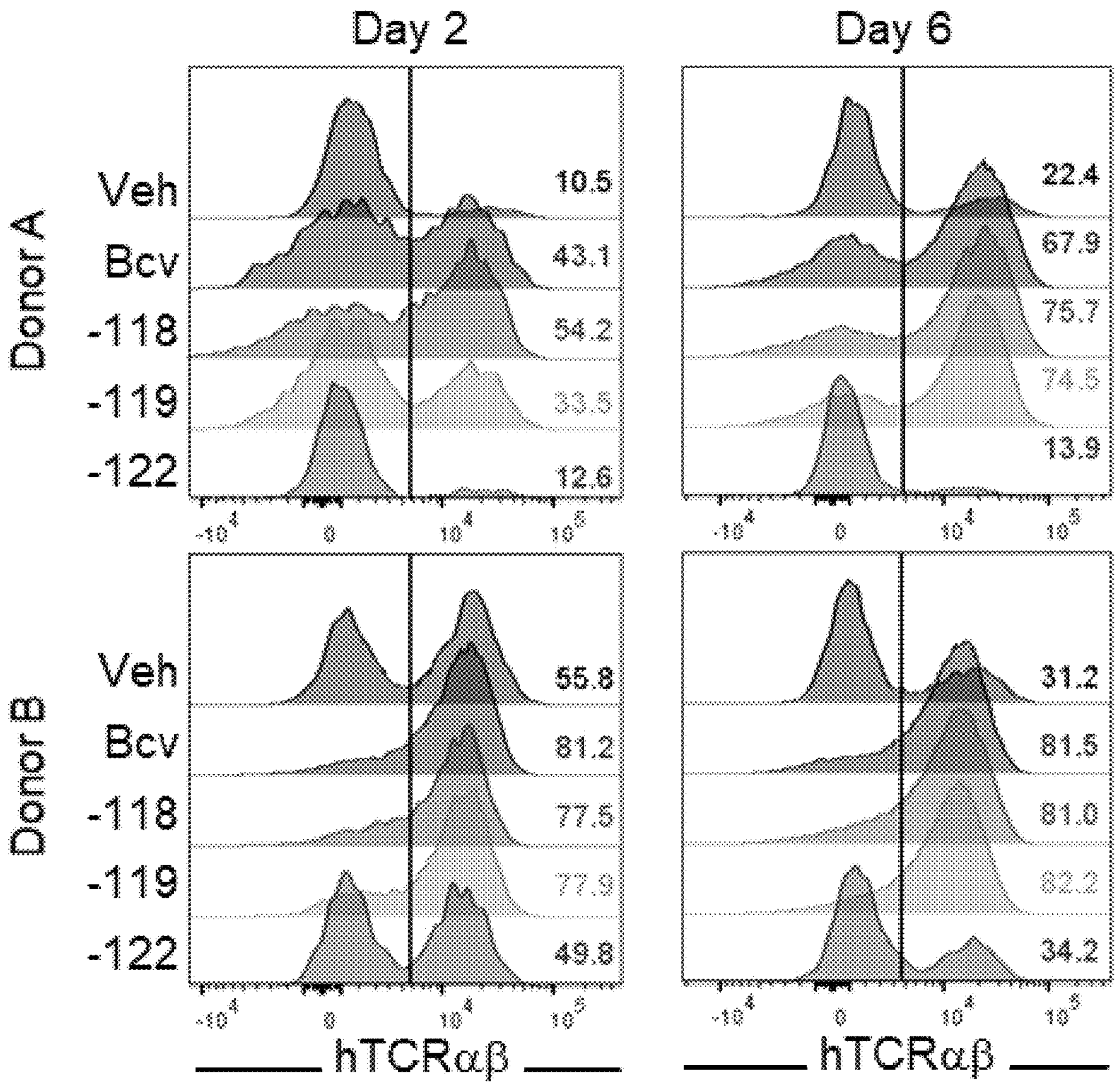
Figure 26B:
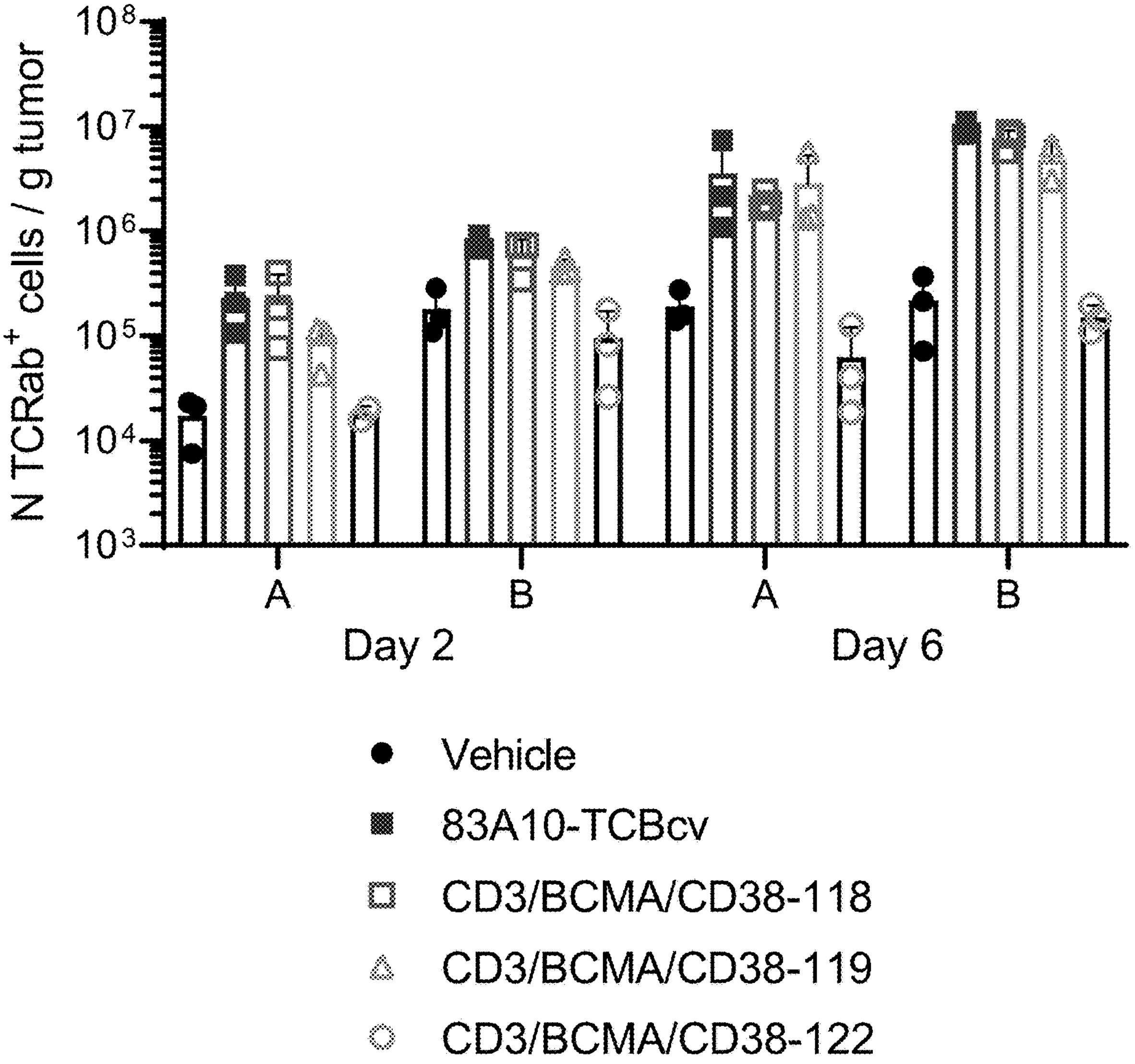
Figure 26C:
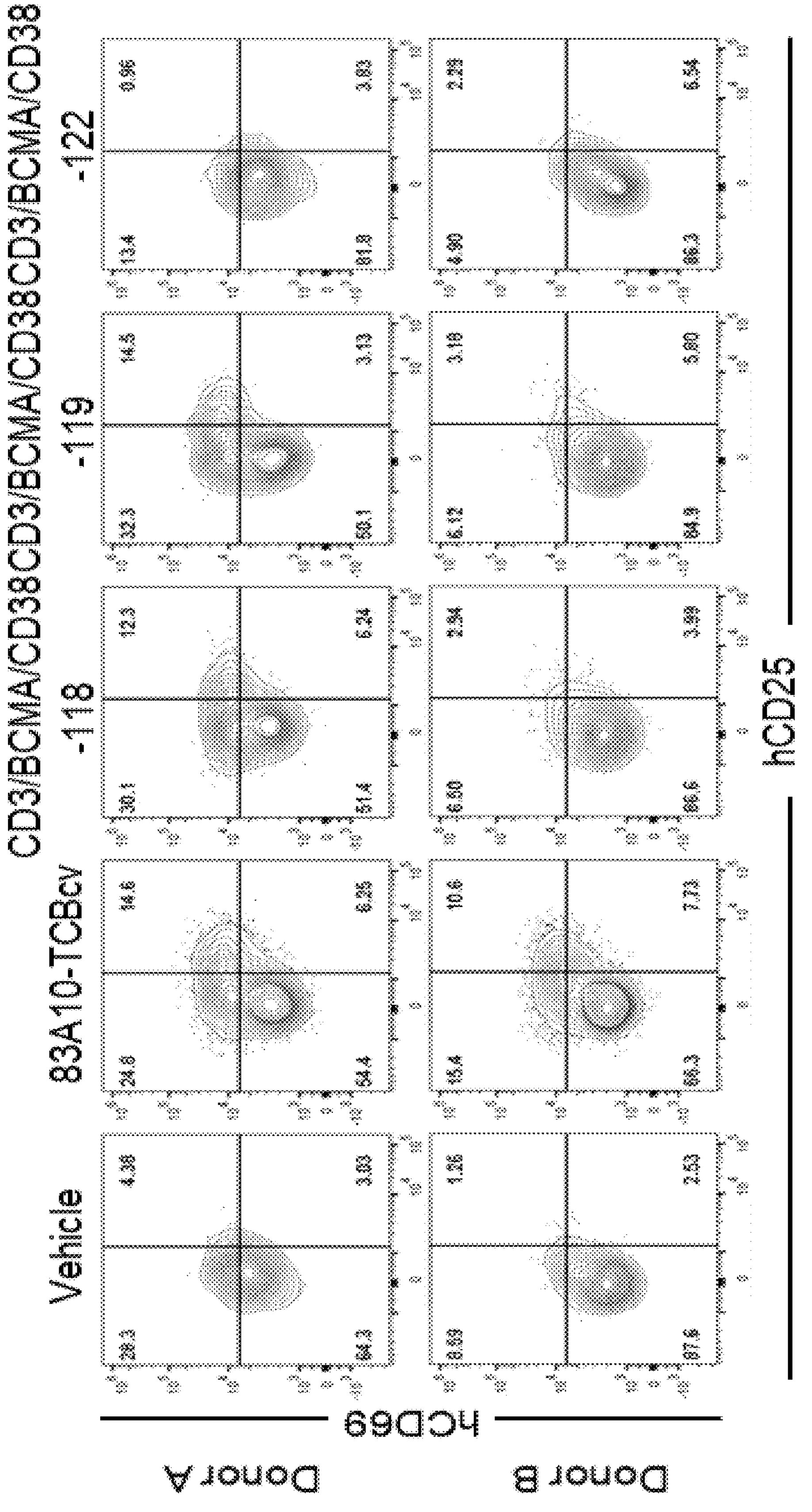
Figure 26D:
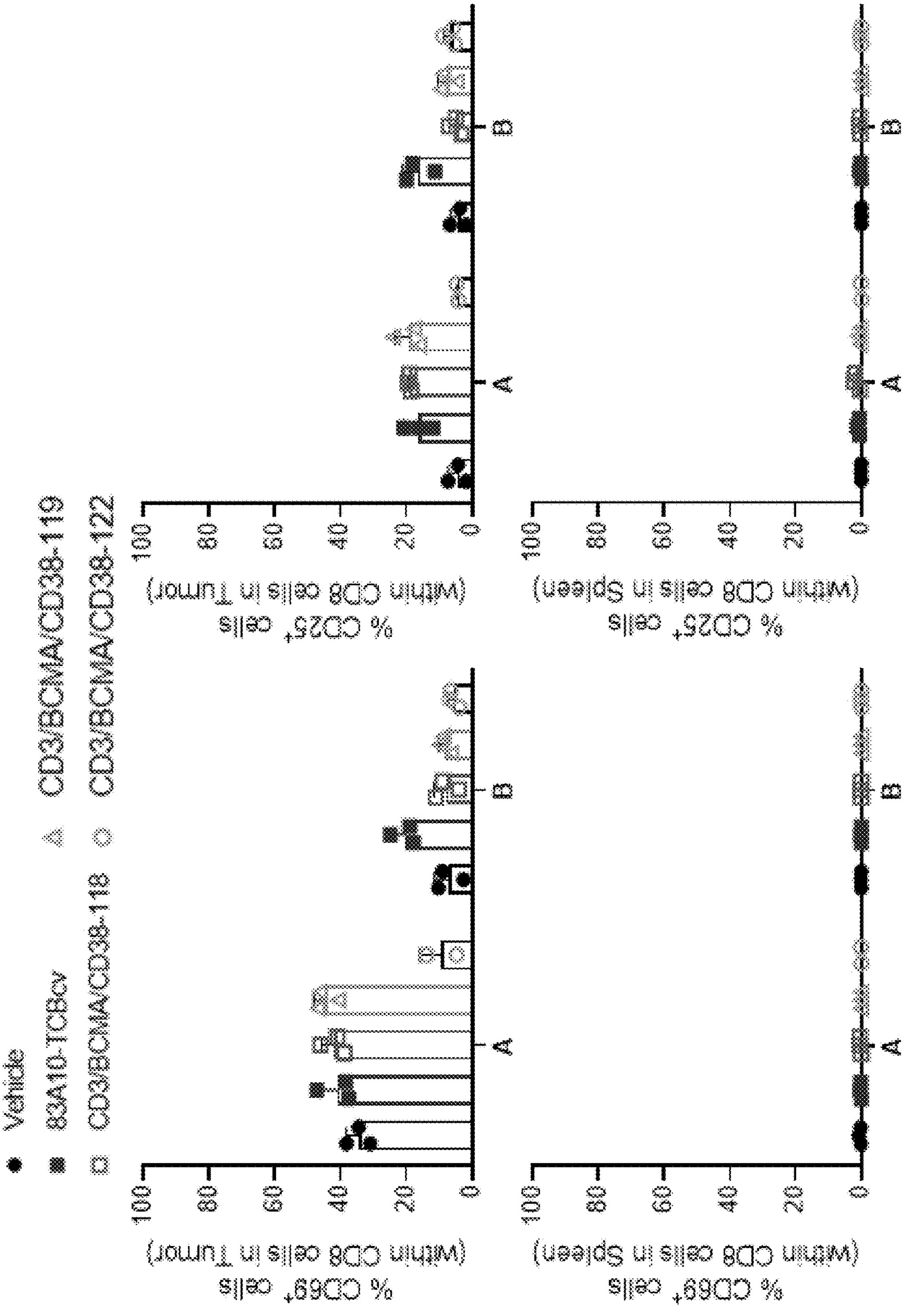

FIGS. 26A-26D. Effectiveness of CD3/BCMA/CD38-118, −119 and 83A10-TCBcv in NCI-H929 tumor control correlated with the degree of T cell infiltration within tumor microenvironment. NCG female mice engrafted with NCI-H929 MM tumor cells and inoculated i.p. with PBMCs from 2 healthy human donors (Donor A and Donor B) were treated with a single dose i.v. of molecules at 0.1 mg/kg on day 0, when the average tumor volume reached approximately 180 $mm^3$. After 2 or 6 days, tumors and spleens of treated mice were harvested and analyzed ex vivo by flow cytometry (n=2-3 mice/group/timepoint). A. Histogram plots show the expression of human TCRαβ in gated human $CD45^+$ cells on day 2 (left) and 6 (right) post single dose in the tumor (FIG. 26A). Numbers indicate the % of positive cells. Legend from top to bottom: Vehicle, 83A10-TCBcv, CD3/BCMA/CD38-118, CD3/BCMA/CD38-119, CD3/BCMA/CD38-122. B. Graph depicts number of human TCRαβ cells per gram of tumor at the indicated day and PBMC donor (FIG. 26B). Mean±SD are shown. C. Contour plots show the expression of human CD69 vs human CD25 in tumor infiltrating CD8+ T cells at day 2 post dosing with the indicated molecules (FIG. 26C). Numbers within plots indicate percentages. D. Graphs show the % of human CD69 (left) and human CD25 (right) positive CD8 T cells in the tumor (top) and in the spleen (bottom) at day 2 post single dose (FIG. 26D). Mean±SD are shown.

Figure 27:
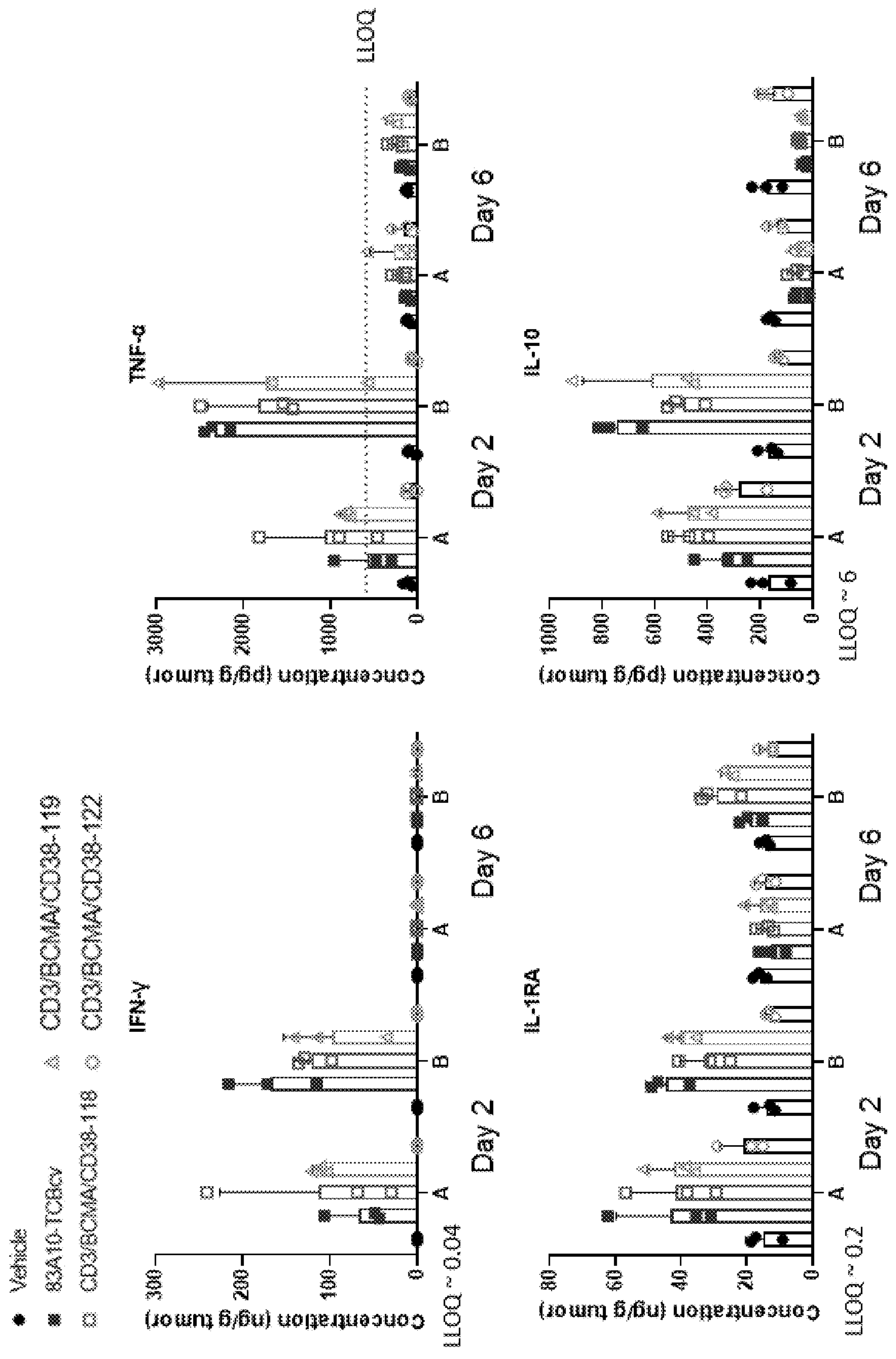

FIG. 27. CD3/BCMA/CD38 candidates induce secretion of human inflammatory cytokines in the tumor microenvironment. NCG female mice engrafted with NCI-H929 MM tumor cells and inoculated i.p. with PBMCs from 2 healthy human donors (Donor A and Donor B) were treated with a single dose i.v. of molecules at 0.1 mg/kg on day 0, when the average tumor volume reached around 180 mm3. After 2 or 6 days, tumors of treated mice were harvested, and tumor supernatant was recovered. Cytokine detection analysis was performed on tumor supernatant using Luminex with a Cytokine & Chemokine 34-Plex Human Kit (n=2-3 mice/group/timepoint). Graphs display the concentration of the indicated cytokine in the tumor supernatant normalized per gram of tumor at day 2 or 6 post dosing with the indicated molecules. Mean±SD are shown.

Figure 28A:
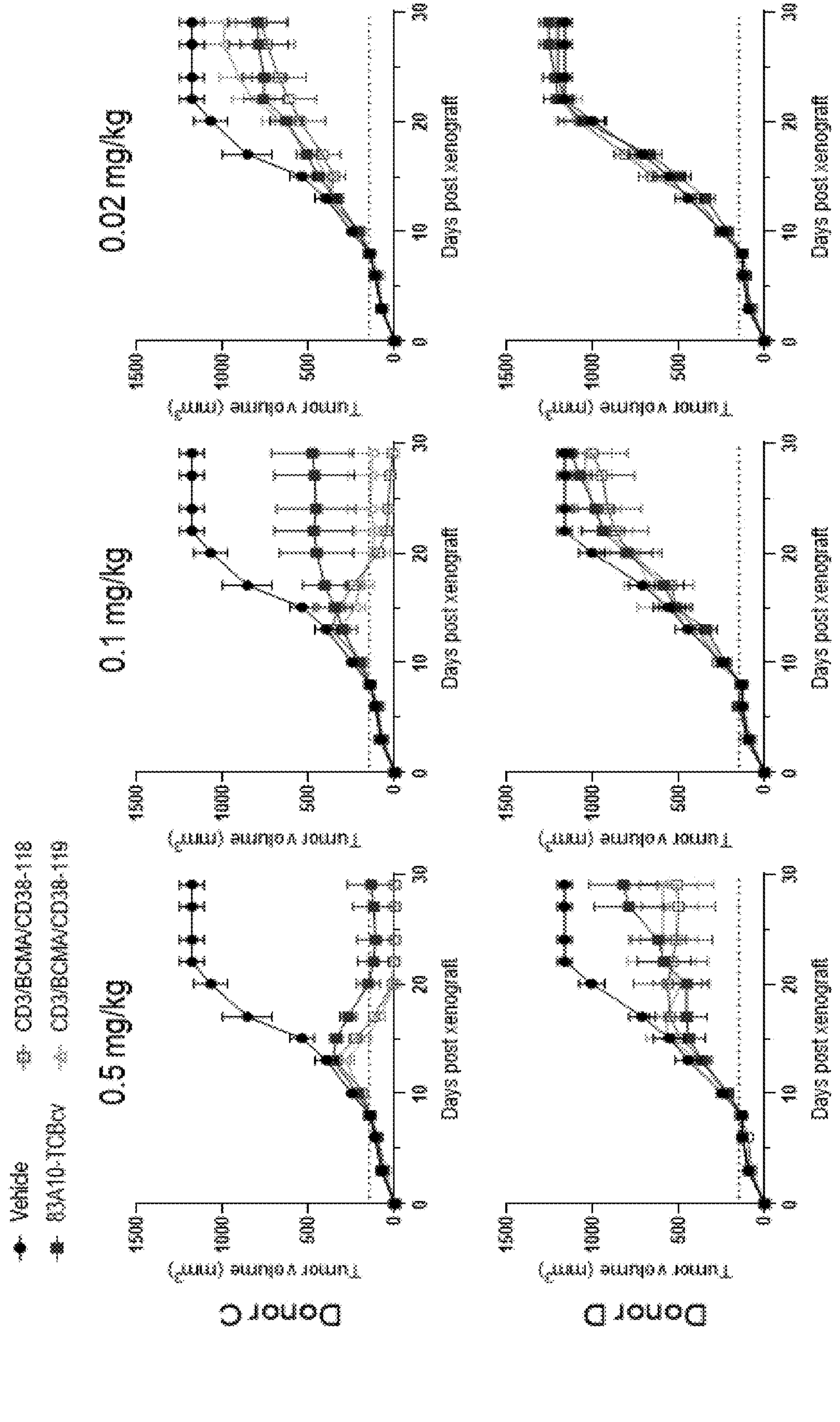
Figure 28B:
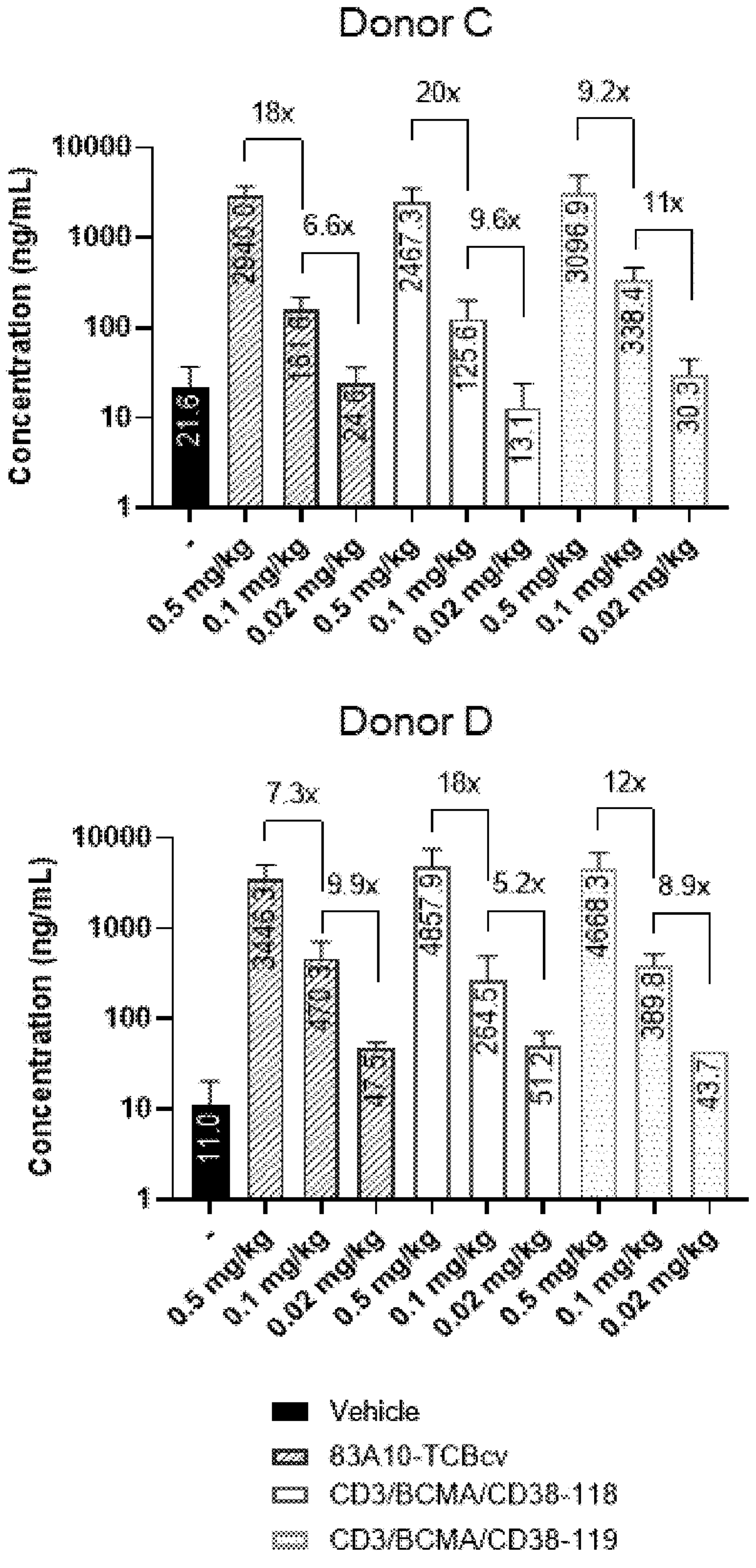

FIGS. 28A-28B. CD3/BCMA/CD38 candidates are at least equally potent to 83A10-TCBcv in the control of BCMAlow CD38low KMS-12-BM tumors. NSG female mice were engrafted on day 0 s.c. with $1\times10^7$ KMS-12-BM MM tumor cells (CD38low and BCMAlow) and inoculated i.p. with $1\times10^7$ PBMCs from 2 healthy human donors (Donor C: n=8 mice/group and Donor D: n=8 mice/group). Mice were randomized at day 8 when the average tumor volume reached around 150 $mm^3$ and treatments injected i.v.

once per week for 3 weeks on days 9, 16 and 23. A. KMS-12-BM tumor growth following treatment at 0.5 mg/kg dose (left); 0.1 mg/kg dose (middle) or 0.02 mg/kg dose (right) in NSG mice inoculated with Donor C (top) or Donor D (bottom) PBMCs (n=8 mice/group) (FIG. 28A). Mean±SEM are shown with Last Observation Carried Forward (LOCF). B. Serum concentrations (ng/mL) of the indicated molecules at the indicated doses on day 23 or 30 post treatment (at through exposure, either prior $3^{rd}$ dose (day 23) or one week later) in NSG mice inoculated with Donor C (top) or Donor D (bottom) PBMCs (n=3-6 mice/group) (FIG. 28B). Concentration of molecules was determined using a human BCMA-specific antigen capture ELISA (a method to quantify anti-BCMA human IgG). Mean±SD are shown, with values within bar representing mean concentrations and values above representing fold differences.

Figure 29A:
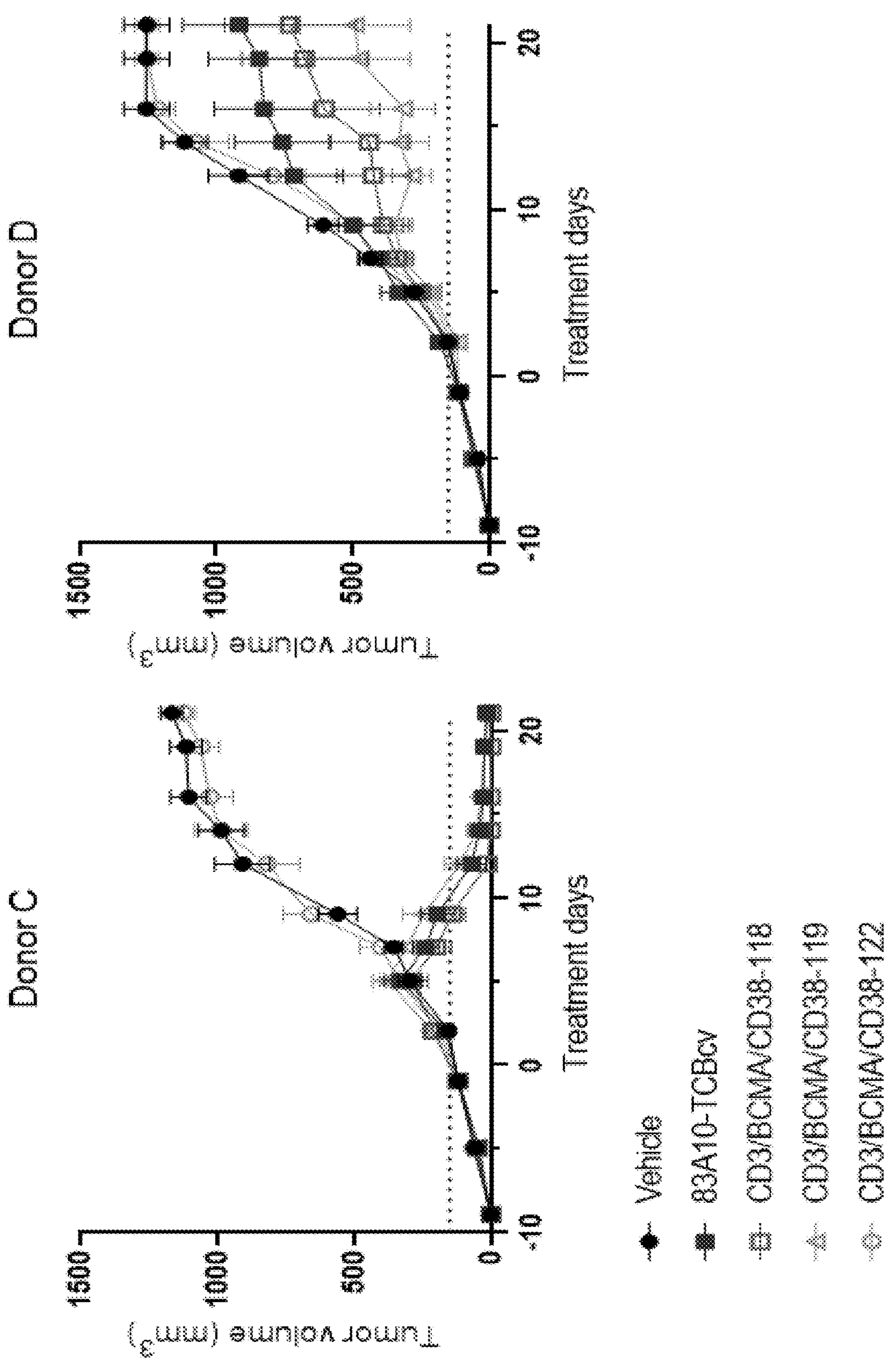
Figure 29B:
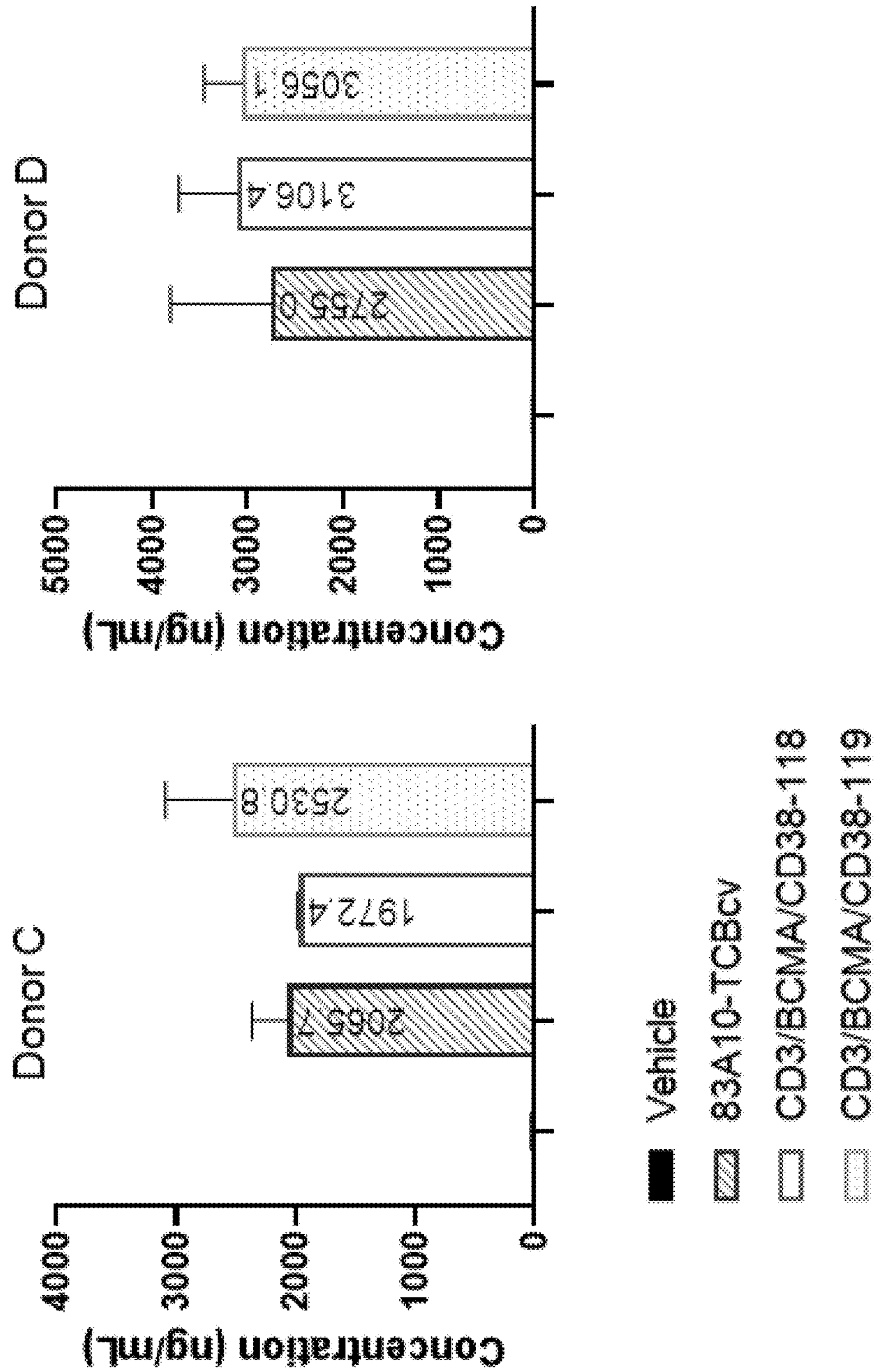

FIGS. 29A-29B. Treatment with CD3/BCMA/CD38 candidates at 0.5 mg/kg leads to complete KMS-12-BM tumor regression for one PBMC donor. NSG female mice were engrafted on day −9 s.c. with $1\times10^7$ KMS-12-BM MM tumor cells (CD38low and BCMAlow) and inoculated i.p. with $1\times10^7$ PBMCs from 2 healthy human donors (Donor C: n=8 mice/group and Donor D: n=8 mice/group). Mice were randomized at day −1 when the average tumor volume reached around 120 mm3 and treatments injected i.v. once per week for 3 weeks on days 0, 7 and 14. A. KMS-12-BM tumor growth following treatment at 0.5 mg/kg dose in NSG mice inoculated with Donor C (left) or Donor D (right) PBMCs (n=8 mice/group) (FIG. 29A). Mean±SEM are shown with Last Observation Carried Forward (LOCF). B. Serum concentrations (ng/mL) of the indicated molecules on day 6 post treatment (after one intravenous injection) in NSG mice inoculated with Donor C (left) or Donor D (right) PBMCs (n=3-4 mice/group) (FIG. 29B). Concentration of molecules was determined using a human BCMA-specific antigen capture ELISA (a method to quantify anti-BCMA human IgG). Mean±SD are shown, with values within bar representing mean concentrations.

Figure 30A:
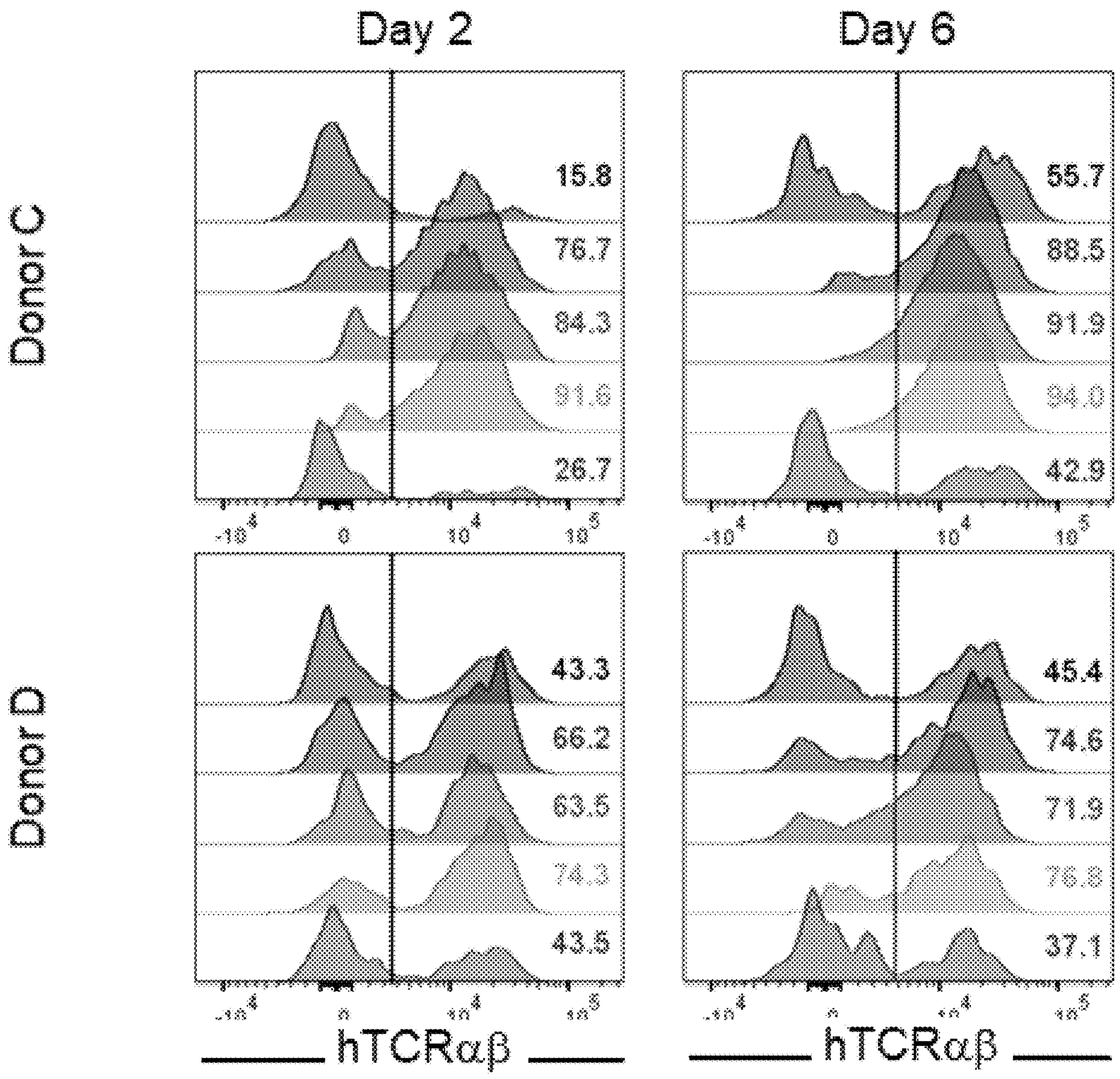
Figure 30B:
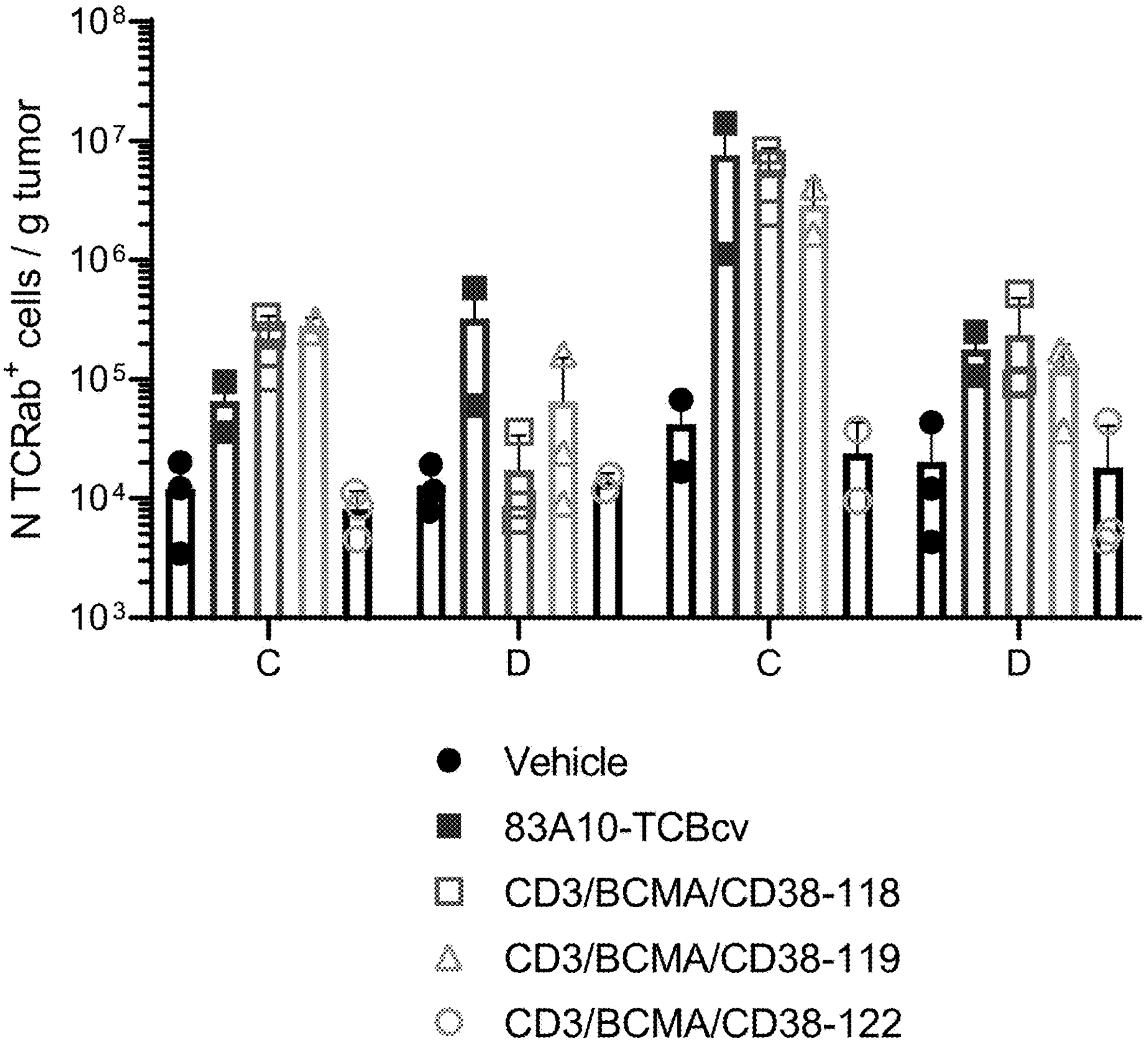
Figure 30C:
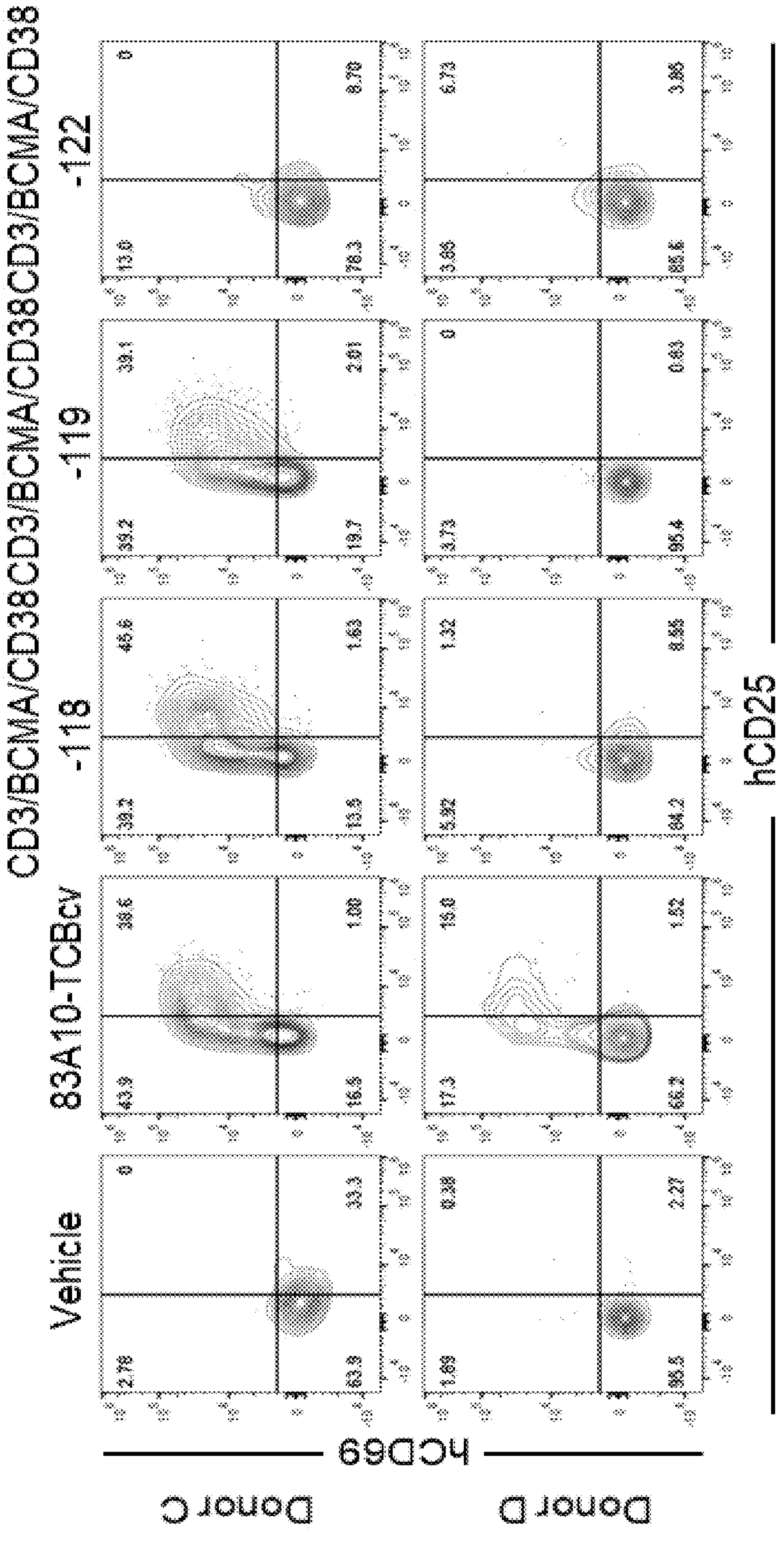
Figure 30D:
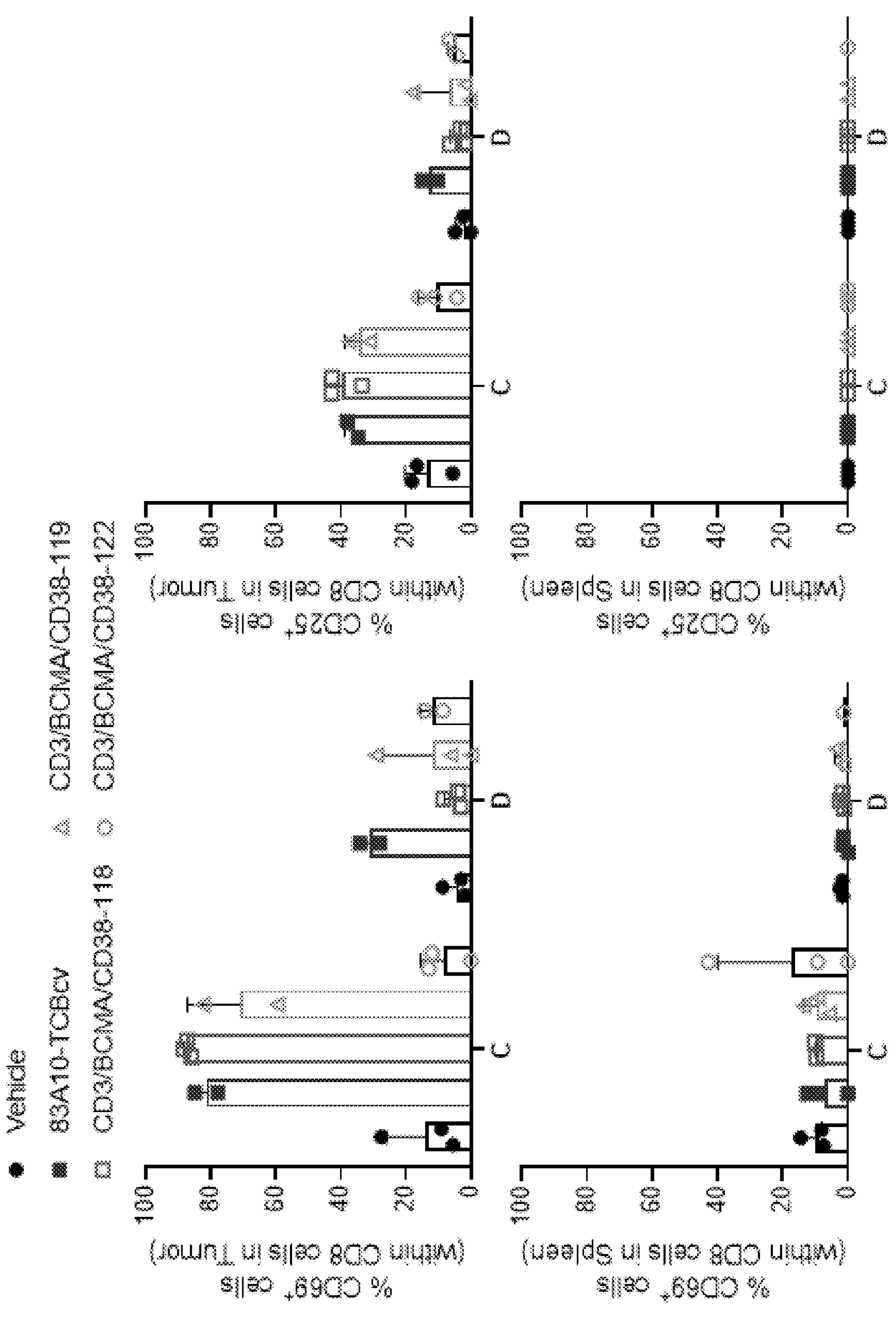

FIGS. 30A-30D. Treatment efficacy of CD3/BCMA/CD38 candidates correlated with the degree of T cell infiltration and activation status within tumor microenvironment. NSG female mice engrafted with KMS-12-BM MM tumor cells and inoculated i.p. with PBMCs from 2 healthy human donors (Donor C and Donor D) were treated with a single dose i.v. of molecules at 0.5 mg/kg on day 0, when the average tumor volume reached around 120 $mm^3$. After 2 or 6 days, tumors and spleens of treated mice were harvested and analyzed ex vivo by flow cytometry (n=2-3 mice/group/timepoint). A. Histogram plots show the expression of human TCRαβ in gated human $CD45^+$ cells on day 2 (left) and 6 (right) post single dose in the tumor (FIG. 30A). Numbers indicate the % of positive cells. Legend from top to bottom: Vehicle, 83A10-TCBcv, CD3/BCMA/CD38-118, CD3/BCMA/CD38-119, CD3/BCMA/CD38-122. B. Graph depicts number of human TCRαβ cells per gram of tumor at the indicated day and PBMC donor (FIG. 30B). Mean±SD are shown. C. Contour plots show the expression of human CD69 vs human CD25 in tumor infiltrating CD8*T cells at day 2 post dosing with the indicated molecules (FIG. 30C). Numbers within plots indicate percentages. D. Graphs show the % of human CD69 (left) and human CD25 (right) positive CD8 T cells in the tumor (top) and in the spleen (bottom) at day 2 post single dose (FIG. 30D). Mean±SD are shown.

Figure 31:
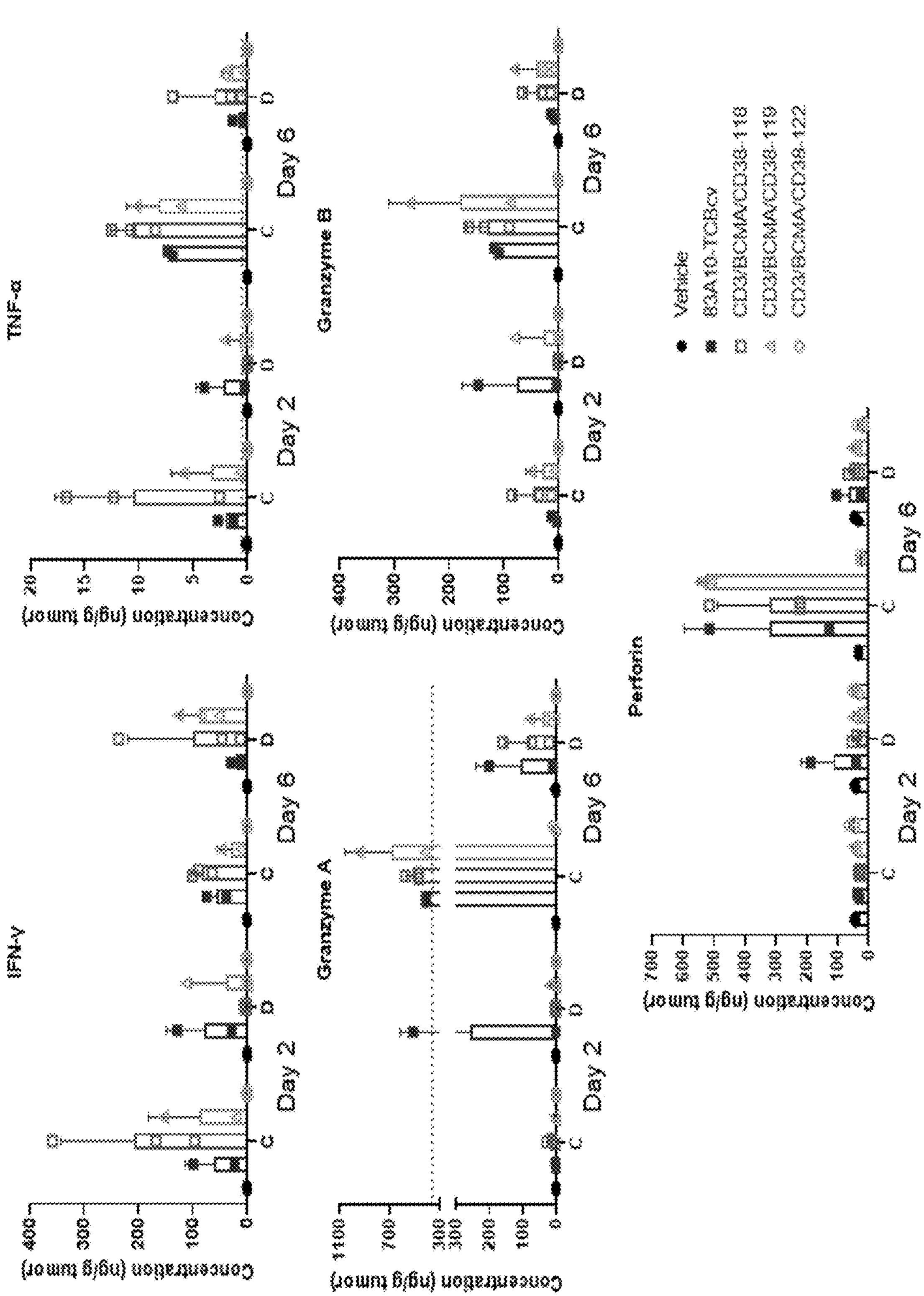

FIG. 31. CD3/BCMA/CD38 candidates induce secretion of human cytotoxic cytokines in the tumor microenvironment. NSG female mice engrafted with KMS-12-BM MM tumor cells and inoculated i.p. with PBMCs from 2 healthy human donors (Donor C and Donor D) were treated with a single dose i.v. of molecules at 0.5 mg/kg on day 0, when the average tumor volume reached around 120 $mm^3$. After 2 or 6 days, tumors of treated mice were harvested, and tumor supernatant was recovered. Cytokine detection analysis was performed on tumor supernatant using Luminex with a Cytokine & Chemokine 34-Plex Human Kit (n=2-3 mice/group/timepoint). Graphs display the concentration (in ng) of the indicated cytokine in the tumor supernatant normalized per gram of tumor at day 2 or 6 post dosing with the indicated molecules. Mean±SD are shown.

Figure 32:
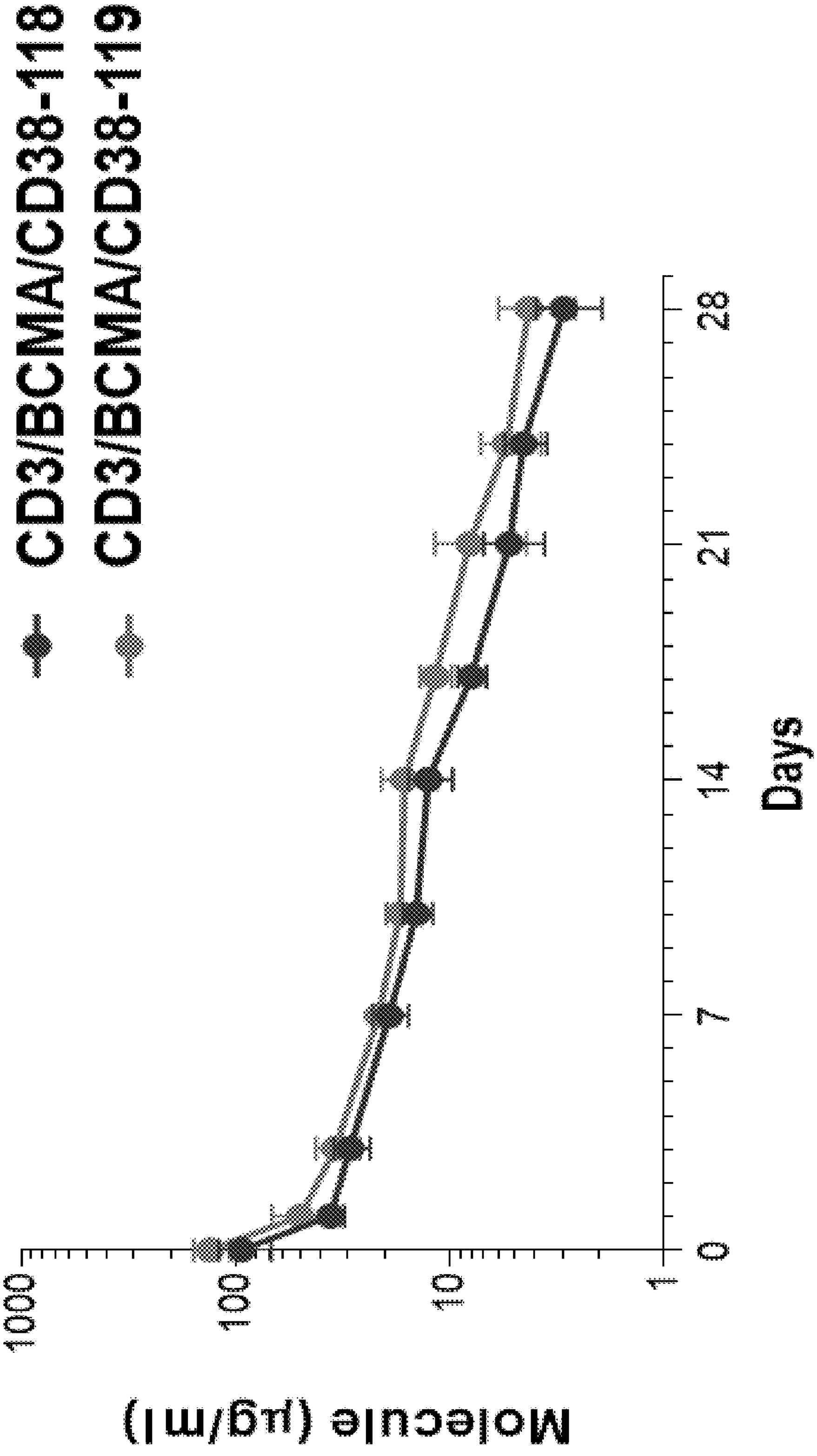

FIG. 32. Pharmacokinetic evaluation of CD3/BCMA/CD38-118 and CD3/BCMA/CD38-119 in TG32 SCID mice. TG32 SCID mice were injected IV with a single dose of CD3/BCMA/CD38-118 and CD3/BCMA/CD38-119 at 5 mg/kg and plasma evaluated for TREAT concentration. Data are plotted as mean+/−SD of 6 mice.

Figure 33:
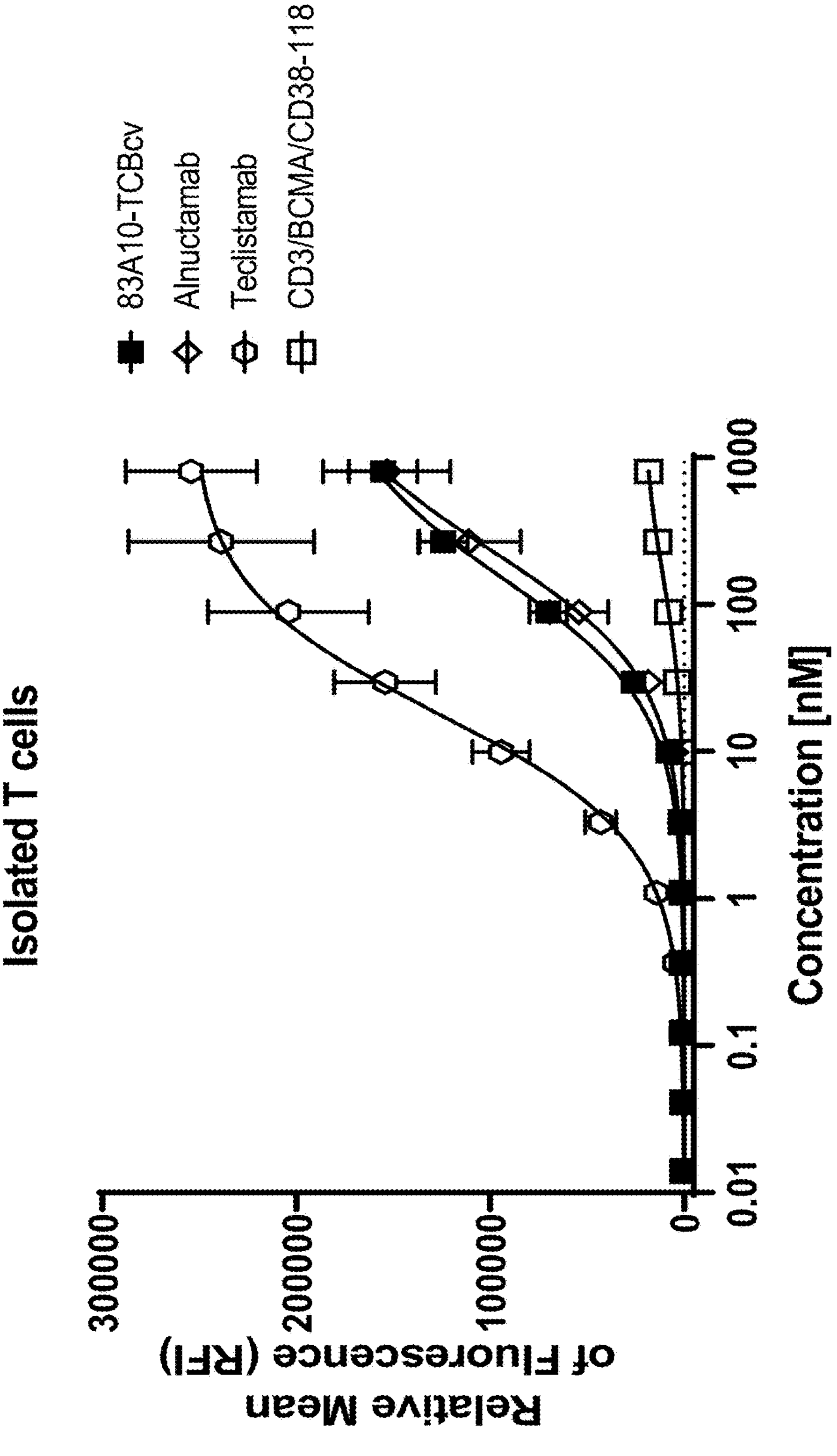

FIG. 33. CD3/BCMA/CD38-118 binds to CD3-expressing T cells. The binding of CD3/BCMA/CD38-118 and CD3×BCMA benchmarks 83A10-TCBcv, alnuctamab and teclistamab, was evaluated by flow cytometry on isolated human T cells. Each point is the mean+/−standard deviation of five to six donors from two individual experiments. Experimental setup and analysis are described in Example 22.

Figure 34A:
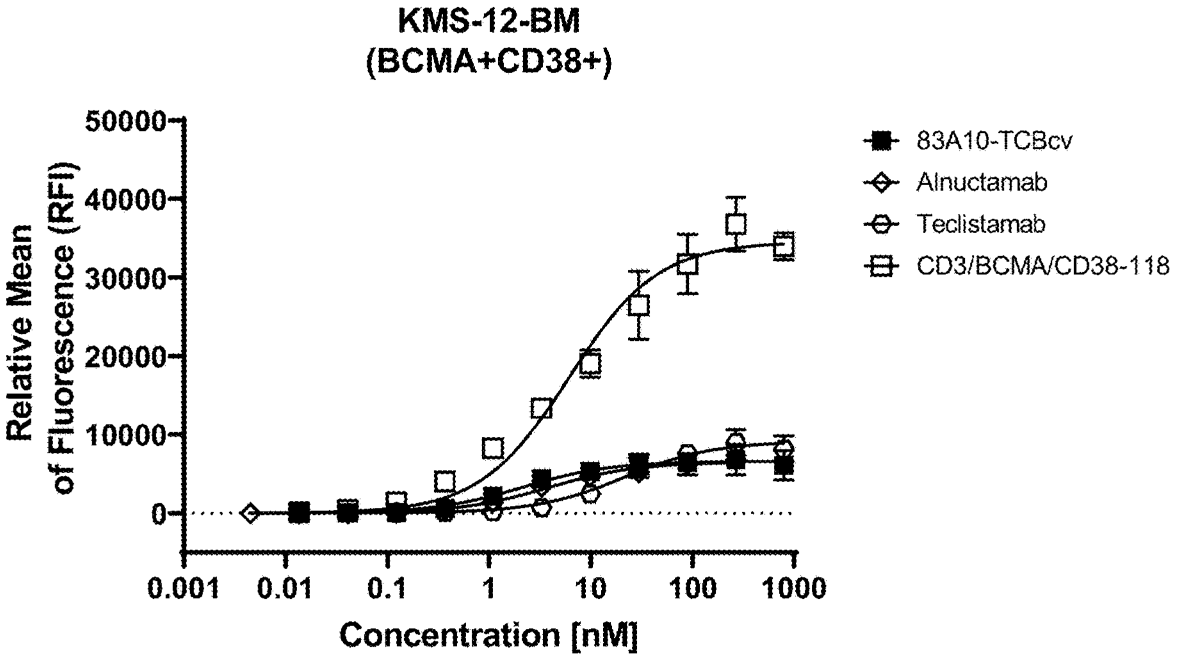
Figure 34B:
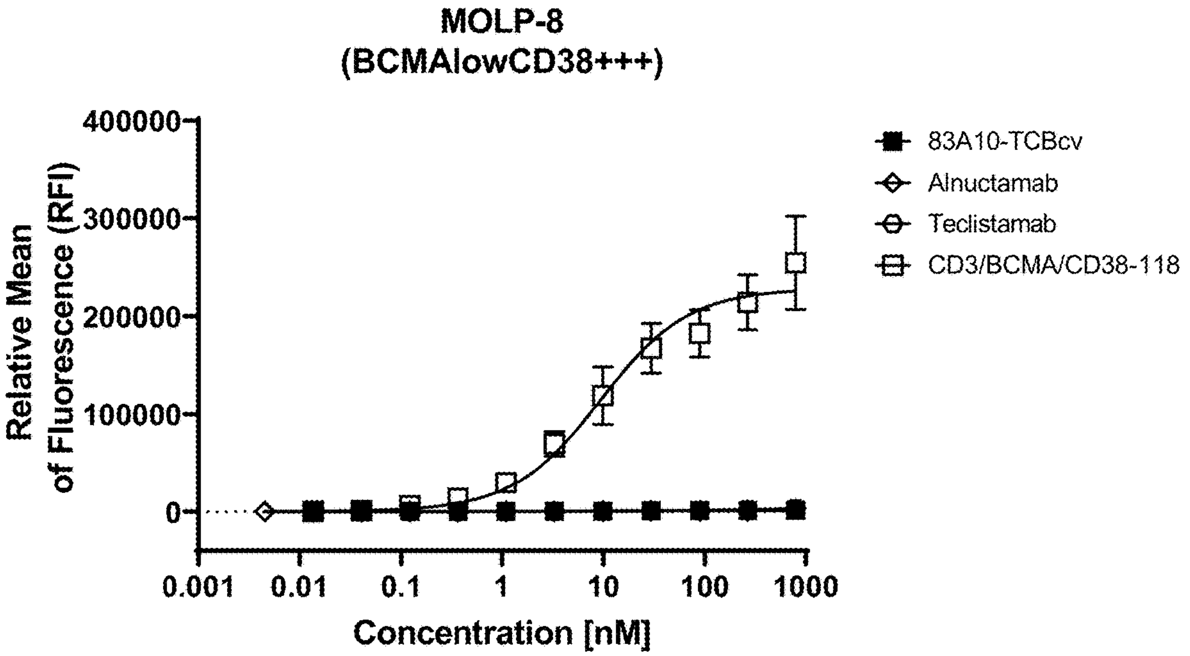
Figure 34C:
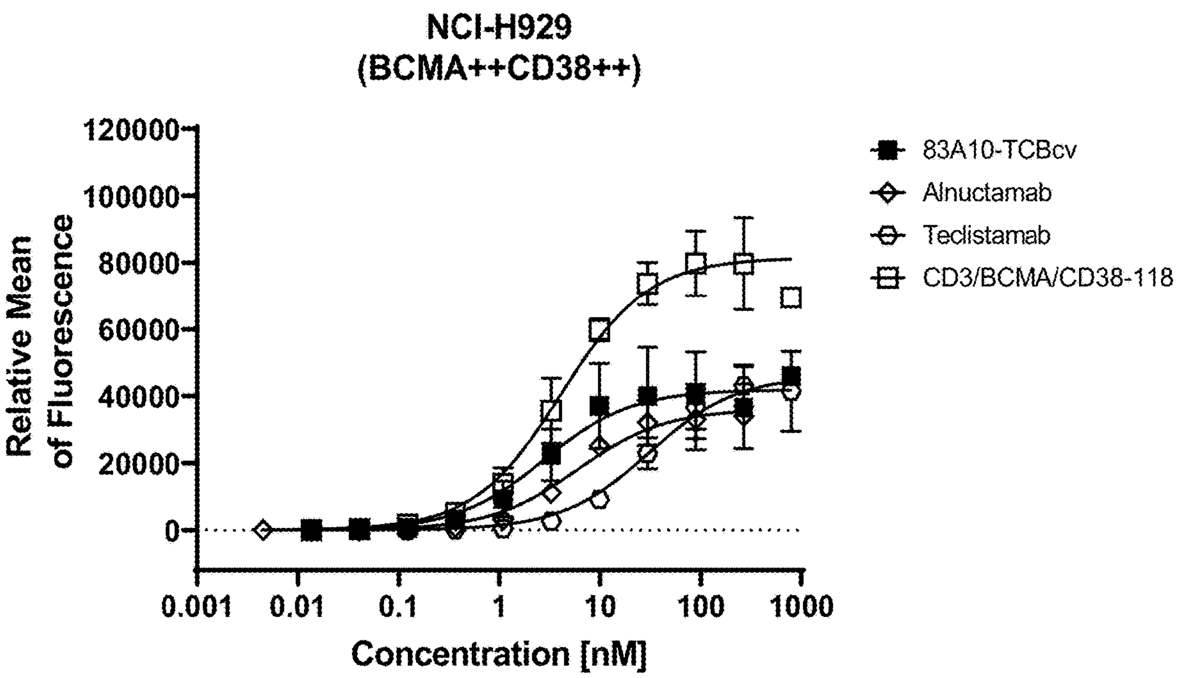
Figure 34D:
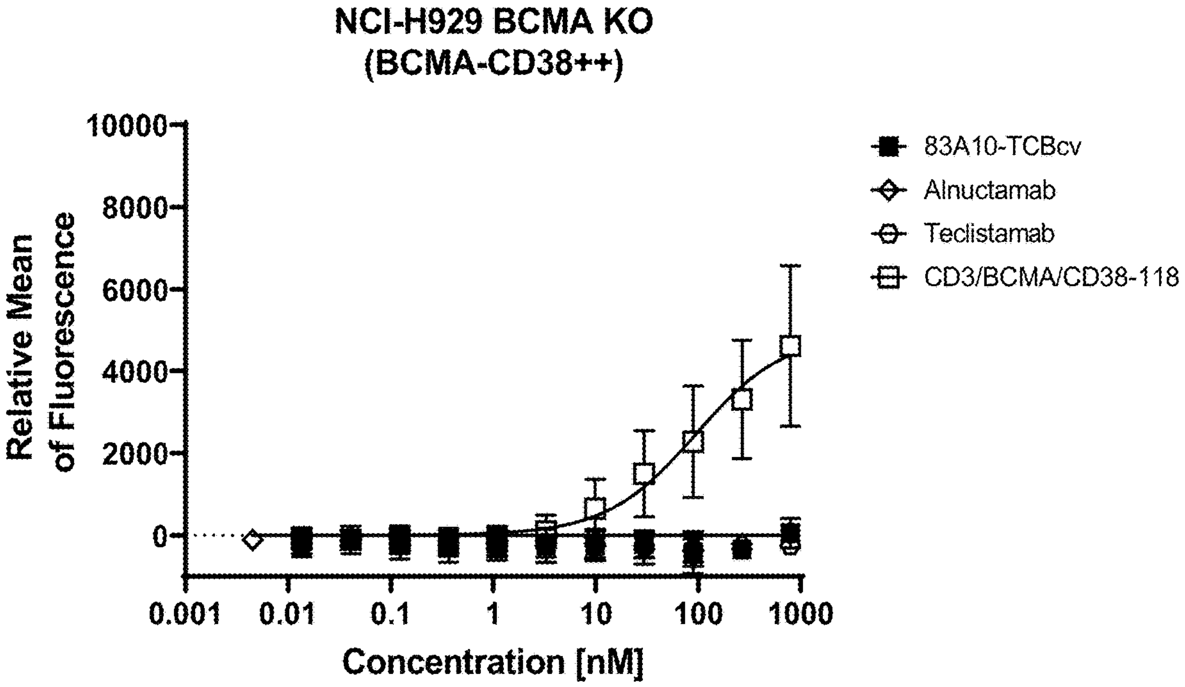
Figure 34E:
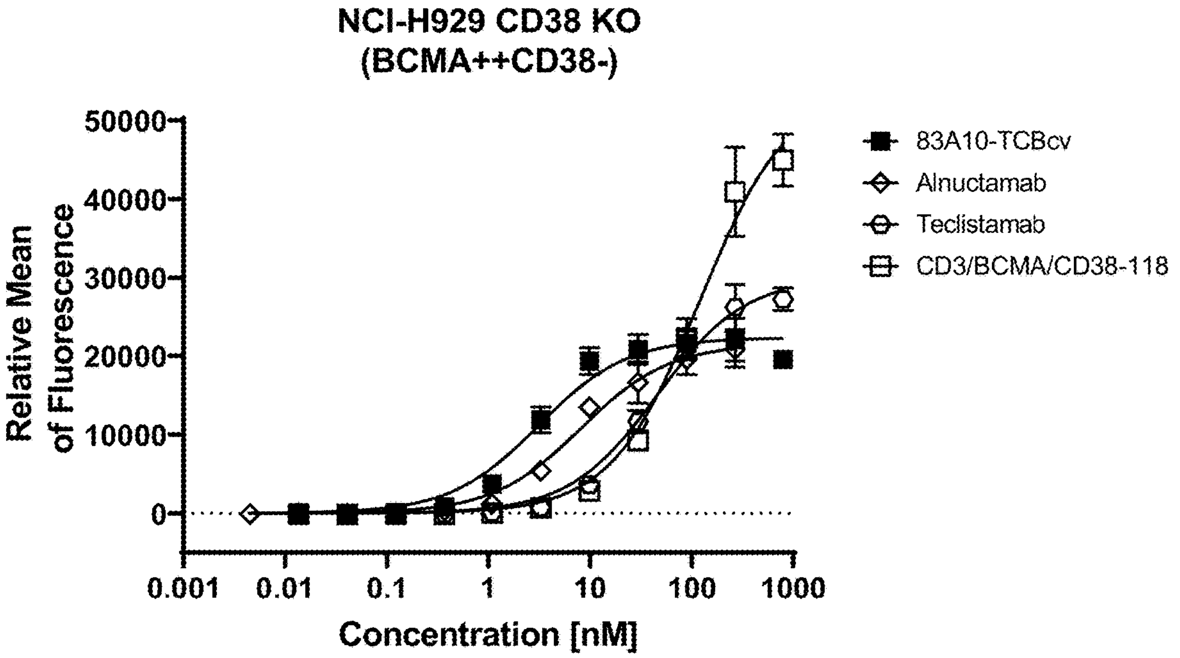

FIGS. 34A-34E. CD3/BCMA/CD38-118 binds to cell lines displaying variable expression of CD38 and BCMA or lacking one antigen. The binding of CD3/BCMA/CD38-118 and CD3×BCMA benchmarks 83A10-TCBcv, alnuctamab and Teclistamab, was evaluated by flow cytometry on different cell lines displaying variable expression of CD38 and BCMA, KMS-12-BM (FIG. 34A), MOLP-8 (FIG. 34B), NCI-H929 WT (FIG. 34C), NCI-H929 BCMA KO (FIG. 34D), NCI-H929 CD38 KO (FIG. 34E). Each point is the mean+/−standard deviation of three measurements from three individual experiments. Experimental setup and analysis are described in Example 22.

Figure 35A:
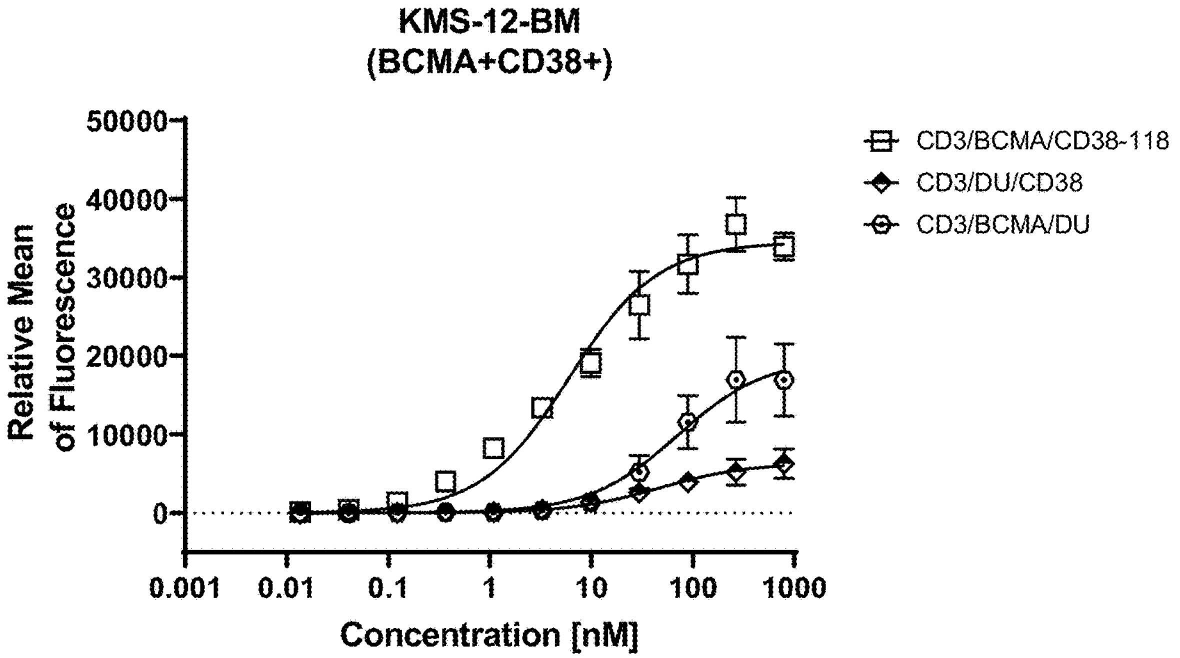
Figure 35B:
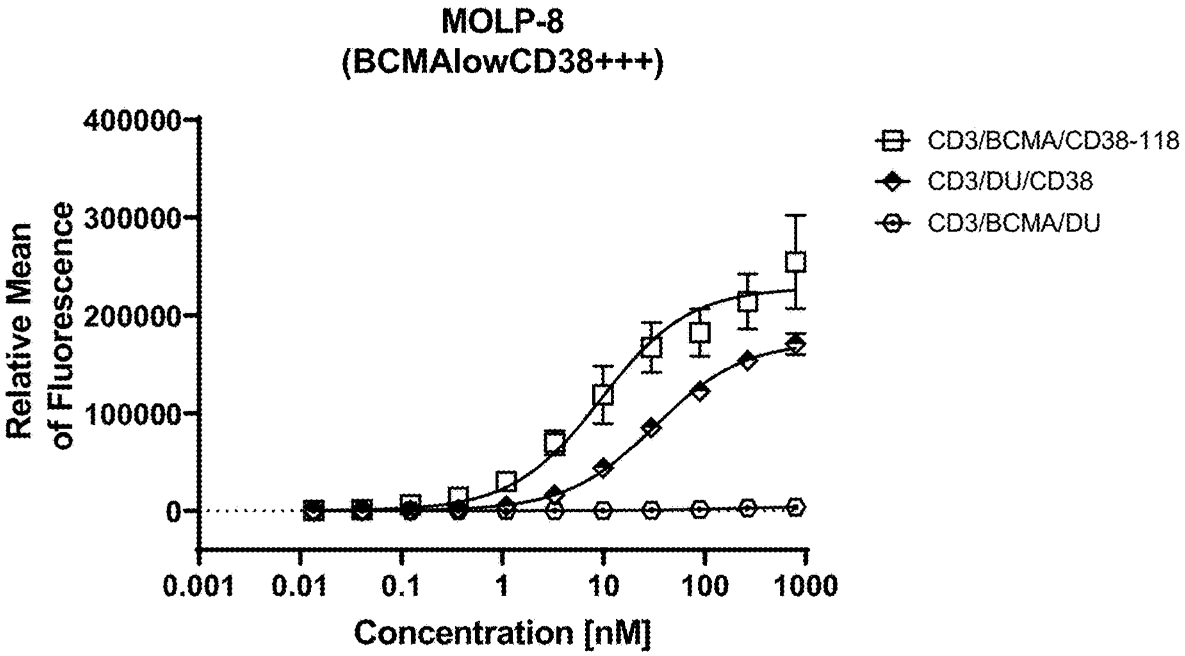
Figure 35C:
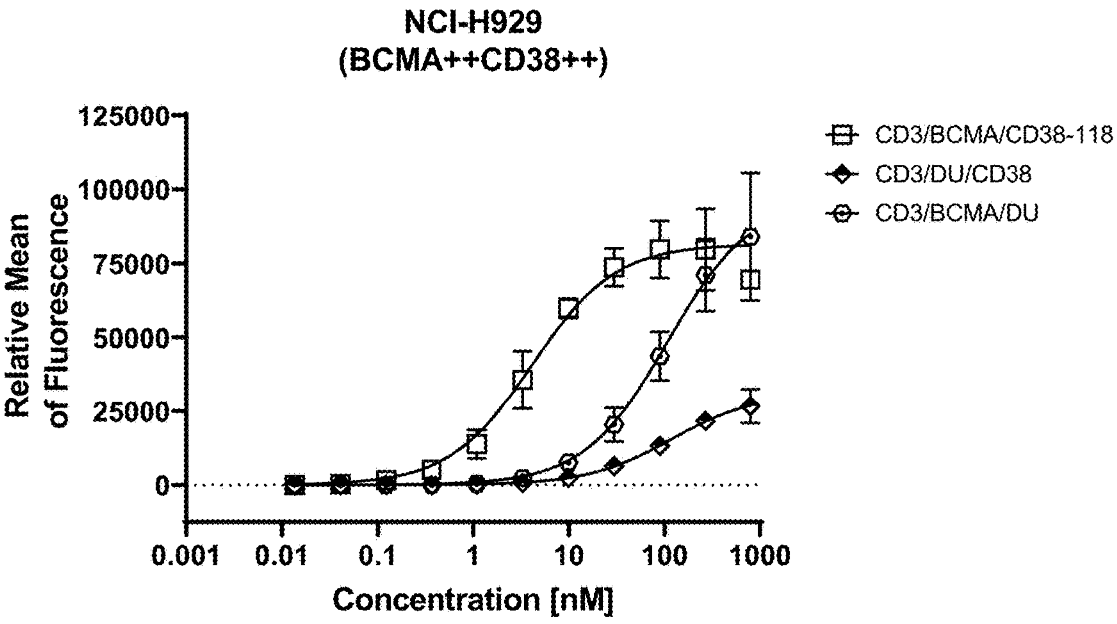
Figure 35D:
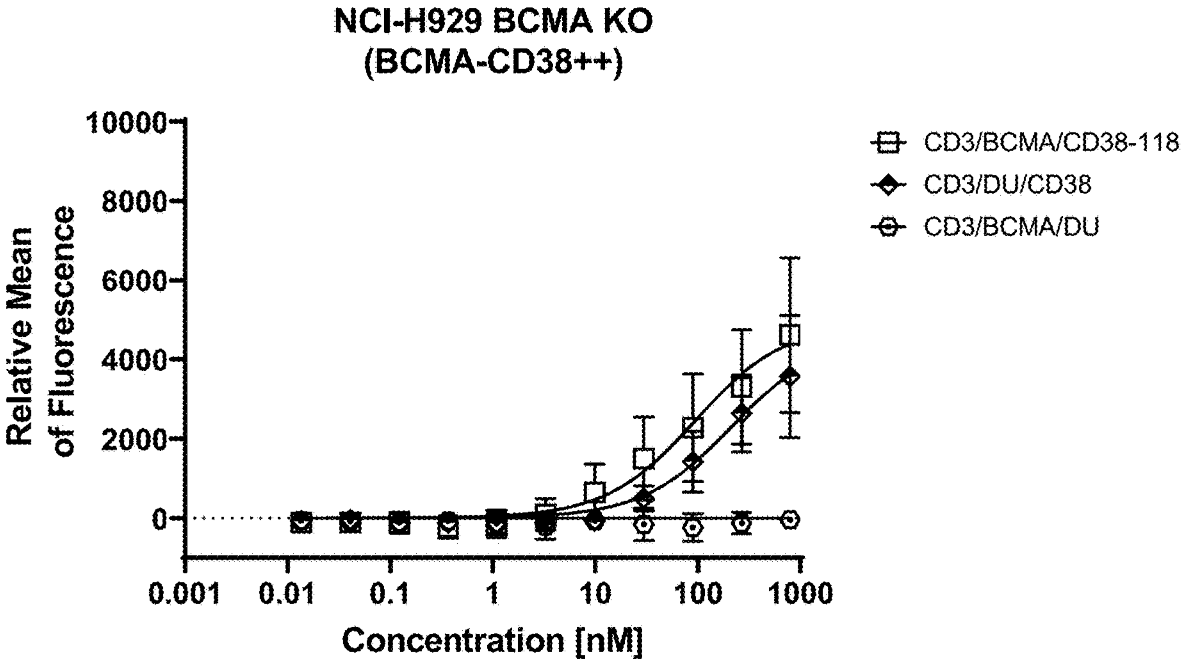
Figure 35E:
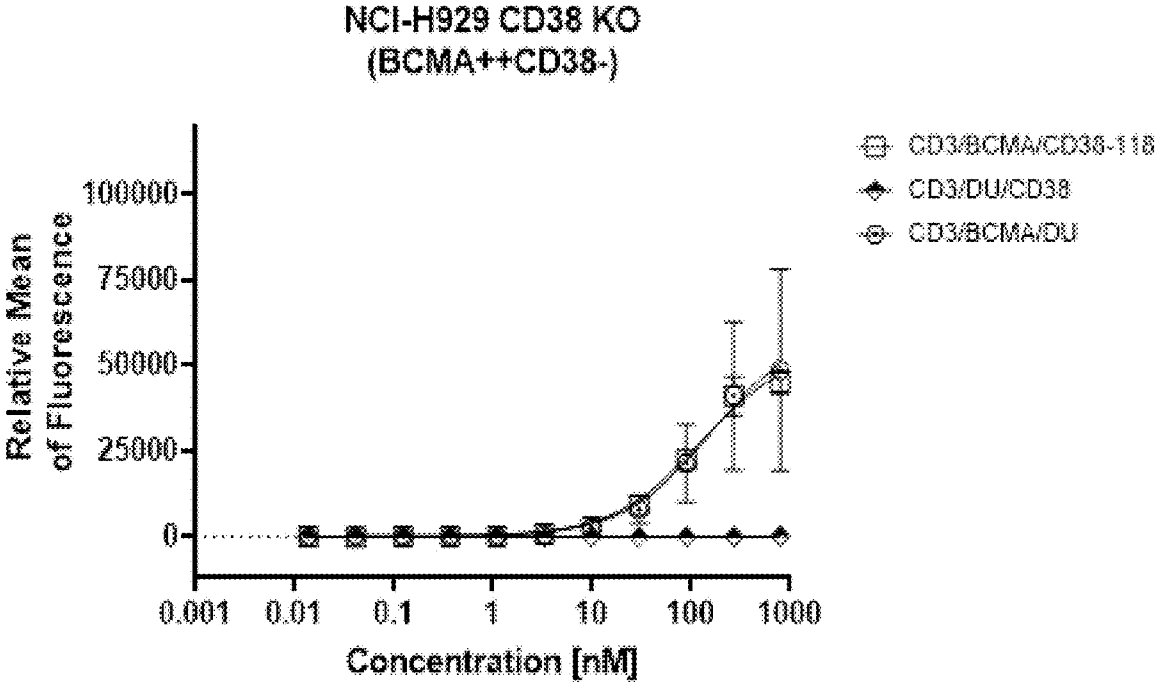

FIGS. 35A-35E. CD3/BCMA/CD38-118 shows higher bindings to cell lines displaying variable expression of CD38 and BCMA compared to control molecules lacking either the BCMA or the CD38 binder. The binding of CD3/BCMA/CD38-118 and controls, CD3/BCMA/CD38-149 and CD3/BCMA/CD38-151, was evaluated by flow cytometry on different cell lines displaying variable expression of CD38 and BCMA, KMS-12-BM (FIG. 35A), MOLP-8 (FIG. 35B), NCI-H929 WT (FIG. 35C), NCI-H929 BCMA KO (FIG. 35D), NCI-H929 CD38 KO (FIG. 35E). Each point is the mean+/−standard deviation of three measurements from three individual experiments. Experimental setup and analysis are described in Example 22.

Figure 36A:
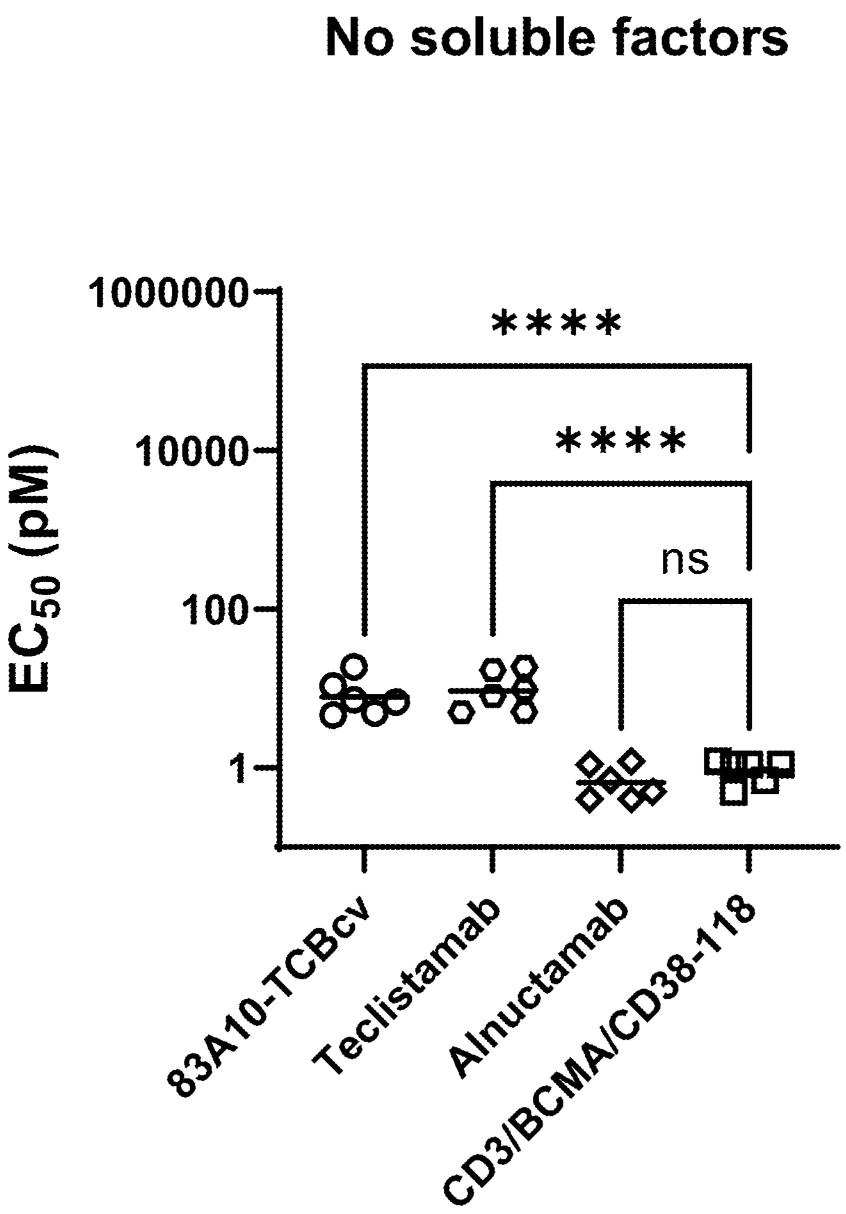
Figure 36B:
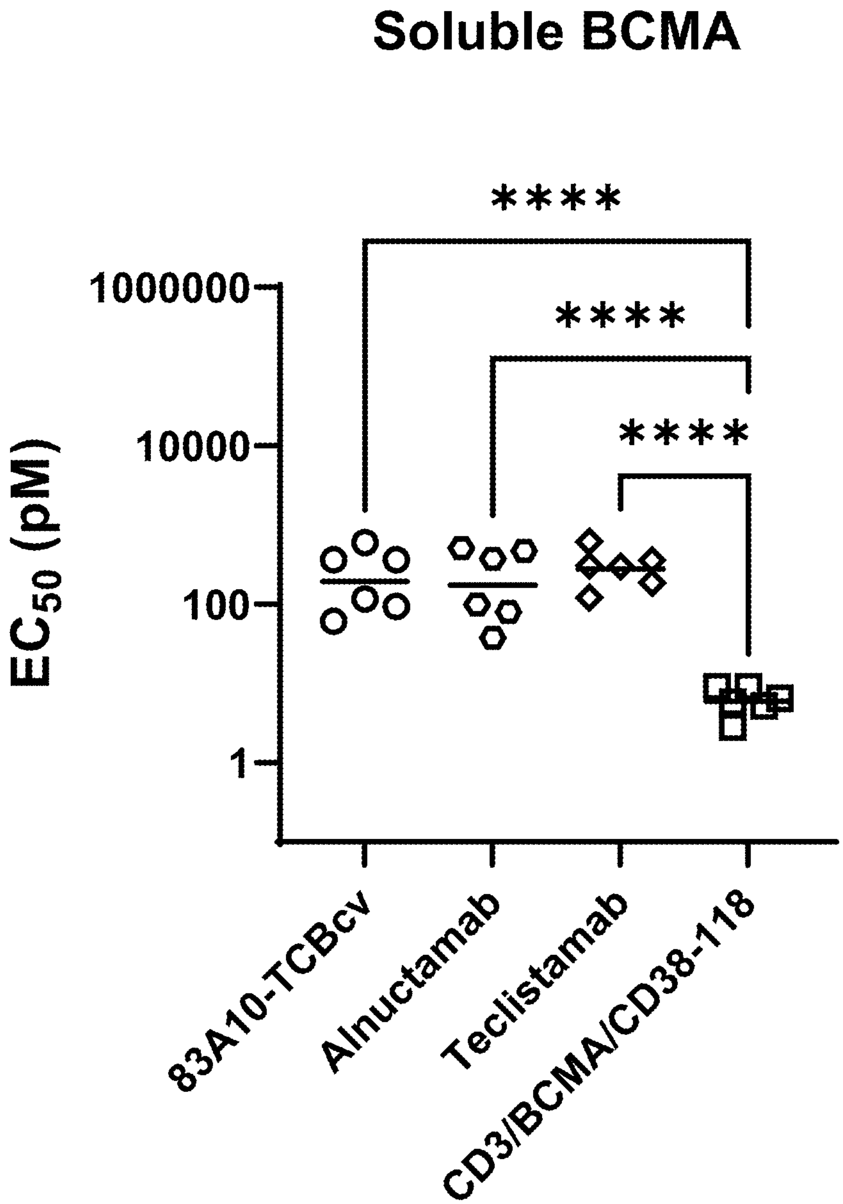
Figure 36C:
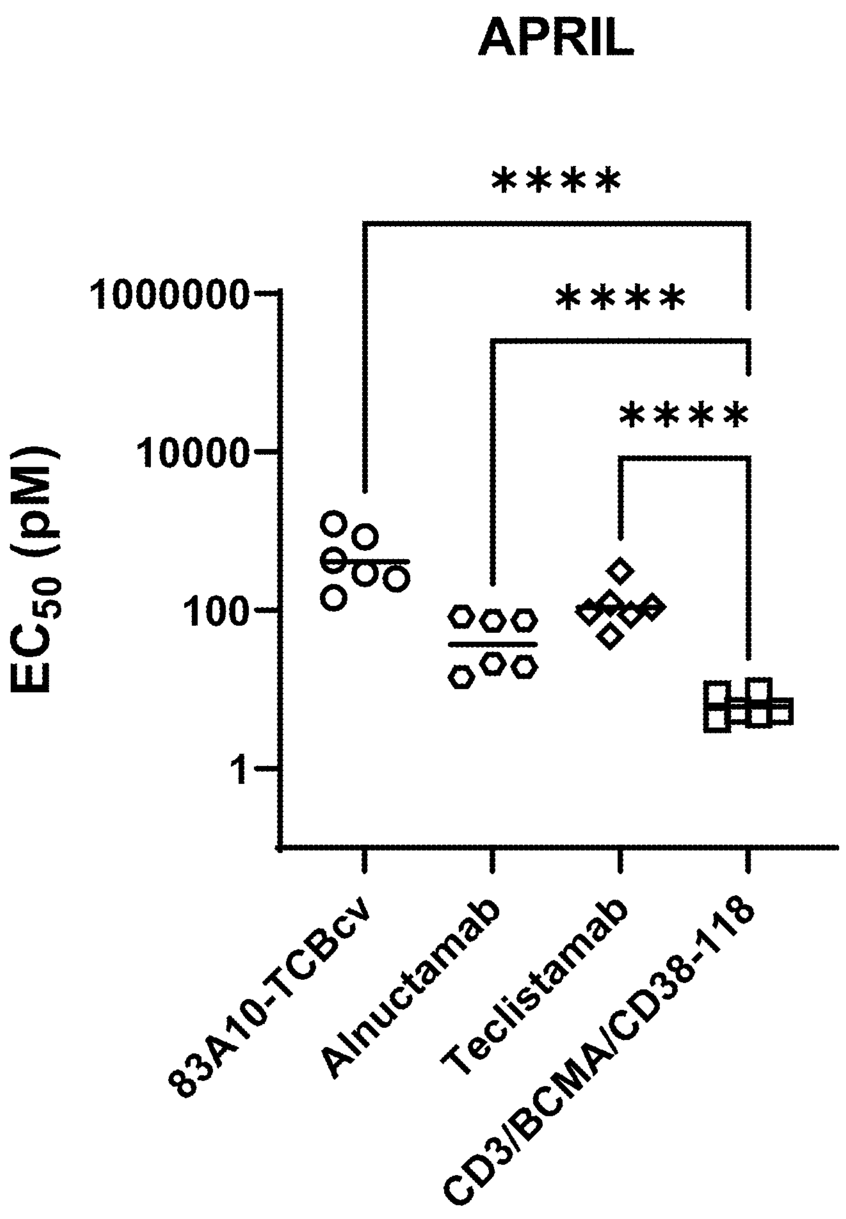
Figure 36D:
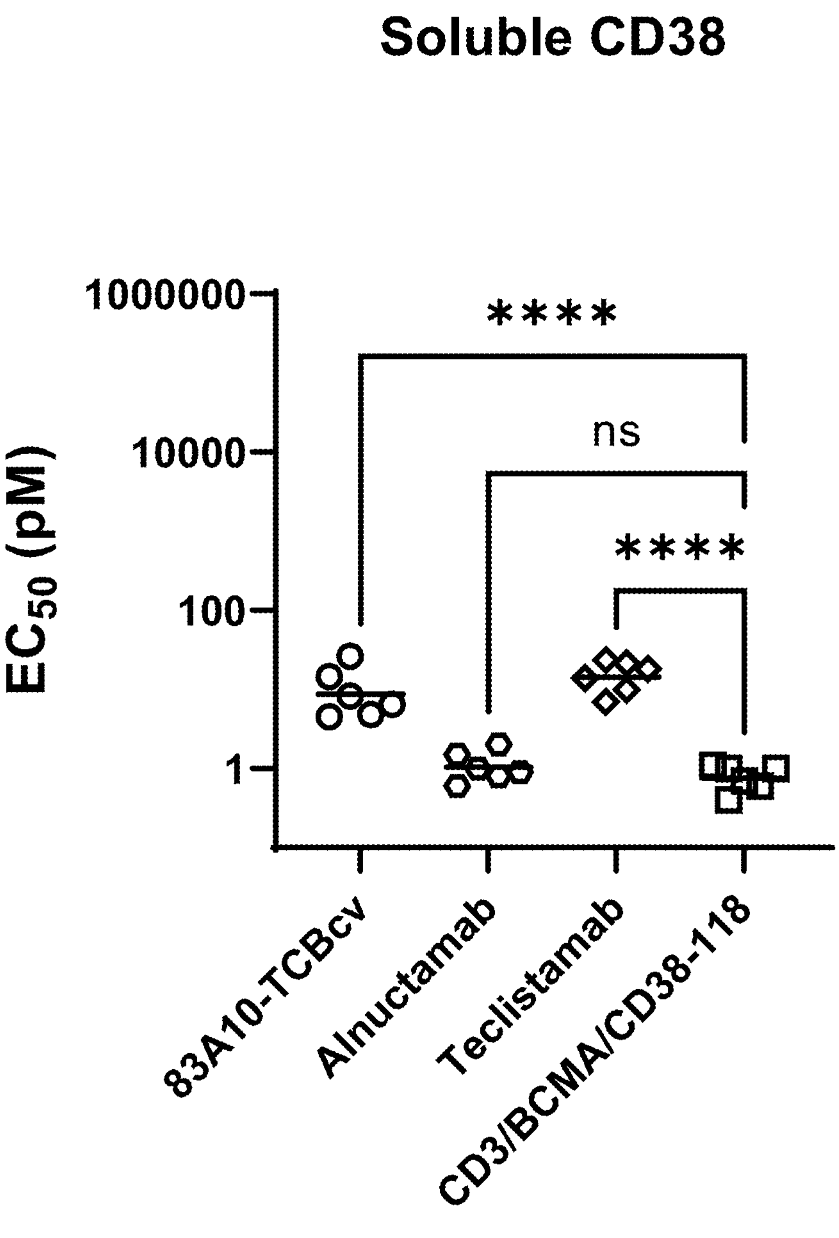
Figure 36E:
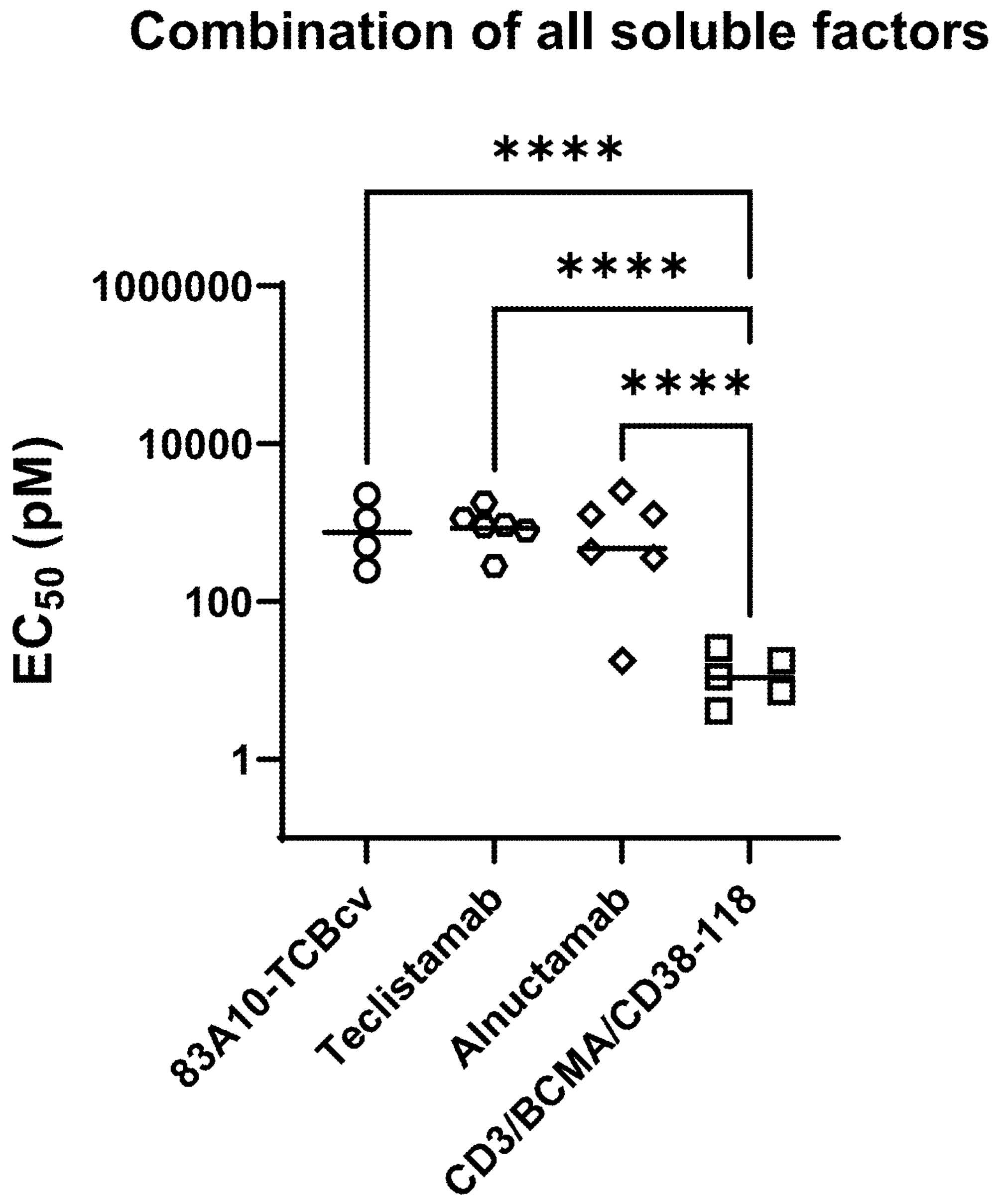

FIGS. 36A-36E. CD3/BCMA/CD38-118 induces the most potent in vitro killing of KMS-12-BM in the absence or presence of individual soluble factors. The ability of CD3/BCMA/CD38-118 and CD3×BCMA benchmarks 83A10-TCBcv, alnuctamab and teclistamab to trigger T cell mediated killing of KMS-12-BM was assessed in a Redirected Lysis assay with a 5:1 Effector-to-target ratio in the absence (FIG. 36A) or presence of individual soluble factors (Soluble BCMA: FIG. 36B; APRIL: FIG. 36C; Soluble CD38: FIG. 36D; and combination of all soluble factors: FIG. 36E) and measured by Flow Cytometry after 48 hours of incubation. Percentages of killing to no Ab and associated half maximum effective killing concentration ($EC_{50}$) values were determined from the Redirected Lysis assay. Each dot represents the $EC_{50}$ value for one individual donor. Bar shows the mean of the dataset. Means were compared using a Mixed-effect model (when some values were missing) or a paired One-way ANOVA (when all values were included) analysis followed by Tukey HSD post-hoc comparison. #p-value<0.0001 **** for CD3/BCMA/CD38-118 vs all other molecules with soluble factors. Experimental setup and analysis are described in Example 22.

Figure 37A:
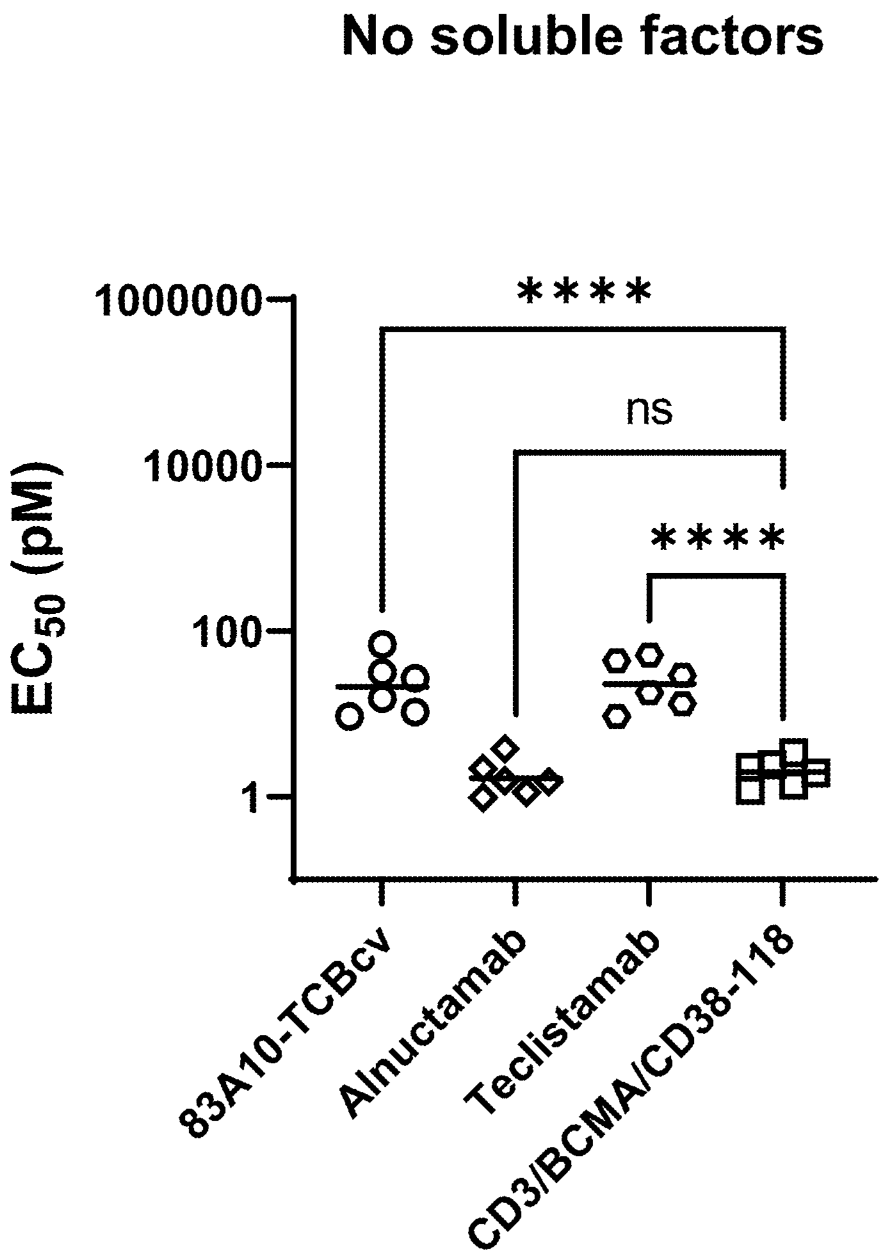
Figure 37B:
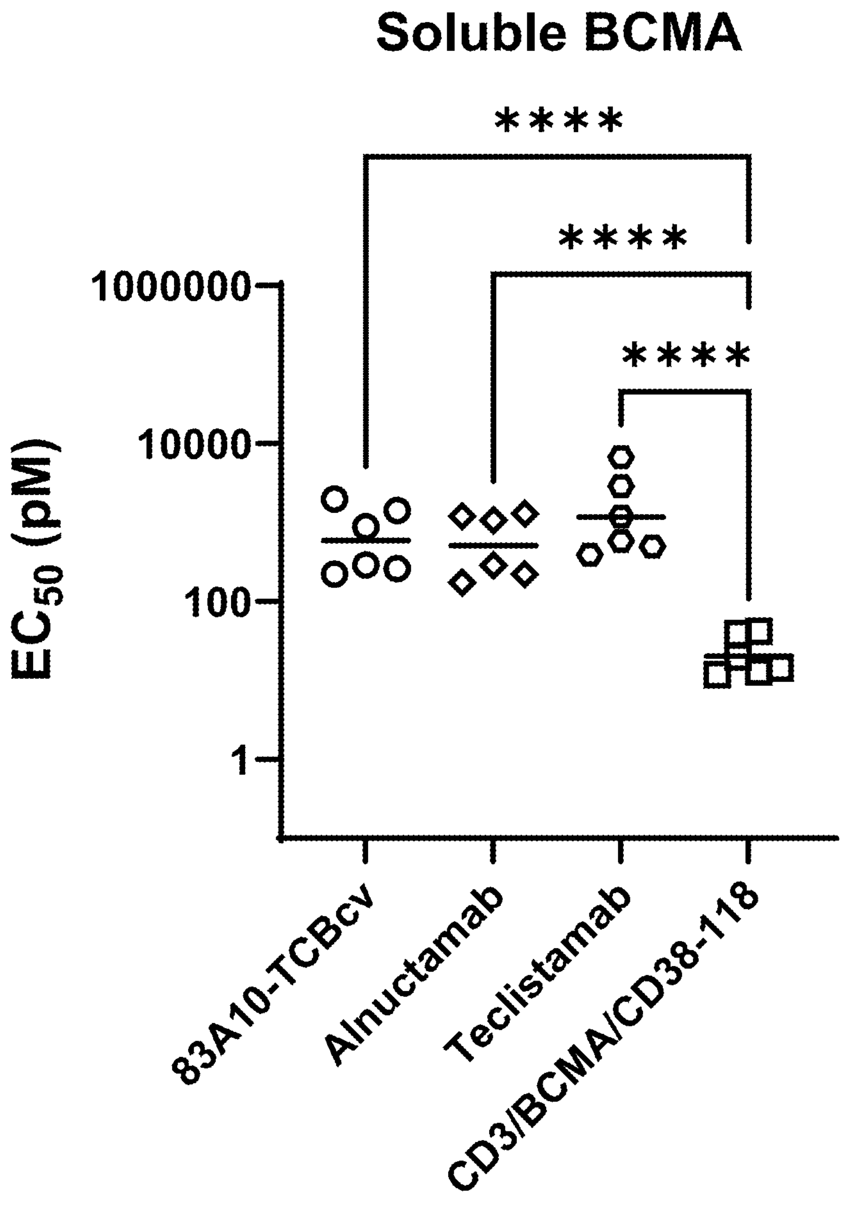
Figure 37C:
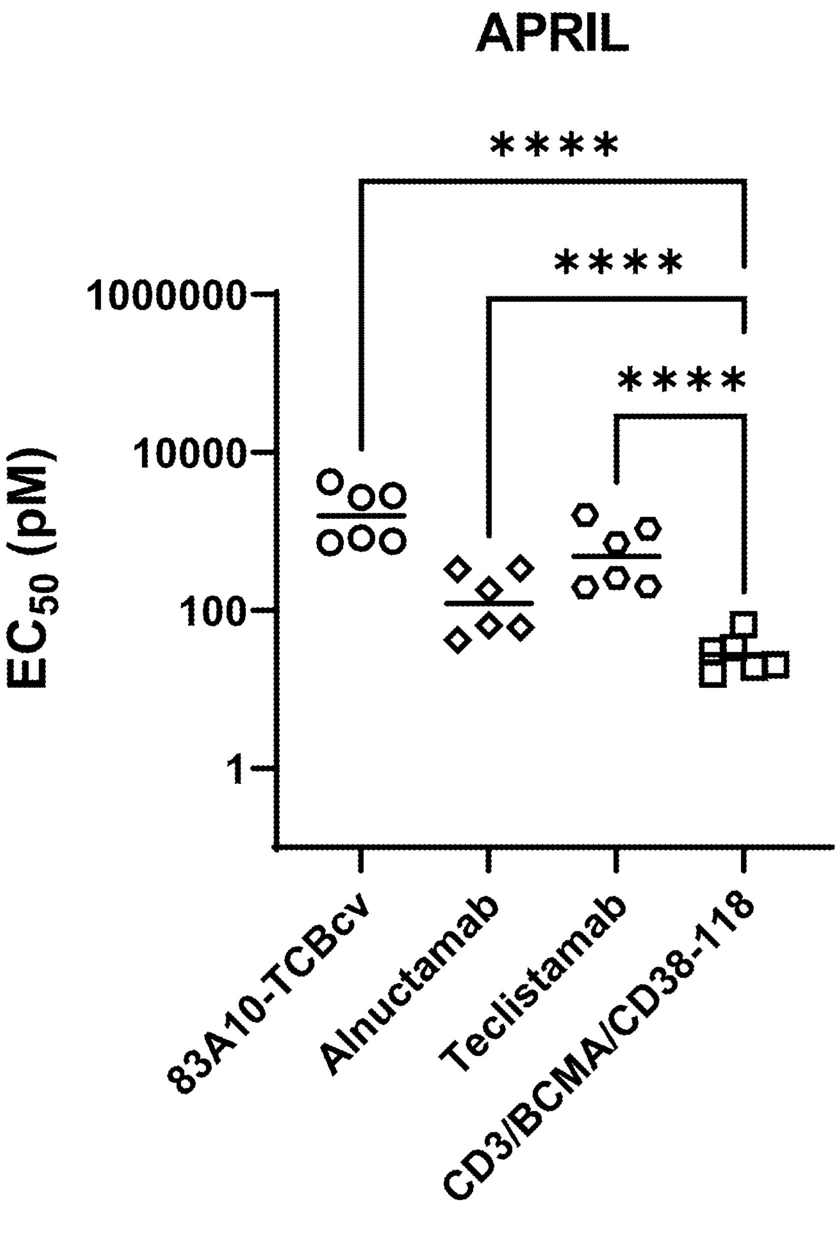
Figure 37D:
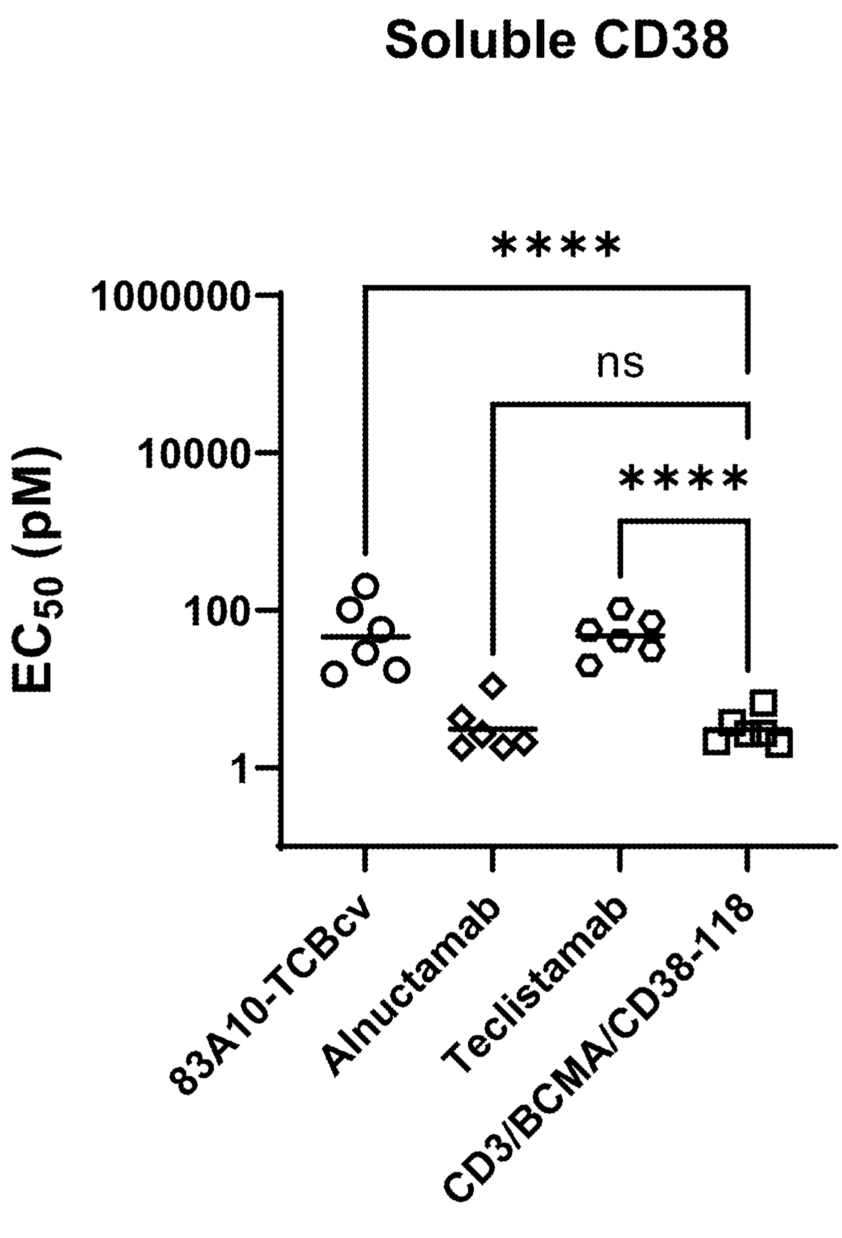
Figure 37E:
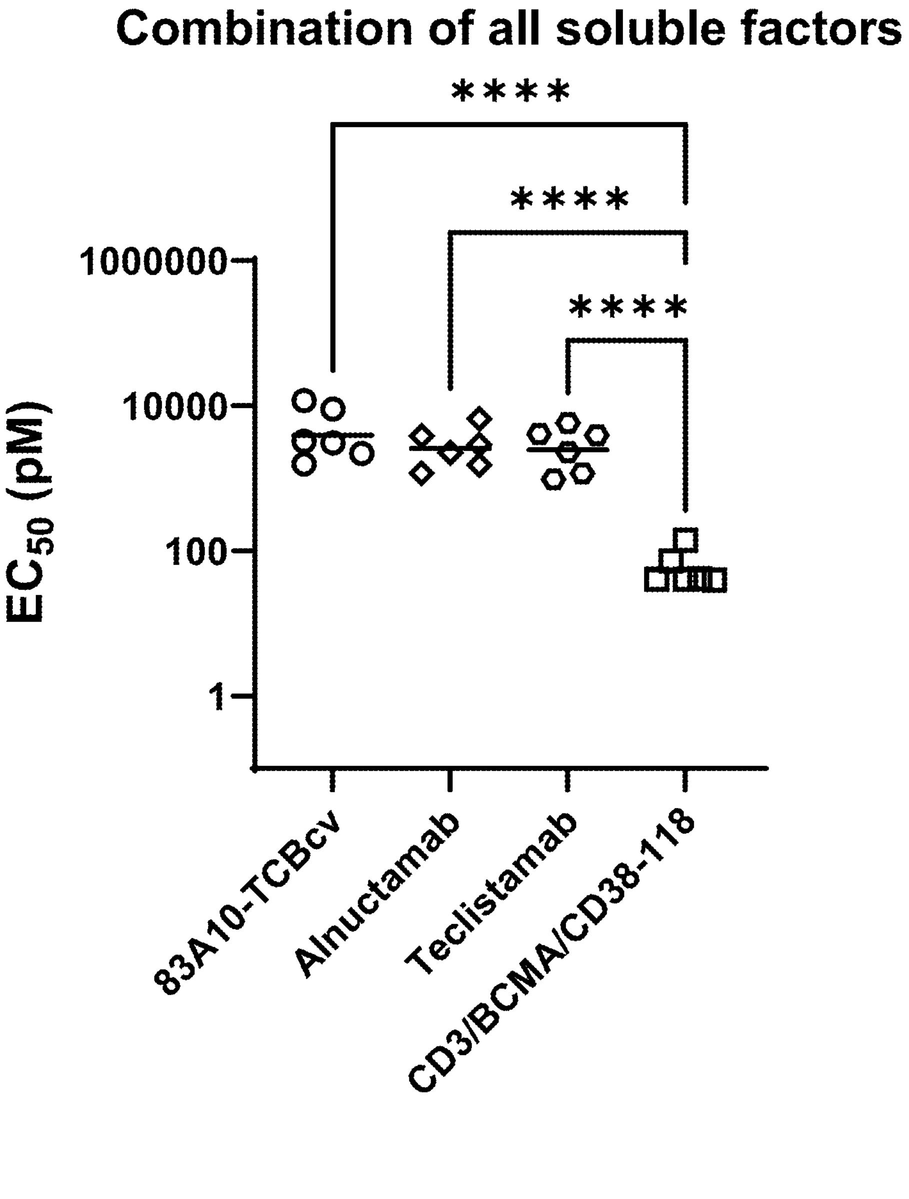

FIGS. 37A-37E. CD3/BCMA/CD38-118 induces the most potent in vitro killing of KMS-12-BM in the absence or presence of individual soluble factors. The ability of CD3/BCMA/CD38-118 and CD3×BCMA benchmarks 83A10-TCBcv, alnuctamab and teclistamab to trigger T cell mediated killing of KMS-12-BM was assessed in a Redirected Lysis assay with a 5:1 Effector-to-target ratio in the absence (FIG. 37A) or presence of individual soluble factors (Soluble BCMA: FIG. 37B; APRIL: FIG. 37C; Soluble CD38: FIG. 37D; and combination of all soluble factors: FIG. 37E) and measured by Flow Cytometry after 48 hours of incubation. Percentages of Cytotoxicity and associated half maximum effective killing concentration ($EC_{50}$) values were determined from the Redirected Lysis assay. Each dot represents the $EC_{50}$ value for one individual donor. Bar shows the mean of the dataset. Means were compared using a Mixed-effect model (when some values were missing) or a paired One-way ANOVA (when all values were included) analysis followed by Tukey HSD post-hoc comparison. #p-value<0.0001 **** for CD3/BCMA/CD38-118 vs all other molecules with soluble factors. Experimental setup and analysis are described in Example 22.

Figure 38A:
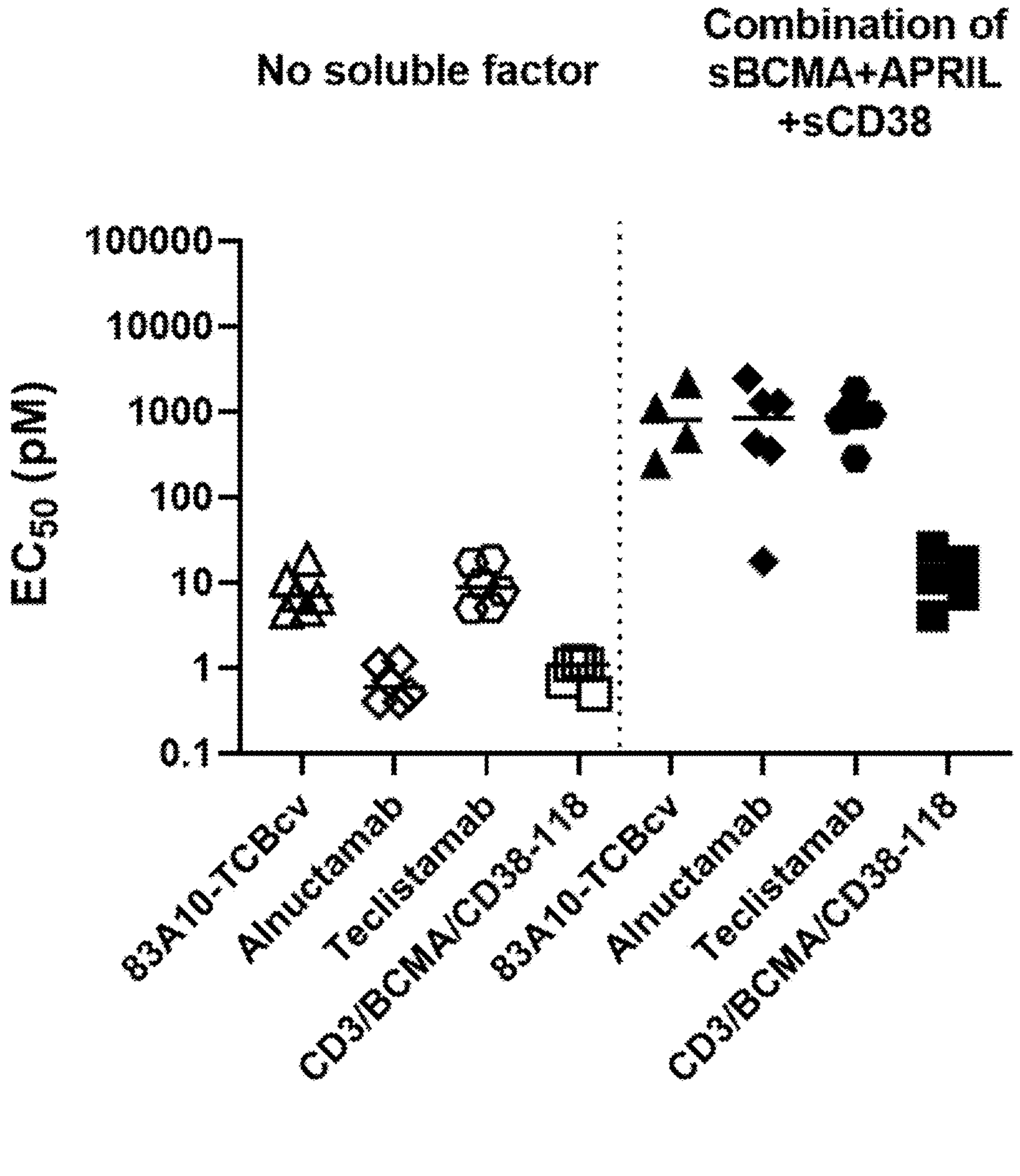
Figure 38B:
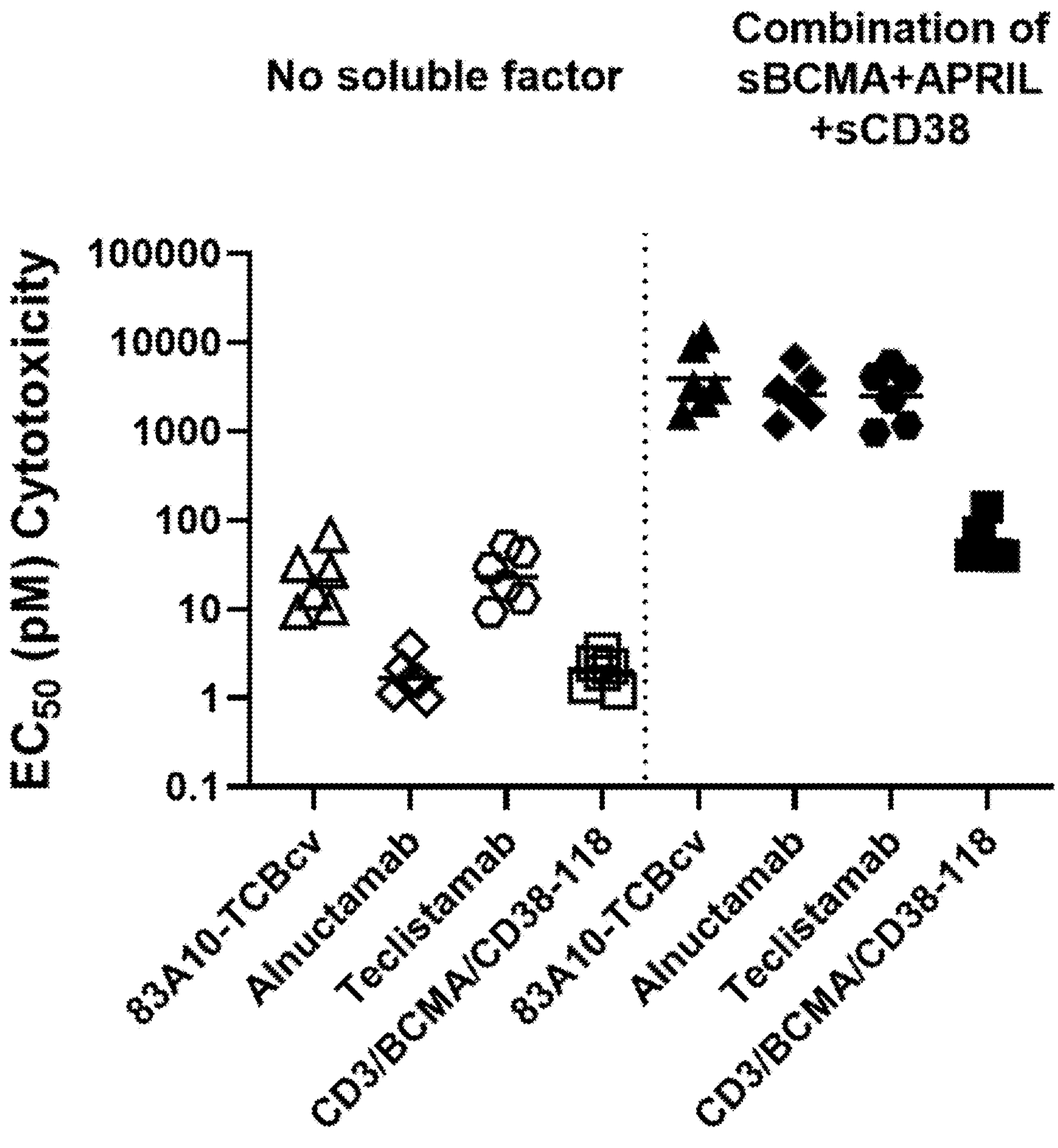

FIGS. 38A-38B. CD3/BCMA/CD38-118 induces the most potent in vitro killing of KMS-12-BM in the presence of competing soluble factors. The ability of CD3/BCMA/CD38-118 and CD3×BCMA benchmarks 83A10-TCBcv, alnuctamab and teclistamab to trigger T cell mediated killing of KMS-12-BM was assessed in a Redirected Lysis assay with a 5:1 Effector-to-target ratio in the absence (left, empty white symbol) or presence of a combination of soluble factors (right; soluble BCMA, soluble CD38 and APRIL, full black symbol) and measured by Flow Cytometry after 48 hours of incubation. Percentages of killing to No Ab (FIG. 38A), percentages of Cytotoxicity (FIG. 38B), and associated half maximum effective killing concentration ($EC_{50}$) values were determined from the Redirected Lysis assay. Each dot represents the $EC_{50}$ value for one individual donor. Bar shows the mean of the dataset. Means were compared using a Mixed-effect model (when some values were missing) or a paired One-way ANOVA (when all values were included) analysis followed by Tukey HSD post-hoc comparison. Experimental setup and analysis are described in Example 22.

FIGS. 39A-39F. CD3/BCMA/CD38-118 induces the most potent in vitro killing against all cell lines. The ability of CD3/BCMA/CD38-118 and CD3×BCMA benchmarks 83A10-TCBcv, alnuctamab and teclistamab to trigger T cell mediated killing of multiple myeloma cell lines was assessed in a Redirected Lysis assay with a 5:1 Effector-to-target ratio using isolated T cells on KMS-12-BM (FIGS. 39A and 39D), MOLP-8 (FIGS. 39B and 39E) and NCI-H929 (FIGS. 39C and 39F) cells and measured by Flow Cytometry after 48 hours of incubation. Percentages of killing to No Ab (FIGS. 39A, 39B, and 39C), percentages of Cytotoxicity (FIGS. 39D, 39E, and 39F), and associated half maximum effective killing concentration ($EC_{50}$) values were determined from the Redirected Lysis assay. Each dot represents the $EC_{50}$ value for one individual donor. Lines show the mean of the dataset. Means were compared using a Mixed-effect model (when some values were missing) or a paired One-way ANOVA (when all values were included) analysis followed by Tukey HSD post-hoc comparison. Ns: not statistically different; *: p=0.05-0.01; : p=0.01-0.001; *: p=0.001-0.0001; ****: p<0.0001. Experimental setup and analysis are described in Example 22.

FIGS. 40A-40F. CD3/BCMA/CD38-118 induces a higher killing potency against all cell lines compared to the combination of bispecific antibodies with the same binders. The ability of CD3/BCMA/CD38-118 and controls, CD3/BCMA/CD38-149, CD3/BCMA/CD38-151 and a combination of both, to trigger T cell mediated killing of multiple myeloma cell lines was assessed in a Redirected Lysis assay with a 5:1 Effector-to-target ratio using isolated T cells on KMS-12-BM (FIGS. 40A and 40D), MOLP-8 (FIGS. 40B and 40E) and NCI-H929 (FIGS. 40C and 40F) cells and measured by Flow Cytometry after 48 hours of incubation. Percentages of killing to No Ab (FIGS. 40A, 40B, and 40C), percentages of Cytotoxicity (FIGS. 40D, 40E, and 40F), and associated half maximum effective killing concentration ($EC_{50}$) values were determined from the Redirected Lysis assay. Each dot represents the $EC_{50}$ value for one individual donor. Bar shows the mean of the dataset. Means were compared using a Mixed-effect model (when some values were missing) or a paired One-way ANOVA (when all values were included) analysis followed by Tukey HSD post-hoc comparison. Ns: not statistically different; *: p=0.05-0.01; : p=0.01-0.001; *: p0.001-0.0001; ****: p<0.0001. NQ: not quantifiable. Experimental setup and analysis are described in Example 22.

FIGS. 41A-41D. CD3/BCMA/CD38-118 demonstrates statistically superior killing to the combination of teclistamab with daratumumab. The ability of CD3/BCMA/CD38-118 and benchmarks, daratumumab, teclistamab and a combination of both, to trigger the killing of multiple myeloma cell lines was assessed in a MmoAK assay with a 5:1 effector-to-target ratio using human PBMCs on KMS-12-BM cells and measured by Flow Cytometry after 48 hours of incubation. Two concentrations, 10 (FIGS. 41A and 41C) and 100 (FIGS. 41B and 41D) pM of CD3/BCMA/CD38-118 or teclistamab were evaluated with a single dose of daratumumab at 100 nM. Percentage of killing to No Ab (FIGS. 41A and 41B) and percentage of cytotoxicity (FIGS. 41C and 41D) were assessed after the incubation. Each dot represents one individual donor. Bars shows the mean of the dataset. Means were compared using a paired One-way ANOVA analysis followed by Tukey HSD post-hoc comparison. Ns: not statistically different; *: p=0.05-0.01; : p=0.01-0.001; *: p0.001-0.0001; ****: p<0.0001. Experimental setup and analysis are described in Example 22.

Figure 42A:
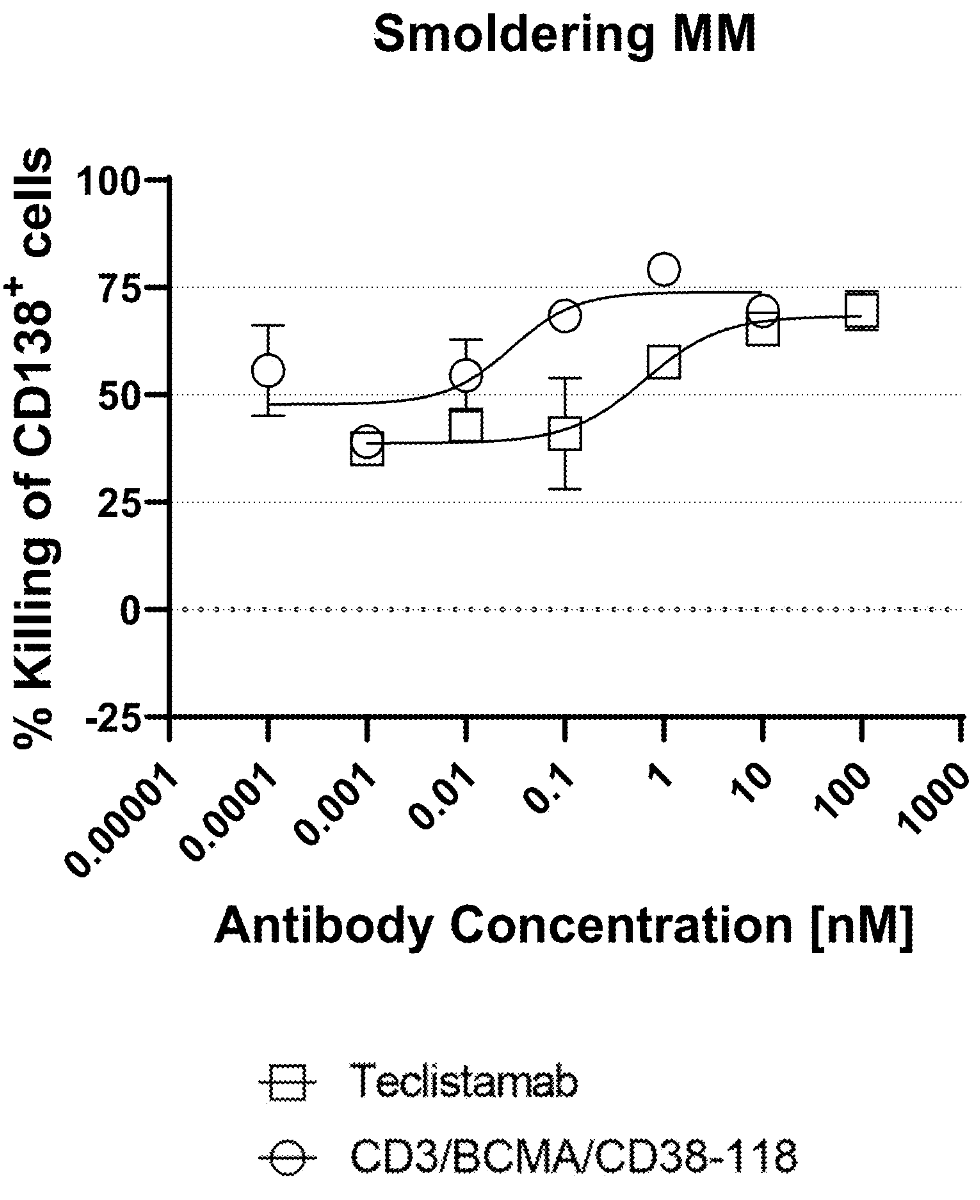
Figure 42B:
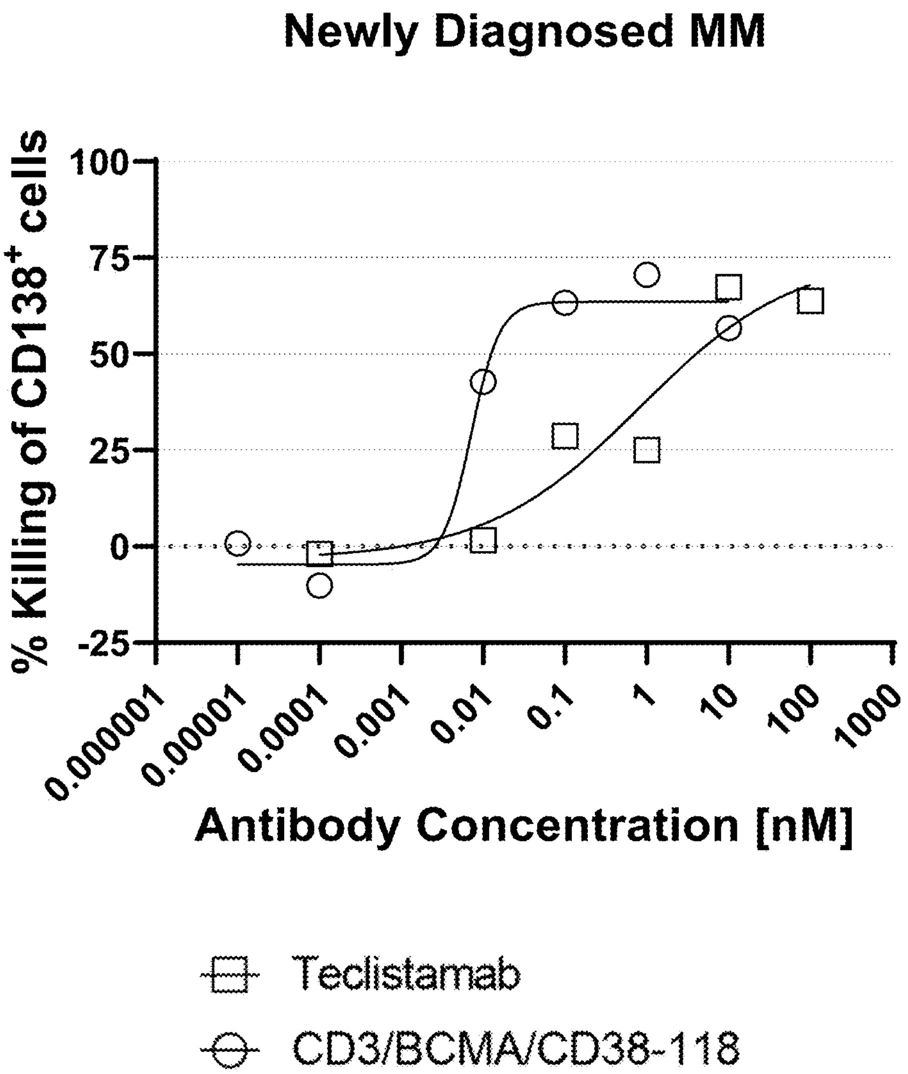
Figure 42C:
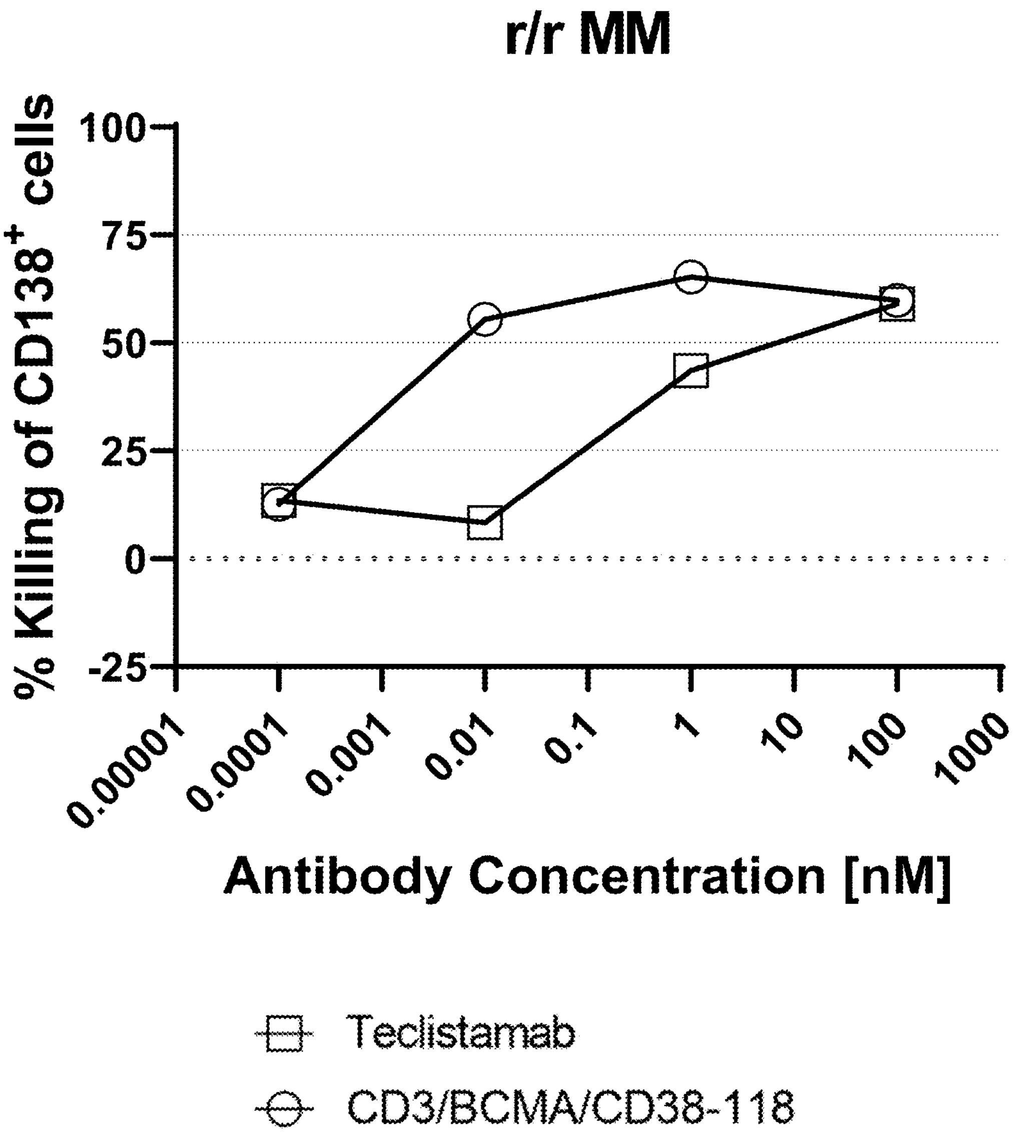
Figure 42D:
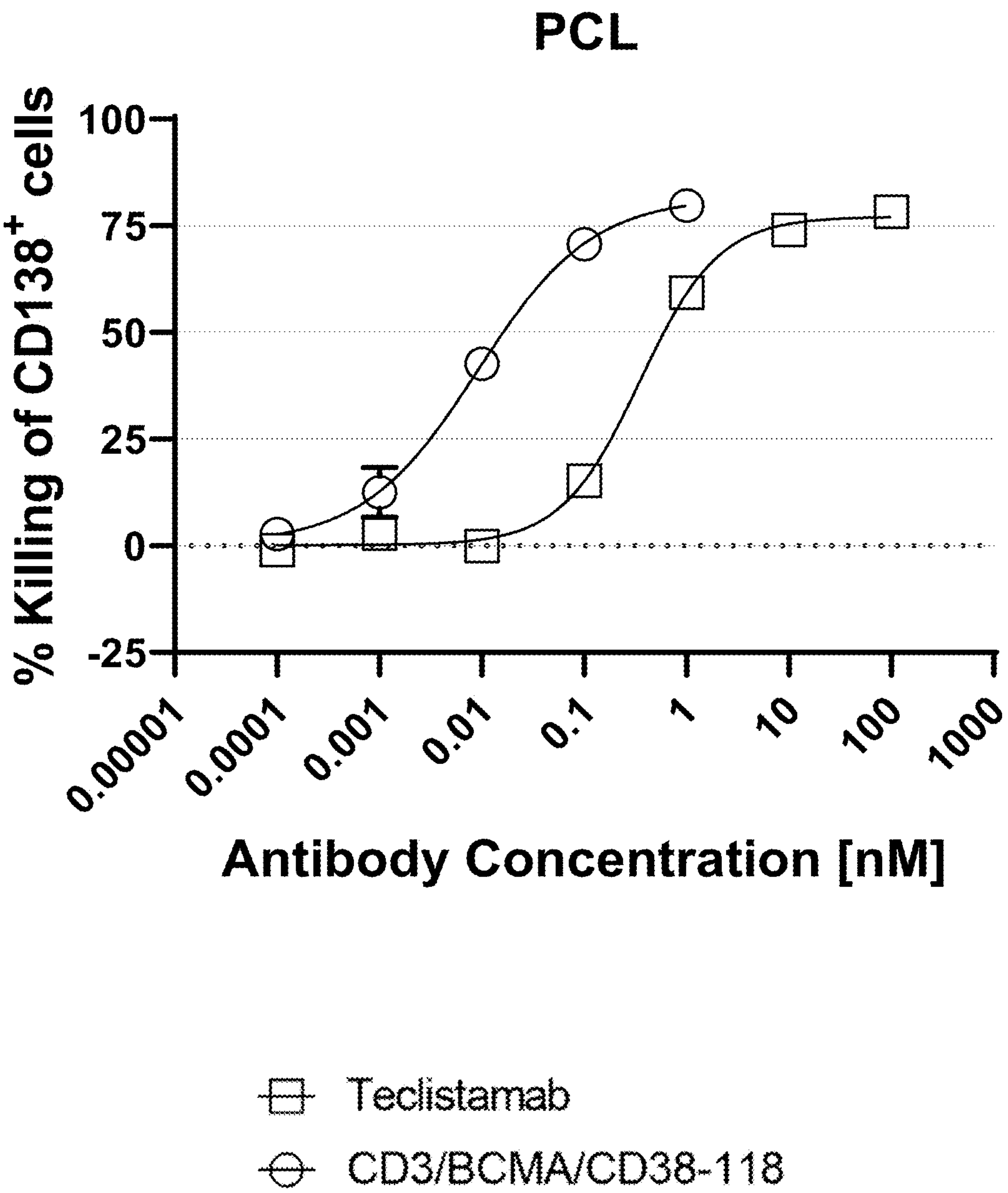

FIGS. 42A-42D. CD3/BCMA/CD38-118 induces the killing of $CD138^+$ cells within MM patient samples. BMMC from four individual donors (FIG. 42A, Smoldering MM; FIG. 42B, Newly Diagnosed MM; FIG. 42C, r/r MM; FIG. 42D, Plasma Cell Leukemia (PCL)) were cultured in RPMI 10% Human serum, 3 ng/ml recombinant human IL-6 and treated with varying concentrations of CD3/BCMA/CD38-118, benchmark (Teclistamab) and negative control (CD3/BCMA/CD38-085, not shown) for 17-22 hours. Absolute counts of live $CD138^+$ cells were extracted and normalized to the no antibody condition to calculate the % killing compared to no antibody. Each dot represents the mean+/− standard error of the mean of 2 replicated measurements for one individual donor (except for B and C where simplicates were used). Experimental setup and analysis are described in Example 22.

Figure 43:
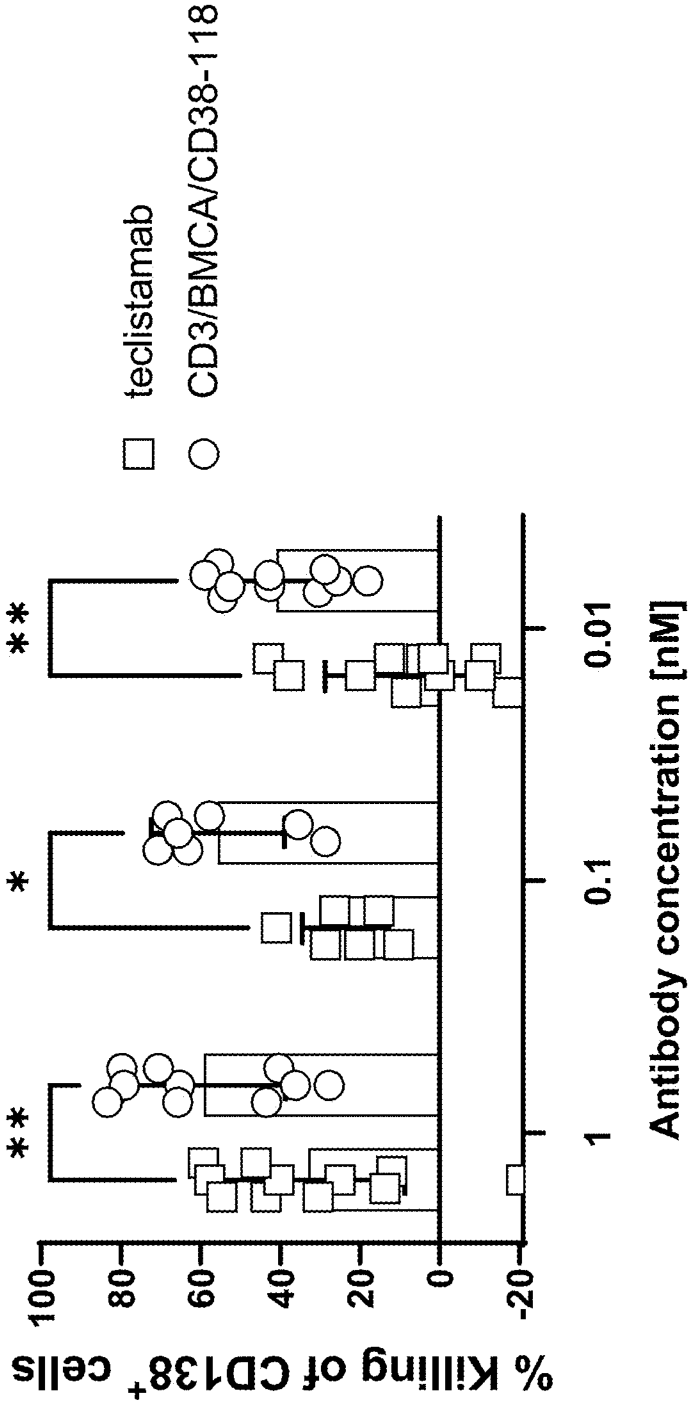

FIG. 43. CD3/BCMA/CD38-118 induces superior killing of $CD138^+$ cells to teclistamab within MM patient samples.

BMMC from six to eleven individual donors were cultured in RPMI 10% Human serum, 3 ng/ml recombinant human IL-6 and treated with varying concentrations of CD3/BCMA/CD38-118, CD3×BCMA benchmark (Teclistamab) and negative controls (not shown) for 17-22 hours. Absolute counts of live $CD138^+$ cells were extracted and normalized to the no antibody condition to calculate the % killing compared to no antibody. Each dot represents an individual donor. Bars show the means+/−standard deviation of the different donors for specific concentrations. Experimental setup and analysis are described in Example 22.

Figure 44A:
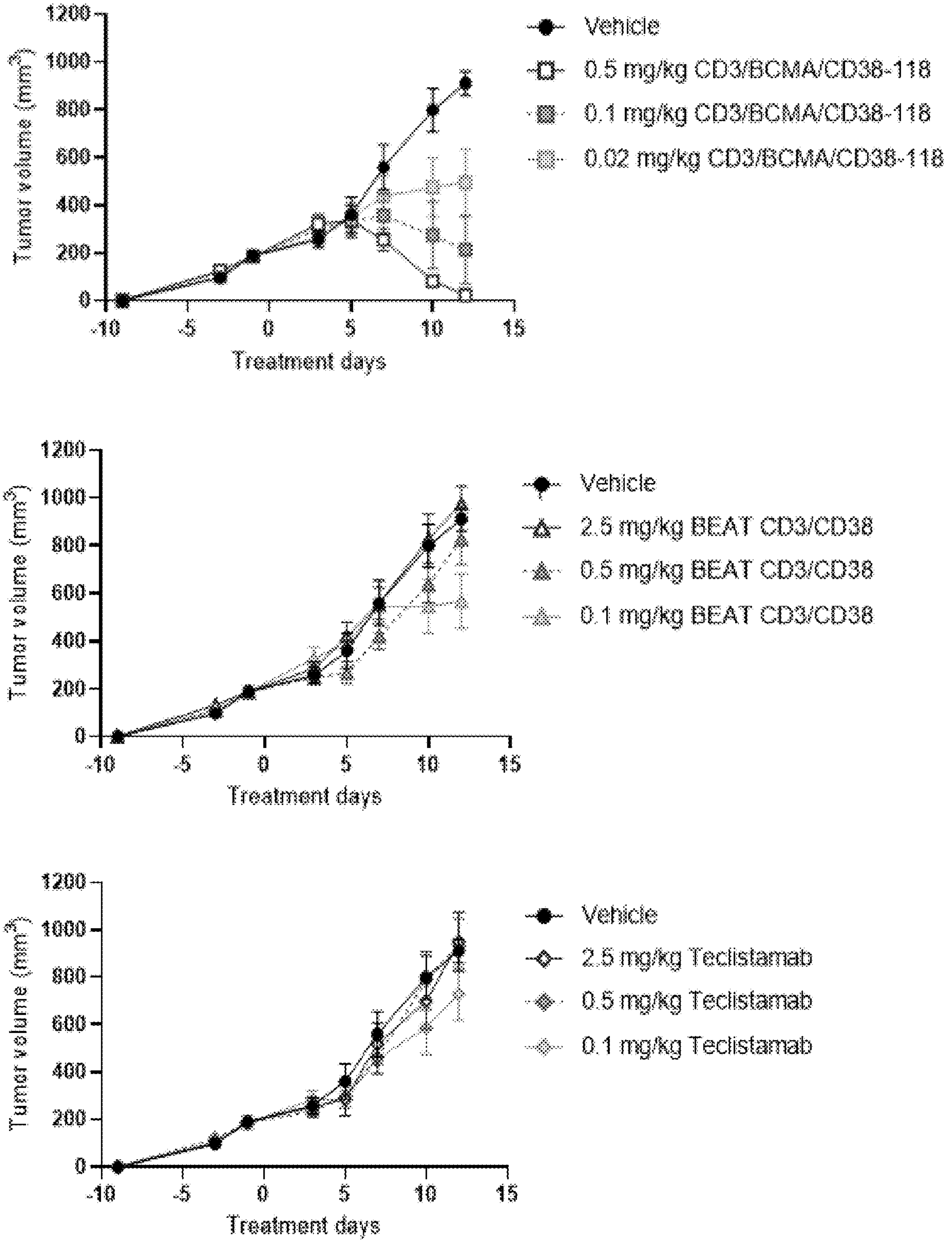
Figure 44B:
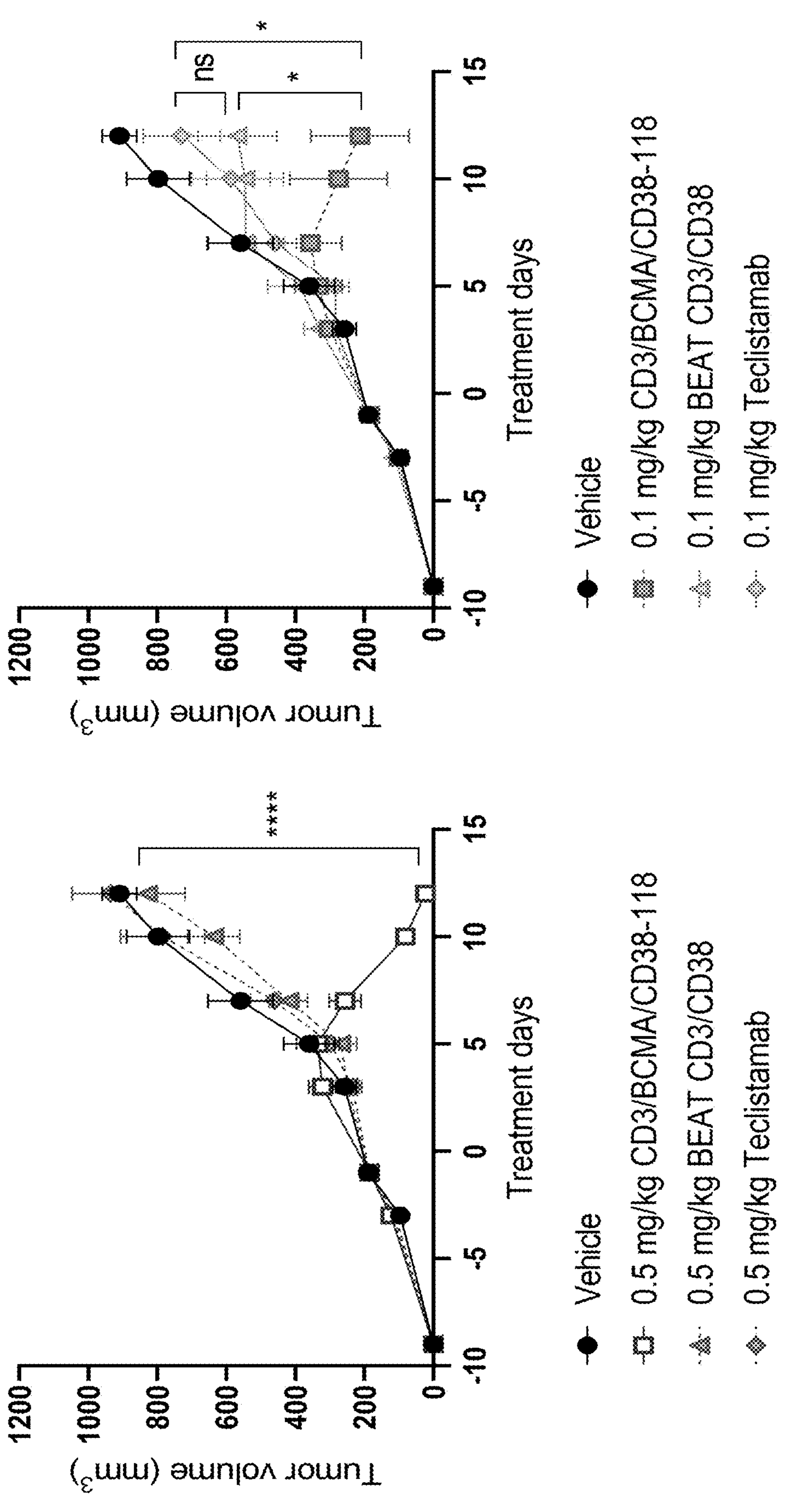
Figure 44C:
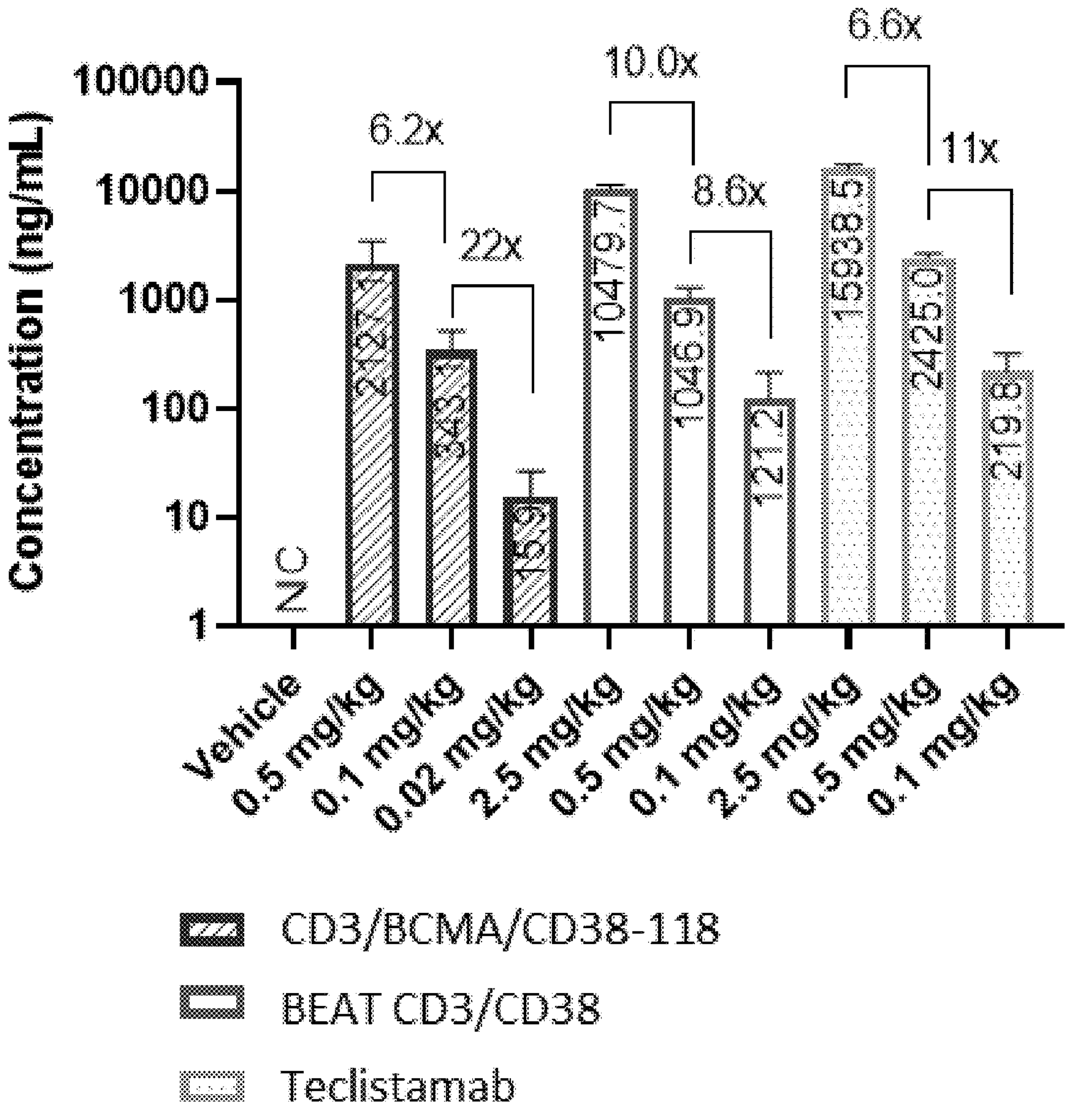

FIGS. 44A-44C. While CD3/BCMA/CD38-118 controls KMS-12-BM tumors in a dose dependent manner, BEAT CD3/CD38 and Teclistamab fail to delay tumor progression at high doses. NSG female mice were engrafted on day −9 s.c. with $1\times10^7$ KMS-12-BM MM tumor cells ($CD38^{low}$ and $BCMA^{low}$) and inoculated i.p. with $1\times10^7$ PBMCs from a healthy human donor (Donor C). Mice were randomized at day −1 when the average tumor volume reached around 187 $mm^3$ and treatments injected i.v. once per week for 3 weeks on days 0, 7 and 14. A. KMS-12-BM tumor growth following treatment with CD3/BCMA/CD38-118 (top); BEAT CD3/CD38 (middle) or Teclistamab (bottom) at the indicated doses in NSG mice inoculated with Donor C PBMCs (n=8 mice/group) (FIG. 44A). Mean±SEM are shown with Last Observation Carried Forward (LOCF). B. KMS-12-BM tumor growth following treatment with the indicated molecules at 0.5 mg/kg (left) or 0.1 mg/kg (right) dose in NSG mice inoculated with Donor C PBMCs (n=8 mice/group) (FIG. 44B). Mean±SEM are shown with Last Observation Carried Forward (LOCF). C. Serum concentrations (ng/mL) of the indicated molecules at the indicated doses on day 13, 14 or 21 (at trough exposure, either prior $3^{rd}$ dose (day 13/14) or one week later) in NSG mice inoculated with Donor C PBMCs (n=4-7 mice/group) (FIG. 44C). Mean±SD are shown, with values within bar representing mean concentrations and values above representing fold differences. NIC=no interpolated concentration.

Figure 45A:
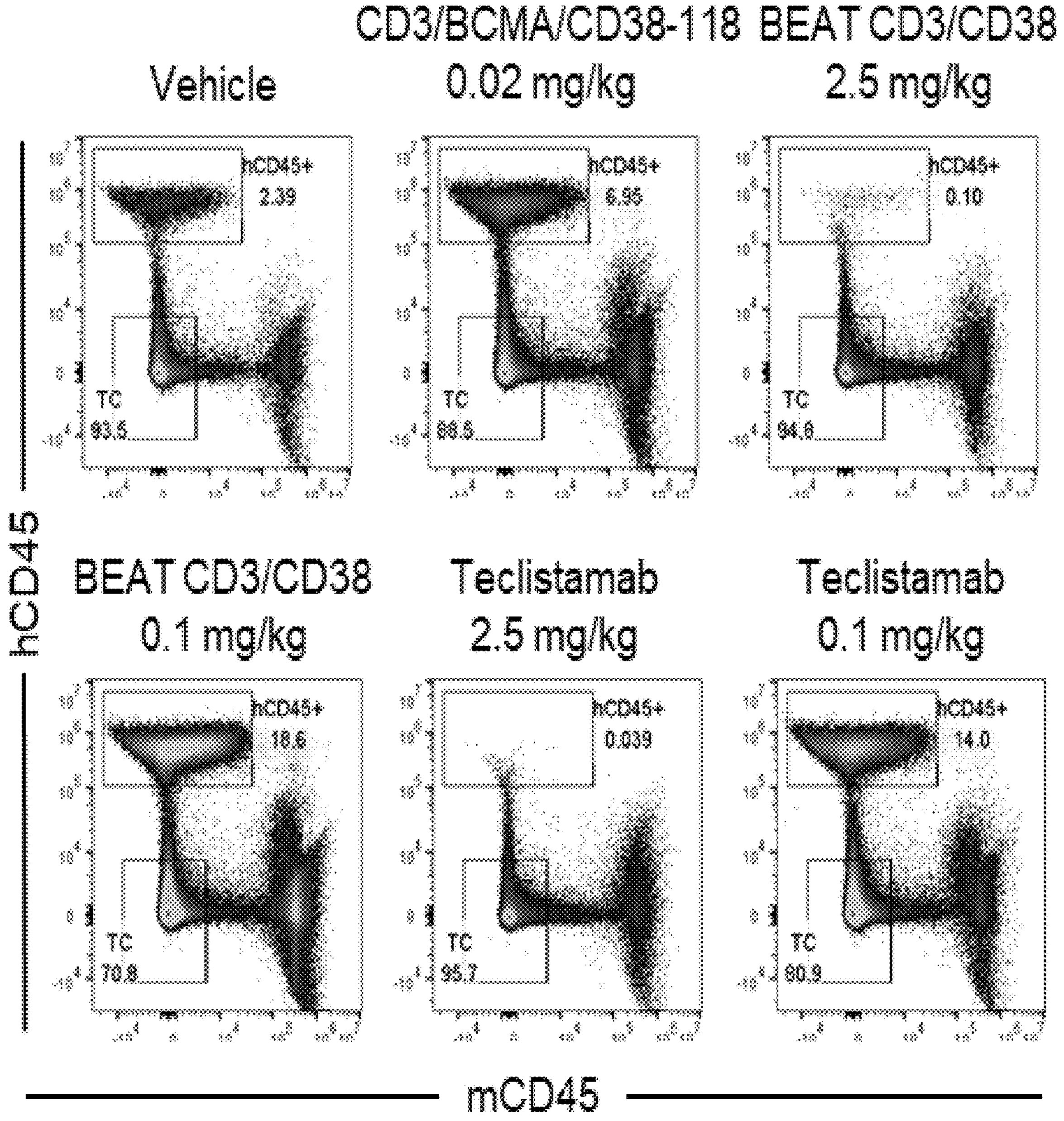
Figure 45B:
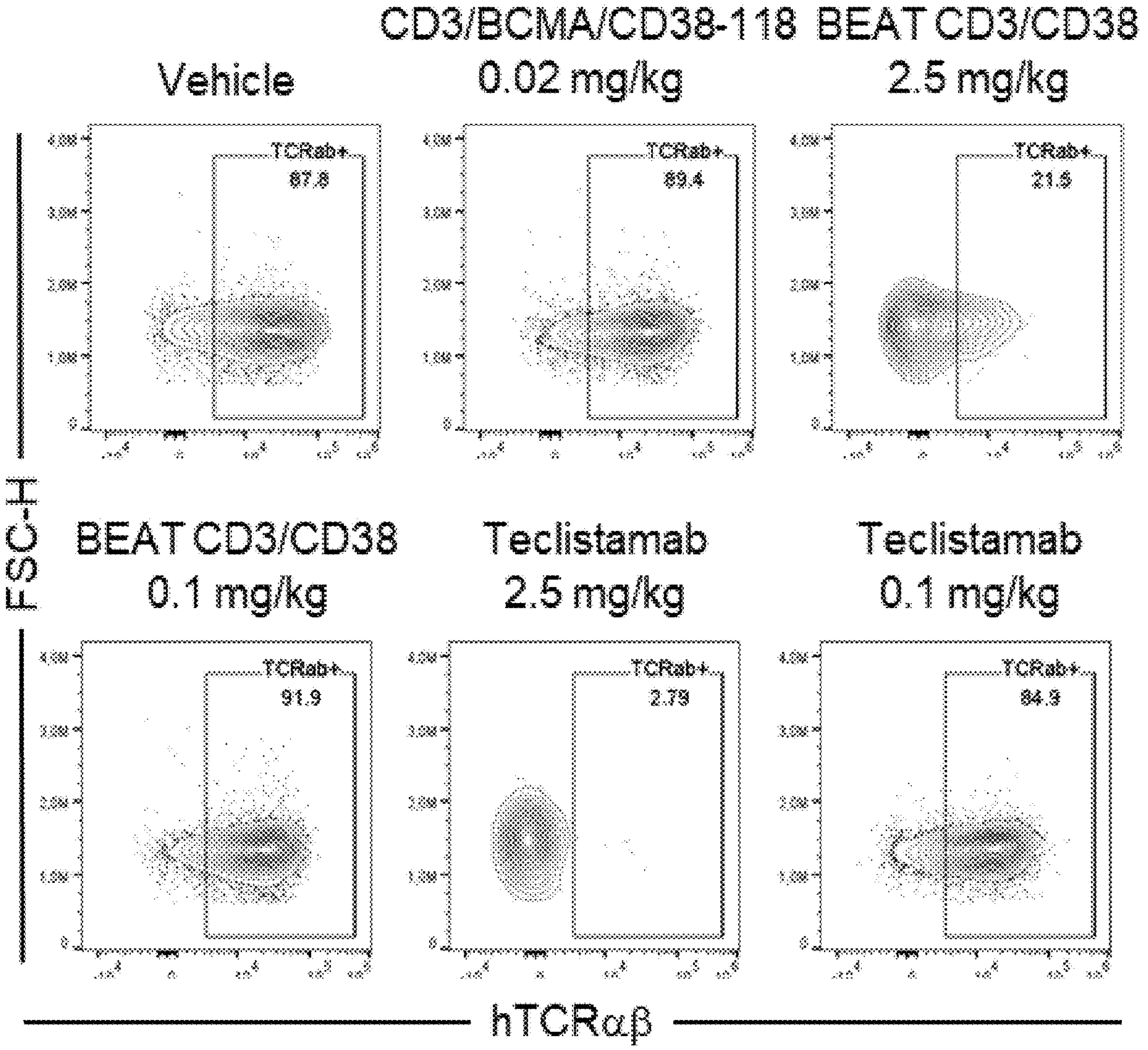
Figure 45C:
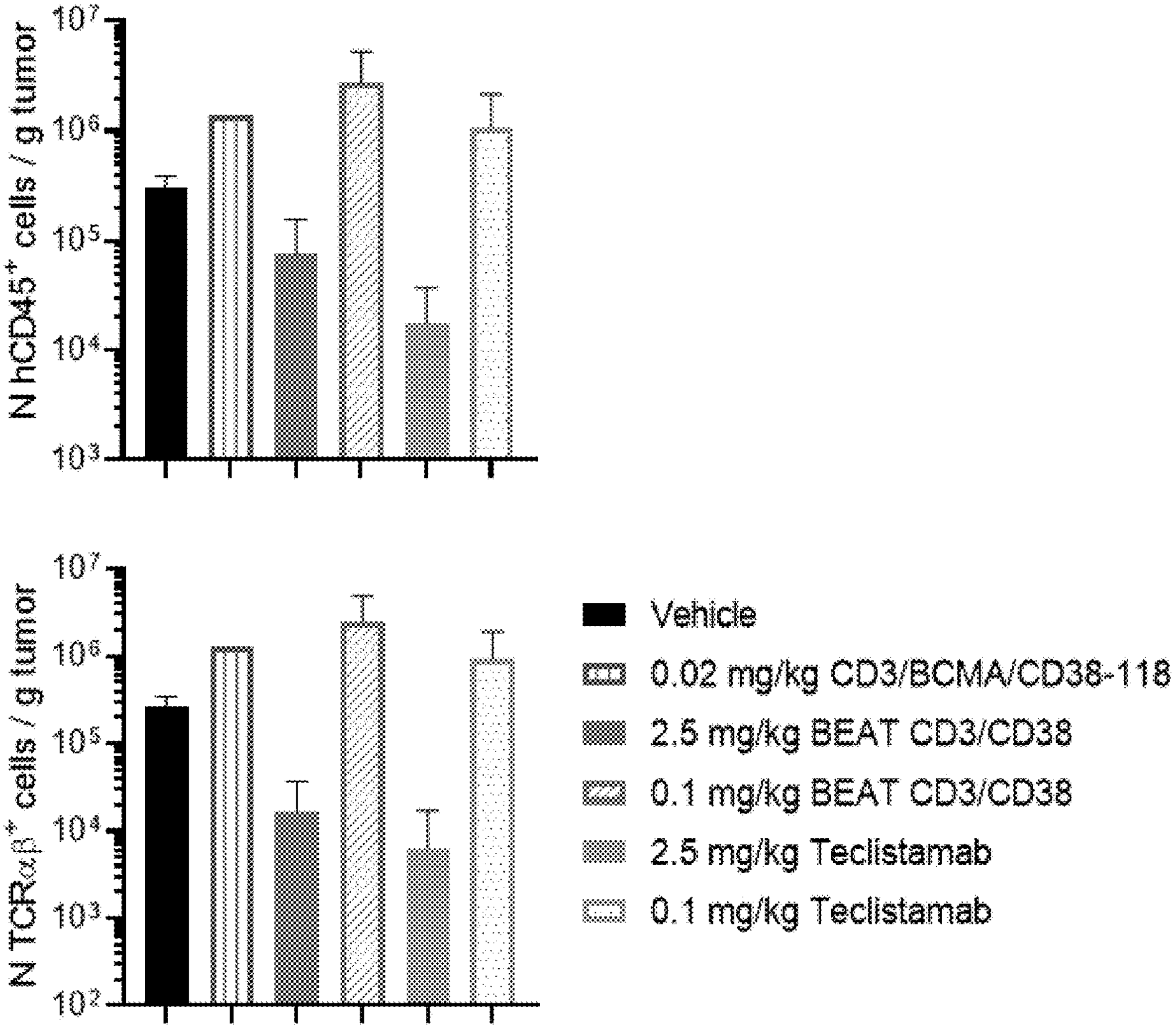
Figure 45D:
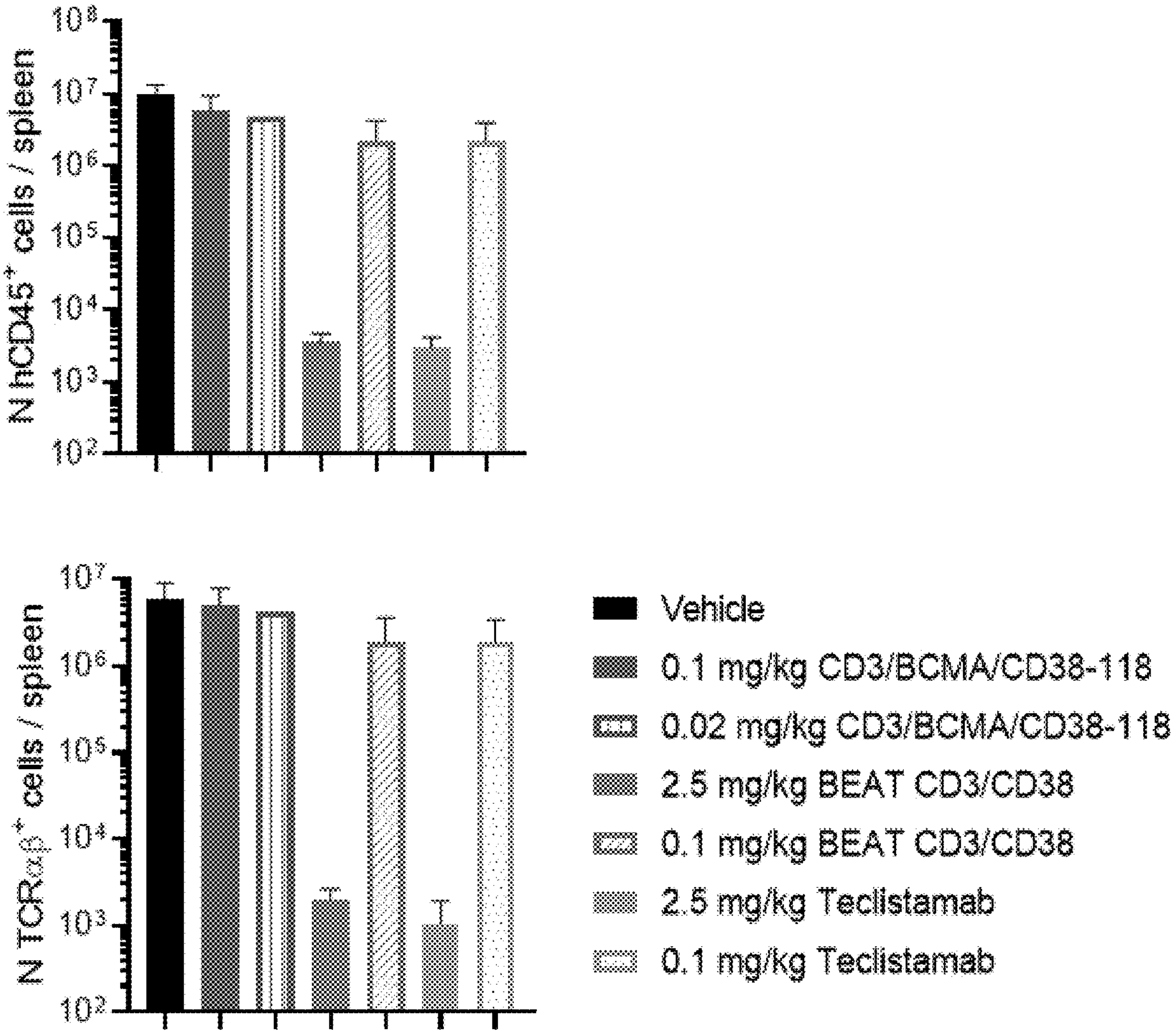

FIGS. 45A-45D. High doses of BEAT CD3/CD38 and Teclistamab induce reduction of the T cell compartment within the tumor microenvironment and in the periphery. NSG female mice engrafted with KMS-12-BM MM tumor cells and inoculated i.p. with PBMCs from a healthy human donor (Donor C) were treated i.v. with the indicated molecules at indicated doses on day zero, when the average tumor volume reached around 187 $mm^3$, and then once per week for 3 weeks. At day 13, tumors and spleens of treated mice were harvested and analysed ex vivo by flow cytometry (n=2-3 mice/group). A. Greyscale Pseudocolour plots show the expression of human CD45 vs mouse CD45 in gated live cells in the tumor (FIG. 45A). Numbers within plots indicate percentages of positive cells. B. Contour plots show the expression of human TCRab in tumor infiltrating $CD45^+$ cells (FIG. 45B). Numbers within plots indicate percentages of positive cells. C. Graphs depict number of human $CD45^+$ (top) and human $TCRab^+$ (bottom) cells per gram of tumor (FIG. 45C). Mean±SD are shown. D. Graphs depict number of human $CD45^+$ (top) and human $TCRab^+$ (bottom) cells in the spleen of treated mice (FIG. 45D). Mean±SD are shown.

FIGS. 46A-46D. Treatment with BEAT CD3/CD38+IVIG rescued the T cell compartment and improved in vivo efficacy against KMS-12-BM tumors. NSG female mice were engrafted on day −9 s.c. with $1\times10^7$ KMS-12-BM MM tumor cells and inoculated i.p. with $1\times10^7$ PBMCs from a healthy human donor (Donor E). Mice were randomized at day −1 when the average tumor volume reached around 120 $mm^3$ and injected i.v. on the same day with 200 mg/kg of IVIG (Privigen) or PBS, and then twice per week. Dosing (i.v.) of Vehicle, CD3/BCMA/CD38-118 at 0.5 mg/kg or BEAT CD3/CD38 at 0.5 mg/kg was performed on day zero and day seven. A. KMS-12-BM tumor growth curves following treatment with the indicated molecules in the presence or absence of IVIG in NSG mice inoculated with Donor E PBMCs (n=3-5 mice/group) (FIG. 46A). Mean±SEM are shown. B. Tumor volume of KMS-12-BM tumors at day 11 post treatment (study endpoint) with indicated molecules±IVIG (FIG. 46B). Mean±SD is shown. C, D. At day 11, tumors and spleens of treated mice were harvested and analysed ex vivo by flow cytometry (n=3-5 mice/group). C. Greyscale Pseudocolour plots show the expression of human CD45 vs mouse CD45 in gated live cells in the tumor (FIG. 46C). Numbers within plots indicate percentages of positive cells. D. Graphs depict number of human $CD45^+$ cells within gated live cells (top) and human $TCRab^+$ cells in gated human $CD45^+$ cells (bottom) per gram of tumor (FIG. 46D) or in the spleen (FIG. 46D (continuation)) of treated mice. Mean±SD are shown.

Figure 47A:
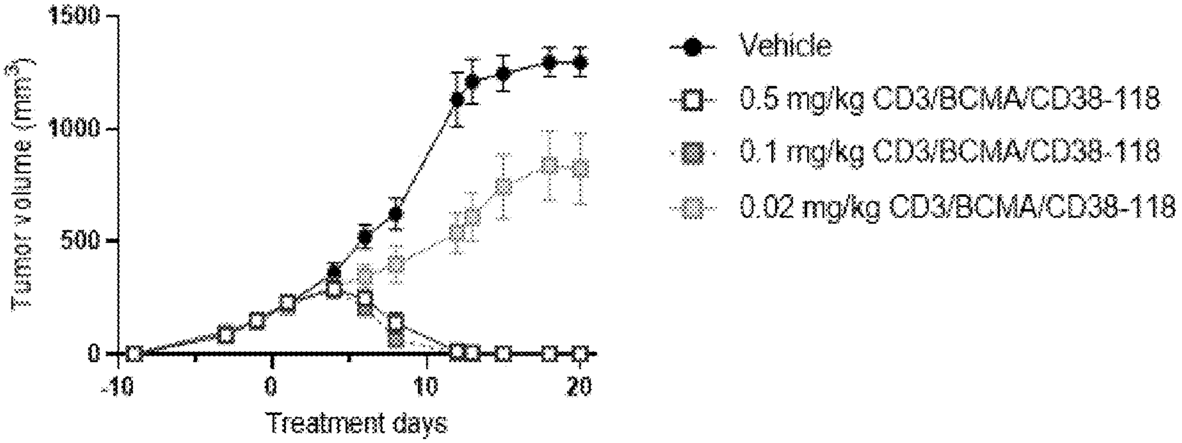
Figure 47A:
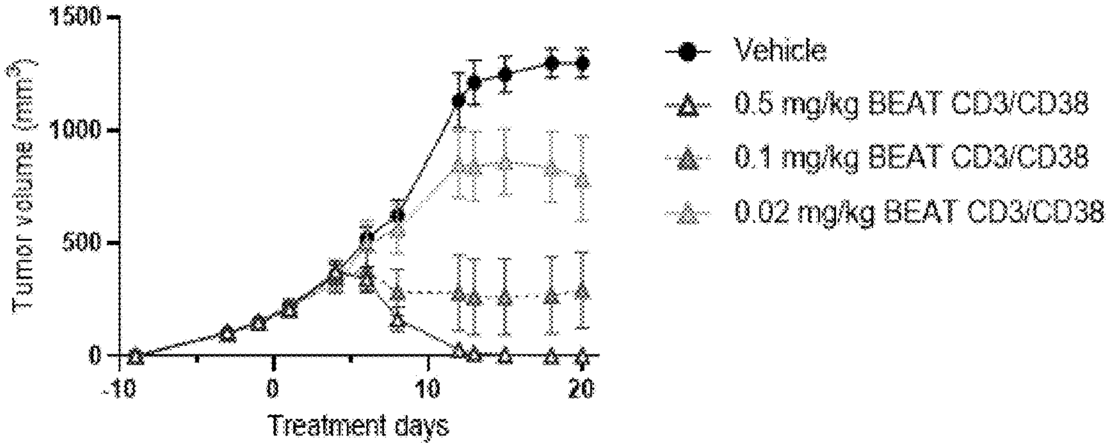
Figure 47A:
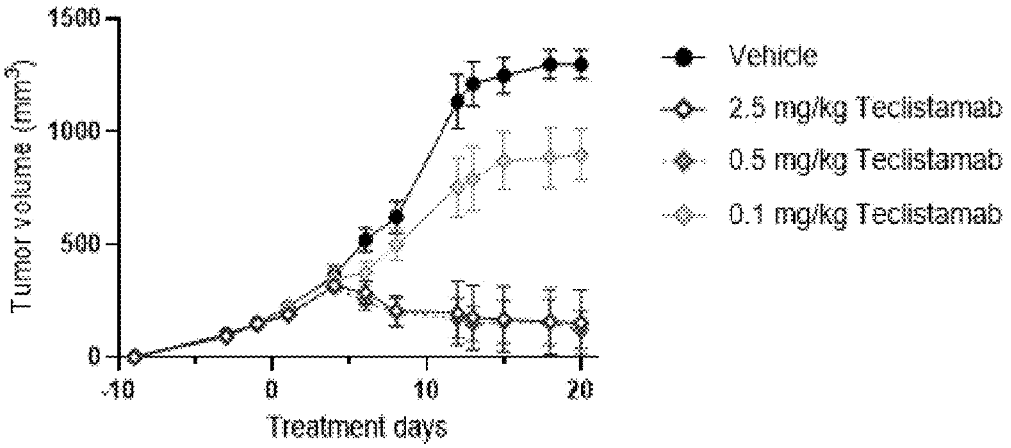
Figure 47B:
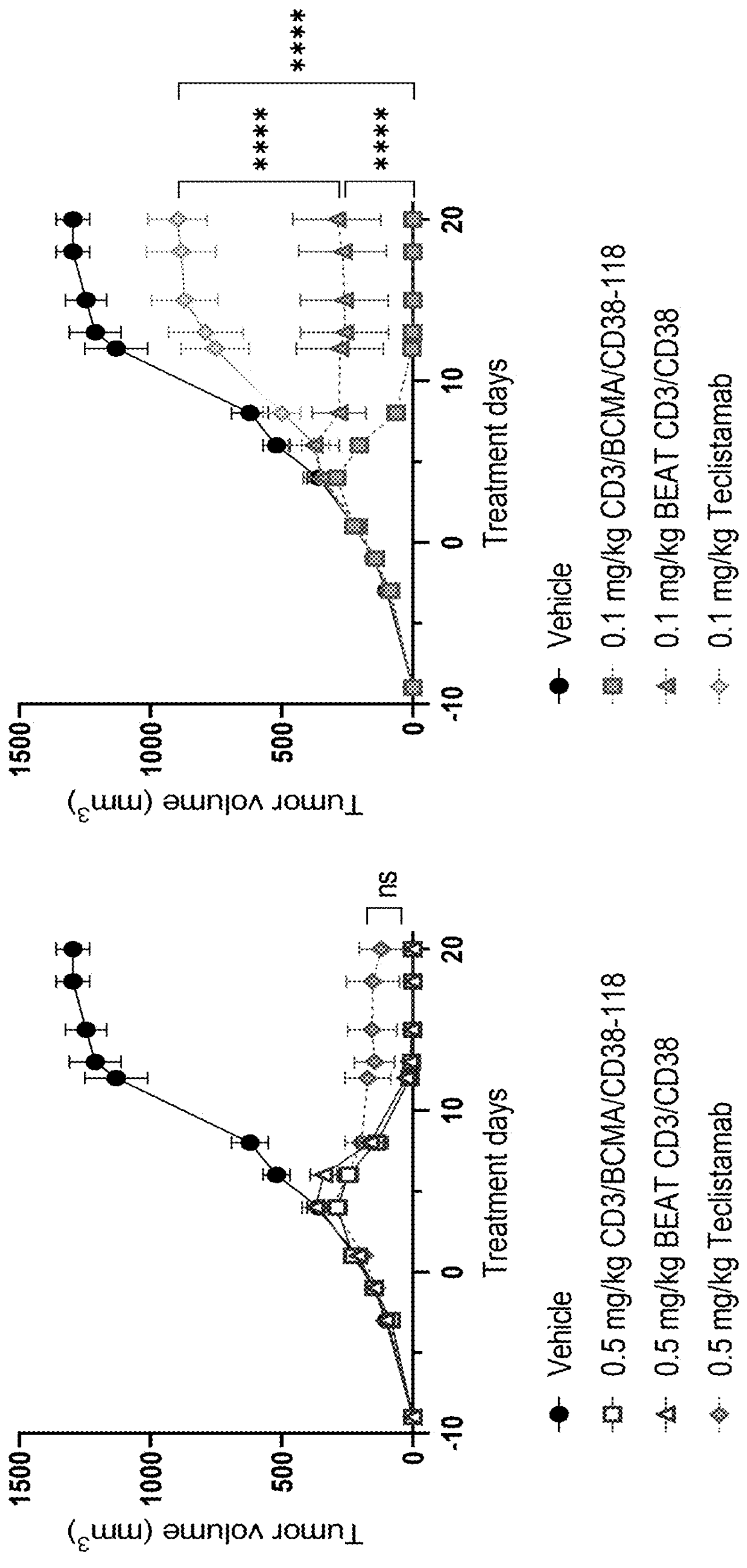
Figure 47C:
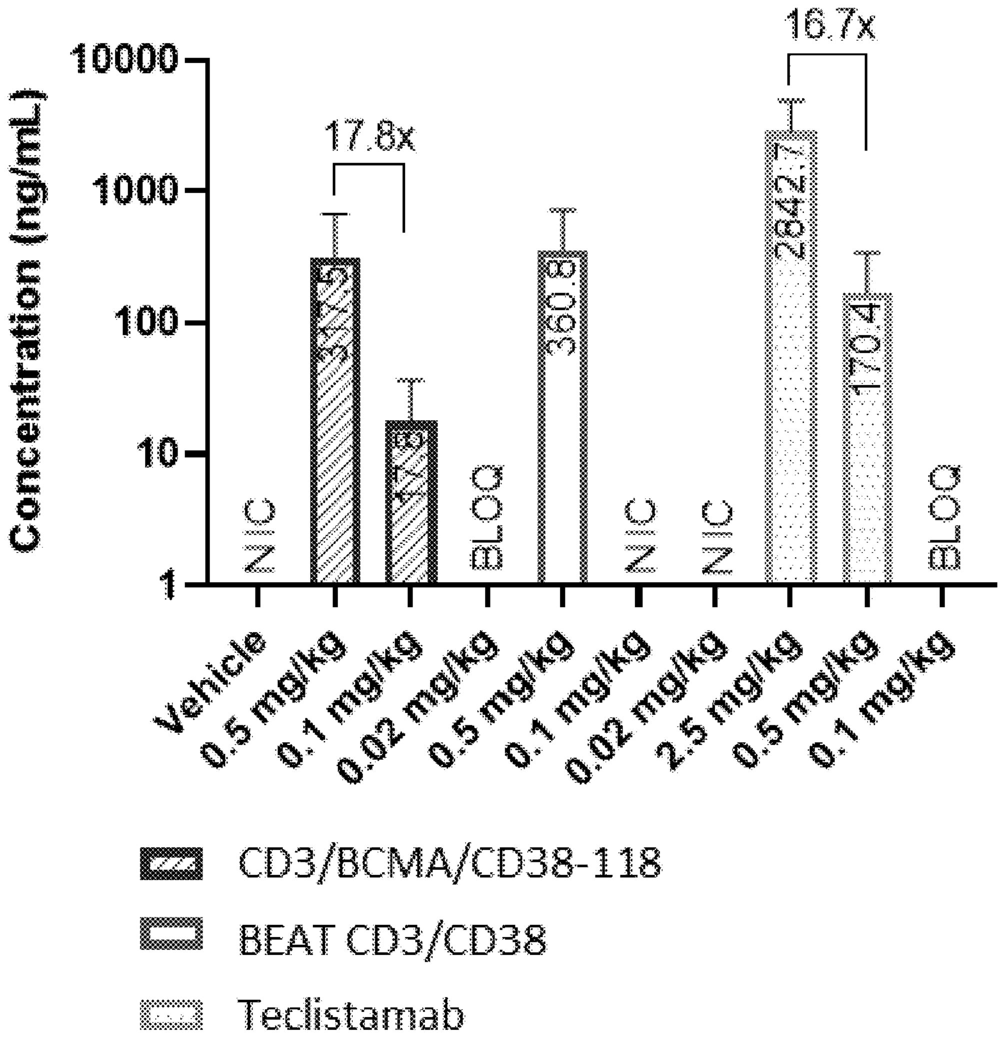

FIGS. 47A-47C. In the presence of IVIG, CD3/BCMA/CD38-118, BEAT CD3/CD38 and Teclistamab all induce regression of KMS-12-BM tumors at highest doses. NSG female mice were engrafted on day −9 s.c. with $1\times10^7$ KMS-12-BM MM tumor cells and inoculated i.p. with $1\times10^7$ PBMCs from a healthy human donor (Donor C). Mice were randomized at day −1 when the average tumor volume reached around 147 $mm^3$ and injected i.v. on the same day with 200 mg/kg of IVIG (Privigen), and then once per week for 3 weeks (day −1, 6 and 13). Dosing (i.v.) of Vehicle, CD3/BCMA/CD38-118 and BEAT CD3/CD38 at 0.5, 0.1 and 0.02 mg/kg and Teclistamab at 2.5, 0.5 and 0.1 mg/kg was performed on day 0, 7 and 14 (once per week for 3 weeks). A. KMS-12-BM tumor growth following treatment with CD3/BCMA/CD38-118 (top); BEAT CD3/CD38 (middle) or Teclistamab (bottom) at the indicated doses in NSG mice inoculated with Donor C PBMCs (n=6-8 mice/group) (FIG. 47A). Mean±SEM are shown with Last Observation Carried Forward (LOCF). B. KMS-12-BM tumor growth following treatment with the indicated molecules at 0.5 mg/kg (left) or 0.1 mg/kg (right) dose in NSG mice inoculated with Donor C PBMCs (n=6-8 mice/group) (FIG. 47B). Mean±SEM are shown with Last Observation Carried Forward (LOCF). C. Serum concentrations (ng/mL) of the indicated molecules at the indicated doses on day 21 (at through exposure, 1 week post $3^{rd}$ dose) in NSG mice inoculated with Donor C PBMCs (n=6-8 mice/group) (FIG. 47C). Mean±SD are shown, with values within bar representing mean concentrations and values above representing fold differences. NIC=no interpolated concentration; BLOQ=below limit of quantification.

Figure 48A:
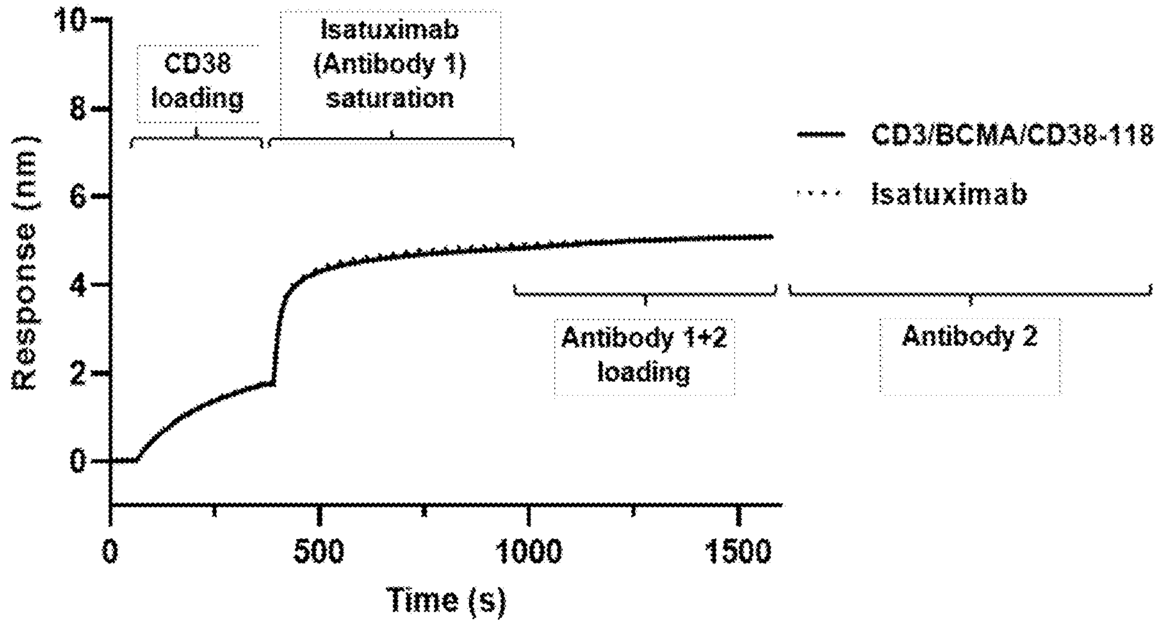
Figure 48B:
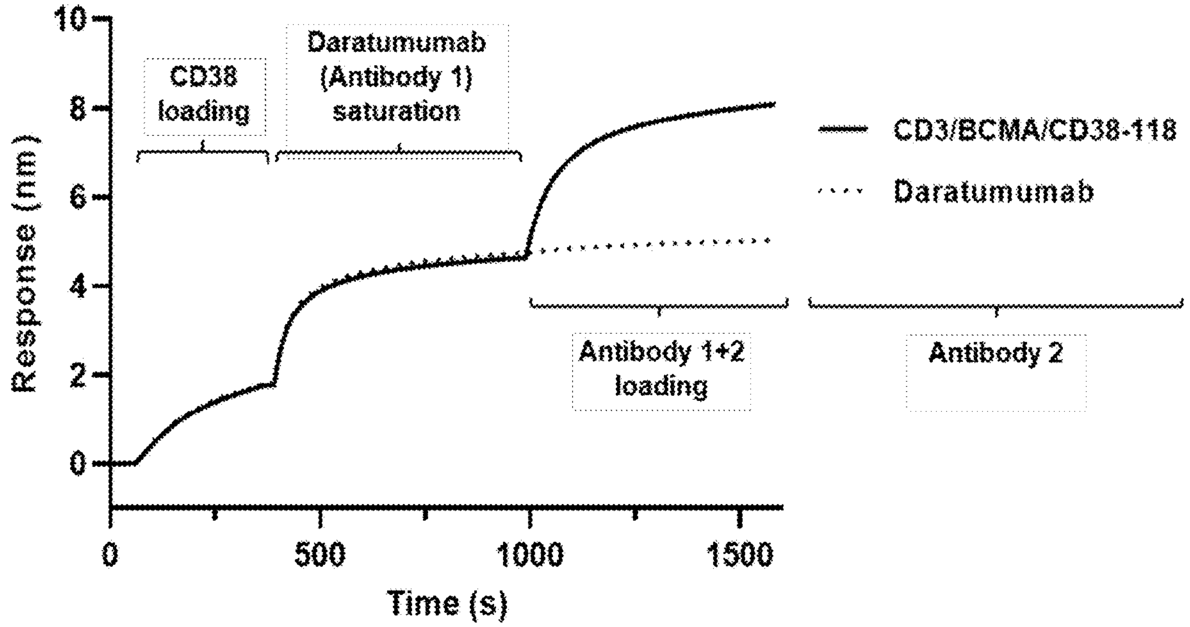

FIGS. 48A-48B. Competition of CD3/BCMA/CD38-118 to isatuximab and to daratumumab for binding to recombinant human CD38 using Octet Bio-Layer Interferometry. Biotinylated human CD38-avi-his protein was loaded on a streptavidin SA Biosensor. CD38 loaded biosensor was dipped into a solution of antibody 1 at 200 nM in kinetic buffer to reach saturation of the surface. Then, saturated biosensor was dipped into a pre-mixed solution of antibody 1 and antibody 2 at 200 nM final concentration each (competition phase). Same experimental procedure was performed using a solution of antibody 1 at 400 nM alone in the competition phase as control for surface saturation. Plots show binding to the sensor tip as a wavelength shift (Response, in nm; y-axis) vs. time (x-axis) for A) isatuximab (FIG. 48A) and B) daratumumab (FIG. 48B) as antibody 1 (saturating antibody), respectively. Curves are labelled by antibody name.

Figure 49:
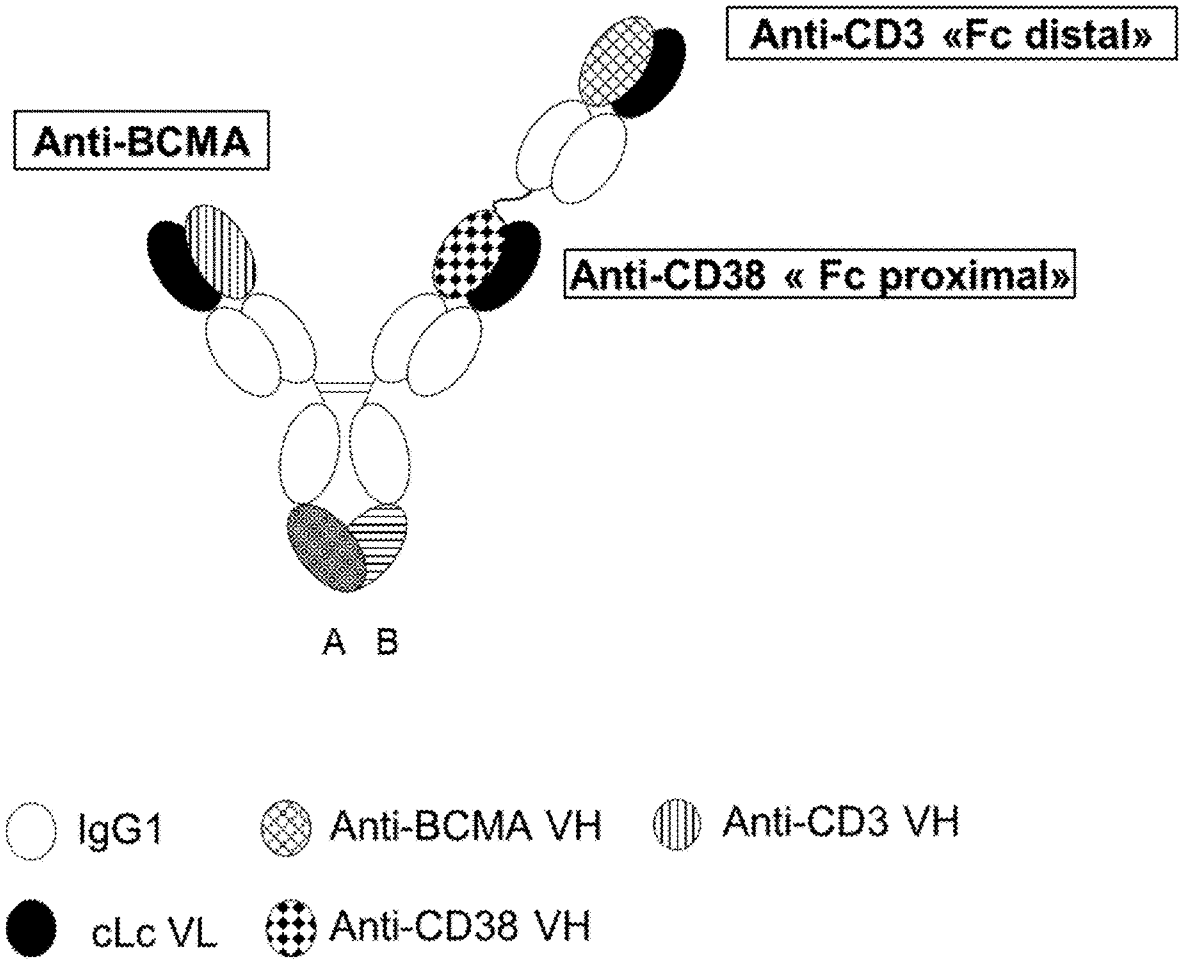

FIG. 49. Schematic drawing of additional CD3/BCMA/CD38 trispecific antibodies. CD3/BCMA/CD38 antibodies were constructed with three Fabs targeting three separate antigens, whereby the "Fc distal" Fab domain was fused to the N-terminus of the VH domain of the "Fc proximal" Fab. In this configuration D, CD3/BCMA/CD38, the CD3 binding arm in the outer, Fc distal position of the B arm and the CD38 binder in the "Fc proximal" position of the B arm, while the BCMA binder is place on the A arm.

Figure 50A:
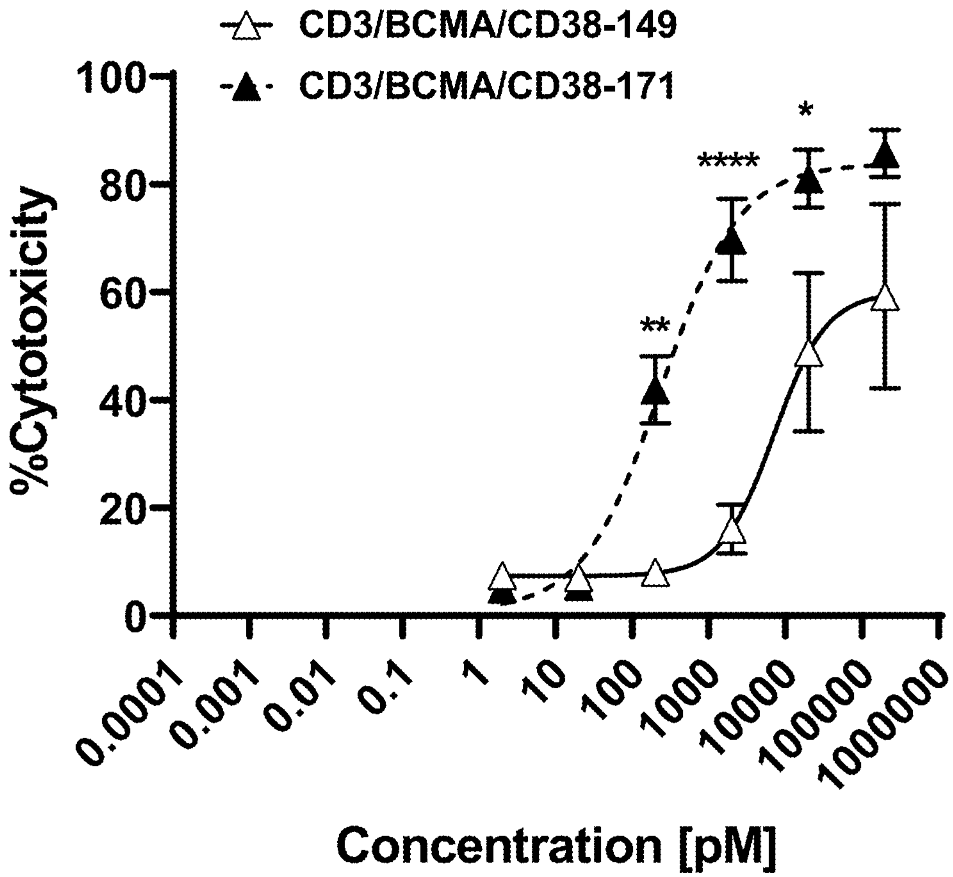
Figure 50B:
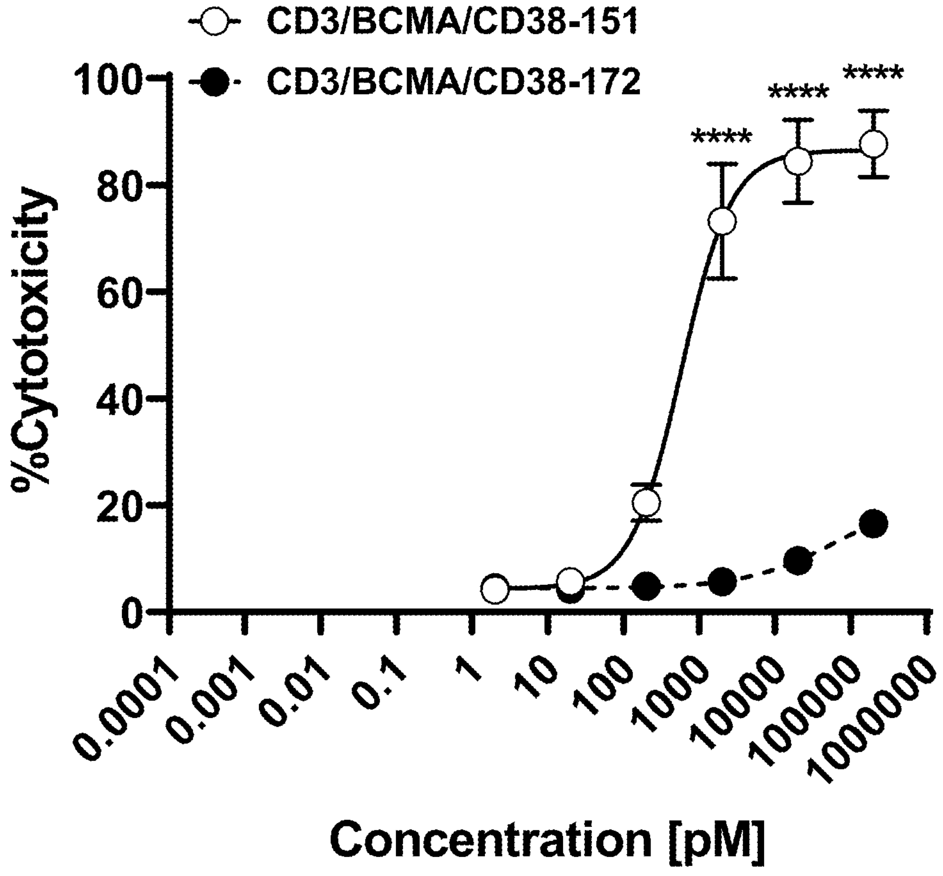
Figure 50C:
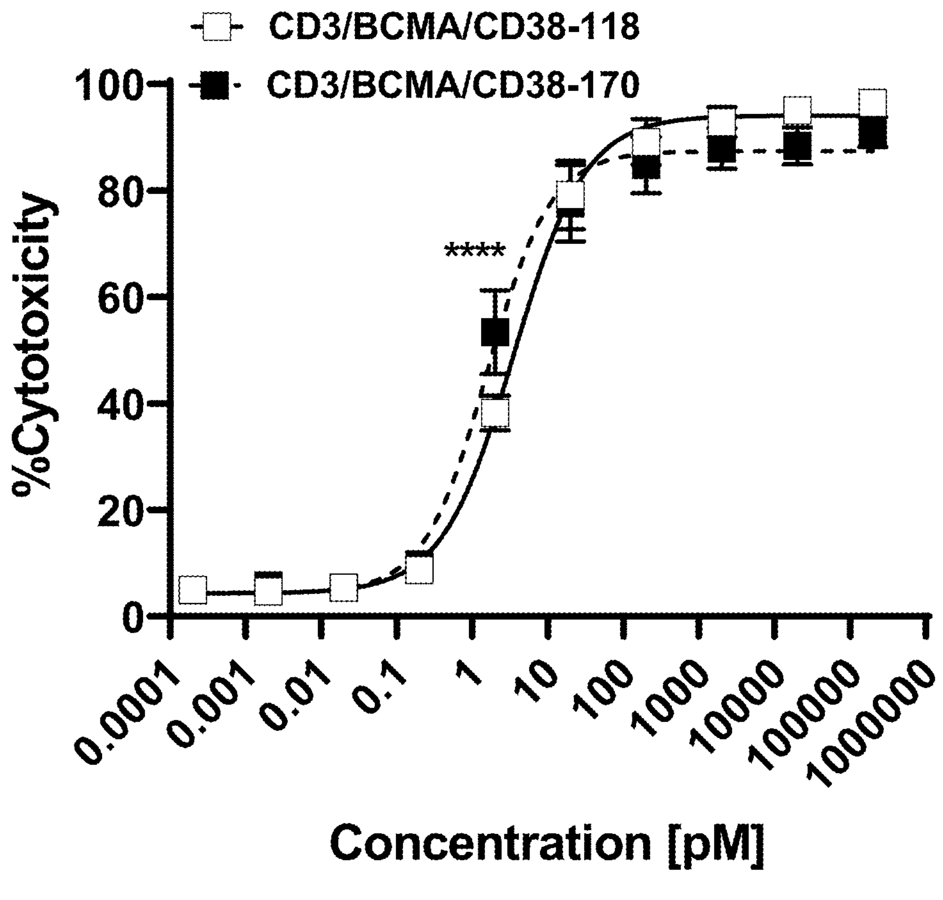

FIGS. 50A-50C. The positioning of binders in CD3/BCMA/CD38 antibodies affects their cytotoxic killing potency. The ability of CD3/BCMA/CD38-118 and control antibodies CD3/BCMA/CD38-149, -151, -170, -171 and -172 to trigger T cell mediated killing of KMS-12-BM tumor cells was assessed in a redirected lysis assay with a 5:1 effector-to-target ratio using isolated T cells. The percentage of cytotoxicity at different concentrations is shown for CD3/BCMA/CD38-149 and CD3/BCMA/CD38-171, FIG. 50A; CD3/BCMA/CD38-151 and CD3/BCMA/CD38-172, FIG. 50B; CD3/BCMA/CD38-118 and CD3/BCMA/CD38-170, FIG. 50C. Each curve is a nonlinear logistic 4PL model with variable slope and symbols represent Mean+/−SEM for six individual T cell donors. Percentages of killing were compared using a paired two-way ANOVA analysis followed by a Sidak's multiple comparisons test (*: p=0.05-0.01; : p=0.01-0.001; *: p0.001-0.0001; ****: p<0.0001). Experimental setup and analysis are described in Example 25b.

Figure 51A:
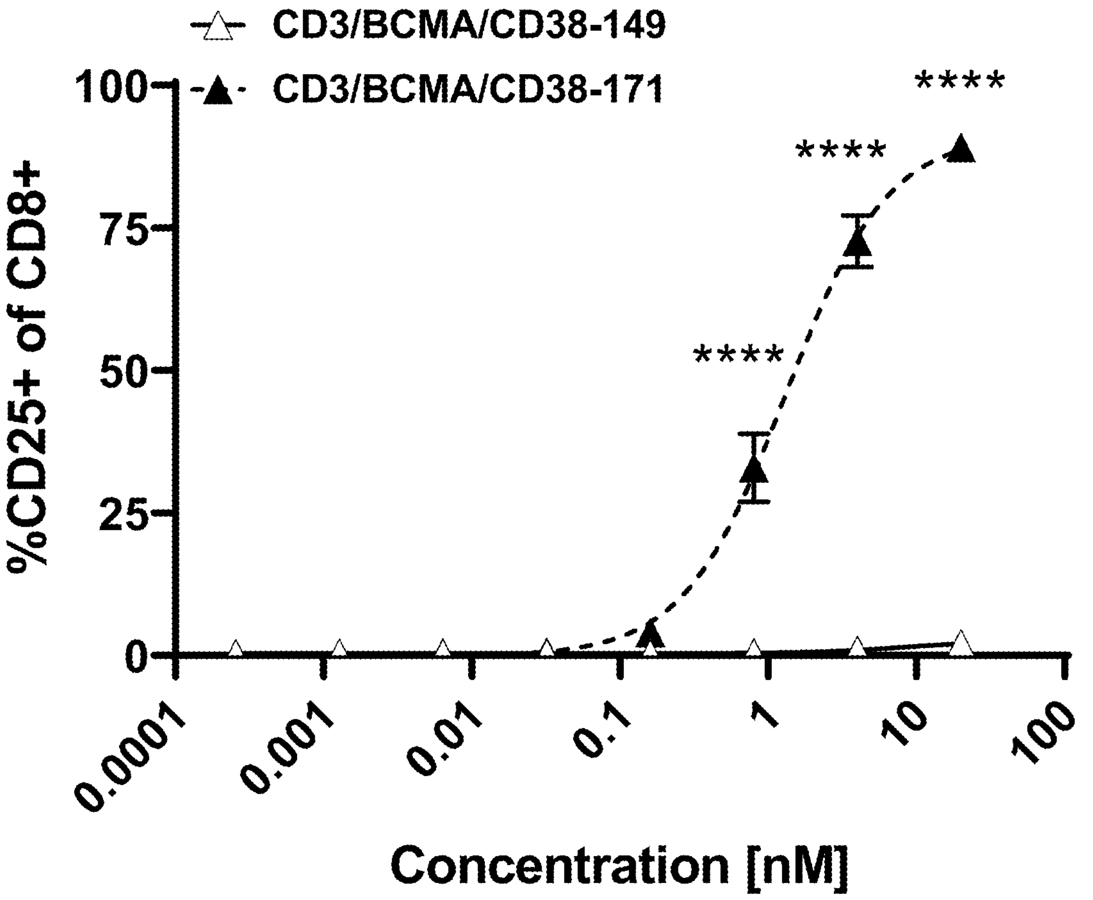
Figure 51B:
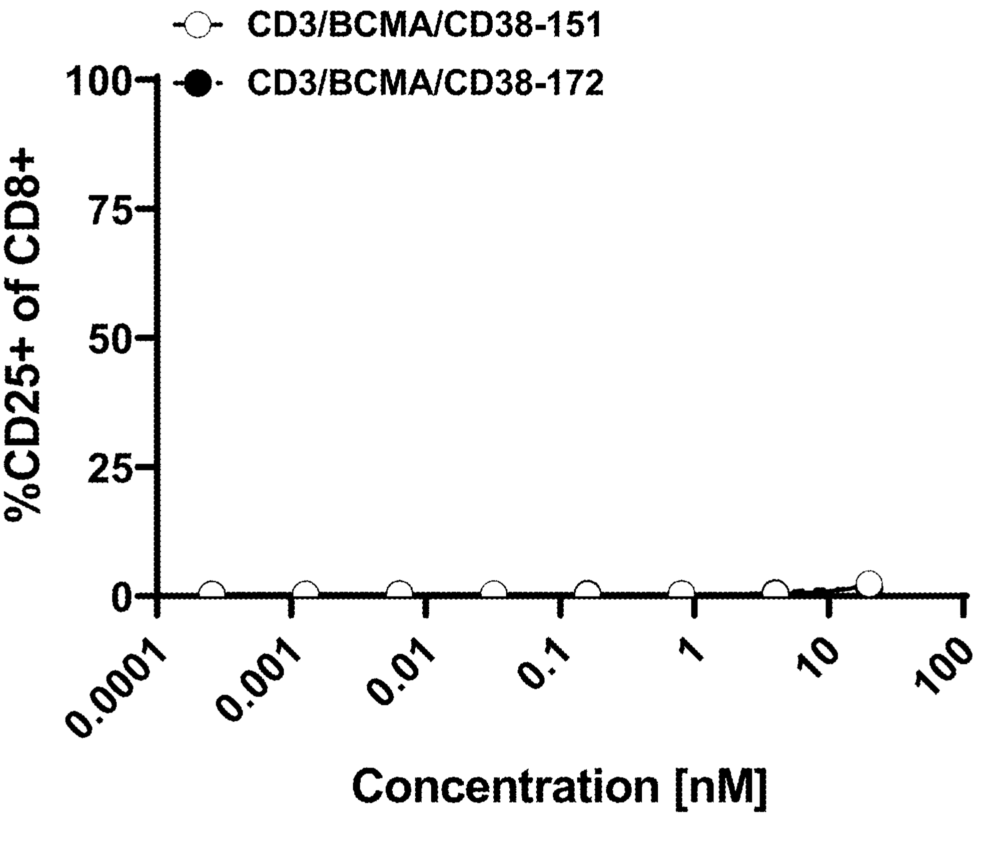
Figure 51C:
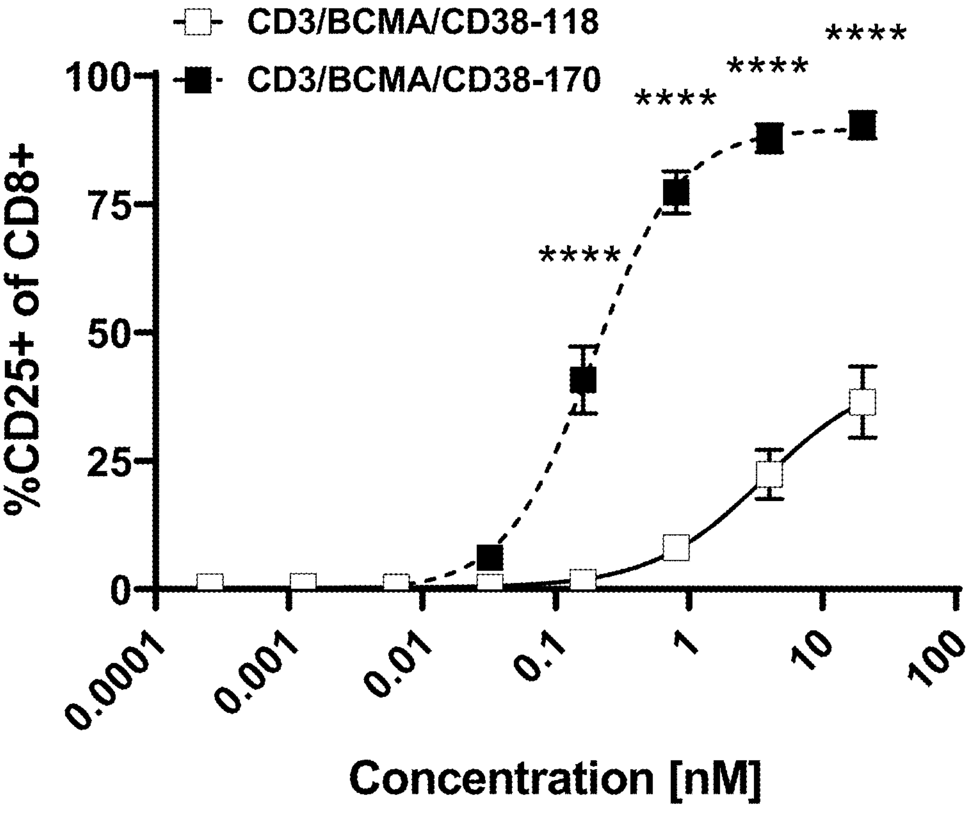

FIG. 51A-51C. The positioning of binders in CD3/BCMA/CD38 antibodies affects their on-target off-tumor T cell activation. The propensity of CD3/BCMA/CD38-118 and control antibodies CD3/BCMA/CD38-149, -151, -170, -171 and -172 to induce on-target off-tumor T cell activation was evaluated by measuring the upregulation of CD25 activation marker on CD8+ T cells in a high density PBMC assay. The percentage of CD8+ T cells expressing CD25 is shown for CD3/BCMA/CD38-149 and CD3/BCMA/CD38-171, FIG. 51A; CD3/BCMA/CD38-151 and CD3/BCMA/CD38-172, FIG. 51B; CD3/BCMA/CD38-118 and CD3/BCMA/CD38-170, FIG. 51C. Each curve is a nonlinear logistic 4PL model with variable slope and symbols represent Mean+/−SEM for six individual donors. Percentages of CD8+ T cells expressing CD25 were compared using a paired two-way ANOVA analysis followed by a Sidak's multiple comparisons test (*: p=0.05-0.01; : p=0.01-0.001; *: p0.001-0.0001; ****: p<0.0001). Experimental setup and analysis are described in Example 25b.

Figure 52A:
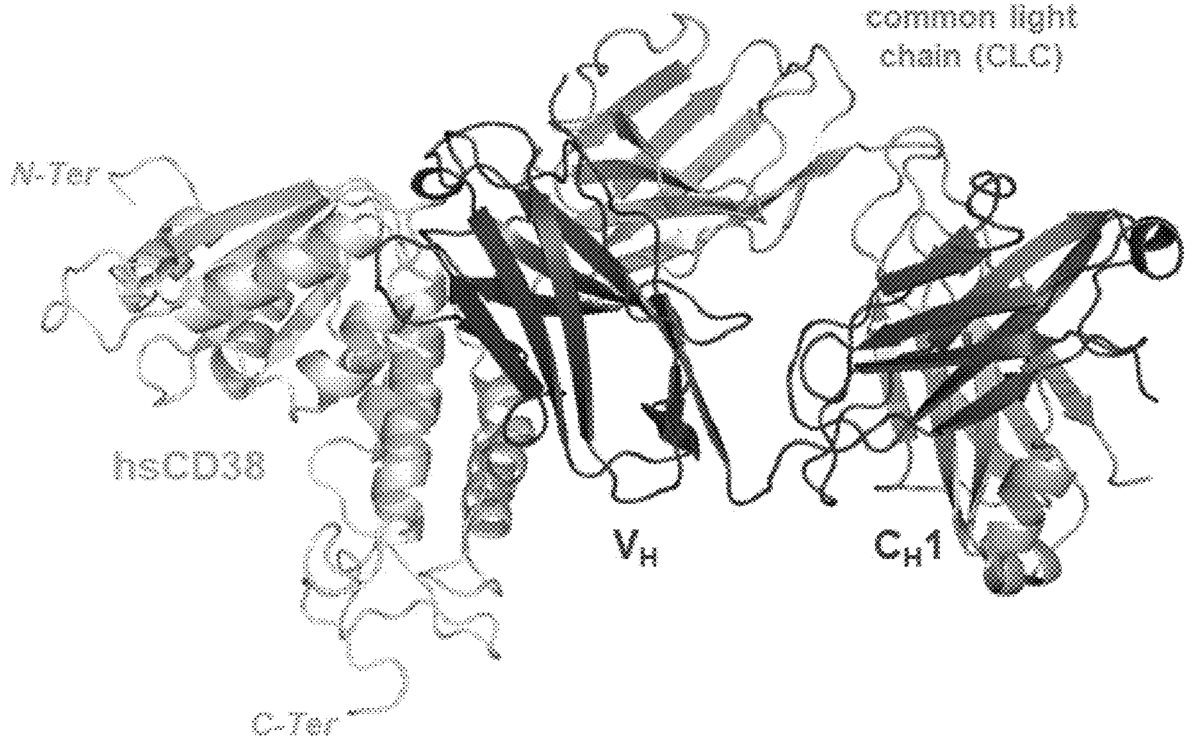
Figure 52B:
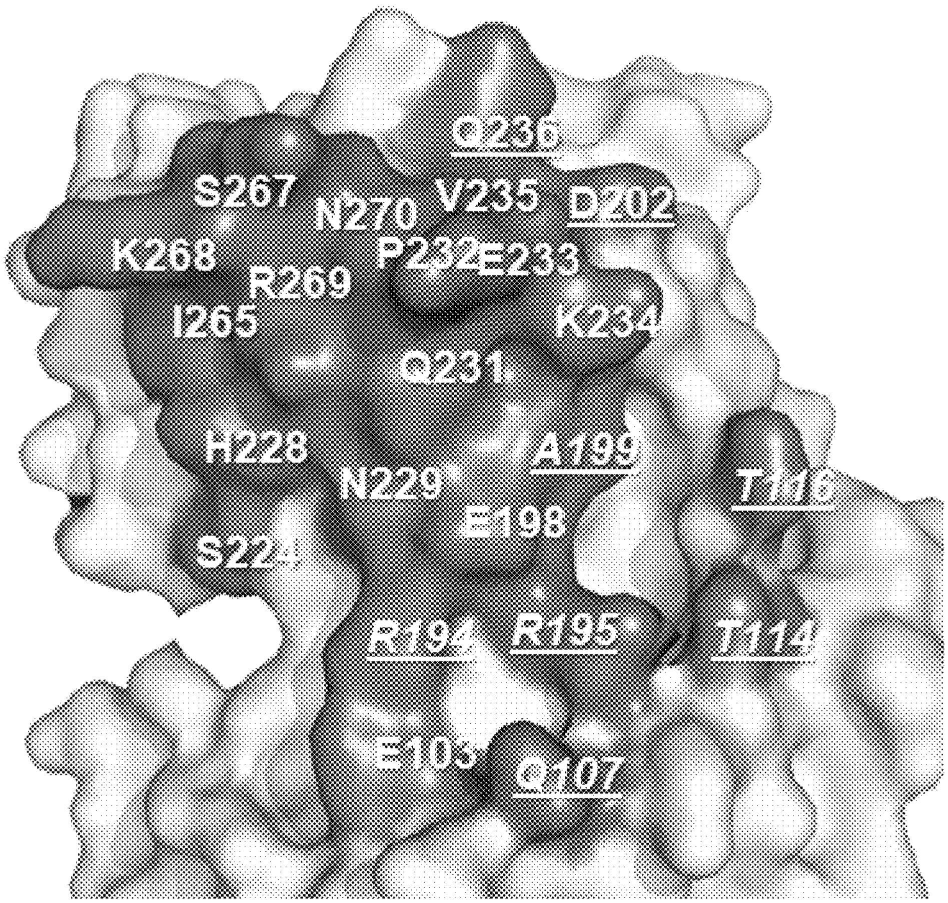
Figure 52C:
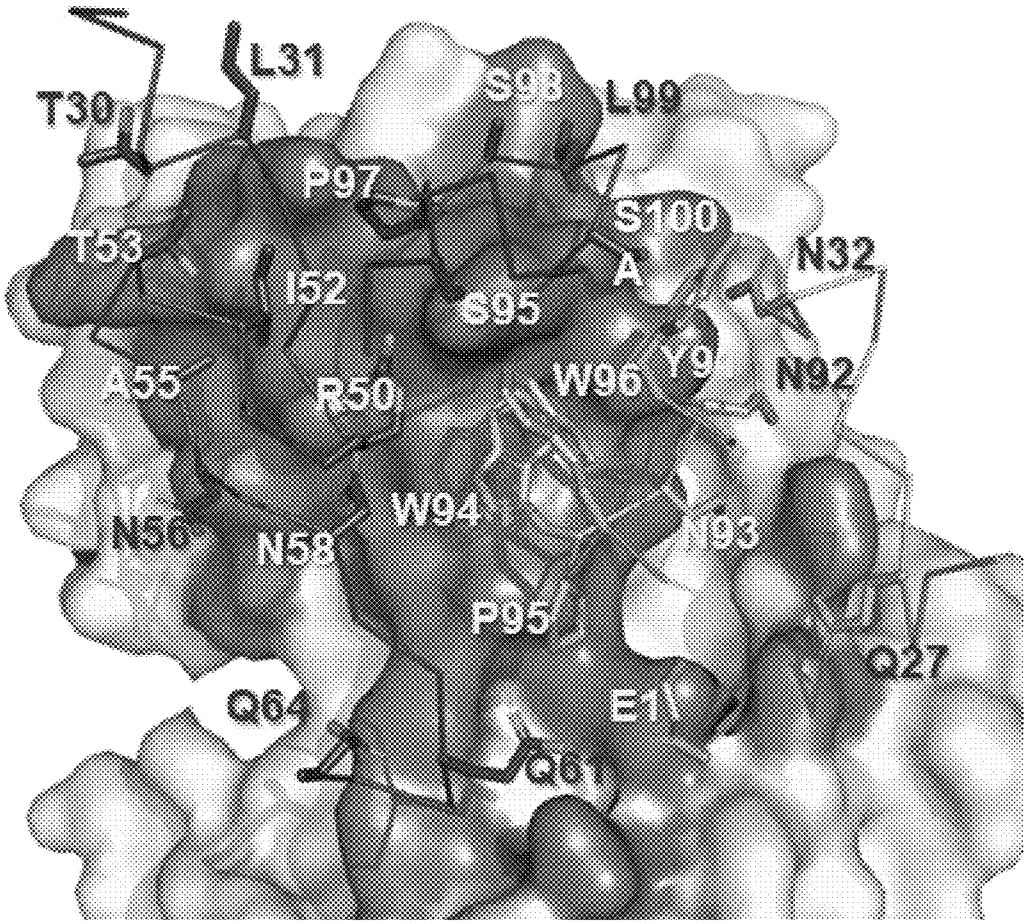

FIGS. 52A-52C. Crystal structure of human CD38 in complex with the anti-CD38-B3. (FIG. 52A) The overall structure of anti-CD38-B3/hsCD38 complex. hsCD38 is shaded in light gray, Fab heavy chain in black and Fab light chain in gray. (FIG. 52B) Footprint of anti-CD38-B3 on CD38 highlighting CD38 residues interacting with B3. Residues underlined correspond to residues shared between the epitope of B3 and daratumumab. Residues in italic and underlined correspond to residues shared between the epitope of anti-CD38-B3 and isatuximab. (FIG. 52C) Surface representation of the anti-CD38-B3 epitope on CD38 with side chains of interacting residues from B3 shown as stick. HCDRs in dark gray and LCDRs in gray. Experimental setup and analysis are described in Example 26.

Figure 53A:
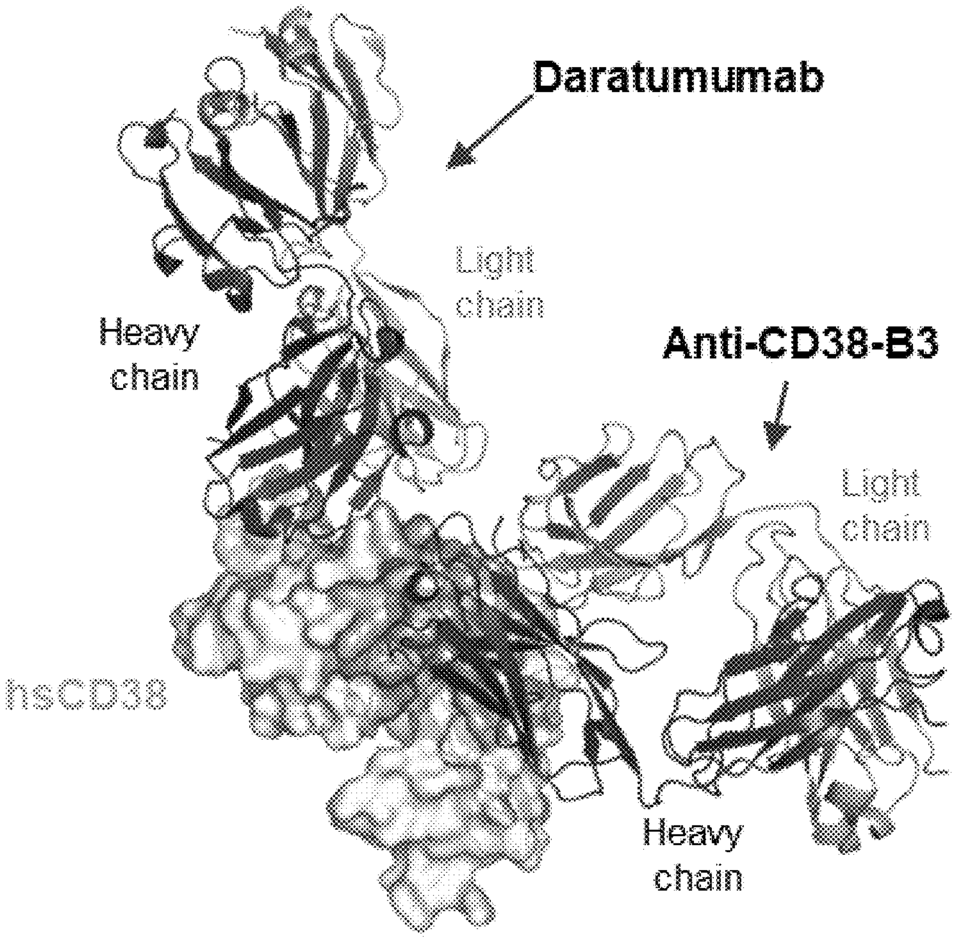
Figure 53B:
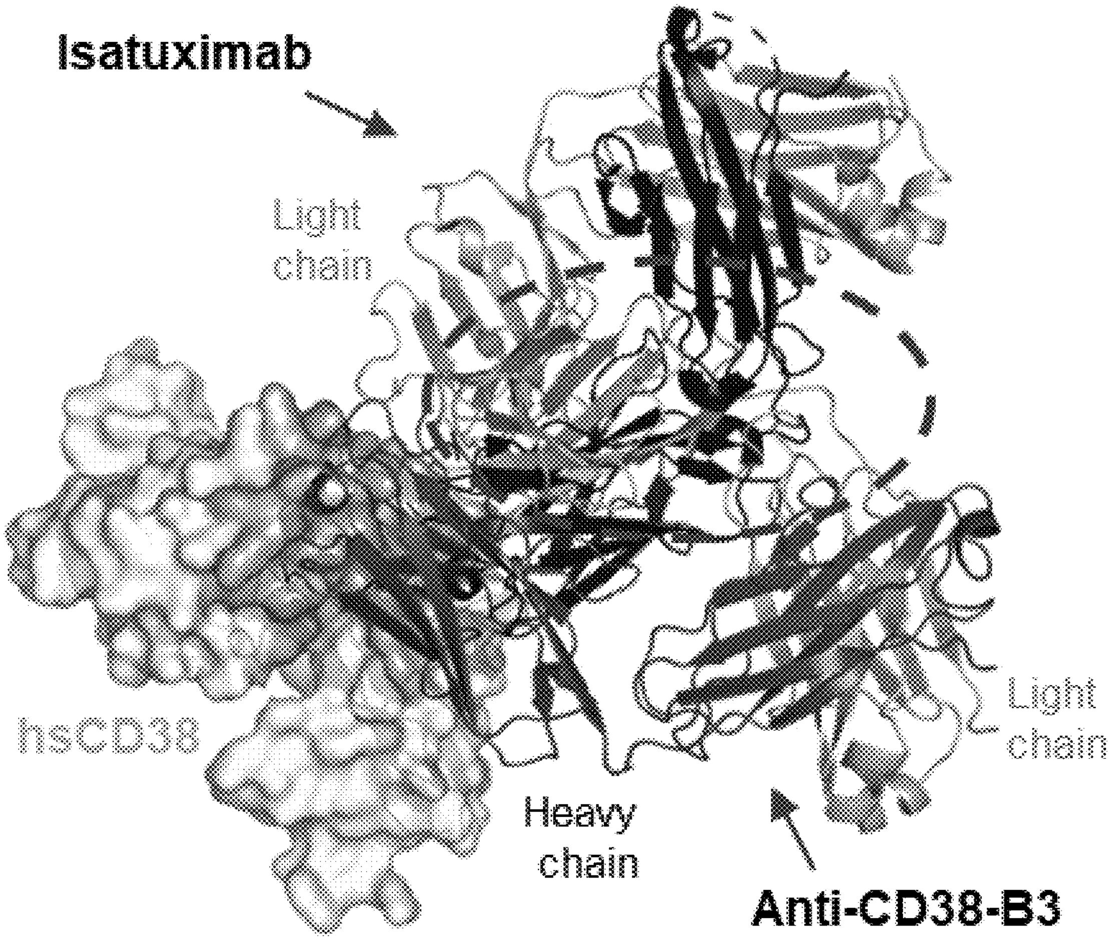
Figure 53C:
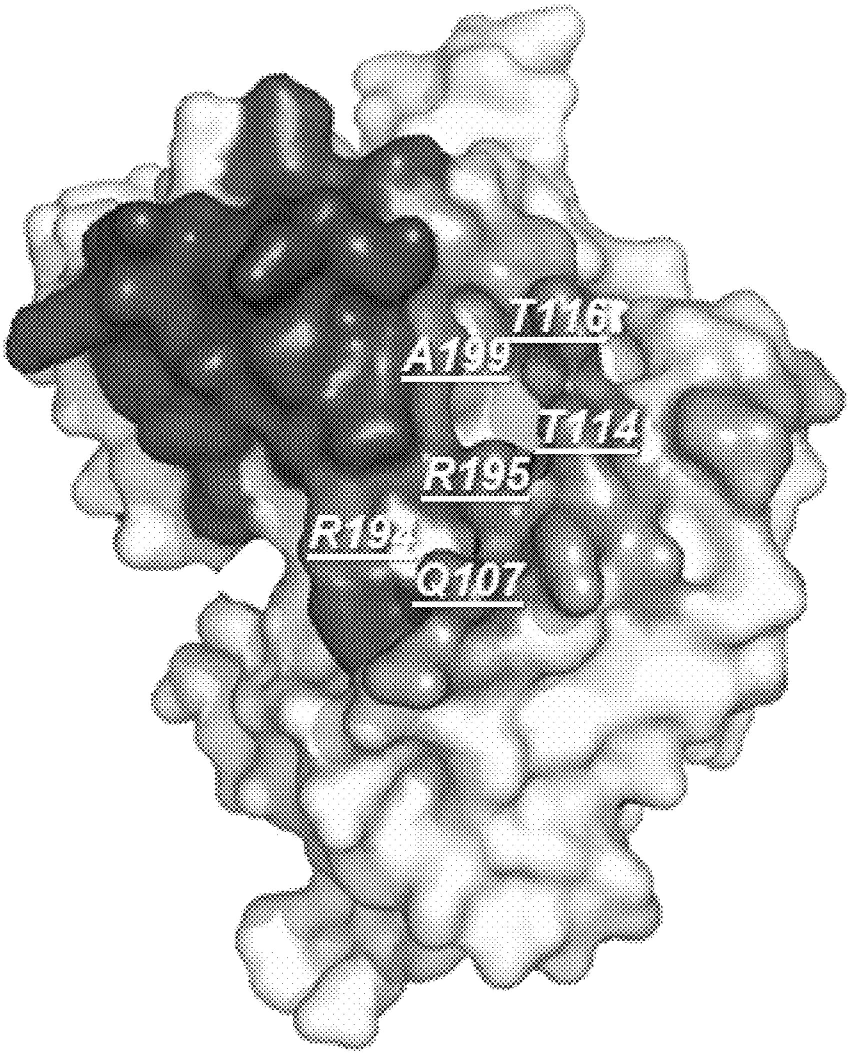

FIGS. 53A-53C. Anti-CD38-B3, isatuximab and daratumumab bind to distinct epitope on CD38. (FIG. 53A) The binding modes of anti-CD38-B3 Fab and daratumumab (PDB 7DHA). (FIG. 53B) The binding modes of anti-CD38-B3 Fab and isatuximab (PDB 4CMH). The light chain of the anti-CD38-B3 Fab sterically clashes with the heavy chain of isatuximab. The steric collision of the two antibodies is indicated with a dashed ellipse. (FIG. 53C) Surface representation of the epitopes of anti-CD38-B3 (dark gray) and isatuximab (gray) on CD38 with residues shared in both epitopes highlighted.

EXAMPLE 1: GENERATION OF ANTI-CD3 ANTIBODIES

Materials and Methods

Recombinant Human CD3Ve Protein (SEQ ID NO: 606)

The CD3γ-CD3E complex (comprising residues 23-103 for CD3γ, a linker, and residues 23-118 for CD3ε, hereafter referred to as recombinant human CD3γε protein) was expressed as a fusion protein in an *E. Coli* expression system according to published information (Arnett et al., 2004, PNAS, 101 (46): 16268-16273). The protein was refolded from inclusion bodies and purified via affinity chromatography (using an affinity resin generated with OKT3 monoclonal antibody) and size exclusion chromatography.

Recombinant human CD3γε protein was biotinylated using the EZ-Link™ Sulfo-NHS-LC-Biotin No-Weigh™ Format kit (ThermoFisher Scientific, catalog NO: A39257). Briefly, recombinant human CD3γε protein was dialyzed at 4° C. against acetate buffer pH 5.0 followed by incubation with a 50-fold molar excess of biotin for 2 hours on ice. Biotinylated recombinant human CD3γε protein was then dialyzed against PBS at 4° C.

Transient expression of full-length human CD3εδ, human CD3εγ and cynomolgus monkey CD3εδ in CHO-S cell line The human codon-optimized extracellular domain sequences of human CD3ε (Uniprot ID P07766 residues 1-126), human CD3δ (Uniprot ID P04234 residues 1-105), human CD3γ (Unipro ID P09693 residues 1-116), cynomolgus monkey CD3ε (Uniprot ID Q95L15 residues 1-105) and cynomolgus monkey CD3δ (Uniprot ID Q95L18 residues 1-117), each fused to part of the extracellular domain, full transmembrane and cytosolic domain of mouse CD80 (Uniprot ID Q00609 residues 237-306) resulted in the constructs comprising sequences as provided in SEQ ID: 610-614. For protein expression, the plasmids were co-transfected (SEQ ID NO: 611 with SEQ ID NO: 612; SEQ ID NO: 610 with SEQ ID NO: 612 or SEQ ID NO: 613 with SEQ ID NO: 614) into suspension-adapted CHO-S cells (cGMP banked, Invitrogen, catalog NO: A1136401) using Polyethyleneimine (PEI; Polysciences). Briefly, cells were prepared at 2 million cells per ml in CD CHO (Gibco). Cells were then transfected with a DNA-PEI mixture at 37° C. Four hours post-transfection, the cell culture was diluted 1:1 in PowerCHO 2 (Lonza) supplemented with 4 mM L-Glutamine and incubated with orbital shaking at 37° C., 5% C02 and 80% humidity. The expression of the target antigens was assessed by monitoring the expression of the eGFP reporter protein with a fluorescence microscope.

Generation of Pools of CD3e Knockout (KO) HPB-ALL Cells

The HPB-ALL CD3 KO cell line was derived from original HPB-ALL cells (DSMZ, catalog NO: ACC483, Lot15) by targeting the first exon of the CD3 gene using clustered regularly interspaced short palindromic repeats (CRISPR)/Cas9 technology, as described by Ran et al (Ran et al., 2013, Cell, 154: 1380-1389). The HPB-ALL cell line was transfected using Neon electroporator (Invitrogen Life Technologies) following the manufacturer's instructions. Following transfection, the cells were stained with anti-CD3 antibody (OKT3 clone, ThermoFisher, catalog NO: 14-0037-85) and CD3 knock-out cells were sorted using Melody FACS sorter (BD) to generate a pool of CD3 knock-out cells. The lack of CD3 expression was further verified by Flow Cytometry using Qifikit (DAKO, catalog NO: K007811-8).

Library Generation

The library used herein was of synthetic origin with a diversity restricted to the heavy chain (CDR-H1, CDR-H2 and CDR-H3) and a fixed VK3-15/JK1 light chain (SEQ ID NO: 1). The library contained 4 different sub libraries based on VH1-69, VH3-23, VH3-15, and VH3-53 antibody germlines. CDRs have been randomized using Trimer oligonucleotides. Primers used for diversifying CDR-H1 and CDR-H2 were designed for each sub libraries and encoded germline-specific naturally occurring diversity at Kabat residues 27-35 and 50-58, respectively. CDR-H3 has been randomized using a pool of oligonucleotides encoding 15 CDR-H3 lengths (6-20) and length-specific naturally occurring diversity at Kabat residues 95-102. Diversified scFv fragments have been pooled to mimic natural CDR-H3 length distribution and cloned into the pNGLEN (in-house modified pUC119 phagemid vector) and the resulting ligation reaction electroporated into *E. coli* TG1 cells. Each sub-library had diversity between $1.2\times10^{10}$ and $1.7\times10^{10}$, the four sub-libraries reached a total diversity of $5.6\times10^{10}$.

Library Panning

The panning strategies consisted either in four rounds of selection using recombinant CD3 protein, or two rounds using recombinant CD3 protein followed by two or three rounds using CD3-expressing cells.

Purified phage particles from individual or pooled sub-libraries ($10^{12}$ plaque-forming units) were blocked in 1 ml of phosphate buffered saline (PBS) containing 3% (w/v) skimmed milk (3% MPBS) for 1 h at room temperature (RT). 2×100 μl magnetic Dynabeads™ MyOne™ Streptavidin C1 beads (Invitrogen, catalog NO: 65002) were blocked in the same conditions. Phages were depleted against pre-blocked beads for 1 h at RT. The other aliquot of pre-blocked beads was incubated with 100 nM of biotinylated recombinant human CD3εδ protein (Creative Biomart, catalog NO: CD3E & CD3D-377H) or biotinylated recombinant human CD3γε protein produced in house (SEQ ID NO: 606) for 30 min at RT. Then, depleted phages were incubated with pre-coated beads for 2 h at RT. Beads were washed five times with PBS containing 0.1% (v/v) TWEEN® (polysorbate) (PBS-TWEEN® 0.1%) and twice with PBS. Phages were eluted with 100 mM triethylamine for 10 min at RT and neutralized using Tris-HCl 1 M pH 8. Eluted phages were used to infect 10 ml of exponentially growing *E. coli* TG1 cells. Infected cells were grown in 2YT medium for 1 h at 37° C. and 100 rotations per minute (RPM), then spread on 2YTAG (2YT medium supplemented with 100 μg/ml ampicillin and 2% glucose) agar plates and incubated overnight (ON) at 30° C. Colonies were scrapped off the plates into 10 ml of 2YT and 15% glycerol (v/v) was added for storage at −80° C. TG1 cells from glycerol stocks were grown at 37° C. and 240 RPM in 2YTAG medium until OD at 600 nm reached 0.5. Cells were then superinfected with the M13K07 helper phage using a multiplicity of infection (MOI) of 10 for 1 h at 37° C. and 100 RPM. Culture medium was then changed for 2YTAK (2YT medium supplemented with 100 μg/ml ampicillin and 50 μg/ml kanamycin) and cells were further cultured ON at 30° C. and 280 RPM. Alternatively, eluted phages were used to infect 2 ml of exponentially growing *E. coli* TG1 cells. Infected cells were grown in 2YT medium for 1 h at 37° C. and 100 RPM, then grown in 2YT medium supplemented with 2% glucose for 1 h at 37° C. and 240 RPM. Cells were then superinfected with the M13K07 helper and phages produced as described above. The next day, 10 μl of phage containing cell-free supernatant were used for the subsequent round of selection.

For cell-based panning, $2\text{-}10\times10^7$ non-expressing cells (CHO, HEK, or CD3E knockout HPB-ALL) and $2\text{-}10\times10^7$ CD3ε-expressing cells (HPB-ALL or CHO cells transiently expressing the membrane-bound extracellular domains of cynomolgus monkey CD3ε (SEQ ID NO: 613) and CD3δ (SEQ ID NO: 614) were blocked with PBS/BSA 3% supplemented with 0.1% azide to avoid receptor internalization for 1 h at RT. Phages were deselected against non-expressing cells for 1 h at RT. The deselected phages were then incubated with CD3ε-expressing cells for 2 h at RT. To remove non-specific phages, cells were washed four times with PBS-Tween 0.1% and twice with PBS. Phages were eluted with citric acid 76 mM, pH 2.0 for 10 min at RT and neutralized using Tris-HCl 1 M pH 8. Eluted phages were used to exponentially growing *E. coli* TG1 cells. Phage amplification was performed as described above.

scFv Screening by Flow Cytometry

The binding of scFv clones to CHO cells transiently expressing the membrane-bound extracellular domains of human CD3ε (SEQ ID NO: 610) and CD3δ (SEQ ID NO: 611) or CD3γ (SEQ ID NO: 612) was assessed by flow cytometry. Individual *E. coli* colonies from the fourth or fifth round of selection were picked and grown in 2YT medium supplemented with 100 μg/ml ampicillin and 0.1% glucose in 96-well deepwell plates. scFv expression was induced by addition of 0.02 mM of IPTG and incubation ON at 30° C. and 260 RPM. Cells were centrifuged and periplasmic extracts were obtained by resuspending the bacterial pellets in TES buffer (50 mM Tris-HCl pH 8; 1 mM EDTA pH 8; 20% sucrose) followed by incubation on ice for 30 min. Cellular debris were removed by centrifugation, and the scFv containing supernatants were used in flow cytometry experiment. CD3-expressing and non-transfected CHO cells were seeded at a density of 105 cells/well in microtiter plates. Next, the plates were centrifuged to remove the cell supernatant and 100 μl of periplasmic extract previously diluted 1:1 in PBS containing 3% (w/v) bovine serum albumin (PBS-BSA 3%) was added to each well and the plates further incubated for 30 min at 4° C. Cells were then washed with PBS-BSA 3% and incubated with a biotin-chicken anti-c-Myc antibody (*Gallus* Immunotech catalog NO: ACMYC-B) diluted at 1:200 in PBS-BSA 3% for 30 min at 4° C. Next, cells were washed with PBS-BSA 3% and incubated with streptavidin APC (eBioscience, catalog NO: 17-4317) diluted at 1:100 in PBS-BSA 3% for 30 min at 4° C. Finally, cell fluorescence was measured using a FACSCalibur flow cytometer (BD biosciences).

IgG1 LALA Expression cDNAs encoding the different antibody constant regions were gene synthetized by GENEART AG (Regensburg, Germany) and modified using standard molecular biology techniques. PCR products were digested with appropriate DNA restriction enzymes, purified, and ligated in modified pcDNA3.1 plasmids (Invitrogen) which carried a CMV promoter and a bovine hormone poly-adenylation (poly(A)). The expression vectors also carried oriP, which is the origin of plasmid replication of Epstein-Barr virus, and the murine VJ2C leader peptide for secretion of the encoded polypeptide chain. For reformatting scFv library clones into human IgG1 LALA (human IgG1 with L234A and L235A substitutions, EU numbering) format, each scFv clone in its phage library vector was used to amplify its individual VH cDNAs by PCR, next the VH PCR product was cloned in the modified pcDNA 3.1 vector described above upstream of a cDNA encoding a human IgG1 heavy chain CH1 domain, whereas the fixed VK3-15/JK1 light chain (SEQ ID NO: 1) was cloned in the modified pcDNA 3.1 vector 108escribeed above upstream of a cDNA encoding a human kappa constant light chain domain.

For IgG1 LALA expression, equal quantities of heavy chain and light chain vectors were co-transfected into suspension-adapted HEK293-EBNA cells (ATCC, catalog NO: CRL-10852) using polyethylenimine (PEI) linear (Polysciences Inc., catalog NO: 24314). Typically, cells were prepared at 8 million cells per ml in RPMI 1640 (Biowest, catalog NO: L0501) supplemented with 0.1% Pluronic F-68 (ThermoScientific, catalog NO: 24040032). Cells were then transfected with a DNA-PEI mixture. Four hours post-transfection, the cell culture was diluted 1:1 in BalanceCD HEK293 (Irvine Scientific, catalog NO: 91165) supplemented with 4 mM L-Glutamine and incubated for 5 days with orbital shaking at 37° C., 5% C02 and 80% humidity. Cell-free culture supernatants containing the recombinant proteins were prepared by centrifugation followed by filtration and used for further purification. IgG1 LALA proteins were purified using CaptivA® Protein A Affinity Resin (Repligen, catalog NO: CA-PRI-0100). Affinity resin was added to the filtered culture supernatants and incubated ON at 4° C. with gentle mixing. The next day, resin beads were collected into Poly-Prep® chromatography columns (Bio-Rad Laboratories), washed with PBS, and the recombinant proteins eluted with an acidic buffer (typically glycine 0.1 M pH 3). After neutralization with 1/10 volume of Tris-HCl pH 8, preparations were buffer-exchanged into PBS.

Screening of anti-CD3 IgG1 LALA clones on CD3-expressing cells

The screening of anti-CD3 antibodies produced as human IgG1-LALA consisted of binding studies on HPB-ALLwild-type and CD3 knockout (KO) HPB-ALL cell lines for selectivity, and on primary isolated PBMC using flow cytometry.

Binding to HPB-ALL and CD3e knockout HPB-ALL cells

Cells were plated at $1\times10^5$ cells/well in a 96-well round-bottom plate (TPP, catalog NO: 92097). The plate was centrifuged at 350 g for 3 min at 4° C. and the cells were resuspended in 100 μl of cold FACS buffer (PBS 1×, supplemented with 2.5% heat inactivated fetal calf serum, 2 mM EDTA and 0.05% sodium azide) containing increasing concentrations of anti-CD3 IgG1-LALA antibodies. Stained cells were incubated for 30 min at 4° C., washed twice with FACS buffer at 350 g for 3 min and resuspended in 100 μl of a cocktail of Goat polyclonal anti-human IgG PE secondary antibody (ThermoFisher Scientific, catalog NO: 12-4998-82) diluted 1/200 in FACS buffer for 30 min. Cells were then washed twice and resuspended in 100 μl of FACS buffer containing SYTOX Green dead cell stain (ThermoFisher Scientific, catalog NO: S34860) diluted 1/2000. Samples were acquired on a CytoFlex instruments (Beckman Coulter). Cells were gated based on size on FSC vs SSC and debris, doublets and dead cells were excluded. Cells were analyzed for PE-geometric mean (geomean) fluorescence intensity using FlowJo software. Only samples showing at least 200 cells in final gate were considered in the further steps of the analysis. PE-geometric mean (geomean) fluorescence intensity values were finally plotted using Prism software (GraphPad) and binding status were summarized in Table 1.

Binding to CD4. Human T Cells in PBMCs

Human PBMC were harvested from buffy coats/Apheresis filters obtained from La Chaux-de-Fonds/Bern (Switzerland) Transfusion Center using ficoll density gradient isolation and frozen the day of the harvest.

On the day prior to the assay, cells were thawed in pre-warmed complete RPMI medium (RPMI supplemented with 10% heat inactivated fetal calf serum, 1% Glutamine, 1% Non-essential Amino Acids, 1% Sodium Pyruvate, and 1% Penicillin/Streptomycin) and rested overnight at $1\times10^6$ cells/ml. On the day of the assay, cells were plated at $1\times10^5$ cells/well in a 96-well round-bottom plate. The plate was centrifuged at 350 g for 3 min at 4° C. and the cells were resuspended in 100 μl of cold FACS buffer containing serial dilutions of anti-CD3 IgG1-LALA antibodies starting from 800 nM and diluted by 3 or 10-fold. Cells were incubated for 30 min at 4° C., washed twice with FACS buffer at 350 g for 3 min and resuspended in 100 μl of a cocktail of goat polyclonal anti-human IgG PE secondary antibody (ThermoFisher Scientific, catalog NO: 12-4998-82, 1/200) and co-staining antibody for human CD4-ALEXA FLUOR® 700 (ThermoFisher Scientific, catalog NO: 56-0048-82, 1/100) diluted in FACS buffer for 30 minutes. Cells were then washed twice and resuspended in 100 μl of FACS buffer containing SYTOX Green dead cell stain (ThermoFisher Scientific, catalog NO: S34860) diluted 1/2000. Samples were acquired on a CytoFlex instruments (Beckman Coulter). Cells were gated based on size on FSC vs SSC and debris, doublets and dead cells were excluded. Finally, CD4+ T cell population was analyzed for PE-geometric mean (geomean) fluorescence intensity using FlowJo software. PE-geometric mean (geomean) fluorescence intensity values were finally plotted using Prism software (GraphPad) as depicted in FIG. 1A and binding status were summarized in Table 1.

Screening of Anti-CD3 IgG1 LALA Clones for T Cell Activation

To evaluate the potential of anti-CD3 antibodies produced as human IgG1-LALA to induce T cell activation, additional screenings were performed using a T cell activation assay. Serial dilutions of anti-CD3 IgG1-LALA antibodies starting from 200 nM and diluted by 3 or 10-fold were coated in PBS in 96-well flat-bottom plates (TPP, catalog NO: 92096). Plates were then incubated overnight at 4° C. Frozen isolated human T cells were thawed in pre-warmed complete RPMI medium and rested overnight at $1\times10^6$ cells/ml. On the day of the assay, plates were washed twice in PBS and primary T cells were harvested, counted, and plated at $1\times10^5$ cells/well (100 μl). After 48 h of incubation at 37° C., 5% CO2, plates were centrifuged (350 g, 5 min), cells were then transferred to a 96-well round-bottom plate, washed and resuspended in 100 μl of a cocktail of antibodies for human CD4-PE-eFluor610 (ThermoFisher Scientific, catalog NO: 61-0049-42, 1/200), CD8-ALEXA FLUOR® 700 (BioLegend, catalog NO: 344724, 1/100), CD25-PE and CD69-PE-Cy7 (ThermoFisher Scientific, catalog NOs: 12-0259-42 and 25-0699-42, respectively, 1/100) diluted in FACS buffer and incubated for 30 min at 4° C. Cells were then washed twice and resuspended in 100 μl of FACS buffer containing SYTOX Green dead cell stain (ThermoFisher Scientific, catalog NO: S34860) diluted 1/2000. Samples were acquired on a CytoFlex Instruments (Beckman Coulter). Cells were gated based on size FSC vs SSC and debris and doublets were excluded. Finally, cells negative for the viability staining were gated, and $CD4^+$ population was analyzed for PE-geometric mean (geomean) fluorescence intensity using FlowJo software. T cell activation was determined by evaluating the CD69 positive expression gated on $CD4^+$ T cells. Percentages of activated $CD69^+$ of $CD4^+$ T cells values were finally plotted using Prism software (GraphPad) as depicted in FIG. 1B and binding status were summarized in Table 1. A total of eight independent experiments were performed.

Results and Conclusions

Phage Display Panning and scFv Screening by Flow Cytometry

Phage display libraries based on a fixed Vκ3-15/Jκ1 light chain (SEQ ID NO: 1) were panned against CD3ε, and phage display output screened by flow-cytometry. ScFv clones showing specific binding to CD3ε-expressing CHO cells were sequenced and unique sequences were expressed as IgG1 LALA for further characterization.

Screening of Anti-CD3 IgG1 LALA Antibodies for T Cell Binding and T Cell Activation Results in FIGS. 1A-1B and Table 1 show that among all 48 binders screened for binding to HPB-ALL wild-type, CD3 knockout (KO) HPB-ALL cell lines, and T cells, only one clone, anti-CD3-UCP06-C1 (heavy chain SEQ ID NO: 34), herein also referred as anti-CD3-C1 or anti-CD3-UCP06-C1 IgG1 LALA showed consistent binding to CD4+ T cells (FIG. 1A) and demonstrated specificity, exemplified by binding to HBP-ALL wildtype but not to CD3 KO HPB-ALL cell line (Table 1). Screening for T cell activation also confirmed that most of the clones were not inducing the upregulation of activation markers on CD4+ T cells such as CD69 except for the candidate anti-CD3-C1 (FIG. 1B). Few clones, such as anti-CD3-UCP07-H1, anti-CD3-UCP07-B2, anti-CD3-UCP07-D2, anti-CD3-UCP07-F3 and anti-CD3-UCP07-B4, showed non-specific binding and stained positive on both HPB-ALL wild-type and CD3 KO cells. Two other clones, namely anti-CD3-UCP05-D1 and anti-CD3-UCP08-B1, showed a specific binding to CD3 but an inability to induce T cell activation. Table 1 summarizes anti-CD3 candidates and the result of the screening for CD3 binding and T cell activation. FIGS. 1A-11B shows binding and T cell activation of anti-CD3-C1 and other anti-CD3 candidates selected as example.

TABLE 1

Overview of developed anti-CD3 IgG1 LALA antibodies and their binding to HPB-ALL, HPB-ALL CD3 KO cells and human $CD4^+$ T cells, as well as their capacity to activate and upregulate CD69 expression on $CD4^+$ T cells. Table shows the heavy chain sequence identification numbers (SEQ ID NO), binding to HPB-ALL, HPB-ALL CD3 KO and $CD4^+$ T cells, as well as $CD4^+$ T cell activation of developed anti-CD3 IgG1-LALA antibodies as determined from Flow Cytometry experiments.

| | | In-vitro binding | | | |
|---|---|---|---|---|---|
| Clone name | Clone heavy chain SEQ ID NO | Binding to HPB-ALL WT at 800 nM | Binding to HPB-ALL CD3 KO or CHO cells not expressing CD3 at 800 nM | Binding to human CD4+ T cells at 800 nM | In vitro T cell activation CD69 upregulation on CD4+ T cells |
| Anti-CD3-UCP02-A3 IgG1LALA | SEQ ID NO: 2 | No | No | No | No |
| Anti-CD3-UCP02-B2 IgG1LALA | SEQ ID NO: 3 | No | No | No | No |
| Anti-CD3-UCP02-D2 IgG1LALA | SEQ ID NO: 4 | No | No | No | No |
| Anti-CD3-UCP02-F2 IgG1LALA | SEQ ID NO: 5 | Yes | No | No | No |
| Anti-CD3-UCP02-H2 IgG1LALA | SEQ ID NO: 6 | No | No | No | No |
| Anti-CD3-UCP03-A3 IgG1LALA | SEQ ID NO: 7 | No | No | No | No |
| Anti-CD3-UCP03-A4 IgG1LALA | SEQ ID NO: 8 | No | No | No | No |
| Anti-CD3-UCP03-B1 IgG1LALA | SEQ ID NO: 9 | No | No | No | No |
| Anti-CD3-UCP03-C1 IgG1LALA | SEQ ID NO: 10 | No | No | No | No |
| Anti-CD3-UCP03-C3 IgG1LALA | SEQ ID NO: 11 | No | No | No | No |
| Anti-CD3-UCP03-C5 IgG1LALA | SEQ ID NO: 12 | No | No | No | No |
| Anti-CD3-UCP03-E1 IgG1LALA | SEQ ID NO: 13 | No | No | No | No |
| Anti-CD3-UCP03-E2 IgG1LALA | SEQ ID NO: 14 | No | No | No | No |
| Anti-CD3-UCP03-E4 IgG1LALA | SEQ ID NO: 15 | No | No | No | No |
| Anti-CD3-UCP03-F1 IgG1LALA | SEQ ID NO: 16 | No | No | No | No |
| Anti-CD3-UCP03-F2 IgG1LALA | SEQ ID NO: 17 | No | No | No | No |
| Anti-CD3-UCP03-F4 IgG1LALA | SEQ ID NO: 18 | No | No | No | No |
| Anti-CD3-UCP03-G2 IgG1LALA | SEQ ID NO: 19 | No | No | No | No |

TABLE 1-continued

Overview of developed anti-CD3 IgG1 LALA antibodies and their binding to HPB-ALL, HPB-ALL CD3 KO cells and human $CD4^+$ T cells, as well as their capacity to activate and upregulate CD69 expression on $CD4^+$ T cells. Table shows the heavy chain sequence identification numbers (SEQ ID NO), binding to HPB-ALL, HPB-ALL CD3 KO and $CD4^+$ T cells, as well as $CD4^+$ T cell activation of developed anti-CD3 IgG1-LALA antibodies as determined from Flow Cytometry experiments.

| | | In-vitro binding | | | |
|---|---|---|---|---|---|
| Clone name | Clone heavy chain SEQ ID NO | Binding to HPB-ALL WT at 800 nM | Binding to HPB-ALL CD3 KO or CHO cells not expressing CD3 at 800 nM | Binding to human CD4+ T cells at 800 nM | In vitro T cell activation CD69 upregulation on CD4+ T cells |
| Anti-CD3-UCP03-G3 IgG1LALA | SEQ ID NO: 20 | No | No | No | No |
| Anti-CD3-UCP03-G4 IgG1LALA | SEQ ID NO: 21 | No | No | No | No |
| Anti-CD3-UCP03-H2 IgG1LALA | SEQ ID NO: 22 | No | No | No | No |
| Anti-CD3-UCP03-H3 IgG1LALA | SEQ ID NO: 23 | No | No | No | No |
| Anti-CD3-UCP05-A1 IgG1LALA | SEQ ID NO: 24 | No | No | No | No |
| Anti-CD3-UCP05-A2 IgG1LALA | SEQ ID NO: 25 | No | No | No | No |
| Anti-CD3-UCP05-C1 IgG1LALA | SEQ ID NO: 26 | No | No | No | No |
| Anti-CD3-UCP05-D1 IgG1LALA | SEQ ID NO: 27 | Yes | No | Yes | No |
| Anti-CD3-UCP05-D2 IgG1LALA | SEQ ID NO: 28 | No | No | No | No |
| Anti-CD3-UCP05-F1 IgG1LALA | SEQ ID NO: 29 | No | No | No | No |
| Anti-CD3-UCP05-G2 IgG1LALA | SEQ ID NO: 30 | No | No | No | No |
| Anti-CD3-UCP05-H1 IgG1LALA | SEQ ID NO: 31 | No | No | No | No |
| Anti-CD3-UCP05-H2 IgG1LALA | SEQ ID NO: 32 | No | No | No | No |
| Anti-CD3-UCP06-A1 IgG1LALA | SEQ ID NO: 33 | No | No | NT | No |
| Anti-CD3-UCP06-C1 IgG1LALA | SEQ ID NO: 34 | Yes | No | Yes | Yes |
| Anti-CD3-UCP07-A1 IgG1LALA | SEQ ID NO: 35 | No | No | NT | NT |
| Anti-CD3-UCP07-A3 IgG1LALA | SEQ ID NO: 36 | No | No | NT | NT |
| Anti-CD3-UCP07-A4 IgG1LALA | SEQ ID NO: 37 | No | No | NT | NT |
| Anti-CD3-UCP07-B2 IgG1LALA | SEQ ID NO: 38 | Yes | Yes | No | No |
| Anti-CD3-UCP07-B3 IgG1LALA | SEQ ID NO: 39 | No | No | NT | NT |
| Anti-CD3-UCP07-B4 IgG1LALA | SEQ ID NO: 40 | Yes | Yes | No | No |
| Anti-CD3-UCP07-C3 IgG1LALA | SEQ ID NO: 41 | No | No | NT | NT |
| Anti-CD3-UCP07-D1 IgG1LALA | SEQ ID NO: 42 | No | No | NT | NT |
| Anti-CD3-UCP07-D2 IgG1LALA | SEQ ID NO: 43 | Yes | Yes | NT | No |
| Anti-CD3-UCP07-E1 IgG1LALA | SEQ ID NO: 44 | No | No | NT | NT |
| Anti-CD3-UCP07-E2 IgG1LALA | SEQ ID NO: 45 | No | No | NT | NT |
| Anti-CD3-UCP07-F2 IgG1LALA | SEQ ID NO: 46 | No | No | NT | NT |
| Anti-CD3-UCP07-F3 IgG1LALA | SEQ ID NO: 47 | Yes | Yes | No | No |
| Anti-CD3-UCP07-H1 IgG1LALA | SEQ ID NO: 48 | Yes | Yes | No | No |
| Anti-CD3-UCP08-B1 IgG1LALA | SEQ ID NO: 49 | NT | NT | Yes | No |

NT = not tested.

EXAMPLE 2: OPTIMIZATION OF ANTI-CD3-C1 ANTIBODY

Material and Methods

Library Generation and Panning

Three affinity maturation libraries were generated for anti-CD3-C1 clone (heavy chain SEQ ID NO: 34) by introducing diversity in CDRs' heavy chain. CDR-H1, CDR-H2 and CDR-H3 were randomized using degenerated NNK codon oligonucleotides (wherein N is any of the four deoxyribonucleotides and K is G or T) at Kabat residues 27-35, 50-58, 95-101 minus 2, respectively. Each library was generated using a pool of overlapping oligonucleotides containing 5 consecutive degenerated codons. The resulting three library PCR products were cloned into the pNGLEN (in-house modified pUC119 phagemid vector) and the resulting ligation reaction electroporated into *E. coli* TG1 cells. Transformed cells were spread on 2YTAG plates and incubated ON at 30° C. Colonies were scrapped off the plates into 10 ml of 2YT medium and 15% glycerol (final concentration) was added for storage at −80° C. Phages were produced and purified by two precipitations steps with one-third v/v of 20% PEG-6000, 2.5 M NaCl and resuspended in PBS.

Phage display panning was performed as described in Example 1 with the following modifications. The three libraries were incubated with beads pre-coated with 100 nM, 50 nM, and 10 nM of biotinylated recombinant human CD3εδ protein (Creative Biomart, catalog NO: CD3E & CD3D-377H) or biotinylated recombinant human CD3γε protein produced in house (SEQ ID NO: 606), for round 1, round 2 and round 3, respectively.

Affinity screening by SPR

Surface Plasmon Resonance (SPR) analysis was used to confirm specific binding activity of the scFv clones. Measurements were performed on a Biacore 8K+ instrument (Cytiva Life Sciences) using the Biacore 8K+ Control Software at 25° C. and analyzed with the Biacore Insight Evaluation Software (v3.0). Recombinant human CD3εδ protein (Creative Biomart, catalog NO: CD3E & CD3D-376H) was diluted to a final concentration of 1 μg/ml in acetate buffer pH 4.5 (Cytiva Life Sciences, catalog NO: BR100530) and subsequently immobilized on flow-path 2 on the eight channels, to around 650-900 resonance units (abbreviated RU) on a Series S CM5 Sensor Chip (Cytiva Life Sciences, catalog NO: BR100012) using an amine coupling kit (Cytiva Life Sciences, catalog NO: BR100050). HBS-EP+(Cytiva Life Sciences, catalog NO: BR100669) was used as running buffer. Filtered periplasmic extracts were injected directly on the covalently coupled human CD3εδ Series S CM5 Sensor Chip. Samples were injected on the flow-paths 1 and 2 (flow-path 1 being used as reference) at a 30 μl/min flow rate for 3 min, followed by a dissociation time of 3 min in running buffer. After each binding event, surface was regenerated with 10 mM Glycine pH 1.5 solution (Cytiva Life Sciences, catalog NO: BR100354) injected for 50 s at 30 μl/min on both flow-paths. Each measurement included zero-concentration samples as well as irrelevant scFv periplasmic extracts for referencing and specificity, respectively.

IgG1 LALA Bivalent Binding Affinity to CD3 by BLI

ScFv library clones were reformatted into human IgG1 LALA as described in Example 1. Apparent bivalent affinities of the IgG1 LALA to human CD3εδ protein were assessed by Bio-Layer Interferometry (BLI). Measurements were done on an OctetRED96e instrument (Sartorius) and analyzed using the Data Analyis HT version 11.1 software (Octet, Sartorius). Biotinylated recombinant human CD3εδ protein (Creative Biomart, catalog NO: CD3E & CD3D-377H) was diluted at 1 μg/ml in kinetic buffer (Sartorius, catalog NO: 18-1105) and subsequently immobilized on a streptavidin SA Biosensor (ForteBio, catalog NO: 15-5019), previously soaked in kinetic buffer for 10 min, to around 0.5-0.8 nm response level. Streptavidin biosensor coated with biotinylated human CD3εδ protein was first dipped into kinetic buffer for 2 min (baseline), followed by a second dip into a solution of IgG1 LALA at concentrations between 1.6 nM and 100 nM in kinetic buffer for 5 min. Dissociation in kinetic buffer was monitored for 10 min. All steps were performed at 25° C. and 1000 RPM shaking. Fresh streptavidin biosensors were coated with biotinylated human CD3εδ protein prior to each cycle. Each measurement included zero-concentration samples for referencing. Experimental data were processed using the 1:1 fitting model on association and dissociation.

Screening of affinity matured anti-CD3 IgG1 LALA clones for binding to CD3-expressing cells and for T cell activation The screening of C1-affinity matured anti-human CD3 candidates produced as human IgG1-LALA was followed by similar binding studies on HPB-ALL wild-type and CD3 knockout (KO) HPB-ALL cell line for selectivity, and on primary isolated PBMC, and activation studies on primary isolated T cells using flow cytometry. The same methodologies and material were used as described in Example 1.

Results and Conclusions

Affinity maturation of anti-CD3-C1 (heavy chain SEQ ID NO: 34) involved diversification of CDR-H1 (Kabat positions 27-35), CDR-H2 (Kabat positions 50-58) and CDR-H3 (Kabat positions 95-101 minus 2) in three individual libraries. ScFv clones having a slower off-rate than the parental clone anti-CD3-C1 as measured by SPR were isolated. ScFv clones were reformatted and expressed as IgG1 LALA and bivalent affinity to human CD3εδ (Creative Biomart, catalog NO: CD3E & CD3D-377H) was measured by BLI. From this assessment, one clone, anti-CD3-C1-UCP01-D6 (heavy chain SEQ ID NO: 55), herein also referred as anti-CD3-C1-D6, had the highest affinity to human CD3εδ with dissociation constant ($K_D$) measured at 0.26 nM. Heavy chain sequence identification numbers (SEQ ID NO), bivalent binding affinity to human CD3εδ by Octet BLI, binding to human $CD4^+$ T cells assessed by flow cytometry, and $CD4^+$ T cell activation assessed by the upregulation of activation marker CD69, are reported in Table 2. All C1 affinity matured anti-CD3 binders showed binding to CD3-expressing cells ($CD4^+$ T cells) and induced the upregulation of activation markers on $CD4^+$ T cells such as CD69 with significant improvement compared to the parental anti-CD3-UCP06-C1 clone. Five clones, anti-CD3-C1-UCP01-D6, herein also referred as anti-CD3-C1-D6, anti-CD3-C1-UCP01-E10, herein also referred as anti-CD3-C1-E10, anti-CD3-C1-UCP01-F10, herein also referred as anti-CD3-C1-F10, anti-CD3-C1-UCP01-H10, herein also referred as anti-CD3-C1-H10 and anti-CD3-C1-UCP01-E12, herein also referred as anti-CD3-C1-E12, were selected for incorporation into a CD3×BCMA bispecific tool molecule to assess T-cell redirected killing (Example 3) based on sequence, binding and T cell activation profiles. Specificity for CD3 was confirmed by the lack of binding to CD3 KO HPB-ALL cell line (FIG. 2).

TABLE 2

Overview of developed anti-CD3-C1 optimized candidates and their relative bivalent affinity to recombinant human CD3εδ protein as assessed by Octet BLI, as well as of their relative binding to human $CD4^+$ T cells and their capacity to upregulate CD69 on $CD4^+$ T cells. Table shows the heavy chain sequence identification numbers (SEQ ID NO), the CDR randomization library from which the clones derive, the bivalent binding affinity ($K_D$) to recombinant human CDεδ protein assessed by Octet BLI, the binding to human $CD4^+$ T cells assessed by flow cytometry, and the $CD4^+$ T cell activation status (%$CD69^+$ upregulation on CD4 T cells at 48 h) of anti-CD3-C1-optimized candidates in IgG1-LALA.

| CDR randomization library | Clone name | Clone heavy chain SEQ ID NO | Human CD3εδ bivalent $K_D$ (nM) measured by Octet BLI | In-vitro binding to human CD4+ T cells (MFI) at 800 nM | In vitro CD4+ T cell activation at 200 nM (%CD69+ at 48 h) |
|---|---|---|---|---|---|
| CDR-H2 | Anti-CD3-UCP06-C1 IgG1LALA | SEQ ID NO: 34 | 1.75 | 45182 | 19% |
| CDR-H2 | Anti-CD3-C1-UCP01-B6 IgG1LALA | SEQ ID NO: 50 | 0.88 | 108571 | 50% |
| CDR-H2 | Anti-CD3-C1-UCP01-B9 IgG1LALA | SEQ ID NO: 51 | 1.04 | 107775 | 57% |
| CDR-H2 | Anti-CD3-C1-UCP01-C11 IgG1LALA | SEQ ID NO: 52 | 0.91 | 118548 | 47% |
| CDR-H2 | Anti-CD3-C1-UCP01-D1 IgG1LALA | SEQ ID NO: 53 | 1.73 | 52800 | 6% |
| CDR-H2 | Anti-CD3-C1-UCP01-D4 IgG1LALA | SEQ ID NO: 54 | 0.62 | 125939 | 4% |
| CDR-H2 | Anti-CD3-C1-UCP01-D6 IgG1LALA | SEQ ID NO: 55 | 0.26 | 178361 | 69% |
| CDR-H2 | Anti-CD3-C1-UCP01-E6 IgG1LALA | SEQ ID NO: 56 | 0.45 | 230552 | 73% |
| CDR-H2 | Anti-CD3-C1-UCP01-E7 IgG1LALA | SEQ ID NO: 57 | 1.53 | 82786 | 17% |
| CDR-H2 | Anti-CD3-C1-UCP01-E10 IgG1LALA | SEQ ID NO: 58 | 0.84 | 100374 | 25% |
| CDR-H2 | Anti-CD3-C1-UCP01-E11 IgG1LALA | SEQ ID NO: 59 | 0.93 | 91829 | 39% |
| CDR-H2 | Anti-CD3-C1-UCP01-E12 IgG1LALA | SEQ ID NO: 60 | 0.41 | 149337 | 54% |
| CDR-H2 | Anti-CD3-C1-UCP01-F1 IgG1LALA | SEQ ID NO: 61 | 1.08 | 81291 | 36% |
| CDR-H2 | Anti-CD3-C1-UCP01-F10 IgG1LALA | SEQ ID NO: 62 | 0.47 | 149830 | 69% |
| CDR-H2 | Anti-CD3-C1-UCP01-F12 IgG1LALA | SEQ ID NO: 63 | 0.66 | 107956 | 51% |
| CDR-H2 | Anti-CD3-C1-UCP01-G12 IgG1LALA | SEQ ID NO: 64 | 0.70 | 120639 | 61% |
| CDR-H2 | Anti-CD3-C1-UCP01-H9 IgG1LALA | SEQ ID NO: 65 | 0.87 | 132976 | 36% |
| CDR-H2 | Anti-CD3-C1-UCP01-H10 IgG1LALA | SEQ ID NO: 66 | 0.55 | 151247 | 58% |
| CDR-H2 | Anti-CD3-C1-UCP02-E1 IgG1LALA | SEQ ID NO: 67 | 0.35 | 150526 | 56% |

EXAMPLE 3: EXPRESSION AND CHARACTERIZATION OF TOOL MOLECULES FOR OPTIMIZED CD3-C1 BINDER CHARACTERIZATION

Material and Methods

Construction of Expression Vectors for Transient Mammalian Cell Expression cDNAs encoding the different polypeptide chains in part or in full were first gene synthetized by GENEART (Regensburg, Germany) or Twist Biosciences (San Francisco, USA) and modified using standard molecular biology techniques. PCR products were ligated in a modified pcDNA3.1 plasmid (Invitrogen AG, Zug, Switzerland) carrying a CMV promoter and a bovine hormone poly-adenylation (poly(A)) using standard molecular biology techniques. All polypeptide chains were independently cloned in an expression vector where secretion is driven by a murine IgGκ light chain leader peptide.

Expression of Antibody Constructs in CHO-S (cGMP Banked)

For expression of antibody constructs CHO-S cells, engineered chains vectors and a vector encoding Epstein-Barr Virus (EBV) nuclear antigen-1 (EBNA-1) were co-transfected into CHO-S cells (cGMP banked, Invitrogen, catalog NO: A1136401), using Polyethyleneimine (PEI; Polysciences). Typically, cells were prepared at 8 million cells per ml in CD-CHO media (Gibco). Cells were then transfected with a DNA-PEI mixture at 37° C. Four hours post-transfection, the cell culture was diluted 1:1 in PowerCHO™ 2 (Lonza) supplemented with 4 mM L-Glutamine and incubated for 14 days with orbital shaking at 32° C., 5% C02 and 80% humidity. Clarified cell culture supernatants containing the recombinant proteins were prepared by centrifugation followed by filtration and used for further purification.

Expression of Antibody Constructs in HEK293-EBNA Cells

For expression of antibody constructs in HEK293-EBNA cells, engineered chains vectors encoding the heavy and light chains were co-transfected into suspension-adapted HEK293-EBNA cells (ATCC, cat no CRL-10852) using PEI. Typically, cells were prepared 25 at 8 million cells per ml in RPMI supplemented with 0.1% Pluronic F-68. Cells were then transfected with a DNA-PEI mixture. Four hours post-transfection, the cell culture was diluted 1:1 in EX-CELL® 293 supplemented with Phenol Red and 4 mM L-Glutamine and incubated for 5 days with orbital shaking at 37° C., 5% C02 and 80% humidity. Cell-free culture supernatants containing the recombinant proteins were prepared by centrifugation followed by filtration and used for further purification.

Purification of Antibody Constructs

Supernatants (from HEK293-EBNA or CHO-S cells) were optionally conditioned with 0.1 volume (V) of sodium phosphate 1 M, pH 6.0 prior purification or used directly without conditioning. KanCapA resin (KANEKA, Belgium) was added to conditioned supernatants. Mixtures were incubated overnight at 4° C. with stirring. After incubation, bound proteins were washed with 10 column volumes (CVs) of PBS pH 7.4, followed by 2 CVs of sodium acetate 170 mM, pH 5.0, then eluted in multiple steps of 50 mM sodium acetate, pH 4.3, 4.1 and/or pH 3.9 and neutralized with 0.1V of 1 M Tris-HCl pH 8.0. At this stage, the recombinant proteins were either carried over to a second step of purification by cation exchange as described further, or the elution fractions were dialyzed to PBS, pH 7.4 or Histidine, 25 mM, pH 6.0, 150 mM NaCl, sterile-filtered and analyzed by Size-Exclusion—High Performance Liquid Chromatography (SE-HPLC) (TSKgel G3000SWXL, 5 μm, 7.8 mm×30 cm L, 5 μm particles and 250 Å pores (Tosoh Bioscience, catalog NO: 08541) at room temperature with 0.1 M sodium phosphate buffer, 0.15 M sodium chloride, pH 6.8 as eluent at 1 ml/min flow rate on HPLC Alliance 2695 (Waters) or Acquity Arc HPLC (Waters) with column heater and either UV/Vis detector (2487 or 2489 from Waters) or PDA detector (2996 or 2998 from Waters)) and SDS-PAGE (NuPAGE Bis-Tris 4-12% acrylamide, Invitrogen AG, Basel, Switzerland). Eluate with <95% main peak in SE-HPLC or eluates without prior analysis were further purified by cation exchange chromatography. The HiTrap HP SP column (1 mL bed volume) was pre-equilibrated in 50 mM sodium acetate buffer pH 5.5 and operated on an AKTA Pure™ chromatography system (both column and instrument from Cytiva Life Sciences) at a flow rate of 1 ml/min. Elution was performed using a linear gradient from 0 to 500 mM NaCl in sodium acetate 50 mM, pH 5.5. Pooled elution fractions corresponding to the main peak were analyzed by SE-HPLC and SDS-PAGE under reducing and non-reducing conditions. The Multi-Cartridge System Endosafe-MCS from Charles River utilizing a Limulus amebocyte lysate (LAL)-based assay was used to confirm a bacterial endotoxin level inferior to 5 EU/mg. Typically, for purified antibodies the content of aggregated forms was lower than 5% and the purity measured by SE-HPLC was superior to 94%.

Redirected Lysis (RDL) Assay

The screening of anti-CD3-C1-optimized candidates was followed by in format testing for tumor killing potency. 2+1 BEAT with BCMA binders were generated as described above and their killing potency was assessed in a Redirected Lysis (RDL) assay using the Multiple Myeloma NCI-H929 cell line.

Human peripheral blood mononuclear cells (PBMC) were isolated from buffy coats of healthy donors obtained from La Chaux-de-Fonds/Bern (Switzerland) Transfusion Center using ficoll density gradient isolation and frozen in CryoStor10 cell freezing medium (Stemcell, catalog NO: 07930). Cells were thawed in a pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $1\times10^6$ cells/ml. Ten thousand target cells (NCI-H929 cell line, Sigma, catalog NO: 95050415) were labelled with proliferation dye eFluor670 (ThermoFisher Scientific, catalog NO: 65-0840-85) and co-cultured with fifty thousand PBMC reaching an effector-to-target ratio of 5:1. Serial dilutions of 2+1 anti-CD3-C1-UCP01-X/BCMA candidates (where X stands for the affinity matured variants of anti-CD3 C1 binder), and control antibodies starting from 200 nM and diluted by 10-fold were added and the co-culture incubated for 48 hours, at 37° C., 5% CO2. After the incubation period, the RDL assay readout was evaluated by two different methods: by measuring T cell cytotoxic activity against target cells and by measuring the increase in expression of the activation marker CD69 on $CD4^+$ T cells. Tumor cell killing was determined by measuring the absolute count of live target cells ($eFluor670^+$ cells) and calculated as % of target killing=[1−(Sample absolute counts)/(absolute counts in the presence of target cells alone)]×100. Specific tumor cell killing was calculated as % of specific killing=% target killing (sample)−unspecific % target killing (in absence of antibody). T cell activation was determined by evaluating the percentage of CD69 positive cells gated on $CD4^+$ T cells. Percentages of Specific Killing and percentages of $CD69^+$ of $CD4^+$ T cells were finally plotted using Prism software (GraphPad).

Results and Conclusions

Control and tool molecules required to compare T cell activation and killing potency of novel CD3 binders were designed by the combination of the CD3 binders as Fab and BCMA double dAb from the art on a silenced BEAT Fc backbone (LALA mutations, Hezareh et al., 2001, J Virol, 75(24): 12161-12168) as depicted in FIG. 3. The negative control ABC-DUxBCMA had an irrelevant binder in place of the CD3 binding Fab. The constructs were produced in CHO-S cells with the chain assemblies detailed in Table 3.

All control molecules were purified with protein A followed by an optional purification by cation exchange chromatography. The yields and purities for the control and tool molecules are reported in Table 4.

TABLE 3

Sequence combinations for tool and control molecules used in characterizing T cell activation.

| Construct | Chain 1 | Chain 2 | Chain 3 |
|---|---|---|---|
| TNB-F2B BEAT Fc | SEQ ID NO: 571 | SEQ ID NO: 572 | SEQ ID NO: 1 |
| Negative control = ABC-DUxBCMA | SEQ ID NO: 519 | SEQ ID NO: 520 | SEQ ID NO: 521 |
| Anti-CD3-C1-UCP01-D6xBCMA | SEQ ID NO: 515 | SEQ ID NO: 516 | SEQ ID NO: 1 |
| Anti-CD3-C1-UCP01-E10xBCMA | SEQ ID NO: 509 | SEQ ID NO: 510 | SEQ ID NO: 1 |

TABLE 3-continued

Sequence combinations for tool and control molecules used in characterizing T cell activation.

| Construct | Chain 1 | Chain 2 | Chain 3 |
|---|---|---|---|
| Anti-CD3-C1-UCP01-H10xBCMA | SEQ ID NO: 513 | SEQ ID NO: 514 | SEQ ID NO: 1 |
| Anti-CD3-C1-UCP01-F10xBCMA | SEQ ID NO: 511 | SEQ ID NO: 512 | SEQ ID NO: 1 |
| Anti-CD3-C1-UCP01-E12xBCMA | SEQ ID NO: 517 | SEQ ID NO: 518 | SEQ ID NO: 1 |
| 83A10-TCBcv_aCD3xTNB-BCMA BEAT Fc | SEQ ID NO: 506 | SEQ ID NO: 507 | SEQ ID NO: 508 |

TABLE 4

Description and production data for control antibodies in CD3-FabxBCMA-dAb-dAb format used for characterization of T cell activation and killing potency of novel CD3 binders.

| Construct | TNB-F2B BEAT Fc | 83A10-TCBcv_aCD3xTNB-BCMA BEAT Fc | Negative control = ABC-DUxBCMA | Anti-CD3-C1-UCP01-D6xBCMA | Anti-CD3-C1-UCP01-E10xBCMA | Anti-CD3-C1-UCP01-H10xBCMA | Anti-CD3-C1-UCP01-F10xBCMA | Anti-CD3-C1-UCP01-E12xBCMA |
|---|---|---|---|---|---|---|---|---|
| CD3 binder | TNB-F2B | 83A10-TCBcv_aCD3 | ABC-DU | Anti-CD3-C1-UCP01-D6 | Anti-CD3-C1-UCP01-E10 | Anti-CD3-C1-UCP01-H10 | Anti-CD3-C1-UCP01-F10 | Anti-CD3-C1-UCP01-E12 |
| BCMA binder | TNB-BCMA-dAb-dAb | TNB-BCMA-dAb-dAb | TNB-BCMA-dAb-dAb | TNB-BCMA-dAb-dAb | TNB-BCMA-dAb-dAb | TNB-BCMA-dAb-dAb | TNB-BCMA-dAb-dAb | TNB-BCMA-dAb-dAb |
| Yield (mg/L) | 56-78 | 31 | 31 | 18 | 11 | 14 | 10 | 13 |
| Final Purity (% monomer) | 98-100 | 99 | 99 | 96 | 96 | 94 | 94 | 96 |

Results in FIGS. 4A-4B show that all candidates triggered the killing of BCMA-expressing tumor cells (FIG. 4A) and the activation of $CD4^+$ T cells (FIG. 4B). In particular, the 2+1 candidate anti-CD3-C1-UCP01-D6×BCMA showed the best killing potency among affinity matured variants. Importantly, this candidate showed a similar profile compared to the positive control 83A10-TCBcv_aCD3×TNB-BCMA BEAT Fc. Similarly, T cell activation data (FIG. 4B) confirmed the similarity between the candidate and the positive control 83A10-TCBcv_aCD3×TNB-BCMA BEAT Fc at inducing CD69 upregulation on CD4+ T cells in presence of BCMA-expressing tumor cells.

EXAMPLE 4: EPITOPE MAPPING FOR CD3 γε TARGETED BY ANTI-CD3-C1-D6 IGG1 LALA USING HDX MASS SPECTROMETRY

Materials and Methods

Pepsin/XIII digestion and LC-MS

The HDX-MS experiment was performed on a customized platform consisting of a custom HDX automation system for deuterium labeling and quenching, a Waters Acquity Binary Solvent Manager for sample digestion and trapping, a second Waters Acquity Binary Solvent Manager for analytical gradient, and a Thermo Q Exactive HF mass spectrometer for peptide identification and mass measurement.

4.3 μg of recombinant human CD3γε protein (SEQ ID NO:606) as described in Example 1 in 100 μL control buffer (50 mM phosphate, 100 mM sodium chloride at pH 7.4) was denatured by adding 100 μL of 4 M guanidine HCl, 0.85 M TCEP (final pH was 2.5) and incubating the mixture for 3 min at 4° C. Then, the mixture was subjected to on-column pepsin/XIII digestion using in-house packed column (2.1×30 mm, NBA2014002, NovaBioAssays, Woburn, MA). The resultant peptides were trapped and desalted on an ACQUITY UPLC BEH C18 VanGuard pre-column (130 Å, 1.7 μm, 2.1 mm×5 mm, 186003975, Waters) for 3.5 min at 160 μL/min. Peptides were then eluted from the trap using a 2-32% gradient of acetonitrile (with 0.3% formic acid) over 12.5 min at a flow rate of 150 μL/min and were separated on a 50×1 mm C8 column (3 μm, NBA2014015, NovaBioAssays). Solvent A was 0.3% formic acid in water. The eluted peptides were analyzed by a Thermo Q Exactive HF mass spectrometry in full MS/ddMS2 mode. The injection valve, enzyme column and their related connecting tubings were inside a cooling box maintained at 4° C. The second switching valve, C8 column and their related connecting stainless steel tubings were inside a chilled circulating box maintained at −6° C. Peptide identification was done through searching MS/MS data against the recombinant human CD3γε protein sequence (SEQ ID NO: 606) with Protein Metrics. The mass tolerance for the precursor and product ions were 10 ppm and 0.02 Da, respectively.

HDX with Pepsin/XIII Digestion

The anti-CD3-C1-D6 IgG1 LALA was concentrated using Amicon™ Ultra 0.5 mL 30 kDa Centrifugal Filter (MilliporeSigma). 10 μL recombinant human CD3γε protein ((SEQ ID NO: 606, 4.3 μg) or 10 μL recombinant human CD3γε protein (SEQ ID NO:606) mixed with anti-CD3-C1-D6 IgG1 LALA mixture (4.3 μg: 18.5 μg) was incubated with 90 μL deuterium oxide labeling buffer (50 mM sodium phosphate, 100 mM sodium chloride at pD 7.0) for 0 s, 15 s, 60 s, 600 s, and 3600 s at 4° C. Hydrogen/deuterium exchange was quenched by adding 100 μL of 4 M guanidine HCl, 0.85 M TCEP (final pH was 2.5). Subsequently, the quenched samples were subjected to on-column pepsin/XIII digestion and LC-MS analysis as described above. The mass spectra were recorded in MS only mode. Raw MS data was processed using HDX WorkBench, software for the analysis of H/D exchange MS data (J. Am. Soc. Mass Spectrom. 2012, 23 (9), 1512-1521). The deuterium levels were calculated using the average mass difference between the deuterated peptide and its native form (t0).

Results and Conclusions

The HDX-MS experiment performed to identify the epitope of anti-CD3-C1-D6 resulting in 100% sequence coverage was achieved for recombinant human CD3γε protein (SEQ ID NO: 606). Recombinant human CD3γε protein showed significant reduction in deuterium uptakes upon binding to anti-CD3-C1-D6 at AA182-197, YVCYPRG-SKPEDANFY (SEQ ID NO: 726), indicating that this was the main epitope on recombinant human CD3γε protein upon binding to anti-CD3-C1-D6 IgG1 LALA. This peptide belonged to the CD3 E peptide of the recombinant protein, indicating that the epsilon chain only of the construct was involved in binding to C1-D6. FIG. 5 shows the differential heat map comparing hydrogen/deuterium exchange of recombinant human CD3γε protein alone to that of recombinant human CD3γε protein mixed with anti-CD3-C1-D6 IgG1 LALA.

EXAMPLE 5: GENERATION OF ANTI-BCMA ANTIBODIES

Materials and Methods

Transient Expression of Full-Length Human and Cynomolgus Monkey BCMA in CHO-SV Cell Line The human codon-optimized sequences of the full-length human BCMA (UniProt sequence ID Q02223; residues 1-184; SEQ ID NO: 615) and of the full-length cynomolgus monkey BCMA (UniProt sequence ID A0A2K5UD97; residues 1-183; SEQ ID NO: 616) were cloned in a modified pcDNA™3.1 plasmid (ThermoFisher Scientific, catalog no. V79020). For protein expression, the plasmids were transfected into suspension-adapted CHO-S cells (cGMP banked, Invitrogen, catalog NO: A1136401) using Polyethyleneimine (PEI; Polysciences). Briefly, cells were prepared at 2 million cells per ml in CD CHO (Gibco). Cells were then transfected with a DNA-PEI mixture at 37° C. Four hours post-transfection, the cell culture was diluted 1:1 Power-CHO 2 (Lonza) supplemented with 4 mM L-Glutamine and incubated with orbital shaking at 37° C., 5% C02 and 80% humidity. The expression of the target antigens was assessed by monitoring the expression of the eGFP reporter protein with a fluorescence microscope.

Library Panning

The panning strategies consisted in four rounds of selection using recombinant human BCMA protein, or two rounds using recombinant human BCMA protein either followed by two rounds using recombinant cynomolgus monkey BCMA protein or cynomolgus monkey BCMA-expressing CHO cells.

Purified phage particles from each sub-library described in Example 1 have been pooled ($2.5\times10^{11}$ plaque-forming units/sub-library) and blocked with phosphate buffered saline (PBS) containing 3% (w/v) skimmed milk (3% MPBS) for 1 h at room temperature (RT). Two first rounds of selection were carried out using magnetic Dynabeads™ MyOne™ Streptavidin C1 beads (Invitrogen, catalog NO: 65002). Beads were blocked with phosphate buffered saline (PBS) containing 3% (w/v) skimmed milk (3% MPBS) for 1 h at room temperature (RT). Phages were deselected against pre-blocked beads for 1 h at RT. Deselected phages were incubated with 100 nM of biotinylated recombinant human BCMA protein (Acrobiosystems, catalog NO: BCA-H82E4) for 2 h at RT. Antigen bound phages were captured on streptavidin beads for 30 min at RT and beads were washed five times with PBS containing 0.1% (v/v) TWEEN® (PBS-TWEEN® 0.1%) and twice with PBS. Phages were eluted with 100 mM triethylamine for 10 min at RT and neutralized using Tris-HCl 1 M pH 8. Eluted phages were used to infect 10 ml of exponentially growing *E. coli* TG1 cells. Infected cells were grown in 2YT medium for 1 h at 37° C. and 100 rotation per minute (RPM), then spread on 2YTAG (2TY medium supplemented with 100 μg/ml ampicillin and 2% glucose) agar plates and incubated overnight (ON) at 30° C. Colonies were scrapped off the plates into 10 ml of 2YT and 15% glycerol (v/v) was added for storage at −80° C. TG1 cells from glycerol stocks were grown at 37° C. and 240 RPM in 2YTAG medium until OD at 600 nm reached 0.5. Cells were then superinfected with the M13K07 helper phage using a multiplicity of infection (MOI) of 10 for 1 h at 37° C. and 100 RPM. Culture medium was then changed for 2YTAK (2YT medium supplemented with 100 μg/ml ampicillin and 50 μg/ml kanamycin) and cells were further cultured ON at 30° C. and 280 RPM. Alternatively, eluted phages were used to infect 2 ml of exponentially growing *E. coli* TG1 cells. Infected cells were grown in 2YT medium for 1 h at 37° C. and 100 RPM, then grown in 2YT medium supplemented with 2% glucose for 1 h at 37° C. and 240 RPM. Cells were then superinfected with the M13K07 helper and phages produced as described above. The next day, 10 μl of phage containing cell-free supernatant were used for the subsequent round of selection.

For panning against recombinant cynomolgus monkey BCMA protein, magnetic Protein G Dynabeads® (Invitrogen, catalog NO: 10003D) and 200 nM of human IgG1 were mixed in 3% MPBS and incubated for 1 h at RT. Blocked phages were deselected against IgG1 coated beads for 1 h at RT. Phages were then incubated with 100 nM of recombinant cynomolgus monkey BCMA Fc fusion protein (Acrobiosystems, catalog NO: BCA-C5253) for 2 h at RT. Antigen bound phages were captured on Protein G beads for 30 min at RT and the following steps were performed as described above.

For cell-based panning, phage particles were blocked with phosphate buffered saline (PBS) containing 3% (w/v) Bovine Serum Albumin (PBS/BSA 3%) for 1 h at RT. $2\times10^7$ non-transfected CHO cells and $2\times10^7$ CHO cells transiently expressing cynomolgus monkey BCMA protein (SEQ ID NO: 616) were blocked with PBS/BSA 3% supplemented with 0.1% azide to avoid receptor internalization for 1 h at RT. Phages were deselected against non-transfected cells for 1 h at RT. The deselected phages were then incubated with the transfected cells for 2 h at RT. To remove non-specific phages, cells were washed four times with PBS-TWEEN® 0.1% and twice with PBS. Phages were eluted with citric acid 76 mM, pH 2.0 for 10 min at RT and neutralized using Tris-HCl 1 M pH 8. The following steps were performed as described above.

scFv Screening by SPR

Surface Plasmon Resonance (SPR) analysis was used to confirm specific binding activity of the scFv clones. Measurements were performed on a Biacore 8K+ instrument (Cytiva Life Sciences) using the Biacore 8K+ Control Software at 25° C. and analyzed with the Biacore Insight Evaluation Software (v3.0). Biotinylated recombinant human BCMA protein (Acrobiosystems, catalog NO: BCA-H82E4) or recombinant cynomolgus monkey BCMA Fc fusion protein (Acrobiosystems, catalog NO: BCA-C52H7) were diluted to a final concentration of 10 μg/ml in acetate buffer pH 4.5 (Cytiva Life Sciences, catalog NO:

BR100530) and subsequently immobilized on flow-path 2 on the eight channels, to around 200 and 250 resonance units (abbreviated RU) respectively, on Series S CM5 Sensor Chips (Cytiva Life Sciences, catalog NO: BR100012) using an amine coupling kit (Cytiva Life Sciences, catalog NO: BR100050). HBS-EP+(Cytiva Life Sciences, catalog NO: BR100669) was used as running buffer. Filtered periplasmic extracts were injected directly on the covalently coupled human BCMA Series S CM5 Sensor Chip or to the covalently coupled cynomolgus monkey BCMA Series S CM5 Sensor Chip. Samples were injected on the flow-paths 1 and 2 (flow-path 1 being used as reference) at a 30 μl/min flow rate for 3 min, followed by a dissociation time of 3 min in running buffer. After each binding event, surface was regenerated with 10 mM Glycine pH 1.5 solution (Cytiva Life Sciences, catalog NO: BR100354) injected for 50 s at 30 μl/min on both flow-paths. Each measurement included zero-concentration samples as well as irrelevant scFv periplasmic extracts for referencing and specificity, respectively.

scFv Screening by Flow Cytometry

The binding of scFv clones to CHO cells transiently expressing human BCMA protein (SEQ ID NO: 615) or cynomolgus monkey BCMA protein (SEQ ID NO: 616) was assessed by flow cytometry as described in Example 1.

Fab Expression cDNAs encoding the different antibody constant regions were gene synthetized by Geneart AG (Regensburg, Germany) and modified using standard molecular biology techniques. PCR products were digested with appropriate DNA restriction enzymes, purified, and ligated in modified pcDNA3.1 plasmids (Invitrogen) which carried a CMV promoter and a bovine hormone poly-adenylation (poly(A)). The expression vectors also carried oriP, which is the origin of plasmid replication of Epstein-Barr virus, and the murine VJ2C leader peptide for secretion of the encoded polypeptide chain. For reformatting scFv library clones into human IgG1 Fab fragments, each scFv clone in its phage library vector was used to amplify its individual VH cDNAs by PCR, next the VH PCR product was cloned in the modified pcDNA 3.1 vector described above upstream of a cDNA encoding a human IgG1 heavy chain CH1 domain, whereas the fixed Vκ3-15/Jκ1 light chain (SEQ ID NO: 1) was cloned in the modified pcDNA 3.1 vector described above upstream of a cDNA encoding a human kappa constant light chain domain.

For Fab expression, equal quantities of heavy chain and light chain vectors were co-transfected into suspension-adapted HEK293-EBNA cells (ATCC, catalog NO: CRL-10852) using polyethyleneimine (PEI) linear (Polysciences Inc., catalog NO: 24314). Typically, cells were prepared at 8 million cells per ml in RPMI 1640 (Biowest, catalog NO: L0501) supplemented with 0.1% Pluronic F-68 (Thermo-Scientific, catalog NO: 24040032). Cells were then transfected with a DNA-PEI mixture. Four hours post-transfection, the cell culture was diluted 1:1 in BalanceCD HEK293 (Irvine Scientific, catalog NO: 91165) supplemented with 4 mM L-Glutamine and incubated for 5 days with orbital shaking at 37° C., 5% C02 and 80% humidity. Cell-free culture supernatants containing the recombinant proteins were prepared by centrifugation followed by filtration and used for further purification. Fab proteins were purified using CaptureSelect™ IgG-CH1 Affinity Matrix (Thermo-Scientific, catalog NO: 194320050). Affinity resin was added to the filtered culture supernatants and incubated ON at 4° C. with gentle mixing. The next day, resin beads were collected into Poly-Prep columns (Bio-Rad Laboratories), washed with PBS, and the recombinant proteins eluted with an acidic buffer (typically glycine 0.1 M pH 3). After neutralization with 1/10 volume of Tris-HCl pH 8, preparations were buffer-exchanged into PBS.

Fab binding affinities for BCMA

Surface plasmon resonance (SPR) was used to measure the binding affinities of the Fab fragments for human and cynomolgus monkey BCMA. Affinities were measured on a Biacore T200 instrument (Cytiva Life Sciences) at 25° C. and analyzed with the Biacore T200 Evaluation Software (v3.1). Measurements were performed on Series S CM5 Sensor Chips (Cytiva Life Sciences, catalog NO: BR100530). Recombinant human BCMA protein (Acrobiosystems, catalog NO: BCA-H522γ) and recombinant cynomolgus monkey BCMA protein (Acrobiosystems, catalog NO: BCA-C52H7) were covalently immobilized to around 200 RU on flow-path 2 and flow-path 3 respectively of the Sensor Chip surface using a commercially available amine coupling kit (Cytiva Life Sciences, catalog NO: BR100050). Fab fragments were injected in single cycle kinetic at different concentrations ranging from 15.6 to 1000 nM, in HBS-EP+ buffer (Cytiva Life Sciences, catalog NO: BR100669) at a flow rate of 30 μl/min for 3 min on flow-path 1, 2, 3 and 4 (flow-path 1 being used as reference). Dissociation was monitored for 5 min. After each cycle, the Series S CM5 Sensor Chip surface coated with recombinant BCMA proteins was regenerated with 30 μl of 10 mM Glycine pH 1.5 (Cytiva Life Sciences, catalog NO: BR100354). Experimental data were processed using the 1:1 Langmuir kinetic fitting model. Measurements included zero-concentration samples for referencing. $Chi^2$, U- and residual values were used to evaluate the quality of a fit between the experimental data and individual binding models.

APRIL and BAFF Blocking Assay

The ability of the Fab fragments to block the interaction between human BCMA and human APRIL, as well as between human BCMA and human BAFF was assessed by Surface Plasmon Resonance (SPR). Measurements were performed on a Biacore 8K+ instrument (Cytiva Life Sciences) using the Biacore 8K+ Control Software at room temperature and analyzed with the Biacore Insight Evaluation Software (v3.0). HBS-EP+ buffer (Cytiva Life Sciences, catalog NO: BR100669) was used as running buffer. His-tagged recombinant human APRIL protein (Acrobiosystems, catalog NO: APL-H5244) or his-tagged recombinant human BAFF protein (Acrobiosystems, catalog NO: BAF-H5248) was immobilized to around 65 RU or to around 10 RU respectively on flow-path 2 of a Series S CM5 Sensor Chip (Cytiva Life Sciences, catalog NO: BR100530) previously coated with anti-histidine antibody (Cytiva Life Sciences, catalog NO: 28995056). A pre-mixed solution of 50 nM recombinant human BCMA Fc fusion protein (Acrobiosystems, catalog NO: BCA-H5254) and 25 nM Fab in HBS-EP+ buffer was injected for 3 min on flow-path 1 and flow-path 2 (flow-path 1 being used as reference) of immobilized human APRIL or of immobilized human BAFF Sensor Chip, followed by 3 min dissociation in running buffer. Same experimental procedure was performed using pre-mixed solutions of 50 nM recombinant human BCMA Fc fusion protein and 50 nM or 200 nM of Fab or with 50 nM recombinant human BCMA Fc fusion protein alone. Anti-histidine antibody surface was regenerated using 30 μl of 10 mM glycine-HCl pH 1.5 (Cytiva Life Sciences, catalog NO: BR100354) injected on both flow-paths at the end of each cycle.

Results and Conclusions

ScFv clones showing specific binding to recombinant human BCMA protein and to recombinant cynomolgus monkey BCMA protein by SPR, or scFv clones showing specific binding to human BCMA-expressing CHO cells and cynomolgus monkey BCMA expressing CHO cells, were sequenced and unique sequences were reformatted in Fab fragment for further characterization. Biochemical characterization included assessment of binding affinities and functional assessment was performed using human BCMA/APRIL and BCMA/BAFF blocking assays.

Fab Binding Affinities for BCMA

Fifteen Fab clones showed binding affinities to human BCMA with an equilibrium dissociation constant ($K_D$) below 2 μM as determined by SPR. Heavy chain sequence identification numbers and binding affinities of the mentioned clones are reported in Table 5. Clone anti-BCMA-PP02-D3 (SEQ ID NO: 78), herein also referred to as anti-BCMA-D3 showed affinities to human BCMA of 15 nM and to cynomolgus monkey BCMA of 40 nM. Clone anti-BCMA-PP02-E6 (SEQ ID NO: 79), herein also referred to as anti-BCMA-E6 showed affinities to human BCMA of 18 nM and to cynomolgus monkey BCMA of 52 nM.

TABLE 5

Overview of the developed anti-BCMA Fabs and their relative affinity to recombinant human and cynomolgus monkey BCMA proteins as assessed by SPR. Table shows clones heavy chain sequence identification numbers, affinity ($K_D$) to recombinant human BCMA protein and affinity ($K_D$) to recombinant cynomolgus monkey BCMA protein for developed anti-BCMA Fabs.

| Clone name | Clone heavy chain SEQ ID NO | Human BCMA $K_D$ (nM) | Cynomolgus monkey BCMA $K_D$ (nM) |
|---|---|---|---|
| anti-BCMA-UCP01-A8 FAB | SEQ ID NO: 68 | 235 | NB |
| anti-BCMA-UCP01-A10 FAB | SEQ ID NO: 69 | 214 | >2000 |
| anti-BCMA-UCP01-C2 FAB | SEQ ID NO: 70 | 336 | NB |
| anti-BCMA-UCP01-E8 FAB | SEQ ID NO: 71 | 1745 | NB |
| anti-BCMA-UCP01-E9 FAB | SEQ ID NO: 72 | 10 | 236 |
| anti-BCMA-UCP01-F9 FAB | SEQ ID NO: 73 | 617 | NB |
| anti-BCMA-PP02-A3 FAB | SEQ ID NO: 74 | 318 | >2000 |
| anti-BCMA-PP02-B4 FAB | SEQ ID NO: 75 | 648 | 58 |
| anti-BCMA-PP02-C2 FAB | SEQ ID NO: 76 | 915 | NB |
| anti-BCMA-PP02-C4 FAB | SEQ ID NO: 77 | 608 | 114 |
| anti-BCMA-PP02-D3 FAB | SEQ ID NO: 78 | 15 | 40 |
| anti-BCMA-PP02-E6 FAB | SEQ ID NO: 79 | 18 | 52 |
| anti-BCMA-PP02-F1 FAB | SEQ ID NO: 80 | 145 | 598 |
| anti-BCMA-PP03-C4 FAB | SEQ ID NO: 81 | 549 | 109 |
| anti-BCMA-PP03-E4 FAB | SEQ ID NO: 82 | 582 | 696 |

NB = no measurable binding.

APRIL and BAFF Blocking Assay

Fab fragments were tested at blocking the interaction between human BCMA and human APRIL or between human BCMA and human BAFF using SPR. Anti-BCMA-D3 and anti-BCMA-E6 Fab fragments tested to block the interaction between human BCMA and human APRIL, as well as between human BCMA and human BAFF. An increase in concentration of Fab in pre-mixed solutions of recombinant BCMA-Fc protein and anti-BCMA-D3 Fab or in pre-mixed solutions of recombinant BCMA-Fc protein and anti-BCMA-E6 Fab resulted in a decrease in binding response (in RU, Y-axis) of BCMA-Fc to immobilized recombinant APRIL protein or to immobilized recombinant BAFF protein. Complete blocking of human BCMA/human APRIL interaction, as well as complete blocking of human BCMA/human BAFF interaction was observed when excess molar ratio of anti-BCMA-D3/human BCMA or excess molar ratio of anti-BCMA-E6 Fab/human BCMA was used. Blocking of the interaction between recombinant human BCMA protein and recombinant human APRIL protein and blocking of the interaction between recombinant human BCMA protein and recombinant human BAFF protein upon binding of Fab clones anti-BCMA-D3 and anti-BCMA-E6 to human BCMA protein is illustrated in FIGS. 6A-6D.

EXAMPLE 6: OPTIMIZATION OF ANTI-BCMA-D3 AND ANTI-BCMA-E6

Materials and Methods

Library Generation and Panning

Five affinity maturation libraries were generated for both anti-BCMA-D3 (SEQ ID NO: 78) and anti-BCMA-E6 (SEQ ID NO: 79) by introducing diversity in the CDRs of the heavy chain. CDR-H1, CDR-H2 and CDR-H3 were randomized using degenerated NNK codon oligonucleotides (wherein N is any of the four deoxyribonucleotides and K is G or T) at Kabat residues 27-35, 50-58, 95-101 minus 2, respectively. Each library was generated using a pool of overlapping oligonucleotides containing 5 consecutive degenerated codons. CDR-H1 and CDR-H2 were also diversified using Trimer oligonucleotide at position Kabat 27-35 and 50-58 respectively. Libraries were prepared as described in Example.

Phage display panning was performed as described in Example 1 with the following modifications. Libraries were incubated with beads pre-coated with 20 nM, 2 nM, and 0.2 nM of biotinylated recombinant human BCMA protein (Acrobiosystems, catalog NO: BCA-H82E4), for round 1, round 2 and round 3, respectively. After 1 h incubation, 1 μM of non-biotinylated recombinant human BCMA protein (Acrobiosystems, catalog NO: BCA-H522γ) was added for 3 h at RT during rounds 2 and 3.

Affinity Screening by SPR

SPR analysis was used to confirm specific binding activity of the new scFv clones and rank the positive clones according to their binding profile. Measurements were performed as described in Example with the following modifications. Recombinant human BCMA protein (Acrobiosystems, catalog NO: BCA-H522γ) was diluted to a final concentration of 200 nM in acetate buffer pH 4.5 (Cytiva Life Sciences, catalog NO: BR100350) and subsequently immobilized on flow-path 2 of the eight channels to around 700-1000 RU on a Series S CM5 sensor CHIP (Cytiva Life Sciences, catalog NO: BR100530) using an amine coupling kit (Cytiva Life Sciences, catalog NO: BR100050). Filtered periplasmic extracts were injected directly on the covalently coupled human BCMA Sensor Chip on the flow-path 1 and 2 (flow-path 1 being used as reference) for 3 min. Dissociation in HBS-EP+ buffer was monitored for 3 min. The scFv clones showing the best binding profiles were reformatted in Fab fragments as described in Example.

Fab Binding Affinities to Recombinant BCMA Protein

Surface plasmon resonance (SPR) was used to measure the binding affinities of the Fab fragments for human and cynomolgus monkey BCMA. Measurements were performed on a Biacore 8K+ instrument (Cytiva Life Sciences) using the Biacore 8K+ Control Software at 25° C. and analyzed with the Biacore Insight Evaluation Software (v3.0). Affinity measurements of the anti-BCMA-D3 optimized Fabs to human and cynomolgus monkey BCMA proteins were performed on Series S CM5 Sensor Chip (Cytiva Life Sciences, catalog NO: BR100530) previously coated with anti-human IgG (Fc) antibody using a Human Antibody Capture Kit (Cytiva Life Sciences, catalog NO: 29234600). Around 120 RU of recombinant human BCMA Fc fusion protein (Acrobiosystems, catalog NO: BC7-H5254) or around 145 RU of recombinant cynomolgus monkey BCMA Fc fusion protein (Acrobiosystems, catalog NO: BCA-C5253) was captured on flow-path 2 of the anti-human IgG (Fc) antibody coated Sensor Chip. Fabs were injected in single cycle kinetic at different concentrations ranging from 0.16 to 10 nM, in HBS-EP+ buffer (Cytiva Life Sciences, catalog NO: BR100669) at a flow rate of 30 μl/min for 3 min on flow-path 1 and 2 (flow-path 1 being used as reference). Dissociation was monitored for 10 min. After each cycle, the surface was regenerated with 60 µl of 3 M $MgCl_2$. Affinity measurements of the anti-BCMA-E6 optimized Fabs to human and cynomolgus monkey BCMA proteins were performed on a Series S Biotin CAPture Chip (Cytiva Life Sciences, catalog NO: 28920234). Around 20 RU of biotinylated recombinant human BCMA protein (Acrobiosystems, catalog NO: BCA-H82E4) or around 55 RU of biotinylated recombinant cynomolgus monkey BCMA Fc fusion protein (Acrobiosystems, catalog NO: BCA-C82F4) was captured on flow-path 2 of a Series CAP Sensor Chip. Fabs were injected in single cycle kinetic at different concentrations ranging from 0.2 to 50 nM, in HBS-EP+ buffer (Cytiva Life Sciences, catalog NO: BR100669) at a flow rate of 30 µl/min for 3 min on flow-path 1 and 2 (flow-path 1 being used as reference). Dissociation was monitored for 10 min. After each cycle, the surface was regenerated with 60 µl of regeneration solution provided with Series S Biotin CAPture Kit (Cytiva Life Sciences, catalog NO: 28920234). Experimental data were processed using the 1:1 Langmuir kinetic fitting model. Measurements included zero-concentration samples for referencing. $Chi^2$ and residual values were used to evaluate the quality of a fit between the experimental data and individual binding models.

Screening of anti-BCMA Fab fragments for binding to BCMA-expressing cells

The screening of anti-BCMA antibodies produced as Fab fragments was performed by binding studies on NCI-H929 wild-type and using BCMA KO NCI-H929 cells to measure non-specific binding.

In brief, cells were harvested, counted, and plated at $1 \times 10^5$ cells/well in a 96-well round-bottom plate (TPP, catalog NO: 92097). The plate was centrifuged at 350 g for 3 min at 4° C. and the cells were resuspended in 100 µl of cold FACS buffer containing serial dilutions of anti-BCMA Fab antibodies starting from 800 nM and diluted by 3-fold. Cells were incubated for 30 min at 4° C., washed twice with cold FACS buffer at 350 g for 3 min and resuspended in 50 µl of polyclonal anti-human IgG Fab PE secondary antibody (ThermoFisher Scientific, catalog NO: MA1-10377, 1/200) diluted in FACS buffer. Cells were then washed twice and resuspended in 100 µl of FACS buffer containing SYTOX Green dead cell stain (ThermoFisher Scientific, catalog NO: S34860). Samples were acquired on a CytoFlex instrument (Beckman Coulter). Cells were gated based on size FSC vs SSC and debris and doublets were excluded. Finally, cells negative for the viability staining were gated, and living cells were analyzed for PE-geometric mean (geomean) fluorescence intensity using FlowJo software. Relative geomean fluorescence intensity (RFI) was calculated by subtracting fluorescence of the isotype control (An irrelevant Fab) to the fluorescence of the anti-BCMA. Relative geomean fluorescence intensity values were finally plotted using Prism software (GraphPad). Equilibrium dissociation constant values ($K_D$) was determined by using one-site binding curve fitting on non-transformed data (Prism). The $K_D$ and Maximum binding (Maximum RFI) values are summarized in Table 6.

Results and Conclusions

Affinity maturation of anti-BCMA-D3 clone (heavy chain SEQ ID NO: 78) and of anti-BCMA-E6 clone (heavy chain SEQ ID NO: 79) involved diversification of CDR-H1 (Kabat positions 27-35), CDR-H2 (Kabat positions 50-58) and CDR-H3 (Kabat positions 95-101 minus 2) in five individual libraries. ScFv clones having a slower off-rate than their respective parental clone (anti-BCMA-D3 or anti-BCMA-E6) as measured by SPR were isolated. ScFv clones were reformatted and expressed as Fab fragments and affinities to recombinant human BCMA protein and to recombinant cynomolgus monkey BCMA protein were measured by SPR. One clone, anti-BCMA-D3-MP04-E11 (heavy chain SEQ ID NO: 93), herein also referred as anti-BCMA-D3-E11, had the highest affinities of the anti-BCMA-D3 optimized clones to human and cynomolgus monkey BCMA, with $K_D$ measured at 0.01 nM for both proteins and was selected for the generation of CD3/BCMA/CD38 antibodies described herein. Three clones, namely clone anti-BCMA-E6-PP02-B1 (heavy chain SEQ ID NO: 101), herein also referred as anti-BCMA-E6-B1, clone anti-BCMA-E6-PP02-E6 (heavy chain SEQ ID NO: 105), herein also referred as anti-BCMA-E6-E6 and clone anti-BCMA-E6-PP02-G6 (heavy chain SEQ ID NO: 108), herein also referred as anti-BCMA-E6-G6, showed varying increase in affinity to human and cynomolgus BCMA as compared to parental anti-BCMA-E6 clone and were also selected for the generation of CD3/BCMA/CD38 antibodies described herein. $K_D$ values for anti-BCMA-E6-B1, anti-BCMA-E6-E6 and anti-BCMA-E6-G6 were measured at 0.182 nM, 0.169 nM, and 0.330 nM, respectively for human BCMA protein and at 0.510 nM, 0.615 nM, and 2.26 nM, respectively for cynomolgus monkey BCMA protein. Heavy chain sequence identification numbers, binding affinity of the developed anti-BCMA-D3-optimized and anti-BCMA-E6-optimized clones to human and cynomolgus monkey BCMA proteins and binding affinity to H929 cells are reported in Table 6. FIG. 7 shows that all Fab fragments showed binding to BCMA-expressing NCI-H929 cells as shown in Table 6. Few clones, anti-BCMA-D3-MP04-E11, anti-BCMA-E6-PP02-B1, anti-BCMA-E6-PP02-E6 and anti-BCMA-E6-PP02-G6 were selected based on their strong binding properties ($K_D$ and maximum binding) with significant improvement compared to their respective parental clones. Specificity was also confirmed by the lack of binding to BCMA KO NCI-H929 cell line.

TABLE 6

Overview of developed anti-BCMA-D3- and anti-BCMA-E6- optimized Fabs and their relative affinity to recombinant human BCMA and to recombinant cynomolgus monkey BCMA by SPR, as well as their relative binding affinity to NCI-H929 cells. Table 6 shows clones heavy chain sequence identification numbers (SEQ ID NO), CDR randomization library from which the clones derive, binding affinity ($K_D$) for developed anti-BCMA-D3- and anti-BCMA-E6- optimized Fabs to recombinant human BCMA protein and to recombinant cynomolgus monkey protein by SPR, as well as binding affinity ($K_D$) and Maximum binding values (RFI) determined from Flow Cytometry experiments on NCI-H929 cell line. $K_D$ and Maximum binding values on NCI-H929 cell line are average values derived from two independent experiments.

| CDR randomization library | Clone name | Clone heavy chain SEQ ID NO | Human BCMA SPR $K_D$ (nM) | Cynomolgus monkey BCMA SPR $K_D$ (nM) | $K_D$ on NCI-H929 (nM) | Maximum binding on NCI-H929 (RFI) |
|---|---|---|---|---|---|---|
| CDR-H2 | Anti-BCMA-D3-MP03-G7 FAB | SEQ ID NO: 83 | 0.41 | 0.31 | 29.49 | 21530 |

TABLE 6-continued

Overview of developed anti-BCMA-D3- and anti-BCMA-E6- optimized Fabs and their relative affinity to recombinant human BCMA and to recombinant cynomolgus monkey BCMA by SPR, as well as their relative binding affinity to NCI-H929 cells. Table 6 shows clones heavy chain sequence identification numbers (SEQ ID NO), CDR randomization library from which the clones derive, binding affinity ($K_D$) for developed anti-BCMA-D3- and anti-BCMA-E6- optimized Fabs to recombinant human BCMA protein and to recombinant cynomolgus monkey protein by SPR, as well as binding affinity ($K_D$) and Maximum binding values (RFI) determined from Flow Cytometry experiments on NCI-H929 cell line. $K_D$ and Maximum binding values on NCI-H929 cell line are average values derived from two independent experiments.

| CDR randomization library | Clone name | Clone heavy chain SEQ ID NO | Human BCMA SPR $K_D$ (nM) | Cynomolgus monkey BCMA SPR $K_D$ (nM) | $K_D$ on NCI-H929 (nM) | Maximum binding on NCI-H929 (RFI) |
|---|---|---|---|---|---|---|
| CDR-H2 | Anti-BCMA-D3-MP04-A2 FAB | SEQ ID NO: 84 | 0.03 | 0.01 | 7.68 | 21478 |
| CDR-H2 | Anti-BCMA-D3-MP04-B11a FAB | SEQ ID NO: 85 | 0.14 | 0.24 | 6.03 | 23663 |
| CDR-H2 | Anti-BCMA-D3-MP04-B11b FAB | SEQ ID NO: 86 | 0.52 | 0.79 | 14.12 | 23316 |
| CDR-H2 | Anti-BCMA-D3-MP04-B11c FAB | SEQ ID NO: 87 | 0.16 | 0.34 | 3.9 | 22905 |
| CDR-H2 | Anti-BCMA-D3-MP04-B11d FAB | SEQ ID NO: 88 | 5.43 | 4.85 | NT | NT |
| CDR-H2 | Anti-BCMA-D3-MP04-C2 FAB | SEQ ID NO: 89 | 0.03 | 0.02 | 6.49 | 24557 |
| CDR-H2 | Anti-BCMA-D3-MP04-C8a FAB | SEQ ID NO: 90 | 0.09 | 0.17 | 3.65 | 26528 |
| CDR-H2 | Anti-BCMA-D3-MP04-C8b FAB | SEQ ID NO: 91 | 0.03 | 0.11 | 7.39 | 28295 |
| CDR-H2 | Anti-BCMA-D3-MP04-D4 FAB | SEQ ID NO: 92 | 0.02 | 0.01 | 8.84 | 25299 |
| CDR-H2 | Anti-BCMA-D3-MP04-E11 FAB | SEQ ID NO: 93 | 0.01 | 0.01 | 13.45 | 31842 |
| CDR-H2 | Anti-BCMA-D3-MP04-F3 FAB | SEQ ID NO: 94 | 0.64 | 3.03 | 7.12 | 19546 |
| CDR-H2 | Anti-BCMA-D3-MP04-G7 FAB | SEQ ID NO: 95 | 0.08 | 0.14 | 5.82 | 27035 |
| CDR-H3 | Anti-BCMA-D3-MP05-A9 FAB | SEQ ID NO: 96 | 2.3 | 6.54 | NT | NT |
| CDR-H3 | Anti-BCMA-D3-MP05-C1a FAB | SEQ ID NO: 97 | 1.03 | 1.03 | NT | NT |
| CDR-H3 | Anti-BCMA-D3-MP05-C1b FAB | SEQ ID NO: 98 | 2.22 | 5.86 | NT | NT |
| CDR-H3 | Anti-BCMA-D3-MP05-F4 FAB | SEQ ID NO: 99 | 0.78 | 2.83 | 11.85 | 29941 |
| CDR-H2 | Anti-BCMA-E6-PP02-A3 FAB | SEQ ID NO: 100 | 0.33 | 0.915 | 6.37 | 40163 |
| CDR-H2 | Anti-BCMA-E6-PP02-B1 FAB | SEQ ID NO: 101 | 0.182 | 0.51 | 3.72 | 34715 |
| CDR-H2 | Anti-BCMA-E6-PP02-B4 FAB | SEQ ID NO: 102 | 0.086 | 0.857 | 5.49 | 43536 |
| CDR-H2 | Anti-BCMA-E6-PP02-C7 FAB | SEQ ID NO: 103 | 0.3 | 1.19 | 6.83 | 38616 |
| CDR-H2 | Anti-BCMA-E6-PP02-D2 FAB | SEQ ID NO: 104 | 0.342 | 0.97 | 6.58 | 36313 |
| CDR-H2 | Anti-BCMA-E6-PP02-E6 FAB | SEQ ID NO: 105 | 0.169 | 0.615 | 5.13 | 43245 |
| CDR-H2 | Anti-BCMA-E6-PP02-F7 FAB | SEQ ID NO: 106 | 0.22 | 0.964 | 5.53 | 44707 |
| CDR-H2 | Anti-BCMA-E6-PP02-G2 FAB | SEQ ID NO: 107 | 0.176 | 0.728 | 5.22 | 40502 |
| CDR-H2 | Anti-BCMA-E6-PP02-G6 FAB | SEQ ID NO: 108 | 0.33 | 2.26 | 5.78 | 46477 |
| CDR-H2 | Anti-BCMA-E6-PP02-G7 FAB | SEQ ID NO: 109 | 0.061 | 0.237 | 4.86 | 39367 |

NB = no measurable binding.

NT = not tested.

EXAMPLE 7: GENERATION OF ANTI-CD38 ANTIBODIES

Materials and Methods

Recombinant Target Antigens cDNA for human and cynomolgus monkey CD38 were obtained from Source Biosciences (Erwin-Negelein-Haus, Germany, Cat. NO: IRAU37D11, 4309086), their extracellular regions (UniProt accession No: P28907 residues 43-300 and Uniprot accession No: Q5VANO, residues 43-301 (residue 44 was deleted), respectively) were PCR amplified and cloned into an in-house expression vector derived from pcDNA3.1 (Invitrogen AG). This expression vector encompassed a Kozak sequence, and a start codon followed by the murine IgGκ light chain leader peptide at the 5' end and a 6-His-tag at the 3' end of its multiple cloning site. The soluble extracellular region of human CD38 (residues 43 to 300, SEQ ID NO: 607) and cynomolgus monkey CD38 (residues 43-301, SEQ ID NO: 608) fused to a 6-His-tag were expressed as follows. Briefly, one volume of RPMI 1640 medium (PAA Laboratories) containing HEK cells, 0.1% Pluronic acid (Invitrogen AG), expression vector and polyethyleneimine (JetPEI®, Polyplus-transfection, Illkirch, France) was incubated in a shake flask at 37° C., 5% $CO_2$ and 80% humidity. One volume of Ex-Cell 293 medium supplemented with 6 mM glutamine was added to the mixture after 4 h and incubation continued further for a total of 5 days. Post-production clarified supernatant was obtained by centrifugation and filtrated using 0.2 μm filters, pH was adjusted at 7.4 (4° C.) using Tris 1 M pH 8.7. Ni-Sepharose Excell beads (GE Healthcare) were added to the clarified supernatant and incubated overnight at 4° C. under agitation. The solution was loaded on an Econo-Column (Bio-Rad Laboratories) for gravity-flow purification. The beads were subsequently washed with 1×PBS, pH 7.4 (1 or 2×10 CV) and 1×PBS, pH 7.4 supplemented with 20 mM imidazole (10 CV). The protein was, depending on the batch, either eluted with 1×PBS, pH 7.4 supplemented with 500 mM imidazole or eluted by increasing stepwise the concentration in imidazole (40 mM, 80 mM, and 250 mM imidazole). Fractions of interest were pooled and dialyzed twice against 1×PBS, pH 7.4 at 4° C. The protein was concentrated and sterile filtered using 0.22 μm filters. Protein quality was assessed by SDS-PAGE, SE-HPLC, endotoxin measurement and ELISA. Briefly, SE-HPLC was performed using a Tosoh Bioscience TSKgel G3000SWxl column (catalog NO: 08541, Tosoh Bioscience) at room temperature with 0.1 M sodium phosphate buffer, 0.15 M sodium chloride, pH 6.8 as eluent at 1 ml/min flow rate, on a Waters Alliance 2695 HPLC system with a Waters 2998 PDA detector (Waters), monitoring at 214 nm and 280 nm. The Multi-Cartridge System Endosafe-MCS from Charles River utilizing a Limulus amebocyte lysate (LAL)-based assay was used to confirm a bacterial endotoxin level inferior to 0.5 EU/mg. These proteins are referred herein as human CD38-C-His and cynomolgus monkey CD38-C-His and are described as SEQ ID NO: 607 and SEQ ID NO: 608, respectively.

Daratumumab Fab Expression and Purification

For daratumumab Fab expression (SEQ ID NO: 609 and SEQ ID NO: 566), equal quantities of heavy chain and light chain vectors were co-transfected into suspension-adapted HEK293-EBNA cells (ATCC, cat no CRL-10852) using PEI. Typically, cells were prepared 25 at 8 million cells per ml in RPMI supplemented with 0.1% Pluronic F-68. Cells were then transfected with a DNA-PEI mixture. Four hours post-transfection, the cell culture was diluted 1:1 in EX-CELL® 293 supplemented with Phenol Red and 4 mM L-Glutamine and incubated for 5 days with orbital shaking at 37° C., 5% C02 and 80% humidity. Cell-free culture supernatants containing the recombinant proteins were prepared by centrifugation followed by filtration and used for further purification. The Fab was purified using Protein A (RepliGen CaptivA PrimAB, catalog NO: CA-PRI). Affinity resin was added to the filtered culture supernatants and incubated ON at 4° C. with gentle mixing. The next day, resin beads were collected into Poly-Prep columns (Bio-Rad Laboratories), washed with PBS, and the recombinant proteins eluted with an acidic buffer (typically glycine 0.1 M pH 3.5). After neutralization with 1/10 volume of Tris-HCl pH 8, preparations were buffer-exchanged into PBS.

Transient expression of full-length human and cynomolgus monkey CD38 in CHO-S cell line The human codon-optimized sequences of the full-length human CD38 (UniProt sequence ID P28907; residues 1-300; SEQ ID NO: 617), of the full-length cynomolgus monkey CD38 (accession number: Q5VAN0; residues 1-301; SEQ ID NO: 618) were cloned in a modified pcDNA™3.1 plasmid (ThermoFisher Scientific, catalog NO: V79020). Transfection and protein expression were done in suspension-adapted CHO-S cells (cGMP banked, Invitrogen, catalog NO: A1136401) as described in Example 1. Human and cynomolgus monkey CD38 proteins as described herein have SEQ ID NO: 617 and SEQ ID NO: 618, respectively.

Library Panning

The panning was performed as described in the Example with the following modifications. The first panning strategy consisted in three rounds of selection using biotinylated recombinant human CD38 protein (Acrobiosystems, catalog NO: CD8-H82E7). The second panning strategy consisted in two rounds of selection using biotinylated recombinant human CD38 protein followed by two rounds using CHO cells transiently expressing human CD38 protein (SEQ ID NO: 617) or cynomolgus monkey CD38 protein (SEQ ID NO: 618).

scFv Screening by SPR

Surface Plasmon Resonance (SPR) analysis was used to confirm specific binding activity of the scFv clones. Measurements were performed on a Biacore 2000 instrument (Cytiva Life Sciences) using the Biacore 2000 Control Software v3.2 at room temperature and analyzed with the Biacore T200 Evaluation Software (v3.1). Commercially available recombinant human CD38 protein (Acrobiosystems, catalog NO: CD8-H5224) and recombinant cynomolgus monkey CD38 protein (R&D Systems, catalog NO: 9834-AC-050), or recombinant human CD38 extracellular domain (ECD)-C-his (SEQ ID NO: 607) and recombinant cynomolgus CD38-ECD-C-his (SEQ ID NO: 608) proteins produced in house were individually diluted to a final concentration of 200 nM in acetate buffer pH 4.5 (Cytiva Life Sciences, catalog NO: BR100350) and subsequently immobilized on flow-path 2 and 3 respectively, to a level of about one 1500 resonance units (abbreviated RU) on CM5 Sensor Chips (Cytiva Life Sciences, catalog NO: BR100012) using an amine coupling kit (Cytiva Life Sciences, catalog NO: BR100050). Flow-path 4 was similarly immobilized with commercially available recombinant mouse CD38 protein (Creative Biomart, catalog NO: CD38-3112M) or with an irrelevant antigen. HBS-EP (Cytiva Life Sciences, catalog NO: BR100188) was used as running buffer. Filtered periplasmic extracts were injected directly on the covalently coupled human CD38-his and cynomolgus CD38-his CM5 Sensor Chip. Samples were injected on the flow-path 1, 2, 3 and 4 (flow-path 1 being used as reference) at a 30 μl/min flow rate for 3 min, followed by a dissociation time of 5 min in running buffer. After each binding event, surface was regenerated with 10 mM Glycine pH 1.5 solution (Cytiva Life Sciences, catalog NO: BR100354) injected for 1 min at 30 μl/min. Each measurement included zero-concentration samples as well as irrelevant scFv periplasmic extracts for referencing and specificity, respectively.

scFv Screening by Flow Cytometry

The binding of scFv clones to CHO cells transiently expressing human CD38 protein (SEQ ID NO: 617) was assessed by flow cytometry as described Example 1.

Fab binding affinities for CD38

Human IgG1 Fab fragments were expressed and purified as described in Example. Surface plasmon resonance (SPR) was used to measure the binding affinities of the Fab fragments for human and cynomolgus monkey CD38. Affinities were measured on a Biacore T200 instrument (Cytiva Life Sciences) at 25° C. and analyzed with the Biacore T200 Evaluation Software (v3.1). Measurements to human CD38 were performed on Series S Sensor Chips SA (Cytiva Life Sciences, catalog NO: BR100531) or on Series S Biotin CAPture Chips (Cytiva Life Sciences, catalog NO: 28920234) using commercially available recombinant biotinylated human CD38 (Acrobiosystems, catalog NO: CD8-H82E7). Measurements to cynomolgus monkey CD38 were performed on Series S CM5 sensor chips (Cytiva Life Sciences, catalog NO: BR100530) previously immobilized with anti-histidine antibody (Cytiva Life Sciences, catalog NO: 28995056) using recombinant cynomolgus monkey CD38-ECD-C-his protein produced in house (SEQ ID NO: 617).

The affinities to human and cynomolgus monkey CD38 were assessed by immobilizing CD38 and using Fab fragments as analyte. Biotinylated recombinant human CD38 protein was immobilized to around 160 RU on flow-path 2 of a Series S Sensor Chip SA or to around 100 RU on flow-path 2 of a Series S Biotin CAPture Chip and recombinant cynomolgus monkey CD38-his protein was immobilized to around 50-100 RU on flow-path 2 of a Series S CM5 Sensor Chip previously coated with anti-histidine antibody. Fab fragments were injected in single cycle kinetic at different concentrations ranging from 7.8 to 2000 nM, in HBS-EP+ buffer (Cytiva Life Sciences, catalog NO: BR100669) at a flow rate of 30 μl/min for 3 min on flow-path 1 and 2 (flow-path 1 being used as reference). Dissociation was monitored for 5 min. After each cycle, the Series S Sensor Chip SA coated with biotinylated recombinant human CD38 protein surface was regenerated with 60 μl of 10 mM Glycine pH1.5 (Cytiva Life Sciences, catalog NO: BR100354) while Series S Biotin CAPture Chip and Series S CM5 Sensor Chip coated with anti-histidin antibody surfaces were regenerated using regeneration solution provided with Biotin CAPture kit (Cytiva Life Sciences, catalog NO: 28920234) and His Capture kit (Cytiva Life Sciences, catalog NO: 28995056) respectively. Experimental data were processed using the 1:1 Langmuir kinetic fitting model. Measurements included zero-concentration samples for referencing. $Chi^2$, U- and residual values were used to evaluate the quality of a fit between the experimental data and individual binding models Epitope Binning Epitope binning of Fab fragments on human CD38 was assessed using Bio-Layer Interferometry (BLI). Measurements were done on an OctetRED96e instrument (Sartorius) and analyzed using the Data Analysis HT version 11.1 software (Octet, Sartorius). Biotinylated human CD38-avi-his protein (Acrobiosystems, catalog NO: CD8-H82E7) was loaded at 1 μg/ml in kinetic buffer for 5 min (Sartorius, catalog NO: 18-1105) on a streptavidin SA Biosensor (Sartorius, catalog NO: 15-5019) previously soaked in kinetic buffer for 10 min. Streptavidin biosensor coated with biotinylated human CD38 antigen was dipped into a solution of 200 nM of Fab antibody 1 (Ab1) for 10 min to reach saturation of the CD38 coated surface, followed by a successive dip into a mixed solution of 200 nM of Ab1 and 200 nM of Fab antibody 2 (Ab2) for 5 min (competition phase). Same experimental procedure was performed using 400 nM of Ab1 alone in the competition phase as control for surface saturation. All steps were performed at 25° C. and 1000 RPM shaking. Fresh streptavidin biosensors were coated with biotinylated human CD38 before each cycle.

Results and Conclusions

ScFv clones showing specific binding to both recombinant human CD38 and recombinant cynomolgus monkey CD38 proteins by SPR as well as specific binding to human CD38 CHO cells were sequenced and unique sequences showing the best binding profiles on SPR were reformatted in Fab fragment for binding affinity measurement.

Fab binding affinities to CD38

Twenty-seven Fab clones showed binding affinities to recombinant human and cynomolgus monkey CD38 proteins with an equilibrium dissociation constant ($K_D$) below 2 μM as determined by SPR. Clone anti-CD38-UCP03-B3 (heavy chain SEQ ID NO: 110), herein also referred as anti-CD38-B3 showed affinities to human CD38 and cynomolgus monkey CD38 of 115 nM and 170 nM respectively. Clone anti-CD38-UCP01-E2 (heavy chain SEQ ID NO: 111), herein also referred as anti-CD38-E2 showed affinities to human CD38 and cynomolgus monkey CD38 of 110 nM and 89 nM respectively. Heavy chain sequence identification numbers and binding affinities of developed anti-CD38 clones are reported in Table 7.

TABLE 7

Relative affinity of developed anti-CD38 Fabs to human and cynomolgus monkey CD38. Table shows clones heavy chain sequence identification numbers (SEQ ID NO), affinity ($K_D$) to recombinant human CD38 protein and affinity ($K_D$) to recombinant cynomolgus monkey CD38 protein for developed anti-CD38 Fabs.

| Clone name | Clone heavy chain SEQ ID NO | Human CD38 $K_D$ (nM) | Cynomolgus monkey CD38 $K_D$ (nM) |
|---|---|---|---|
| Anti-CD38-UCP01-B1 Fab | SEQ ID NO: 619 | 193 | 102 |
| Anti-CD38-UCP01-D1 Fab | SEQ ID NO: 620 | 666 | NB |
| Anti-CD38-UCP01-F1 Fab | SEQ ID NO: 621 | 429 | 393 |
| Anti-CD38-UCP01-G1 Fab | SEQ ID NO: 622 | 1124 | 283 |
| Anti-CD38-UCP01-H1 Fab | SEQ ID NO: 623 | 437 | 352 |
| Anti-CD38-UCP01-C2 Fab | SEQ ID NO: 624 | 85.3 | 53.5 |
| Anti-CD38-UCP01-E2 FAB | SEQ ID NO: 111 | 110 | 89 |
| Anti-CD38-UCP02-A7 Fab | SEQ ID NO: 625 | 71.14 | low binding |
| Anti-CD38-UCP02-B1 Fab | SEQ ID NO: 626 | 595 | low binding |
| Anti-CD38-UCP02-B7 Fab | SEQ ID NO: 627 | 1709 | NT |
| Anti-CD38-UCP02-C3 Fab | SEQ ID NO: 628 | 305.1 | 187.7 |
| Anti-CD38-UCP02-D1 Fab | SEQ ID NO: 629 | 132.9 | 78 |
| Anti-CD38-UCP02-D5 Fab | SEQ ID NO: 630 | 192 | 33.5 |
| Anti-CD38-UCP02-E5 Fab | SEQ ID NO: 631 | 0.03 | low binding |
| Anti-CD38-UCP02-F2 Fab | SEQ ID NO: 632 | 14.16 | 13.96 |
| Anti-CD38-UCP02-F5 Fab | SEQ ID NO: 633 | 71.08 | 55.22 |
| Anti-CD38-UCP02-F6 Fab | SEQ ID NO: 634 | 389.2 | low binding |
| Anti-CD38-UCP02-H1 Fab | SEQ ID NO: 635 | 153.9 | 2.7 |
| Anti-CD38-UCP03-B3 FAB | SEQ ID NO: 110 | 115 | 170 |
| Anti-CD38-UCP03-C3 Fab | SEQ ID NO: 636 | 117 | 465 |

TABLE 7-continued

Relative affinity of developed anti-CD38 Fabs to human and cynomolgus monkey CD38. Table shows clones heavy chain sequence identification numbers (SEQ ID NO), affinity ($K_D$) to recombinant human CD38 protein and affinity ($K_D$) to recombinant cynomolgus monkey CD38 protein for developed anti-CD38 Fabs.

| Clone name | Clone heavy chain SEQ ID NO | Human CD38 $K_D$ (nM) | Cynomolgus monkey CD38 $K_D$ (nM) |
|---|---|---|---|
| Anti-CD38-UCP03-H5 Fab | SEQ ID NO: 637 | 141.6 | 11 |
| Anti-CD38-UCP03-B6 Fab | SEQ ID NO: 638 | 225 | 829 |
| Anti-CD38-UCP03-E3 Fab | SEQ ID NO: 639 | 300 | 195 |
| Anti-CD38-UCP03-A6 Fab | SEQ ID NO: 640 | 410 | 525 |
| Anti-CD38-UCP03-C2 Fab | SEQ ID NO: 641 | 1388 | 628 |
| Anti-CD38-UCP03-H2 Fab | SEQ ID NO: 642 | 1850 | 672 |
| Anti-CD38-UCP03-H3 Fab | SEQ ID NO: 643 | 810 | 178 |

Epitope Binning

To assess competition of anti-CD38 clones on CD38, epitope binning assay using anti-CD38 Fab fragments, daratumumab Fab fragment produced in house (SEQ ID NO: 566 and SEQ ID NO: 609) and recombinant human CD38 protein was performed using Octet Bio-Layer Interferometry (BLI). An increase in binding response (in nm, Y-axis) upon dipping of CD38 coated Biosensor previously saturated with Ab1 antibody into a pre-mixed solution of Ab1/Ab2 antibodies indicates that Ab1 and Ab2 antibodies are not competing for binding to CD38, and thereby do not recognize overlapping epitopes on CD38. FIGS. 8A-8B shows that anti-CD38-E2 and anti-CD38-B3 clones do not compete for binding to CD38 and thereby do not recognize overlapping epitopes on CD38. FIG. 8C also shows that anti-CD38-E2 and anti-CD38-B3 do not compete with daratumumab Fab for binding to CD38 and thereby do not recognize overlapping epitopes on CD38.

EXAMPLE 8: OPTIMIZATION OF ANTI-CD38-E2 AND ANTI-CD38-B3

Material and Methods

Recombinant Target Antigens

Recombinant human CD38-ECD-C-his protein (SEQ ID NO: 607), herein also referred to as recombinant human CD38 protein, and recombinant cynomolgus monkey CD38-ECD-C-his protein (SEQ ID NO: 608), herein also referred to as recombinant cynomolgus monkey CD38 protein, were produced in house as described in Example.

Library Generation and Selection

Five affinity maturation libraries were generated for both anti-CD38-B3 (SEQ ID NO: 110) and anti-CD38-E2 (SEQ ID NO: 111) clones by introducing diversity in CDRs' of the heavy chain. CDR-H1, CDR-H2 and CDR-H3 were randomized using degenerated NNK codon oligonucleotides (wherein N is any of the four deoxyribonucleotides and K is G or T) at Kabat residues 27-35, 50-58, 95-101 minus 2, respectively. Each library was generated using a pool of overlapping oligonucleotides containing 5 consecutive degenerated codons. CDR-H1 and CDR-H2 were also diversified using Trimer oligonucleotide at position Kabat 27-35 and 50-58 respectively. Libraries were prepared as described in Example.

Phage display panning was performed as described in Example 5 with the following modifications. Libraries were incubated with beads pre-coated with 50 nM, 5 nM, and 0.5 nM of biotinylated recombinant human CD38 protein (Acrobiosystems, catalog NO: CD8-H82E7), for round 1, round 2 and round 3, respectively. After 1 h incubation, 1 μM of non-biotinylated recombinant human CD38 protein produced in house (SEQ ID NO: 607) was added for 3 h at RT during rounds 2 and 3.

Affinity Screening by SPR

SPR analysis was used to confirm specific binding activity of the new scFv clones and rank the positive clones according to their binding profile. Measurements were performed as described in Example with the following modifications. Measurements were performed on a Biacore T200 instrument (Cytiva Life Sciences) and analyzed with the Biacore T200 Evaluation Software (v3.1) or on a Biacore 8K+ instrument (Cytiva Life Sciences) using the Biacore 8K+ Control Software and analyzed with the Biacore Insight Evaluation Software (v3.0). Commercially available recombinant human CD38 protein (Acrobiosystems, catalog NO: CD8-H224) or recombinant human CD38 protein produced in house (SEQ ID NO: 607) was diluted to a final concentration of 200 nM in acetate buffer pH 4.5 (Cytiva Life Sciences, catalog NO: BR100350) and subsequently immobilized on flow-path 2 to levels of about 1300 RU or 250 RU on Series S CM5 Sensor Chips (Cytiva Life Sciences, catalog NO: BR100530) using an amine coupling kit (Cytiva Life Sciences, catalog NO: BR100050). Filtered periplasmic extracts were injected directly on the covalently coupled human CD38 CM5 Sensor Chips on the flow-path 1 and 2 (flow-path 1 being used as reference) for 3 min. Dissociation in HBS-EP+ buffer was monitored for 3 to 10 min. The scFv clones showing the best binding profiles were reformatted in Fab fragments as described in Example.

Fab Binding Affinities to CD38

Affinities of the Fab to human and cynomolgus monkey CD38 were measured by SPR as described in Example with following modifications. Measurements were performed at 25° C. on a Biacore T200 instrument (Cytiva Life Sciences) and analyzed with the Biacore T200 Evaluation Software (v3.1) or on a Biacore 8K+ instrument (Cytiva Life Sciences) using the Biacore 8K+ Control Software and analyzed with the Biacore Insight Evaluation Software (v3.0). Affinities of the Fab to human CD38 were performed on Series S Biotin CAPture Chips (Cytiva Life Sciences, catalog NO: 28920234) immobilized with recombinant biotinylated human CD38 (Acrobiosystems, catalog NO: CD8-H82E7) on flow-path 2 to levels between 50 to 70 RU. Fabs were injected in single cycle kinetic for 3 min with concentrations ranging from 1.95 nM to 500 nM. Measurements to cynomolgus monkey CD38 were performed on Series S CM5 Sensor Chips (Cytiva Life Sciences, catalog NO: BR100530) previously immobilized with anti-histidine antibody (Cytiva Life Sciences, catalog NO: 28995056). Recombinant cynomolgus monkey CD38-ECD-C-his protein produced in house (SEQ ID NO: 608) was immobilized on flow-path 2 to levels of around 50 RU. Fabs were injected in single cycle kinetics for 3 min with concentrations ranging from 1.48 nM to 120 nM or from 1.95 nM to 500 nM. Dissociation was monitored for 5 to 10 min.

Results and Conclusions

Affinity maturation of anti-CD38-B3 clone (heavy chain SEQ ID NO: 110) and of anti-CD38-E2 clone (heavy chain SEQ ID NO: 111) involved diversification of CDR-H1 (Kabat positions 27-35), CDR-H2 (Kabat positions 50-58) and CDR-H3 (Kabat positions 95-101 minus 2) in five individual libraries. ScFv clones having a slower off-rate than their respective parental clone (anti-CD38-E2 or anti- CD38-B3) as measured by SPR were isolated. ScFv clones were reformatted and expressed as Fab fragments and affinities to recombinant human CD38 protein and to recombinant cynomolgus monkey CD38 protein were measured by SPR. One clone, anti-CD38-B3-PP11-C11 (heavy chain SEQ ID NO: 113), herein also referred as anti-CD38-B3-C11, showed increase in affinity to human and cynomolgus CD38 as compared to parental anti-CD38-B3 clone, with $K_D$ measured at 5.4 nM and 25 nM respectively, and was selected for the generation of CD3/BCMA/CD38 antibodies described herein. One clone, anti-CD38-E2-UCP02-A5 (heavy chain SEQ ID NO: 122), herein also referred as anti-CD38-E2-A5, showed increased affinities to human and cynomolgus monkey CD38 as compared to parental anti-CD38-E2 clone, with $K_D$ measured at 23.6 nM and 4.4 nM respectively, and was also selected for the generation of CD3/BCMA/CD38 antibodies described herein.

Heavy chain sequence identification numbers and binding affinities to recombinant human and cynomolgus monkey CD38 proteins of the mentioned clones are reported in Table 8.

TABLE 8

Overview of developed anti-CD38-B3- and anti-CD38-E2- optimized Fabs and their relative affinity to human and cynomolgus monkey CD38 measured by Surface Plasmon Resonance. Table shows clones heavy chain sequence identification numbers (SEQ ID NO), affinity ($K_D$) to recombinant human CD38 protein and affinity ($K_D$) to recombinant cynomolgus monkey CD38 protein for developed anti-CD38-B3- and anti-CD38-E2- optimized Fabs.

| Library | Clone name | Clone heavy chain SEQ ID NO | Human CD38 $K_D$ (nM), Fab as analyte | Cynomolgus monkey CD38 $K_D$ (nM), Fab as analyte |
|---|---|---|---|---|
| CDR-H1 | Anti-CD38-B3-PP11-A2 FAB | SEQ ID NO: 112 | 38.4 | 62.5 |
| CDR-H3 | Anti-CD38-B3-PP11-C11 FAB | SEQ ID NO: 113 | 5.4 | 25 |
| CDR-H1 | Anti-CD38-B3-PP11-D1a FAB | SEQ ID NO: 114 | 10 | 9.6 |
| CDR-H1 | Anti-CD38-B3-PP11-D1b FAB | SEQ ID NO: 115 | 5.8 | 14.6 |
| CDR-H3 | Anti-CD38-B3-PP11-D11a FAB | SEQ ID NO: 116 | 8.2 | 17.3 |
| CDR-H1 | Anti-CD38-B3-PP11-E1 FAB | SEQ ID NO: 117 | 10.5 | 26.3 |
| CDR-H3 | Anti-CD38-B3-PP11-E11 FAB | SEQ ID NO: 118 | 2 | 8.9 |
| CDR-H1 | Anti-CD38-B3-PP11-H1a FAB | SEQ ID NO: 119 | 15.3 | 17.9 |
| CDR-H3 | Anti-CD38-B3-PP11-H10 FAB | SEQ ID NO: 120 | 6.2 | 22.7 |
| CDR-H1 | Anti-CD38-E2-UCP01-A10 FAB | SEQ ID NO: 121 | 9.4 | 8.6 |
| CDR-H2 | Anti-CD38-E2-UCP02-A5 FAB | SEQ ID NO: 122 | 23.6 | 4.4 |
| CDR-H2 | Anti-CD38-E2-UCP02-D6 FAB | SEQ ID NO: 123 | 4.9 | 1.1 |
| CDR-H2 | Anti-CD38-E2-UCP02-E7 FAB | SEQ ID NO: 124 | 2.2 | 1.8 |
| CDR-H2 | Anti-CD38-E2-UCP02-F3 FAB | SEQ ID NO: 125 | 3.5 | 2.4 |
| CDR-H2 | Anti-CD38-E2-UCP02-F8 FAB | SEQ ID NO: 126 | 17.6 | 24.5 |
| CDR-H2 | Anti-CD38-E2-UCP02-G8 FAB | SEQ ID NO: 127 | 5.2 | 4.2 |

EXAMPLE 9: DESIGN OF CD3/BCMA/CD38 ANTIBODIES

CD3/BCMA/CD38 antibodies according to the invention comprise of a first antigen binding site that binds to human CD3, a second binding site to human BCMA and a third antigen binding site that binds human CD38. CD3/BCMA/CD38 trispecific antibodies can be designed utilizing two novel architectures. In the first one, configuration BO ("BTB Outer": CDR binder in the outer position of the BEAT BTB arm), the CD3 and BCMA binding arm are located on the same arm of the BEAT antibody, whereby the CD3 binding arm is in the Fc distal position, and the BCMA arm of high affinity is in the Fc proximal position, and the two are fused via a flexible linker (SEQ ID NO: 605). The high affinity BCMA binder in the Fc proximal position in the BO configuration may drive the formation of a short immunological synapse joining the effector cell to tumor cell. The CD38 binding arm is on the A arm of the BEAT (FIG. 9A).

In configuration C, the CD3 binding arm is on the first arm of the bispecific antibody, and the two tumor-associated antigen (TAA) binding arms are on the same arm of the BEAT, the B arm. The two are linked via a flexible linker (SEQ ID NO: 604), whereby a Fab targeted to CD38 is fused to the C-terminus of a BCMA-binding arm, with the aim of binding tumor cells with high avidity (FIG. 9B).

We provide herein heterodimeric antibodies including the ones selected from the group comprising CD3/BCMA/CD38-43, CD3/BCMA/CD38-86, CD3/BCMA/CD38-92, CD3/BCMA/CD38-93, CD3/BCMA/CD38-103, CD3/BCMA/CD38-114, CD3/BCMA/CD38-115, CD3/BCMA/CD38-116, CD3/BCMA/CD38-117, CD3/BCMA/CD38-118, CD3/BCMA/CD38-119.

In particular:

CD3/BCMA/CD38-43 is a combination of SEQ ID NO:522, SEQ ID NO:523 and SEQ ID NO:1

CD3/BCMA/CD38-86 is a combination of SEQ ID NO:530, SEQ ID NO:531 and SEQ ID NO:1

CD3/BCMA/CD38-92 is a combination of SEQ ID NO:532, SEQ ID NO:533 and SEQ ID NO:1

CD3/BCMA/CD38-93 is a combination of SEQ ID NO:534, SEQ ID NO:535 and SEQ ID NO:1

CD3/BCMA/CD38-103 is a combination of SEQ ID NO:536, SEQ ID NO:537 and SEQ ID NO:1

CD3/BCMA/CD38-114 is a combination of SEQ ID NO:538, SEQ ID NO:539 and SEQ ID NO:1

CD3/BCMA/CD38-115 is a combination of SEQ ID NO:540, SEQ ID NO:541 and SEQ ID NO:1

CD3/BCMA/CD38-116 is a combination of SEQ ID NO:542, SEQ ID NO:543 and SEQ ID NO:1

CD3/BCMA/CD38-117 is a combination of SEQ ID NO:544, SEQ ID NO:545 and SEQ ID NO:1

CD3/BCMA/CD38-118 is a combination of SEQ ID NO:546, SEQ ID NO:547 and SEQ ID NO:1

CD3/BCMA/CD38-119 is a combination of SEQ ID NO:548, SEQ ID NO:549 and SEQ ID NO:1

Trispecific antibodies are a group of engineered antibody derivatives which recognize 3 different target antigens. The TREAT trispecific antibody technology is based on BEAT® platform. The BEAT® platform is based on the replacement of the protein-protein interface of the CH3 domain pair of the antibody Fc region with the protein-protein interface of the T cell receptor (TCR) α-β constant region (Skegro et al., J Biol Chem, 2017, 292(23):9745-9759; Stutz et al., J Biol Chem, 2020, 295(28):9392-9408). The resulting BEAT interface drives preferential formation and purification of heterodimeric bispecific or trispecific antibodies (bsAbs or TriAbs) over the homodimer contaminants. In addition, CD3/BCMA/CD38 antibodies make use of a Fab CD38 binding arm as Fab unit, of a Fab BCMA binding arm and of a Fab CD3 binding arm that all utilize a common light chain to prevent light chain mispairing, a common challenge associated with bsAb and even more so TriAbs platforms. Additional engineering has also been performed to allow an easier and faster purification process, natural conformation in antibody structure, stability, and binding to neonatal Fc receptor (FcRn) was retained maximizing the serum half-life of CD3/BCMA/CD38 antibodies (Skegro et al., J Biol Chem, 2017, 292(23):9745-9759; Stutz et al., J Biol Chem, 2020, 295(28):9392-9408).

EXAMPLE 10: CD3/BCMA/CD38 ANTIBODIES HEAVY CHAIN AND LIGHT CHAIN AMINO ACID COMBINATIONS

Materials and Methods

To enable the analysis of the effects of varying the format, affinities and CD38 epitope on in vitro pharmacology, the combination as described in Table 9 were expressed and purified as described in Example.

Results and Conclusions

Table 9 below lists the combinations of chains used for the expression of CD3/BCMA/CD38 trispecific antibodies.

TABLE 9

SEQ ID of CD3/BCMA/CD38 antibodies

| CD3/BCMA/ CD38- | Chain 1 | Chain 2 | Chain 3 |
|---|---|---|---|
| 043 | SEQ ID NO: 522 | SEQ ID NO: 523 | SEQ ID NO: 1 |
| 086 | SEQ ID NO: 530 | SEQ ID NO: 531 | SEQ ID NO: 1 |
| 092 | SEQ ID NO: 532 | SEQ ID NO: 533 | SEQ ID NO: 1 |
| 093 | SEQ ID NO: 534 | SEQ ID NO: 535 | SEQ ID NO: 1 |
| 103 | SEQ ID NO: 536 | SEQ ID NO: 537 | SEQ ID NO: 1 |
| 114 | SEQ ID NO: 538 | SEQ ID NO: 539 | SEQ ID NO: 1 |
| 115 | SEQ ID NO: 540 | SEQ ID NO: 541 | SEQ ID NO: 1 |

TABLE 9-continued

SEQ ID of CD3/BCMA/CD38 antibodies

| CD3/BCMA/ CD38- | Chain 1 | Chain 2 | Chain 3 |
|---|---|---|---|
| 116 | SEQ ID NO: 542 | SEQ ID NO: 543 | SEQ ID NO: 1 |
| 117 | SEQ ID NO: 544 | SEQ ID NO: 545 | SEQ ID NO: 1 |
| 118 | SEQ ID NO: 546 | SEQ ID NO: 547 | SEQ ID NO: 1 |
| 119 | SEQ ID NO: 548 | SEQ ID NO: 549 | SEQ ID NO: 1 |

EXAMPLE 11: EXPRESSION AND CHARACTERIZATION OF CD3/BCMA/CD38 ANTIBODIES PRODUCED IN CHO CELLS

Materials and Methods

To enable the analysis of the effects of varying the format, affinities and CD38 epitope on in vitro pharmacology, the combinations as described in Table 9 were expressed and purified as described in Example.

Results and Conclusions

CD3/BCMA/CD38 antibodies were successfully produced in CHO-S cells and were highly monodisperse with percentages of main peak ranging from between 95.05-99.93% by SE-HPLC post-purification according to the protocol described in Example.

Details of the format, binders, titers, and final purity are given in Table 10.

TABLE 10

Expression and characterization of CD3/BCMA/CD38 antibodies in CHO-S cells

| CD3/BCMA/CD38_ | 043 | 086 | 092 | 093 | 103 | 114 | 115 | 116 | 117 | 118 | 119 |
|---|---|---|---|---|---|---|---|---|---|---|---|
| Format | BO | C | C | C | C | C | C | C | BO | BO | BO |
| CD3 binder | C1-D6 | C1-D6 | C1-D6 | C1-D6 | C1-D6 | C1-D6 | C1-D6 | C1-D6 | C1-D6 | C1-D6 | C1-D6 |
| CD38 binder | E2 | B3-C11 | B3-C11 | B3-C11 | B3-C11 | E2-A5 | B3-C11 | B3 | E2-A5 | B3-C11 | B3 |
| BCMA binder | D3-E11 | D3-E11 | E6-E6 | E6-G6 | E6-B1-N82aS | E6-G6-N82aS | E6-G6-N82aS | E6-G6 N82aS | E6-G6-N82aS | E6-G6 N82aS | E6-G6 N82aS |
| Protein A purification yield (mg/L) | 42 | N/A | 45 | 30.6 | 57.7 | 44.88 | 52.8 | N/A | 72.6 | 34.32 | 47.3 |
| Purity post-Protein SE-HPLC) A (% monomer by | 92.42 | 90.37 | 95.57 | 95.05 | 94.77 | 92.96 | 93.84 | N/A | 85.75 | 94.94 | 94.53 |
| Final Purity (% monomer by SE-HPLC) | 98.37 | 99.93 | 95.57 | 95.05 | 99.47 | 98.42 | 99.26 | 99.3 | 99.01 | 99.36 | 99.77 |

EXAMPLE 12: EXPRESSION AND CHARACTERIZATION OF CONTROL MOLECULES FOR THE CHARACTERIZATION OF CD3/BCMA/CD38 TREATs

Materials and Methods

Control molecules described below were produced according to the protocol described in Example.

Results and Conclusions

Control molecules according to the sequence combinations detailed in Table 11 were additionally tested that used an irrelevant binder, dubbed G6DU, in place of the CD3 binding Fab, in place of the BCMA and CD38 binding Fabs or in place of the three binding Fabs (isotype control) as detailed in Table 12. Other controls included bispecific antibodies targeting BCMA and CD3 but not CD38 with two different BCMA binders used in trispecific antibodies.

TABLE 11

| SEQ ID of CD3/BCMA/CD38 control antibodies | | | |
| --- | --- | --- | --- |
| CD3/BCMA/ CD38_ | Chain 1 | Chain 2 | Chain 3 |
| 082 | SEQ ID NO: 526 | SEQ ID NO: 527 | SEQ ID NO: 1 |
| 085 | SEQ ID NO: 528 | SEQ ID NO: 529 | SEQ ID NO: 1 |
| 120 | SEQ ID NO: 550 | SEQ ID NO: 551 | SEQ ID NO: 1 |
| 121 | SEQ ID NO: 552 | SEQ ID NO: 553 | SEQ ID NO: 1 |
| 122 | SEQ ID NO: 554 | SEQ ID NO: 555 | SEQ ID NO: 1 |
| 044 | SEQ ID NO: 524 | SEQ ID NO: 525 | SEQ ID NO: 1 |
| 123 | SEQ ID NO: 556 | SEQ ID NO: 557 | SEQ ID NO: 1 |

Control antibodies were designed and successfully produced in CHO-S cells and were highly monodisperse with percentages of main peak ranging from between 96-100% as measured by SE-HPLC post-purification (Table 12).

TABLE 12

| Description and characterization of control molecules used to characterize CD3/BCMA/CD38 molecules. | | | | | | | |
| --- | --- | --- | --- | --- | --- | --- | --- |
| CD3/BCMA/CD38- | 082 | 085 | 120 | 121 | 122 | 044 | 123 |
| Format | C | N/A | C | BO | BO | BEAT | BEAT |
| CD3 binder | C1-D6 | G6DU | G6DU | G6DU | C1-D6 | C1-D6 | C1-D6 |
| CD38 binder | G6DU | G6DU | B3-C11 | B3-C11 | G6DU | None | None |
| BCMA binder | G6DU | G6DU | E6-G6-N82aS | E6-G6-N82aS | G6DU | D3-E11 | E6-G6-N82aS |
| Purification yield (mg/L) | 31-38 | N/A | 16 | 19 | 15 | 19-101 | 16 |
| Final Purity (% monomer by SE-HPLC) | 98-99 | 96-98 | 99 | 99 | 100 | 97-99 | 100 |

EXAMPLE 13: SCREENING FOR TUMOR KILLING POTENCY OF CD3/BCMA/CD38 ANTIBODIES IN PRESENCE AND ABSENCE OF SOLUBLE BCMA, AND ON-TARGET OFF-TUMOR ACTIVITY

EXAMPLE 13 (A): RDL ASSAY WITH KMS-12-BM TUMOR CELLS EXPRESSING LOW LEVELS OF BCMA AND CD38 AND THE EFFECT OF SOLUBLE BCMA ON KILLING POTENCY

Materials and Methods

Several constructs of TREAT CD3/BCMA/CD38 described in Example 10, holding the same binders targeting CD3 and CD38 and different E6-affinity matured binders targeting BCMA, E6-E6 (CD3/BCMA/CD38-092), E6-G6 (CD3/BCMA/CD38-093) and E6-B1 (CD3/BCMA/CD38-103) were tested for tumor killing efficacy and potency of KMS-12-BM cells using flow cytometry. It is known that levels of circulating soluble BCMA in blood from Multiple Myeloma patients is significantly higher than levels of circulating soluble BCMA in blood from Healthy donors (average of 89.91 ng/ml and 8.04 ng/ml, respectively (Pillarisetti et al, 2020)). In circulation, soluble BCMA could bind to the anti-BCMA binder of the CD3/BCMA/CD38 TREAT, presenting a potential sink risk and decreasing the possibility of the molecule to bind to tumor cells, therefore impacting the killing potency. The killing activity of those TREAT was therefore evaluated in the presence of high levels of soluble BCMA (150 ng/ml), above the average of the levels observed in the blood of Multiple Myeloma patients.

83A10-TCBcv

The comparator molecule 83A10-TCBcv (comprising SEQ ID NO: 558, SEQ ID NO: 559, SEQ ID NO:560 and SEQ ID NO:561) was produced and purified as detailed in Example 3.

RDL Assay with KMS-12-BM Tumor Cells Expressing Low Levels of BCMA and CD38 and the Effect of Soluble BCMA on Killing Potency Human peripheral blood mononuclear cells (PBMC) were isolated from buffy coats of healthy donors obtained from La Chaux-de-Fonds/Bern (Switzerland) Transfusion Center using ficoll density gradient isolation and frozen in CryoStor10 cell freezing medium (Stemcell, #07930). Cells were thawed in a pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $2\times10^6$ cells/ml. Twenty thousand target cells (KMS-12-BM, DSMZ, ACC 551) labelled with Cell Proliferation Dye eFluor 670 (ThermoFisher Scientific, 65-0840-85) were co-cultured with one hundred thousand PBMC labelled with Cell Proliferation Dye eFluor 450 (ThermoFisher Scientific, 65-0842-85) reaching an effector-to-target ratio of 5:1. Serial dilutions of CD3/BCMA/CD38 candidates starting from 20 nM and diluted by 10-fold, and control antibody (Negative control (CD3/BCMA/CD38_085)(not shown) were incubated in co-culture for 72 h, at 37° C., 5% $CO_2$. After the incubation period, the RDL assay readout was evaluated by measuring T cell cytotoxic activity against target cells. Tumor cell killing was determined by measuring the absolute count of live target cells (eFluor670+ cells) and calculated as % of target killing=[1−(Sample absolute counts)/(absolute counts in the presence of target cells alone)]×100. Specific tumor cell killing was calculated as % of specific killing=% target killing (sample)−unspecific % target killing (in absence of antibody). Half maximal effective concentration or $EC_{50}$ was calculated from the specific killing values using Sigmoidal dose response Nonlinear regression. Some values were excluded based on goodness of fit ($R^2 > 0.8$), on percentage of tumor cells spontaneous killing (assay window), out-of-range $EC_{50}$ values and inappropriate percentages of killing (<20% or >130%).

Using the same protocol, additional experiments were conducted in presence of soluble BCMA, supplemented at 150 ng/ml final concentration. In these experiments, the starting dose used was 200 nM.

Means $EC_{50}$ are reported in pM in Table 13. A total of two independent experiments were performed with each candidate for a total of three donors.

Results and Conclusions

The comparison between TREAT CD3/BCMA/CD38 holding the same binders targeting CD3 and CD38 and different E6-affinity matured binders targeting BCMA, E6-E6, E6-G6 and E6-B1 respectively showed that CD3/BCMA/CD38-093 triggered the most efficient killing of KMS-12-BM, in the presence of 150 ng/ml of soluble BCMA, suggesting that this candidate is less affected by soluble BCMA compared to other candidates and retained strong killing potency even in presence of soluble BCMA. The BCMA anti-BCMA E6-G6 binder present in CD3/BCMA/CD38-093 was therefore selected for further optimization of CD3/BCMA/CD38 molecules.

All candidates were able to trigger strong killing of tumor cell lines with EC50 ranging from 0.4 to 25.4 pM. They all induced the killing of all three cell lines expressing variable levels of CD38 and BCMA. Comparisons between molecules with matching binders such as CD3/BCMA/CD38-115 (C) and -118 (BO) for instance, showed that the format BO impacts positively the tumor cell lines killing for all cell lines, demonstrating an increase of killing potency of 3-fold (−118 versus −115 on KMS-12-BM). The affinity of the anti-CD38 binders impacted the killing potency on all cell lines, as observed for candidates −118 and −119, demonstrating an increase in killing potency of 8.3-fold (−118 versus −119 on KMS-12-BM).

Comparison between the format C molecules with different CD38 binding arms, CD3/BCMA/CD38-093 and CD3/BCMA/CD38-114, showed that anti-CD38-B3-C11 binder increased the killing potency of the molecule on all cell lines compared to anti-CD38-E2-A5 binder (between 5.3-9.1-fold lower EC50). This is also true when these binders are in format BO, but to a lesser extent, with 1.7-2.3-fold difference observed on EC50 between CD3/BCMA/CD38-117 (E2-A5) and CD3/BCMA/CD38-118 (B3-C11). Comparison between CD3/BCMA/CD38-086 and CD3/BCMA/CD38-093 showed that the candidate with anti-BCMA-E6-G6 binder was less affected by soluble BCMA compared to other candidate and retained strong killing potency even in presence of soluble BCMA.

TABLE 13

CD3/BCMA/CD38-093 candidate trigger the most potent KMS-12-BM cell killing in the presence of soluble BCMA in Redirected Lysis assay. The table shows Mean of EC50 of specific killing determined from Redirected Lysis experiments on KMS-12-BM cell line incubated with or without soluble BCMA (150 ng/ml). A total of three PBMC donors were tested in two independent experiments.

| | | | | | Mean $EC_{50}$ (pM) | |
|---|---|---|---|---|---|---|
| Treatment | Type | CD3 | BCMA | CD38 | no sBCMA | sBCMA |
| CD3/BCMA/CD38-092 | TREAT C | C1-D6 | E6-E6 | B3-C11 | 3.3 | 49.5 |
| CD3/BCMA/CD38-093 | TREAT C | C1-D6 | E6-G6 | B3-C11 | 4.1 | 28.4 |
| CD3/BCMA/CD38-103* | TREAT C | C1-D6 | E6-B1 | B3-C11 | 4.0 | 47.5 |

*To note, mutation N82aS prevents the binding to Protein A.

EXAMPLE 13 (B): RDL OF NCI-H929, MOLP-8 AND KMS-12-BM TUMOR CELLS EXPRESSING VARIOUS LEVELS OF BCMA AND CD38 AND THE EFFECT OF SOLUBLE BCMA ON KILLING POTENCY

Materials and Methods

Additional antibodies described in Example 10 (−043, −086, −114, −115, −116, −117, −118, −119) were tested along with previously selected CD3/BCMA/CD38 constructs (−093) and benchmarks (BEAT CD3/CD38, TNB-F2B BEAT Fc, 83A10-TCBcv). The CD3/BCMA/CD38 were tested for tumor killing potency in RDL assays on multiple myeloma cell lines NCI-H929, MOLP-8 and KMS-12-BM (in the absence or presence of soluble BCMA) and for on-target off-tumor T cell activation in a high density PBMC assay using flow cytometry as readouts.

Assays were performed following the same methodologies and material as described above.

Results and Conclusions

Multiple CD3/BCMA/CD38 candidates were tested for killing potency on three multiple myeloma cell lines, KMS-12-BM (characterized as BCMA and CD38 low-expressing cells), MOLP-8 (characterized as BCMA low- and CD38 high-expressing cells) and NCI-H929 (characterized as BCMA and CD38 medium-expressing cells) in comparison with three benchmarks: BEAT CD3/CD38, 83A10-TCBcv and TNB-F2B BEAT Fc. All EC50 values for killing potency are reported in Table 14.

The mutation N82aS was introduced in several candidates to prevent binding to Protein A, such as CD3/BCMA/CD38-115 candidate. The comparison between molecules sharing the same format and binders showed that the mutation N82aS did not change the killing potency of the candidate (−115 versus −093).

All CD3/BCMA/CD38 candidates reported in Table 14 induced potent T-cell redirected killing and demonstrated superior killing potency, with lower $EC_{50}$ values, compared to benchmarks TNB-F2B BEAT Fc (except for −116 only on KMS-12-BM tumor cells). A group of candidates displayed higher capability at inducing T-cell mediated cytotoxicity, consistently on all cell lines: CD3/BCMA/CD38-117, −118, −119 with BO format and CD3/BCMA/CD38-115 with C format. One candidate, CD3/BCMA/CD38-118, triggered significantly stronger killing compared to benchmark 83A10-TCBcv and BEAT CD3/CD38 on all cell lines.

Candidates CD3/BCMA/CD38-043, −93, −115, −117, −118, −119 also showed important anti-tumor killing in the presence of 150 ng/ml of soluble BCMA. The killing potency of CD3/BCMA/CD38-086 with anti-BCMA-D3-E11 binder was more affected by the presence of soluble BCMA as compared to the TREAT with the higher affinity anti-BCMA-E6-G6 binder, CD3/BCMA/CD38-093.

TABLE 14

Among pre-selected CD3/BCMA/CD38 candidates, −118 triggers most potent KMS-12-BM cell killing in the presence of soluble BCMA in Redirected Lysis assay. The table shows Mean +/− Standard Deviation of $EC_{50}$ of specific killing determined from Redirected Lysis experiments on NCI-H929, MOLP-8 and KMS-12-BM cell lines incubated (with or without soluble BCMA (150 ng/ml) for KMS-12-BM cell line). A total of six PBMC donors were tested in three independent experiments. * To note, mutation N82aS (Kabat numbering) in the VH that prevents the binding to Protein A.

| Treatment | Type | CD3 | BCMA | CD38 | NCI-H929 Mean $EC_{50}$ (pM) | NCI-H929 SD $EC_{50}$ (pM) | MOLP-8 Mean $EC_{50}$ (pM) | MOLP-8 SD $EC_{50}$ (pM) | KMS-12-BM no soluble Mean $EC_{50}$ (pM) | KMS-12-BM no soluble SD $EC_{50}$ (pM) | KMS-12-BM sBCMA Mean $EC_{50}$ (pM) | KMS-12-BM sBCMA SD $EC_{50}$ (pM) |
|---|---|---|---|---|---|---|---|---|---|---|---|---|
| BEAT CD3/CD38 | BEAT 1.0 | CD3 | None | CD38 | 6.5 | 4.8 | 3.1 | 3.0 | 3.2 | 1.0 | 3.5 | 1.2 |
| TNB-F2B BEAT Fc | Benchmark CD3 × BCMA | CD3 | BCMA | None | 265.1 | 104.7 | 100.4 | 62.8 | 25.1 | 10.3 | 112.4 | 111.0 |
| 83A10-TCBcv | Benchmark CD3 × BCMA | CD3 | BCMA | None | 3.4 | 1.5 | 29.0 | 9.7 | 3.1 | 1.1 | 48.0 | 40 |
| CD3/BCMA/ CD38-043 | TREAT BO | C1-D6 | D3-E11 | E2 | 15.6 | 12.3 | 1.5 | 1.1 | 0.6 | 0.4 | 24.7 | 19.8 |
| CD3/BCMA/ CD38-086 | TREAT C | C1-D6 | D3-E11 | B3-C11 | 16.6 | 15.8 | 3.0 | 2.2 | 2.2 | 1.2 | 45.2 | 35.4 |
| CD3/BCMA/ CD38-093 | TREAT C | C1-D6 | E6-G6 | B3-C11 | 1.7 | 0.8 | 1.3 | 0.9 | 1.3 | 0.7 | 10.6 | 3.2 |
| CD3/BCMA/ CD38-114* | TREAT C | C1-D6 | E6-G6 | E2-A5 | 9.0 | 4.1 | 11.8 | 7.0 | 8.5 | 5.7 | 46.1 | 17.3 |
| CD3/BCMA/ CD38-115* | TREAT C | C1-D6 | E6-G6 | B3-C11 | 1.7 | 1.0 | 1.7 | 0.9 | 1.2 | 0.7 | 4.6 | 1.8 |
| CD3/BCMA/ CD38-116* | TREAT C | C1-D6 | E6-G6 | B3 | 8.9 | 4.1 | 7.6 | 5.8 | 25.4 | 15.8 | 197.5 | 91.6 |
| CD3/BCMA/ CD38-117* | TREAT BO | C1-D6 | E6-G6 | E2-A5 | 2.0 | 1.3 | 1.3 | 0.5 | 0.9 | 0.6 | 3.3 | 1.5 |
| CD3/BCMA/ CD38-118* | TREAT BO | C1-D6 | E6-G6 | B3-C11 | 1.2 | 0.9 | 0.7 | 0.7 | 0.4 | 0.2 | 3.0 | 1.0 |
| CD3/BCMA/ CD38-119* | TREAT BO | C1-D6 | E6-G6 | B3 | 3.2 | 1.4 | 4.9 | 4.7 | 3.3 | 1.3 | 26.1 | 9.0 |

Taken together, those data suggest that T-cell mediated killing of the best candidates, CD3/BCMA/CD38-115, −117, −118, −119 is enhanced by dual binding to the two target antigens. Moreover, the TREAT CD3/BCMA/CD38 with the CD3 binding arm in outer position showed superior killing. In conclusion, cytotoxic activity of CD3/BCMA/CD38 candidates was superior compared to the bispecific benchmarks.

EXAMPLE 13 (C): ON-TARGET OFF-TUMOR ACTIVITY

Materials and Methods

Low on target off-tumor activity in vitro is expected to be associated with a more favorable safety profile of biotherapeutic antibodies in the clinic. To this end, CD3/BCMA/CD38 TREAT candidates were tested for their ability to induce T cell response in the absence of tumor cells in an in vitro high density PBMC assay. Activated lymphocytes were identified based on the expression of CD25 or CD69 activation markers in CD4 and CD8 live T cell populations. Human peripheral blood mononuclear cells (PBMC) were isolated from buffy coats of healthy donors obtained from La Chaux-de-Fonds/Bern (Switzerland) Transfusion Centers using ficoll density gradient isolation and frozen in CryoStor10 cell freezing medium (Stemcell, #07930). PBMCs were thawed in pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and incubated for 48 h at 37° C., 5% CO2, at $10 \times 10^6$ cells/ml in a 6-well plate (TPP, 92006, 3 ml/well). Then, PBMC were harvested and plated at $1 \times 10^5$ cells/well in a 96-well plate in presence of serial dilutions of CD3/BCMA/CD38 candidates, benchmarks (BEAT CD3/CD38, 83A10-TCBcv, TNB-F2B BEAT Fc) and controls (CD3/BCMA/CD38-085, Phytohemagglutinin (Sigma-Aldrich, L2646), coated anti-CD3 (ThermoFisher, 16-0037-85) and soluble anti-CD28 (BioXcell, BE0291)) starting from 200 nM and diluted by 5-fold for 48 additional hours at 37° C., 5% CO2. After the incubation, plates were centrifuged (350 g, 5 min), supernatants were frozen for further cytokines quantification. Cells were then transferred to a 96-well round-bottom plate, washed and resuspended in 25 µl of a cocktail of antibodies for human CD4-PE-eFluor610 (ThermoFisher Scientific, catalog NO: 61-0049-42), CD8-ALEXA FLUOR® 700 (BD Pharmingen, catalog NO: 557945), CD25-PE and CD69-PE-Cy7 (ThermoFisher Scientific, catalog NOs: 12-0259-42 and 25-0699-42, respectively) diluted 1/100 in FACS buffer and FcR Blocking Reagent (1/250, Miltenyi Biotec, catalog NO: 130-059-901), and incubated for 30 min at 4° C. Cells were washed twice and resuspended in 100 µl of FACS buffer containing SYTOX Green dead cell stain (ThermoFisher Scientific, catalog NO: S34860) diluted 1/2000. Samples were acquired on a CytoFlex instrument (Beckman Coulter).

Cells were gated based on size FSC vs SSC and debris and doublets were excluded. Finally, cells negative for the viability staining were gated. T cell activation was determined by evaluating the percentage of CD25 or CD69 positive cells gated on $CD4^+$ or $CD8^+$ T cells. Percentages of activated T cells values ($CD69^+$ of CD4 or CD8 T cells, $CD25^+$ of CD4 or CD8 T cells) were extracted. From those data, two parameters were determined: the threshold of activation and the Maximum activation. The threshold of activation is defined by the first dose showing statistically significant activation ($CD69^+$ or $CD25^+$ upregulation on CD4+ or $CD8^+$ T cells) compared to the negative control (CD3/BCMA/CD38_085) and the Maximum activation is the Mean+/−Standard Deviation of Percentage of activated cells (highest activation observed among tested doses). Both parameters were obtained using JMP software (SAS), the threshold of activation was determined using Nested Least Square model followed by a Dunnet post-hoc comparison compared to Negative control (CD3/BCMA/CD38_085), $p\text{-value}<0.05$ was considered as statistically significant. Both Maximum activation and threshold of activation values are summarized in Table 15 and Table 16, respectively. Two independent experiments were performed with each candidate for a total of four donors.

Results and Conclusions

Results from Table 15 show that CD3/BCMA/CD38-117, -118 and -119 candidates induced minimal T cell activation associated with on-target off-tumor activity with 9.8-24.0% upregulation of CD25 marker on $CD4^+$ and $CD8^+$ T cells and 11.1-45.9% upregulation of CD69 marker on $CD4^+$ and $CD8^+$ T cells, while positive controls such as anti-CD3/anti-CD28 induced more upregulation (61.1-77.6% upregulation of CD25 and 43.7-70.9% upregulation of CD69). Furthermore, CD3/BCMA/CD38-117, -118 and -119 candidates, in the absence of tumor cells, induced T cell activation associated with on-target off-tumor activity to a lesser extent compared to candidates −086, −114, −115 (threshold of activation of 8 or 200 nM, respectively for −117, −118 and -119 and 1.6 nM for −086, −114, −115). Moreover, all controls (−044, −082, −085, −120, −121, -122, −123) show very limited upregulation of CD25 and CD69 on $CD4^+$ and $CD8^+$ T cells compared to the negative control. Taken together, this suggests that format BO (−117, −118, −119) is less prone to induce on-target off-tumor activity compared to format C (−086, −114, −115).

TABLE 15

CD3/BCMA/CD38-118 and −119 candidates induce minimal T cell activation associated with on-target off-tumor activity compared to positive controls. The table shows the Mean +/− Standard Deviation of Maximum activation determined from High-Density PBMC experiments and measured by the percentage of CD69 and CD25 upregulation on CD8 and CD4 T cells. A total of 4 PBMC donors were tested in two independent experiments. * To note, mutation N82aS prevents the binding to Protein A.

| | | | | | $CD25^+CD4^+$ | | $CD25^+CD8^+$ | | $CD69^+CD4^+$ | | $CD69^+CD8^+$ | |
|---|---|---|---|---|---|---|---|---|---|---|---|---|
| Treatment | Type | CD3 | BCMA | CD38 | Average | +/− SD | Average | +/− SD | Average | +/− SD | Average | +/− SD |
| no Antibody | N/A | N/A | N/A | N/A | 4.05 | 1.24 | 0.65 | 0.46 | 1.21 | 1.31 | 0.90 | 0.38 |
| Negative control (CD3/BCMA/CD38_085) | N/A | G6 DU | G6 DU | G6 DU | 4.09 | 1.42 | 0.91 | 0.46 | 1.37 | 1.37 | 1.05 | 0.31 |
| anti-CD3 + anti-CD28 | N/A | N/A | N/A | N/A | 77.59 | 13.93 | 61.11 | 10.15 | 70.94 | 11.87 | 43.72 | 10.14 |
| PHA | N/A | N/A | N/A | N/A | 46.26 | 4.97 | 29.49 | 10.07 | 55.60 | 10.06 | 28.00 | 8.33 |
| 83A10-TCBcv | Bench mark CD3 × BCMA | CD3 | BCMA | None | 22.47 | 9.22 | 21.46 | 15.06 | 39.70 | 12.45 | 23.49 | 6.51 |
| CD3/BCMA/CD38-043 | TREAT BO | C1-D6 | D3-E11 | E2 | 17.46 | 6.15 | 17.57 | 8.90 | 39.92 | 12.52 | 21.94 | 1.67 |
| CD3/BCMA/CD38-044 | BEAT | C1-D6 | D3-E11 | None | 11.95 | 2.42 | 14.51 | 9.16 | 35.37 | 11.26 | 19.40 | 3.22 |
| CD3/BCMA/CD38-082 | TREAT C | C1-D6 | G6 DU | G6 DU | 4.17 | 1.46 | 1.79 | 1.42 | 2.02 | 1.16 | 3.23 | 0.98 |
| CD3/BCMA/CD38-086 | TREAT C | C1-D6 | D3-E11 | B3-C11 | 64.14 | 18.30 | 69.77 | 6.90 | 67.40 | 14.11 | 47.75 | 10.59 |
| CD3/BCMA/CD38-114* | TREAT C | C1-D6 | E6-G6 | E2-A5 | 69.34 | 10.14 | 74.14 | 9.27 | 69.72 | 13.00 | 53.86 | 9.73 |
| CD3/BCMA/CD38-115* | TREAT C | C1-D6 | E6-G6 | B3-C11 | 49.54 | 11.69 | 62.90 | 8.31 | 66.99 | 18.75 | 52.81 | 12.73 |
| CD3/BCMA/CD38-116* | TREAT C | C1-D6 | E6-G6 | B3 | 24.29 | 8.32 | 39.62 | 11.86 | 50.22 | 21.01 | 37.83 | 7.66 |
| CD3/BCMA/CD38-117* | TREAT BO | C1-D6 | E6-G6 | E2-A5 | 22.87 | 5.32 | 24.03 | 10.72 | 45.91 | 14.60 | 24.28 | 5.56 |
| CD3/BCMA/CD38-118* | TREAT BO | C1-D6 | E6-G6 | B3-C11 | 19.31 | 6.00 | 20.91 | 7.39 | 42.20 | 19.03 | 25.32 | 3.96 |
| CD3/BCMA/CD38-119* | TREAT BO | C1-D6 | E6-G6 | B3 | 9.81 | 3.46 | 11.50 | 5.63 | 20.42 | 10.87 | 11.11 | 2.87 |
| CD3/BCMA/CD38-120* | TREAT C | G6 DU | E6-G6 | B3-C11 | 4.36 | 1.55 | 1.06 | 0.80 | 1.23 | 0.84 | 0.91 | 0.40 |
| CD3/BCMA/CD38-121* | TREAT BO | G6 DU | E6-G6 | B3-C11 | 4.47 | 2.13 | 0.78 | 0.56 | 2.89 | 3.78 | 1.22 | 1.12 |
| CD3/BCMA/CD38-122 | TREAT BO | C1-D6 | G6 DU | G6 DU | 4.24 | 1.76 | 0.83 | 0.20 | 2.20 | 2.30 | 1.58 | 0.79 |
| CD3/BCMA/CD38-123* | BEAT | C1-D6 | E6-G6 | None | 9.14 | 1.50 | 12.38 | 7.67 | 19.62 | 9.97 | 14.84 | 3.77 |

TABLE 16

CD3/BCMA/CD38 −117, −118 and −119 candidates induce T cell activation associated with on-target off-tumor activity to a lesser extent compared to candidates −086, −114 and −115. The table shows the threshold of activation in nM (except for anti-CD3 + anti-CD28 and PHA, dose in ug/ml) determined from High-Density PBMC experiments and measured by the percentage of CD69 and CD25 upregulation on CD8 and CD4 T cells. * To note, mutation N82aS in the VH prevents the binding to Protein A.

| Treatment (nM except for positive controls) | Type | CD3 | BCMA | CD38 | $CD69^+$ of $CD4^+$ T cells | $CD25^+$ of $CD4^+$ T cells | $CD69^+$ of $CD8^+$ T cells | $CD25^+$ of $CD8^+$ T cells |
|---|---|---|---|---|---|---|---|---|
| anti-CD3 + anti-CD28 or PHA | N/A | N/A | N/A | N/A | <5 | <5 | <5 | <5 |
| 83A10-TCBcv | Benchmark CD3 × BCMA | CD3 | BCMA | None | 40 | 200 | 40 | 40 |
| CD3/BCMA/CD38-043 | TREAT BO | C1-D6 | D3-E11 | E2 | 40 | 200 | 8 | 40 |
| CD3/BCMA/CD38-086 | TREAT C | C1-D6 | D3-E11 | B3-C11 | 1.6 | 8 | 1.6 | 1.6 |
| CD3/BCMA/CD38-114* | TREAT C | C1-D6 | E6-G6 | E2-A5 | 1.6 | 1.6 | 1.6 | 1.6 |
| CD3/BCMA/CD38-115* | TREAT C | C1-D6 | E6-G6 | B3-C11 | 1.6 | 1.6 | 1.6 | 1.6 |
| CD3/BCMA/CD38-116* | TREAT C | C1-D6 | E6-G6 | B3 | 40 | 200 | 8 | 40 |
| CD3/BCMA/CD38-117* | TREAT BO | C1-D6 | E6-G6 | E2-A5 | 8 | 40 | 8 | 8 |
| CD3/BCMA/CD38-118* | TREAT BO | C1-D6 | E6-G6 | B3-C11 | 8 | 40 | 8 | 8 |
| CD3/BCMA/CD38-119* | TREAT BO | C1-D6 | E6-G6 | B3 | >200 | >200 | 200 | 200 |

EXAMPLE 14: CD3/BCMA/CD38 ANTIBODIES DIFFERENTIAL SCANNING CALORIMETRY (DSC) PROFILES

Materials and Methods

Differential Scanning Calorimetry (DSC)

The thermal stabilities of antibodies were compared using calorimetric measurements. Calorimetric measurements were carried out on a MicroCal PEAQ-DSC differential scanning calorimeter (Malvern Instruments, UK). The cell volume was 0.128 ml, the heating rate was 1° C./min and the excess pressure was kept at 64 psi. All protein fragments were used at a concentration of 1-2 mg/ml in PBS (pH 7.4). The molar heat capacity of each protein was estimated by comparison with duplicate samples containing identical buffer from which the protein had been omitted. The partial molar heat capacities and melting curves were analyzed using standard procedures. Thermograms were baseline corrected and concentration normalized before being further analyzed using a Non-Two State model.

The expected melting profiles for the human IgG subclasses are known (Garber E & Demarest S J (2007) Biochem Biophys Res Commun, 355(3): 751-7) and all profiles have been shown to contain three unfolding transitions corresponding to the independent unfolding of the CH2, CH3 and Fab domains. Of the four human IgG subclasses, IGHG1 has the most stable CH3 domain (~85° C.); while other subclasses CH3 domains are less stable, although none are known to melt below 70° C. Similarly, all subclasses are known to have a melting temperature of ~70° C. for the CH2 domain.

Results and Conclusions

Thermal stability of CD3/BCMA/CD38-115, CD3/BCMA/CD38-117, CD3/BCMA/CD38-118, CD3/BCMA/CD38-119 antibodies was assessed by differential scanning calorimetry. CD3/BCMA/CD38-115 showed a thermal transition (Tm) for the BEAT Fc domain at 70.09° C., (overlap of Tm of the CH2 and CH3 domains, in line with published data reported in Skegro et al., J Biol Chem, 2017, 292(23): 9745-9759) and at 83.22° C. for the Fabs. Similarly, CD3/BCMA/CD38-117 showed a thermal transition (Tm) for the BEAT Fc domain at 69.89° C. and at 82.78° C. for the Fabs. CD3/BCMA/CD38-118 showed a thermal transition (Tm) for the BEAT Fc domain at 69.99° C. and at 83.1° C. for the Fabs. CD3/BCMA/CD38-119 showed a thermal transition (Tm) for the BEAT Fc domain at 70.05° C. and at 82.81° C. and 86.6° C. for the Fabs as summarized in Table 17 and the corresponding thermograms are shown in FIGS. 10A-10D.

TABLE 17

Transition temperatures measured by DSC for selected TREAT CD3/BCMA/CD38

| Name | Total Area (kcal/mole) | Tm1 (° C.) | Tm2 (° C.) | Tm3 (° C.) |
|---|---|---|---|---|
| TREAT CD3/BCMA/CD38-115 | 1660 | 70.09 | 83.22 | N/A |
| TREAT CD3/BCMA/CD38-117 | 1550 | 69.89 | 82.78 | N/A |
| TREAT CD3/BCMA/CD38-118 | 1660 | 69.99 | 83.1 | N/A |
| TREAT CD3/BCMA/CD38-119 | 1530 | 70.05 | 82.81 | 86.6 |

EXAMPLE 15: TARGET BINDING OF CD3/BCMA/CD38 ANTIBODIES

Materials and Methods

Affinity measurements by SPR

Affinities of CD3/BCMA/CD38 antibodies for their three targets (CD3, CD38 and BCMA) were measured by Surface Plasmon Resonance (SPR) on a Biacore 8K+ instrument (Cytiva Life Sciences) at 25° C. and analyzed with the Biacore Insight Evaluation Software (v3). Measurements were performed on a CAP Sensor Chip using the Biotin CAPture kit (Cytiva Life Sciences, catalog NO: 28920234). The Biotin CAPture kit contains the reagents and sensor chip allowing for reversible attachment of biotinylated molecules to analyze interactions with the Biacore system. The biotinylated ligands, CD3, CD38, or BCMA, are captured on the sensor surface via the Biotin CAPture Reagent, a modified streptavidin that can be reversibly attached to the chip surface (d3.cytivalifesciences.com/prod/IFU/28924234.pdf). Following measurement of the interaction of CD3/BCMA/CD38 with the immobilized ligand, the surface can be regenerated to initiate a new cycle of ligand immobilization and interaction analysis.

Affinity of CD3/BCMA/CD38 Antibodies to Human CD3ε6

To measure the binding affinity of CD3/BCMA/CD38 antibodies to CD3εδ with CD3εδ as ligand, Recombinant Human CD3E & CD3D Protein, His-Avi-tagged, Biotinylated (CD3ε5, 10-16 RU) was immobilized on a Series S Biotin CAPture chip after adding 2500-5000 RU of CAPture reagent. CD3εδ was immobilized at a flow rate of 10 μL/min and at a concentration of 33.1 nM for 24 s. CD3/BCMA/CD38 antibodies were injected in concentration series at a flow rate of 30 μl/min and in HBS-EP+ buffer at 25° C. The time for association was 3 min and the time for dissociation was 5 min.

Affinity of CD3/BCMA/CD38 antibodies to human CD38

To measure the binding affinity of CD3/BCMA/CD38 antibodies to CD38 with CD38 as ligand, Biotinylated Human CD38 Protein, Avitag™, His Tag (CD38, 16-55 RU) was immobilized on a Series S Biotin CAPture chip after adding 2500-5000 RU of CAPture reagent. CD38 was immobilized at a flow rate of 10 μL/min and at a concentration of 32 nM for 50 s. CD3/BCMA/CD38 antibodies were injected in concentration series at a flow rate of 30 μl/min and in HBS-EP+ buffer at 25° C. The time for association was 3 min and the time for dissociation was 10 min.

Affinity of CD3/BCMA/CD38 Antibodies to Human BCMA

To measure the binding affinity of CD3/BCMA/CD38 antibodies to BCMA with BCMA as ligand, Biotinylated Human BCMA/TNFRSF17 Protein, His, Avitag™ DMF Filed (BCMA, 6-8 RU) was immobilized on a Series S Biotin CAPture chip after adding 2500-5000 RU of CAPture reagent. BCMA was immobilized at a flow rate of 10 μL/min and at a concentration of 52 nM for 12 s. CD3/BCMA/CD38 antibodies were injected in concentration series at a flow rate of 30 μl/min and in HBS-EP+ buffer at 25° C. The time for association was 4 min and the time for dissociation was 10 min.

Results and Conclusions

The binding affinity of CD3/BCMA/CD38 antibodies for human CD3εδ, BCMA and CD38 proteins were determined by surface plasmon resonance. CD3/BCMA/CD38 antibodies were engineered with Fab binding arms to CD3ε (C1-D6 Fab), BCMA (E6-G6 N82aS Fab) and CD38 (B3-C11, B3 or E2-A5 Fabs). Binding affinities were measured on immobilized human CD3, CD38, or BCMA at various CD3/BCMA/CD38 concentrations on a Biacore 8K+ instrument at 25° C. The CD3×BCMA bispecific antibody 83A10-TCBcv (Seckinger et al, 2017) was included as a reference molecule in all experiments. CD3/BCMA/CD38 antibodies $K_D$ values for the 1:1 interaction with human CD3, human BCMA and human CD38 were measured as listed in Table 18.

TABLE 18

Target binding of CD3/BCMA/CD38 antibodies and benchmark 83A10-TCBcv. Table shows binding affinities ($K_D$) measured using SPR for CD3/BCMA/CD38 antibodies and 83A10-TCBcv benchmark antibody to recombinant human CD3εδ protein, recombinant human BCMA and recombinant human CD38 protein, respectively.

| Target Binding (SPR, nM) | CD3/BCMA/CD38-115 | CD3/BCMA/CD38-117 | CD3/BCMA/CD38-118 | CD3/BCMA/CD38-119 | 83A10-TCBcv |
|---|---|---|---|---|---|
| human CD3εδ (FIG. 11) | 15.8 ± 1.9 | 30.0 ± 2.3 | 41.4 ± 2.8 | 44.8 ± 4.1 | 12.1 ± 1.3 (8.0 ± 0.9 using 1:1 kinetics fit) |
| human CD38 (FIG. 12) | 1.5 ± 0.3 | 8.1 ± 0.6 | 2.7 ± 0.2 | 36.8 ± 1.9 | Not applicable |
| human BCMA (FIG. 13) | 1.10 ± 0.06 | 1.71 ± 0.03 | 1.87 ± 0.11 | 1.92 ± 0.40 | 0.074 ± 0.010 |

Data represents average $K_D$ value ± standard deviation from at least two measurements.

FIGS. 11A-11D (for CD3εδ), FIGS. 12A-12D (for CD38) and FIGS. 13A-13D (for BCMA) show representative binding sensorgrams of CD3/BCMA/CD38 antibodies to their targets. These measurements confirmed that the CD3/BCMA/CD38 bound the three target antigens, with higher affinities to the tumor-associated antigens BCMA and CD38, and lower affinity to CD3.

EXAMPLE 16: FC SILENCING OF CD3/BCMA/CD38 ANTIBODIES

Materials and Methods

Binding affinity of CD3/BCMA/CD38 and trastuzumab IgG1 to human Fc receptors Measurements were conducted on a Biacore 8K+ instrument (Cytiva Life Sciences) and analyzed with the Biacore Insight Evaluation software (v2.0). Measurements included zero concentration samples for referencing. The binding kinetics constants of CD3/BCMA/CD38 to the recombinant human FcγRI extracellular domain (ECD) (Acrobiosystems, catalog no. FCA-H82E8) and to the in-house produced recombinant human FcγRIIa ECD (SEQ ID NO: 601), recombinant human FcγRIIb ECD (SEQ ID NO:600), recombinant human FcγRIIIa ECD (SEQ ID NO: 599) and recombinant human FcRn ECD (SEQ ID NO: 602 and SEQ ID NO: 603) were compared to the binding kinetics constants of the in-house produced clinically validated IgG1 reference antibody trastuzumab. Table 21

Procedure for FcγRI, FcγRIIa, FcγRIIb, FcγRIIIa measurements

Measurements were conducted via Protein G capture of the antibodies using a commercial Protein G coated Sensor Chip (Series S Protein G sensor CHIP, Cytiva, catalog no. 29179315). Each assay consisted of one replicate of each antibody sample. The Series S Protein G Sensor Chip was docked in the instrument and 290 to 380 RU of CD3/BCMA/CD38 or trastuzumab IgG1 antibodies, previously diluted to a final concentration of 4 μg/mL in HBS-EP+ buffer (Cytiva, catalog no. BR100669) were captured on flow-path 2. Human FcγRI ECD (Acrobiosystems, catalog no. FCA-H82E8), human FcγRIIa ECD (batch no. P1749), human FcγRIIb ECD (batch no. P1739), and human FcγRIIIa ECD (batch no. P1304) were injected on flow-path 1 and flow-path 2 (flow-path 1 being used as the reference) according to experimental settings described in Table 19. For analysis of the binding to CD3/BCMA/CD38 and trastuzumab IgG1, human FcγRI ECD, human FcγRIIa ECD, human FcγRIIb ECD, and human FcγRIIIa ECD were prepared in a 2× or 3× dilution series in HBS-EP+ buffer, pH 7.4, at a final 1× concentration and injected in order A-I as described in Table 20.

Procedure for FcRn measurements

Measurements were conducted via Protein L capture of the antibodies using a commercial Protein L coated Sensor Chip (Series S Protein L Sensor CHIP, Cytiva, catalog no. 29205138). All antibody samples were measured in three independent assays. Each assay consisted of one replicate of each antibody sample. The Series S Protein L Sensor Chip was docked in the instrument and 150-250 RU of CD3/BCMA/CD38 or trastuzumab IgG1 antibodies, previously diluted to a final concentration of 5 μg/mL in HBS-EP+ buffer (Cytiva, catalog no. BR100669), adjusted to pH 6.0 with HCl, were captured on flow-path 2. Recombinant human FcRn ECD and 32 microglobulin was injected on flow-path 1 and flow-path 2 (flow-path 1 being used as the reference) according to experimental settings described in Table 19. For analysis of the binding to CD3/BCMA/CD38 and trastuzumab IgG1, human FcRn ECD was prepared in a 2× dilution series in HBS-EP+ buffer pH 6.0 at a final 1× concentration and injected in order A-I as described in Table 20.

TABLE 19

Experimental settings for affinity measurements of CD3/BCMA/CD38 and trastuzumab IgG1 to human Fc receptors.

| Affinity measurement | FcγRI | FcγRIIa, FcγRIIb, FcγRIIIa | FcRn |
|---|---|---|---|
| Instrument | | Biacore 8K+ | |
| Sensor Chip | Series S Protein G sensor CHIP | | Series S Protein L sensor CHIP |
| Immobilized ligand | | N/A | |
| Flow path of immobilization | | N/A | |
| Captured ligands (RU) | CD3/BCMA/CD38 (340-390 RU) and Trastuzumab (380-1800 RU) | CD3/BCMA/CD38 (7500-7660 RU) Trastuzumab (970-1080 RU) | CD3/BCMA/CD38 and Trastuzumab (300-360 RU) |
| Flow path of capture | | 2 | |
| Flow rate of capture (μL/min) | | 10 | |
| Concentration of capture molecule (μg/mL) | 4 | CD3/BCMA/CD38: 4 Trastuzumab: 3 | CD3/BCMA/CD38: 4 |
| Capture injection time (s) | 25 | 20 | 30 |
| Analyte | FcγRI | FcγRIIa, FcγRIIb, FcγRIIIa | FcRn |
| Flow rate of injection (μL/min) | | 30 | |
| Running buffer | HBS-EP + pH 7.4 | | HBS-EP + pH 6 |
| Running temperature | | 25° C. | |
| Sample compartment temperature | | 25° C. | |
| Flow path of injection | | 1 > 2 | |
| Injection time (min) | 4.5 | 2 | 3 |
| Dissociation time (min) | 12 | 2 | 10 |
| Capture regeneration | 10 mM Glycine pH 1.5, 60 s | | 10 mM Glycine pH 1.7, 120 s |
| Experimental data fit method | Kinetics 1:1, default parameters | Steady state affinity | Steady state affinity |
| Reference subtraction | Double: reference surface without ligand and blank (running buffer injection) | | |

TABLE 20

Fc receptors sample injection series

| Fc receptor analyte | Fc receptor protein concentrations (nM) A | B | C | D | E | F | G | H | I |
|---|---|---|---|---|---|---|---|---|---|
| FcγRI | 0 | 0.78 | 1.56 | 3.12 | 6.25 | 12.5 | 25 | 50 | — |
| FcγRIIa | 0 | 39 | 78 | 156 | 312 | 625 | 1250 | 2500 | 5000 |
| FcγRIIb | 0 | 39 | 78 | 156 | 312 | 625 | 1250 | 2500 | 5000 |
| FcγRIIIa | 0 | 3.125 | 6.25 | 12.5 | 25 | 50 | 100 | 200 | 400 |
| FcRn | 0 | 15.6 | 31.25 | 62.5 | 125 | 250 | 500 | 1000 | 2000 |

Results and Conclusions

To prevent Fcγ receptor-mediated T cell activation in the absence of target cell engagement and ADCC and CDC against T cells, L234 Å/L235A (LALA)/P329A substitutions were introduced into the CH2 domains of BEAT CD38/CD3 molecules. The double mutation LALA has been shown to reduce the binding of human IgG1 molecules to human CD64, CD32a and CD16a (Hezareh et al., 2001, J Virol, 75(24): 12161-12168), while only slightly reducing the binding of the IgG Fc domain to FcRn, which occurs at the IgG CH2-CH3 interface (Wines et al., J Immunol., 2001; 166(3):1781-9). In addition to abolishing the binding to FcγR, the L234A, L235A double mutation has been shown to abolish binding to C1q (Hezareh et al., 2001, J Virol, 75(24): 12161-12168). C1q is the recognition subunit of C1, the complex that triggers activation of the classical pathway of complement. LALA only mutations in BEAT Fc reduce both ADCC and CDC functions but do not fully abolish binding to Fc receptors, therefore we have added P329A, a mutation which by itself reduces binding to Fc receptors (Shields et al. J. Biol. Chem, 2001, 276(9), 6591-6604), to further silence the Fc of CD3/BCMA/CD38 constructs. As a result, no binding could be observed to FcγRIa, IIa (SEQ ID NO:601), IIIa (SEQ ID NO: 599) and IIb (SEQ ID NO: 600) as shown in Table 21 below up to the maximum concentrations mentioned in table 20. Binding to FcRn (SEQ ID NO:602 and SEQ ID NO: 603) was conserved similarly to the benchmark antibody trastuzumab IgG1.

FIGS. 14A-14E shows representative, individual binding sensorgrams of CD3/BCMA/CD38 antibodies-115 (FIG. 14A), -117 (FIG. 14B), -118 (FIG. 14C) and -119 (FIG. 14D) to the different Fc receptors tested in this example, or lack of binding thereof, as well as the orientation and immobilization technique used for the analysis.

20 mM Na-Acetate buffer (pH 4.3, pre-filtered through 0.22 μm "Rapid"-Filtermax ("Rapid"-Filtermax, PES, 0.22 μm, TPP, cat. No. 99255)) using Zeba Spin Desalting Columns (Zeba™ Spin Desalting Columns, 7K MWCO, ThermoFisher, cat. No. 89882), followed by adjustment of the concentration to 0.4 mg/ml using sodium acetate buffer (Sodium acetate, anhydrous, for molecular biology, >99%, Sigma, cat. No. S2889-1 kg). A pre-mixed 4:1 volume ratio of capture:non-capture IgG solution was added to a solution of 20 nm unconjugated gold Sols nanoparticles (AuNP, pre-diluted 0.67-fold in H2O) to a final 1:9 volume ratio of coating solution:AuNP. AuNP were coated for 1 hr at room temperature, followed by blocking of empty sites on AuNP by addition of thiolated PEG (Poly (ethylene glycol) methyl ether thiol, Sigma-Aldrich, cat. No. 729140-1G) at a final concentration of 0.1 μM. Coated AuNP were then stored at 4° C. until use.

AC-SINS measurement: Pre-coated AuNP solution was centrifuged at 20000 rcf at 4° C. for 10 min. Around 95% of the supernatant was removed using a pipette. AuNP were then resuspended into 10% of the initial volume in PBS. 10 μl of the resuspended AuNP was mixed to 100 μl of the test antibody (CD3/BCMA/CD38-115, 117, 118 or 119), previously diluted at a concentration of 100 μg/ml, into a 96-well polypropylene plate (Nunc™ 96-well Polypropylene Storage Microplates, ThermoFisher, cat. no. 249946). After 1 h incubation at room temperature at 700 RPM on a plate shaker, 100 μl of the solutions were transferred into a clear UV-Transparent 96-well polystyrene plate (Corning® 96-well Clear Flat Bottom UV-Transparent Microplate, without Lid, Nonsterile, Corning, cat. No. 3635) and absorbance data were collected from 450 nm to 650 nm at an increment of 1 nm on a Synergy Neo plate reader (Synergy Neo HTS Multi Mode Reader, BioTek Instruments).

TABLE 21

Binding to Fc receptors of CD3/BCMA/CD38 antibodies and benchmark antibody trastuzumab.

| | Affinity to human Fc receptor ($K_D$, nM ± standard deviation) | | | | |
|---|---|---|---|---|---|
| | CD3/BCMA/CD38-115 (P1854) | CD3/BCMA/CD38-117 (P1842) | CD3/BCMA/CD38-118 (P1854) | CD3/BCMA/CD38-119 (P1842) | Trastuzumab (pJFR148) |
| Human FcγRI | Not Binding | Not Binding | Not Binding | Not Binding | 0.196 ± 0.006 |
| Human FcγRIIA | Not Binding | Not Binding | Not Binding | Not Binding | 550 ± 20 |
| Human FcγRIIB | Not Binding | Not Binding | Not Binding | Not Binding | 2070 ± 90 |
| Human FcγRIIIA | Not Binding | Not Binding | Not Binding | Not Binding | 106 ± 3 |
| Human FcRn | 250 ± 21 | 235 ± 13 | 221 ± 16 | 240 ± 9 | 231 ± 15 |

EXAMPLE 17: AC-SINS OF CD3/BCMA/CD38 CANDIDATES

Materials and Methods

Affinity-Capture Self-Interaction Nanoparticle Spectroscopy (AC-SINS)

Prior to coating of gold particles, polyclonal goat anti-human IgG Fc antibodies (AffiniPure Goat Anti-Human IgG, Fcγ fragment specific, Jackson ImmunoResearch, cat. No. 109-005-098-JIR; "capture") and ChromPure goat non-specific antibodies (ChromPure Goat IgG, whole molecule, polyclonal, Jackson ImmunoResearch, cat no. 005-000-003; "non-capture") were buffer exchanged into freshly prepared Raw absorbance data were exported into Excel and analyzed using the Excel macro used by Tessier P. lab, University of Michigan (Liu et al., 2013, mAbs, doi: 10.4161/mabs.27431). Briefly, "[ . . . ] The macro first identifies the wavelength of maximum absorbance in the raw data, then stores the 20 data points around that wavelength in an array. Each point is averaged with the points directly before and after it to reduce error from noise. Using the Linest function in Excel, a second-order polynomial is fitted to this set of data. The coefficients are used to calculate the wavelength where the slope is equal to zero and the macro then determines whether this point is a maximum or minimum. In the case of a maximum, the calculated wavelength is returned [ . . . ]" (Liu et al., 2013, mAbs, doi: 10.4161/mabs.27431).

Each antibody was measured in duplicate and the plasmon wavelength shift (Δλmax) of each antibody was calculated by subtracting the plasmon wavelength at maximum absorbance (λmax) of PBS from the average λmax of the antibody.

Results and Conclusions

Propensity of a selection of CD3/BCMA/CD38 to self-associate was assessed by Affinity-Capture Self-Interaction Nanoparticle Spectroscopy (FIG. 15). CD3/BCMA/CD38-118 and CD3/BCMA/CD38-119 showed very low propensity to self-associate as judged by low plasmon wavelength shift (Δλmax) value, whereas CD3/BCMA/CD38-115 and CD3/BCMA/CD38-117 had high plasmon wavelength shift compatible with high propensity to self-associate (FIG. 15). To the inventors' surprise, CD3/BCMA/CD38-118 showed a better developability profile related to propensity to self-associate than CD3/BCMA/CD38-115, despite the two constructs being a combination of the same three binders, although in a different spatial orientation. This property confers an advantage to CD3/BCMA/CD38-118 and CD3/BCMA/CD38-119 for their development as antibody therapeutics.

EXAMPLE 18: FURTHER CHARACTERIZATION OF CD3/BCMA/CD38 ANTIBODIES

EXAMPLE 18 (A): BINDING TO HUMAN PRIMARY T CELLS

Materials and Methods

Human PBMC were harvested from buffy coats/apheresis filters obtained from La Chaux-de-Fonds/Bern (Switzerland) Transfusion Center using Ficoll® density gradient isolation. T cells were isolated (StemCell Technologies, 17951) and frozen the same day of the harvest. Cells were thawed in pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $2\times10^6$ cells/ml. Cells were plated at $1\times10^5$ cells/well in a 96-well round-bottom plate. The plate was centrifuged at 350 g for 3 min at 4° C. and the cells were resuspended in 100 μl of cold FACS buffer containing serial dilutions of CD3/BCMA/CD38-118 and -119 candidates, benchmarks (BEAT CD3/CD38, 83A10-TCBcv, TNB-F2B BEAT Fc) and control (CD3/BCMA/CD38-085) starting from 800 nM and diluted by 3-fold. Cells were incubated for 30 min at 4° C., washed twice with FACS buffer at 350 g for 3 min and resuspended in 25 μl of a cocktail of monoclonal anti-human IgG ALEXA FLUOR® 647 secondary antibody (Biolegend, 409316) and co-staining antibodies for human CD38 (Anti-CD38 multi-epitope, Cytognos, CYT-38F2) diluted 1/200 and 1/10 in FACS buffer, respectively. Cells were incubated for 30 min at 4° C. Cells were then washed twice and resuspended in 50 μl of FACS buffer containing SYTOX Blue dead cell stain (ThermoFisher Scientific, S34857) diluted 1/2000. Samples were acquired on an iQue Screener Plus instrument (IntelliCyt). Cells were gated based on size on FSC vs SSC and debris and doublets were excluded. Finally, viable cells were gated on CD38-T cells. This population was analyzed for ALEXA FLUOR® 647-geometric mean (geomean) fluorescence intensity using iQue Forecyt® software. Only samples showing at least 200 cells in final gate were considered in the further steps of the analysis. Relative geomean fluorescence intensity (RFI) was calculated by subtracting fluorescence of negative control (CD3/BCMA/CD38_085) to fluorescence of treatments at each dilution. Relative geomean fluorescence intensity values were finally plotted using Prism software (GraphPad). Equilibrium dissociation constant values ($K_D$) and maximum binding were determined by using one-site binding curve fitting on non-transformed data (Prism). The Relative geomean fluorescence intensity and $K_D$ was plotted using Prism software (GraphPad) as depicted in FIGS. 16A-16B. $K_D$ and Maximum binding values are summarized in Table 22. Two independent experiments were performed with each candidate with a total of six donors.

Results and Conclusions

The binding curves of CD3/BCMA/CD38 candidates and benchmarks on primary human CD38− T cells are shown in FIG. 16A and associated Equilibrium dissociation constant ($K_D$) values in FIGS. 16B, as well as reported in Table 22 together with Maximum binding. CD3/BCMA/CD38-118 and -119 candidates displayed comparable binding curves than BEAT CD3/CD38 with $K_D$ measurements of 152.2±51.1 nM (CD3/BCMA/CD38-118), 133.5±40.3 nM (CD3/BCMA/CD38-119) and 152.6±40.9 nM (BEAT CD3/CD38) respectively as well as Maximum binding (CD3/BCMA/CD38-118 12'000±3'000 RFI; CD3/BCMA/CD38-119 18'000±3'000 RFI; BEAT CD3/CD38 40'000±8'000 RFI) whereas benchmarks show very different $K_D$ and Maximum binding: 83A10-TCBcv ($K_D$ 80.0±10.6; Maximum binding 103'000±13'000 RFI) and TNB-F2B BEAT Fc ($K_D$ Not Quantifiable; Maximum binding 60±20 RFI).

TABLE 22

CD3/BCMA/CD38 candidates bind to human CD38 negative T cells. The table shows $K_D$ in nM and Maximum binding (Relative Fluorescence Intensity, RFI) values on T cells determined by Flow Cytometry experiments. Each value is the Mean +/− Standard Deviation of six T cell donors from two independent experiments.

| Molecule | Max binding (RFI) | $K_D$ (nM) |
|---|---|---|
| BEAT CD3/CD38 | 40'000 ± 8'000 | 152.6 ± 40.9 |
| TNB-F2B BEAT Fc | 60 ± 30 | N.Q. |
| 83A10-TCBcv | 103'000 ± 14'000 | 80.0 ± 10.6 |
| CD3/BCMA/CD38-118 | 12'000 ± 3'000 | 152.2 ± 51.1 |
| CD3/BCMA/CD38-119 | 18'000 ± 3'000 | 133.5 ± 40.3 |

N.Q. stands for not quantifiable (No binding or bad quality of fit).

EXAMPLE 18 (B): BINDING TO MULTIPLE MYELOMA CELL LINES

Materials and Methods

NCI-H929, MOLP-8 and KMS-12-BM were plated at $1\times10^5$ cells/well in a 96-well round-bottom plates. The plates were centrifuged at 350 g for 3 min at 4° C. and the cells were resuspended in 100 μl of cold FACS buffer containing serial dilutions of CD3/BCMA/CD38-118 and -119 candidates, benchmark (83A10-TCBcv) and control (CD3/BCMA/CD38-085) starting from 800 nM and diluted by 3. Cells were incubated for 30 min at 4° C., washed twice with FACS buffer at 350 g for 3 min and resuspended in 25 μl of a monoclonal anti-human IgG ALEXA FLUOR® 647 secondary antibody (Biolegend, 409316) diluted 1/200 in FACS buffer. Cells were then washed twice and resuspended in 50 μl of FACS buffer containing SYTOX Blue dead cell stain (ThermoFisher Scientific, S34857) diluted 1/2000. Samples were acquired on an iQue Screener Plus instrument (IntelliCyt). Cells were gated based on size on FSC vs SSC and debris, doublets and dead cells were excluded. Population was analyzed for ALEXA FLUOR® 647-geometric mean (geomean) fluorescence intensity using iQue Forecyt® software. Only samples showing at least 200 cells in final gate were considered in the further steps of the analysis. Relative geomean fluorescence intensity (RFI) was calculated by subtracting fluorescence of isotype control to fluorescence of treatments at each dilution. Relative geomean fluorescence intensity values were finally plotted using Prism software (GraphPad). Equilibrium dissociation constant values ($K_D$) and maximum binding were determined by using one-site binding curve fitting on non-transformed data (Prism). The Relative geomean fluorescence intensity was plotted using Prism software (GraphPad) as depicted in FIGS. 17A-17C. $K_D$ and Maximum binding values are summarized in Table 23. Three independent experiments were performed with each candidate.

Results and Conclusions

Results from FIGS. 17A-17C show the binding curves of CD3/BCMA/CD38 candidates and benchmarks on multiple myeloma cell lines displaying variable expression of CD38 and BCMA. Associated Equilibrium dissociation constant ($K_D$) values and Maximum binding are reported in Table 23.

CD3/BCMA/CD38 candidates displayed superior maximum binding compared to CD3×BCMA benchmark 83A10-TCBcv on all cell lines. On the KMS-12-BM cell line (characterized as BCMA and CD38 low-expressing cells), the increase in maximum binding compared with 83A10-TCBcv was 2.6-fold and 1.5-fold higher for candidates CD3/BCMA/CD38-118 and -119 respectively (FIG. 17A). On the MOLP-8 cell line (characterized as BCMA low- and CD38 high-expressing cells), the CD3/BCMA/CD38 candidates displayed 80-fold or 44-fold higher maximum binding compared to 83A10-TCBcv (FIG. 17B). On NCI-H929 cells (characterized as BCMA and CD38 medium-expressing cells), the maximum binding was 1.5-fold and 1.3-fold higher for candidates CD3/BCMA/CD38-118 and -119 respectively compared with the CD3×BCMA benchmark 83A10-TCBcv (FIG. 17C). CD3/BCMA/CD38 candidates displayed comparable binding curves with low nanomolar range Kr measurements of 7 and 12 nM on KMS-12-BM, 3 and 31 nM on MOLP-8 and 3 and 12 nM on NCI-H929, whereas 83A10-TCBcv displayed the same range of binding than CD3/BCMA/CD38-118 candidate with 2, 5 and 4 nM, respectively.

TABLE 23

CD3/BCMA/CD38 candidates bind to cell lines displaying variable expression of CD38 and BCMA.
The table shows $K_D$ in nM and Maximum binding values on cell lines displaying variable expression of CD38 and BCMA, KMS-12-BM, MOLP-8 and NCI-H929, determined by Flow Cytometry. Each value is the Mean of 3 measurements from 3 individual experiments.

| | KMS-12-BM | | MOLP-8 | | NCI-H929 WT | |
|---|---|---|---|---|---|---|
| | Max binding (RFI) | $K_D$ (nM) | Max binding (RFI) | $K_D$ (nM) | Max binding (RFI) | $K_D$ (nM) |
| 83A10-TCBcv | 40,132 | 2 | 11,112 | 5 | 218,894 | 4 |
| CD3/BCMA/ CD38-118 | 104,284 | 7 | 891,877 | 3 | 322,578 | 3 |
| CD3/BCMA/ CD38-119 | 61,483 | 12 | 490,400 | 31 | 293,847 | 12 |

Taken together, the data suggest that CD3/BCMA/CD38-118 and -119 candidates are likely to bind preferentially to BCMA and CD38 expressing tumor cells with high apparent binding affinities rather than to T cells.

EXAMPLE 18 (C): STATISTICAL ANALYSIS FROM RDL ASSAY OF NCI-H929, MOLP-8 AND KMS-12-BM TUMOR CELLS expressing various levels of BCMA and CD38

Materials and Methods

Assays were performed following the same methodologies and material as described above.

Additionally, statistical analyses were applied to compare the killing potency of CD3/BCMA/CD38-118 and -119 candidates to each benchmark (BEAT CD3/CD38, 83A10-TCBcv, TNB-F2B BEAT Fc) on NCI-H929, MOLP-8 and KMS-12-BM multiple myeloma cell lines. EC50 Specific Killing previously extracted were plotted using Prism software (GraphPad) as depicted in FIGS. 18A-18C and summarized (Mean+/−Standard Deviation) in Table 24. Means EC50 were compared using a paired One-way ANOVA followed by Tukey HSD post-hoc comparison (*P<0.05).

Results and Conclusions

CD3/BCMA/CD38-118 and -119 were tested for their in vitro killing potency against myeloma cell lines KMS-12-BM, MOLP-8 and NCI-H929 with varying levels of CD38 and BCMA expression in a RDL assay. As shown in FIGS. 18A-18C, CD3/BCMA/CD38-118 and -119 induced potent killing of all myeloma cell lines tested indicating that killing mediated by redirected T cell cytotoxic activity induces an efficient cytotoxic activity against these cell lines. $EC_{50}$ values for CD3/BCMA/CD38-118 mediated killing of KMS-12-BM, MOLP-8 and NCI-H929 were determined as 0.4±0.2, 0.7±0.7 and 1.2±0.9 pM, respectively (Table 24). CD3/BCMA/CD38-118 exhibited a significant 41.4-fold increase of killing potency compared to the 83A10-TCBcv antibody against MOLP-8 (characterized as BCMA low- and CD38 high-expressing cells) cells. Cytotoxic activity of CD3/BCMA/CD38-118 was also superior to 83A10-TCBcv redirected lysis of KMS-12-BM (characterized as BCMA and CD38 low-expressing cells) and NCI-H929 (characterized as BCMA and CD38 med-expressing cells) cells showing 7.8 or 2.8-fold lower $EC_{50}$ values, respectively (Table 24). CD3/BCMA/CD38-119 triggered superior killing compared to benchmark 83A10-TCBcv of the MOLP-8 cell line (significant 5.9-fold decrease of $EC_{50}$) and comparable killing of KMS-12-BM and NCI-H929 cell lines. TNB-F2B BEAT Fc triggered the weakest killing potency compared to other treatments (statistically significant on all cell lines). Overall, data analysis showed potent cytotoxic activity of CD3/BCMA/CD38-118 and -119 with $EC_{50}$ values in the low picomolar range against myeloma cell lines with varying levels of CD38 and BCMA expression. Cytotoxic activity of CD3/BCMA/CD38-118 and -119 with binding arms to CD38 and BCMA is strongly enhanced compared to the benchmarks, BEAT CD3/CD38, targeting only CD38 and TNB-F2B BEAT Fc and 83A10-TCBcv, targeting only BCMA.

TABLE 24

CD3/BCMA/CD38-118 candidate induces the most potent in vitro killing of Multiple Myeloma cell lines displaying variable expression of CD38 and BCMA. The table shows half maximum effective killing concentration ($EC_{50}$) values determined from Redirected Lysis assay on multiple cell lines displaying variable expression of CD38 and BCMA, KMS-12-BM, MOLP-8 or NCI-H929, for 72 h and using an Effector-to-Target ratio of 5:1. Each $EC_{50}$ value is the Mean +/− Standard Deviation of five-six measurements from three individual experiments. Means were compared using a paired One-way ANOVA followed by Tukey HSD post-hoc comparison.

| Treatment | Type | Anti-CD38 | Specific Killing $EC_{50}$ ± SD [pM] KMS-12-BM | MOLP-8 | NCI-H929 |
|---|---|---|---|---|---|
| BEAT CD3/CD38 | CD3 × CD38 | h9G7 | 3.2 ± 1 * | 3.1 ± 3 *# | 6.5 ± 4.8 * |
| TNB-F2B BEAT Fc | CD3 × BCMA | None | 25.1 ± 10.3 | 100.4 ± 62.8 | 265.1 ± 104.7 |
| 83A10-TCBcv | CD3 × BCMA | None | 3.1 ± 1.1 * | 29 ± 9.7 + | 3.4 ± 1.5 * |
| CD3/BCMA/CD38-118 | TREAT BO | B3-C11 | 0.4 ± 0.2 *#+ | 0.7 ± 0.7 *#+ | 1.2 ± 0.9 *#+ |
| CD3/BCMA/CD38-119 | TREAT BO | B3 | 3.3 ± 1.3 * | 4.9 ± 4.7 *# | 3.2 ± 1.4 * |

N.Q. stands for not quantifiable (No binding or poor quality of fit).

* stands for statistically significant compared to TNB-F2B BEAT Fc.

stands for statistically significant compared to 83A10-TCBcv.

+ stands for statistically significant compared to BEAT CD3/CD38.

EXAMPLE 18 (D): T CELL ACTIVATION AND PROLIFERATION ANALYSES FROM RDL ASSAY OF KMS-12-BM TUMOR CELLS EXPRESSING LOW LEVELS OF BCMA AND CD38

Materials and Methods

To evaluate whether CD3/BCMA/CD38-118 and -119 candidates induced activation and proliferation of T cells, additional readouts were monitored by Flow Cytometry in parallel of target cell killing. Cells were stained with anti-human CD4-BrilliantViolet785 (BioLegend, Scientific, 317442, 1/100 dilution), CD8-APC-eFluor780 (ThermoFisher Scientific, 47-0087-42, 1/200 dilution) and CD25-PE-Cyanine7 (ThermoFisher Scientific, 25-0259-42, 1/100 dilution) diluted in FACS buffer. As described above, samples were acquired on an iQue instruments (Beckman Coulter). Specifically, PBMC were gated on eFluor670-/eFluor450*cells, then $CD4^+$ and $CD8^+$ T cells were gated. T cell activation was determined by evaluating the percentage of CD25 positive cells gated on $CD4^+$ or $CD8^+$ T cells and proliferation was assessed using the method of dye dilution through multiple rounds of cell division (loss of eF450 labelling). Percentages of activated T cells values ($CD25^+$ of CD4 or CD8 T cells) as well as percentages of proliferation (Proliferation of $CD4^+$ or $CD8^+$ T cells) were extracted. Half maximal effective concentration or $EC_{50}$ of activation or proliferation were calculated from the percentages extracted using Sigmoidal dose response Nonlinear regression. $EC_{50}$ values determined on KMS-12-BM multiple myeloma cell line are depicted in FIG. 19. Statistical analysis was also conducted and Means $EC_{50}$ were compared using a paired One-way ANOVA followed by Tukey HSD post-hoc comparison.

Results and Conclusions

Analysis of the activation marker CD25 expression on $CD4^+$ and $CD8^+$ T cells in the KMS-12-BM RDL assay revealed a CD25 upregulation with $EC_{50}$ values of 28 and 5 pM and an induction of proliferation at $EC_{50}$ values of 19 and 4 pM for CD3/BCMA/CD38-118, showing a higher induction of proliferation and activation of cytotoxic $CD8^+$ T cells compared to 83A10-TCBcv. CD3/BCMA/CD38-118 demonstrated comparable T cell activation and proliferation compared to BEAT CD3/CD38. CD3/BCMA/CD38-119 induced comparable T cell activation and proliferation compared to TNB-F2B BEAT Fc. CD3/BCMA/CD38-119 induced lower $CD4^+$ T cell activation and proliferation compared to BEAT CD3/CD38 and 83A10-TCBcv.

EXAMPLE 18 (E): RDL ASSAY OF KMS-12-BM TUMOR CELLS EXPRESSING LOW LEVELS OF BCMA AND CD38 AND THE EFFECT OF SOLUBLE APRIL AND CD38 ON KILLING POTENCY

Materials and Methods

It is known that levels of circulating soluble CD38 and APRIL in blood from Multiple Myeloma patients is significantly higher than levels of circulating soluble CD38 and APRIL in blood from Healthy donors (average of 100 ng/ml and 15 ng/ml for soluble APRIL, respectively (Moreaux et al, 2004); average of 0.4 ng/ml and 0.1 ng/ml for soluble CD38, respectively (Zuch de Zafra et al, 2019). In circulation, soluble CD38 or APRIL present a potential sink risk, decreasing the possibility of the molecule to bind to tumor cells, therefore impacting the killing potency. The killing activity of these CD3/BCMA/CD38 TREATs was evaluated as described in Example 13, in the presence of high levels of soluble APRIL and CD38, supplemented at 100 ng/ml or 2.8 ng/ml final concentrations, respectively. In these experiments, the starting dose used was 200 nM. Means $EC_{50}$ and Standard Deviations are reported in pM in Table 25, as well as the fold difference compared to the absence of soluble receptors. Two independent experiments were performed with each candidate for a total of six donors.

Results and Conclusions

As shown in Table 25, CD3/BCMA/CD38-118 and -119 candidates were less affected by the presence of soluble APRIL compared to the benchmark 83A10-TCBcv (63-fold higher $EC_{50}$ of killing in the presence of APRIL). Soluble CD38 did not affect the killing potency of any molecule.

TABLE 25

CD3/BCMA/CD38 candidates trigger KMS-12-BM cell killing in the presence of soluble APRIL or soluble CD38 in Redirected Lysis assay. The table shows Mean +/− Standard Deviation of $EC_{50}$ of killing determined from Redirected Lysis experiments on KMS-12-BM cell line incubated with or without APRIL or soluble CD38 (100 ng/ml and 2.8 ng/ml, respectively). The fold-difference was calculated to indicate the impact on killing potency (Mean $EC_{50}$ with soluble molecule/Mean $EC_{50}$ without soluble molecule). The table shows data from three donors from one representative experiment out of two.

| | $EC_{50}$ (pM) | | | Fold difference $EC_{50}$ | |
|---|---|---|---|---|---|
| Molecule | No soluble | APRIL (100 ng/ml) | sCD38 (2.8 ng/ml) | APRIL (100 ng/ml) | sCD38 (2.8 ng/ml) |
| BEAT CD3/CD38 | 4.1 ± 1.3 | 4.4 ± 1.2 | 2.9 ± 0.9 | 1 | 1 |
| TNB-F2B BEAT Fc | 31.9 ± 9.4 | 273.5 ± 154.8 | 15.6 ± 6.2 | 9 | 0.5 |
| 83A10-TCBcv | 2.5 ± 0 | 154.3 ± 53.3 | 2.5 ± 0.5 | 63 | 1 |
| CD3/BCMA/CD38-118 | 0.5 ± 0.3 | 3 ± 0.8 | 0.8 ± 0.7 | 6 | 2 |
| CD3/BCMA/CD38-119 | 5.4 ± 3 | 42.8 ± 20.3 | 4.7 ± 2.8 | 8 | 1 |

EXAMPLE 18 (F): CYTOKINE QUANTIFICATION ANALYSES FROM ON-TARGET OFF-TUMOR ACTIVITY

Materials and Methods

The protocol of on-target off-tumor assay was previously described in Example 13. From the same experiments, cytokines were quantified using Meso Scale Discovery V-PLEX Custom Human Biomarkers (Human IL-2, IL-6, IL-10, IFN-gamma, TNF-alpha) kit (MesoScale Discovery, K151A9H-2) following the manufacturer's instructions. Quantification values were plotted using Prism software (GraphPad) as depicted in FIGS. 20A-20E. From those data, the threshold of cytokine induction was determined. The threshold of induction is defined by the first dose showing significant cytokine release and was obtained using JMP software (SAS), using Nested Least Square model followed by a Dunnet post-hoc comparison compared to Negative control (CD3/BCMA/CD38_085), p-value<0.05 was considered as statistically significant. The benchmark 83A10-TCBcv was used as reference. The CD3/BCMA/CD38-118 and 119 candidates were compared against the positive control, PHA stimulated PBMCs. Threshold of induction values are summarized in Table 26.

Results and Conclusions

Human IL-2, IL-6, IL-10, IFN-gamma, and TNF-alpha soluble markers were quantified from high-density PBMC assay. Results from FIGS. 20A-20E show that CD3/BCMA/CD38-118 and -119 candidates do induce some cytokine release however to a much lower extent compared to the positive control (PHA). As summarized in Table 26, the thresholds of cytokine induction show that CD3/BCMA/CD38-118 and -119 candidates induced cytokine release associated with on-target off-tumor activity at concentrations of 8 to 200 nM.

TABLE 26

CD3/BCMA/CD38-118 and -119 candidates induce Cytokine release associated with on-target off-tumor activity to a similar or lesser extent compared to benchmark 83A10-TCBcv. The table shows the threshold of activation in nM (except for anti-CD3 + anti-CD28 and PHA) determined from High-Density PBMC experiments and measured by the cytokine release of IFN-gamma, TNF-alpha, IL-2, IL-6, and IL-10.

| Sample | IFN-gamma | TNF-alpha | IL-2 | IL-6 | IL-10 |
|---|---|---|---|---|---|
| CD3/CD38/BCMA-118 | 40 | 40 | >200 | >200 | 8 |
| CD3/CD38/BCMA-119 | 200 | 200 | >200 | >200 | >200 |
| 83A10-TCBcv | 40 | 200 | 8 | 200 | 40 |

EXAMPLE 18 (G): BINDING TO RED BLOOD CELLS

Materials and Methods

One hundred microliters of freshly EDTA-drawn whole blood (Bern transfusion center, 92000) was incubated in a 96-well round-bottom plate with a dose-response (800, 9.88, 0.12 nM) of CD3/BCMA/CD38-118, −119 candidates or benchmarks (BEAT CD3/CD38, 83A10-TCBcv, TNB-F2B BEAT Fc, daratumumab (SEQ ID NO:565 and SEQ ID NO:566), magrolimab (SEQ ID NO:567 and SEQ ID NO:568)) and Fab anti-human IgG (H+L) Alexa-Fluor488 secondary antibody (Jackson ImmunoResearch Europe Ltd, 109-547-003) for 20 min at 4° C. After the incubation, each condition was diluted 1/1600 in a new 96-well round-bottom plate in FACS buffer containing azide. Cells were then washed twice and resuspended in 200 μl of FACS buffer containing azide. Samples were acquired on a CytoFlex instrument (Beckman Coulter). Cells were gated based on size on FSC vs and analyzed for ALEXA FLUOR® 488-geometric mean (geomean) fluorescence intensity using FlowJo software. Only samples showing at least 500 events in final gate were considered in the further steps of the analysis. Geometric mean fluorescence intensity values were finally plotted using Prism software (GraphPad) as depicted in FIGS. 21A-21B. Area Under the Curve (AUC) of a dose response curve was determined for each donor. Means were compared using a paired One-way ANOVA followed by Dunnett post-hoc comparison to daratumumab (*$P<0.05$). Two independent experiments were performed with each candidate for a total of six donors.

Results and Conclusions

FIG. 21A shows that none of the antibodies tested, including CD3/BCMA/CD38 candidate-118 and -119, showed binding to red blood cells in human whole blood except the positive control magrolimab and daratumumab at the highest dose (800 nM). FIG. 21B displays the Area under the curves (AUC) for each treatment and highlights that magrolimab and daratumumab showed significant binding to red blood cells whereas CD3/BCMA/CD38 candidate-118 and -119, as well as BEAT CD3/CD38, 83A10-TCBcv, and TNB-F2B BEAT Fc did not bind to red blood cells.

EXAMPLE 18 (H): HEMAGGLUTINATION

Materials and Methods

CD3/BCMA/CD38-118 and -119 candidates or controls (BEAT CD3/CD38, 83A10-TCBcv, TNB-F2B BEAT Fc, daratumumab, magrolimab) were prepared 3× concentrated in sterile PBS. Fifty microliters of a 0.8% red blood cell suspension prepared from fresh whole blood and 25 μl of each antibody dilution (220, 1.25 and 0.07 nM) was then added in each column of the ID-card Coombs anti-IgG. The cards were incubated at 37° C. for 15 minutes and then were centrifuged in the ID-20 centrifuge. Each microtube of the ID-card contains anti-human globulin anti-IgG (rabbit) within a gel matrix. The gel column acts as a filter that traps agglutinated red blood cells as they pass through the gel column during the centrifugation of the card. The gel column separates agglutinated red blood cells from non-agglutinated red blood cells based on size. Any agglutinated red blood cells are captured at the top of or along the gel column, and non-agglutinated red blood cells descend to the bottom of the microtube 25 forming a pellet. Extent of agglutination was scored from 0 (no agglutination) to 4 (complete agglutination) as depicted in FIG. 22. Two independent experiments were performed with each candidate for a total of six donors.

Results and Conclusions

FIG. 22 shows that none of the antibodies tested, including CD3/BCMA/CD38-118 and -119 candidates, sensitized red blood cells to hemagglutination except magrolimab and daratumumab treatments at the two highest dose (220 and 1.25 nM). The positive control, magrolimab, sensitized red blood cells to hemagglutination at maximum levels at 220 nM and 1.25 nM, as well as partially at 0.007 nM. Daratumumab partially sensitized red blood cells to hemagglutination at 220 nM and 1.25 nM. CD3/BCMA/CD38-118 and -119 candidates as well as 83A10-TCBcv and TNB-F2B BEAT Fc did not sensitize red blood cells to hemagglutination.

EXAMPLE 18 (I): MULTIPLE MODES OF ACTION KILLING ASSAY

Materials and Methods

To further compare the killing potency of CD3/BCMA/CD38-118, −119 candidates with anti-CD38 benchmarks, an assay that recapitulates Multiple Modes of Action of Killing (Fc-mediated, T cell-mediated, complement-mediated) using NCI-H929 multiple myeloma cell line was used.

Human peripheral blood mononuclear cells (PBMC) were isolated from buffy coats of healthy donors obtained from La Chaux-de-Fonds/Bern (Switzerland) Transfusion Center using ficoll density gradient isolation and frozen in CryoStor10 medium (Stemcell, catalog NO: 07930). Cells were thawed in a pre-warmed complete RPMI medium (RPMI supplemented with 10% heat inactivated fetal calf serum, 1% L-Glutamine and 1% Penicillin/Streptomycin) and rested overnight at $2\times10^6$ cells/ml. On the day of the assay, target cells (NCI-H929 cell line, Sigma, catalog NO: 95050415) were labelled with 2 μM of proliferation dye eFluor670 (ThermoFisher Scientific, catalog NO: 56-0048-82), prepared at $4\times10^5$ cells/ml and $2\times10^4$ cells (50 μl) were plated in RPMI containing 2% L-Glutamine and 2% Penicillin/Streptomycin. Following this step, PBMC were prepared in 100% human Serum (Sigma, catalog NO: SLCD4040) and 200 units/ml of IL-2 (Roche, Proleukin) at $1\times10^6$ cells/ml and $1\times10^5$ PBMC (100 μl) were plated reaching a effector-to-target ratio of 5:1. Then, serial dilutions of CD3/BCMA/CD38 candidates, benchmarks (daratumumab, isatuximab (SEQ ID NO: 569 and SEQ ID NO:

570), 83A10-TCBcv) or control (CD3/BCMA/CD38-085), starting from 80 nM for anti-CD38 benchmarks and 2 nM for CD3/BCMA/CD38 candidates and 83A10-TCBcv, then diluted by 10 or 5, respectively, were incubated in the co-culture for 48 h, at 37° C., 5% CO2.

At the end of the incubation, tumor cell killing was assessed using flow cytometry, by measuring absolute count of live target cells (eFluor670$^+$ cells) and calculated as % of target killing=[1−(Sample absolute counts)/(absolute counts in the presence of target cells alone)]×100. Half maximal effective concentration or $EC_{50}$ was calculated from the target killing values using Prism (GraphPad). Some values were excluded based on goodness of fit ($R^2$>0.7), on percentage of tumor cells spontaneous killing (assay window), out-of-range $EC_{50}$ values and inappropriate percentages of killing (<20%). Target killing curves were finally plotted using Prism software (GraphPad) as depicted in FIGS. 23A, as well as EC50 of killing (FIG. 23B) and Area Under the Curve (AUC) of a dose response curve, determined for each donor (FIG. 23C). Means EC50 (5-8 donors) were compared using Kruskal-Wallis followed by Dunn's post-hoc comparison and Means AUC using a paired One-way ANOVA test followed by Tukey's post-hoc comparison. A total of three independent experiments were performed with each candidate for a total of nine donors.

Results and Conclusions

CD3/BCMA/CD38-118 demonstrated a statistically significant superior killing of multiple myeloma NCI-H929 cell line in Multiple Modes of Action Killing assay compared to anti-CD38 benchmarks, daratumumab and isatuximab, as shown in FIG. 23A. As depicted on FIG. 23B, the killing induced by CD3/BCMA/CD38-118 ($EC_{50}$ of 6.2±5.8 pM) is significantly higher compared to the killing triggered by daratumumab ($EC_{50}$ of 94.5±19.8 pM) and isatuximab ($EC_{50}$ of 61.1±64.7 pM). No significant difference was observed with other treatments. When calculating the AUC (FIG. 23C), CD3/BCMA/CD38-118 candidate triggered superior killing compared to anti-CD38 benchmarks but also compared to CD3/BCMA/CD38-119 candidate. Finally, CD3/BCMA/CD38-119 candidate triggered a significant superior killing compared to isatuximab.

EXAMPLE 19: EFFICACY OF TREAT CD3/BCMA/CD38-118 AND CD3/BCMA/CD38-119 IN AN IN VIVO NCI-H929 TUMOR MOUSE MODEL IN COMPARISON TO 83A10-TCBCV BENCHMARK ANTIBODY

Materials and Methods

Animal Husbandry

In vivo experiments were performed at Crown Bioscience Inc. (Beijing, China) in 6-7-week-old female NCG (NOD-Prkdc$^{em26cd52}$Il2rg$^{em26cd22}$/NjuCrl) mice from GemPharmatech Co., Ltd. All mice were maintained under standardized environmental conditions and housed in polysulfone IVC cages with autoclaved crushed corncob bedding (20-26° C. temperature, 40-70% relative humidity, 12 hours light/dark cycle). Mice received irradiated food (standard rodent chow) and 0.22 am-filtered drinking water ad libitum. Animal welfare was monitored daily (cage side observations) and weekly clinical observations.

NCI-H929 subcutaneous tumor with systemic PBMC humanized mouse model

Two experiments were conducted at Crown Bioscience Inc. (Beijing, China) Study 1 and Study 2.

Study 1. Dose escalation of TREAT CD3/BCMA/CD38 candidates and 83A10-TCBcv in NCI-H929 tumors.

NCG female mice were engrafted subcutaneously (s.c.) with 1×10$^7$ NCI-H929 MM tumor cells and inoculated intraperitoneally (i.p.) with 1×10$^7$ PBMCs from 2 healthy human donors (Donor A and Donor B) on the same day (9 mice per group; 10 groups; 2 donors; 180 mice total). Mice were randomized based on the tumor volume 10 days after the xenograft and were injected intravenously (i.v.) with Vehicle, 83A10-TCBcv, CD3/BCMA/CD38-118 and CD3/BCMA/CD38-119 molecules at 0.5, 0.1 and 0.02 mg/kg once per week for 3 weeks. Tumor volume was evaluated based on tumor size measurement with a caliper three times per week. Mouse plasma was collected on day 13 or 14 to determine the molecule's trough concentration using a human BCMA-specific antigen capture ELISA (a method to quantify anti-BCMA human IgG, please refer to ELISA assay section of the material and methods). This experiment was done only once.

Study 2. TREAT CD3/BCMA/CD38-118 and CD3/BCMA/CD38-119 efficacy and pharmacodynamic study in NCI-H929 tumors. NCG female mice were engrafted s.c. with 1×10$^7$ NCI-H929 MM tumor cells and inoculated i.p. with 1×10$^7$ PBMCs from 2 healthy human donors (Donor A and Donor B) on the same day (15 mice per group; 5 groups; 2 donors; 150 mice total). Mice were randomized based on the tumor volume 11 days after the xenograft and were injected i.v. with Vehicle, 83A10-TCBcv, CD3/BCMA/CD38-118, CD3/BCMA/CD38-119 and CD3/BCMA/CD38-122 molecules at 0.1 mg/kg once per week for 3 weeks. The molecule's trough concentration was determined in plasma at day 14 using a human BCMA-specific antigen capture ELISA (please refer to ELISA assay section of the material and methods). Ex vivo analysis was performed at day 2 and day 6 following a single dose of molecules (n=2-3 mice/group/timepoint). Mice serum, spleens and tumors were harvested. FACS analysis was performed on spleens and tumors. Human cytokine detection was performed with Luminex assay on serum and tumor supernatant. This experiment was done only once.

ELISA assay

Plasma concentrations of each molecule were determined using a human BCMA-specific antigen capture ELISA. In brief, 96-well ELISA plate is coated with human BCMA-His Tag protein (Acrobiosystems, Ref. BCA-H522γ) at 2 μg/mL overnight and non-specific sites are saturated with blocking buffer the next day. Next the serum samples (containing CD3/BCMA/CD38 candidates or 83A10-TCBcv) are applied and incubated at room temperature (RT) for 2 h. After the unbound antibody is washed away, antibody bound to BCMA is then detected using a horseradish peroxidase (HRP)-conjugated goat anti-human IgG Fc (Abcam, Ref. ab97225), incubated at RT for 1 h. The signal is then generated through the action of HRP enzyme on the TMB (Tetramethylbenzidine) substrate and the absorbance read on a spectrophotometer using 450 nm as the primary wavelength and 570 nm as the reference wavelength. Data were analyzed using Excel and GraphPad Prism 9.

Sample Preparation for Flow Cytometry

Tumors were harvested and dissociated with enzymatic cocktail from human tumor dissociation kit (Miltenyi Biotec, Ref. 130-095-929) in a GentleMACS dissociator. Cell suspensions were then filtered using a 70 μm cell strainer and centrifuged. Tumor supernatant was recovered (for cytokine analysis) and cell pellet was resuspended, cells counted and adjusted to $10\times10^7$ cells/mL in PBS supplemented with 10% FCS and 40 mM EDTA (FACS buffer). Spleens were processed on the GentleMACS dissociator (program m_spleen_04) and resulting cell suspension was filtered through a 70 μM nylon cell strainer. Next, red blood cells were lysed using RBC Lysing Buffer (Beyotime, Ref. C3702), cells were counted and adjusted to $10\times10^7$ cells/mL in FACS buffer. Tumor and spleen suspensions were then stained for immune cell profiling. In brief, cell suspensions were incubated with human Fc Block for 10 min at 4° C. in FACS buffer, followed by surface staining with antibody cocktail (including viability dye) for 30 min at 4° C. in FACS buffer. Samples were acquired on a BD flow cytometer and data were analyzed using FlowJo v10.7.2 and GraphPad Prism 9.

Luminex Assay

Serum and tumor supernatant samples were assessed by Multiplex Luminex quantification according to the manufacturer's instructions (Invitrogen). Briefly, magnetic beads, samples, standards, and blanks were added to the plates and incubated at RT for 2 h. Next, detection antibody was added to the plates and incubated for 1 h at RT, before incubating with streptavidin-PE solution (30 min at RT). The plates were then washed, and the reading buffer was added before acquisition with a Luminex LX200 instrument. Luminex data were analyzed using the Luminex 200™ software to calculate standard curves using regression method of 5P logistic curve fitting by an automated procedure and determine the sample concentrations (in μg/ml) from the standard curve. Then the Luminex xPONENT software was used to output a report, including the concentration of each well and standard curves, which was further analyzed using Excel and GraphPad Prism 9. Cytokine concentration was normalized to the upper (ULOQ) and lower (LLOQ) limit of quantification.

Statistical Analysis

Data were analyzed using GraphPad Prism 9 software. Differences in tumor volume were determined using a two-way analysis of variance (ANOVA) with Tukey's multiple comparison test, n=9 mice per group. P value <0.05 was considered statistically significant, with the level of significancy represented by asterisks as followed: ns p>0.05; * p<0.05; ** p<0.01; *  p<0.001; ** p<0.0001.

Results and Conclusions

The in vivo efficacy of CD3/BCMA/CD38 candidates in comparison to the CD3×BCMA bispecific reference antibody 83A10-TCBcv was evaluated at various dose levels in a subcutaneous NCI-H929 tumor xenograft model in NCG mice in a therapeutic setting. Human myeloma NCI-H929 tumor cells with high expression levels of BCMA ($58\times10^3$ sABC: specific Antibody-Binding Capacity units) and CD38 ($130\times10^3$ sABC) were injected subcutaneously (s.c.) in NCG mice ($1\times10^7$ cells). In parallel, human PBMCs from 2 healthy human donors A and B were injected intraperitoneally (i.p) on the same day ($1\times10^7$ cells). Mice were randomized 10 days after tumor cell injection when the average tumor volume reached 150 mm3 in various treatment groups of PBMCs injected from donor A (n=9) and B (n=9), two donors were used to account for variability in response expected with PBMCs. Therapeutic treatments of CD3/BCMA/CD38 candidates or 83A10-TCBcv were injected intravenously (i.v.) on days 0, 7 and 14 at 0.5, 0.1 or 0.02 mg/kg. Mice in the vehicle control group were injected i.v. with a mixture of PBS and CD3/BCMA/CD38 candidates reconstitution buffer.

Three weeks post treatment start, CD3/BCMA/CD38-118 or -119 induced complete regression of NCI-H929 tumors at the 0.5 mg/kg dose for both PBMC donors, similar to the 83A10-TCBcv bispecific BCMA CD3 antibody (FIG. 24A, left). At a dose level of 0.1 mg/kg, while CD3/BCMA/CD38 candidates and 83A10-TCBcv still induce substantially tumor regression in donor B inoculated mice (in 100% or 77.7% of treated mice, respectively), only a partial control of NCI-H929 tumors could be observed in mice inoculated with donor A (FIG. 24A, middle). At this dose (0.1 mg/kg) in donor A, CD3/BCMA/CD38-118 showed significantly higher efficacy compared to 83A10-TCBcv (FIG. 24A, top middle; Table 27), with tumor regression observed in 5 out of 9 mice in CD3/BCMA/CD38-118 treated mice, compared to 0 out of 9 mice in 83A10-TCBcv treated mice. Treatment of NCG mice with a low dose (0.02 mg/kg) of CD3/BCMA/CD38 candidates or 83A10-TCBcv resulted in weak but statistically significant inhibition of NCI-H929 tumor growth compared to the vehicle control, observed to a larger extent in donor B inoculated mice (FIG. 24A, right; Table 27). The majority of vehicle and low dose treated mice were sacrificed between days 9 and 13 due to high tumor load.

TABLE 27

Statistical analysis of FIG. 24 (A). Differences in tumor volume were determined using a two-way analysis of variance (ANOVA) with Tukey's multiple comparison test, n = 9 mice per group. P value < 0.05 was considered statistically significant, with the level of significancy represented by asterisks as followed: ns p ≥ 0.05; * p < 0.05;  p < 0.01; * p < 0.001; **** p < 0.0001

| | Donor A | | | | Donor B | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| Vehicle vs. 0.5 mg/kg 83A10-TCBcv | 1413 | 1197 to 1629 | **** | <0.0001 | 1458 | 1317 to 1598 | **** | <0.0001 |
| Vehicle vs. 0.1 mg/kg 83A10-TCBcv | 683.1 | 467.4 to 898.9 | **** | <0.0001 | 1384 | 1244 to 1525 | **** | <0.0001 |
| Vehicle vs. 0.02 mg/kg 83A10-TCBcv | 117.5 | −98.31 to 333.3 | ns | 0.7798 | 265.6 | 125.2 to 406.1 | **** | <0.0001 |
| Vehicle vs. 0.5 mg/kg CD3/BCMA/CD38-118 | 1433 | 1217 to 1649 | **** | <0.0001 | 1460 | 1319 to 1600 | **** | <0.0001 |
| Vehicle vs. 0.1 mg/kg CD3/BCMA/CD38-118 | 1187 | 971.2 to 1403 | **** | <0.0001 | 1469 | 1328 to 1609 | **** | <0.0001 |
| Vehicle vs. 0.02 mg/kg CD3/BCMA/CD38-118 | 241.9 | 26.06 to 457.6 | * | 0.0145 | 605.7 | 465.3 to 746.2 | **** | <0.0001 |

TABLE 27-continued

Statistical analysis of FIG. 24 (A). Differences in tumor volume were determined using a two-way analysis of variance (ANOVA) with Tukey's multiple comparison test, n = 9 mice per group. P value < 0.05 was considered statistically significant, with the level of significancy represented by asterisks as followed: ns p ≥ 0.05; * p < 0.05;  p < 0.01; * p < 0.001; **** p < 0.0001

| | Donor A | | | | Donor B | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| Vehicle vs. 0.5 mg/kg CD3/BCMA/CD38-119 | 1434 | 1218 to 1650 | **** | <0.0001 | 1457 | 1317 to 1598 | **** | <0.0001 |
| Vehicle vs. 0.1 mg/kg CD3/BCMA/CD38-119 | 885.4 | 669.6 to 1101 | **** | <0.0001 | 1465 | 1324 to 1605 | **** | <0.0001 |
| Vehicle vs. 0.02 mg/kg CD3/BCMA/CD38-119 | −125.8 | −341.6 to 89.94 | ns | 0.7026 | 825.3 | 684.8 to 965.7 | **** | <0.0001 |
| 0.5 mg/kg 83A10-TCBcv vs. 0.1 mg/kg 83A10-TCBcv | −729.7 | 945.5 to −513.9 | **** | <0.0001 | −73.48 | −213.9 to 66.97 | ns | 0.8176 |
| 0.5 mg/kg 83A10-TCBcv vs. 0.02 mg/kg 83A10-TCBcv | −1295 | 1511 to −1080 | **** | <0.0001 | −1192 | −1333 to −1052 | **** | <0.0001 |
| 0.5 mg/kg 83A10-TCBcv vs. 0.5 mg/kg CD3/BCMA/CD38-118 | 20.16 | 195.6 to 236.0 | ns | >0.9999 | 2.039 | −138.4 to 142.5 | ns | >0.9999 |
| 0.5 mg/kg EM-801 vs. 0.1 mg/kg CD3/BCMA/CD38-118 | −225.8 | −441.6 to −10.02 | * | 0.0318 | 10.98 | −129.5 to 151.4 | ns | >0.9999 |
| 0.5 mg/kg 83A10-TCBcv vs. 0.02 mg/kg CD3/BCMA/CD38-118 | −1171 | −1387 to −955.2 | **** | <0.0001 | −852.1 | −992.6 to −711.7 | **** | <0.0001 |
| 0.5 mg/kg 83A10-TCBcv vs. 0.5 mg/kg CD3/BCMA/CD38-119 | 21.08 | 194.7 to 236.9 | ns | >0.9999 | −0.4046 | 140.9 to 140.1 | ns | >0.9999 |
| 0.5 mg/kg 83A10-TCBcv vs. 0.1 mg/kg CD3/BCMA/CD38-119 | −527.4 | 743.2 to −311.7 | **** | <0.0001 | 6.696 | 133.8 to 147.2 | ns | >0.9999 |
| 0.5 mg/kg 83A10-TCBcv vs. 0.02 mg/kg CD3/BCMA/CD38-119 | −1539 | 1754 to −1323 | **** | <0.0001 | −632.6 | −773.0 to −492.1 | **** | <0.0001 |
| 0.1 mg/kg 83A10-TCBcv vs. 0.02 mg/kg 83A10-TCBcv | −565.7 | 781.5 to −349.9 | **** | <0.0001 | −1119 | −1259 to −978.3 | **** | <0.0001 |
| 0.1 mg/kg 83A10-TCBcv vs. 0.5 mg/kg CD3/BCMA/CD38-118 | 749.8 | 534.0 to 965.6 | **** | <0.0001 | 75.52 | −64.94 to 216.0 | ns | 0.7921 |
| 0.1 mg/kg 83A10-TCBcv vs. 0.1 mg/kg CD3/BCMA/CD38-118 | 503.9 | 288.1 to 719.6 | **** | <0.0001 | 84.46 | 56.00 to 224.9 | ns | 0.6638 |
| 0.1 mg/kg 83A10-TCBcv vs. 0.02 mg/kg CD3/BCMA/CD38-118 | −441.3 | −657.1 to −225.5 | **** | <0.0001 | −778.6 | 919.1 to −638.2 | **** | <0.0001 |
| 0.1 mg/kg 83A10-TCBcv vs. 0.5 mg/kg CD3/BCMA/CD38-119 | 750.7 | 535.0 to 966.5 | **** | <0.0001 | 73.08 | −67.38 to 213.5 | ns | 0.8225 |
| 0.1 mg/kg 83A10-TCBcv vs. 0.1 mg/kg CD3/BCMA/CD38-119 | 202.2 | −13.57 to 418.0 | ns | 0.0882 | 80.18 | 60.28 to 220.6 | ns | 0.7282 |
| 0.1 mg/kg 83A10-TCBcv vs. 0.02 mg/kg CD3/BCMA/CD38-119 | −809 | 1025 to −593.2 | **** | <0.0001 | −559.1 | −699.5 to −418.6 | **** | <0.0001 |
| 0.02 mg/kg 83A10-TCBcv vs. 0.5 mg/kg CD3/BCMA/CD38-118 | 1315 | 1100 to 1531 | **** | <0.0001 | 1194 | 1054 to 1335 | **** | <0.0001 |
| 0.02 mg/kg 83A10-TCBcv vs. 0.1 mg/kg CD3/BCMA/CD38-118 | 1070 | 853.7 to 1285 | **** | <0.0001 | 1203 | 1063 to 1344 | **** | <0.0001 |
| 0.02 mg/kg 83A10-TCBcv vs. 0.02 mg/kg CD3/BCMA/CD38-118 | 124.4 | −91.41 to 340.2 | ns | 0.7168 | 340.1 | 199.6 to 480.5 | **** | <0.0001 |
| 0.02 mg/kg 83A10-TCBcv vs. 0.5 mg/kg CD3/BCMA/CD38-119 | 1316 | 1101 to 1532 | **** | <0.0001 | 1192 | 1051 to 1332 | **** | <0.0001 |
| 0.02 mg/kg 83A10-TCBcv vs. 0.1 mg/kg CD3/BCMA/CD38-119 | 767.9 | 552.1 to 983.7 | **** | <0.0001 | 1199 | 1058 to 1339 | **** | <0.0001 |
| 0.02 mg/kg 83A10-TCBcv vs. 0.02 mg/kg CD3/BCMA/CD38-119 | −243.3 | 459.1 to −27.53 | * | 0.0135 | 559.6 | 419.2 to 700.1 | **** | <0.0001 |

TABLE 27-continued

Statistical analysis of FIG. 24 (A). Differences in tumor volume were determined using a two-way analysis of variance (ANOVA) with Tukey's multiple comparison test, n = 9 mice per group. P value < 0.05 was considered statistically significant, with the level of significancy represented by asterisks as followed: ns p ≥ 0.05; * p < 0.05;  p < 0.01; * p < 0.001; **** p < 0.0001

| | Donor A | | | | Donor B | | | |
|---|---|---|---|---|---|---|---|---|
| Group comparison | Mean Diff. (mm³) | 95.00% CI of diff. (mm³) | Summary | Adjusted P Value | Mean Diff. (mm³) | 95.00% CI of diff. (mm³) | Summary | Adjusted P Value |
| 0.5 mg/kg CD3/BCMA/CD38-118 vs. 0.1 mg/kg CD3/BCMA/CD38-118 | −246 | −461.8 to −30.18 | * | 0.0117 | 8.938 | −131.5 to 149.4 | ns | >0.9999 |
| 0.5 mg/kg CD3/BCMA/CD38-118 vs. 0.02 mg/kg CD3/BCMA/CD38-118 | −1191 | −1407 to −975.3 | **** | <0.0001 | −854.2 | −994.6 to −713.7 | **** | <0.0001 |
| 0.5 mg/kg CD3/BCMA/CD38-118 vs. 0.5 mg/kg CD3/BCMA/CD38-119 | 0.9164 | −214.9 to 216.7 | ns | >0.9999 | −2.443 | −142.9 to 138.0 | ns | >0.9999 |
| 0.5 mg/kg CD3/BCMA/CD38-118 vs. 0.1 mg/kg CD3/BCMA/CD38-119 | −547.6 | −763.4 to −331.8 | **** | <0.0001 | 4.657 | −135.8 to 145.1 | ns | >0.9999 |
| 0.5 mg/kg CD3/BCMA/CD38-118 vs. 0.02 mg/kg CD3/BCMA/CD38-119 | −1559 | −1775 to −1343 | **** | <0.0001 | -634.6 | −775.1 to −494.2 | **** | <0.0001 |
| 0.1 mg/kg CD3/BCMA/CD38-118 vs. 0.02 mg/kg CD3/BCMA/CD38-118 | −945.1 | −1161 to −729.4 | **** | <0.0001 | −863.1 | −1004 to −722.6 | **** | <0.0001 |
| 0.1 mg/kg CD3/BCMA/CD38-118 vs. 0.5 mg/kg CD3/BCMA/CD38-119 | 246.9 | 31.10 to 462.7 | * | 0.0112 | −11.38 | −151.8 to 129.1 | ns | >0.9999 |
| 0.1 mg/kg CD3/BCMA/CD38-118 vs. 0.1 mg/kg CD3/BCMA/CD38-119 | −301.6 | −517.4 to −85.84 | *** | 0.0004 | −4.281 | −144.7 to 136.2 | ns | >0.9999 |
| 0.1 mg/kg CD3/BCMA/CD38-118 vs. 0.02 mg/kg CD3/BCMA/CD38-119 | −1313 | −1529 to −1097 | **** | <0.0001 | −643.6 | −784.0 to −503.1 | **** | <0.0001 |
| 0.02 mg/kg CD3/BCMA/CD38-118 vs. 0.5 mg/kg CD3/BCMA/CD38-119 | 1192 | 976.2 to 1408 | **** | <0.0001 | 851.7 | 711.3 to 992.2 | **** | <0.0001 |
| 0.02 mg/kg CD3/BCMA/CD38-118 vs. 0.1 mg/kg CD3/BCMA/CD38-119 | 643.5 | 427.7 to 859.3 | **** | <0.0001 | 858.8 | 718.4 to 999.3 | **** | <0.0001 |
| 0.02 mg/kg CD3/BCMA/CD38-118 vs. 0.02 mg/kg CD3/BCMA/CD38-119 | −367.7 | −583.5 to −151.9 | **** | <0.0001 | 219.5 | 79.09 to 360.0 | **** | <0.0001 |
| 0.5 mg/kg CD3/BCMA/CD38-119 vs. 0.1 mg/kg CD3/BCMA/CD38-119 | −548.5 | −764.3 to −332.7 | **** | <0.0001 | 7.1 | −133.4 to 147.6 | ns | >0.9999 |
| 0.5 mg/kg CD3/BCMA/CD38-119 vs. 0.02 mg/kg CD3/BCMA/CD38-119 | −1560 | −1776 to −1344 | **** | <0.0001 | −632.2 | −772.6 to −491.7 | **** | <0.0001 |
| 0.1 mg/kg CD3/BCMA/CD38-119 vs. 0.02 mg/kg CD3/BCMA/CD38-119 | −1011 | −1227 to −795.4 | **** | <0.0001 | −639.3 | −779.7 to −498.8 | **** | <0.0001 |

Plasma concentrations of CD3/BCMA/CD38 candidates or 83A10-TCBcv were determined on day 13 or 14 prior to 3rd dose using an ELISA method developed to quantify anti-BCMA human IgG. Plasma levels at 0.5 mg/kg dosing of CD3/BCMA/CD38 candidates were determined at around 3500 ng/ml, with 83A10-TCBcv showing similar levels with a concentration of around 2900 ng/ml (FIG. 24B). Dose to exposure of CD3/BCMA/CD38 candidates was relatively linear between 0.5 and 0.1 mg/kg dosing with 4 to 6-fold reduced plasma concentrations at 0.1 mg/kg (FIG. 24B). Lower tumor inhibition observed in mice inoculated with donor A PBMCs was not due to lower plasma antibody concentrations at this dose (0.1 mg/kg), given that trough concentrations were roughly similar between both PBMC donor inoculated mice (FIG. 24B). Dosing at 0.02 mg/kg resulted in poor PK exposure of CD3/BCMA/CD38 candidates compared to higher doses with low plasma concentrations, indicating that target mediated drug disposition may be relevant at lower doses.

In summary, these data show that CD3/BCMA/CD38 candidates controlled NCI-H929 tumor growth in a dose dependent manner when used as a therapeutic treatment in a human myeloma xenograft model in NCG mice. At dose levels of 0.1 mg/kg, CD3/BCMA/CD38-118 and -119 induced regression of established NCI-H929 tumors in 77% and 66% of mice in a therapeutic setting, respectively (pool of donor A and B data). In comparison, treatment with 83A10-TCBcv at 0.1 mg/kg showed significantly lower efficacy in the control of NCI-H929 tumors, with regression observed in only 39% of tumors (pool of donor A and B data).

The in vivo efficacy of CD3/BCMA/CD38 candidates at 0.1 mg/kg was re-evaluated in a separate experiment in which a CD3 dummy control (CD3/BCMA/CD38-122—lacking the CD38 and BCMA binding arms) was included (FIGS. 25A-25B). Human myeloma NCI-H929 tumor cells were injected subcutaneously (s.c.) in NCG mice ($1\times10^7$ cells) and inoculated intraperitoneally (i.p) with human PBMCs from 2 healthy human donors A and B on the same day ($1\times10^7$ cells). Mice were randomized 11 days after tumor cell injection when the average tumor volume reached 180 $mm^3$ in various treatment groups of PBMCs injected from donor A (n=9) and B (n=9). Therapeutic treatments of CD3/BCMA/CD38 candidates or 83A10-TCBcv were injected intravenously (i.v.) on days 0, 7 and 14 at 0.1 mg/kg. Mice in the vehicle control group were injected i.v. with a mixture of PBS and CD3/BCMA/CD38 candidates reconstitution buffer.

While a faster tumor growth kinetics (compared to the previous study) led to an overall lower efficacy, partial NCI-H929 tumor control was still observed upon treatment with CD3/BCMA/CD38 candidates or 83A10-TCBcv at 0.1 mg/kg (FIG. 25A). Three weeks post treatment start, both CD3/BCMA/CD38-118 and -119 substantially delayed the progression of NCI-H929 tumors, to a larger extent in mice that received donor B PBMCs (FIG. 25A, right). Treatment with 83A10-TCBcv showed significantly lower NCI-H929 tumor control compared to CD3/BCMA/CD38-118 in both PBMC donor inoculated mice (FIG. 25A, Table 28). Finally, administration of CD3/BCMA/CD38-122 at 0.1 mg/kg showed no control of NCI-H929 tumor progression (similar to vehicle treated mice) in both PBMC donors (FIG. 25A). The latter demonstrates that the target antigen binding arms are crucial for the tumor killing efficacy of CD3/BCMA/CD38 candidates.

and spleens were harvested at day 2 and day 6 following a single dose of molecules at 0.1 mg/kg and FACS analysis was performed (n=2-3 mice/group/timepoint). At either day 2 or day 6 post dosing, treatment with CD3/BCMA/CD38-118, CD3/BCMA/CD38-119 or 83A10-TCBcv resulted in a selective infiltration of human $TCR\alpha\beta^+$ cells (surrogate marker for CD3 T cells) in the tumor microenvironment compared to control treated groups (FIG. 26A). The extent of $TCR\alpha\beta^+$ cell infiltration varied between PBMC donors, with mice inoculated with donor B, which showed the highest tumor growth inhibition, also showing highest degree of T cell infiltration in the tumor (FIG. 3A, bottom). Treatment with CD3/BCMA/CD38-122 did not induce increased presence of $TCR\alpha\beta^+$ cells in the tumor, demonstrating that binding to CD3 only is not sufficient to increase tumor infiltration of T cells. At day 6 post single dose, numbers of infiltrating T cells per gram of tumor were 35 to 50-fold higher in mice treated with CD3/BCMA/CD38 candidates or 83A10-TCBcv, compared to control treated groups in mice inoculated with donor B (FIG. 26B). This data showed that T cell engager efficacy (CD3/BCMA/CD38 candidates or 83A10-TCBcv) correlates with the degree of T cell infiltration within the tumor microenvironment.

Compared to CD3/BCMA/CD38-122 treated mice, tumor infiltrating CD8*T cells showed higher expression of human CD69 and human CD25 (T cell activation markers) in mice treated with CD3/BCMA/CD38 candidates or 83A10-

TABLE 28

Statistical analysis of FIG. 25 (A). Differences in tumor volume were determined using a two-way analysis of variance (ANOVA) with Tukey's multiple comparison test, n = 9 mice per group. P value < 0.05 was considered statistically significant, with the level of significancy represented by asterisks as followed: ns $p \geq 0.05$; * $p < 0.05$;  $p < 0.01$; * $p < 0.001$; **** $p < 0.0001$.

| | Donor A | | | | Donor B | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| Vehicle vs. 83A10-TCBcv | 213.8 | 57.77 to 369.8 | ** | 0.0019 | 665.5 | 510.3 to 820.8 | **** | <0.0001 |
| Vehicle vs. CD3/BCMA/CD38-118 | 489.2 | 333.1 to 645.2 | **** | <0.0001 | 942.6 | 787.4 to 1098 | **** | <0.0001 |
| Vehicle vs. CD3/BCMA/CD38-119 | 270.6 | 114.5 to 426.6 | **** | <0.0001 | 872.1 | 716.9 to 1027 | **** | <0.0001 |
| Vehicle vs. CD3/BCMA/CD38-122 | 8.525 | −147.5 to 164.6 | ns | 0.9999 | 37.46 | −117.8 to 192.7 | ns | 0.9645 |
| 83A10-TCBcv vs. CD3/BCMA/CD38-118 | 275.4 | 119.3 to 431.4 | **** | <0.0001 | 277 | 121.8 to 432.3 | **** | <0.0001 |
| 83A10-TCBcv vs. CD3/BCMA/CD38-119 | 56.78 | −99.26 to 212.8 | ns | 0.8566 | 206.6 | 51.37 to 361.8 | ** | 0.0028 |
| 83A10-TCBcv vs. CD3/BCMA/CD38-122 | −205.3 | −361.3 to −49.24 | ** | 0.0032 | −628.1 | −783.3 to −472.9 | **** | <0.0001 |
| CD3/BCMA/CD38-118 vs. CD3/BCMA/CD38-119 | −218.6 | −374.6 to −62.54 | ** | 0.0013 | −70.45 | −225.7 to 84.78 | ns | 0.7257 |
| CD3/BCMA/CD38-118 vs. CD3/BCMA/CD38-122 | −480.7 | −636.7 to −324.6 | **** | <0.0001 | −905.1 | −1060 to −749.9 | **** | <0.0001 |
| CD3/BCMA/CD38-119 vs. CD3/BCMA/CD38_122 | −262.1 | −418.1 to −106.0 | **** | <0.0001 | −834.7 | −989.9 to −679.4 | **** | <0.0001 |

Plasma concentrations of CD3/BCMA/CD38 candidates were 1.7 to 1.9-fold higher than plasma levels of 83A10-TCBcv at trough exposure (day 14 prior to $3^{rd}$ dose) (FIG. 25B). Thus, superior efficacy of CD3/BCMA/CD38 candidates correlated with slightly better trough plasma concentrations compared to the benchmark 83A10-TCBcv.

To understand the mechanistic action of CD3/BCMA/CD38 candidates, immune cell profiling (ICP) was performed early post treatment (FIGS. 26A-26B). Mice tumors TCBcv at day 2 post single dose (FIG. 26C and FIG. 26D, top). However, $CD8^+$ T cells found in the periphery (spleen) had no expression of the activation markers CD69 and CD25 (FIG. 26D, bottom), thus no evidence for on-target non-tumor specific activation was observed.

Finally, the immune cell profiling FACS data was corroborated with cytokine analysis in the tumor supernatant using Luminex assay (FIG. 27). Consistent with intratumor T cell activation, human IFN-$\gamma$ and TNF-$\alpha$ were specifically induced in the tumor by T cell engagers early post first dose (day 2), to a larger extent in donor B inoculated mice (FIG. 27, top). Additional inflammatory cytokines, such as human IL-IRA and IL-10, were also specifically detected in the tumor microenvironment upon treatment with CD3/BCMA/CD38 candidates or 83A10-TCBcv (FIG. 27, bottom).

In conclusion, the degree of efficacy of CD3/BCMA/CD38 candidates (0.1 mg/kg) in NCI-H929 tumor control correlated with the degree of T cell infiltration within the tumor microenvironment. No evidence for systemic T cell activation could be observed 2 days following first dose, suggesting that on target binding to BCMA/CD38 expressing cells is required to activate T cells in vivo. These in vivo data demonstrate that CD3/BCMA/CD38 candidates possess a potent cytotoxic potential against CD38 and BCMA high expressing tumor cells.

EXAMPLE 20: EFFICACY OF TREAT CD3/BCMA/CD38-118 AND CD3/BCMA/CD38-119 IN AN IN VIVO BCMA$^{LOW}$ CD38$^{LOW}$ KMS-12-BM TUMOR MOUSE MODEL

Material and Methods

Animal Husbandry

In vivo experiments were performed in female 6-8-week-old immune-deficient NSG (NOD·Cg-Prkdcsc$^{scid}$ Il2rg$^{tm1\,Wjl}$/SzJ) mice from CHARLES RIVER LABORATORIES France. All mice were maintained under standardized environmental conditions in rodent cages (20±1° C. room temperature, 50±10% relative humidity, 12 hours light dark cycle). Mice received irradiated food and bedding and 0.22 am-filtered drinking water. Animal experiments were conducted in accordance with protocols approved by the veterinary authorities of the Canton de Vaud, Switzerland.

KSM-12-BM Subcutaneous Tumor with Systemic PBMC Humanized Mouse Model

Two experiments were conducted and were named respectively KMS_10 and KMS_11 studies.

KMS_10 study. Dose escalation of TREAT CD3/BCMA/CD38 candidates in KMS-12-BM tumors. NSG female mice were engrafted subcutaneously (s.c.) with $1\times10^7$ KMS-12-BM MM tumor cells and inoculated intraperitoneally (i.p.) with $1\times10^7$ PBMCs from 2 healthy human donors (Donor C and Donor D) on the same day (8 mice per group; 10 groups; 2 donors; 160 mice total). Mice were randomized based on the tumor volume 8 days after the xenograft and were injected intravenously (i.v.) on the following day with Vehicle, 83A10-TCBcv, CD3/BCMA/CD38-118 and CD3/BCMA/CD38-119 molecules at 0.5, 0.1 and 0.02 mg/kg once per week for 3 weeks. Tumor volume was evaluated based on tumor size measurement with a caliper three times per week. Mouse serum was collected on day 23 or 30 to determine the molecule's trough concentration using a human BCMA-specific antigen capture ELISA (a method to quantify anti-BCMA human IgG, please refer to ELISA assay section of the material and methods). If mice reached a tumor volume of 1000 mm$^3$ before study termination, collection of corresponding samples was done either prior 3$^{rd}$ dose (day 23) or one week later (day 30). This experiment was done only once.

KMS_11 study. TREAT CD3/BCMA/CD38-118 and CD3/BCMA/CD38-119 efficacy and pharmacodynamic study in KMS-12-BM tumors. NSG female mice were engrafted s.c. with $1\times10^7$ KMS-12-BM MM tumor cells and inoculated i.p. with $1\times10^7$ PBMCs from 2 healthy human donors (Donor C and Donor D) on the same day (14 mice per group; 5 groups; 2 donors; 140 mice total). Mice were randomized based on the tumor volume 8 days after the xenograft and were injected i.v. on the following day with Vehicle, 83A10-TCBcv, CD3/BCMA/CD38-118, CD3/BCMA/CD38-119 and CD3/BCMA/CD38-122 molecules at 0.5 mg/kg once per week for 3 weeks. Ex vivo analysis was performed at day 2 and day 6 following a single dose of molecules (n=2-3 mice/group/timepoint). Mice serum, spleens and tumors were harvested. The molecule's trough concentration was determined in serum at day 6 using a human BCMA-specific antigen capture ELISA (please refer to ELISA assay section of the material and methods). FACS analysis was performed on spleens and tumors. Human cytokine detection was performed with Luminex assay on serum and tumor supernatant. This experiment was done only once.

ELISA Assay

Serum concentrations of each molecule were determined using a human BCMA-specific antigen capture ELISA. In brief, 96-well ELISA plate is coated with BCMA-His Tag protein (produced in house: P1658-hsBCMA-ECD(A1-M54)-Avi-His) at 2 μg/mL overnight and non-specific sites are saturated with blocking buffer the next day. Next the serum samples (containing CD3/BCMA/CD38 candidates or 83A10-TCBcv) are applied and incubated at room temperature (RT) for 2 h. After the unbound antibody is washed away, antibody bound to BCMA is then detected using a horseradish peroxidase (HRP)-conjugated anti-human IgG Fc F(ab')2 fragment (Jackson ImmunoResearch, Ref. 109-035-170), incubated at RT for 1 h. Wells are washed between all steps with Phosphate Buffered Saline (PBS) supplemented with 0.05% TWEEN® 20 and the signal is generated through the action of HRP enzyme on the TMB (Tetramethylbenzidine) substrate. The reaction is then stopped by the addition of 2N $H_2SO_4$ solution and the absorbance read on a spectrophotometer using 450 nm as the primary wavelength and 570 nm as the reference wavelength. Data were analyzed using Excel and GraphPad Prism 9.

Sample Preparation for Flow Cytometry

Tumors were harvested and dissociated with enzymatic cocktail from human tumor dissociation kit (Miltenyi Biotec, Ref. 130-095-929) in a GentleMACS dissociator. Cell suspensions were then filtered using a 70 μm cell strainer and centrifuged. Tumor supernatant was recovered (for cytokine analysis) and cell pellet was resuspended, cells counted and adjusted to $10\times10^6$ cells/mL in PBS supplemented with 2% FCS (FACS buffer). Cell suspensions from spleen were obtained by mashing through a 70 μM nylon cell strainer, cells were counted and resuspended in FACS buffer. Tumor and spleen suspensions were then stained for immune cell profiling. In brief, cell suspensions were incubated with viability dye, human, and mouse Fc Block for 15 min at 4° C. in FACS buffer, followed by surface staining with antibody cocktail (or relative controls) for 30 min at 4° C. in FACS buffer. Samples were acquired on the Northern lights instrument (CYTEK) and data were analyzed using FlowJo v10.7.2 and GraphPad Prism 9.

Luminex Assay

Serum and tumor supernatant samples were assessed by Multiplex Luminex quantification according to the manufacturer's instructions. Briefly, magnetic beads, samples, standards, and blanks were added to the plates and incubated overnight. The next day, detection antibody was added to the plates and incubated for 30 min at room temperature, before incubating with streptavidin-PE solution (30 min at RT). The plates were then washed, and the reading buffer was added before acquisition with a Luminex LX200 instrument. Luminex data were analyzed using ProcartaPlex Analyst 1.0 software. Cytokine concentration was normalized to the upper (ULOQ) and lower (LLOQ) limit of quantification. Data were analyzed using Excel and GraphPad Prism 9.

Statistical Analysis

Data were analyzed using GraphPad Prism 9 software. Differences in tumor volume were determined using a two-way analysis of variance (ANOVA) with Tukey's multiple comparison test, n=8 mice per group. P value <0.05 was considered statistically significant, with the level of significancy represented by asterisks as followed: ns p>0.05; * p<0.05; ** p<0.01; *  p<0.001; ** p<0.0001.

Results and Conclusions

The in vivo efficacy of CD3/BCMA/CD38 candidates in comparison to the CD3×BCMA bispecific reference antibody 83A10-TCBcv was evaluated at various dose levels in a subcutaneous KMS-12-BM tumor xenograft model in NSG mice in a therapeutic setting. Human myeloma KMS-12-BM tumor cells with low/moderate expression levels of BCMA ($9\times10^3$ sABC: specific Antibody-Binding Capacity units) and CD38 ($27\times10^3$ sABC) were injected subcutaneously (s.c.) in NSG mice ($1\times10^7$ cells). In parallel, human PBMCs from 2 healthy human donors C and D were injected intraperitoneally (i.p) on the same day ($1\times10^7$ cells). Mice were randomized 8 days after tumor cell injection when the average tumor volume reached 150 mm3 in various treatment groups of PBMCs injected from donor C (n=8) and D (n=8). Therapeutic treatments of CD3/BCMA/CD38 candidates or 83A10-TCBcv were injected intravenously (i.v.) on days 9, 16 and 23 at 0.5, 0.1 and 0.02 mg/kg. Mice in the vehicle control group were injected i.v. with a mixture of PBS and CD3/BCMA/CD38 candidates reconstitution buffer.

Three weeks post treatment start, CD3/BCMA/CD38-118 or -119 induced complete regression of KMS-12-BM tumors inoculated with donor C PBMCs in 100% of the treated mice at the 0.5 mg/kg dose, similar to the 83A10-TCBcv bispecific BCMA CD3 antibody, which lead to the regression of 87.5% of tumors (FIG. 28A, top left). At a dose level of 0.1 mg/kg, both CD3/BCMA/CD38 candidates showed significantly higher efficacy compared to 83A10-TCBcv (FIG. 28A, top middle; Table 29). Treatment of NSG mice with a low dose of 0.02 mg/kg CD3/BCMA/CD38 candidates or 83A10-TCBcv resulted in weak but statistically significant inhibition of KMS-12-BM tumor growth compared to the vehicle control (FIG. 28A, top right; Table 29).

Following inoculation of donor D PBMCs, top doses of CD3/BCMA/CD38 candidates controlled tumor progression similarly to 83A10-TCBcv. CD3/BCMA/CD38 candidates lead to partial control of KMS-12-BM tumors with tumor regression seen in 50% of treated mice at the 0.5 mg/kg (FIG. 28A, bottom left). Treatment with CD3/BCMA/CD38 candidates or 83A10-TCBcv at either 0.1 or 0.02 mg/kg did not significantly inhibit the growth of KMS-12-BM tumors in mice inoculated with PBMCs from donor D (FIG. 28A, bottom middle and right; Table 29).

TABLE 29

Statistical analysis of FIG. 28 (A). Differences in tumor volume were determined using a two-way analysis of variance (ANOVA) with Tukey's multiple comparison test, n = 8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| | Donor C | | | | Donor D | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| Vehicle vs. 0.5 mg/kg 83A10-TCBcv | 464.1 | 363.4 to 564.8 | **** | <0.0001 | 221.7 | 92.71 to 350.7 | **** | <0.0001 |
| Vehicle vs. 0.1 mg/kg 83A10-TCBcv | 326.8 | 222.9 to 430.8 | **** | <0.0001 | 76.32 | −52.70 to 205.3 | ns | 0.6853 |
| Vehicle vs. 0.02 mg/kg 83A10-TCBcv | 198.8 | 98.11 to 299.4 | **** | <0.0001 | −4.482 | 133.5 to 124.5 | ns | >0.9999 |
| Vehicle vs. 0.5 mg/kg CD3/BCMA/CD38-118 | 534.2 | 433.6 to 634.9 | **** | <0.0001 | 262.6 | 133.6 to 391.6 | **** | <0.0001 |
| Vehicle vs. 0.1 mg/kg CD3/BCMA/CD38-118 | 500.6 | 400.0 to 601.3 | **** | <0.0001 | 104.8 | −24.19 to 233.8 | ns | 0.2301 |
| Vehicle vs. 0.02 mg/kg CD3/BCMA/CD38-118 | 241 | 140.3 to 341.6 | **** | <0.0001 | −22.91 | −151.9 to 106.1 | ns | >0.9999 |
| Vehicle vs. 0.5 mg/kg CD3/BCMA/CD38-119 | 549.8 | 449.2 to 650.5 | **** | <0.0001 | 231.1 | 102.1 to 360.1 | **** | <0.0001 |
| Vehicle vs. 0.1 mg/kg CD3/BCMA/CD38-119 | 482.1 | 381.5 to 582.8 | **** | <0.0001 | 77.43 | −51.59 to 206.4 | ns | 0.6668 |
| Vehicle vs. 0.02 mg/kg CD3/BCMA/CD38-119 | 158.9 | 58.24 to 259.6 | **** | <0.0001 | 23.98 | −153.0 to 105.0 | ns | 0.9999 |
| 0.5 mg/kg 83A10-TCBcv vs. 0.1 mg/kg EM-801 | −137.3 | −237.9 to −36.61 | *** | 0.0007 | −145.4 | −270.0 to −20.76 | ** | 0.0086 |
| 0.5 mg/kg 83A10-TCBcv vs. 0.02 mg/kg EM-801 | −265.3 | −362.6 to −168.1 | **** | <0.0001 | −226.2 | 350.8 to −101.6 | **** | <0.0001 |
| 0.5 mg/kg 83A10-TCBcv vs. 0.5 mg/kg CD3/BCMA/CD38-118 | 70.14 | −27.10 to 167.4 | ns | 0.3979 | 40.89 | 83.75 to 165.5 | ns | 0.9897 |
| 0.5 mg/kg 83A10-TCBcv vs. 0.1 mg/kg CD3/BCMA/CD38-118 | 36.53 | 60.72 to 133.8 | ns | 0.9736 | −116.9 | −241.5 to 7.745 | ns | 0.0877 |
| 0.5 mg/kg 83A10-TCBcv vs. 0.02 mg/kg CD3/BCMA/CD38-118 | −223.1 | −320.4 to −125.9 | **** | <0.0001 | −244.6 | −369.3 to −120.0 | **** | <0.0001 |
| 0.5 mg/kg 83A10-TCBcv vs. 0.5 mg/kg CD3/BCMA/CD38-119 | 85.73 | 11.52 to 183.0 | ns | 0.1392 | 9.382 | −115.3 to 134.0 | ns | >0.9999 |
| 0.5 mg/kg 83A10-TCBcv vs. 0.1 mg/kg CD3/BCMA/CD38-119 | 18.03 | 79.21 to 115.3 | ns | 0.9999 | −144.3 | −268.9 to −19.65 | ** | 0.0096 |

TABLE 29-continued

Statistical analysis of FIG. 28 (A). Differences in tumor volume were determined using a two-way analysis of variance (ANOVA) with Tukey's multiple comparison test, n = 8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| | Donor C | | | | Donor D | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| 0.5 mg/kg 83A10-TCBcv vs. 0.02 mg/kg CD3/BCMA/CD38-119 | −305.2 | −402.4 to −208.0 | **** | <0.0001 | −245.7 | −370.3 to −121.1 | **** | <0.0001 |
| 0.1 mg/kg 83A10-TCBcv vs. 0.02 mg/kg EM-801 | −128.1 | −228.7 to −27.42 | ** | 0.0024 | −80.8 | −205.4 to 43.84 | ns | 0.5593 |
| 0.1 mg/kg 83A10-TCBcv vs. 0.5 mg/kg CD3/BCMA/CD38-118 | 207.4 | 106.7 to 308.1 | **** | <0.0001 | 186.3 | 61.65 to 310.9 | *** | 0.0001 |
| 0.1 mg/kg 83A10-TCBcv vs. 0.1 mg/kg CD3/BCMA/CD38-118 | 173.8 | 73.13 to 274.4 | **** | <0.0001 | 28.51 | 96.14 to 153.1 | ns | 0.9994 |
| 0.1 mg/kg 83A10-TCBcv vs. 0.02 mg/kg CD3/BCMA/CD38-118 | −85.88 | −186.5 to 14.77 | ns | 0.1726 | −99.23 | −223.9 to 25.41 | ns | 0.2564 |
| 0.1 mg/kg 83A10-TCBcv vs. 0.5 mg/kg CD3/BCMA/CD38-119 | 223 | 122.3 to 323.6 | **** | <0.0001 | 154.8 | 30.14 to 279.4 | ** | 0.0035 |
| 0.1 mg/kg 83A10-TCBcv vs. 0.1 mg/kg CD3/BCMA/CD38-119 | 155.3 | 54.64 to 255.9 | **** | <0.0001 | 1.107 | −123.5 to 125.7 | ns | >0.9999 |
| 0.1 mg/kg 83A10-TCBcv vs. 0.02 mg/kg CD3/BCMA/CD38-119 | −167.9 | −268.6 to −67.29 | **** | <0.0001 | −100.3 | −224.9 to 24.34 | ns | 0.2424 |
| 0.02 mg/kg 83A10-TCBcv vs. 0.5 mg/kg CD3/BCMA/CD38-118 | 335.5 | 238.2 to 432.7 | **** | <0.0001 | 267.1 | 142.5 to 391.7 | **** | <0.0001 |
| 0.02 mg/kg 83A10-TCBcv vs. 0.1 mg/kg CD3/BCMA/CD38-118 | 301.9 | 204.6 to 399.1 | **** | <0.0001 | 109.3 | −15.33 to 233.9 | ns | 0.1443 |
| 0.02 mg/kg 83A10-TCBcv vs. 0.02 mg/kg CD3/BCMA/CD38-118 | 42.19 | −55.05 to 139.4 | ns | 0.9343 | −18.43 | 143.1 to 106.2 | ns | >0.9999 |
| 0.02 mg/kg 83A10-TCBcv vs. 0.5 mg/kg CD3/BCMA/CD38-119 | 351.1 | 253.8 to 448.3 | **** | <0.0001 | 235.6 | 110.9 to 360.2 | **** | <0.0001 |
| 0.02 mg/kg 83A10-TCBcv vs. 0.1 mg/kg CD3/BCMA/CD38-119 | 283.4 | 186.1 to 380.6 | **** | <0.0001 | 81.91 | −42.73 to 206.5 | ns | 0.5391 |
| 0.02 mg/kg 83A10-TCBcv vs. 0.02 mg/kg CD3/BCMA/CD38-119 | −39.87 | 137.1 to 57.37 | ns | 0.9536 | −19.5 | −144.1 to 105.1 | ns | >0.9999 |
| 0.5 mg/kg CD3/BCMA/CD38-118 vs. 0.1 mg/kg CD3/BCMA/CD38-118 | −33.62 | −130.9 to 63.63 | ns | 0.985 | −157.8 | −282.4 to −33.15 | ** | 0.0026 |
| 0.5 mg/kg CD3/BCMA/CD38-118 vs. 0.02 mg/kg CD3/BCMA/CD38-118 | −293.3 | −390.5 to −196.0 | **** | <0.0001 | 285.5 | −410.2 to −160.9 | **** | <0.0001 |
| 0.5 mg/kg CD3/BCMA/CD38-118 vs. 0.5 mg/kg CD3/BCMA/CD38-119 | 15.58 | −81.66 to 112.8 | ns | >0.9999 | −31.51 | −156.2 to 93.13 | ns | 0.9986 |
| 0.5 mg/kg CD3/BCMA/CD38-118 vs. 0.1 mg/kg CD3/BCMA/CD38-119 | −52.11 | 149.4 to 45.13 | ns | 0.7957 | −185.2 | −309.8 to −60.55 | *** | 0.0001 |
| 0.5 mg/kg CD3/BCMA/CD38-118 vs. 0.02 mg/kg CD3/BCMA/CD38-119 | −375.3 | 472.6 to −278.1 | **** | <0.0001 | −286.6 | −411.2 to −162.0 | **** | <0.0001 |
| 0.1 mg/kg CD3/BCMA/CD38-118 vs. 0.02 mg/kg CD3/BCMA/CD38-118 | −259.7 | −356.9 to −162.4 | **** | <0.0001 | −127.7 | −252.4 to −3.092 | * | 0.0394 |
| 0.1 mg/kg CD3/BCMA/CD38-118 vs. 0.5 mg/kg CD3/BCMA/CD38-119 | 49.2 | −48.04 to 146.4 | ns | 0.8459 | 126.3 | 1.637 to 250.9 | * | 0.0441 |
| 0.1 mg/kg CD3/BCMA/CD38-118 vs. 0.1 mg/kg CD3/BCMA/CD38-119 | −18.49 | −115.7 to 78.75 | ns | 0.9999 | −27.4 | −152.0 to 97.24 | ns | 0.9995 |
| 0.1 mg/kg CD3/BCMA/CD38-118 vs. 0.02 mg/kg CD3/BCMA/CD38-119 | −341.7 | 439.0 to −244.5 | **** | <0.0001 | −128.8 | −253.4 to −4.163 | * | 0.0362 |
| 0.02 mg/kg CD3/BCMA/CD38-118 vs. 0.5 mg/kg CD3/BCMA/CD38-119 | 308.9 | 211.6 to 406.1 | **** | <0.0001 | 254 | 129.4 to 378.7 | **** | <0.0001 |
| 0.02 mg/kg CD3/BCMA/CD38-118 vs. 0.1 mg/kg CD3/BCMA/CD38-119 | 241.2 | 143.9 to 338.4 | **** | <0.0001 | 100.3 | −24.31 to 225.0 | ns | 0.2419 |
| 0.02 mg/kg CD3/BCMA/CD38-118 vs. 0.02 mg/kg CD3/BCMA/CD38-119 | −82.06 | −179.3 to 15.18 | ns | 0.1848 | −1.071 | −125.7 to 123.6 | ns | >0.9999 |
| 0.5 mg/kg CD3/BCMA/CD38-119 vs. 0.1 mg/kg CD3/BCMA/CD38-119 | 67.69 | −164.9 to 29.55 | ns | 0.4519 | −153.7 | −278.3 to −29.04 | ** | 0.0039 |
| 0.5 mg/kg CD3/BCMA/CD38-119 vs. 0.02 mg/kg CD3/BCMA/CD38-119 | −390.9 | −488.2 to −293.7 | **** | <0.0001 | −255.1 | −379.7 to −130.4 | **** | <0.0001 |

TABLE 29-continued

Statistical analysis of FIG. 28 (A). Differences in tumor volume were determined using a two-way analysis of variance (ANOVA) with Tukey's multiple comparison test, n = 8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| | Donor C | | | | Donor D | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| 0.1 mg/kg CD3/BCMA/CD38-119 vs. 0.02 mg/kg CD3/BCMA/CD38-119 | 323.2 | −420.5 to −226.0 | **** | <0.0001 | 101.4 | −226.0 to 23.24 | ns | 0.2284 |

Lower tumor inhibition observed in mice inoculated with donor D PBMCs was not due to lower serum antibody concentrations, given that trough concentrations were 1.2 to 1.9-fold higher compared to donor C inoculated mice (FIG. 28B). Serum levels at 0.5 mg/kg dosing of CD3/BCMA/CD38 candidates were determined on day 23 or 30 at around 3000 ng/ml (FIG. 28B), similarly to 83A10-TCBcv levels. Dose to exposure of CD3/BCMA/CD38 candidates molecule was not linear between 0.5 and 0.1 mg/kg dosing with 9 to 20-fold reduced serum concentrations at 0.1 mg/kg one week after the $2^{nd}$ or $3^{rd}$ dose (FIG. 28B). Dosing at 0.02 mg/kg resulted in poor PK exposure of CD3/BCMA/CD38 candidates compared to the 0.5 mg/kg dose with low serum concentrations of around 30 ng/ml.

In summary, these data show that CD3/BCMA/CD38 candidates controlled KMS-12-BM tumor growth in a dose dependent manner with superior killing potency to benchmark 83A10-TCBcv (a published CD3×BCMA engager, ref: Seckinger et al.) when used as a therapeutic treatment in a human myeloma xenograft model in NSG mice. At dose levels of 0.5 mg/kg, CD3/BCMA/CD38 candidates induced complete regression of established KMS-12-BM tumors in 62.5% of mice in a therapeutic setting (pool of donor C and D data).

The in vivo efficacy of CD3/BCMA/CD38 candidates at 0.5 mg/kg was re-evaluated in a separate experiment in which a CD3 dummy control (CD3/BCMA/CD38-122—lacking the CD38 and BCMA binding arms) was included (FIGS. 29A-29B). Human myeloma KMS-12-BM tumor cells were injected subcutaneously (s.c.) in NSG mice ($1\times10^7$ cells) and inoculated intraperitoneally (i.p) with human PBMCs from 2 healthy human donors C and D on the same day ($1\times10^7$ cells). Mice were randomized 8 days after tumor cell injection when the average tumor volume reached 120 mm3 in various treatment groups of PBMCs injected from donor C (n=8) and D (n=8). Therapeutic treatments of CD3/BCMA/CD38 candidates or 83A10-TCBcv were injected intravenously (i.v.) on days 0, 7 and 14 at 0.5 mg/kg. Mice in the vehicle control group were injected i.v. with a mixture of PBS and CD3/BCMA/CD38 candidates reconstitution buffer.

As previously observed, three weeks post treatment start, CD3/BCMA/CD38-118 and -119 induced complete regression of KMS-12-BM tumors inoculated with donor C PBMCs in 100% and 87.5% of treated mice, respectively. Similarly, 83A10-TCBcv bispecific BCMA CD3 antibody led to the regression of 75% of tumors (FIG. 29A, left). Upon inoculation of donor D PBMCs, CD3/BCMA/CD38 candidates partially controlled KMS-12-BM tumors, with tumor regression seen in 37.5 to 50% of treated mice. Treatment with 83A10-TCBcv induced significantly lower tumor regression (25% of treated mice) (FIG. 29A, right; Table 30). Finally, administration of CD3/BCMA/CD38-122 at 0.5 mg/kg showed no control of KMS-12-BM tumor progression (similar to vehicle treated mice) in both PBMC donors (FIG. 29A), demonstrating that the target antigen binding arms are crucial for the tumor killing efficacy of CD3/BCMA/CD38 candidates.

Serum concentrations of CD3/BCMA/CD38 candidates or 83A10-TCBcv were determined on day 6 at around 2000 ng/ml (Donor C) and around 3000 ng/ml (Donor D) in similar levels across all treatment groups (FIG. 29B). Therefore, CD3/BCMA/CD38 candidates outperform 83A10-TCBcv in the control of KMS-12-BM tumors (donor D), despite having similar trough exposures.

TABLE 30

Statistical analysis of FIG. 29 (A). Differences in tumor volume were determined using a two-way analysis of variance (ANOVA) with Tukey's multiple comparison test, n = 8 mice per group. P value <0.05 was considered statistically significant, with the level of significancy represented by asterisks as followed: ns p ≥ 0.05; * p < 0.05;  p < 0.01; * p < 0.001; **** p < 0.0001.

| | Donor C | | | | Donor D | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| Vehicle vs. 83A10-TCBcv | 462.3 | 408.4 to 516.3 | **** | <0.0001 | 148.6 | 35.54 to 261.6 | ** | 0.0033 |
| Vehicle vs. CD3/BCMA/CD38-118 | 482.6 | 428.7 to 536.5 | **** | <0.0001 | 271.2 | 158.2 to 384.3 | **** | <0.0001 |
| Vehicle vs. CD3/BCMA/CD38-119 | 439 | 385.1 to 492.9 | **** | <0.0001 | 363.7 | 250.7 to 476.8 | **** | <0.0001 |
| Vehicle vs. CD3/BCMA/CD38_122 | 3.498 | −50.44 to 57.43 | ns | 0.9998 | 33.49 | −79.56 to 146.5 | ns | 0.927 |
| 83A10-TCBcv vs. CD3/BCMA/CD38-118 | 20.28 | −33.66 to 74.22 | ns | 0.8413 | 122.7 | 9.613 to 235.7 | * | 0.0258 |

TABLE 30-continued

Statistical analysis of FIG. 29 (A). Differences in tumor volume were determined using a two-way analysis of variance (ANOVA) with Tukey's multiple comparison test, n = 8 mice per group. P value <0.05 was considered statistically significant, with the level of significancy represented by asterisks as followed: ns p ≥ 0.05; * p < 0.05;  p < 0.01; * p < 0.001; **** p < 0.0001.

| | Donor C | | | | Donor D | | | |
|---|---|---|---|---|---|---|---|---|
| Group comparison | Mean Diff. ($mm^3$) | 95.00% CI of diff. ($mm^3$) | Summary | Adjusted P Value | Mean Diff. ($mm^3$) | 95.00% CI of diff. ($mm^3$) | Summary | Adjusted P Value |
| 83A10-TCBcv vs. CD3/BCMA/CD38-119 | −23.33 | −77.27 to 30.61 | ns | 0.76 | 215.2 | 102.1 to 328.2 | **** | <0.0001 |
| 83A10-TCBcv vs. CD3/BCMA/CD38_122 | −458.8 | −512.8 to −404.9 | **** | <0.0001 | −115.1 | −228.1 to −2.045 | * | 0.0437 |
| CD3/BCMA/CD38-118 vs. CD3/BCMA/CD38-119 | −43.61 | −97.55 to 10.33 | ns | 0.1761 | 92.5 | −20.55 to 205.5 | ns | 0.1665 |
| CD3/BCMA/CD38-118 VS. CD3/BCMA/CD38_122 | −479.1 | −533.0 to −425.2 | **** | <0.0001 | −237.8 | −350.8 to −124.7 | **** | <0.0001 |
| CD3/BCMA/CD38-119 VS. CD3/BCMA/CD38_122 | −435.5 | −489.4 to −381.6 | **** | <0.0001 | −330.3 | −443.3 to −217.2 | **** | <0.0001 |

To understand the mechanistic action of CD3/BCMA/CD38 candidates, immune cell profiling (ICP) was performed early post treatment (FIGS. 30A-30D). Mice tumors and spleens were harvested at day 2 and day 6 following a single dose of molecules at 0.5 mg/kg and FACS analysis was performed (n=2-3 mice/group/timepoint). At either day 2 or day 6 post dosing, treatment with CD3/BCMA/CD38-118, CD3/BCMA/CD38-119 or 83A10-TCBcv resulted in a selective infiltration of human $TCR\alpha\beta^+$ cells (surrogate marker for CD3 T cells) in the tumor microenvironment compared to the vehicle or CD3/BCMA/CD38-122 treated groups (FIG. 30A). The extent of $TCR\alpha\beta^+$ cell infiltration varied between PBMC donors, with mice inoculated with donor C, which showed the highest tumor growth inhibition also showing highest degree of T cell infiltration in the tumor (FIG. 30A, top). Treatment with CD3/BCMA/CD38-122 did not induce increased presence of $TCR\alpha\beta^+$ cells in the tumor, demonstrating that binding to CD3 only is not sufficient to increase tumor infiltration of T cells. The numbers of infiltrating T cells per gram of tumor were also increased in mice inoculated with donor C upon treatment with CD3/BCMA/CD38 candidates (20 and 100-fold increase compared to control treated groups at day 2 and 6, respectively) (FIG. 30B). This data showed that T cell engager efficacy (CD3/BCMA/CD38 candidates or 83A10-TCBcv) correlates with the degree of T cell infiltration within the tumor microenvironment.

At day 2 post single dose, tumor infiltrating $CD8^+$ T cells showed higher expression of human CD69 and human CD25 (T cell activation markers) in mice treated with CD3/BCMA/CD38 candidates or 83A10-TCBcv, compared to vehicle or CD3/BCMA/CD38-122 treated groups (FIG. 30C and FIG. 30D, top). Intratumor T cell activation was mostly observed in mice inoculated with donor C PBMCs, showing that the treatment efficacy of CD3/BCMA/CD38 candidates also correlate with greater T cell activation status within the tumor. In addition, $CD8^+$ T cells found in the periphery (spleen) at day 2 showed little to no expression of the activation markers CD69 and CD25 (FIG. 30D, bottom), thus no evidence for systemic T cell activation was observed.

Finally, the immune cell profiling FACS data was corroborated with cytokine analysis in the tumor supernatant using Luminex assay (FIG. 31). Consistent with intratumor T cell activation, human IFN-γ and TNF-α were specifically induced in the tumor by T cell engagers at both day 2 and 6 post first dose, to a larger extent in donor C inoculated mice (FIG. 31, top). In addition, perforin and granzymes (cytotoxic molecules) were also elevated in the tumor at day 6, especially in mice inoculated with donor C PBMCs (FIG. 31, middle and bottom). This data indicates that CD3/BCMA/CD38 candidates or 83A10-TCBcv substantially induce secretion of human cytotoxic cytokines in the tumor microenvironment.

In conclusion, the degree of efficacy of CD3/BCMA/CD38 candidates (0.5 mg/kg) in KMS-12-BM tumor control correlated with the degree of T cell infiltration and activation status within the tumor microenvironment. No evidence for systemic T cell activation could be observed 2 days following first dose suggesting that on target binding to BCMA/CD38 expressing cells is required to activate T cells in vivo. These in vivo data demonstrate that CD3/BCMA/CD38 candidates possess a potent cytotoxic potential against CD38 and BCMA low expressing tumor cells.

EXAMPLE 21: PK OF CD3/BCMA/CD38-118 AND CD3/BCMA/CD38-119 IN TG32/SCID MICE

Material and Methods

Animal Husbandry and Blood Sampling

In vivo experiments were performed at Jackson laboratories (Bar Harbor, Maine, USA) in accordance to JAX IACUC protocols. TG32/SCID refers to B6·Cg-FcgrttmlDcr Prkdcscid Tg(FCGRT)32Dcr/DcrJ (Tg32 SCID, JAX stock #018441.

ELISA Assay

25 μL blood samples were collected from each mouse according to the bleeding schedule shown in the table below at 5m, 1d, 3d, 5d, 7d, 10d, 14d, 17d, 21d, 24d, and 28d. The blood samples were collected into 1 μL $K_3$EDTA, processed to plasma, diluted 1/10 in 50% glycerol in PBS, transferred into specialized 96 well storage plates, and stored at −20° C. All plasma samples were assessed via Mabtech (3850-1AD-6) hIgG Fc ELISA to quantify human IgG Fc activity.

PK Calculations

All PK calculations were performed using Phoenix WinNonLin (Certara, USA). Statistical analysis and graphing was conducted using GraphPad Prism 9 software.

Results and Conclusions

The in vivo PK of CD3/BCMA/CD38-118 and CD3/BCMA/CD38-119 was evaluated in TG32/SCID mice expressing human neonatal Fc receptors (FcRn). Blood samples were collected for 4 weeks and analyzed for TREAT concentration. Both TREATs had similar PK profiles with distribution and elimination (see FIG. 32) broadly comparable. When PK parameters were calculated both had elimination half-lives in excess of one week in this model (Table 31). Based on this data both TREATs interact with human FcRn to give elimination half-lives supportive of weekly dosing.

TABLE 31

Pharmacokinetic Parameters of CD3/BCMA/CD38-118 and CD3/BCMA/CD38-119 in TG32 SCID mice. TG32 SCID mice were injected IV with a single dose of CD3/BCMA/CD38-118 and CD3/BCMA/CD38-119 at 5 mg/kg and plasma evaluated for TREAT concentration. PK parameters are reported as mean +/− SD of 6 mice.

| Molecule | Half-Life (days) | Cmax (μg/ml) | AUC (μg · days/ml) |
|---|---|---|---|
| CD3/BCMA/CD38-118 | 7.6 ± 0.9 | 95 ± 26 | 417 ± 75 |
| CD3/BCMA/CD38-119 | 8.3 ± 1.7 | 132 ± 26 | 529 ± 79 |

EXAMPLE 22: FURTHER CHARACTERIZATION OF CD3/BCMA/CD38 ANTIBODIES

EXAMPLE 22 (A): EXPRESSION AND CHARACTERIZATION OF ADDITIONAL CONTROL MOLECULES FOR THE CHARACTERIZATION OF CD3/BCMA/CD38 TREATS

Materials and Methods

Alnuctamab (Batch pALB205 and P2078) Expression and Purification

For alnuctamab batch pALB205 (Recommended INN: List 85; WHO Drug Information, Vol. 35, No. 1, 2021), filtered and conditioned supernatant obtained as detailed in example 3 was incubated with mAbSelectSURE resin (Cytiva life sciences) overnight at 4° C. with stirring. After incubation, bound proteins were washed with 10 column volumes (CVs) of PBS pH 7.4, followed by elution in 100 mM Glycine pH 3.0. The resulting eluate was further purified by Cation Exchange Chromatography. The HiTrap HP SP column (1 mL bed volume) was pre-equilibrated in 50 mM sodium acetate buffer pH 5.5 and operated on an AKTA Pure™ chromatography system (both column and instrument from Cytiva Life Sciences) at a flow rate of 1 ml/min. The protein A eluate was diluted in 50 mM sodium acetate pH 5.5 prior to injection onto the column. Elution was thereafter performed using a linear gradient from 0 to 250 mM NaCl in sodium acetate 50 mM, pH 5.5 over 30 CVs. Selected fractions from the cation exchange eluate corresponding to alnuctamab as judged by SDS-PAGE were pooled and further purified by Size Exclusion Chromatography on a HiLoad Superdex 200 16-60 PrepGrade column operated in PBS, pH 7.4 on AKTA Pure™ chromatography system (both column and instrument from Cytiva Life Sciences). Fractions corresponding to the main peak were pooled and analyzed as previously described for other recombinant antibody constructs.

For alnuctamab batch P2078 (Recommended INN: List 85; WHO Drug Information, Vol. 35, No. 1, 2021), protein A magnetic beads (GenScript Protein A Magnetic Beads) were added to the culture one day prior to the harvest and incubated overnight at 32° C. under appropriate agitation. Beads were collected using a magnetic wand (AmMag™ Wand Sleeve D12) and placed on a magnetic separation stand. The beads were first washed in 1×PBS, pH 7.4 until all visible cell debris are removed and the proteins were eluted with a step elution protocol, using sequentially 50 mM sodium acetate pH 4.1. The PA eluate was neutralized by adding 5% (v/v) of 1M Tris-HCl, pH 8.0 and further purified by cation exchange chromatography (CEX). A two-step chromatography sequence was used. In a first step, desalting column (HiPrep 26/10 desalting, Cytiva) was used for buffer exchange. After equilibration of the desalting column with 50 mM sodium acetate buffer pH 5.5, purified antibodies were injected onto the column. Then automated monitoring of the UV signal together with the used of the versatile valve V9H-V was used to specifically inject antibodies to an Hitrap HP SP cation exchange chromatography column (5 mL bed volume, Cytiva). After complete loading of the sample, the CEX chromatography was performed using a linear gradient from 0 to 300 mM NaCl in sodium acetate 50 mM, pH 5.5 over 40 CVs. Collected fractions were analyzed by SE-HPLC and selected based on apparent purity. Fractions of interest were then pooled and buffer exchanged in 5 mM Histidine, 4% sucrose (w/v) pH 6.0 and 0.01% TWEEN® 80 (v/v). The purified antibodies were stored at -80° C. after sterile filtration on 0.2 μm filter.

Teclistamab production (batch pALB203 and P2095) purification

Teclistamab (Recommended INN: List 82, WHO Drug Information, Vol. 33, No. 3, 2019) was expressed as two separate monoclonal antibodies binding BCMA or CD3 and further reconstituted as described previously (Labrijn et al., Nat. Prot, 2014, 9(10):2450-63). After reconstitution of the bispecific antibody, the latter was further purified, transferred to appropriate buffers, and characterized as described in Example 3 for all other antibody-based constructs.

Additional control molecules in TREAT format purification

Control molecules described in this example were produced according to the protocol detailed in Example 3. Control molecules according to the sequence combinations detailed in Table 32 were additionally tested. Here an irrelevant binder was used, dubbed G6DU, in place of the CD3, BCMA or CD38 binding arms or in place of either combination of two binding arms as detailed in Table 33. Other controls included bispecific antibodies targeting BCMA and CD3 but not CD38 with two different BCMA binders used in trispecific antibodies. All these additional controls were dialyzed to Histidine, 25 mM, 150 mM NaCl, pH 6.0.

TABLE 32

SEQ ID of CD3/BCMA/CD38 control antibodies.

| CD3/BCMA/ CD38_ | Chain 1 | Chain 2 | Chain 3 |
|---|---|---|---|
| 147 | SEQ ID NO: 548 | SEQ ID NO: 553 | SEQ ID NO: 1 |
| 149 | SEQ ID NO: 546 | SEQ ID NO: 555 | SEQ ID NO: 1 |
| 150 | SEQ ID NO: 548 | SEQ ID NO: 555 | SEQ ID NO: 1 |
| 151 | SEQ ID NO: 528 | SEQ ID NO: 547 | SEQ ID NO: 1 |
| 156 | SEQ ID NO: 548 | SEQ ID NO: 529 | SEQ ID NO: 1 |
| 157 | SEQ ID NO: 546 | SEQ ID NO: 529 | SEQ ID NO: 1 |
| 158 | SEQ ID NO: 528 | SEQ ID NO: 553 | SEQ ID NO: 1 |

Results and Conclusions

Production and Characterization of Alnuctamab and Teclistamab

Alnuctamab is a CD3×BCMA bispecific in a 2+1 format, based on an Fc with L234 Å/L235 Å/P329G (EU numbering) mutations. Alnuctamab was produced in CHO cells with plasmid DNA encoding the four chains as identified in the International Non-Proprietary Nomenclature List (Recommended INN: List 85; WHO Drug Information, Vol. 35, No. 1, 2021). Following three steps of purification by protein A, Cation Exchange Chromatography and Size Exclusion Chromatography (for batch pALB205 only), batch pALB205 and batch P2078 of alnuctamab had a purity of 94.6% and 96.43%, respectively, as judged by SE-HPLC.

Teclistamab is a CD3×BCMA bispecific based on the IgG4-F234 Å/L235 Å/S228P (EU numbering) Fc and was produced first as two separate mAbs in CHO cells with plasmid DNA encoding the heavy and light chains of the BCMA- and CD3-binding arm, respectively and identified in the International Non-Proprietary Nomenclature List (Recommended INN: List 82, WHO Drug Information, Vol. 33, No. 3, 2019). The bispecific antibody was reconstituted as previously described (Labrijn et al., Nat. Prot, 2014, 9(10):2450-63) following protein A purification. After a subsequent purification step by Cation Exchange Chromatography, batch pALB203 and batch P2095 of teclistamab had a purity of 98.8% and 99.51%, as judged by SE-HPLC.

Production and characterization of additional control molecules for CD3/BCMA/CD38 TREATs characterization Additional control antibodies in the TREAT format according to Table 32 were designed and successfully produced in CHO-S cells and displayed percentages of main peak in SE-HPLC ranging from between 95.90-99.22% post-purification (Table 33). Other controls further used in this example have been described in Example 12.

TABLE 33

Description and characterization of control molecules used to characterize CD3/BCMA/CD38 molecules.

| CD3/BCMA/CD38– | 147 | 149 | 150 | 151 | 156 | 157 | 158 |
|---|---|---|---|---|---|---|---|
| BATCH ID | P1936 | pTHM145 | pTHM146 | pARE312 | pTHM147 | pTHM148 | pTHM149 |
| CD3 binder or dummy | G6DU | C1-D6 | C1-D6 | C1-D6 | G6DU | G6DU | G6DU |
| CD38 binder or dummy | B3 | B3-C11 | B3 | G6DU | B3 | B3-C11 | G6DU |
| BCMA binder or dummy | E6-G6-N82aS | G6DU | G6DU | E6-G6-N82aS | G6DU | G6DU | E6-G6-N82aS |
| yield (mg/L) | 26 | 27.2 | 47.3 | 24.5 | 57.8 | 44.1 | 52.2 |
| Final Purity (% monomer) | 98.91 | 97.15 | 98.18 | 99.22 | 98.2 | 96.89 | 95.90 |

All additional controls were deemed of suitable quality for further use in in vitro characterization of CD3/BCMA/CD38 antibodies.

EXAMPLE 22 (B): MULTIPLE MYELOMA CELL LINES EXPRESS VARIOUS LEVELS OF CD38 AND BCMA

Material and Methods

Generation of Pools of BCMA and CD38 Knockout (KO) NCI-H929 Cells

The NCI-H929 BCMA KO and CD38 KO cell lines were derived from original NCI-H929 cells (95050415, lot 17AO27, Sigma from ECACC) by targeting the first exon of the BCMA gene or CD38 gene using clustered regularly interspaced short palindromic repeats (CRISPR)/Cas9 technology, as described by Ran et al [Ran et al., 2013, Cell, 154: 1380-1389]. The NCI-H929 cell line was transfected using 4D-Nucleofector (Lonza) following the manufacturer's recommendation. Following transfection, the cells were stained with anti-BCMA antibody (269-020, Ancell) or CD38 antibody (12-0389-42, HIT2 clone, eBioscience) and knock-out cells were sorted using Melody FACS sorter (BD) to generate a pool of knock-out cells. The lack of BCMA or CD38 expression was further verified by Flow Cytometry using Qifikit (DAKO, catalog NO: K007811-8) and mapping breakpoint analysis using TA-cloning and Sanger sequencing and ICE-Synthego analysis software.

Characterization of Multiple Myeloma Cell Lines and Primary T Cells Using Specific Antibody Binding Capacity Assay Expression levels of human CD38 and human BCMA on cell surface were determined using QIFIKIT flow cytometry (DAKO) according to the manufacturer's instructions. This method allows the quantification of antigenic sites on cell surface by providing an antibody binding per cell value. Mouse anti-human CD38 (Clone HIT2), anti-human BCMA (Clone ANC3B1) and mouse isotype Immunoglobulin (Ig) G1 were used as primary antibodies on KMS-12-BM, MOLP-8, NCI-H929, NCI-H929 CD38 KO and NCI-H929 BCMA KO cell lines. One hundred thousand cells per well were stained with primary antibodies at saturating concentration and after incubation and washes, were then incubated with the secondary anti-mouse Ig-FITC antibody, at a saturating concentration as well as the beads for the calibration curve. Samples were acquired on a flow-cytometer (Cytoflex) and data were analyzed with Flow cytometry software (CytExpert) according to the manufacturer's instructions.

Results and Conclusions

The expression of BCMA and CD38 on the evaluated cancer cell lines was in agreement with published data showing that myeloma cells express BCMA as well as CD38 as described by Uhlen et al [Uhlen et al., 2017, Science, 357(6352):eaan2507]. CD38 and BCMA levels for KMS-12-BM, MOLP-8 and NCI-H929 were consistent across experiments. NCI-H929 CD38 KO cells express BCMA ($51\times10^3$ sABC) but do not express CD38. NCI H929 BCMA KO cells express CD38 ($26\times10^3$ sABC) and do not express detectable levels of BCMA. The relative expression of CD3 and CD38 was also determined on human isolated primary human T cells which expressed high levels of CD3 ($67\times10^3$ sABC), low levels of CD38 ($1.8\times10^3$ sABC) and no detectable levels of BCMA.

The mean and standard deviation of sABC values for each cell line are summarized in the Table 34.

TABLE 34

All cell lines and primary T cells express CD38 and BCMA levels aligned with literature. The table shows sABC values determined by Flow Cytometry experiments. Each value is the mean +/− standard deviation of three to six measurements from three independent experiments.

| Cell line | Mean CD38 sABC ± SD $10^3$ | Mean BCMA sABC ± SD $10^3$ | Mean CD3 sABC ± SD $10^3$ | Nomenclature for example |
|---|---|---|---|---|
| KMS-12-BM | 28 ± 2 | 9 ± 0.2 | Not applicable | BCMA+CD38+ |
| NCI-H929 | 85 ± 19 | 52 ± 13 | Not applicable | BCMA++CD38++ |
| MOLP-8 | 512 ± 184 | 3.2 ± 0.4 | Not applicable | BCMAlowCD38+++ |
| NCI-H929 BCMA KO | 26 ± 4 | BLQ | Not applicable | BCMA−CD38++ |
| NCI-H929 CD38 KO | BLQ | 51 ± 12 | Not applicable | BCMA++CD38− |
| Human T cells | 1.8 ± 0.7 | Not applicable | 66.9 ± 4.3 | Not applicable |

BLQ stands for Below limit of quantification, SD, for standard deviation, MM, for multiple myeloma.
Not applicable stands for that it has not been measured.

EXAMPLE 22 (C): CD3/BCMA/CD38-118 AND CD3×BCMA BENCHMARKS BIND TO HUMAN PRIMARY CD38-NEGATIVE T CELLS

Material and Methods

Binding to human primary T cells

Human PBMCs were harvested from buffy coats obtained from La Chaux-de-Fonds/Bern (Switzerland) Transfusion Center using Ficoll density gradient isolation. T cells were isolated (StemCell Technologies, 17951) from PBMCs and frozen in CryoStor10 cell freezing medium (StemCell, #07930). Cells were thawed in pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $1.5\times10^6$ cells/ml. Cells were plated at $1\times10^5$ cells/well in 96-well round-bottom plates. The plates were centrifuged at 350 g for 3 min at 4° C. and cells washed twice with DPBS. Cells were resuspended in 25 µl of LIVE/DEAD Fixable Near-IR Dead Cell Stain (ThermoFisher Scientific, L34976) diluted at 1/1'000 in DPBS and incubated 20 min at 4° C. After two washes in FACS buffer with azide, the cells were resuspended in 100 µl of cold FACS buffer containing serial dilutions of CD3/BCMA/CD38-118, benchmarks (83A10-TCBcv, alnuctamab, teclistamab) and control antibodies (CD3/BCMA/CD38-85 (negative control irrelevant TREAT)) starting from 800 nM and diluted by 3. Cells were incubated for 30 min at 4° C., then washed twice with FACS buffer at 350 g for 3 min, resuspended in 50 µl of a cocktail of monoclonal anti-human IgG PE secondary antibody (Biolegend, 366904) and co-staining antibodies for human CD38 (Anti-CD38 FITC multi-epitope, Cytognos, CYT-38F2) diluted respectively 1/50 and 1/10 in FACS buffer and incubated 20 min at 4° C. Cells were then washed twice and resuspended in 25 µl of FACS buffer with azide. Samples were acquired on an iQue Screener Plus instrument (IntelliCyt). Cells were gated based on size on FSC vs SSC and debris, doublets and dead cells were excluded. Finally, viable cells were gated on CD38-T cells. The population was analyzed for PE-geometric mean (geomean) fluorescence intensity (MFI) using iQue Forecyt® software. Only samples showing at least 2'000 cells in final gate were considered in the further steps of the analysis. Relative geometric mean fluorescence intensity (RFI) was calculated per donor by subtracting the mean of MFI of the negative control from the MFI of the sample at each dilution. RFI values were finally plotted using Prism software (GraphPad). Equilibrium dissociation constant values ($K_D$) and maximum binding were determined by using one-site binding curve fitting on non-transformed data (Prism). The RFI was plotted using Prism software (GraphPad) as depicted in FIG. 33. $K_D$ and maximum binding values are summarized in Table 35. Two independent experiments were performed.

Results and Conclusions

The binding curves of CD3/BCMA/CD38-118 and benchmarks on primary human CD38− T cells are shown in FIG. 33 and associated Equilibrium dissociation constant ($K_D$) values in Table 35 together with maximum binding. CD3/BCMA/CD38-118 displayed lower maximum binding on CD38− T cells compared to CD3×BCMA benchmarks 83A10-TCBcv, alnuctamab and teclistamab whereas CD3/BCMA/CD38-118 showed a binding affinity of 160 nM, similar to 83A10-TCBcv (155 nM), lower compared to alnuctamab (252 nM) and higher compared to teclistamab (18 nM).

TABLE 35

CD3/BCMA/CD38-118 binds to human CD38 negative T cells. The table shows $K_D$ in nM and maximum binding (Relative Fluorescence Intensity, RFI) values on CD38- T cells determined by Flow Cytometry experiments. Each value is the mean +/- standard deviation of five to six T cell donors from two independent experiments.

| Molecule | Maximum binding ($10^3$ RFI) | $K_D$ (nM) |
|---|---|---|
| 83A10-TCBcv | 155 ± 18 | 155 ± 29 |
| alnuctamab | 153 ± 33 | 252 ± 25 |
| teclistamab | 258 ± 38 | 18 ± 2 |
| CD3/BCMA/CD38-118 | 18 ± 5 | 160 ± 36 |

EXAMPLE 22 (D): CD3/BCMA/CD38-118 AND CD3×BCMA BENCHMARKS AND CONTROL BINDING TO MULTIPLE MYELOMA AND BCMA- OR CD38-KNOCKOUT (KO) CELL LINES

Material and Methods

Binding to Multiple Myeloma and BCMA- or CD38-Knockout (KO) Cell Lines

To evaluate how CD3/BCMA/CD38-118 binds to BCMA and CD38 compared to CD3×BCMA benchmarks (83A10-TCBcv, alnuctamab, teclistamab) and assess the avidity effect when two tumor associated antigens are targeted, cell-based affinity assays were conducted on cell lines displaying variable expression of CD38 and BCMA or lacking one of the antigens (KO cell lines).

NCI-H929 wild-type (WT) (Sigma, 95050415, lot 17AO27), NCI-H929 BCMA KO (derived from Sigma, 95050415, lot 17AO27), NCI-H929 CD38 KO (derived from Sigma, 95050415, lot 17AO27), MOLP-8 (DSMZ, ACC 569, lot 14) and KMS-12-BM (DSMZ, ACC 551, lot 9) were plated at $1\times10^5$ cells/well in 96-well round-bottom plates. The plates were centrifuged at 350 g for 3 min at 4° C. and cells washed twice with DPBS.

Cells were resuspended in 25 μl of LIVE/DEAD Fixable Near-IR Dead Cell Stain (ThermoFisher Scientific, L34976) diluted at 1/1'000 in DPBS and incubated 20 min at 4° C. After two washes in FACS buffer with azide, the cells were resuspended in 100 μl of cold FACS buffer containing serial dilutions of CD3/BCMA/CD38-118, benchmarks (83A10-TCBcv, alnuctamab, teclistamab) and control antibodies (CD3/BCMA/CD38-85 (negative control irrelevant TREAT), CD3/BCMA/CD38-149 (C1-D6/irrelevant binder G6DU/B3-C11 or CD3/DU/CD38) and CD3/BCMA/CD38-151 (C1-D6/E6-G6/irrelevant binder G6DU or CD3/BCMA/DU)) starting from 800 nM (except for alnuctamab, starting dose was 266 nM) and diluted by 3. Cells were incubated for 30 min at 4° C., then washed twice with FACS buffer at 350 g for 3 min, resuspended in 50 μl of a monoclonal anti-human IgG APC secondary antibody (Biolegend, 366906) diluted 1/400 in FACS buffer with azide and incubated 20 min at 4° C. Cells were then washed twice and resuspended in 25 μl of FACS buffer with azide. Samples were acquired on an iQue Screener Plus instrument (IntelliCyt). Cells were gated based on size on FSC vs SSC and debris, doublets and dead cells were excluded. Population was analyzed for APC-geometric mean (geomean) fluorescence intensity (MFI) using iQue Forecyt® software. Only samples showing at least 2'000 cells in final gate were considered in the further steps of the analysis. Relative geometric mean fluorescence intensity (RFI) was calculated by subtracting the MFI of the negative control from the MFI of the sample at each dilution. RFI values were finally plotted using Prism software (GraphPad). Equilibrium dissociation constant values ($K_D$) and maximum binding were determined by using one-site binding curve fitting on non-transformed data (Prism). The RFI was plotted using Prism software (GraphPad) as depicted in FIGS. 34A-34E and FIGS. 35A-35E. $K_D$ and maximum binding values are summarized in Table 36 and Table 37. Three independent experiments were performed.

Results and Conclusions

Results in FIGS. 34A-34E show the binding curves of CD3/BCMA/CD38-118 and benchmarks on multiple myeloma cell lines displaying variable expression of CD38 and BCMA (FIG. 34A: KMS-12-BM, FIG. 34B: MOLP-8, FIG. 34C: NCI-H929 WT, FIG. 34D: NCI-H929 BCMA KO, FIG. 34E: NCI-H929 CD38 KO). Associated $K_D$ values and maximum binding are reported in Table 36.

CD3/BCMA/CD38-118 displayed superior maximum binding on all cell lines compared to CD3×BCMA benchmarks 83A10-TCBcv, alnuctamab and teclistamab. On the KMS-12-BM cell line (characterized as BCMA and CD38 low-expressing cells), the maximum binding of CD3/BCMA/CD38-118 was 5.3-, 5.3- and 4.1-fold higher compared to 83A10-TCBcv, alnuctamab and teclistamab respectively. On the MOLP-8 cell line (characterized as BCMA low- and CD38 high-expressing cells), CD3/BCMA/CD38-118 displayed 203-, 354, 110-fold higher maximum binding compared to 83A10-TCBcv, alnuctamab and teclistamab. On the NCI-H929 WT cell line (characterized as BCMA and CD38 medium-expressing cells), the maximum binding of CD3/BCMA/CD38-118 was 2.0-, 2.4-, 1.8-fold higher compared to the CD3×BCMA benchmarks 83A10-TCBcv, alnuctamab and teclistamab. On the NCI-H929 BCMA KO cell line (characterized as BCMA negative and CD38 medium-expressing cells), 83A10-TCBcv, alnuctamab and teclistamab displayed no-to-minimal binding (<2000 RFI) whereas candidate CD3/BCMA/CD38-118 showed a maximum binding of 4'611 RFI. On the NCI-H929 CD38 KO cell line (characterized as CD38 negative and BCMA medium-expressing cells), the increase in maximum binding compared to 83A10-TCBcv, alnuctamab and teclistamab was 2.0-, 2.2-, 1.7-fold for CD3/BCMA/CD38-118.

CD3/BCMA/CD38-118 candidate displayed a strong binding affinity in the low nanomolar range with a $K_D$ of 6.1 nM on KMS-12-BM. 83A10-TCBcv and alnuctamab displayed the same range of binding as CD3/BCMA/CD38-118 to KMS-12-BM with $K_D$ values of 2.3 and 3.9 nM. On the NCI-H929 cell line, CD3/BCMA/CD38 showed a binding affinity of 4.8 nM, similar to 83A10-TCBcv (2.7 nM) and alnuctamab (6.0 nM). On MOLP-8, while CD3/BCMA/CD38-118 candidate displayed a binding with low nanomolar range $K_D$ measurements of 9.6 nM, 83A10-TCBcv and alnuctamab showed minimal binding on cells ($K_D$ not quantifiable). Teclistamab showed overall lower binding affinities to the three cell lines with $K_D$ values of 21.8 nM for KMS-12-BM, 95.8 nM for MOLP-8 and 30.4 nM for NCI-H929 cells. On NCI-H929 BCMA KO cells, the CD3/BCMA/CD38-118 candidate displayed the strongest binding, with mid nanomolar range $K_D$measurement of 120.6 nM, whereas 83A10-TCBcv, alnuctamab and teclistamab displayed minimal-to-no binding ($K_D$ not quantifiable). On NCI-H929 CD38 KO cells, CD3/BCMA/CD38-118 displayed comparable binding curves with mid nanomolar range $K_D$ measurements of 126.2 nM, whereas CD3×BCMA benchmarks, 83A10-TCBcv, alnuctamab and teclistamab, showed binding with higher $K_D$ values of 3.2, 8.1 and 46.3 nM however 2-fold lower maximum binding, respectively.

TABLE 36

Binding of CD3/BCMA/CD38-118 and CD3 × BCMA benchmarks 83A10-TCBcv, alnuctamab and teclistamab to cell lines displaying variable expression of CD38 and BCMA. The table shows $K_D$ in nM and maximum binding values in RFI on KMS-12-BM, MOLP-8, NCI-H929 WT, NCI-H929 BCMA KO and NCI-H929 CD38 KO, determined by flow cytometry. Each value is the mean of three measurements from three individual experiments. NQ stands for Not Quantifiable.

| | KMS-12-BM | | MOLP-8 | | NCI-H929 WT | | NCI-H929 BCMA KO | | NCI-H929 CD38 KO | |
|---|---|---|---|---|---|---|---|---|---|---|
| | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) |
| 83A10-TCBcv | 6,949 | 2.3 | 1,252 | NQ | 40,821 | 2.7 | No binding (255) | NQ | 22,829 | 3.2 |
| alnuctamab | 6,876 | 3.9 | 719 | NQ | 34,282 | 6.0 | No binding (101) | NQ | 21,228 | 8.1 |
| teclistamab | 8,964 | 21.8 | 2,321 | 95.8 | 44,698 | 30.4 | No binding (104) | NQ | 27,992 | 46.3 |
| CD3/BCMA/CD38-118 | 36,781 | 6.1 | 254,225 | 9.6 | 81,386 | 4.8 | 4,611 | 120.6 | 46,398 | 126.2 |

Results in FIGS. 35A-35E show the binding curves of CD3/BCMA/CD38-118 candidate and control molecules CD3/BCMA/CD38-149 (C1-D6/irrelevant binder G6DU/B3-C11) and CD3/BCMA/CD38-151 (C1-D6/E6-G6/irrelevant binder G6DU) on multiple myeloma cell lines displaying variable expression of CD38 and BCMA (FIG. 35A: KMS-12-BM, FIG. 35B: MOLP-8, FIG. 35C: NCI-H929 WT, FIG. 35D: NCI-H929 BCMA KO, FIG. 35E: NCI-H929 CD38 KO). Associated $K_D$ values and maximum binding are reported in Table 37.

CD3/BCMA/CD38-118 and control antibodies showed binding on all cell lines except NCI-H929 KO lines for each control molecule, as designed. CD3/BCMA/CD38-118 displayed superior maximum binding compared to control molecules CD3/BCMA/CD38-149 (CD3/DU/CD38) and CD3/BCMA/CD38-151 (CD3/BCMA/DU) on the KMS-12-BM cell line (characterized as BCMA and CD38 low-expressing cells) on the MOLP-8 cell line (characterized as BCMA low- and CD38 high-expressing cells), and on the NCI-H929 WT cell line. On the NCI-H929 BCMA KO cell line, the maximum binding was similar for CD3/BCMA/CD38-118 and the CD3/BCMA/CD38-149 control. On the CD38 KO cell line, the maximum binding was similar for CD3/BCMA/CD38-118 candidate and CD3/BCMA/CD38-151 control, as expected.

CD3/BCMA/CD38-118 displayed a strong binding in low nanomolar range with $K_D$ measurements of 6.1 nM on KMS-12-BM, 9.6 nM on MOLP-8 and 4.8 nM on NCI-H929 WT, while CD3/DU/CD38 and CD3/BCMA/DU displayed binding in a higher nanomolar range as compared to CD3/BCMA/CD38-118 candidate with 45.6 nM and 71.2 nM, 32.1 nM and 260.1 nM, and 117.6 nM and 105.1 nM, respectively. On NCI-H929 BCMA KO, CD3/BCMA/CD38-118 candidate and CD3/DU/CD38 control showed similar binding, in nanomolar range with $K_D$ measurements of 120.6 nM and 214.8 nM, respectively whereas CD3/BCMA/DU displayed no binding ($K_D$ not quantifiable). On NCI-H929 CD38 KO, CD3/BCMA/CD38-118 and CD3/BCMA/DU control showed similar binding, in nanomolar range with $K_D$ measurements of 126.2 nM and 147.8 nM, respectively whereas CD3/BCMA/CD38-149 displayed no binding ($K_D$ not quantifiable).

TABLE 37

Binding of CD3/BCMA/CD38 candidate and controls, CD3/DU/CD38 and CD3/BCMA/DU, to cell lines displaying variable expression of CD38 and BCMA. The table shows $K_D$ in nM and maximum binding values in RFI on cell lines displaying variable expression of CD38 and BCMA, KMS-12-BM, MOLP-8, NCI-H929 WT, NCI-H929 BCMA KO and NCI-H929 CD38 KO, determined by flow cytometry. Each value is the mean of 3 measurements from 3 individual experiments. G6DU stands for an irrelevant binder, dubbed G6DU, in place of the BCMA or CD38 binding arms as detailed in Example 22(a). NQ stands for Not Quantifiable.

| | KMS-12-BM | | MOLP-8 | | NCI-H929 WT | | NCI-H929 BCMA KO | | NCI-H929 CD38 KO | |
|---|---|---|---|---|---|---|---|---|---|---|
| | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) |
| CD3/BCMA/CD38-118 (C1-D6/E6-G6/B3-C11) | 36,781 | 6.1 | 254,225 | 9.6 | 81,386 | 4.8 | 4,611 | 120.6 | 46,398 | 126.2 |
| CD3/BCMA/CD38-149 (C1-D6/G6DU/B3-C11 or CD3/DU/CD38) | 6,273 | 45.6 | 165,651 | 32.1 | 26,757 | 117.6 | 3,565 | 214.8 | 123 | NQ |
| CD3/BCMA/CD38-151 | 17,444 | 71.2 | 3,623 | 260.1 | 83,978 | 105.1 | 88 | NQ | 48,478 | 147.8 |

TABLE 37-continued

Binding of CD3/BCMA/CD38 candidate and controls, CD3/DU/CD38 and CD3/BCMA/DU, to cell lines displaying variable expression of CD38 and BCMA. The table shows $K_D$ in nM and maximum binding values in RFI on cell lines displaying variable expression of CD38 and BCMA, KMS-12-BM, MOLP-8, NCI-H929 WT, NCI-H929 BCMA KO and NCI-H929 CD38 KO, determined by flow cytometry. Each value is the mean of 3 measurements from 3 individual experiments. G6DU stands for an irrelevant binder, dubbed G6DU, in place of the BCMA or CD38 binding arms as detailed in Example 22(a). NQ stands for Not Quantifiable.

| | KMS-12-BM | | MOLP-8 | | NCI-H929 WT | | NCI-H929 BCMA KO | | NCI-H929 CD38 KO | |
|---|---|---|---|---|---|---|---|---|---|---|
| | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) | Maximum binding (RFI) | $K_D$ (nM) |
| (C1-D6/E6-G6/G6DU or CD3/BCMA/DU) | | | | | | | | | | |

Taken together, the data show that CD3/BCMA/CD38-118 candidate demonstrated a lower binding to T cells (lower maximum binding) compared to teclistamab, alnuctamab and 83A10-TCBcv. CD3/BCMA/CD38-118 also showed the strongest binding ability towards all multiple myeloma cell lines tested compared to CD3×BCMA benchmarks. Specifically, maximum binding to multiple myeloma cell lines was higher and the $K_D$ was lower for CD3/BCMA/CD38-118 compared to teclistamab on all cell lines. CD3/BCMA/CD38-118 showed higher maximum binding with similar affinity on KMS-12-BM cells and NCI-H929 WT cells but higher affinity on MOLP-8 cells) compared to alnuctamab. The different control molecules holding one irrelevant binder arm as well as binding studies using KO cell lines illustrate the avidity effect induced by the binding to two antigens. The CD38 binder is essential to allow binding towards cells not expressing BCMA and increases substantially the binding to low BCMA expressing cells. CD3/BCMA/CD38-118 format shows strong synergism when both antigens are expressed.

EXAMPLE 22 (E): CD3/BCMA/CD38-118 TRIGGERS TUMOR LYSIS IN THE PRESENCE OF SOLUBLE BCMA, CD38 AND APRIL

Material and Methods

RDL Assay with KMS-12-BM Tumor Cells Expressing Low Levels of BCMA and CD38 and the Effect of Soluble BCMA, CD38 and APRIL on Killing Potency To evaluate how CD3/BCMA/CD38-118 killing potency may be affected by individual or concomitant presence of soluble factors (soluble BCMA, soluble CD38 and APRIL) compared to CD3×BCMA benchmarks (83A10-TCBcv, alnuctamab, teclistamab), RDL assays were conducted on the multiple myeloma KMS-12-BM cell line in presence or absence of the soluble factors alone or in combination.

Human peripheral blood mononuclear cells (PBMCs) were isolated from buffy coats of heathy donors obtained from Epalinges (Switzerland) Transfusion Center using Ficoll density gradient isolation and frozen in CryoStor10 cell freezing medium (StemCell, #07930). Cells were thawed in a pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $1.5\times10^6$ cells/ml. Twenty thousand target cells (KMS-12-BM, DSMZ, ACC 551, lot 9) labelled with Cell Proliferation Dye eFluor 670 (ThermoFisher Scientific, 65-0840-85) were plated with one hundred thousand PBMCs labelled with Cell Proliferation Dye eFluor 450 (ThermoFisher Scientific, 65-0842-85) reaching an effector-to-target ratio of 5:1. Serial dilutions of CD3/BCMA/CD38-118, benchmarks (83A10-TCBcv, alnuctamab, teclistamab) starting from 20 nM and diluted by 4-fold and control antibody (CD3/BCMA/CD38-85, Negative control), were added. The assay was performed in the presence or absence of soluble BCMA, soluble CD38 and APRIL at 150, 2.8 and 100 ng/ml final concentrations. Plates were incubated for 48 h, at 37° C., 5% $CO_2$ in a humidified atmosphere. After the incubation period, the RDL assay readout was evaluated by measuring T cell cytotoxic activity against target cells. Tumor cell killing was determined by measuring the absolute count of live target cells (eFluor670+ cells) using the LIVE/DEAD Fixable Green Dead Cell Stain (ThermoFisher Scientific, L34970), and calculated as % of Killing to No Ab=[1−(Sample absolute counts)/(absolute counts in the presence of target and effector cells without treatment)]×100. Percentage of cytotoxicity was also determined by measuring the % Dead Target or percentage of eFluor670+ L/D Green+ cells. Half maximal effective concentrations or $EC_{50}$ were calculated from the killing curves using Sigmoidal dose response nonlinear regression. Values were excluded based on goodness of fit ($R^2>0.7$), on percentage of tumor cells spontaneous killing (assay window), out-of-range $EC_{50}$ values or low percentages of maximum killing (<25%). Additionally, statistical analysis was applied to compare the killing potency of CD3/BCMA/CD38-118 candidate to each benchmark (83A10-TCBcv, Alnuctamab, Teclistamab). Mean EC50 were compared using a Mixed-effects model (REML) or paired One-way ANOVA analysis followed by Tukey HSD post-hoc comparison (*P<0.05).

$EC_{50}$ values were plotted using Prism software (GraphPad) as depicted in FIGS. 36A-36E (% Killing to No Ab) and FIGS. 37A-37E (% Cytotoxicity) for individual conditions and in FIGS. 38A-38B for the comparison between no soluble factor and the combination of soluble CD38, soluble BCMA and APRIL (A, % Killing to No Ab; B, % Cytotoxicity). Means of $EC_{50}$ values and fold-difference are summarized in Table 38 and Table 39 (% Killing to No Ab) and Table 40 and Table 41 (% Cytotoxicity). Two independent experiments were performed with a total of six donors.

Results and Conclusions

When the percentages of killing to No Ab was used as readout for killing (FIGS. 36A-36E, FIGS. 38A and Table 38 and Table 39), CD3/BCMA/CD38-118 candidate and alnuctamab showed the most efficient killing of KMS-12-BM in the absence of any soluble marker or in the presence of soluble CD38 with subpicomolar $EC_{50}$ values of 0.9 and 0.8 pM for CD3/BCMA/CD38-118 and 0.7 and 1.1 pM for alnuctamab. In the presence of soluble BCMA, APRIL or the combination of all three factors, CD3/BCMA/CD38-118 showed the strongest killing potency, with $EC_{50}$ values of 6.4, 6.3 and 13.2 pM, whereas alnuctamab displayed higher $EC_{50}$ values of 262, 47.6 and 970 pM. In particular, in the presence of the combination of soluble factors, the fold-difference compared to the absence of soluble factors for CD3/BCMA/CD38-118 reached 14-fold whereas it reached 1357-fold for alnuctamab. Other benchmarks also showed a decline in the killing potency in presence of soluble factors. While CD3×BCMA benchmark 83A10-TCBcv and teclistamab displayed a strong killing with low picomolar range $EC_{50}$ values of 8.8 and 10.6 pM, in the absence of soluble factors or in the presence of soluble CD38, their killing potency was reduced in the presence of soluble BCMA, APRIL or the combination of all factors with high picomolar range $EC_{50}$ values 266, 532 and 1'026 pM for 83A10-TCBcv and 314, 130 and 972 pM for teclistamab. In the presence of the combination of all three factors, the fold-difference compared to the absence of soluble factors for 83A10-TCBcv and teclistamab reached 116-fold and 92-fold.

When the percentage of cytotoxicity was used as readout for killing, the results were very similar. FIGS. 37A-37E, FIG. 38B and Table 40 and Table 41 show that CD3/BCMA/CD38-118 and alnuctamab showed the most efficient killing potency against KMS-12-BM in the absence of any soluble marker or in the presence of soluble CD38 with subpicomolar $EC_{50}$ values of 2.1 and 3.3 pM for CD3/BCMA/CD38-118 and 1.9 and 3.9 pM for alnuctamab. However, in the presence of soluble BCMA, APRIL or the combination of all three factors, CD3/BCMA/CD38-118 showed the strongest killing potency, with an $EC_{50}$ value of 23.3, 31.1 and 62.5 pM, whereas alnuctamab displayed a higher $EC_{50}$ value of 706, 171 and 3'060 pM.

Particularly, in the presence of the combination of soluble factors, the fold-difference compared to no soluble factors for CD3/BCMA/CD38-118 reached 30-fold whereas it was 1'647-fold for alnuctamab. Other benchmarks also showed a decline in their killing potency in presence of soluble BCMA, APRIL or the soluble factors. While 83A10-TCBcv and teclistamab displayed a killing potency with picomolar $EC_{50}$ values of 27.1 and 27.4 pM, respectively in the absence of soluble factors or 70.4 and 54.2 pM in the presence of soluble CD38, their potency was reduced in the presence of soluble BCMA, APRIL or the combination of all factors with subnanomolar range $EC_{50}$ value of 842, 2'018 and 5'144 pM for 83A10-TCBcv and 2047, 677 and 3'038 pM for teclistamab. In the presence of the combination of all three factors, the fold-difference compared to no soluble factors for 83A10-TCBcv and teclistamab reached 190-fold and 111-fold, respectively.

TABLE 38

CD3/BCMA/CD38-118 candidate induces the most potent in vitro killing of a Multiple Myeloma cell line in presence of soluble factors. The table shows half maximum effective killing concentration ($EC_{50}$) values using % killing to No Ab parameter determined from Redirected Lysis assay on KMS-12-BM cell line for 48 h and using an Effector-to-Target ratio of 5:1. Each $EC_{50}$ value is the mean +/− standard deviation of four-to-six measurements from two individual experiments.

| | % Killing to No Ab $EC_{50}$ ± SD [pM] | | | |
|---|---|---|---|---|
| Soluble factors/ Treatments | CD3/BCMA/ CD38-118 | 83A10-TCBcv | Alnuctamab | Teclistamab |
| None | 0.9 ± 0.3 | 8.8 ± 5.3 | 0.7 ± 0.4 | 10.6 ± 5.9 |
| sBCMA | 6.4 ± 2.4 | 266 ± 211 | 262 ± 214 | 314 ± 171 |
| APRIL | 6.3 ± 2.2 | 532 ± 420 | 47.6 ± 32.5 | 130 ± 94 |
| sCD38 | 0.8 ± 0.3 | 10.8 ± 8.4 | 1.1 ± 0.5 | 15.6 ± 6.5 |
| sBCMA + APRIL + sCD38 | 13.2 ± 8.7 | 1'026 ± 885 | 970 ± 898 | 972 ± 493 |

TABLE 39

CD3/BCMA/CD38-118 candidate induces the most potent in vitro killing of a Multiple Myeloma cell line in presence of soluble factors in term of fold-difference to no soluble factor condition. The table shows fold-difference to no soluble factor condition of half maximum effective killing concentration ($EC_{50}$) reported above. Fold differences were calculated using more decimals than shown.

| | Fold difference to no soluble factor condition ($EC_{50}$ from % Killing to No Ab) | | | |
|---|---|---|---|---|
| Soluble factors/ Treatments | CD3/BCMA/ CD38-118 | 83A10-TCBcv | Alnuctamab | Teclistamab |
| sBCMA | 7 | 30 | 367 | 30 |
| APRIL | 7 | 60 | 67 | 12 |
| sCD38 | 1 | 1 | 2 | 1 |
| sBCMA + APRIL + sCD38 | 14 | 116 | 1357 | 92 |

TABLE 40

CD3/BCMA/CD38-118 candidate induces the most potent in vitro killing of a Multiple Myeloma cell line in presence of soluble factors. The table shows half maximum effective killing concentration ($EC_{50}$) values using % cytotoxicity readout, determined from Redirected Lysis assay on KMS-12-BM cell line for 48 h and using an Effector-to-Target ratio of 5:1. Each $EC_{50}$ value is the mean +/− standard deviation of six measurements (from 6 different donors) from two independent experiments.

| | % Cytotoxicity $EC_{50}$ ± SD [pM] | | | |
|---|---|---|---|---|
| Soluble factors/ Treatments | CD3/BCMA/ CD38-118 | 83A10- TCBcv | Alnuctamab | Teclistamab |
| None | 2.1 ± 0.8 | 27.1 ± 22.2 | 1.9 ± 1.0 | 27.4 ± 17.1 |
| sBCMA | 23.3 ± 13.7 | 842 ± 730 | 706 ± 530 | 2'047 ± 2'486 |
| APRIL | 31.1 ± 18.6 | 2'018 ± 1'480 | 171 ± 138 | 677 ± 582 |
| sCD38 | 3.3 ± 1.7 | 70.4 ± 72.2 | 3.9 ± 3.5 | 54.2 ± 30.6 |
| sBCMA + APRIL + sCD38 | 62.5 ± 40.4 | 5'144 ± 4'182 | 3'060 ± 2'008 | 3'038 ± 1'889 |

TABLE 41

CD3/BCMA/CD38-118 candidate induces the most potent in vitro killing of a Multiple Myeloma cell line in presence of soluble factors in term of fold-difference to no soluble factor condition. The table shows fold-difference to no soluble factor condition of half maximum effective killing concentration ($EC_{50}$) reported above. Fold differences were calculated using more decimals than shown.

| | Fold difference to no soluble factor condition (EC50 from % Cytotoxicity) | | | |
|---|---|---|---|---|
| Soluble factors/ Treatments | CD3/BCMA/ CD38-118 | 83A10- TCBcv | Alnuctamab | Teclistamab |
| sBCMA | 11 | 31 | 380 | 75 |
| APRIL | 15 | 74 | 92 | 25 |
| sCD38 | 2 | 3 | 2 | 2 |
| sBCMA + APRIL + sCD38 | 30 | 190 | 1647 | 111 |

Taken together, these data show that CD3/BCMA/CD38-118 killed with similar killing potency compared to alnuctamab in the absence of soluble factors, and better killing potency compared to 83A10-TCBcv and teclistamab in the KMS-12-BM cell line. All molecules containing anti-BCMA binder were affected by the presence of soluble BCMA, APRIL or the combination of soluble factors, which reduced their killing potency. CD3/BCMA/CD38-118 candidate retained a better killing potency with around 14/30-fold increase of $EC_{50}$ value of killing compared to the condition with no soluble factors. Other benchmarks showed over a 100-fold increase of respective $EC_{50}$ value of killing in the presence of soluble factors. Statistical analysis showed that CD3/BCMA/CD38-118 killing potency in the presence of the soluble BCMA, APRIL or the combination of soluble factors was significantly higher compared to the killing potency of any of the CD3×BCMA benchmarks.

EXAMPLE 22 (F): RDL ASSAY WITH T CELLS AND MULTIPLE MYELOMA TUMOR CELLS EXPRESSING VARIOUS LEVELS OF BCMA AND CD38

Material and Methods

RDL assay with T cells and multiple myeloma tumor cells expressing various levels of BCMA and CD38

To evaluate CD3/BCMA/CD38-118 killing potency compared to CD3×BCMA benchmarks (83A10-TCBcv, alnuctamab, teclistamab), RDL assays using isolated T cells were conducted on multiple myeloma KMS-12-BM, MOLP-8 and NCI-H929 cell lines.

Human peripheral blood mononuclear cells (PBMCs) were isolated from buffy coats of heathy donors obtained from Epalinges (Switzerland) Transfusion Center using Ficoll density gradient isolation and frozen in CryoStor10 cell freezing medium (StemCell, #07930). Cells were thawed in a pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $1.5 \times 10^6$ cells/ml. Twenty thousand target cells (KMS-12-BM, DSMZ, ACC 551, lot 9; MOLP-8, DSMZ, ACC 569, lot 14; NCI-H929, Sigma, 95050415, lot 17AO27) labelled with Cell Proliferation Dye eFluor 670 (ThermoFisher Scientific, 65-0840-85) were plated with one hundred thousand T cells freshly isolated using EasySep™ Human T Cell Isolation Kit (StemCell, #17951) reaching an effector-to-target ratio of 5:1. Serial dilutions of CD3/BCMA/CD38-118, benchmarks (83A10-TCBcv, alnuctamab, teclistamab) or control antibodies (CD3/BCMA/CD38-149 (C1-D6/irrelevant binder G6DU/B3-C11 or CD3/DU/CD38) and CD3/BCMA/CD38-151 (C1-D6/E6-G6/irrelevant binder G6DU or CD3/BCMA/DU)) starting from 20 nM and diluted by 10-fold, and a single dose of control antibody (CD3/BCMA/CD38-85, negative control) were added. Plates were incubated for 48 h, at 37° C., 5% $CO_2$ in a humidified atmosphere. After the incubation period, the RDL assay readout was evaluated by measuring T cell cytotoxic activity against target cells. Tumor cell killing was determined by measuring the absolute count of live target cells (eFluor670+ cells) using the LIVE/DEAD Fixable Green Dead Cell Stain (ThermoFisher Scientific, L34970), and calculated as % of Killing to No Ab=[1−(Sample absolute counts)/(absolute counts in the presence of target and effector cells without treatment)]×100. Percentages of cytotoxicity was also determined by measuring the % Dead Target or percentage of eFluor670+L/D Green+ cells. Half maximal effective concentrations or $EC_{50}$ were calculated from the killing values using Sigmoidal dose response nonlinear regression. Values were excluded based on goodness of fit ($R^2$>0.7), on percentage of tumor cells spontaneous killing (assay window), out-of-range $EC_{50}$ values and low percentages of killing (<25%). Statistical analyses were applied to compare the killing potency of CD3/BCMA/CD38-118 candidate to each benchmark (83A10-TCBcv, alnuctamab, teclistamab) and control antibodies. Means EC50 were compared using a using a Paired One-way ANOVA followed by Tukey HSD post-hoc comparison (*P<0.05).

$EC_{50}$ values were plotted using Prism software (GraphPad) as depicted in FIGS. 39A-39C and FIGS. 40A-40C (% Killing to No Ab) and FIGS. 39D-39F and FIGS. 40D-40F (% Cytotoxicity) and means of EC50 values are summarized in pM in Table 42 and Table 44 (% Killing to No Ab) and Table 43 and Table 45 (% Cytotoxicity). A total of three independent experiments were performed with a total of six donors.

Results and Conclusions

Figure 39A:
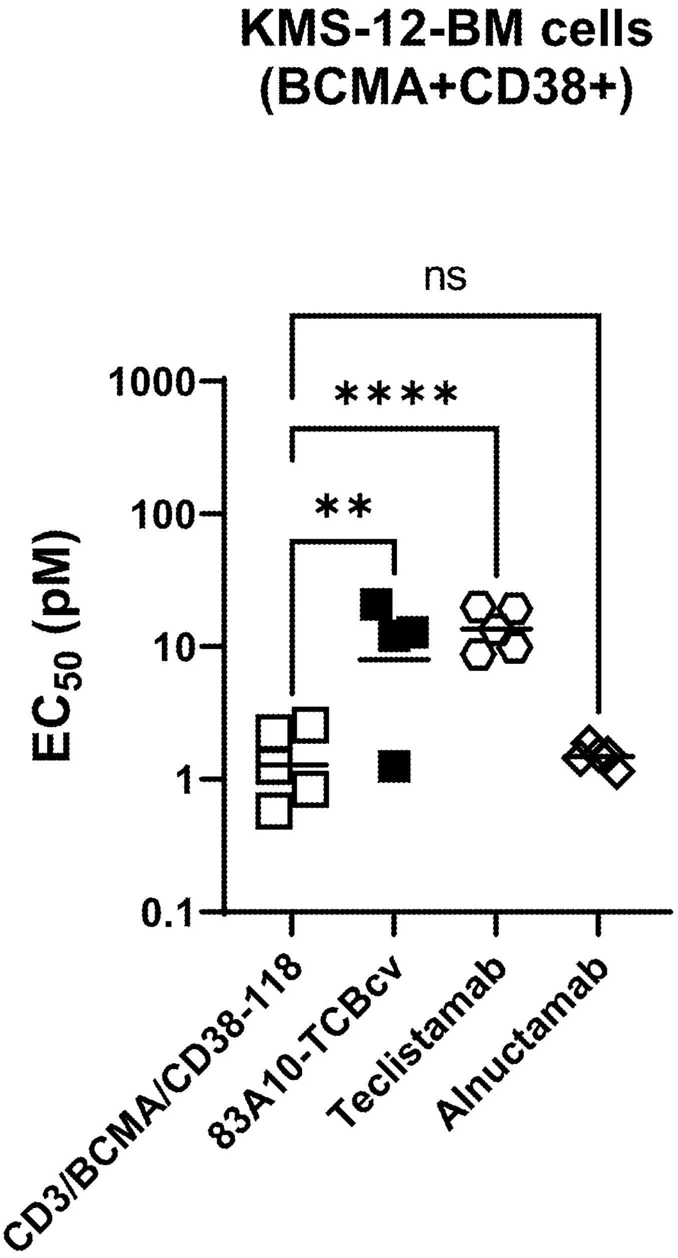
Figure 39B:
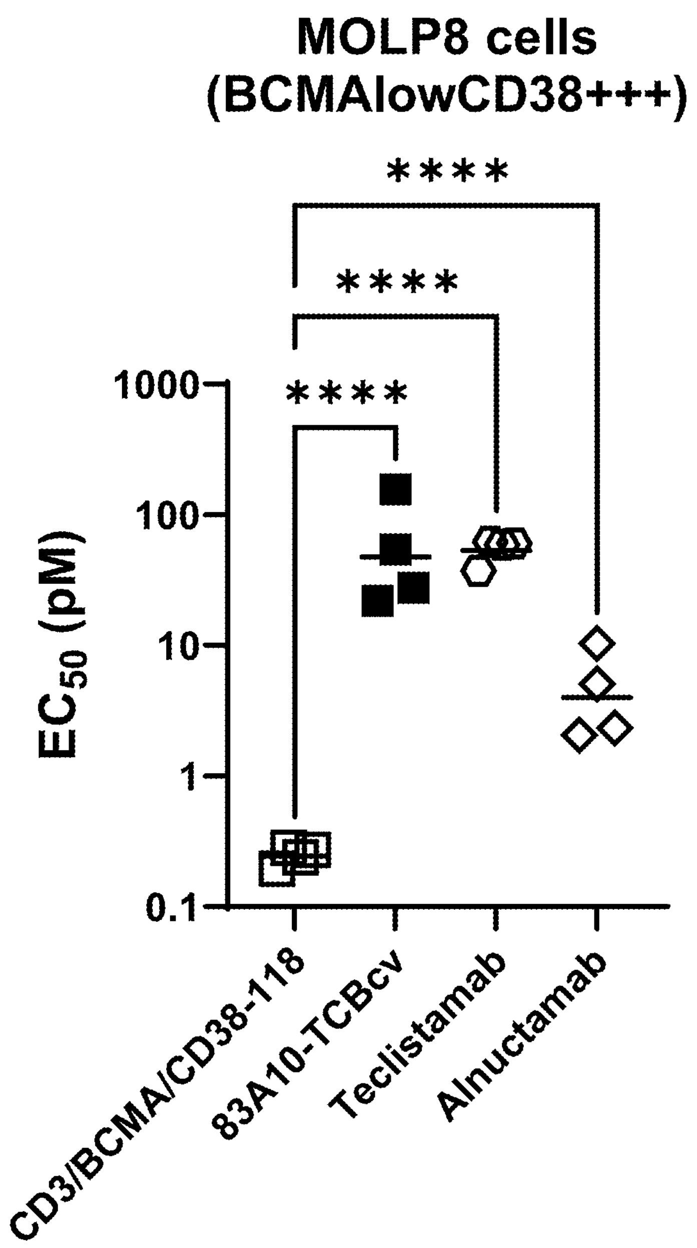
Figure 39C:
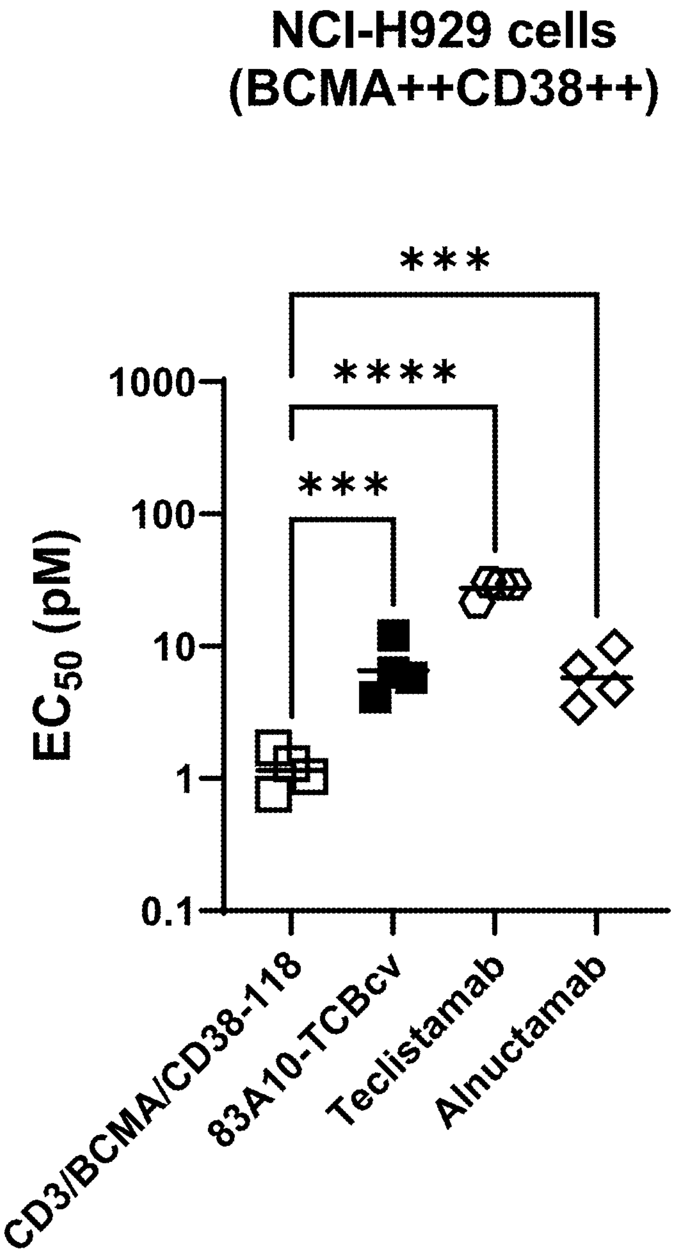

Considering the percentages of Killing to No Ab, results in FIGS. 39A-39C shows the $EC_{50}$ values for CD3/BCMA/CD38-118 and CD3×BCMA benchmarks of killing in the KMS-12-BM (FIG. 39A), MOLP-8 (FIG. 39B) and NCI-H929 (FIG. 39C) cell lines. Means of the $EC_{50}$ values are reported in Table 42. CD3/BCMA/CD38-118 and alnuctamab showed comparable killing potency of KMS-12-BM, characterized as BCMA and CD38 low-expressing cells, and superior to the killing potency of 83A10-TCBcv and teclistamab, with $EC_{50}$ values of 1.5 pM (CD3/BCMA/CD38-118), 1.5 pM (alnuctamab), 11.7 (83A10-TCBcv) and 14.3 pM (teclistamab). On the MOLP-8 cell line, characterized as BCMA low- and CD38 high-expressing cells, CD3/BCMA/CD38-118 showed very strong killing potency with subpicomolar $EC_{50}$ value of 0.2 pM whereas CD3×BCMA benchmarks triggered killing with higher $EC_{50}$ values of 5.0 pM for alnuctamab, 65.1 pM for 83A10-TCBcv and 54.7 pM for teclistamab. On the NCI-H929 cell line, characterized as BCMA and CD38 medium-expressing cells, CD3/BCMA/CD38-118 showed a superior killing potency compared to benchmarks, with low picomolar $EC_{50}$ value of 1.2 pM whereas CD3×BCMA benchmarks triggered killing with higher $EC_{50}$ values of 6.2 pM for alnuctamab, 7.1 pM for 83A10-TCBcv and 27.7 pM for teclistamab.

TABLE 42

CD3/BCMA/CD38-118 candidate induces strong in vitro killing of Multiple Myeloma cell lines compared to benchmarks (% Killing to No Ab). The table shows half maximum effective killing concentration ($EC_{50}$) values using % Killing to No Ab parameter determined from Redirected Lysis assay with T cells on KMS-12-BM, MOLP-8 and NCI-H929 cell lines for 48 h and using an Effector-to-Target ratio of 5:1. Each $EC_{50}$ value is the mean +/− standard deviation of maximum five included measurements (from 6 different donors) from three independent experiments.

| | % Killing to No Ab $EC_{50}$ ± SD [pM] | | | |
|---|---|---|---|---|
| Cell lines/ Treatments | CD3/BCMA/ CD38-118 | 83A10-TCBcv | Alnuctamab | Teclistamab |
| KMS-12-BM | 1.5 ± 0.9 | 11.7 ± 8.0 | 1.5 ± 0.3 | 14.3 ± 5.2 |
| MOLP-8 | 0.2 ± 0.0 | 65.1 ± 62.4 | 5.0 ± 3.8 | 54.7 ± 11.7 |
| NCI-H929 | 1.2 ± 0.4 | 7.1 ± 3.4 | 6.2 ± 2.8 | 27.7 ± 4.2 |

Figure 39D:
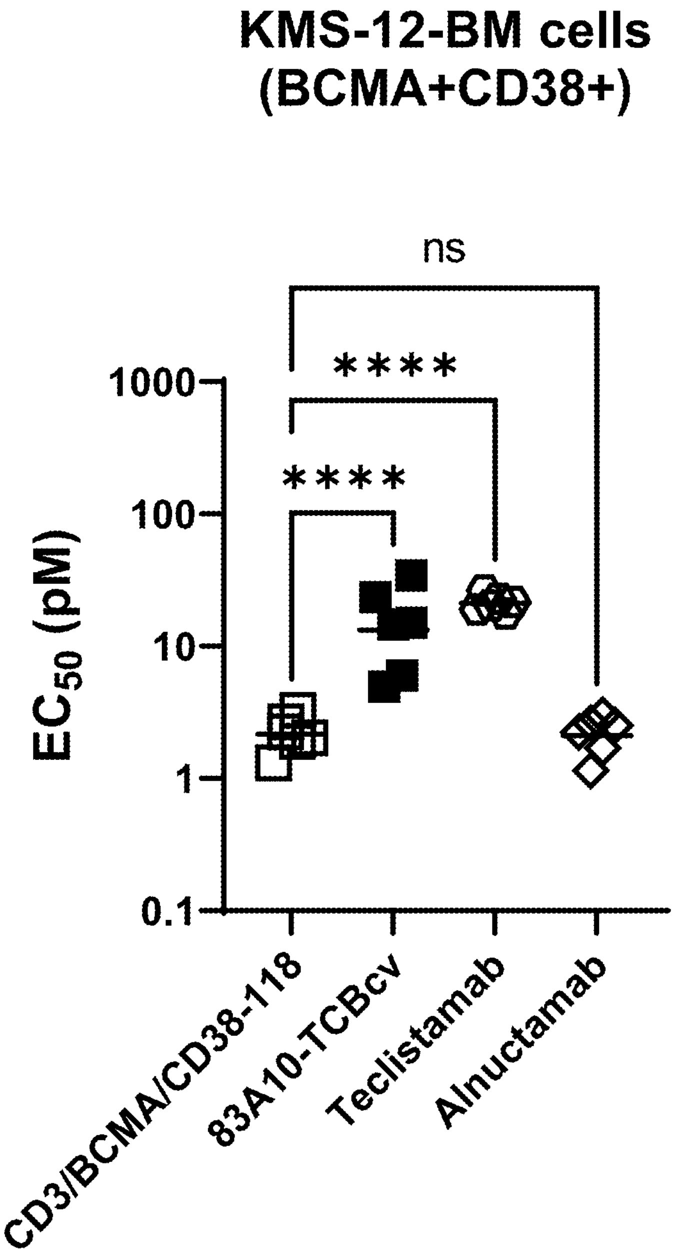
Figure 39E:
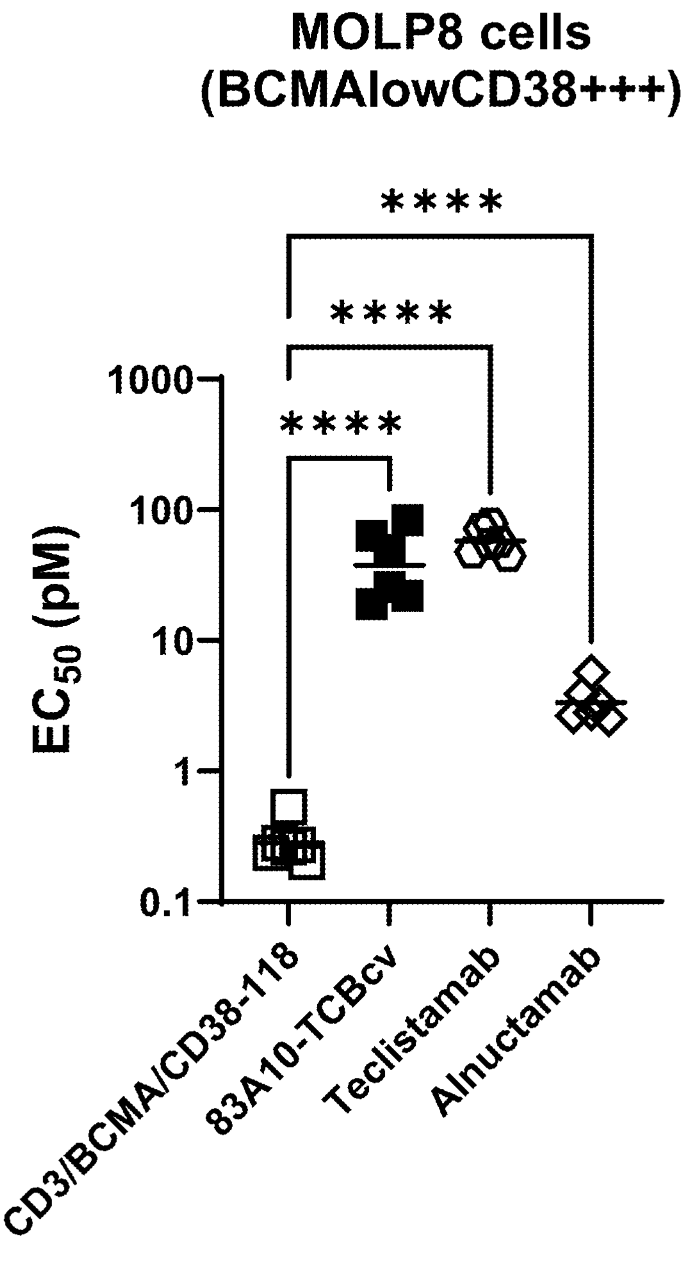
Figure 39F:
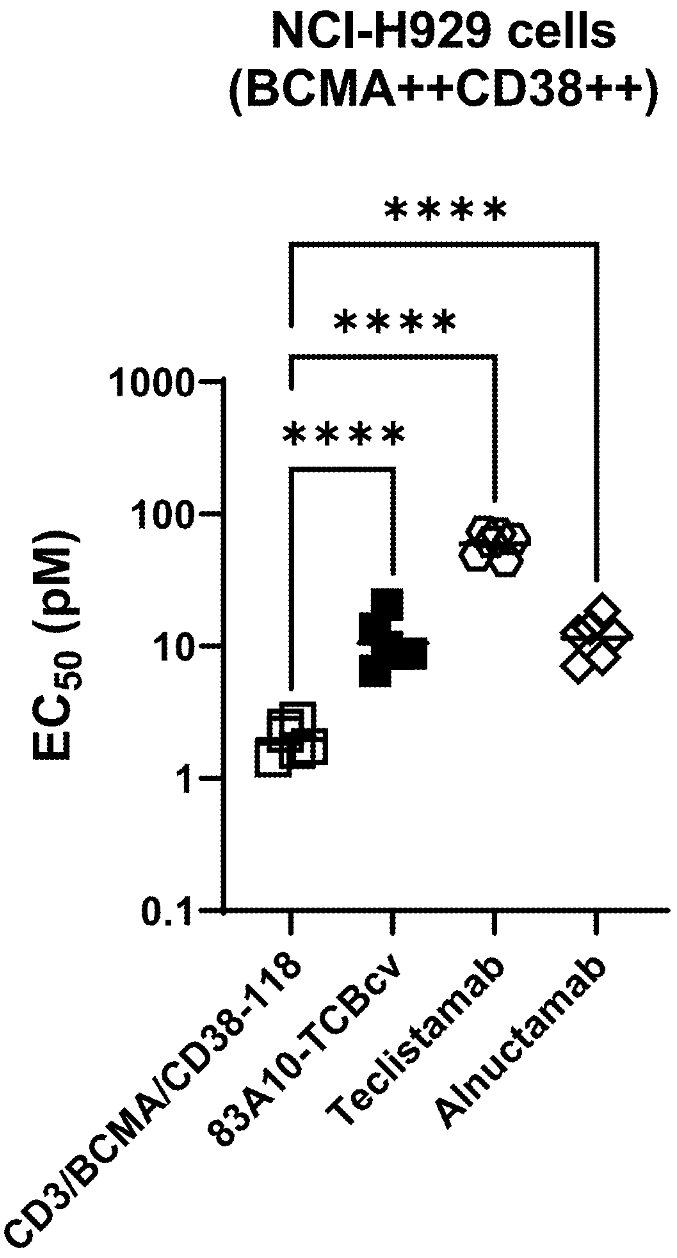

When the percentage of cytotoxicity was used as readout for killing, the results were very similar. FIGS. 39D-39F show the $EC_{50}$ values for CD3/BCMA/CD38-118 and CD3×BCMA benchmarks killing of the KMS-12-BM (FIG. 39D), MOLP-8 (FIG. 39E) and NCI-H929 (FIG. 39F) cell lines. Means of $EC_{50}$ values are reported in Table 43. CD3/BCMA/CD38-118 and alnuctamab showed a comparable killing potency against KMS-12-BM cells, characterized as BCMA and CD38 low-expressing cells, and superior to the killing potency of 83A10-TCBcv and teclistamab, with $EC_{50}$ values of 2.2 pM, 2.2 pM, 16.4 and 21.3 pM respectively. On the MOLP-8 cell line, characterized as BCMA low- and CD38 high-expressing cells, CD3/BCMA/CD38-118 showed very strong killing potency with subpicomolar $EC_{50}$ value of 0.3 pM whereas CD3×BCMA benchmarks triggered killing with higher $EC_{50}$ value of 3.5 pM for alnuctamab, 43.8 pM for 83A10-TCBcv and 58.9 pM for teclistamab. On the NCI-H929 cell line, characterized as BCMA and CD38 med-expressing cells, CD3/BCMA/CD38-118 showed a superior killing potency compared to benchmarks, with low picomolar $EC_{50}$ value of 2.0 pM whereas CD3×BCMA benchmarks triggered killing with higher $EC_{50}$ value of 12.1 pM for alnuctamab, 11.4 pM for 83A10-TCBcv and 60.5 pM for teclistamab.

TABLE 43

CD3/BCMA/CD38-118 candidate induces strong in vitro killing of Multiple Myeloma cell lines compared to benchmarks (% Cytotoxicity). The table shows half maximum effective killing concentration ($EC_{50}$) values using % Cytotoxicity parameter determined from Redirected Lysis assay with T cells on KMS-12-BM, MOLP-8 and NCI-H929 cell lines for 48 h and using an Effector-to-Target ratio of 5:1. Each $EC_{50}$ value is the mean +/− standard deviation of six measurements (from six different donors) from three independent experiments.

| | % Cytotoxicity $EC_{50}$ ± SD [pM] | | | |
|---|---|---|---|---|
| Cell lines/ Treatments | CD3/BCMA/ CD38-118 | 83A10-TCBcv | Alnuctamab | Teclistamab |
| KMS-12-BM | 2.2 ± 0.7 | 16.4 ± 11.1 | 2.2 ± 0.7 | 21.3 ± 3.1 |
| MOLP-8 | 0.3 ± 0.1 | 43.8 ± 26.2 | 3.5 ± 1.2 | 58.9 ± 13.5 |
| NCI-H929 | 2.0 ± 0.5 | 11.4 ± 5.1 | 12.1 ± 4.1 | 60.5 ± 11.7 |

As shown in the FIGS. 39A-39F, for both % Killing to No Ab and % Cytotoxicity, the CD3/BCMA/CD38-118 candidate statistically triggered the strongest killing potency compared to other CD3×BCMA treatments, 83A10-TCBcv, alnuctamab and teclistamab, against MOLP-8 and NCI-H929 cell lines as well as on the KMS-12-BM cell line compared to 83A10-TCBcv and teclistamab.

Figure 40A:
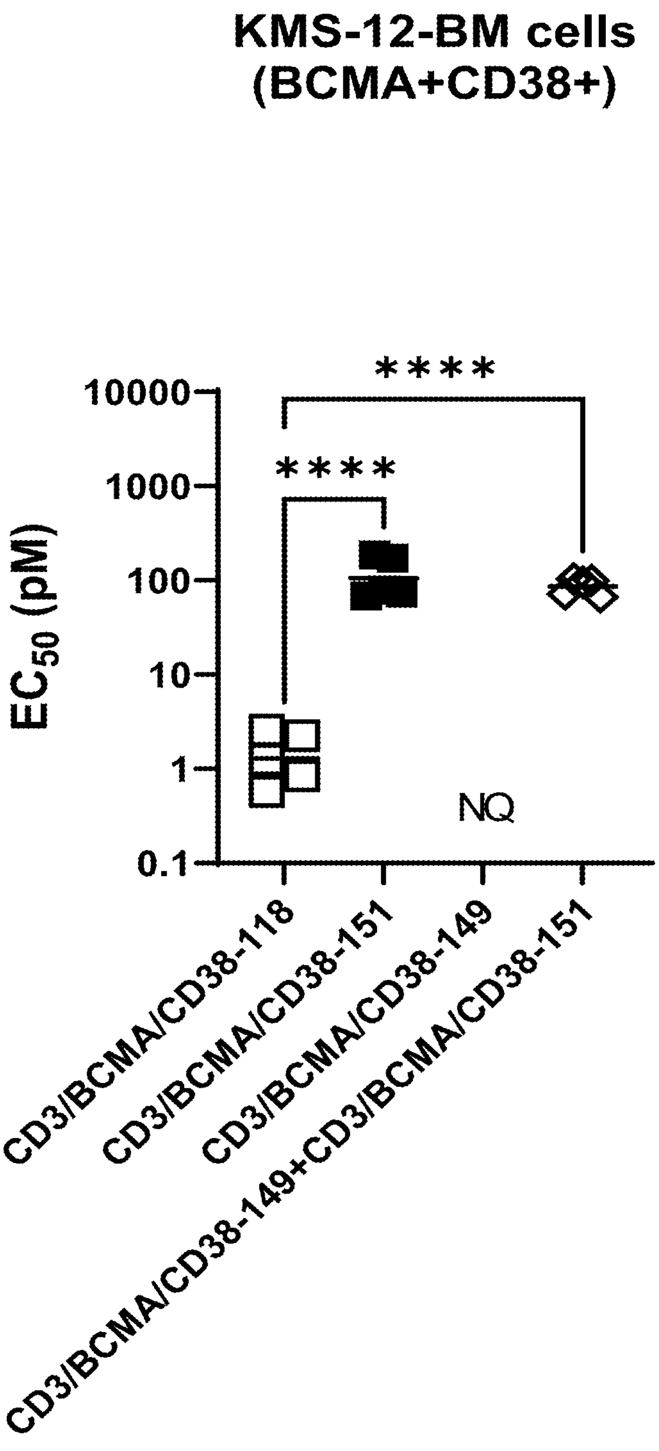
Figure 40B:
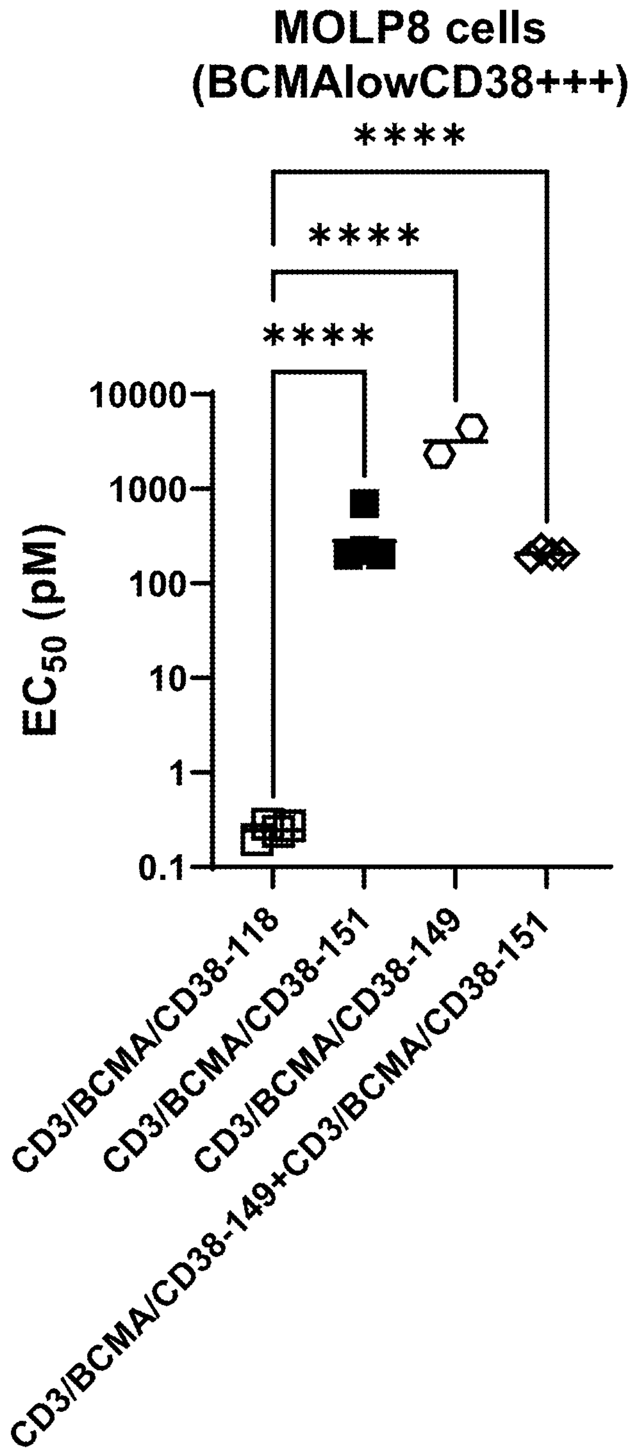
Figure 40C:
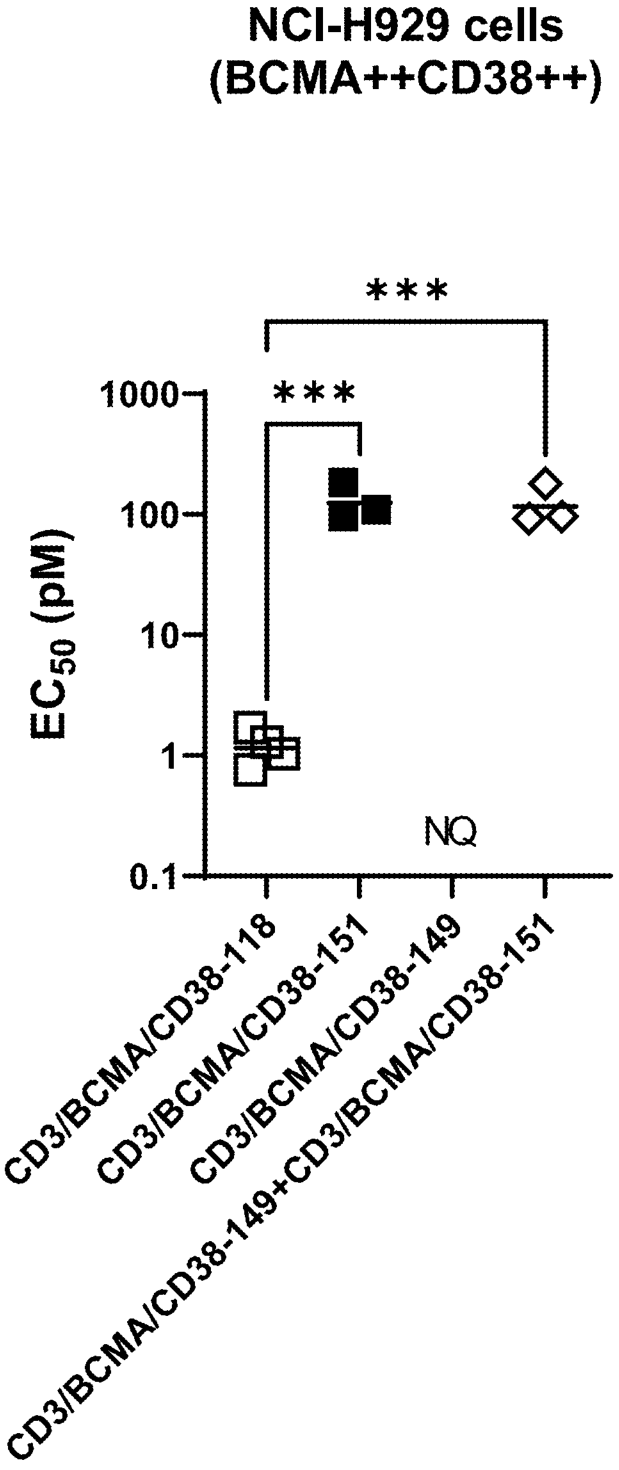

Considering the percentages of Killing to No Ab, results in FIGS. 40A-40C show the $EC_{50}$ values for CD3/BCMA/CD38-118 and control molecules for the KMS-12-BM (FIG. 40A), MOLP-8 (FIG. 40B) and NCI-H929 (FIG. 40C) cell lines. Means of $EC_{50}$ values are reported in Table 44. CD3/BCMA/CD38-118 showed superior killing potency compared to the control molecules, CD3/BCMA/CD38-149 (CD3/DU/CD38) and CD3/BCMA/CD38-151 (CD3/BCMA/DU), or the combination of -149 and -151 against all cell lines.

Taken together and considering both parameters, % Killing to No Ab and % Cytotoxicity, data show that CD3/BCMA/CD38-118 demonstrated a statistically superior killing potency against all cell lines compared to the control molecules CD3/BCMA/CD38-151(C1-D6/E6-G6/irrelevant binder G6DU), CD3/BCMA/CD38-149 and the combination of CD3/BCMA/CD38-151 and CD3/BCMA/CD38-149. This confirms the previous observation of avidity effect induced by the binding to two antigens, leading to a strong killing against CD38− and BCMA-expressing multiple myeloma cells, with various expression levels.

TABLE 44

CD3/BCMA/CD38-118 induces strong in vitro killing of Multiple Myeloma cell lines compared to controls (% Killing to No Ab). The table shows half maximum effective killing concentration (EC50) values using % Killing to No Ab parameter determined from Redirected Lysis assay with T cells on KMS-12-BM, MOLP-8 and NCI-H929 cell lines for 48 h and using an Effector-to-Target ratio of 5:1. Each EC50 value is the mean +/− standard deviation of maximum five included donors from three independent experiments. NQ stands for not quantifiable.

| | % Killing to No Ab $EC_{50}$ ± SD [pM] | | | |
|---|---|---|---|---|
| Cell lines/ Treatments | CD3/BCMA/ CD38-118 | CD3/BCMA/CD38-151 (C1-D6/E6-G6/ G6DU or CD3/BCMA/DU) | CD3/BCMA/CD38-149 (C1-D6/G6DU/ B3-C11 or CD3/DU/CD38) | CD3/BCMA/CD38-149 + CD3/BCMA/CD38-151 |
| KMS-12-BM | 1.5 ± 0.9 | 116 ± 58 | NQ | 87 ± 17 |
| MOLP-8 | 0.2 ± 0.0 | 330 ± 247 | 3'353 ± 1471 | 207 ± 17 |
| NCI-H929 | 1.2 ± 0.4 | 130 ± 47 | NQ | 123 ± 50 |

Figure 40D:
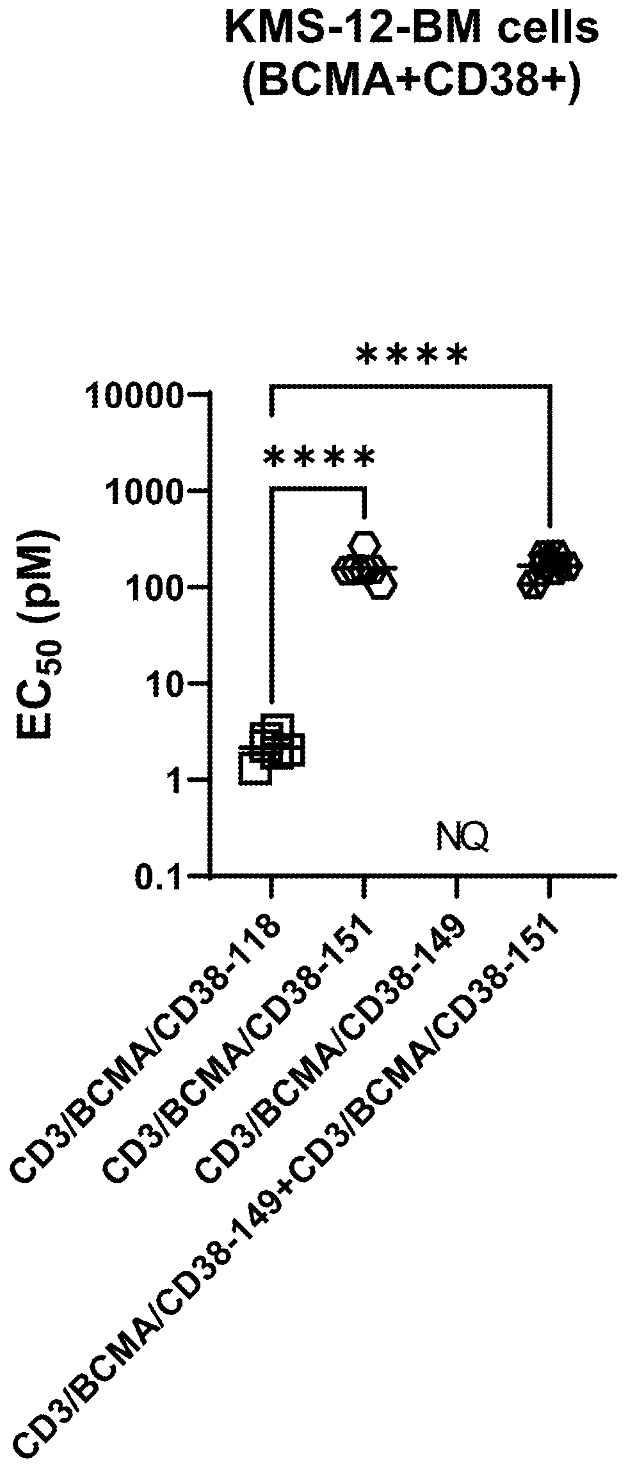
Figure 40E:
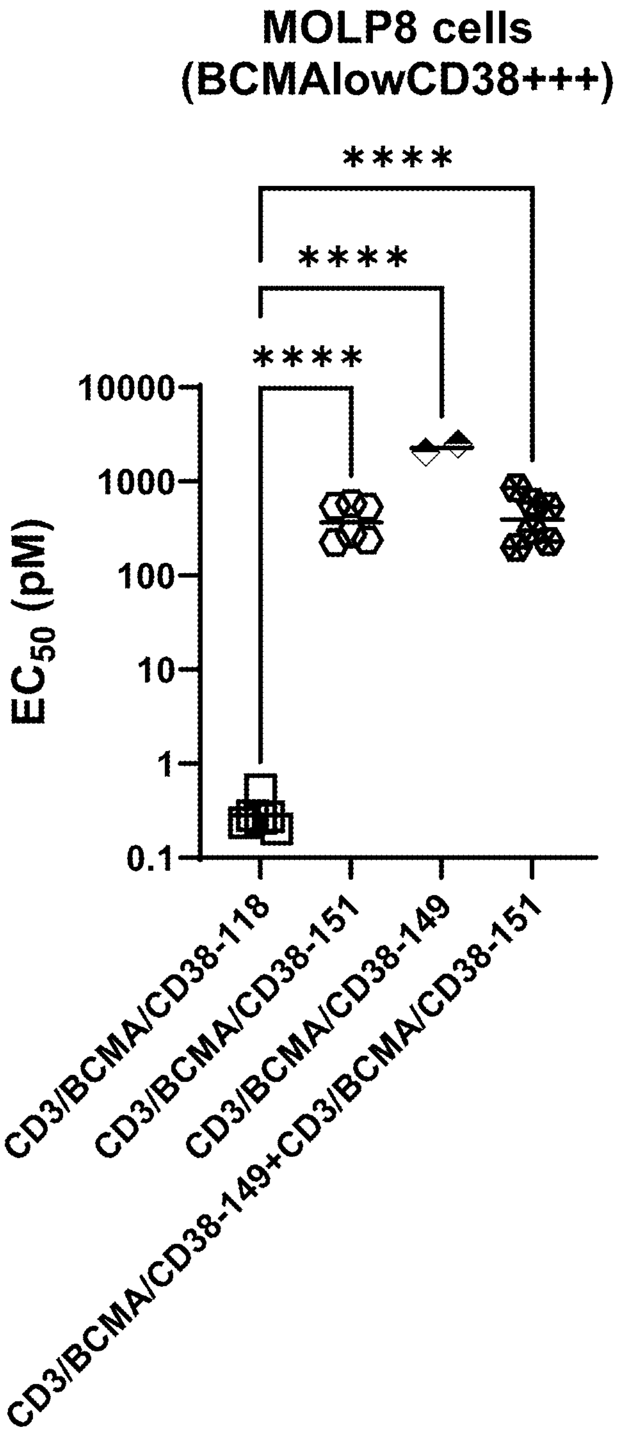
Figure 40F:
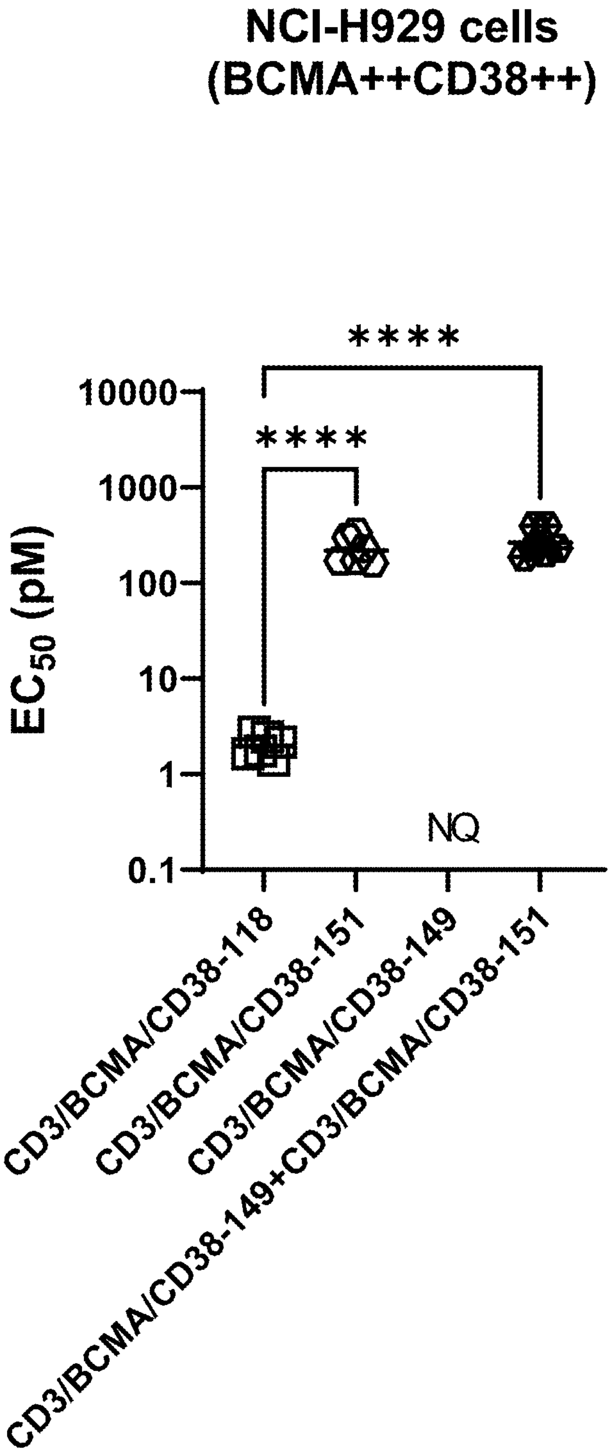

When the percentage of cytotoxicity was used as the readout for killing, the results were very similar. FIGS. 40D-40F show the $EC_{50}$ values for CD3/BCMA/CD38-118 and control molecules for the KMS-12-BM (FIG. 40D), MOLP-8 (FIG. 40E) and NCI-H929 (FIG. 40F) cell lines. Means of $EC_{50}$ values are reported in Table 45. CD3/BCMA/CD38-118 triggered superior killing potency compared to control molecules, CD3/BCMA/CD38-149 (CD3/DU/CD38) and CD3/BCMA/CD38-151 (CD3/BCMA/DU), or the combination of -149 and -151 against all cell lines.

Moreover, CD3/BCMA/CD38-118 candidate statistically triggered the strongest killing potency compared to other CD3×BCMA treatments, 83A10-TCBcv, alnuctamab and teclistamab, against MOLP-8 and NCI-H929 cell lines as well as on the KMS-12-BM cell line compared to 83A10-TCBcv and teclistamab. CD3/BCMA/CD38-118 enabled the potent killing of low expressing BCMA cells, such as MOLP-8 and KMS-12-BM multiple myeloma cell lines, an expression level that can also be found in patient as described by Seckinger et al [Seckinger et al., 2017, Cancer Cell, 31: 396-410].

TABLE 45

CD3/BCMA/CD38-118 shows strong in vitro killing potency of Multiple Myeloma cell lines compared to controls (% Cytotoxicity). The table shows half maximum effective killing concentration ($EC_{50}$) values using % Cytotoxicity parameter determined from Redirected Lysis assay with T cells on KMS-12-BM, MOLP-8 and NCI-H929 cell lines for 48 h and using an Effector-to-Target ratio of 5:1. Each $EC_{50}$ value is the mean +/− standard deviation of maximum six included donors from three individual experiments. NQ stands for not quantifiable.

| | % Cytotoxicity $EC_{50}$ ± SD [pM] | | | |
|---|---|---|---|---|
| Cell lines/ Treatments | CD3/BCMA/ CD38-118 | CD3/BCMA/CD38-151 (C1-D6/E6-G6/ G6DU or CD3/BCMA/DU) | CD3/BCMA/CD38-149 (C1-D6/G6DU/ B3-C11 or CD3/DU/CD38) | CD3/BCMA/CD38-149 + CD3/BCMA/CD38-151 |
| KMS-12-BM | 2.2 ± 0.7 | 164 ± 56 | NQ | 172 ± 42 |
| MOLP-8 | 0.3 ± 0.1 | 399 ± 169 | 2'278 ± 320 | 452 ± 254 |
| NCI-H929 | 2.0 ± 0.5 | 229 ± 75 | NQ | 276 ± 95 |

EXAMPLE 22 (G): MMOAK ASSAY WITH HUMAN PBMCS AND MULTIPLE MYELOMA KMS-12-BM TUMOR CELLS

Materials and Methods

To evaluate the killing potency of CD3/BCMA/CD38-118 compared to the combination of the CD3×BCMA benchmark teclistamab and the anti-CD38 monoclonal benchmark daratumumab, MMoAK assays using human PBMCs were conducted on multiple myeloma KMS-12-BM cell line.

Human peripheral blood mononuclear cells (PBMCs) were isolated from buffy coats of heathy donors obtained from Epalinges (Switzerland) Transfusion Center using Ficoll density gradient isolation and frozen in CryoStor10 cell freezing medium (StemCell, #07930). Cells were thawed in a pre-warmed complete RPMI medium (RPMI supplemented with 10% heat inactivated fetal calf serum, 1% L-Glutamine, 1% Non-essential Amino Acids, 1% Sodium Pyruvate, and 1% Penicillin/Streptomycin) and rested overnight at $1.5 \times 10^6$ cells/ml. Twenty thousand target cells (KMS-12-BM, DSMZ, ACC 551, lot 9) labelled with cell proliferation dye eFluor 670 (ThermoFisher Scientific, 65-0840-85) were plated with one hundred thousand PBMC cells labelled with Cell Proliferation Dye eFluor 450 (ThermoFisher Scientific, 65-0842-85) reaching an effector-to-target ratio of 5:1. Serial dilutions of CD3/BCMA/CD38-118 and teclistamab starting from 10 nM, diluted by 10-fold, and a single dose of control antibodies (human IgG1 or CD3/BCMA/CD38-85, negative control) were added. Plates were incubated for 48 h, at 37° C., 5% $CO_2$ in a humidified atmosphere. Two different readouts were used to evaluate the killing of tumor target cells. The percentage of killing to No Ab (normalized to the no antibody condition) was determined by measuring the absolute count of live target cells (eFluor670+ cells) using the LIVE/DEAD fixable green dead cell Stain (ThermoFisher Scientific, L34970), and calculated as % of Killing to No Ab=[1−(Sample absolute counts)/(absolute counts in the presence of target and effector cells without treatment)]×100. The percentage of cytotoxicity was determined by measuring the % dead target or percentage of eFluor670+L/D green$^+$ cells. Two concentrations, 10 and 100 pM of CD3/BCMA/CD38-118 or teclistamab were chosen to evaluate the killing of CD3/BCMA/CD38-118 compared to the combination of teclistamab and daratumumab, which was dosed at 100 nM. Killing values from 10 pM and 100 pM concentrations were plotted in histograms. Statistical analyses were conducted on those plotted values (9 donors) using a donor-paired Repeated measures ANOVA test, followed by post-hoc Tukey's HSD comparisons (*P<0.05).

Figure 41A:
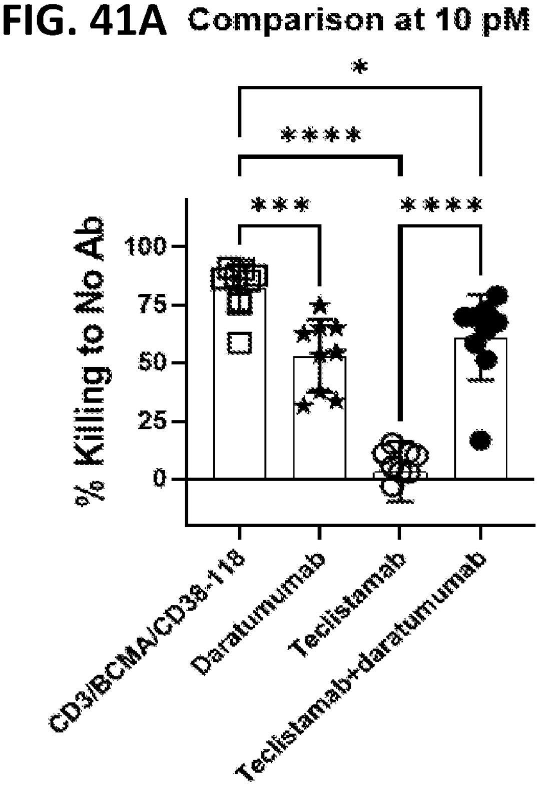
Figure 41B:
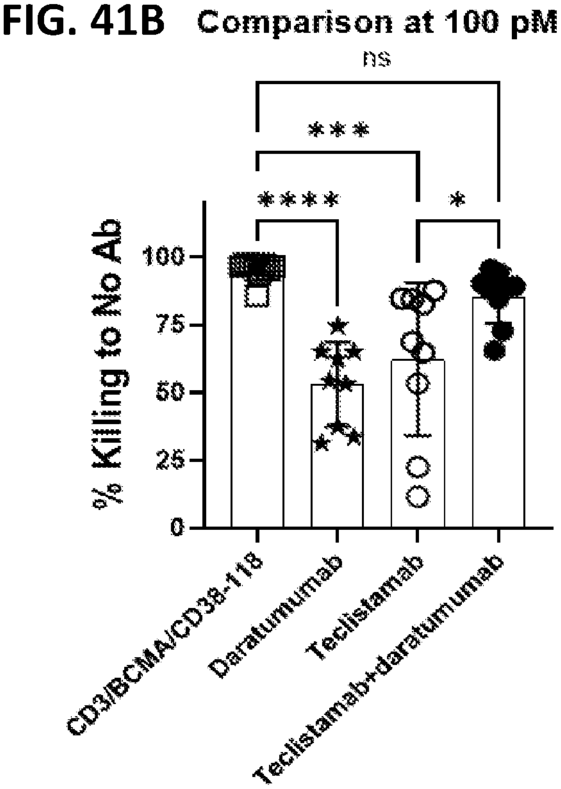
Figure 41C:
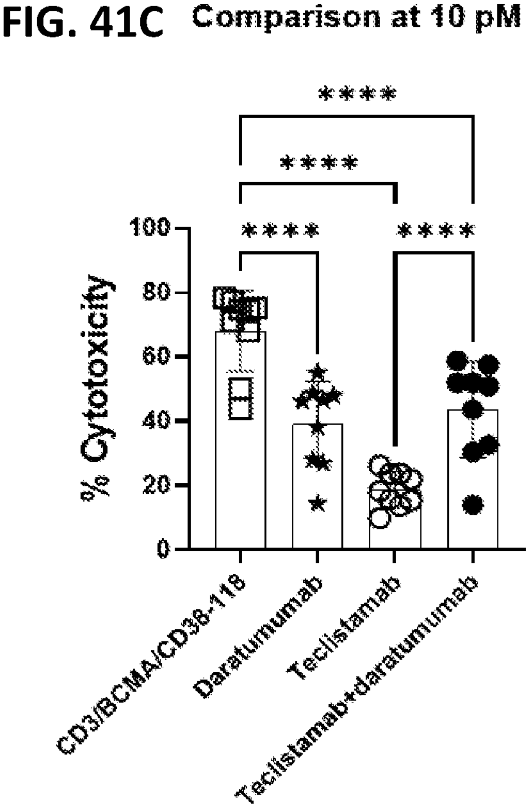
Figure 41D:
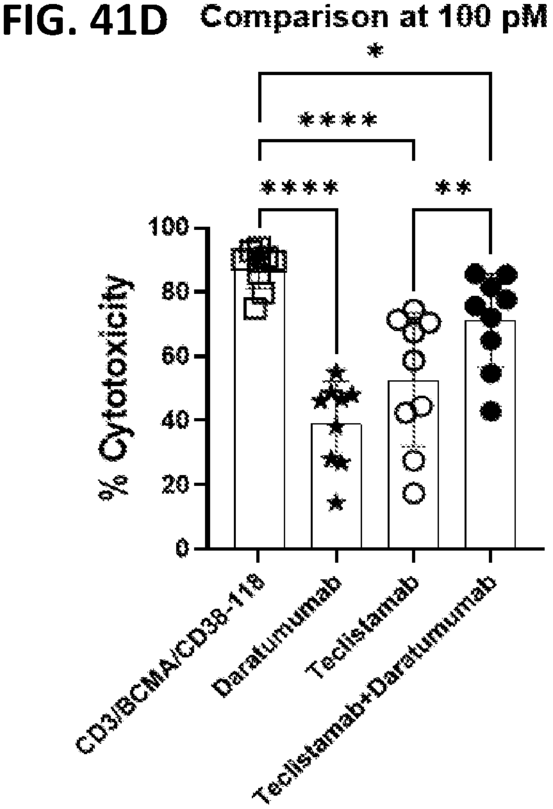

Killing values induced by 10 pM or 100 pM of CD3/BCMA/CD38-118 and teclistamab, as well as daratumumab at 100 nM and the combination of teclistamab and daratumumab were plotted using Prism software (GraphPad) as depicted in FIG. 41A and FIG. 41B (% killing to No Ab) and FIG. 41C and FIG. 41D (% cytotoxicity), 10 pM results are presented in FIGS. 41A-41C and 100 pM results FIG. 41B and FIG. 41D. Three independent experiments were performed.

Results and Conclusions

Considering the percentages of killing to No Ab, results in FIG. 41A and FIG. 41B show the percentage of killing for CD3/BCMA/CD38-118 (at 10 or 100 pM), daratumumab at 100 nM, teclistamab (at 10 or 100 pM) and the combination of daratumumab and teclistamab. At 10 and 100 pM, the killing of teclistamab was slightly improved when combined with daratumumab at 100 nM as described by Frerichs et al [Frerichs et al., 2020, Clin. Cancer Res., 26(9):2203-15]. At 10 pM (FIG. 41A), CD3/BCMA/CD38-118 showed statistically superior killing of KMS-12-BM cells compared to daratumumab, teclistamab and the combination of both. At 100 pM (FIG. 41B), CD3/BCMA/CD38-118 showed statistically superior killing compared to daratumumab and teclistamab. Comparison of CD3/BCMA/CD38-118 to the combination of both was not statistically different at this concentration (p-value=0.5082).

When the percentage of cytotoxicity was used as readout for killing, the results were very similar. FIG. 41C and FIG. 41D show the percentage of killing for CD3/BCMA/CD38-118 (at 10 or 100 pM), daratumumab at 100 nM, teclistamab (at 10 or 100 pM) and the combination of daratumumab and teclistamab. At 10 and 100 pM, the killing of teclistamab was slightly improved when combined with daratumumab at 100 nM. At 10 pM (FIG. 41C) and 100 pM (FIG. 41D) concentrations, CD3/BCMA/CD38-118 showed statistically superior killing of KMS-12-BM cells compared to daratumumab, teclistamab and the combination of both.

Taken together and considering both percentage of killing to No Ab and percentage of cytotoxicity, CD3/BCMA/CD38-118 demonstrated a statistically superior killing potency against the KMS-12-BM cell line compared to daratumumab at 100 nM, teclistamab at 10 or 100 pM and the combination of daratumumab at 100 nM and teclistamab at 10 or 100 pM.

EXAMPLE 22 (H): KILLING ASSAYS USING PATIENT SAMPLES

Material and Methods

Killing Assays Using Patient Samples

To further characterize CD3/BCMA/CD38-118 compared to a CD3×BCMA benchmark (teclistamab), killing assays were conducted on Bone Marrow Mononuclear Cells (BMMC) or blood samples from patients with Multiple Myeloma (Newly Diagnosed, smoldering and relapse/refractory) as well as patients with Plasma Cell Leukemia (PCL) and Waldenstrom macroglobulinemia to test the ability of CD3/BCMA/CD38-118 to kill multiple myeloma cells by redirecting patient T cells.

BMMC were isolated from bone marrow aspirate or PBMC from blood of patient samples, collected from the University Hospital of Geneva, Switzerland and the Oxford University Hospitals (OUH, UK) using Ficoll density gradient isolation. The assay was conducted in complete RPMI medium (RPMI supplemented with 10% human serum, 3 ng/ml of IL-6, 1% L-Glutamine, 1% Non-Essential Amino Acids, 1% Sodium Pyruvate and 1% Penicillin/Streptomycin). One to two hundred thousand cells were incubated with serial dilutions of CD3/BCMA/CD38-118, benchmarks (teclistamab) starting from 10 to 100 nM and diluted by 10-fold, and a single dose of control antibodies (CD3/BCMA/CD38-85, human IgG4, human IgG1). Plates were incubated for 17-22 h at 37° C., 5% $CO_2$ in a humidified atmosphere. After the incubation period, the killing assay readout was evaluated by measuring T cell cytotoxic activity against CD138$^+$ cells with a 10-colour panel including a CD138 marker for tumor cells. Tumor cell killing was determined by measuring the absolute count of live CD138$^+$ cells using the LIVE/DEAD Fixable Blue Dead Cell Stain (ThermoFisher Scientific, L23105, 1/500), and calculated as % of Killing to No Ab=[1−(absolute living $CD138^+$ counts)/(absolute living $CD138^+$ counts in BMMCs without treatment)]×100. Killing curves were plotted using Prism software (GraphPad) as depicted in FIGS. 42A-42D (% Killing of CD138+ cells to No Ab). Percentages of killing to No Ab shown in FIG. 43 were compared using a paired two-way ANOVA model followed by Sidak's multiple post-hoc comparison (*P<0.05). The list of samples is summarized in the Table 46. Eleven independent experiments were performed with eleven patient samples.

TABLE 46

List of patient samples included in the study (nomenclature in FIG. 42A-D)

| Sample ID | Patient status |
|---|---|
| Sample 1 | Plasma Cell Leukemia (PCL) |
| Sample 2 | Waldenstrom macroglobulinemia |
| Sample 3 | Relapsed/Refractory Multiple Myeloma (r/r MM) |
| Sample 4 | Smoldering Multiple Myeloma (Smoldering MM) |
| Sample 5 | Smoldering Multiple Myeloma (Smoldering MM) |
| Sample 6 | Multiple Myeloma - Newly diagnosed |
| Sample 7 | Multiple Myeloma - Newly diagnosed |
| Sample 8 | Multiple Myeloma - Newly diagnosed |
| Sample 9 | Relapsed/Refractory Multiple Myeloma (r/r MM) |
| Sample 10 | Relapsed/Refractory Multiple Myeloma (r/r MM) |
| Sample 11 | Multiple Myeloma - Newly diagnosed |

Results and Conclusion

Results in FIGS. 42A-42D show the killing curves of CD138+ cells in four patient samples for CD3/BCMA/CD38-118 and the CD3×BCMA benchmark teclistamab. Across all samples tested from various diseases, Smoldering MM (A), Newly Diagnosed MM (B), r/r MM (C) and PCL (D), CD3/BCMA/CD38-118 showed superior killing potency compared to teclistamab. FIGS. 42B and 42D show the killing curves of $CD138^+$ cells in a patient sample with Newly diagnosed MM and Plasma Cell Leukemia (PCL), $EC_{50}$ values of killing associated with those curves shows a 115- or 38-fold increase of killing potency for CD3/BCMA/CD38-118 (EC50=7.2 and 9.1 pM) compared to teclistamab (EC50=829 and 351.7 pM). Additionally, as shown in FIG. 43, CD3/BCMA/CD38-118 candidate statistically triggered the strongest killing potency compared to teclistamab, for each tested concentration. At 0.1 and 0.01 nM, teclistamab showed around 8-24% killing of $CD138^+$ cells, while CD3/BCMA/CD38-118 maintained 41-56% of killing at the lowest dose.

EXAMPLE 23: EFFICACY OF TREAT CD3/BCMA/CD38-118, BEAT CD3/CD38 AND TECLISTAMAB IN AN IN VIVO $BCMA^{LOW}$ $CD38^{LOW}$ KMS-12-BM TUMOR MOUSE MODEL

Material and Methods

Animal Husbandry and Blood Sampling

In vivo experiments were performed in female 6-7-week-old immune-deficient NSG (NOD·Cg-$Prkdc^{scid}Il2rg^{tm1Wjl}$/SzJ) mice from CHARLES RIVER LABORATORIES France. All mice were maintained under standardized environmental conditions in rodent cages (20±1° C. room temperature, 50±10% relative humidity, 12 hours light dark cycle). Mice received irradiated food and bedding and 0.22 am-filtered drinking water. Animal experiments were conducted in accordance with protocols approved by the veterinary authorities of the Canton de Vaud, Switzerland. Exclusion criteria: if animals demonstrated signs of graft versus host disease (GVHD), a common effect in systemic peripheral blood mononuclear cells (PBMCs) humanized mice, they were euthanized before study endpoint (or before tumor volume reached 1000 $mm^3$) and were excluded from the analysis.

KSM-12-BM Subcutaneous Tumor with Systemic PBMC Humanized Mouse Model

Three experiments were conducted and were named respectively KMS_12, KMS_13 and KMS_14 studies. KMS_12 study. Dose escalation of TREAT CD3/BCMA/CD38-118, BEAT CD3/CD38 and Teclistamab in KMS-12-BM tumors. NSG female mice were engrafted subcutaneously (s.c.) with $1\times10^7$ KMS-12-BM multiple myeloma (MM) tumor cells and inoculated intraperitoneally (i.p.) with $1\times10^7$ PBMCs from a healthy human donor (Donor C) on the same day (8 mice per group; 10 groups). Mice were randomized based on the tumor volume 8 days after the xenograft and were injected intravenously (i.v.) on the following day with Vehicle, CD3/BCMA/CD38-118 (at 0.5, 0.1 and 0.02 mg/kg), BEAT CD3/CD38 and Teclistamab (at 2.5, 0.5 and 0.1 mg/kg) once per week for 3 weeks. Tumor volume was evaluated based on tumor size measurement with a caliper three times per week. Ex vivo analysis was performed on day 13 (n=2-3 mice per group) in selected groups. Spleens and tumors were harvested and FACS analysis was performed. Mouse serum was collected on day 13, 14 or 21 to determine the molecule's trough concentration using a specific capture ELISA method for each molecule (please refer to ELISA assay section of the material and methods). When mice reached a tumor volume of 1000 $mm^3$ before study termination (day 21), collection of corresponding samples was done prior to third dose (day 13/14). This experiment was done once.

KMS_13 study. Evaluation of the in vivo efficacy of BEAT CD3/CD38 in KMS-12-BM tumors, in the presence or absence of intravenous immunoglobulin (IVIG). NSG female mice were engrafted s.c. with $1\times10^7$ KMS-12-BM tumor cells and inoculated i.p. with $1\times10^7$ PBMCs from a healthy human donor (Donor E) on the same day (3-5 mice per group; 5 groups). Mice were randomized based on the tumor volume 8 days after the xenograft and were injected i.v. on the same day (day −1) with 200 mg/kg of IVIG (Privigen) or PBS and then twice per week. Dosing (i.v.) of Vehicle, CD3/BCMA/CD38-118 at 0.5 mg/kg or BEAT CD3/CD38 at 0.5 mg/kg was performed on day zero and day seven. Mice treated with CD3/BCMA/CD38-118 were evaluated in the absence of IVIG, while the Vehicle and BEAT CD3/CD38 treated groups were evaluated both in the presence and absence of IVIG. Tumor volume was evaluated based on tumor size measurement with a caliper three times per week. Ex vivo analysis was performed on day 11 (n=3-5 mice per group). Spleens and tumors were harvested and FACS analysis was performed. This experiment was done once.

KMS_14 study. Dose escalation of TREAT CD3/BCMA/CD38-118, BEAT CD3/CD38 and Teclistamab in KMS-12-BM tumors, in the presence of IVIG. NSG female mice were engrafted s.c. with $1\times10^7$ KMS-12-BM tumor cells and inoculated i.p. with $1\times10^7$ PBMCs from a healthy human donor (Donor C) on the same day (6-8 mice per group; 10 groups). Mice were randomized based on the tumor volume 8 days after the xenograft and were injected i.v. on the same day (day −1) with 200 mg/kg of IVIG (Privigen) and then once per week for 3 weeks (day −1, 6 and 13). Dosing (i.v.) of Vehicle, CD3/BCMA/CD38-118 and BEAT CD3/CD38 at 0.5, 0.1 and 0.02 mg/kg and Teclistamab at 2.5, 0.5 and 0.1 mg/kg was performed on day 0, 7 and 14 (once per week for 3 weeks). Tumor volume was evaluated based on tumor size measurement with a caliper three times per week. Mouse serum was collected on day 21 (1 week post last dose) to determine the molecule's trough concentration using a specific capture ELISA method for each molecule (please refer to ELISA assay section of the material and methods). This experiment was done once.

T Cell Engager Pharmacokinetics

Serum concentrations of each molecule were determined using a specific antigen capture ELISA. In brief, a 96-well Meso Scale Discovery (MSD) plate (MSD, Ref. L15XA-3) is coated overnight at 2-8° C. with target antigen: BCMA Protein, His Tag (ACRO Biosystems, Ref. BCA-H522γ) for CD3/BCMA/CD38-118 (at 2 μg/mL) and Teclistamab (at 1 μg/mL); or CD38 Protein, His Tag (ACRO Biosystems, Ref. CD8-H82E7) for BEAT CD3/CD38 (at 1 μg/mL). The next day, non-specific sites are saturated with 1% (w/v) casein blocking buffer (Thermo Scientific, Ref. 37583) for 1 h at room temperature (RT). Next, the target antigen immobilized on the surface of the 96-well MSD plate is used to capture antibody in the diluted serum samples (standards, quality controls and study samples) for 1 h at RT. Bound antibody is detected with sulfo-tagged detection antibody for 1 h at RT: Sulfo-tagged anti-ID CD38 (P1188: GBR1342_aID(9G7)_6B12, generated in house) for CD3/BCMA/CD38-118 or Biotinylated anti-ID CD3 IgG (P1362: GBR430aID (SP34), generated in house) +Streptavidin Sulfo-Tag (MSD, Ref. R32AD-1) for BEAT CD3/CD38 and Teclistamab. Wells are washed between all steps with Phosphate Buffered Saline (PBS) supplemented with 0.1% TWEEN®-20 (Sigma, Ref. P1379). Positive signal is measured by an Electrochemiluminescence (ECL) response generated following the addition of 2×MSD Read Buffer T (MSD, Ref. R92TC-2) using an MSD plate reader: electricity is applied to the plate electrodes by the MSD instrument leading to light emission by SULFO-TAG labels. Light intensity is then measured at ~620 nm and is proportional to the concentration of antibody in the samples. The concentration of antibody in unknown samples is then interpolated from calibration curve using four parameter regression model with 1/Y2 weighting. Data were analyzed using Excel and GraphPad Prism 9.

Sample Preparation for Flow Cytometry

Tumors were harvested and dissociated with enzymatic cocktail from human tumor dissociation kit (Miltenyi Biotec, Ref. 130-095-929) in a GentleMACS dissociator. Cell suspensions were then filtered using a 70 μm cell strainer and centrifuged. Tumor supernatant was discarded and cell pellet was resuspended, cells counted and adjusted to $10\times10^6$ cell/mL in PBS supplemented with 2% FCS (FACS buffer). Cell suspensions from spleen were obtained by mashing through a 70 μM nylon cell strainer. Red blood cells (RBCs) were lysed with RBC lysis buffer (eBioscience, Ref. 00-4300-54) for 4 min at RT and the reaction was stopped with RMPI 10% FBS followed by centrifugation. The cell pellet was resuspended, cells were counted and resuspended in FACS buffer at $10\times10^6$ cell/mL. Tumor and spleen cell suspensions were then stained for immune cell profiling. In brief, cell suspensions were incubated with viability dye, human, and mouse Fc Block for 15 min at 4° C. in FACS buffer, followed by surface staining with antibody cocktail (or relative controls) for 30 min at 4° C. in FACS buffer. Samples were acquired on the Northern lights instrument (CYTEK) and data were analyzed using FlowJo v10.7.2 and GraphPad Prism 9.

Statistical Analysis

Data were analyzed using GraphPad Prism 9 software. Differences in tumor volume were determined using a one-way (for a given day) or two-way (for the entire treatment days) analysis of variance (ANOVA) with Tukey's multiple comparison test. P value <0.05 was considered statistically significant, with the level of significancy represented by asterisks as followed: ns p>0.05; * p<0.05;  p<0.01; * p<0.001; **** p<0.0001. The percentage (%) of Tumor growth inhibition (TGI), an indication of antitumor activity, was calculated as: TGI (%)=100×(1−T/C), where T and C are the mean tumor volume of the treated and vehicle control groups, respectively, on a given day. For the datasets where animals reached maximum tumor size (1000 $mm^3$) prior to study endpoint, last observation carried forward (LOCF) was used to display the tumor volumes in graphs and to calculate the percentage of TGI.

Results and Conclusions

The in vivo efficacy of CD3/BCMA/CD38-118 in comparison to BEAT CD3/CD38 and the CD3×BCMA bispecific reference antibody teclistamab (Pillarisetti K. et al., 2020) was evaluated at various dose levels in a subcutaneous KMS-12-BM tumor xenograft model in NSG mice in a therapeutic setting. Human myeloma KMS-12-BM tumor cells with low expression levels of BCMA and CD38 were injected subcutaneously (s.c.) in NSG mice ($1\times10^7$ cells). In parallel, human PBMCs from a healthy human donor (Donor C) were injected intraperitoneally (i.p) on the same day ($1\times10^7$ cells). Mice were randomized 8 days after tumor cell injection when the average tumor volume reached 187 mm3 in various treatment groups (day −1). Therapeutic treatments of CD3/BCMA/CD38-118 (at 0.5, 0.1 and 0.02 mg/kg), BEAT CD3/CD38 and teclistamab (at 2.5, 0.5 and 0.1 mg/kg) were injected intravenously (i.v.) on the following day and once per week for 3 weeks (day 0, 7 and 14).

As previously observed, 12 days post treatment start, CD3/BCMA/CD38-118 induced KMS-12-BM tumor regression in a dose dependent manner (FIG. 44A, top), with 97.4%, 76.5% and 45.5% of tumor growth inhibition (TGI, compared to vehicle) in mice treated with 0.5, 0.1 and 0.02 mg/kg doses, respectively. In contrast, treatment with BEAT CD3/CD38 or teclistamab failed to control tumor progression even at highest doses (FIG. 44A, middle and bottom). At 2.5 mg/kg, the TGI compared to vehicle was −7.1% for BEAT CD3/CD38 and −4.6% for teclistamab, showing no differences compared to control mice (Table 47). Surprisingly, while not statistically significant compared to vehicle treated mice, low doses (0.1 mg/kg) of BEAT CD3/CD38 and teclistamab showed a trend for higher efficacy compared to top doses (with 37% and 19.8% of TGI, respectively) (FIG. 44A, Table 47).

At a dose level of 0.5 or 0.1 mg/kg, BEAT CD3/CD38 and teclistamab did not significantly inhibit the growth of KMS-12-BM tumors in NSG mice, while CD3/BCMA/CD38-118 showed considerably higher potency at both doses (FIG. 44B, Table 47).

TABLE 47

Statistical analysis of FIG. 43 (A, B). Differences in tumor volume were determined using a two-way analysis of variance (ANOVA) with Tukey's multiple comparison test, n = 8 mice per group. P value < 0.05 was considered statistically significant, with the level of significancy represented by asterisks as followed: ns $p \geq 0.05$; * $p < 0.05$;  $p < 0.01$; * $p < 0.001$; **** $p < 0.0001$.

| Group comparison | Mean Diff. ($mm^3$) | 95.00% CI of diff. | Summary | Adjusted P Value |
|---|---|---|---|---|
| Vehicle vs. 0.5 mg/kg CD3/BCMA/CD38-118 | 230.5 | 125.4 to 335.6 | **** | <0.0001 |
| Vehicle vs. 0.1 mg/kg CD3/BCMA/CD38-118 | 176 | 70.94 to 281.1 | **** | <0.0001 |
| Vehicle vs. 0.02 mg/kg CD3/BCMA/CD38-118 | 104.5 | −0.5785 to 209.6 | ns | 0.0527 |
| Vehicle vs. 2.5 mg/kg BEAT CD3/CD38 | −27.52 | −132.6 to 77.57 | ns | 0.9981 |
| Vehicle vs. 0.5 mg/kg BEAT CD3/CD38 | 59.1 | −45.98 to 164.2 | ns | 0.7436 |
| Vehicle vs. 0.1 mg/kg BEAT CD3/CD38 | 61.83 | −43.25 to 166.9 | ns | 0.69 |
| Vehicle vs. 2.5 mg/kg Teclistamab | 21.93 | −83.16 to 127.0 | ns | 0.9997 |
| Vehicle vs. 0.5 mg/kg Teclistamab | 19.05 | −86.04 to 124.1 | ns | >0.9999 |
| Vehicle vs. 0.1 mg/kg Teclistamab | 67.69 | −37.39 to 172.8 | ns | 0.5666 |
| 0.5 mg/kg CD3/BCMA/CD38-118 vs. 0.1 mg/kg CD3/BCMA/CD38-118 | −54.49 | −159.6 to 50.59 | ns | 0.8241 |
| 0.5 mg/kg CD3/BCMA/CD38-118 vs. 0.02 mg/kg CD3/BCMA/CD38-118 | −126 | −231.1 to −20.93 | ** | 0.006 |
| 0.5 mg/kg CD3/BCMA/CD38-118 vs. 2.5 mg/kg BEAT CD3/CD38 | −258 | −363.1 to −153.0 | **** | <0.0001 |
| 0.5 mg/kg CD3/BCMA/CD38-118 vs. 0.5 mg/kg BEAT CD3/CD38 | −171.4 | −276.5 to −66.33 | **** | <0.0001 |
| 0.5 mg/kg CD3/BCMA/CD38-118 vs. 0.1 mg/kg BEAT CD3/CD38 | −168.7 | −273.8 to −63.60 | **** | <0.0001 |
| 0.5 mg/kg CD3/BCMA/CD38-118 vs. 2.5 mg/kg Teclistamab | −208.6 | −313.7 to −103.5 | **** | <0.0001 |
| 0.5 mg/kg CD3/BCMA/CD38-118 vs. 0.5 mg/kg Teclistamab | −211.5 | −316.6 to −106.4 | **** | <0.0001 |
| 0.5 mg/kg CD3/BCMA/CD38-118 vs. 0.1 mg/kg Teclistamab | −162.8 | −267.9 to −57.74 | **** | <0.0001 |
| 0.1 mg/kg CD3/BCMA/CD38-118 vs. 0.02 mg/kg CD3/BCMA/CD38-118 | −71.52 | −176.6 to 33.57 | ns | 0.4845 |
| 0.1 mg/kg CD3/BCMA/CD38-118 vs. 2.5 mg/kg BEAT CD3/CD38 | −203.5 | −308.6 to −98.46 | **** | <0.0001 |
| 0.1 mg/kg CD3/BCMA/CD38-118 vs. 0.5 mg/kg BEAT CD3/CD38 | −116.9 | −222.0 to −11.84 | * | 0.0159 |
| 0.1 mg/kg CD3/BCMA/CD38-118 vs. 0.1 mg/kg BEAT CD3/CD38 | −114.2 | −219.3 to −9.106 | * | 0.021 |
| 0.1 mg/kg CD3/BCMA/CD38-118 vs. 2.5 mg/kg Teclistamab | −154.1 | −259.2 to −49.02 | *** | 0.0002 |
| 0.1 mg/kg CD3/BCMA/CD38-118 vs. 0.5 mg/kg Teclistamab | −157 | −262.1 to 51.89 | *** | 0.0001 |
| 0.1 mg/kg CD3/BCMA/CD38-118 vs. 0.1 mg/kg Teclistamab | −108.3 | −213.4 to −3.248 | * | 0.0371 |
| 0.02 mg/kg CD3/BCMA/CD38-118 vs. 2.5 mg/kg BEAT CD3/CD38 | −132 | −237.1 to −26.94 | ** | 0.003 |
| 0.02 mg/kg CD3/BCMA/CD38-118 vs. 0.5 mg/kg BEAT CD3/CD38 | −45.4 | −150.5 to 59.68 | ns | 0.9352 |
| 0.02 mg/kg CD3/BCMA/CD38-118 vs. 0.1 mg/kg BEAT CD3/CD38 | −42.67 | −147.8 to 62.41 | ns | 0.9557 |
| 0.02 mg/kg CD3/BCMA/CD38-118 vs. 2.5 mg/kg Teclistamab | −82.58 | −187.7 to 22.50 | ns | 0.2726 |
| 0.02 mg/kg CD3/BCMA/CD38-118 vs. 0.5 mg/kg Teclistamab | −85.46 | −190.5 to 19.63 | ns | 0.228 |
| 0.02 mg/kg CD3/BCMA/CD38-118 vs. 0.1 mg/kg Teclistamab | −36.82 | −141.9 to 68.27 | ns | 0.9833 |
| 2.5 mg/kg BEAT CD3/CD38 vs. 0.5 mg/kg BEAT CD3/CD38 | 86.62 | −18.46 to 191.7 | ns | 0.2114 |
| 2.5 mg/kg BEAT CD3/CD38 vs. 0.1 mg/kg BEAT CD3/CD38 | 89.35 | −15.73 to 194.4 | ns | 0.1757 |
| 2.5 mg/kg BEAT CD3/CD38 vs. 2.5 mg/kg Teclistamab | 49.44 | −55.64 to 154.5 | ns | 0.8941 |
| 2.5 mg/kg BEAT CD3/CD38 vs. 0.5 mg/kg Teclistamab | 46.57 | −58.52 to 151.7 | ns | 0.9247 |
| 2.5 mg/kg BEAT CD3/CD38 vs. 0.1 mg/kg Teclistamab | 95.21 | −9.875 to 200.3 | ns | 0.1142 |
| 0.5 mg/kg BEAT CD3/CD38 vs. 0.1 mg/kg BEAT CD3/CD38 | 2.73 | −102.4 to 107.8 | ns | >0.9999 |

TABLE 47-continued

Statistical analysis of FIG. 43 (A, B). Differences in tumor volume were determined using a two-way analysis of variance (ANOVA) with Tukey's multiple comparison test, n = 8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| Group comparison | Mean Diff. ($mm^3$) | 95.00% CI of diff. | Summary | Adjusted P Value |
|---|---|---|---|---|
| 0.5 mg/kg BEAT CD3/CD38 vs. 2.5 mg/kg Teclistamab | −37.18 | −142.3 to 67.91 | ns | 0.9822 |
| 0.5 mg/kg BEAT CD3/CD38 vs. 0.5 mg/kg Teclistamab | −40.06 | −145.1 to 65.03 | ns | 0.9705 |
| 0.5 mg/kg BEAT CD3/CD38 vs. 0.1 mg/kg Teclistamab | 8.587 | −96.50 to 113.7 | ns | >0.9999 |
| 0.1 mg/kg BEAT CD3/CD38 vs. 2.5 mg/kg Teclistamab | −39.91 | −145.0 to 65.18 | ns | 0.9712 |
| 0.1 mg/kg BEAT CD3/CD38 vs. 0.5 mg/kg Teclistamab | −42.79 | −147.9 to 62.30 | ns | 0.955 |
| 0.1 mg/kg BEAT CD3/CD38 vs. 0.1 mg/kg Teclistamab | 5.858 | −99.23 to 110.9 | ns | >0.9999 |
| 2.5 mg/kg Teclistamab vs. 0.5 mg/kg Teclistamab | −2.877 | −108.0 to 102.2 | ns | >0.9999 |
| 2.5 mg/kg Teclistamab vs. 0.1 mg/kg Teclistamab | 45.77 | −59.32 to 150.9 | ns | 0.932 |
| 0.5 mg/kg Teclistamab vs. 0.1 mg/kg Teclistamab | 48.64 | −56.44 to 153.7 | ns | 0.9033 |

Serum concentrations of all three molecules were determined at day 13/14, prior to a third dose, or 1 week later (day 21). Dose (5-fold) to exposure levels (6 to 11-fold) was relatively linear for most doses and molecules, except for CD3/BCMA/CD38-118 at 0.02 mg/kg (FIG. 44C), as previously observed. At corresponding doses, serum trough concentrations were similar across treatment groups. As such, decreased efficacy of BEAT CD3/CD38 and teclistamab could not be explained by differences in PK, as similar trough levels were observed in mice treated with CD3/BCMA/CD38-118 (FIGS. 44A-44C).

To investigate the cause for the lack of in vivo efficacy of BEAT CD3/CD38 and teclistamab in this model, immune cell profiling was performed on day 13 in tumors and spleens of mice from selected groups (n=2-3 mice/group) (FIGS. 45A-45D). High doses (with no tumor control) and low doses (with a trend for better efficacy) of both molecules were chosen, while only a single low dose treated mouse was selected for CD3/BCMA/CD38-118 since tumors had been cleared at all other doses and complete regression represents high efficacy at this timepoint for this molecule. FACS analysis demonstrated a decrease of both total human leucocytes ($CD45^+$) and human T cells ($TCR\alpha\beta^+$) per gram of tumor in mice treated with 2.5 mg/kg of BEAT CD3/CD38 and teclistamab, compared to vehicle, CD3/BCMA/CD38-118 treated or mice treated with low doses (0.1 mg/kg) of the same molecules (FIGS. 45A, 45B, 45C). Similar data was observed for the high doses of BEAT CD3/CD38 and teclistamab in the spleen (FIG. 45D). A ~3000-fold reduction in the peripheral T cell compartment could be observed compared to vehicle treated mice, which when taken with the reduced levels of T cells seen in the tumor is consistent with depletion of T cells in vivo. Lower doses of BEAT CD3/CD38 and teclistamab did not induce depletion of tumor infiltrating T cells (FIG. 45C), with low efficacy (FIG. 44A) and T cell persistence attributed to low exposure (FIG. 44C).

CD3/BCMA/CD38-118 contains fully Fc silencing mutations (LALA-P329A) (Schlothauer T. et al., 2016), thus lacking Fc/Fcγ receptor (FcγR) interactions and consequently FcγR-mediated effector functions. However, the Fc portion of both BEAT CD3/CD38 (IgG1) and teclistamab (IgG4) is only partially silenced (LALA mutation) (Pillarisetti K. et al., 2020), potentially allowing for residual Fc-mediated activity. Together with the data above, this suggests that failure of tumor control from BEAT CD3/CD38 and teclistamab could be caused by depletion of T cells as a result of residual Fc activity. The treatment-antibody dose dependence of tumor infiltrating T cell depletion is consistent with this explanation and the lack of depletion with CD3/BCMA/CD38-118 implicates the residual Fc activity.

We thus hypothesize that pre-treatment with intravenous immunoglobulin (IVIG), comprising pooled human IgG antibodies from the serum of healthy donors, could provide competition for binding to FcγR on macrophages, preventing binding to treatment antibody and consequent Fc-mediated toxicity.

To corroborate this hypothesis, an experiment was performed comparing the efficacy of BEAT CD3/CD38 in the presence or absence of IVIG in vivo. NSG female mice were engrafted s.c. with $1\times10^7$ KMS-12-BM tumor cells and inoculated i.p. with $1\times10^7$ PBMCs from a healthy human donor (Donor E) on the same day. Mice were randomized 8 days later when the average tumor volume reached 120 mm3 in various treatment groups (day −1) and injected i.v. on the same day with 200 mg/kg of IVIG (Privigen) or PBS and then twice per week. Dosing (i.v.) of Vehicle, CD3/BCMA/CD38-118 at 0.5 mg/kg or BEAT CD3/CD38 at 0.5 mg/kg was performed on day 0 and 7. Mice treated with CD3/BCMA/CD38-118 were evaluated in the absence of IVIG, while the Vehicle and BEAT CD3/CD38 treated groups were evaluated both in the presence and absence of IVIG.

No statistical differences in tumor volume were observed in vehicle treated mice with or without pre-treatment of IVIG in vivo (FIGS. 46A, 46; Table 48), showing that IVIG does not impact the kinetics of KMS-12-BM tumor growth. In the presence of IVIG, treatment with BEAT CD3/CD38 induced tumor regression similarly to CD3/BCMA/CD38-118 (FIG. 46A, Table 48), with 93.1% and 90.8% of tumor growth inhibition at day 11, respectively. In contrast, treatment with BEAT CD3/CD38 without IVIG did not significantly inhibit the growth of KMS-12-BM tumors in NSG mice compared to vehicle treated mice (FIGS. 46A, 46B; Table 48 and Table 49), as previously observed.

TABLE 48

Statistical analysis of FIG. 46(A). Differences in tumor volume were determined using a two-way analysis of variance (ANOVA) with Tukey's multiple comparison test, n = 3-5 mice per group. P value < 0.05 was considered statistically significant, with the level of significancy represented by asterisks as followed: ns p ≥ 0.05; * p < 0.05;  p < 0.01; * p < 0.001; **** p < 0.0001.

| Group comparison | Mean Diff. ($mm^3$) | 95.00% CI of diff. | Summary | Adjusted P Value |
|---|---|---|---|---|
| Vehicle vs. Vehicle + IVIG | 39.75 | −31.86 to 111.4 | ns | 0.5431 |
| Vehicle vs. 0.5 mg/kg CD3/BCMA/CD38-118 | 159.7 | 84.78 to 234.6 | **** | <0.0001 |
| Vehicle vs. 0.5 mg/kg BEAT CD3/CD38 | 44.1 | −27.51 to 115.7 | ns | 0.437 |
| Vehicle vs. 0.5 mg/kg BEAT CD3/CD38 + IVIG | 175 | 103.4 to 246.6 | **** | <0.0001 |
| Vehicle + IVIG vs. 0.5 mg/kg CD3/BCMA/CD38-118 | 119.9 | 54.14 to 185.7 | **** | <0.0001 |
| Vehicle + IVIG vs. 0.5 mg/kg BEAT CD3/CD38 | 4.349 | −57.67 to 66.37 | ns | 0.9997 |
| Vehicle + IVIG vs. 0.5 mg/kg BEAT CD3/CD38 + IVIG | 135.3 | 73.26 to 197.3 | **** | <0.0001 |
| 0.5 mg/kg CD3/BCMA/CD38-118 vs. 0.5 mg/kg BEAT CD3/CD38 | −115.6 | −181.3 to −49.79 | **** | <0.0001 |
| 0.5 mg/kg CD3/BCMA/CD38-118 vs. 0.5 mg/kg BEAT CD3/CD38 + IVIG | 15.36 | −50.42 to 81.14 | ns | 0.9674 |
| 0.5 mg/kg BEAT CD3/CD38 vs. 0.5 mg/kg BEAT CD3/CD38 + IVIG | 130.9 | 68.91 to 192.9 | **** | <0.0001 |

TABLE 49

Statistical analysis of FIG. 46(B). Differences in tumor volume at day 11 (study endpoint) were determined using a one-way analysis of variance (ANOVA) with Tukey's multiple comparison test, n = 3-5 mice per group. P value < 0.05 was considered statistically significant, with the level of significancy represented by asterisks as followed: ns p ≥ 0.05; * p < 0.05;  p < 0.01; * p < 0.001; **** p < 0.0001.

| Group comparison | Mean Diff. ($mm^3$) | 95.00% CI of diff. | Summary | Adjusted P Value |
|---|---|---|---|---|
| Vehicle vs. Vehicle + IVIG | 86.23 | −345.0 to 517.5 | ns | 0.9718 |
| Vehicle vs. 0.5 mg/kg CD3/BCMA/CD38-118 | 729.5 | 278.5 to 1181 | ** | 0.0011 |
| Vehicle vs. 0.5 mg/kg BEAT CD3/CD38 | 130.6 | −300.6 to 561.9 | ns | 0.8847 |
| Vehicle vs. 0.5 mg/kg BEAT CD3/CD38 + IVIG | 747.9 | 316.6 to 1179 | *** | 0.0005 |
| Vehicle + IVIG vs. 0.5 mg/kg CD3/BCMA/CD38-118 | 643.3 | 247.2 to 1039 | ** | 0.001 |
| Vehicle + IVIG vs. 0.5 mg/kg BEAT CD3/CD38 | 44.38 | −329.1 to 417.8 | ns | 0.996 |
| Vehicle + IVIG vs. 0.5 mg/kg BEAT CD3/CD38 + IVIG | 661.6 | 288.2 to 1035 | *** | 0.0004 |
| 0.5 mg/kg CD3/BCMA/CD38-118 vs. 0.5 mg/kg BEAT CD3/CD38 | −598.9 | −995.0 to −202.8 | ** | 0.0021 |
| 0.5 mg/kg CD3/BCMA/CD38-118 vs. 0.5 mg/kg BEAT CD3/CD38 + IVIG | 18.32 | −377.8 to 414.4 | ns | >0.9999 |
| 0.5 mg/kg BEAT CD3/CD38 vs. 0.5 mg/kg BEAT CD3/CD38 + IVIG | 617.2 | 243.8 to 990.7 | *** | 0.0009 |

Flow cytometry was performed on tumors and spleens to evaluate the degree of human immune cell infiltration in the presence/absence of IVIG (FIGS. 46C, 46D). At day 11, a -10-fold reduction of tumor infiltrating T cells (compared to CD3/BCMA/CD38-118) and a -60-fold reduction in the peripheral T cell compartment (compared to vehicle) was observed in mice treated with BEAT CD3/CD38 without IVIG, indicating T cell depletion and corroborating previous results. However, when mice were pre-treated with IVIG, treatment with BEAT CD3/CD38 increased the infiltration of T cells in the tumor microenvironment similarly to CD3/BCMA/CD38-118 (FIG. 46D). In addition, the peripheral T cell compartment was partially rescued upon administration of BEAT CD3/CD38+IVIG (FIG. 46D (continuation)).

In conclusion, IVIG rescued the T cell compartment and restored the in vivo efficacy of BEAT CD3/CD38. This innovative IVIG pre-treatment of humanized mice thus seems to provide competition for receptor engagement and avoid T cell depletion by a mostly silent antibody, providing a better modelling of the clinical situation. This method will thus allow a better pre-clinical modelling of T cell engagers and the direct comparison of antibodies with differing Fc regions/mutations in vivo.

Next, we re-evaluated the in vivo efficacy of CD3/BCMA/CD38-118, BEAT CD3/CD38 and teclistamab against KMS-12-BM tumors in the presence of IVIG (FIGS. 47A-47C). Human myeloma KMS-12-BM tumor cells with low expression levels of BCMA and CD38 were injected subcutaneously (s.c.) in NSG mice ($1\times10^7$ cells). In parallel, human PBMCs from a healthy human donor (Donor C) were injected intraperitoneally (i.p) on the same day ($1\times10^7$ cells). Mice were randomized 8 days after tumor cell injection when the average tumor volume reached 147 $mm^3$ and were injected i.v. on the same day (day −1) with 200 mg/kg of IVIG (Privigen) and then once per week for 3 weeks (day −1, 6 and 13). Dosing (i.v.) of Vehicle, CD3/BCMA/CD38-118 and BEAT CD3/CD38 at 0.5, 0.1 and 0.02 mg/kg and Teclistamab at 2.5, 0.5 and 0.1 mg/kg was performed on day 0, 7 and 14 (once per week for 3 weeks).

CD3/BCMA/CD38-118, BEAT CD3/CD38 and teclistamab were all able to control KMS-12-BM tumors in a dose dependent manner (FIG. 47A). CD3/BCMA/CD38-118 caused complete tumor regression in all 8 mice (8/8, 100% TGI) when dosed at 0.5 and 0.1 mg/kg and only showed a partial, statistically significant, efficacy of 36.5% TGI at a dose of 0.02 mg/kg. BEAT CD3/CD38 caused complete tumor regression in all eight mice (8/8, 100% TGI) when dosed at 0.5 mg/kg and significant tumor growth inhibition of 77.6% at a dose of 0.1 mg/kg, with 3 (out of 7) complete regressions. At a dose of 0.02 mg/kg it showed a significant inhibition of tumor growth of 39.4%. Teclistamab dosed at 2.5 mg/kg caused complete regression of 5/8 tumors with 88.3% TGI. At a dose of 0.5 mg/kg, teclistamab showed a tumor growth inhibition of 90.7% and a TGI of 30.8% at the lowest dose tested, 0.1 mg/kg. Statistics are summarized in Table 50.

When comparing the three molecules evaluated at 0.5 mg/kg no statistical differences were observed, with 100% of TGI for CD3/BCMA/CD38-118 and BEAT CD3/CD38 and 90.7% for teclistamab (FIG. 47B, left; Table 50). However, at a dose of 0.1 mg/kg, CD3/BCMA/CD38-118 showed statistically higher in vivo potency compared to BEAT CD3/CD38 and to an even higher extent compared to teclistamab (FIG. 47B, right; Table 50). At this dose, complete tumor regression was seen in 100% of mice (100% TGI) for CD3/BCMA/CD38-118; in 43% of mice (77.6% TGI) for BEAT CD3/CD38 and in 0% of mice (30.8% TGI) for teclistamab, which showed only partial efficacy.

TABLE 50

Statistical analysis of FIG. 47 (A, B). Differences in tumor volume were determined using a two-way analysis of variance (ANOVA) with Tukey's multiple comparison test, n = 6-8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| Group comparison | Mean Diff. ($mm^3$) | 95.00% CI of diff. | Summary | Adjusted P Value |
|---|---|---|---|---|
| Vehicle vs. 0.5 mg/kg CD3/BCMA/CD38-118 | 583.8 | 489.3 to 678.3 | **** | <0.0001 |
| Vehicle vs. 0.1 mg/kg CD3/BCMA/CD38-118 | 594.9 | 500.4 to 689.4 | **** | <0.0001 |
| Vehicle vs. 0.02 mg/kg CD3/BCMA/CD38-118 | 259.6 | 165.1 to 354.1 | **** | <0.0001 |
| Vehicle vs. 0.5 mg/kg BEAT CD3/CD38 | 564.9 | 470.4 to 659.4 | **** | <0.0001 |
| Vehicle vs. 0.1 mg/kg BEAT CD3/CD38 | 444.5 | 346.7 to 542.3 | **** | <0.0001 |
| Vehicle vs. 0.02 mg/kg BEAT CD3/CD38 | 178.9 | 76.84 to 281.0 | **** | <0.0001 |
| Vehicle vs. 2.5 mg/kg Teclistamab | 506.3 | 411.8 to 600.8 | **** | <0.0001 |
| Vehicle vs. 0.5 mg/kg Teclistamab | 519.8 | 422.0 to 617.6 | **** | <0.0001 |
| Vehicle vs. 0.1 mg/kg Teclistamab | 189.8 | 91.94 to 287.6 | **** | <0.0001 |
| 0.5 mg/kg CD3/BCMA/CD38-118 vs. 0.1 mg/kg CD3/BCMA/CD38-118 | 11.12 | −83.38 to 105.6 | ns | >0.9999 |
| 0.5 mg/kg CD3/BCMA/CD38-118 vs. 0.02 mg/kg CD3/BCMA/CD38-118 | −324.2 | −418.7 to −229.7 | **** | <0.0001 |
| 0.5 mg/kg CD3/BCMA/CD38-118 vs. 0.5 mg/kg BEAT CD3/CD38 | −18.91 | −113.4 to 75.58 | ns | 0.9998 |
| 0.5 mg/kg CD3/BCMA/CD38-118 vs. 0.1 mg/kg BEAT CD3/CD38 | −139.3 | −237.1 to −41.44 | *** | 0.0003 |
| 0.5 mg/kg CD3/BCMA/CD38-118 vs. 0.02 mg/kg BEAT CD3/CD38 | −404.9 | −506.9 to −302.8 | **** | <0.0001 |
| 0.5 mg/kg CD3/BCMA/CD38-118 vs. 2.5 mg/kg Teclistamab | −77.49 | −172.0 to 17.00 | ns | 0.2183 |
| 0.5 mg/kg CD3/BCMA/CD38-118 vs. 0.5 mg/kg Teclistamab | −63.96 | −161.8 to 33.86 | ns | 0.5461 |
| 0.5 mg/kg CD3/BCMA/CD38-118 vs. 0.1 mg/kg Teclistamab | −394 | −491.8 to −296.2 | **** | <0.0001 |
| 0.1 mg/kg CD3/BCMA/CD38-118 vs. 0.02 mg/kg CD3/BCMA/CD38-118 | −335.3 | −429.8 to −240.8 | **** | <0.0001 |
| 0.1 mg/kg CD3/BCMA/CD38-118 vs. 0.5 mg/kg BEAT CD3/CD38 | −30.03 | 124.5 to 64.47 | ns | 0.9918 |
| 0.1 mg/kg CD3/BCMA/CD38-118 vs. 0.1 mg/kg BEAT CD3/CD38 | −150.4 | −248.2 to −52.56 | **** | <0.0001 |
| 0.1 mg/kg CD3/BCMA/CD38-118 vs. 0.02 mg/kg BEAT | −416 | −518.1 | **** | <0.0001 |

TABLE 50-continued

Statistical analysis of FIG. 47 (A, B). Differences in tumor volume were determined using a two-way analysis of variance (ANOVA) with Tukey's multiple comparison test, n = 6-8 mice per group. P value < 0.05 was considered statistically significant, with the level of significancy represented by asterisks as followed: ns p ≥ 0.05; * p < 0.05;  p < 0.01; * p < 0.001; **** p < 0.0001.

| Group comparison | Mean Diff. ($mm^3$) | 95.00% CI of diff. | Summary | Adjusted P Value |
|---|---|---|---|---|
| CD3/CD38 | | to −313.9 | | |
| 0.1 mg/kg CD3/BCMA/CD38-118 vs. 2.5 mg/kg Teclistamab | −88.61 | −183.1 to 5.888 | ns | 0.0878 |
| 0.1 mg/kg CD3/BCMA/CD38-118 vs. 0.5 mg/kg Teclistamab | −75.07 | −172.9 to 22.74 | ns | 0.3063 |
| 0.1 mg/kg CD3/BCMA/CD38-118 vs. 0.1 mg/kg Teclistamab | −405.1 | −503.0 to −307.3 | **** | <0.0001 |
| 0.02 mg/kg CD3/BCMA/CD38-118 vs. 0.5 mg/kg BEAT CD3/CD38 | 305.3 | 210.8 to 399.8 | **** | <0.0001 |
| 0.02 mg/kg CD3/BCMA/CD38-118 vs. 0.1 mg/kg BEAT CD3/CD38 | 185 | 87.16 to 282.8 | **** | <0.0001 |
| 0.02 mg/kg CD3/BCMA/CD38-118 vs. 0.02 mg/kg BEAT CD3/CD38 | −80.65 | −182.7 to 21.41 | ns | 0.2661 |
| 0.02 mg/kg CD3/BCMA/CD38-118 vs. 2.5 mg/kg Teclistamab | 246.7 | 152.2 to 341.2 | **** | <0.0001 |
| 0.02 mg/kg CD3/BCMA/CD38-118 vs. 0.5 mg/kg Teclistamab | 260.3 | 162.5 to 358.1 | **** | <0.0001 |
| 0.02 mg/kg CD3/BCMA/CD38-118 vs. 0.1 mg/kg Teclistamab | −69.8 | −167.6 to 28.01 | ns | 0.4137 |
| 0.5 mg/kg BEAT CD3/CD38 vs. 0.1 mg/kg BEAT CD3/CD38 | −120.3 | −218.2 to −22.53 | ** | 0.0041 |
| 0.5 mg/kg BEAT CD3/CD38 vs. 0.02 mg/kg BEAT CD3/CD38 | −386 | −488.0 to −283.9 | **** | <0.0001 |
| 0.5 mg/kg BEAT CD3/CD38 vs. 2.5 mg/kg Teclistamab | −58.58 | −153.1 to 35.92 | ns | 0.6227 |
| 0.5 mg/kg BEAT CD3/CD38 vs. 0.5 mg/kg Teclistamab | −45.04 | −142.9 to 52.77 | ns | 0.9069 |
| 0.5 mg/kg BEAT CD3/CD38 vs. 0.1 mg/kg Teclistamab | −375.1 | −472.9 to −277.3 | **** | <0.0001 |
| 0.1 mg/kg BEAT CD3/CD38 vs. 0.02 mg/kg BEAT CD3/CD38 | −265.6 | −370.8 to −160.5 | **** | <0.0001 |
| 0.1 mg/kg BEAT CD3/CD38 vs. 2.5 mg/kg Teclistamab | 61.76 | −36.05 to 159.6 | ns | 0.5968 |
| 0.1 mg/kg BEAT CD3/CD38 vs. 0.5 mg/kg Teclistamab | 75.3 | −25.72 to 176.3 | ns | 0.3485 |
| 0.1 mg/kg BEAT CD3/CD38 vs. 0.1 mg/kg Teclistamab | −254.8 | −355.8 to −153.8 | **** | <0.0001 |
| 0.02 mg/kg BEAT CD3/CD38 vs. 2.5 mg/kg Teclistamab | 327.4 | 225.3 to 429.5 | **** | <0.0001 |
| 0.02 mg/kg BEAT CD3/CD38 vs. 0.5 mg/kg Teclistamab | 340.9 | 235.8 to 446.1 | **** | <0.0001 |
| 0.02 mg/kg BEAT CD3/CD38 vs. 0.1 mg/kg Teclistamab | 10.85 | −94.30 to 116.0 | ns | >0.9999 |
| 2.5 mg/kg Teclistamab vs. 0.5 mg/kg Teclistamab | 13.54 | −84.28 to 111.4 | ns | >0.9999 |
| 2.5 mg/kg Teclistamab vs. 0.1 mg/kg Teclistamab | −316.5 | −414.4 to −218.7 | **** | <0.0001 |
| 0.5 mg/kg Teclistamab vs. 0.1 mg/kg Teclistamab | −330.1 | −431.1 to −229.1 | **** | <0.0001 |

The serum concentrations were determined on day 21 (1 week post last dose) using the same previous ELISA methods, excluding any animals which reached maximum tumor size prior to that timepoint. However, the in vivo presence of IVIG impacts the molecule's half-lives (at least for CD3/BCMA/CD38-118; not shown), and the trough concentrations dropped below the limit of quantification for the lower treatment doses (FIG. 47C). Additionally, compared to the trough exposures in the absence of IVIG (FIG. 44C), the dose (5-fold) to exposure levels (17-fold) were no longer linear between treatment doses (FIG. 47C). At a dose of 0.5 mg/kg, PK data showed relatively similar trough concentrations of CD3/BCMA/CD38-118 and BEAT CD3/CD38 with modestly lower exposures of teclistamab (FIG. 47C). On the other hand, at 0.1 mg/kg the trough exposures levels of BEAT CD3/CD38 and teclistamab could not be quantified (FIG. 47C). As such, the differences in potency observed at this dose (0.1 mg/kg; FIG. 47B) cannot be correlated with serum trough concentrations.

In summary, when compared in a clinically relevant model (with IVIG), CD3/BCMA/CD38-118 showed superior potency to the clinical approved CD3×BCMA bispecific antibody teclistamab (Pillarisetti K. et al., 2020) when used as a therapeutic treatment in a human myeloma xenograft model in NSG mice. When compared to BEAT CD3/CD38 differences were smaller with CD3/BCMA/CD38-118 only showing significantly better in vivo efficacy compared to BEAT CD3/CD38 at 0.1 mg/kg, suggesting that the simultaneous targeting of BCMA and CD38 can increase tumor killing capacity in vivo, even against BCMA and CD38 low expressing tumor cells.

EXAMPLE 24: COMPETITION ASSAY OF CD3/BCMA/CD38-118 TO ISATUXIMAB AND TO DARATUMUMAB BY BIO-LAYER INTERFEROMETRY

Materials and Methods

Competition of CD3/BCMA/CD38-118 to isatuximab and to daratumumab for binding to human CD38 was assessed using Octet Bio-Layer Interferometry. Measurements were done on an OctetRED96e instrument (Sartorius) and analyzed using the Data Analysis version 11.1 software (Sartorius). Biotinylated recombinant human CD38-avi-his protein (Acrobiosystems, cat.nb. CD8-H82E7) was loaded at 1 μg/mL in kinetic buffer (Sartorius, catalog NO: 18-1105) for 5 min onto streptavidin SA Biosensor (Sartorius, catalog NO: 18-5019). The CD38 loaded biosensor was then dipped into a saturating solution of isatuximab (SEQ ID NO: 569 and SEQ ID NO: 570) or of daratumumab (Darzalex®, Janssen) at 200 nM for 10 minutes, followed by a successive dip into a mixed solution of 200 nM isatuximab and 200 nM CD3/BCMA/CD38-118, or into a mixed solution of 200 nM daratumumab and 200 nM CD3/BCMA/CD38-118 for 10 minutes. As control for isatuximab or daratumumab saturation of CD38 loaded biosensor surface, the same experimental procedure was performed with a second dip into a solution of 400 nM isatuximab or of 400 nM daratumumab, respectively. Fresh streptavidin biosensors were immobilized with biotinylated human CD38 before each cycle. All steps were performed at 25° C. and 1000 RPM shaking.

Results and Conclusions

To assess whether CD3/BCMA/CD38-118 could still bind human CD38 (hsCD38) previously saturated with isatuximab or with daratumumab, we used Bio-Layer Interferometry. As shown in FIGS. 48A, after saturating recombinant human CD38 protein with isatuximab, CD3/BCMA/CD38-118 was not able to bind recombinant human CD38 protein, as shown by no increase in signal visible upon CD3/BCMA/CD38-118 loading, in the presence of Isatuximab. On the other hand, as shown in FIGS. 48B, after saturating recombinant human CD38 protein with daratumumab, CD3/BCMA/CD38-118 was still able to bind hsCD38, as shown by the increase in signal visible upon CD3/BCMA/CD38-118 loading.

EXAMPLE 25: THE POSITIONING OF BINDERS IN CD3/BCMA/CD38 ANTIBODIES ALLOWS FOR POTENCY OPTIMIZATION AND REDUCTION OF ON-TARGET OFF-TUMOR ACTIVITY

Material and Methods

Generation of Additional Control Molecules

CD3/BCMA/CD38-118 is in the configuration BO, whereby the CD3 binder is in the Fc distal position of the B arm of the BEAT construct, the BCMA binder is in the Fc proximal position of the B arm and the CD38 binder is on the A arm of the BEAT construct (FIG. 9A). To evaluate whether the position of the tumor-associated antigen (TAA) binders relative to the CD3 binder can impact tumor killing potency or on-target off-tumor T cell activation, additional control molecules were produced according to the protocol described in Example and according to the sequence combinations detailed in Table 51. CD3/BCMA/CD38-170 uses the same Fab binding arms as CD3/BCMA/CD38-118 but whereby the positions of the BCMA and CD38 are reversed (FIG. 49). Additional controls were generated that used an irrelevant binder, dubbed G6DU, in place of specific binding Fabs and that displayed the same alternative arrangement of the binders within the trispecific antibody as detailed in Table 52.

TABLE 51

Chain combination of additional CD3/BCMA/CD38 control antibodies

| CD3/BCMA/ CD38- | Chain 1 | Chain 2 | Chain 3 |
|---|---|---|---|
| 170 | SEQ ID NO: 727 | SEQ ID NO: 728 | SEQ ID NO: 1 |
| 171 | SEQ ID NO: 528 | SEQ ID NO: 728 | SEQ ID NO: 1 |
| 172 | SEQ ID NO: 727 | SEQ ID NO: 555 | SEQ ID NO: 1 |

RDL assay with T cells and multiple myeloma KMS-12-BM tumor cells

CD3/BCMA/CD38-118 (previously described in Example 9), -149, –151 (previously described in Example 22a), -170, –171 and -172 antibodies were evaluated for cytotoxic killing potency of the MM cell line KSM-12-BM. The RDL assay was performed as described in Example 22f, except that experiments were conducted with a dose-range starting at 200 nM followed by 10-fold serial dilutions. Percentage of tumor cytotoxicity was determined by measuring the percentage of dead target cells. Percentages of cytotoxicity were plotted and fitted using a nonlinear logistic 4PL model with variable slope. A two-way ANOVA followed by a Sidak's multiple comparisons test was used for statistical comparison. Two independent experiments were performed with a total of six donors.

On-target off-tumor activity

CD3/BCMA/CD38-118, 149, 151, 170, 171 and 172 antibodies were evaluated for on-target off-tumor T cell activation in a high density PBMC assay. The assay was performed as described in example 13, except that experiments were conducted using a dose-range starting at 20 nM followed by 5-fold serial dilutions. The percentage of CD8+ T cells expressing CD25 was plotted and fitted using a nonlinear logistic 4PL model with variable slope. A two-way ANOVA followed by a Sidak's multiple comparisons test was used for statistical comparison. Two independent experiments were performed with a total of six donors.

Results and Conclusions

Control antibodies were designed and successfully produced in CHO-S cells with percentages of purity ranging from 97 to 98%, as measured by SE-HPLC (Table 52).

TABLE 52

Description and characterization of additional CD3/BCMA/CD38 control antibodies (FIG. 49) used to further characterize lead CD3/BCMA/CD38 molecules.

| CD3/BCMA/CD38- | 170 | 171 | 172 |
|---|---|---|---|
| Format | D | D | D |
| CD3 binder | C1-D6 | C1-D6 | C1-D6 |
| CD38 binder | B3-C11 | B3-C11 | G6DU |
| BCMA binder | E6-G6-N82aS | G6DU | E6-G6-N82aS |
| Final Purity (% monomer) | 98 | 97 | 98 |

Newly generated control antibodies (CD3/BCMA/CD38-170, -171 and -172) were compared in an RDL assay and in an HD-PBMC assay to previous constructs (CD3/BCMA/CD38-118, -149 and -151).

To assess the impact of the position of the CD38 binder relative to the CD3 binder, the control antibodies with the CD38 binder either in distal or proximal to the CD3 binder and lacking the BCMA binder (CD3/BCMA/CD38-171 (FIG. 49) versus CD3/BCMA/CD38-149 (FIG. 9A), respectively) were compared. As shown in FIGS. 50A, the control antibody with the CD38 binder proximal to the CD3 binder (CD3/BCMA/CD38-171, configuration D) triggered a statistically higher tumor cell cytotoxicity compared to the control antibody with the CD38 binder distal to the CD3 binder (CD3/BCMA/CD38-149).

The on-target off-tumor T cell activation, as measured by CD25 upregulation on CD8*T cells in a HD-PBMC assay, was also statistically higher for the control antibody with the CD38 binder proximal to the CD3 binder (CD3/BCMA/CD38-171) compared to the control antibody with the CD38 binder distal to the CD3 binder (CD3/BCMA/CD38-149) (FIG. 51A).

The tumor killing potency and on-target off-tumor T cell activation were also evaluated for control antibodies with the BCMA binder either distal or proximal to the CD3 binder and lacking the CD38 binder (CD3/BCMA/CD38-151 (FIG. 9A) versus CD3/BCMA/CD38-172 (FIG. 49), respectively). The control antibody with the BCMA binder proximal to the CD3 binder (CD3/BCMA/CD38-151) induced a significantly higher tumor cytotoxicity than the control antibody with the BCMA binder distal to the CD3 binder (CD3/BCMA/CD38-172, configuration D) (FIG. 50B). However, the on-target off-tumor T cell activation, as measured by CD25 upregulation on CD8*T cells in the HD-PBMC assay, was very low for both antibodies lacking the CD38 binder (FIG. 51B).

To understand whether the spatial arrangement of the binders in the trispecific antibody CD3/BCMA/CD38-118 (FIG. 9A) confers the optimal balance between potency and on-target off-tumor activity, another configuration of CD3/BCMA/CD38-118, in which the CD38 and BCMA binders have been reversed (CD3/BCMA/CD38-170 (FIG. 49)) was produced and both antibodies were evaluated for tumor killing potency and on-target off-tumor T cell activation. CD3/BCMA/CD38-118 and the reversed CD3/BCMA/CD38-170 antibody showed overall similar tumor killing potency (FIG. 50C). However, the CD3/BCMA/CD38-170 antibody, in which the CD38 binder is proximal and the BCMA binder is distal to the CD3 binder, induced significantly higher on-target off-tumor T cell activation compared to the CD3/BCMA/CD38-118 antibody (FIG. 51C).

Taken together, these data demonstrated that an antibody construct with the CD38 binder proximal to the CD3 binder in an antibody construct increases both tumor killing potency and on-target off-tumor T cell activation compared to an antibody in which the CD38 binder is distal to the CD3 binder. The positioning of the BCMA binder proximal to the CD3 binder also increased the tumor killing potency. The on-target off-tumor T cell activation was low for the control molecules with CD3 and BCMA binders but lacking a CD38 binder, most likely due to the lower number of PBMCs expressing BCMA compared to CD38. Finally, the specific positioning of the binders in CD3/BCMA/CD38-118 conferred a similar tumor killing potency and lower on-target off-tumor activity, compared to the reversed CD3/BCMA/CD38-170 antibody.

For CD3/BCMA/CD38 tri-specific constructs, the binding domain with the highest expected on-target off-tumor activity (the CD38 binding domain, due to its expression on immune cells) should be placed further away (or distal) from the CD3 binding domain and the binding domain with the lowest expected on-target off tumor effects (the BCMA binding domain) should be placed in a closer (or proximal) location to the CD3 binding domain.

EXAMPLE 26: EPITOPE MAPPING FOR CD38 TARGETED BY ANTI-CD38-B3 FAB USING X-RAY CRYSTALLOGRAPHY

The present example presents the solved crystal structure of anti-CD38-B3 Fab (SEQ ID NO: 110 and SEQ ID NO: 1) bound to the recombinant human CD38 antigen (SEQ ID NO: 729) at 3.4 Å resolution.

Materials and Methods

Production of CD38 Antigen

Gene Synthesis and Cloning cDNA encoding the human CD38 (hsCD38) extracellular domain (ECD, amino acid residues Arg45-Ile300 of Uniprot entry P28907), containing the following mutations on designed to move the four N-linked glycosylation sites (N100D, N164 Å, N209D and N219D); the ECD was fused to a C-terminal 6-histidine peptide tag,synthesized and cloned into a pcDNA3.1 derived vector (Invitrogen). The expression vector also carries a CMV promoter, a bovine hormone poly-adenylation (poly(A)), the origin of plasmid replication of Epstein-Barr virus (oriP), and the murine VJ2C leader peptide for secretion of the encoded polypeptide chain.

Protein Expression and Purification

*Homo sapiens* (hs) CD38 ECD was expressed in Expi293F™ cells (ThermoFisher) cultured in Expi293 Expression Medium (Thermo Fisher). The day prior to transfection, the cells were centrifuged for 10 minutes at 900 rpm and resuspended in fresh Expi293 Expression medium to a final concentration of $2\times10^6$ viable cells/ml. The next day, the cells were diluted to a final density of $2.5\times10^6$ viable cells/ml and transfected with a DNA-ExpiFectamine™ 293 transfection reagent (ThermoFisher) mixture using 1 μg of DNA and 2.7 μl of transfection agent per 1 ml of culture. Typically, the DNA and ExpiFectamine™ are diluted with 5% final culture volume of Opti-Plex™ Complexation Buffer (ThermoFisher), gently mixed by swirling and the individual reagents incubated for 5 minutes at room temperature. The diluted ExpiFectamine™ 293 Reagent is gently added to the diluted plasmid DNA and the complex incubated at room temperature for 20 minutes. The complex is then transferred to the cells and cells incubated on an orbital shaking platform at 37° C. with 8% CO2. 18-22 hours post-transfection, the cells are supplemented with ExpiFectamine™ 293 Transfection Enhancer 1 and ExpiFectamine™ 293 Transfection Enhancer 2 (ThermoFisher) using a volume corresponding to 0.5% and 5% of the final culture volume for the Enhancer 1 and Enhancer 2, respectively. 5 days post-transfection, cell-free culture supernatant containing the recombinant protein were prepared by centrifugation followed by filtration and used for further purification.

For hsCD38 purification, the cleared supernatant containing the protein of interest was loaded on a 5 mL HisTrap™ Excel column (Cytiva) equilibrated with PBS pH7.4 at 10 mL/min using an Akta™ pure FPLC system (Cytiva). The column was then washed with 7 column volumes of PBS pH 7.4 at 5 mL/min and the protein eluted with a 4-steps gradient with 5%, 20%, 50%, and 100% of elution buffer composed of PBS pH 7.4 and 500 mM Imidazole, each step running over 7 column volumes. Peak fractions were pooled and concentrated using a Centricon® centrifugal filter device (Merck Millipore) equipped with a 10 kDa cut-off membrane. The concentrated sample was further purified by size exclusion chromatography (SEC) using a HiLoad Superdex-200 26/600 (Cytiva) run at 2.8 mL/min and PBS pH 7.4.

Generation of anti-CD38-B3 Fab

Gene Synthesis and Cloning

For expression of the anti-CD38-B3 Fab (SEQ ID NO: 110 and SEQ ID NO: 1), heavy and light chain vectors were constructed as described previously in Example 5. Briefly, cDNAs encoding the variable heavy chain region were amplified by PCR using the scFv clone in its phage library vector. The VH PCR product was cloned in the modified pcDNA 3.1 vector upstream of a cDNA encoding a human IgG1 heavy chain CH1 domain. The fixed Vκ3-15/Jκ1 light chain (SEQ ID NO: 1) was cloned in the modified pcDNA 3.1 vector upstream of a cDNA encoding a human kappa constant light chain domain.

Protein Expression and Purification

For Fab expression, equal quantities of heavy chain and light chain vectors were co-transfected into Expi293F™ cells (ThermoFisher). The expression was then performed as described previously for human CD38 ECD. 5 days post-transfection, cell-free culture supernatant containing the recombinant protein were prepared by centrifugation followed by filtration and used for further purification.

For purification, the cleared supernatant containing the protein of interest was loaded on a CaptureSelect™ CH1-XL (Thermo Scientific™) column equilibrated with PBS pH7.4. Fab was then eluted with glycine 0.1 M pH 3.5. After neutralization with 1/10 volume of Tris-HCl pH 8.0, the eluate was further purified by SEC using a HiLoad Superdex-200 16/600 (Cytiva) equilibrated in PBS pH 7.4.

Crystallization and Structure Determination of the B3/CD38 Complex

For crystallization, the complex of hsCD38 with the anti-CD38-B3 Fab was formed by mixing the receptor with a 1.3-fold excess of Fab followed by purification by SEC using a HiLoad Superdex-200 16/600 (Cytiva) equilibrated in 25 mM HEPES pH7.4, 140 mM NaCl. The Fab/hsCD38 complex was concentrated to ~11 mg/mL. The crystals used for data collection were grown by the sitting drop vapor diffusion method with a reservoir solution containing 18% w/v PEG 4000, 0.1M sodium citrate, 0.2M ammonium acetate, pH 6.0. Drops consisting of 1 μL protein+1 μL precipitant were set up at 20° C., and crystals appeared within 3-7 days. The resulting crystals were cryoprotected by soaking in well solution supplemented with 35% ethylene glycol, then flash cooled and stored in liquid nitrogen until data collection. Diffraction data were collected at the Swiss Light Source (SLS). The data were indexed in P6522 and integrated and scaled using XDS and XSCALE (W. Kabsch, Xds. Acta Crystallogr. D 66, 125-132 (2010)) to 3.4 Å resolution. The structure was determined by molecular replacement with Phaser. The Fab and CD38 from structure with pdb code 7DHA were used as the initial search model and two copies of the anti-CD38-B3 Fab/hsCD38 complex were found in the asymmetric unit. Rigid body refinement, simulated annealing and restrained refinement were carried out in Refmac (G. N. Murshudov, A. A. Vagin, E. J. Dodson, Refinement of macromolecular structures by the maximum-likelihood method. Acta Crystallogr. D 53, 240-255 (1997)). Between rounds of refinement, the model was built and adjusted using Coot (P. Emsley, B. Lohkamp, W. G. Scott, K. Cowtan, Features and development of Coot. Acta Crystallogr. D 66, 486-501 (2010)).

The structure was analyzed with the Protein Interfaces, Surfaces, and Assemblies (PISA) program. All figures were made with PyMol (DeLano Scientific).

Results and Conclusion

To obtain the atomic-level resolution of the epitope/paratope interaction, the crystal structure of the anti-CD38-B3 Fab (SEQ ID NO: 110 and SEQ ID NO: 1) in complex with the ectodomain of hsCD38 antigen (SEQ ID NO: 729) was solved at 3.4 Å resolution.

A representation of the structure of the anti-CD38-B3 Fab bound to CD38 is shown in FIG. 52A. Anti-CD38-B3 Fab buries a total of 1,707 A2 at the interface with hsCD38 (853 A2 for B3 and 854 A2 for CD38). The recognition of CD38 is dominated by the heavy chain, where heavy-chain complementarity-determining region2 (HCDR2) and HCDR3 make extensive hydrogen bond and hydrophobic contacts with CD38. The light-chain, through exposed residues at the tip of LCDR1 and LCDR3, also engages the antigen via hydrogen and hydrophobic interactions. The B3 heavy chain contributes to 68% of the Fab buried surface area, similar to other antibodies against protein antigens.

The anti-CD38-B3 Fab recognises 23 residues of human CD38 via hydrogen bonds, ionic interactions and hydrophobic contacts (FIG. 52B and FIG. 52C). The epitope consists of residues Glu103, Gln107, Thr114, Thr116, Arg194, Arg195, Glu198, Ala199, Asp202, Ser224, His228, Asn229, Gln231, Pro232, Glu233, Lys234, Val235, Gln236, Ile265, Ser267, Lys268, Arg269 and Asn270. The residues within the HCDR2 and HCDR3 of B3, including Arg50, Thr53, Asn56, Asn58, Ser95 and Ser100A make hydrogen bonds with the residues on the surface of CD38, including His228, Gln231, Glu233, Lys268, Arg269. HCDR2 via Ile52, Gly54 and Ala55 make hydrophobic contacts with the residues Lys268 and Arg269. Three hydrophobic residues in HCDR3, Pro97, Leu99 and GIy100B interact with hydrophobic residues on CD38 as well as with surrounding polar residues, including Pro232, Glu233, Lys234, Val235 and Gln236. HCDR1 residues, via the main chain of Thr30 and Leu31 form electrostatic interaction with Asn270. Interestingly, Gln61 and Gln64, residues within the framework region of the anti-CD38-B3 heavy chain, also contribute to the interaction with CD38 by interactions with Gln107, Glu103 and Arg194.

The light chain, through exposed residues at the tip of LCDR1 and LCDR3, also engages the antigen via hydrogen bond, ionic and hydrophobic interactions (FIG. 52C). Asn92 from LCDR3 is the only light chain residue that binds CD38 through a hydrogen bond with Lys234. The light chain also contributes to the hydrophobic interactions where LCDR3 Trp94 interacts with the aliphatic portions of Gln231. The backbone carbonyl oxygen group of Glu1 within the light chain also contribute to the interaction with the side chain of Arg195.

The crystal structure of the B3 binder in complex with CD38 confirmed the results from the competition assay (Example 24): B3 recognizes a distinct but overlapping epitope with daratumumab and isatuximab (2 residues shared between the epitope of B3 and daratumumab, and 6 residues shared between the epitope of B3 and isatuximab) (FIG. 53A). While the binding modes of B3 and daratumumab show that both Fabs can bind simultaneously to the surface of CD38, the binding orientations of B3 and isatuximab clearly cause steric collision between both Fabs, preventing their simultaneous binding to CD38 (FIG. 53B and FIG. 53C).

The invention claimed is:

1. A trispecific antibody that binds to human CD3, human B-cell maturation antigen (BCMA), and human CD38, comprising:

a. a first heavy chain polypeptide, said first heavy chain polypeptide comprising
   i. a first heavy chain variable domain comprising a CDR1 having the amino acid sequence shown as SEQ ID NO: 181, a CDR2 having the amino acid sequence shown as SEQ ID NO: 307, and a CDR3 having the amino acid sequence shown as SEQ ID NO: 433, and
   ii. a second heavy chain variable domain comprising a CDR1 having the amino acid sequence shown as SEQ ID NO: 234, a CDR2 having the amino acid sequence shown as SEQ ID NO: 360, and a CDR3 having the amino acid sequence shown as SEQ ID NO: 486; and b. a second heavy chain polypeptide, said second heavy chain polypeptide comprising a heavy chain variable domain comprising a CDR1 having the amino acid sequence shown as SEQ ID NO: 239, a CDR2 having the amino acid sequence shown as SEQ ID NO: 365, and a CDR3 having the amino acid sequence shown as SEQ ID NO: 491; and c. three light chain polypeptides, each of said light chain polypeptides comprising a light chain variable domain comprising a CDR1 having the amino acid sequence shown as SEQ ID NO: 721, a CDR2 having the amino acid sequence shown as SEQ ID NO: 722, and a CDR3 having the amino acid sequence shown as SEQ ID NO: 723.

2. The trispecific antibody of claim 1, wherein the second heavy chain variable domain of the first heavy chain polypeptide is fused at the N-terminus to the C-terminus of the first heavy chain variable domain of the first heavy chain polypeptide via a peptide linker.

3. The trispecific antibody of claim 1, wherein said trispecific antibody comprises a non-naturally occurring Fc domain.

4. The trispecific antibody of claim 1, wherein one heavy chain polypeptide comprises a first engineered IgG1 CH3 domain and the other heavy chain polypeptide comprises a second engineered IgG1 CH3 domain, wherein said first engineered IgG1 CH3 domain comprises all of the substitutions of the group consisting of: Q347A, S364K, T366V, K370T, K392Y, F405S, Y407V, K409W, and T411 N according to EU numbering, and said second engineered IgG1 CH3 domain comprises all of the substitutions of the group consisting of: Q347E, Y349A, L351 F, S364T, T366V, K370T, T394D, V397L, D399E, F405A, Y407S, K409R, and T411R according to EU numbering.

5. The trispecific antibody of claim 1, wherein two of the three light chain polypeptides are covalently linked via disulfide bonding to the first heavy chain polypeptide and the third light chain polypeptide is covalently linked via disulfide bonding to the second heavy chain polypeptide.

6. The trispecific antibody of claim 1, wherein the first heavy chain polypeptide comprises a first heavy chain variable domain comprising the amino acid sequence shown as SEQ ID NO: 592.

7. The trispecific antibody of claim 1, wherein the first heavy chain polypeptide comprises a second heavy chain variable domain comprising the amino acid sequence shown as SEQ ID NO: 591.

8. The trispecific antibody of claim 1, wherein the second heavy chain polypeptide comprises a heavy chain variable domain comprising the amino acid sequence shown as SEQ ID NO: 594.

9. The trispecific antibody of claim 1, wherein the first heavy chain polypeptide comprises a first heavy chain variable domain comprising the amino acid sequence shown as SEQ ID NO: 592, the first heavy chain polypeptide comprises a second heavy chain variable domain comprising the amino acid sequence shown as SEQ ID NO: 591, and the second heavy chain polypeptide comprises a heavy chain variable domain comprising the amino acid sequence shown as SEQ ID NO: 594.

10. A trispecific antibody that binds to human CD3, human BCMA, and human CD38, comprising:

(i) a first polypeptide comprising the amino acid sequence shown as SEQ ID NO: 546;

(ii) a second polypeptide comprising the amino acid sequence shown as SEQ ID NO: 547; and (iii) a third, a fourth, and a fifth polypeptide each comprising the amino acid sequence shown as SEQ ID NO: 1.

* * * * *